US007129042B2

(12) United States Patent
Gillim-Ross et al.

(10) Patent No.: US 7,129,042 B2
(45) Date of Patent: Oct. 31, 2006

(54) COMPOSITIONS AND METHODS FOR DETECTING SEVERE ACUTE RESPIRATORY SYNDROME CORONAVIRUS

(75) Inventors: Laura Gillim-Ross, Mechanicville, NY (US); Jill Taylor, Albany, NY (US); David R. Scholl, Athens, OH (US); David E. Wentworth, Guilderland, NY (US); Joseph D. Jollick, Athens, OH (US)

(73) Assignees: Diagnostic Hybrids, Inc., Athens, OH (US); Health Research Incorporated, Rensselaer, NY (US)

( * ) Notice: Subject to any disclaimer, the term of this patent is extended or adjusted under 35 U.S.C. 154(b) by 0 days.

(21) Appl. No.: 10/699,936

(22) Filed: Nov. 3, 2003

(65) Prior Publication Data

US 2005/0095582 A1 May 5, 2005

(51) Int. Cl.
*C12Q 1/70* (2006.01)
*C12Q 1/18* (2006.01)

(52) U.S. Cl. .......................... 435/5; 435/32; 435/235.1

(58) Field of Classification Search .................... 435/5, 435/32, 235.1; 424/221.1
See application file for complete search history.

(56) References Cited

U.S. PATENT DOCUMENTS

| | | | | |
|---|---|---|---|---|
| 4,244,946 | A | 1/1981 | Rivier et al. | 424/177 |
| 4,949,778 | A | 8/1990 | Saito et al. | 164/468 |
| 5,270,163 | A | 12/1993 | Gold et al. | 435/6 |
| 5,545,806 | A | 8/1996 | Lonberg et al. | 800/2 |
| 5,569,825 | A | 10/1996 | Lonberg et al. | 800/2 |
| 5,625,126 | A | 4/1997 | Lonberg et al. | 800/2 |
| 5,760,029 | A | 6/1998 | Jadhav et al. | 514/211 |
| 6,252,043 | B1 | 6/2001 | Hession et al. | 530/350 |
| 6,376,172 | B1 | 4/2002 | Scholl et al. | 435/5 |
| 6,472,206 | B1 | 10/2002 | Scholl et al. | 435/325 |
| 6,610,474 | B1 | 8/2003 | Huang | 435/5 |

FOREIGN PATENT DOCUMENTS

EP 0 140 308 5/1985

OTHER PUBLICATIONS

Interlab Cell Line Collection (ICLC) on-line catalog. 293T. [online][retreived Jun. 7, 2006] Retreived from the internet <URL: http://wwwsql.iclc.it/test/iclc/det_list.php?line_id=7154&x=19 &y=12>.*

Benbacer et al. (1997) "Interspecies aminopeptidase-*N* chimerase reveal species-specific receptor recognition by canine coronavirus, feline infectious peritonitis virus, and transmissible gastroenteritis virus," J Virol, 71:734-737.

Blondelle et al. (1995) "Soluble combinatorial libraries of organic, peptidomimetic and peptide-diversities," Trends Anal Chem, 14:83-92.

Chaloner-Larsson et al. "Establishment and maintenance of a persistent infection of L132 cells by human coronavirus strain 229E," (1981) Arch Virol, 69:117-129.

Cole et al., (1985) "The EBV-Hybridoma Technique and Its Application to Human Lung Cancer," in *Monoclonal Antibodies and Cancer Therapy,* Alan R. Liss, Inc., pp. 77-96.

Compton et al. (1982) "Coronavirus species specificity: Murine coronavirus binds to a mouse-specific epitope on its carcinoembryonic antigen-related receptor glycoprotein," J Virol, 66:7420-7428.

Cote et al. (1983) "Generation of human monoclonal antibodies reactive with cellular antigens," Proc Natl Acad Sci USA, 80:2026-2030.

de Kruif et al. (1996) "Biosynthetically lipid-modified human scFv fragments from phage display libraries as targeting molecules for immunoliposomes," FEBS Lett, 399:232-236.

Delmas et al. (1992) "Aminopeptidase N is a major receptor for the enteropathogenic coronavirus TGEV," Nature, 357:417-420.

Ding et al. (1995) "Synthesis and biological activity of oligosaccharide libraries," Adv Exp Med Biol, 376:261-269.

Drosten et al. (2003) "Identification of a novel coronavirus in patients with severe acute respiratory syndrome," N Engl J Med, 348:1967-1976.

Dveksler et al. (1991) "Cloning of the mouse hepatitus virus (MHV) receptor: Expression in human and hamster cell lines confers susceptibility to MHV," J Virol, 65:6881-6891.

Dveksler et al. (1995) "Mouse hepatitis virus receptor activities of an MHVR/mph chimera and MHVR mutants lacking N-linked glycosylation of the N-terminal domain," J Virol, 69:543-546.

Dveksler et al. (1996) "Expression of the recombinant anchorless N-terminal domain of mouse hepatitus virus (MHV) receptor makes hamster of human cells susceptible to MHV infection," J Virol, 70:4142-4145.

Ecker and Crook (1995) "Combinatorial drug discovery: Which methods will produce the greatest value?" Bio/Technology 13:351-360.

Fields and Noble (1990) "Solid phase peptide synthesis utilizing 9-fluorenylmethoxycarbonyl amino acids," Intl Peptide Protein Res, 35:161-214.

Fouchier et al. (2003) "Koch's postulates fulfilled for SARS virus," Nature, 423:240.

Gleaves et al. (1992) "Detection of human cytomegalovirus in clinical specimens by centrifugation culture with a nonhuman cell line," J Clin Microbiol 30:1045-8.

Gordon et al. (1994) "Applications of combinatorial technologies to drug discovery. 2. Combinatorial organic synthesis, library screening strategies, and future directions," J Med Chem, 37:1385-1401.

Hambor et al. (1988) "Functional consequences of anti-sense RNA-mediated inhibition of CD8 surface expression in a human T cell clone," J Exp Med, 168:1237-1245.

Holmes and Lai (1996) "Coronaviridae: The Viruses and Their Replication," in *Fields Virology,* Third Edition, Lippincott-Raven, pp. 1075-1093.

(Continued)

*Primary Examiner*—Mary E. Mosher
(74) *Attorney, Agent, or Firm*—Medlen & Carroll LLP

(57) ABSTRACT

The invention provides compositions and methods for detecting the presence of SARS-coronavirus, for screening anti-SARS coronavirus agents and vaccines, and for reducing infection with plus-strand RNA viruses such as SARS-coronavirus.

30 Claims, 86 Drawing Sheets

OTHER PUBLICATIONS

Holmes et al. (2001) "Coronaviruses," in *Fields Virology,* Fourth Edition, Lippincott Williams & Wilkins, Chapter 36, pp. 1187-1203.
Huse et al. (1989) "Generation of a Large Combinatorial Library of the Immunoglobulin Repertoire in Phage Lambda," Science, 246:1275-1281.
Karaoglu et al. (1995) "Functional characterization of Ost3p. Loss of the 34-kD subunit of the *Saccharomyces cerevisiae* oligosaccharyltransferase results in biased underglycosylation of acceptor substrates," J Cell Biol, 130:567-577.
Köhler and Milstein (1975) "Continuous cultures of fused cells secreting antibody of predefined specificity," Nature, 256:495-497.
Koivunen et al. (1994) "Isolation of a highly specific ligand for the $\alpha_5\beta_1$ integrin from a phage display library," J Cell Biol, 124:373-380.
Kolb et al. (1997) "Identification of residues critical for the human coronavirus 229E receptor function of human aminopeptidase N," J Gen Virol, 78:2795-2802.
Kontoyiannis et al. (2003) "Aminopeptidase N inhibitors and SARS," Lancet, 361:1558.
Kozbor et al. (1983) "The production of monoclonal antibodies from human lymphocytes," Immunol Today, 4:72.
Ksiazek et al. (2003) "A novel coronavirus associated with severe acute respiratory syndrome," N Engl J Med, 348:1953-1966.
Kuiken et al. (2003) "Newly discovered coronavirus as the primary cause of severe acute respiratory syndrome," Lancet, 362:263-270.
Liang et al. (1996) "Parallel synthesis and screening of a solid phase carbohydrate library," Science, 274:1520-1522.
Look et al. (1989) "Human myeloid plasma membrane glycoprotein CD13 (gp150) is identical to aminopeptidase N," J Clin Invest, 83:1299-1307.
Markus-Sekura (1988) "Techniques for using antisense oligodeoxyribonucleotides to study gene expression," Anal Biochem, 172:289-295.
Marra et al. (2003) "The genome sequence of the SARS-associated coronavirus," Science, 300:1399-1404.
Meienhofer, (1973) "Peptide synthesis: A review of the solid-phase method," in *Hormonal Proteins and Peptides,* vol. II, Chapter 3, Academic Press (title and copyright pages only).
Murphy and Chanock, (2001) "Immunization against viral diseases" in *Fields Virology,* Fourth Edition, Knipe and Howley, Lippincott Williams & Wilkins, Chapter 16, pp. 435-467.
Nakabayashi et al. (1982) "Growth of human hepatoma cell lines with differentiated function in chemically defined medium," Cancer Res, 42:3858-3863.
Nakabayashi et al. (1984) "Phenotypical stability of a human hepatoma cell line, HuH-7, in long-term culture with chemically defined medium," Gann, 75:151-158 (abstract only).
Nakabayashi et al. (1985) "Hormonal control of $\alpha$-fetoprotein secretion in human hepatoma cell lines proliferating in chemically defined medium," Cancer Res. 45:6379-6383.
Palache et al. (1997) "Immunogenicity and reactogenicity of influenza subunit vaccines produced in MDCK cells or fertilized chicken eggs," J Infect Dis, 176(Suppl I):S20-S23.
Peiris et al. (2003) "Coronavirus as a possible cause of severe acute respiratory syndrome," Lancet, 361:1319-1325.
Poon et al. (2003) "Rapid diagnosis of a coronavirus associated with severe acute respiratory syndrome (SARS)," Clin Chem, 49:953-955.
Poutanen et al. (2003) "Identification of severe acute respiratory syndrome in Canada," N Engl J Med, 348:1995-2005.
Rota et al. (2003) "Characterization of a novel coronavirus associated with severe acute respiratory syndrome," Science, 300:1394-1399.
Sawicki and Sawicki (1995) "Coronavirus use discontinuous extension for synthesis of subgenome-length negative strands," Adv Exp Med Biol, 380:499-506.
Sawicki and Sawicki (1998) "A new model for coronavirus transcription," Adv Exp Biol, 440:215-219.
Sawicki et al. (2001) "The RNA structures engaged in replication and transcription of the A59 strain of mouse hepatitis virus," J Gen Virol, 385-96.
Snijder et al. (2003) "Unique and conserved features of genome and proteome of SARS-coronavirus, an early split-off from the coronavirus group 2 lineage," J Mol Biol, 331:991-1004.
Thiel et al. (2003) "Mechanisms and enzymes involved in SARS coronavirus genome expression," J Gen Virol, 84:2305-2315.
Tresnan et al. (1996) "Feline aminopeptidase N serves as a receptor for feline, canine, porcine, and human coronaviruses in serogroup I," J Virol, 70:8669-8674.
Ward et al. (1989) "Binding activities of a repertoire of single immunoglobulin variable domains secreted from *Escherichia coli,* " Nature, 341:544-546.
Wentworth et al. (2001) "Molecular determinants of species specificity in the coronavirus receptor aminopeptidase N (CD13): Influence of N-Linked glycosylation," J Virol, 75:9741-9752.
Williams et al. (1990) "Purification of the 110-kilodalton glycoprotein receptor for mouse hepatitus virus (MHV)-A59 from mouse liver and identification of a nonfunctional, homologous protein in MHV-resistant SJL/J mice," J Virol, 64:3817-3823.
Williams et al. (1991) "Receptor for mouse hepatitis virus is a member of the carcinoembryonic antigen family of glycoproteins," Proc Natl Acad Sci USA, 88:5533-5536.
Winter and Harris (1993) "Humanized antibodies," Immunol Today, 14:243-246.
Yeager et al. (1992) "Human aminopeptidase N is a receptor for human coronavirus 229E," Nature, 357:420-422 (abstract only).
York et al. (1996) "The structures of arabinoxyloglucans produced by solanaceous plants," Carb Res, 285:99-128.
Yount et al. (2003) "Reverse genetics with a full-length infectious cDNA of severe acute respiratory syndrome coronavirus," Proc Natl Acad Sci USA, 100:12995-13000.
Yu et al. (2003) "Putative hAPN receptor binding sites in SARS CoV spike protein," Acta Pharmacol Sin, 24:481-488.
Zeng et al. (2003) "The complete genome sequence of severe acute respiratory syndrome coronavirus strain HKU-39849 (HK-39)," Exp Biol Med, 228:866-73.

* cited by examiner

A.
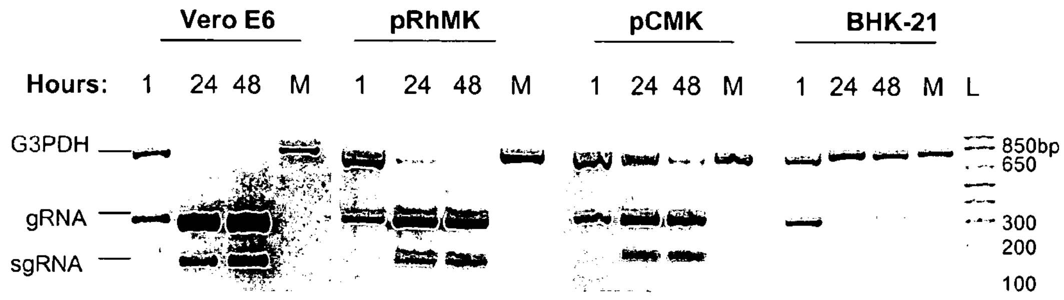
B.
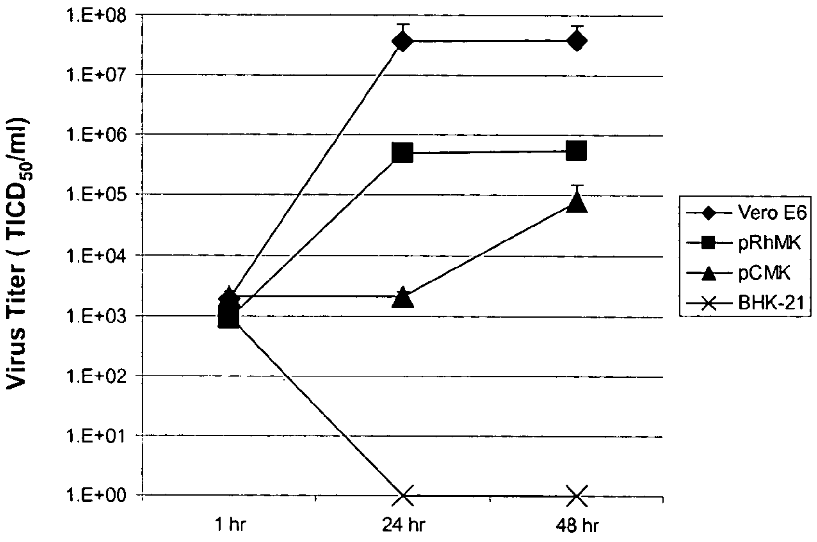
FIG. 2.

A.
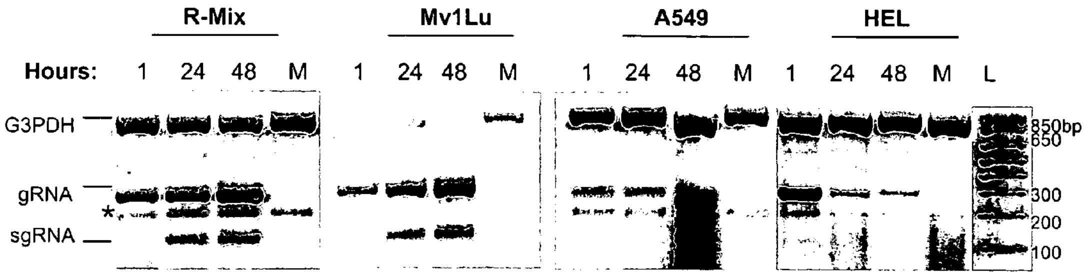
B.
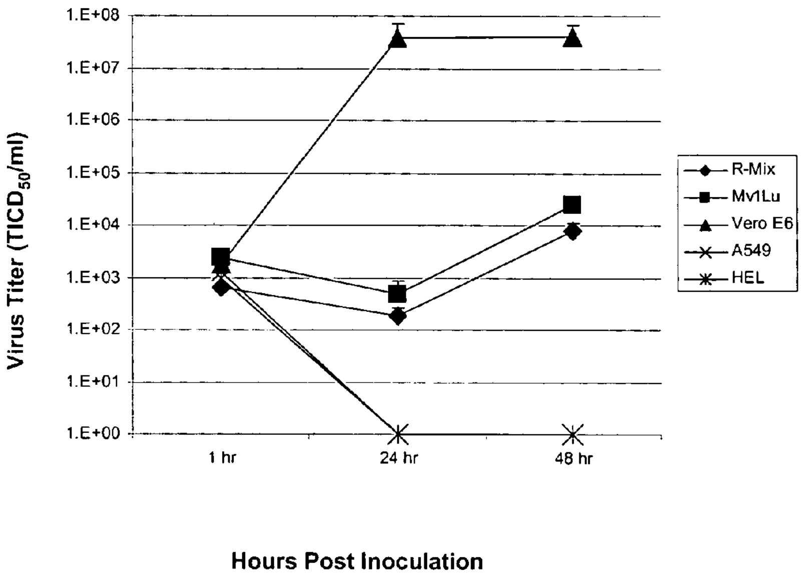
FIG. 4.

A.
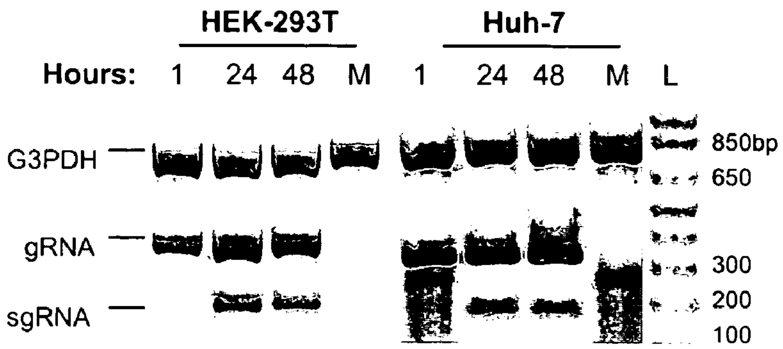
B.
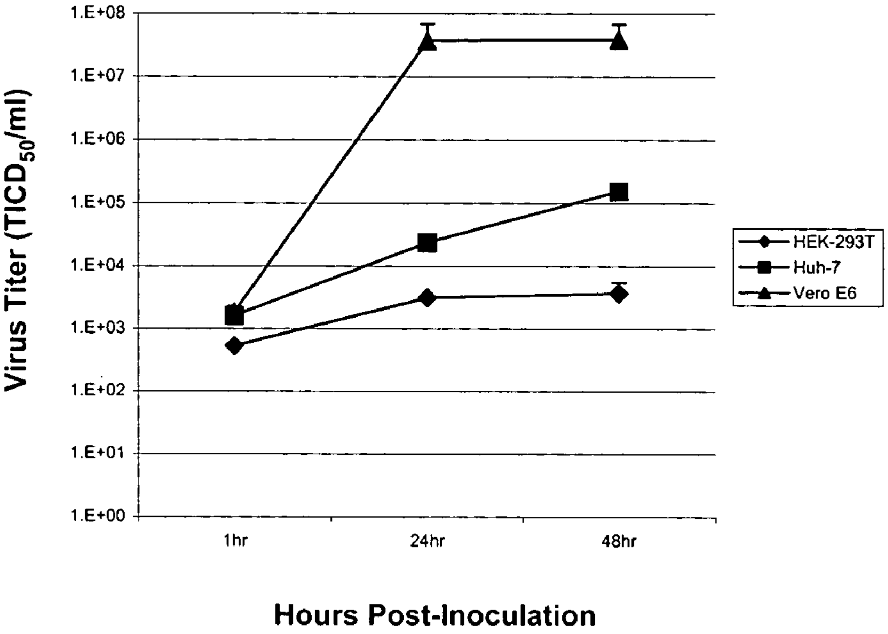
FIG. 5.

A.
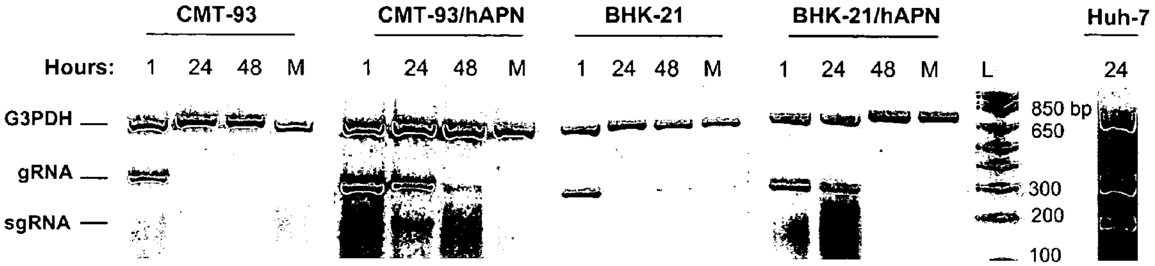
B.
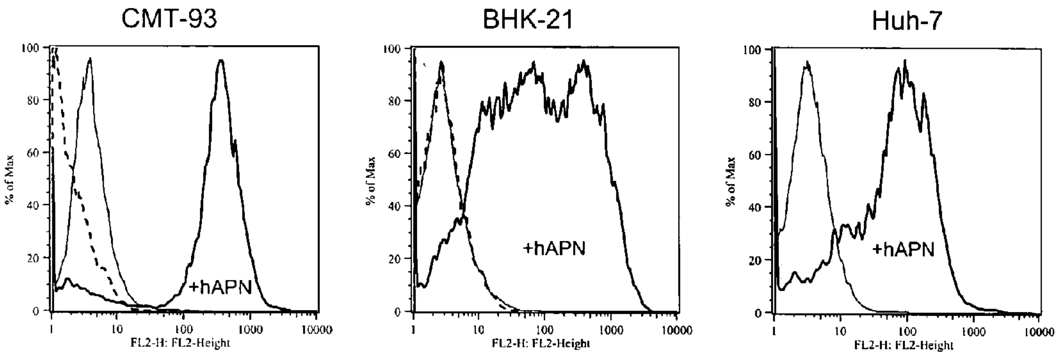
FIG. 6.

FIGURE 7A

```
   1 atattaggtt tttacctacc caggaaaagc caaccaacct cgatctcttg tagatctgtt
  61 ctctaaacga actttaaaat ctgtgtagct gtcgctcggc tgcatgccta gtgcacctac
 121 gcagtataaa caataataaa ttttactgtc gttgacaaga aacgagtaac tcgtccctct
 181 tctgcagact gcttacggtt tcgtccgtgt tgcagtcgat catcagcata cctaggtttc
 241 gtccgggtgt gaccgaaagg taagatggag agccttgttc ttggtgtcaa cgagaaaaca
 301 cacgtccaac tcagtttgcc tgtccttcag gttagagacg tgctagtgcg tggcttcggg
 361 gactctgtgg aagaggccct atcggaggca cgtgaacacc tcaaaaatgg cacttgtggt
 421 ctagtagagc tggaaaaagg cgtactgccc cagcttgaac agccctatgt gttcattaaa
 481 cgttctgatg ccttaagcac caatcacggc cacaaggtcg ttgagctggt tgcagaaatg
 541 gacggcattc agtacggtcg tagcggtata acactgggag tactcgtgcc acatgtgggc
 601 gaaaccccaa ttgcataccg caatgttctt cttcgtaaga acggtaataa gggagccggt
 661 ggtcatagct atggcatcga tctaaagtct tatgacttag gtgacgagct tggcactgat
 721 cccattgaag attatgaaca aaactggaac actaagcatg gcagtggtgc actccgtgaa
 781 ctcactcgtg agctcaatgg aggtgcagtc actcgctatg tcgacaacaa tttctgtggc
 841 ccagatgggt accctcttga ttgcatcaaa gattttctcg cacgcgcggg caagtcaatg
 901 tgcactcttt ccgaacaact tgattacatc gagtcgaaga gaggtgtcta ctgctgccgt
 961 gaccatgagc atgaaattgc ctggttcact gagcgctctg ataagagcta cgagcaccag
1021 acacccttcg aaattaagag tgccaagaaa tttgacactt tcaaagggga atgcccaaag
1081 tttgtgtttc ctcttaactc aaaagtcaaa gtcattcaac cacgtgttga aaagaaaaag
1141 actgagggtt tcatggggcg tatacgctct gtgtaccctg ttgcatctcc acaggagtgt
1201 aacaatatgc acttgtctac cttgatgaaa tgtaatcatt gcgatgaagt ttcatggcag
1261 acgtgcgact ttctgaaagc cacttgtgaa cattgtggca ctgaaaattt agttattgaa
1321 ggacctacta catgtgggta cctacctact aatgctgtag tgaaaatgcc atgtcctgcc
1381 tgtcaagacc cagagattgg acctgagcat agtgttgcag attatcacaa ccactcaaac
1441 attgaaactc gactccgcaa gggaggtagg actagatgtt ttggaggctg tgtgtttgcc
1501 tatgttggct gctataataa gcgtgcctac tgggttcctc gtgctagtgc tgatattggc
1561 tcaggccata ctggcattac tggtgacaat gtggagacct tgaatgagga tctccttgag
1621 atactgagtc gtgaacgtgt taacattaac attgttggcg attttcattt gaatgaagag
1681 gttgccatca ttttggcatc tttctctgct tctacaagtg cctttattga cactataaag
1741 agtcttgatt acaagtcttt caaaaccatt gttgagtcct gcggtaacta taaagttacc
1801 aagggaaagc ccgtaaaagg tgcttggaac attggacaac agagatcagt tttaacacca
1861 ctgtgtggtt ttccctcaca ggctgctggt gttatcagat caatttttgc gcgcacactt
1921 gatgcagcaa accactcaat tcctgatttg caaagagcag ctgtcaccat acttgatggt
1981 atttctgaac agtcattacg tcttgtcgac gccatggttt atacttcaga cctgctcacc
2041 aacagtgtca ttattatggc atatgtaact ggtggtcttg tacaacagac ttctcagtgg
2101 ttgtctaatc ttttgggcac tactgttgaa aaactcaggc ctatctttga atggattgag
2161 gcgaaactta gtgcaggagt tgaatttctc aaggatgctt gggagattct caaatttctc
2221 attacaggtg tttttgacat cgtcaagggt caaatacagg ttgcttcaga taacatcaag
2281 gattgtgtaa aatgcttcat tgatgttgtt aacaaggcac tcgaaatgtg cattgatcaa
2341 gtcactatcg ctggcgcaaa gttgcgatca ctcaacttag gtgaagtctt catcgctcaa
2401 agcaagggac tttaccgtca gtgtatacgt ggcaaggagc agctgcaact actcatgcct
2461 cttaaggcac caaaagaagt aacctttctt gaaggtgatt cacatgacac agtacttacc
2521 tctgaggagg ttgttctcaa gaacggtgaa ctcgaagcac tcgagacgcc cgttgatagc
2581 ttcacaaatg gagctatcgt tggcacacca gtctgtgtaa atggcctcat gctcttagag
2641 attaaggaca aagaacaata ctgcgcattg tctcctggtt tactggctac aaacaatgtc
2701 tttcgcttaa aggggggtgc accaattaaa ggtgtaacct ttggagaaga tactgtttgg
2761 gaagttcaag gttacaagaa tgtgagaatc acatttgagc ttgatgaacg tgttgacaaa
2821 gtgcttaatg aaaagtgctc tgtctacact gttgaatccg gtaccgaagt tactgagttt
2881 gcatgtgttg tagcagaggc tgttgtgaag actttacaac cagtttctga tctccttacc
2941 aacatgggta ttgatcttga tgagtggagt gtagctacat tctacttatt tgatgatgct
3001 ggtgaagaaa acttttcatc acgtatgtat tgttcctttt accctccaga tgaggaagaa
3061 gaggacgatg cagagtgtga ggaagaagaa attgatgaaa cctgtgaaca tgagtacggt
3121 acagaggatg attatcaagg tctccctctg gaatttggtg cctcagctga aacagttcga
3181 gttgaggaag aagaagagga agactggctg gatgatacta ctgagcaatc agagattgag
3241 ccagaaccag aacctacacc tgaagaacca gttaatcagt ttactggtta tttaaaactt
3301 actgacaatg ttgccattaa atgtgttgac atcgttaagg aggcacaaag tgctaatcct
3361 atggtgattg taaatgctgc taacatacac ctgaaacatg gtggtggtgt agcaggtgca
3421 ctcaacaagg caaccaatgg tgccatgcaa aaggagagtg atgattacat taagctaaat
3481 ggccctctta cagtaggagg gtcttgtttg ctttctggac ataatcttgc taagaagtgt
3541 ctgcatgttg ttggacctaa cctaaatgca ggtgaggaca tccagcttct taaggcagca
3601 tatgaaaatt tcaattcaca ggacatctta cttgcaccat tgttgtcagc aggcatattt
```

FIGURE 7B

```
3661 ggtgctaaac cacttcagtc tttacaagtg tgcgtgcaga cggttcgtac acaggtttat
3721 attgcagtca atgacaaagc tctttatgag caggttgtca tggattatct tgataacctg
3781 aagcctagag tggaagcacc taaacaagag gagccaccaa acacagaaga ttccaaaact
3841 gaggagaaat ctgtcgtaca gaagcctgtc gatgtgaagc caaaaattaa ggcctgcatt
3901 gatgaggtta ccacaacact ggaagaaact aagtttctta ccaataagtt actcttgttt
3961 gctgatatca atggtaagct ttaccatgat tctcagaaca tgcttagagg tgaagatatg
4021 tctttccttg agaaggatgc accttacatg gtaggtgatg ttatcactag tggtgatatc
4081 acttgtgttg taataccctc caaaaaggct ggtggcacta ctgagatgct ctcaagagct
4141 ttgaagaaag tgccagttga tgagtatata accacgtacc ctggacaagg atgtgctggt
4201 tatacacttg aggaagctaa gactgctctt aagaaatgca aatctgcatt ttatgtacta
4261 ccttcagaag cacctaatgc taaggaagag attctaggaa ctgtatcctg gaatttgaga
4321 gaaatgcttg ctcatgctga agagacaaga aaattaatgc ctatatgcat ggatgttaga
4381 gccataatgg caaccatcca acgtaagtat aaaggaatta aaattcaaga gggcatcgtt
4441 gactatggtg tccgattctt cttttatact agtaaagagc ctgtagcttc tattattacg
4501 aagctgaact ctctaaatga gccgcttgtc acaatgccaa ttggttatgt gacacatggt
4561 tttaatcttg aagaggctgc gcgctgtatg cgttctctta aagctcctgc cgtagtgtca
4621 gtatcatcac cagatgctgt tactacatat aatggatacc tcacttcgtc atcaaagaca
4681 tctgaggagc actttgtaga aacagtttct ttggctggct cttacagaga ttggtcctat
4741 tcaggacagc gtacagagtt aggtgttgaa tttcttaagc gtggtgacaa aattgtgtac
4801 cacactctgg agagccccgt cgagtttcat cttgacggtg aggttctttc acttgacaaa
4861 ctaaagagtc tcttatccct gcgggaggtt aagactataa aagtgttcac aactgtggac
4921 aacactaatc tccacacaca gcttgtggat atgtctatga catatggaca gcagtttggt
4981 ccaacatact tggatggtgc tgatgttaca aaaattaaac ctcatgtaaa tcatgagggt
5041 aagactttct ttgtactacc tagtgatgac acactacgta gtgaagcttt cgagtactac
5101 catactcttg atgagagttt tcttggtagg tacatgtctg ctttaaacca cacaaagaaa
5161 tggaaatttc ctcaagttgg tggtttaact tcaattaaat gggctgataa caattgttat
5221 ttgtctagtg ttttattagc acttcaacag cttgaagtca aattcaatgc accagcactt
5281 caagaggctt attatagagc ccgtgctggt gatgctgcta acttttgtgc actcatactc
5341 gcttacagta ataaaactgt tggcgagctt ggtgatgtca gagaaactat gacccatctt
5401 ctacagcatg ctaatttgga atctgcaaag cgagttctta atgtggtgtg taaacattgt
5461 ggtcagaaaa ctactacctt aacgggtgta gaagctgtga tgtatatggg tactctatct
5521 tatgataatc ttaagacagg tgtttccatt ccatgtgtgt gtggtcgtga tgctacacaa
5581 tatctagtac aacaagagtc ttcttttgtt atgatgtctg caccacctgc tgagtataaa
5641 ttacagcaag gtacattctt atgtgcgaat gagtacactg gtaactatca gtgtggtcat
5701 tacactcata taactgctaa ggagaccctc tatcgtattg acggagctca ccttacaaag
5761 atgtcagagt acaaaggacc agtgactgat gttttctaca aggaaacatc ttacactaca
5821 accatcaagc ctgtgtcgta taaactcgat ggagttactt acacagagat tgaaccaaaa
5881 ttggatgggt attataaaaa ggataatgct tactatacag agcagcctat agaccttgta
5941 ccaactcaac cattaccaaa tgcgagtttt gataatttca aactcacatg ttctaacaca
6001 aaatttgctg atgatttaaa tcaaatgaca ggcttcacaa agccagcttc acgagagcta
6061 tctgtcacat tcttcccaga cttgaatggc gatgtagtgg ctattgacta tagacactat
6121 tcagcgagtt tcaagaaagg tgctaaatta ctgcataagc caattgtttg gcacattaac
6181 caggctacaa ccaagacaac gttcaaacca aacacttggt gtttacgttg tctttggagt
6241 acaaagccag tagatacttc aaattcattt gaagttctgg cagtagaaga cacacaagga
6301 atggacaatc ttgcttgtga aagtcaacaa cccacctctg aagaagtagt ggaaaatcct
6361 accatacaga aggaagtcat agagtgtgac gtgaaaacta ccgaagttgt aggcaatgtc
6421 atacttaaac catcagatga aggtgttaaa gtaacacaag agttaggtca tgaggatctt
6481 atggctgctt atgtggaaaa cacaagcatt accattaaga aacctaatga gctttcacta
6541 gccttaggtt taaaaacaat tgccactcat ggtattgctg caattaatag tgttccttgg
6601 agtaaaattt tggcttatgt caaaccattc ttaggacaag cagcaattac aacatcaaat
6661 tgcgctaaga gattagcaca acgtgtgttt aacaattata tgccttatgt gtttacatta
6721 ttgttccaat tgtgtacttt tactaaaagt accaattcta gaattagagc ttcactacct
6781 acaactattg ctaaaaatag tgttaagagt gttgctaaat tatgtttgga tgccggcatt
6841 aattatgtga agtcacccaa atttctaaa ttgttcacaa tcgctatgtg gctattgttg
6901 ttaagtattt gcttaggttc tctaatctgt gtaactgctg cttttggtgt actcttatct
6961 aattttggtg ctccttctta ttgtaatggc gttagagaat tgtatcttaa ttcgtctaac
7021 gttactacta tggatttctg tgaaggttct tttccttgca gcatttgttt aagtggatta
7081 gactcccttg attcttatcc agctcttgaa accattcagg tgacgatttc atcgtacaag
7141 ctagacttga caattttagg tctggccgct gagtgggttt tggcatatat gttgttcaca
7201 aaattctttt atttattagg tctttcagct ataatgcagg tgttctttgg ctatttgct
7261 agtcatttca tcagcaattc ttggctcatg tggtttatca ttagtattgt acaaatggca
```

FIGURE 7C

```
7321 cccgtttctg caatggttag gatgtacatc ttctttgctt ctttctacta catatggaag
7381 agctatgttc atatcatgga tggttgcacc tcttcgactt gcatgatgtg ctataagcgc
7441 aatcgtgcca cacgcgttga gtgtacaact attgttaatg gcatgaagag atctttctat
7501 gtctatgcaa atggaggccg tggcttctgc aagactcaca attggaattg tctcaattgt
7561 gacacatttt gcactggtag tacattcatt agtgatgaag ttgctcgtga tttgtcactc
7621 cagtttaaaa gaccaatcaa ccctactgac cagtcatcgt atattgttga tagtgttgct
7681 gtgaaaaatg gcgcgcttca cctctacttt gacaaggctg gtcaaaagac ctatgagaga
7741 catccgctct cccattttgt caatttagac aatttgagag ctaacaacac taaaggttca
7801 ctgcctatta atgtcatagt ttttgatggc aagtccaaat gcgacgagtc tgcttctaag
7861 tctgcttctg tgtactacag tcagctgatg tgccaaccta ttctgttgct tgaccaagtt
7921 cttgtatcag acgttggaga tagtactgaa gtttccgtta agatgtttga tgcttatgtc
7981 gacacctttt cagcaacttt tagtgttcct atggaaaaac ttaaggcact tgttgctaca
8041 gctcacagcg agttagcaaa gggtgtagct ttagatggtg tcctttctac attcgtgtca
8101 gctgcccgac aaggtgttgt tgataccgat gttgacacaa aggatgttat tgaatgtctc
8161 aaactttcac atcactctga cttagaagtg acaggtgaca gttgtaacaa tttcatgctc
8221 acctataata aggttgaaaa catgacgccc agagatcttg gcgcatgtat tgactgtaat
8281 gcaaggcata tcaatgccca agtagcaaaa agtcacaatg tttcactcat ctggaatgta
8341 aaagactaca tgtctttatc tgaacagctg cgtaaacaaa ttcgtagtgc tgccaagaag
8401 aacaacatac cttttagact aacttgtgct acaactagac aggttgtcaa tgtcataact
8461 actaaaatct cactcaaggg tggtaagatt gttagtactt gttttaaact tatgcttaag
8521 gccacattat tgtgcgttct tgctgcattg gtttgttata tcgttatgcc agtacataca
8581 ttgtcaatcc atgatggtta cacaaatgaa atcattggtt acaaagccat tcaggatggt
8641 gtcactcgtg acatcatttc tactgatgat tgttttgcaa ataaacatgc tggttttgac
8701 gcatggttta gccagcgtgg tggttcatac aaaaatgaca aaagctgccc tgtagtagct
8761 gctatcatta caagagagat tggtttcata gtgcctggct taccgggtac tgtgctgaga
8821 gcaatcaatg gtgacttctt gcattttcta cctcgtgttt ttagtgctgt tggcaacatt
8881 tgctacacac cttccaaact cattgagtat agtgattttg ctacctctgc ttgcgttctt
8941 gctgctgagt gtacaatttt taaggatgct atgggcaaac ctgtgccata ttgttatgac
9001 actaatttgc tagagggttc tatttcttat agtgagcttc gtccagacac tcgttatgtg
9061 cttatggatg gttccatcat acagtttcct aacacttacc tggagggttc tgttagagta
9121 gtaacaactt ttgatgctga gtactgtaga catggtacat gcgaaaggtc agaagtaggt
9181 atttgcctat ctaccagtgg tagatgggtt cttaataatg agcattacag agctctatca
9241 ggagttttct gtggtgttga tgcgatgaat ctcatagcta acatctttac tcctcttgtg
9301 caacctgtgg gtgctttaga tgtgtctgct tcagtagtgg ctggtggtat tattgccata
9361 ttggtgactt gtgctgccta ctactttatg aaattcagac gtgtttttgg tgagtacaac
9421 catgttgttg ctgctaatgc acttttgttt ttgatgtctt tcactatact ctgtctggta
9481 ccagcttaca gctttctgcc gggagtctac tcagtctttt acttgtactt gacattctat
9541 ttcaccaatg atgtttcatt cttggctcac cttcaatggt ttgccatgtt ttctcctatt
9601 gtgccttttt ggataacagc aatctatgta ttctgtattt ctctgaagca ctgccattgg
9661 ttctttaaca actatcttag gaaaagagtc atgtttaatg gagttacatt tagtaccttc
9721 gaggaggctg ctttgtgtac ctttttgctc aacaaggaaa tgtacctaaa attgcgtagc
9781 gagacactgt tgccacttac acagtataac aggtatcttg ctctatataa caagtacaag
9841 tatttcagtg gagccttaga tactaccagc tatcgtgaag cagcttgctg ccacttagca
9901 aaggctctaa atgactttag caactcaggt gctgatgttc tctaccaacc accacagaca
9961 tcaatcactt ctgctgttct gcagagtggt tttaggaaaa tggcattccc gtcaggcaaa
10021 gttgaagggt gcatggtaca agtaacctgt ggaactacaa ctcttaatgg attgtggttg
10081 gatgacacag tatactgtcc aagacatgtc atttgcacag cagaagacat gcttaatcct
10141 aactatgaag atctgctcat tcgcaaatcc aaccatagct ttcttgttca ggctggcaat
10201 gttcaacttc gtgttattgg ccattctatg caaaattgtc tgcttaggct taaagttgat
10261 acttctaacc ctaagacacc caagtataaa tttgtccgta tccaacctgg tcaaacattt
10321 tcagttctag catgctacaa tggttcacca tctggtgttt atcagtgtgc catgagacct
10381 aatcatacca ttaaaggttc tttccttaat ggatcatgtg gtagtgttgg ttttaacatt
10441 gattatgatt gcgtgtcttt ctgctatatg catcatatgg agcttccaac aggagtacac
10501 gctggtactg acttagaagg taaattctat ggtccatttg ttgacagaca aactgcacag
10561 gctgcaggta cagacacaac cataacatta aatgttttgg catggctgta tgctgctgtt
10621 atcaatggtg ataggtggtt tcttaataga ttcaccacta ctttgaatga ctttaacctt
10681 gtggcaatga agtacaacta tgaacctttg acacaagatc atgttgacat attgggacct
10741 ctttctgctc aaacaggaat tgccgtctta gatatgtgtg ctgctttgaa agagctgctg
10801 cagaatggta tgaatggtcg tactatcctt ggtagcacta ttttagaaga tgagtttaca
10861 ccatttgatg ttgttagaca atgctctggt gttaccttcc aaggtaagtt caagaaaatt
10921 gttaagggca ctcatcattg gatgctttta actttcttga catcactatt gattcttgtt
10981 caaagtacac agtggtcact gtttttcttt gtttacgaga atgctttctt gccatttact
```

FIGURE 7D

```
11041 cttggtatta tggcaattgc tgcatgtgct atgctgcttg ttaagcataa gcacgcattc
11101 ttgtgcttgt ttctgttacc ttctcttgca acagttgctt actttaatat ggtctacatg
11161 cctgctagct gggtgatgcg tatcatgaca tggcttgaat tggctgacac tagcttgtct
11221 ggttataggc ttaaggattg tgttatgtat gcttcagctt tagttttgct tattctcatg
11281 acagctcgca ctgtttatga tgatgctgct agacgtgttt ggacactgat gaatgtcatt
11341 acacttgttt acaaagtcta ctatggtaat gctttagatc aagctatttc catgtgggcc
11401 ttagttattt ctgtaacctc taactattct ggtgtcgtta cgactatcat gtttttagct
11461 agagctatag tgtttgtgtg tgttgagtat tacccattgt tatttattac tggcaacacc
11521 ttacagtgta tcatgcttgt ttattgtttc ttaggctatt gttgctgctg ctactttggc
11581 cttttctgtt tactcaaccg ttacttcagg cttactcttg gtgtttatga ctacttggtc
11641 tctacacaag aatttaggta tatgaactcc caggggcttt tgcctcctaa gagtagtatt
11701 gatgctttca agcttaacat taagttgttg ggtattggag gtaaaccatg tatcaaggtt
11761 gctactgtac agtctaaaat gtctgacgta aagtgcacat ctgtggtact gctctcggtt
11821 cttcaacaac ttagagtaga gtcatcttct aaattgtggg cacaatgtgt acaactccac
11881 aatgatattc ttcttgcaaa agacacaact gaagctttcg agaagatggt ttctcttttg
11941 tctgttttgc tatccatgca gggtgctgta gacattaata ggttgtgcga ggaaatgctc
12001 gataaccgtg ctactcttca ggctattgct tcagaattta gttctttacc atcatatgcc
12061 gcttatgcca ctgcccagga ggcctatgag caggctgtag ctaatggtga ttctgaagtc
12121 gttctcaaaa agttaaagaa atctttgaat gtggctaaat ctgagtttga ccgtgatgct
12181 gccatgcaac gcaagttgga aaagatggca gatcaggcta tgacccaaat gtacaaacag
12241 gcaagatctg aggacaagag ggcaaaagta actagtgcta tgcaaacaat gctcttcact
12301 atgcttagga agcttgataa tgatgcactt aacaacatta tcaacaatgc gcgtgatggt
12361 tgtgttccac tcaacatcat accattgact acagcagcca aactcatggt tgttgtccct
12421 gattatggta cctacaagaa cacttgtgat ggtaacacct ttacatatgc atctgcactc
12481 tgggaaatcc agcaagttgt tgatgcggat agcaagattg ttcaacttag tgaaattaac
12541 atggacaatt caccaaattt ggcttggcct cttattgtta cagctctaag agccaactca
12601 gctgttaaac tacagaataa tgaactgagt ccagtagcac tacgacagat gtcctgtgcg
12661 gctggtacca cacaaacagc ttgtactgat gacaatgcac ttgcctacta taacaattcg
12721 aagggaggta ggtttgtgct ggcattacta tcagaccacc aagatctcaa atgggctaga
12781 ttccctaaga gtgatggtac aggtacaatt tacacagaac tggaaccacc ttgtaggttt
12841 gttacagaca caccaaaagg gcctaaagtg aaatacttgt acttcatcaa aggcttaaac
12901 aacctaaata gaggtatggt gctgggcagt ttagctgcta cagtacgtct tcaggctgga
12961 aatgctacag aagtacctgc caattcaact gtgctttcct tctgtgcttt tgcagtagac
13021 cctgctaaag catataagga ttacctagca agtggaggac aaccaatcac caactgtgtg
13081 aagatgttgt gtacacacac tggtacagga caggcaatta ctgtaacacc agaagctaac
13141 atggaccaag agtcctttgg tggtgcttca tgttgtctgt attgtagatg ccacattgac
13201 catccaaatc ctaaaggatt ctgtgacttg aaaggtaagt acgtccaaat acctaccact
13261 tgtgctaatg acccagtggg ttttacactt agaaacacag tctgtaccgt ctgcggaatg
13321 tggaaaggtt atggctgtag ttgtgaccaa ctccgcgaac ccttgatgca gtctgcggat
13381 gcatcaacgt ttttaaacgg gtttgcggtg taagtgcagc ccgtcttaca ccgtgcggca
13441 caggcactag tactgatgtc gtctacaggg cttttgatat ttacaacgaa aaagttgctg
13501 gttttgcaaa gttcctaaaa actaattgct gtcgcttcca ggagaaggat gaggaaggca
13561 atttattaga ctcttacttt gtagttaaga ggcatactat gtctaactac caacatgaag
13621 agactattta taacttggtt aaagattgtc cagcggttgc tgtccatgac tttttcaagt
13681 ttagagtaga tggtgacatg gtaccacata tatcacgtca gcgtctaact aaatacacaa
13741 tggctgattt agtctatgct ctacgtcatt ttgatgaggg taattgtgat acattaaaag
13801 aaatactcgt cacatacaat tgctgtgatg atgattattt caataagaag gattggtatg
13861 acttcgtaga gaatcctgac atcttacgcg tatatgctaa cttaggtgag cgtgtacgcc
13921 aatcattatt aaagactgta caattctgcg atgctatgcg tgatgcaggc attgtaggcg
13981 tactgacatt agataatcag gatcttaatg ggaactggta cgatttcggt gatttcgtac
14041 aagtagcacc aggctgcgga gttcctattg tggattcata ttactcattg ctgatgccca
14101 tcctcacttt gactagggca ttggctgctg agtcccatat ggatgctgat ctcgcaaaac
14161 cacttattaa gtgggatttg ctgaaatatg attttacgga agagagactt tgtctcttcg
14221 accgttattt taaatattgg gaccagacat accatcccaa ttgtattaac tgtttggatg
14281 ataggtgtat ccttcattgt gcaaacttta atgtgttatt ttctactgtg tttccaccta
14341 caagttttgg accactagta agaaaaatat ttgtagatgg tgttcctttt gttgtttcaa
14401 ctggatacca ttttcgtgag ttaggagtcg tacataatca ggatgtaaac ttacatagct
14461 cgcgtctcag tttcaaggaa cttttagtgt atgctgctga tccagctatg catgcagctt
14521 ctggcaattt attgctagat aaacgcacta catgcttttc agtagctgca ctaacaaaca
14581 atgttgcttt tcaaactgtc aaacccggta attttaataa agacttttat gactttgctg
14641 tgtctaaagg tttctttaag gaaggaagtt ctgttgaact aaaacacttc ttctttgctc
14701 aggatggcaa cgctgctatc agtgattatg actattatcg ttataatctg ccaacaatgt
```

FIGURE 7E

```
14761 gtgatatcag acaactccta ttcgtagttg aagttgttga taaatacttt gattgttacg
14821 atggtggctg tattaatgcc aaccaagtaa tcgttaacaa tctggataaa tcagctggtt
14881 tcccatttaa taaatggggt aaggctagac tttattatga ctcaatgagt tatgaggatc
14941 aagatgcact tttcgcgtat actaagcgta atgtcatccc tactataact caaatgaatc
15001 ttaagtatgc cattagtgca aagaatagag ctcgcaccgt agctggtgtc tctatctgta
15061 gtactatgac aaatagacag tttcatcaga aattattgaa gtcaatagcc gccactagag
15121 gagctactgt ggtaattgga acaagcaagt tttacggtgg ctggcataat atgttaaaaa
15181 ctgtttacag tgatgtagaa actccacacc ttatgggttg ggattatcca aaatgtgaca
15241 gagccatgcc taacatgctt aggataatgg cctctcttgt tcttgctcgc aaacataaca
15301 cttgctgtaa cttatcacac cgtttctaca ggttagctaa cgagtgtgcg caagtattaa
15361 gtgagatggt catgtgtggc ggctcactat atgttaaacc aggtggaaca tcatccggtg
15421 atgctacaac tgcttatgct aatagtgtct ttaacatttg tcaagctgtt acagccaatg
15481 taaatgcact tctttcaact gatggtaata agatagctga caagtatgtc cgcaatctac
15541 aacacaggct ctatgagtgt ctctatagaa atagggatgt tgatcatgaa ttcgtggatg
15601 agttttacgc ttacctgcgt aaacatttct ccatgatgat tctttctgat gatgccgttg
15661 tgtgctataa cagtaactat gcggctcaag gtttagtagc tagcattaag aactttaagg
15721 cagttcttta ttatcaaaat aatgtgttca tgtctgaggc aaaatgttgg actgagactg
15781 accttactaa aggacctcac gaattttgct cacagcatac aatgctagtt aaacaaggag
15841 atgattacgt gtacctgcct tacccagatc catcaagaat attaggcgca ggctgttttg
15901 tcgatgatat tgtcaaaaca gatggtacac ttatgattga aaggttcgtg tcactggcta
15961 ttgatgctta cccacttaca aaacatccta atcaggagta tgctgatgtc tttcacttgt
16021 atttacaata cattagaaag ttacatgatg agcttactgg ccacatgttg gacatgtatt
16081 ccgtaatgct aactaatgat aacacctcac ggtactggga acctgagttt tatgaggcta
16141 tgtacacacc acatacagtc ttgcaggctg taggtgcttg tgtattgtgc aattcacaga
16201 cttcacttcg ttgcggtgcc tgtattagga gaccattcct atgttgcaag tgctgctatg
16261 accatgtcat ttcaacatca cacaaattag tgttgtctgt taatccctat gtttgcaatg
16321 ccccaggttg tgatgtcact gatgtgacac aactgtatct aggaggtatg agctattatt
16381 gcaagtcaca taagcctccc attagttttc cattatgtgc taatggtcag gtttttggtt
16441 tatacaaaaa cacatgtgta ggcagtgaca atgtcactga cttcaatgcg atagcaacat
16501 gtgattggac taatgctggc gattacatac ttgccaacac ttgtactgag agactcaagc
16561 ttttcgcagc agaaacgctc aaagccactg aggaaacatt taagctgtca tatggtattg
16621 ctactgtacg cgaagtactc tctgacagag aattgcatct ttcatgggag gttggaaaac
16681 ctagaccacc attgaacaga aactatgtct ttactggtta ccgtgtaact aaaaatagta
16741 aagtacagat tggagagtac acctttgaaa aaggtgacta tggtgatgct gttgtgtaca
16801 gaggtactac gacatacaag ttgaatgttg gtgattactt tgtgttgaca tctcacactg
16861 taatgccact tagtgcacct actctagtgc cacaagagca ctatgtgaga attactggct
16921 tgtacccaac actcaacatc tcagatgagt tttctagcaa tgttgcaaat tatcaaaagg
16981 tcggcatgca aaagtactct acactccaag gaccacctgg tactggtaag agtcattttg
17041 ccatcggact tgctctctat tacccatctg ctcgcatagt gtatacggca tgctctcatg
17101 cagctgttga tgccctatgt gaaaaggcat taaaatattt gcccatagat aaatgtagta
17161 gaatcatacc tgcgcgtgcg cgcgtagagt gttttgataa attcaaagtg aattcaacac
17221 tagaacagta tgttttctgc actgtaaatg cattgccaga aacaactgct gacattgtag
17281 tctttgatga aatctctatg gctactaatt atgacttgag tgttgtcaat gctagacttc
17341 gtgcaaaaca ctacgtctat attggcgatc ctgctcaatt accagccccc cgcacattgc
17401 tgactaaagg cacactagaa ccagaatatt ttaattcagt gtgcagactt atgaaaacaa
17461 taggtccaga catgttcctt ggaacttgtc gccgttgtcc tgctgaaatt gttgacactg
17521 tgagtgcttt agtttatgac aataagctaa aagcacacaa ggataagtca gctcaatgct
17581 tcaaaatgtt ctacaaaggt gttattacac atgatgtttc atctgcaatc aacagacctc
17641 aaataggcgt tgtaagagaa tttcttacac gcaatcctgc ttggagaaaa gctgttttta
17701 tctcacctta taattcacag aacgctgtag cttcaaaaat cttaggattg cctacgcaga
17761 ctgttgattc atcacagggt tctgaatatg actatgtcat attcacacaa actactgaaa
17821 cagcacactc ttgtaatgtc aaccgcttca atgtggctat cacaagggca aaaattggca
17881 ttttgtgcat aatgtctgat agagatcttt atgacaaact gcaatttaca agtctagaaa
17941 taccacgtcg caatgtggct acattacaag cagaaaatgt aactggactt tttaaggact
18001 gtagtaagat cattactggt cttcatccta cacaggcacc tacacacctc agcgttgata
18061 taaagttcaa gactgaagga ttatgtgttg acataccagg cataccaaag gacatgacct
18121 accgtagact catctctatg atgggtttca aaatgaatta ccaagtcaat ggttacccta
18181 atatgtttat cacccgcgaa gaagctattc gtcacgttcg tgcgtggatt ggctttgatg
18241 tagagggctg tcatgcaact agagatgctg tgggtactaa cctacctctc cagctaggat
18301 tttctacagg tgttaactta gtagctgtac cgactggtta tgttgacact gaaaataaca
18361 cagaattcac cagagttaat gcaaaacctc caccaggtga ccagtttaaa catcttatac
18421 cactcatgta taaaggcttg ccctggaatg tagtgcgtat taagatagta caaatgctca
```

FIGURE 7F

```
18481 gtgatacact gaaaggattg tcagacagag tcgtgttcgt cctttgggcg catggctttg
18541 agcttacatc aatgaagtac tttgtcaaga ttggacctga aagaacgtgt tgtctgtgtg
18601 acaaacgtgc aacttgcttt tctacttcat cagatactta tgcctgctgg aatcattctg
18661 tgggttttga ctatgtctat aacccattta tgattgatgt tcagcagtgg ggctttacgg
18721 gtaaccttca gagtaaccat gaccaacatt gccaggtaca tggaaatgca catgtggcta
18781 gttgtgatgc tatcatgact agatgtttag cagtccatga gtgctttgtt aagcgcgttg
18841 attggtctgt tgaataccct attataggag atgaactgag ggttaattct gcttgcagaa
18901 aagtacaaca catggttgtg aagtctgcat tgcttgctga taagtttcca gttcttcatg
18961 acattggaaa tccaaaggct atcaagtgtg tgcctcaggc tgaagtagaa tggaagttct
19021 acgatgctca gccatgtagt gacaaagctt acaaaataga ggagctcttc tattcttatg
19081 ctacacatca cgataaattc actgatggtg tttgtttgtt ttggaattgt aacgttgatc
19141 gttacccagc caatgcaatt gtgtgtaggt ttgacacaag agtcttgtca aacttgaact
19201 taccaggctg tgatggtggt agtttgtatg tgaataagca tgcattccac actccagctt
19261 tcgataaaag tgcatttact aatttaaagc aattgccttt cttttactat tctgatagtc
19321 cttgtgagtc tcatggcaaa caagtagtgt cggatattga ttatgttcca ctcaaatctg
19381 ctacgtgtat tacacgatgc aatttaggtg gtgctgtttg cagacaccat gcaaatgagt
19441 accgacagta cttggatgca tataatatga tgatttctgc tggatttagc ctatggattt
19501 acaaacaatt tgatacttat aacctgtgga atacatttac caggttacag agtttagaaa
19561 atgtggctta taatgttgtt aataaaggac actttgatgg acacgccggc gaagcacctg
19621 tttccatcat taataatgct gtttacacaa aggtagatgg tattgatgtg gagatctttg
19681 aaaataagac aacacttcct gttaatgttg catttgagct ttgggctaag cgtaacatta
19741 aaccagtgcc agagattaag atactcaata atttgggtgt tgatatcgct gctaatactg
19801 taatctggga ctacaaaaga gaagccccag cacatgtatc tacaataggt gtctgcacaa
19861 tgactgacat tgccaagaaa cctactgaga gtgcttgttc ttcacttact gtcttgtttg
19921 atggtagagt ggaaggacag gtagaccttt ttagaaacgc ccgtaatggt gttttaataa
19981 cagaaggttc agtcaaaggt ctaacacctt caaagggacc agcacaagct agcgtcaatg
20041 gagtcacatt aattggagaa tcagtaaaaa cacagtttaa ctactttaag aaagtagacg
20101 gcattattca acagttgcct gaaacctact ttactcagag cagagactta gaggatttta
20161 agcccagatc acaaatggaa actgactttc tcgagctcgc tatggatgaa ttcatacagc
20221 gatataagct cgagggctat gccttcgaac acatcgttta tggagatttc agtcatggac
20281 aacttggcgg tcttcattta atgataggct tagccaagcg ctcacaagat tcaccactta
20341 aattagagga ttttatccct atggacagca cagtgaaaaa ttacttcata acagatgcgc
20401 aaacaggttc atcaaaatgt gtgtgttctg tgattgatct tttacttgat gactttgtcg
20461 agataataaa gtcacaagat ttgtcagtga tttcaaaagt ggtcaaggtt acaattgact
20521 atgctgaaat ttcattcatg ctttggtgta aggatggaca tgttgaaacc ttctacccaa
20581 aactacaagc aagtcaagcg tggcaaccag gtgttgcgat gcctaacttg tacaagatgc
20641 aaagaatgct tcttgaaaag tgtgaccttc agaattatgg tgaaaatgct gttataccaa
20701 aaggaataat gatgaatgtc gcaaagtata ctcaactgtg tcaatactta aatacactta
20761 ctttagctgt accctacaac atgagagtta ttcactttgg tgctggctct gataaaggag
20821 ttgcaccagg tacagctgtg ctcagacaat ggttgccaac tggcacacta cttgtcgatt
20881 cagatcttaa tgacttcgtc tccgacgcag attctacttt aattggagac tgtgcaacag
20941 tacatacggc taataaatgg gaccttatta ttagcgatat gtatgaccct aggaccaaac
21001 atgtgacaaa agagaatgac tctaaagaag ggtttttcac ttatctgtgt ggatttataa
21061 agcaaaaact agccctgggt ggttctatag ctgtaaagat aacagagcat tcttggaatg
21121 ctgaccttta caagcttatg ggccatttct catggtggac agcttttgtt acaaatgtaa
21181 atgcatcatc atcggaagca tttttaattg ggctaacta tcttggcaag ccgaaggaac
21241 aaattgatgg ctataccatg catgctaact acattttctg gaggaacaca aatcctatcc
21301 agttgtcttc ctattcactc tttgacatga gcaaatttcc tcttaaatta agaggaactg
21361 ctgtaatgtc tcttaaggag aatcaaatca atgatatgat ttattctctt ctggaaaaag
21421 gtaggcttat cattagagaa aacaacagag ttgtggtttc aagtgatatt cttgttaaca
21481 actaaacgaa catgtttatt ttcttattat ttcttactct cactagtggt agtgaccttg
21541 accggtgcac cactttgat gatgttcaag ctcctaatta cactcaacat acttcatcta
21601 tgaggggggt ttactatcct gatgaaattt ttagatcaga cactctttat ttaactcagg
21661 atttatttct tccattttat tctaatgtta cagggtttca tactattaat catacgtttg
21721 gcaaccctgt catacctttt aaggatggta tttattttgc tgccacagag aaatcaaatg
21781 ttgtccgtgg ttgggttttt ggttctacca tgaacaacaa gtcacagtcg gtgattatta
21841 ttaacaattc tactaatgtt gttatacgag catgtaactt tgaattgtgt gacaaccctt
21901 tctttgctgt ttctaaaccc atgggtacac agacacatac tatgatattc gataatgcat
21961 ttaattgcac tttcgagtac atatctgatg ccttttcgct tgatgtttca gaaaagtcag
22021 gtaattttaa acacttacga gagtttgtgt ttaaaaataa agatgggttt ctctatgttt
22081 ataagggcta tcaacctata gatgtagttc gtgatctacc ttctggtttt aacactttga
22141 aacctatttt taagttgcct cttggtatta acattacaaa ttttagagcc attcttacag
```

FIGURE 7G

```
22201 ccttttcacc tgctcaagac atttggggca cgtcagctgc agcctatttt gttggctatt
22261 taaagccaac tacatttatg ctcaagtatg atgaaaatgg tacaatcaca gatgctgttg
22321 attgttctca aaatccactt gctgaactca aatgctctgt taagagcttt gagattgaca
22381 aaggaattta ccagacctct aatttcaggg ttgttccctc aggagatgtt gtgagattcc
22441 ctaatattac aaacttgtgt ccttttggag aggtttttaa tgctactaaa ttcccttctg
22501 tctatgcatg ggagagaaaa aaaatttcta attgtgttgc tgattactct gtgctctaca
22561 actcaacatt tttttcaacc tttaagtgct atggcgtttc tgccactaag ttgaatgatc
22621 tttgcttctc caatgtctat gcagattctt ttgtagtcaa gggagatgat gtaagacaaa
22681 tagcgccagg acaaactggt gttattgctg attataatta taaattgcca gatgatttca
22741 tgggttgtgt ccttgcttgg aatactagga acattgatgc tacttcaact ggtaattata
22801 attataaata taggtatctt agacatggca agcttaggcc ctttgagaga gacatatcta
22861 atgtgccttt ctcccctgat ggcaaacctt gcaccccacc tgctcttaat tgttattggc
22921 cattaaatga ttatggtttt tacaccacta ctggcattgg ctaccaacct tacagagttg
22981 tagtactttc ttttgaactt ttaaatgcac cggccacggt ttgtggacca aaattatcca
23041 ctgaccttat taagaaccag tgtgtcaatt ttaattttaa tggactcact ggtactggtg
23101 tgttaactcc ttcttcaaag agatttcaac catttcaaca atttggccgt gatgtttctg
23161 atttcactga ttccgttcga gatcctaaaa catctgaaat attagacatt tcaccttgct
23221 cttttggggg tgtaagtgta attacacctg gaacaaatgc ttcatctgaa gttgctgttc
23281 tatatcaaga tgttaactgc actgatgttt ctacagcaat tcatgcagat caactcacac
23341 cagcttggcg catatattct actggaaaca atgtattcca gactcaagca ggctgtctta
23401 taggagctga gcatgtcgac acttcttatg agtgcgacat tcctattgga gctggcattt
23461 gtgctagtta ccatacagtt tctttattac gtagtactag ccaaaaatct attgtggctt
23521 atactatgtc tttaggtgct gatagttcaa ttgcttactc taataacacc attgctatac
23581 ctactaactt ttcaattagc attactacag aagtaatgcc tgtttctatg gctaaaacct
23641 ccgtagattg taatatgtac atctgcggag attctactga atgtgctaat ttgcttctcc
23701 aatatggtag cttttgcaca caactaaatc gtgcactctc aggtattgct gctgaacagg
23761 atcgcaacac acgtgaagtg ttcgctcaag tcaaacaaat gtacaaaacc ccaactttga
23821 aatattttgg tggttttaat ttttcacaaa tattacctga ccctctaaag ccaactaaga
23881 ggtcttttat tgaggacttg ctctttaata aggtgacact cgctgatgct ggcttcatga
23941 agcaatatgg cgaatgccta ggtgatatta atgctagaga tctcatttgt gcgcagaagt
24001 tcaatggact tacagtgttg ccacctctgc tcactgatga tatgattgct gcctacactg
24061 ctgctctagt tagtggtact gccactgctg gatggacatt tggtgctggc gctgctcttc
24121 aaataccttt tgctatgcaa atggcatata ggttcaatgg cattggagtt acccaaaatg
24181 ttctctatga gaaccaaaaa caaatcgcca accaatttaa caaggcgatt agtcaaattc
24241 aagaatcact tacaacaaca tcaactgcat tgggcaagct gcaagacgtt gttaaccaga
24301 atgctcaagc attaaacaca cttgttaaac aacttagctc taattttggt gcaatttcaa
24361 gtgtgctaaa tgatatcctt tcgcgacttg ataaagtcga ggcggaggta caaattgaca
24421 ggttaattac aggcagactt caaagccttc aaacctatgt aacacaacaa ctaatcaggg
24481 ctgctgaaat cagggcttct gctaatcttg ctgctactaa aatgtctgag tgtgttcttg
24541 gacaatcaaa aagagttgac ttttgtggaa agggctacca ccttatgtcc ttcccacaag
24601 cagccccgca tggtgttgtc ttcctacatg tcacgtatgt gccatcccag gagaggaact
24661 tcaccacagc gccagcaatt tgtcatgaag gcaaagcata cttccctcgt gaaggtgttt
24721 ttgtgtttaa tggcacttct tggtttatta cacagaggaa cttcttttct ccacaaataa
24781 ttactacaga caatacattt gtctcaggaa attgtgatgt cgttattggc atcattaaca
24841 acacagttta tgatcctctg caacctgagc tcgactcatt caaagaagag ctggacaagt
24901 acttcaaaaa tcatacatca ccagatgttg atcttggcga catttcaggc attaacgctt
24961 ctgtcgtcaa cattcaaaaa gaaattgacc gcctcaatga ggtcgctaaa aatttaaatg
25021 aatcactcat tgaccttcaa gaattgggaa aatatgagca atatattaaa tggccttggt
25081 atgtttggct cggcttcatt gctggactaa ttgccatcgt catggttaca atcttgcttt
25141 gttgcatgac tagttgttgc agttgcctca agggtgcatg ctcttgtggt tcttgctgca
25201 agtttgatga ggatgactct gagccagttc tcaagggtgt caaattacat tacacataaa
25261 cgaacttatg gatttgttta tgagattttt tactcttgga tcaattactg cacagccagt
25321 aaaaattgac aatgcttctc ctgcaagtac tgttcatgct acagcaacga taccgctaca
25381 agcctcactc cctttcggat ggcttgttat tggcgttgca tttcttgctg tttttcagag
25441 cgctaccaaa ataattgcgc tcaataaaag atggcagcta gccctttata agggcttcca
25501 gttcatttgc aatttactgc tgctatttgt taccatctat tcacatcttt tgcttgtcgc
25561 tgcaggtatg gaggcgcaat ttttgtacct ctatgccttg atatattttc tacaatgcat
25621 caacgcatgt agaattatta tgagatgttg gctttgttgg aagtgcaaat ccaagaaccc
25681 attactttat gatgccaact actttgtttg ctggcacaca cataactatg actactgtat
25741 accatataac agtgtcacag atacaattgt cgttactgaa ggtgacggca tttcaacacc
25801 aaaactcaaa gaagactacc aaattggtgg ttattctgag gataggcact caggtgttaa
25861 agactatgtc gttgtacatg gctatttcac cgaagtttac taccagcttg agtctacaca
```

FIGURE 7H

```
25921 aattactaca gacactggta ttgaaaatgc tacattcttc atctttaaca agcttgttaa
25981 agacccaccg aatgtgcaaa tacacacaat cgacggctct tcaggagttg ctaatccagc
26041 aatggatcca atttatgatg agccgacgac gactactagc gtgcctttgt aagcacaaga
26101 aagtgagtac gaacttatgt actcattcgt ttcggaagaa acaggtacgt taatagttaa
26161 tagcgtactt ctttttcttg ctttcgtggt attcttgcta gtcacactag ccatccttac
26221 tgcgcttcga ttgtgtgcgt actgctgcaa tattgttaac gtgagtttag taaaaccaac
26281 ggtttacgtc tactcgcgtg ttaaaaatct gaactcttct gaaggagttc ctgatcttct
26341 ggtctaaacg aactaactat tattattatt ctgtttggaa ctttaacatt gcttatcatg
26401 gcagacaacg gtactattac cgttgaggag cttaaacaac tcctggaaca atggaaccta
26461 gtaataggtt tcctattcct agcctggatt atgttactac aatttgccta ttctaatcgg
26521 aacaggtttt tgtacataat aaagcttgtt ttcctctggc tcttgtggcc agtaacactt
26581 gcttgttttg tgcttgctgc tgtctacaga attaattggg tgactggcgg gattgcgatt
26641 gcaatggctt gtattgtagg cttgatgtgg cttagctact tcgttgcttc cttcaggctg
26701 tttgctcgta cccgctcaat gtggtcattc aacccagaaa caaacattct tctcaatgtg
26761 cctctccggg ggacaattgt gaccagaccg ctcatggaaa gtgaacttgt cattggtgct
26821 gtgatcattc gtggtcactt gcgaatggcc ggacaccccc tagggcgctg tgacattaag
26881 gacctgccaa aagagatcac tgtggctaca tcacgaacgc tttcttatta caaattagga
26941 gcgtcgcagc gtgtaggcac tgattcaggt tttgctgcat acaaccgcta ccgtattgga
27001 aactataaat taaatacaga ccacgccggt agcaacgaca atattgcttt gctagtacag
27061 taagtgacaa cagatgtttc atcttgttga cttccaggtt acaatagcag agatattgat
27121 tatcattatg aggactttca ggattgctat ttggaatctt gacgttataa taagttcaat
27181 agtgagacaa ttatttaagc ctctaactaa gaagaattat tcggagttag atgatgaaga
27241 acctatggag ttagattatc cataaaacga acatgaaaat tattctcttc ctgacattga
27301 ttgtatttac atcttgcgag ctatatcact atcaggagtg tgttagaggt acgactgtac
27361 tactaaaaga accttgccca tcaggaacat acgagggcaa ttcaccattt caccctcttg
27421 ctgacaataa atttgcacta acttgcacta gcacacactt tgcttttgct tgtgctgacg
27481 gtactcgaca tacctatcag ctgcgtgcaa gatcagtttc accaaaactt ttcatcagac
27541 aagaggaggt tcaacaagag ctctactcgc cactttttct cattgttgct gctctagtat
27601 ttttaatact ttgcttcacc attaagagaa agacagaatg aatgagctca ctttaattga
27661 cttctatttg tgctttttag cctttctgct attccttgtt ttaataatgc ttattatatt
27721 ttggttttca ctcgaaatcc aggatctaga agaaccttgt accaaagtct aaacgaacat
27781 gaaacttctc attgttttga cttgtatttc tctatgcagt tgcatatgca ctgtagtaca
27841 gcgctgtgca tctaataaac ctcatgtgct tgaagatcct tgtaaggtac aacactaggg
27901 gtaatactta tagcactgct tggctttgtg ctctaggaaa ggttttacct tttcatagat
27961 ggcacactat ggttcaaaca tgcacaccta atgttactat caactgtcaa gatccagctg
28021 gtggtgcgct tatagctagg tgttggtacc ttcatgaagg tcaccaaact gctgcattta
28081 gagacgtact tgttgtttta aataaacgaa caaattaaaa tgtctgataa tggaccccaa
28141 tcaaaccaac gtagtgcccc ccgcattaca tttggtggac ccacagattc aactgacaat
28201 aaccagaatg gaggacgcaa tggggcaagg ccaaaacagc gccgacccca aggtttaccc
28261 aataatactg cgtcttggtt cacagctctc actcagcatg gcaaggagga acttagattc
28321 cctcgaggcc agggcgttcc aatcaacacc aatagtggtc cagatgacca aattggctac
28381 taccgaagag ctacccgacg agttcgtggt ggtgacggca aaatgaaaga gctcagcccc
28441 agatggtact tctattacct aggaactggc ccagaagctt cacttcccta cggcgctaac
28501 aaagaaggca tcgtatgggt tgcaactgag ggagccttga atacacccaa agaccacatt
28561 ggcacccgca atcctaataa caatgctgcc accgtgctac aacttcctca aggaacaaca
28621 ttgccaaaag gcttctacgc agagggaagc agaggcggca gtcaagcctc ttctcgctcc
28681 tcatcacgta gtcgcggtaa ttcaagaaat tcaactcctg gcagcagtag gggaaattct
28741 cctgctcgaa tggctagcgg aggtggtgaa actgccctcg cgctattgct gctagacaga
28801 ttgaaccagc ttgagagcaa agtttctggt aaaggccaac aacaacaagg ccaaactgtc
28861 actaagaaat ctgctgctga ggcatctaaa aagcctcgcc aaaaacgtac tgccacaaaa
28921 cagtacaacg tcactcaagc atttgggaga cgtggtccag aacaaaccca aggaaatttc
28981 ggggaccaag acctaatcag acaaggaact gattacaaac attggccgca aattgcacaa
29041 tttgctccaa gtgcctctgc attctttgga atgtcacgca ttggcatgga agtcacacct
29101 tcgggaacat ggctgactta tcatggagcc attaaattgg atgacaaaga tccacaattc
29161 aaagacaacg tcatactgct gaacaagcac attgacgcat acaaaacatt cccaccaaca
29221 gagcctaaaa aggacaaaaa gaaaaagact gatgaagctc agcctttgcc gcagagacaa
29281 aagaagcagc ccactgtgac tcttcttcct gcggctgaca tggatgattt ctccagacaa
29341 cttcaaaatt ccatgagtgg agcttctgct gattcaactc aggcataaac actcatgatg
29401 accacacaag gcagatgggc tatgtaaacg ttttcgcaat tccgtttacg atacatagtc
29461 tactcttgtg cagaatgaat tctcgtaact aaacagcaca agtaggttta gttaacttta
29521 atctcacata gcaatcttta atcaatgtgt aacattaggg aggacttgaa agagccacca
29581 cattttcatc gaggccacgc ggagtacgat cgagggtaca gtgaataatg ctagggagag
```

FIGURE 7I

```
29641 ctgcctatat ggaagagccc taatgtgtaa aattaatttt agtagtgcta tccccatgtg
29701 attttaatag cttcttagga gaatgac
```

FIGURE 8 A 1 atattaggtt tttacctacc caggaaaagc caaccaacct cgatctcttg tagatctgtt
61 ctctaaacga actttaaaat ctgtgtagct gtcgctcggc tgcatgccta gtgcacctac
121 gcagtataaa caataataaa ttttactgtc gttgacaaga aacgagtaac tcgtccctct
181 tctgcagact gcttacggtt tcgtccgtgt tgcagtcgat catcagcata cctaggtttc
241 gtccgggtgt gaccgaaagg taagatggag agccttgttc ttggtgtcaa cgagaaaaca
301 cacgtccaac tcagtttgcc tgtccttcag gttagagacg tgctagtgcg tggcttcggg
361 gactctgtgg aagaggccct atcggaggca cgtgaacacc tcaaaaatgg cacttgtggt
421 ctagtagagc tggaaaaagg cgtactgccc cagcttgaac agccctatgt gttcattaaa
481 cgttctgatg ccttaagcac caatcacggc cacaaggtcg ttgagctggt tgcagaaatg
541 gacggcattc agtacggtcg tagcggtata acactgggag tactcgtgcc acatgtgggc
601 gaaaccccaa ttgcataccg caatgttctt cttcgtaaga acggtaataa gggagccggt
661 ggtcatagct atggcatcga tctaaagtct tatgacttag gtgacgagct tggcactgat
721 cccattgaag attatgaaca aaactggaac actaagcatg gcagtggtgc actccgtgaa
781 ctcactcgtg agctcaatgg aggtgcagtc actcgctatg tcgacaacaa tttctgtggc
841 ccagatgggt accctcttga ttgcatcaaa gattttctcg cacgcgcggg caagtcaatg
901 tgcactcttt ccgaacaact tgattacatc gagtcgaaga gaggtgtcta ctgctgccgt
961 gaccatgagc atgaaattgc ctggttcact gagcgctctg ataagagcta cgagcaccag
1021 acacccttcg aaattaagag tgccaagaaa tttgacactt tcaaagggga atgcccaaag
1081 tttgtgtttc ctcttaactc aaaagtcaaa gtcattcaac cacgtgttga aaagaaaaag
1141 actgagggtt tcatggggcg tatacgctct gtgtaccctg ttgcatctcc acaggagtgt
1201 aacaatatgc acttgtctac cttgatgaaa tgtaatcatt gcgatgaagt ttcatggcag
1261 acgtgcgact ttctgaaagc cacttgtgaa cattgtggca ctgaaaattt agttattgaa
1321 ggacctacta catgtgggta cctacctact aatgctgtag tgaaaatgcc atgtcctgcc
1381 tgtcaagacc cagagattgg acctgagcat agtgttgcag attatcacaa ccactcaaac
1441 attgaaactc gactccgcaa gggaggtagg actagatgtt ttggaggctg tgtgtttgcc
1501 tatgttggct gctataataa gcgtgcctac tgggttcctc gtgctagtgc tgatattggc
1561 tcaggccata ctggcattac tggtgacaat gtggagacct tgaatgagga tctccttgag
1621 atactgagtc gtgaacgtgt taacattaac attgttggcg attttcattt gaatgaagag
1681 gttgccatca ttttggcatc tttctctgct tctacaagtg cctttattga cactataaag
1741 agtcttgatt acaagtcttt caaaaccatt gttgagtcct gcggtaacta taaagttacc
1801 aagggaaagc ccgtaaaagg tgcttggaac attggacaac agagatcagt tttaacacca
1861 ctgtgtggtt ttccctcaca ggctgctggt gttatcagat caatttttgc gcgcacactt
1921 gatgcagcaa accactcaat tcctgatttg caaagagcag ctgtcaccat acttgatggt
1981 atttctgaac agtcattacg tcttgtcgac gccatggttt atacttcaga cctgctcacc
2041 aacagtgtca ttattatggc atatgtaact ggtggtcttg tacaacagac ttctcagtgg
2101 ttgtctaatc ttttgggcac tactgttgaa aaactcaggc ctatctttga atggattgag
2161 gcgaaactta gtgcaggagt tgaatttctc aaggatgctt gggagattct caaatttctc
2221 attacaggtg tttttgacat cgtcaagggt caaatacagg ttgcttcaga taacatcaag
2281 gattgtgtaa aatgcttcat tgatgttgtt aacaaggcac tcgaaatgtg cattgatcaa
2341 gtcactatcg ctggcgcaaa gttgcgatca ctcaacttag gtgaagtctt catcgctcaa
2401 agcaagggac tttaccgtca gtgtatacgt ggcaaggagc agctgcaact actcatgcct
2461 cttaaggcac caaaagaagt aacctttctt gaaggtgatt cacatgacac agtacttacc
2521 tctgaggagg ttgttctcaa gaacggtgaa ctcgaagcac tcgagacgcc cgttgatagc
2581 ttcacaaatg gagctatcgt tggcacacca gtctgtgtaa atggcctcat gctcttagag
2641 attaaggaca aagaacaata ctgcgcattg tctcctggtt tactggctac aaacaatgtc
2701 tttcgcttaa aagggggtgc accaattaaa ggtgtaacct ttggagaaga tactgtttgg
2761 gaagttcaag gttacaagaa tgtgagaatc acatttgagc ttgatgaacg tgttgacaaa
2821 gtgcttaatg aaaagtgctc tgtctacact gttgaatccg gtaccgaagt tactgagttt
2881 gcatgtgttg tagcagaggc tgttgtgaag actttacaac cagtttctga tctccttacc
2941 aacatgggta ttgatcttga tgagtggagt gtagctacat tctacttatt tgatgatgct
3001 ggtgaagaaa acttttcatc acgtatgtat tgttcctttt accctccaga tgaggaagaa

FIGURE 8 B 3061 gaggacgatg cagagtgtga ggaagaagaa attgatgaaa cctgtgaaca tgagtacggt
3121 acagaggatg attatcaagg tctccctctg gaatttggtg cctcagctga aacagttcga
3181 gttgaggaag aagaagagga agactggctg gatgatacta ctgagcaatc agagattgag
3241 ccagaaccag aacctacacc tgaagaacca gttaatcagt ttactggtta tttaaaactt
3301 actgacaatg ttgccattaa atgtgttgac atcgttaagg aggcacaaag tgctaatcct
3361 atggtgattg taaatgctgc taacatacac ctgaaacatg gtggtggtgt agcaggtgca
3421 ctcaacaagg caaccaatgg tgccatgcaa aaggagagtg atgattacat taagctaaat
3481 ggccctctta cagtaggagg gtcttgtttg ctttctggac ataatcttgc taagaagtgt
3541 ctgcatgttg ttggacctaa cctaaatgca ggtgaggaca tccagcttct taaggcagca
3601 tatgaaaatt tcaattcaca ggacatctta cttgcaccat tgttgtcagc aggcatattt
3661 ggtgctaaac cacttcagtc tttacaagtg tgcgtgcaga cggttcgtac acaggtttat
3721 attgcagtca atgacaaagc tctttatgag caggttgtca tggattatct tgataacctg
3781 aagcctagag tggaagcacc taaacaagag gagccaccaa acacagaaga ttccaaaact
3841 gaggagaaat ctgtcgtaca gaagcctgtc gatgtgaagc caaaaattaa ggcctgcatt
3901 gatgaggtta ccacaacact ggaagaaact aagtttctta ccaataagtt actcttgttt
3961 gctgatatca atggtaagct ttaccatgat tctcagaaca tgcttagagg tgaagatatg
4021 tctttccttg agaaggatgc accttacatg gtaggtgatg ttatcactag tggtgatatc
4081 acttgtgttg taataccctc caaaaaggct ggtggcacta ctgagatgct ctcaagagct
4141 ttgaagaaag tgccagttga tgagtatata accacgtacc ctggacaagg atgtgctggt
4201 tatacacttg aggaagctaa gactgctctt aagaaatgca aatctgcatt ttatgtacta
4261 ccttcagaag cacctaatgc taaggaagag attctaggaa ctgtatcctg gaatttgaga
4321 gaaatgcttg ctcatgctga agagacaaga aaattaatgc ctatatgcat ggatgttaga
4381 gccataatgg caaccatcca acgtaagtat aaaggaatta aaattcaaga gggcatcgtt
4441 gactatggtg tccgattctt cttttatact agtaaagagc ctgtagcttc tattattacg
4501 aagctgaact ctctaaatga gccgcttgtc acaatgccaa ttggttatgt gacacatggt
4561 tttaatcttg aagaggctgc gcgctgtatg cgttctctta aagctcctgc cgtagtgtca
4621 gtatcatcac cagatgctgt tactacatat aatggatacc tcacttcgtc atcaaagaca
4681 tctgaggagc actttgtaga aacagtttct ttggctggct cttacagaga ttggtcctat
4741 tcaggacagc gtacagagtt aggtgttgaa tttcttaagc gtggtgacaa aattgtgtac
4801 cacactctgg agagccccgt cgagtttcat cttgacggtg aggttctttc acttgacaaa
4861 ctaaagagtc tcttatccct gcgggaggtt aagactataa aagtgttcac aactgtggac
4921 aacactaatc tccacacaca gcttgtggat atgtctatga catatggaca gcagtttggt
4981 ccaacatact tggatggtgc tgatgttaca aaaattaaac ctcatgtaaa tcatgagggt
5041 aagactttct ttgtactacc tagtgatgac acactacgta gtgaagcttt cgagtactac
5101 catactcttg atgagagttt tcttggtagg tacatgtctg ctttaaacca cacaaagaaa
5161 tggaaatttc ctcaagttgg tggtttaact tcaattaaat gggctgataa caattgttat
5221 ttgtctagtg ttttattagc acttcaacag cttgaagtca aattcaatgc accagcactt
5281 caagaggctt attatagagc ccgtgctggt gatgctgcta acttttgtgc actcatactc
5341 gcttacagta ataaaactgt tggcgagctt ggtgatgtca gagaaactat gacccatctt
5401 ctacagcatg ctaatttgga atctgcaaag cgagttctta atgtggtgtg taaacattgt
5461 ggtcagaaaa ctactacctt aacgggtgta gaagctgtga tgtatatggg tactctatct
5521 tatgataatc ttaagacagg tgtttccatt ccatgtgtgt gtggtcgtga tgctacacaa
5581 tatctagtac aacaagagtc ttcttttgtt atgatgtctg caccacctgc tgagtataaa
5641 ttacagcaag gtacattctt atgtgcgaat gagtacactg gtaactatca gtgtggtcat
5701 tacactcata taactgctaa ggagacccct tatcgtattg acggagctca ccttacaaag
5761 atgtcagagt acaaaggacc agtgactgat gttttctaca aggaaacatc ttacactaca
5821 accatcaagc ctgtgtcgta taaactcgat ggagttactt acacagagat tgaaccaaaa
5881 ttggatgggt attataaaaa ggataatgct tactatacag agcagcctat agaccttgta
5941 ccaactcaac cattaccaaa tgcgagtttt gataatttca aactcacatg ttctaacaca
6001 aaatttgctg atgatttaaa tcaaatgaca ggcttcacaa agccagcttc acgagagcta
6061 tctgtcacat tcttcccaga cttgaatggc gatgtagtgg ctattgacta tagacactat
6121 tcagcgagtt tcaagaaagg tgctaaatta ctgcataagc caattgtttg gcacattaac

FIGURE 8 C 6181 caggctacaa ccaagacaac gttcaaacca aacacttggt gtttacgttg tctttggagt
6241 acaaagccag tagatacttc aaattcattt gaagttctgg cagtagaaga cacacaagga
6301 atggacaatc ttgcttgtga aagtcaacaa cccacctctg aagaagtagt ggaaaatcct
6361 accatacaga aggaagtcat agagtgtgac gtgaaaacta ccgaagttgt aggcaatgtc
6421 atacttaaac catcagatga aggtgttaaa gtaacacaag agttaggtca tgaggatctt
6481 atggctgctt atgtggaaaa cacaagcatt accattaaga aacctaatga gctttcacta
6541 gccttaggtt taaaaacaat tgccactcat ggtattgctg caattaatag tgttccttgg
6601 agtaaaattt tggcttatgt caaaccattc ttaggacaag cagcaattac aacatcaaat
6661 tgcgctaaga gattagcaca acgtgtgttt aacaattata tgccttatgt gtttacatta
6721 ttgttccaat tgtgtacttt tactaaaagt accaattcta gaattagagc ttcactacct
6781 acaactattg ctaaaaatag tgttaagagt gttgctaaat tatgtttgga tgccggcatt
6841 aattatgtga agtcacccaa attttctaaa ttgttcacaa tcgctatgtg gctattgttg
6901 ttaagtattt gcttaggttc tctaatctgt gtaactgctg cttttggtgt actcttatct
6961 aattttggtg ctccttctta ttgtaatggc gttagagaat tgtatcttaa ttcgtctaac
7021 gttactacta tggatttctg tgaaggttct tttccttgca gcatttgttt aagtggatta
7081 gactcccttg attcttatcc agctcttgaa accattcagg tgacgatttc atcgtacaag
7141 ctagacttga caattttagg tctggccgct gagtgggttt tggcatatat gttgttcaca
7201 aaattctttt atttattagg tctttcagct ataatgcagg tgttctttgg ctattttgct
7261 agtcatttca tcagcaattc ttggctcatg tggtttatca ttagtattgt acaaatggca
7321 cccgtttctg caatggttag gatgtacatc ttctttgctt ctttctacta catatggaag
7381 agctatgttc atatcatgga tggttgcacc tcttcgactt gcatgatgtg ctataagcgc
7441 aatcgtgcca cacgcgttga gtgtacaact attgttaatg gcatgaagag atctttctat
7501 gtctatgcaa atggaggccg tggcttctgc aagactcaca attggaattg tctcaattgt
7561 gacacatttt gcactggtag tacattcatt agtgatgaag ttgctcgtga tttgtcactc
7621 cagtttaaaa gaccaatcaa ccctactgac cagtcatcgt atattgttga tagtgttgct
7681 gtgaaaaatg gcgcgcttca cctctacttt gacaaggctg gtcaaaagac ctatgagaga
7741 catccgctct cccattttgt caatttagac aatttgagag ctaacaacac taaaggttca
7801 ctgcctatta atgtcatagt ttttgatggc aagtccaaat gcgacgagtc tgcttctaag
7861 tctgcttctg tgtactacag tcagctgatg tgccaaccta ttctgttgct tgaccaagct
7921 cttgtatcag acgttggaga tagtactgaa gtttccgtta agatgtttga tgcttatgtc
7981 gacacctttt cagcaacttt tagtgttcct atggaaaaac ttaaggcact tgttgctaca
8041 gctcacagcg agttagcaaa gggtgtagct ttagatggtg tcctttctac attcgtgtca
8101 gctgcccgac aaggtgttgt tgataccgat gttgacacaa aggatgttat tgaatgtctc
8161 aaactttcac atcactctga cttagaagtg acaggtgaca gttgtaacaa tttcatgctc
8221 acctataata aggttgaaaa catgacgccc agagatcttg gcgcatgtat tgactgtaat
8281 gcaaggcata tcaatgccca agtagcaaaa agtcacaatg tttcactcat ctggaatgta
8341 aaagactaca tgtctttatc tgaacagctg cgtaaacaaa ttcgtagtgc tgccaagaag
8401 aacaacatac cttttagact aacttgtgct acaactagac aggttgtcaa tgtcataact
8461 actaaaatct cactcaaggg tggtaagatt gttagtactt gttttaaact tatgcttaag
8521 gccacattat tgtgcgttct tgctgcattg gtttgttata tcgttatgcc agtacataca
8581 ttgtcaatcc atgatggtta cacaaatgaa atcattggtt acaaagccat tcaggatggt
8641 gtcactcgtg acatcatttc tactgatgat tgttttgcaa ataaacatgc tggttttgac
8701 gcatggttta gccagcgtgg tggttcatac aaaaatgaca aaagctgccc tgtagtagct
8761 gctatcatta caagagagat tggtttcata gtgcctggct taccgggtac tgtgctgaga
8821 gcaatcaatg gtgacttctt gcattttcta cctcgtgttt ttagtgctgt tggcaacatt
8881 tgctacacac cttccaaact cattgagtat agtgattttg ctacctctgc ttgcgttctt
8941 gctgctgagt gtacaatttt taaggatgct atgggcaaac ctgtgccata ttgttatgac
9001 actaatttgc tagagggttc tatttcttat agtgagcttc gtccagacac tcgttatgtg
9061 cttatggatg gttccatcat acagtttcct aacacttacc tggagggttc tgttagagta
9121 gtaacaactt ttgatgctga gtactgtaga catggtacat gcgaaaggtc agaagtaggt
9181 atttgcctat ctaccagtgg tagatgggtt cttaataatg agcattacag agctctatca
9241 ggagttttct gtggtgttga tgcgatgaat ctcatagcta acatctttac tcctcttgtg

FIGURE 8 D 9301 caacctgtgg gtgctttaga tgtgtctgct tcagtagtgg ctggtggtat tattgccata
9361 ttggtgactt gtgctgccta ctactttatg aaattcagac gtgtttttgg tgagtacaac
9421 catgttgttg ctgctaatgc acttttgttt ttgatgtctt tcactatact ctgtctggta
9481 ccagcttaca gctttctgcc gggagtctac tcagtctttt acttgtactt gacattctat
9541 ttcaccaatg atgtttcatt cttggctcac cttcaatggt ttgccatgtt ttctcctatt
9601 gtgccttttt ggataacagc aatctatgta ttctgtattt ctctgaagca ctgccattgg
9661 ttctttaaca actatcttag gaaaagagtc atgtttaatg gagttacatt tagtaccttc
9721 gaggaggctg ctttgtgtac ctttttgctc aacaaggaaa tgtacctaaa attgcgtagc
9781 gagacactgt tgccacttac acagtataac aggtatcttg ctctatataa caagtacaag
9841 tatttcagtg gagccttaga tactaccagc tatcgtgaag cagcttgctg ccacttagca
9901 aaggctctaa atgactttag caactcaggt gctgatgttc tctaccaacc accacagaca
9961 tcaatcactt ctgctgttct gcagagtggt tttaggaaaa tggcattccc gtcaggcaaa
10021 gttgaagggt gcatggtaca agtaacctgt ggaactacaa ctcttaatgg attgtggttg
10081 gatgacacag tatactgtcc aagacatgtc atttgcacag cagaagacat gcttaatcct
10141 aactatgaag atctgctcat tcgcaaatcc aaccatagct ttcttgttca ggctggcaat
10201 gttcaacttc gtgttattgg ccattctatg caaaattgtc tgcttaggct taaagttgat
10261 acttctaacc ctaagacacc caagtataaa tttgtccgta tccaacctgg tcaaacattt
10321 tcagttctag catgctacaa tggttcacca tctggtgttt atcagtgtgc catgagacct
10381 aatcatacca ttaaaggttc tttccttaat ggatcatgtg gtagtgttgg ttttaacatt
10441 gattatgatt gcgtgtcttt ctgctatatg catcatatgg agcttccaac aggagtacac
10501 gctggtactg acttagaagg taaattctat ggtccatttg ttgacagaca aactgcacag
10561 gctgcaggta cagacacaac cataacatta aatgttttgg catggctgta tgctgctgtt
10621 atcaatggtg ataggtggtt tcttaataga ttcaccacta ctttgaatga ctttaacctt
10681 gtggcaatga agtacaacta tgaacctttg acacaagatc atgttgacat attgggacct
10741 ctttctgctc aaacaggaat tgccgtctta gatatgtgtg ctgctttgaa agagctgctg
10801 cagaatggta tgaatggtcg tactatcctt ggtagcacta ttttagaaga tgagtttaca
10861 ccatttgatg ttgttagaca atgctctggt gttaccttcc aaggtaagtt caagaaaatt
10921 gttaagggca ctcatcattg gatgctttta actttcttga catcactatt gattcttgtt
10981 caaagtacac agtggtcact gtttttcttt gtttacgaga atgctttctt gccatttact
11041 cttggtatta tggcaattgc tgcatgtgct atgctgcttg ttaagcataa gcacgcattc
11101 ttgtgcttgt ttctgttacc ttctcttgca acagttgctt actttaatat ggtctacatg
11161 cctgctagct gggtgatgcg tatcatgaca tggcttgaat tggctgacac tagcttgtct
11221 ggttataggc ttaaggattg tgttatgtat gcttcagctt tagttttgct tattctcatg
11281 acagctcgca ctgtttatga tgatgctgct agacgtgttt ggacactgat gaatgtcatt
11341 acacttgttt acaaagtcta ctatggtaat gctttagatc aagctatttc catgtgggcc
11401 ttagttattt ctgtaacctc taactattct ggtgtcgtta cgactatcat gtttttagct
11461 agagctatag tgtttgtgtg tgttgagtat tacccattgt tatttattac tggcaacacc
11521 ttacagtgta tcatgcttgt ttattgtttc ttaggctatt gttgctgctg ctactttggc
11581 cttttctgtt tactcaaccg ttacttcagg cttactcttg gtgtttatga ctacttggtc
11641 tctacacaag aatttaggta tatgaactcc caggggcttt tgcctcctaa gagtagtatt
11701 gatgctttca agcttaacat taagttgttg ggtattggag gtaaaccatg tatcaaggtt
11761 gctactgtac agtctaaaat gtctgacgta aagtgcacat ctgtggtact gctctcggtt
11821 cttcaacaac ttagagtaga gtcatcttct aaattgtggg cacaatgtgt acaactccac
11881 aatgatattc ttcttgcaaa agacacaact gaagctttcg agaagatggt ttctcttttg
11941 tctgttttgc tatccatgca gggtgctgta gacattaata ggttgtgcga ggaaatgctc
12001 gataaccgtg ctactcttca ggctattgct tcagaattta gttctttacc atcatatgcc
12061 gcttatgcca ctgcccagga ggcctatgag caggctgtag ctaatggtga ttctgaagtc
12121 gttctcaaaa agttaaagaa atctttgaat gtggctaaat ctgagtttga ccgtgatgct
12181 gccatgcaac gcaagttgga aaagatggca gatcaggcta tgacccaaat gtacaaacag
12241 gcaagatctg aggacaagag ggcaaaagta actagtgcta tgcaaacaat gctcttcact
12301 atgcttagga agcttgataa tgatgcactt aacaacatta tcaacaatgc gcgtgatggt
12361 tgtgttccac tcaacatcat accattgact acagcagcca aactcatggt tgttgtccct

FIGURE 8 E 12421 gattatggta cctacaagaa cacttgtgat ggtaacacct ttacatatgc atctgcactc
12481 tgggaaatcc agcaagttgt tgatgcggat agcaagattg ttcaacttag tgaaattaac
12541 atggacaatt caccaaattt ggcttggcct cttattgtta cagctctaag agccaactca
12601 gctgttaaac tacagaataa tgaactgagt ccagtagcac tacgacagat gtcctgtgcg
12661 gctggtacca cacaaacagc ttgtactgat gacaatgcac ttgcctacta taacaattcg
12721 aagggaggta ggtttgtgct ggcattacta tcagaccacc aagatctcaa atgggctaga
12781 ttccctaaga gtgatggtac aggtacaatt tacacagaac tggaaccacc ttgtaggttt
12841 gttacagaca caccaaaagg gcctaaagtg aaatacttgt acttcatcaa aggcttaaac
12901 aacctaaata gaggtatggt gctgggcagt ttagctgcta cagtacgtct tcaggctgga
12961 aatgctacag aagtacctgc caattcaact gtgctttcct tctgtgcttt tgcagtagac
13021 cctgctaaag catataagga ttacctagca agtggaggac aaccaatcac caactgtgtg
13081 aagatgttgt gtacacacac tggtacagga caggcaatta ctgtaacacc agaagctaac
13141 atggaccaag agtcctttgg tggtgcttca tgttgtctgt attgtagatg ccacattgac
13201 catccaaatc ctaaaggatt ctgtgacttg aaaggtaagt acgtccaaat acctaccact
13261 tgtgctaatg acccagtggg ttttacactt agaaacacag tctgtaccgt ctgcggaatg
13321 tggaaaggtt atggctgtag ttgtgaccaa ctccgcgaac ccttgatgca gtctgcggat
13381 gcatcaacgt ttttaaacgg gtttgcggtg taagtgcagc ccgtcttaca ccgtgcggca
13441 caggcactag tactgatgtc gtctacaggg cttttgatat ttacaacgaa aaagttgctg
13501 gttttgcaaa gttcctaaaa actaattgct gtcgcttcca ggagaaggat gaggaaggca
13561 atttattaga ctcttacttt gtagttaaga ggcatactat gtctaactac caacatgaag
13621 agactattta taacttggtt aaagattgtc cagcggttgc tgtccatgac tttttcaagt
13681 ttagagtaga tggtgacatg gtaccacata tatcacgtca gcgtctaact aaatacacaa
13741 tggctgattt agtctatgct ctacgtcatt ttgatgaggg taattgtgat acattaaaag
13801 aaatactcgt cacatacaat tgctgtgatg atgattattt caataagaag gattggtatg
13861 acttcgtaga gaatcctgac atcttacgcg tatatgctaa cttaggtgag cgtgtacgcc
13921 aatcattatt aaagactgta caattctgcg atgctatgcg tgatgcaggc attgtaggcg
13981 tactgacatt agataatcag gatcttaatg ggaactggta cgatttcggt gatttcgtac
14041 aagtagcacc aggctgcgga gttcctattg tggattcata ttactcattg ctgatgccca
14101 tcctcacttt gactagggca ttggctgctg agtcccatat ggatgctgat ctcgcaaaac
14161 cacttattaa gtgggatttg ctgaaatatg attttacgga agagagactt tgtctcttcg
14221 accgttattt taaatattgg gaccagacat accatcccaa ttgtattaac tgtttggatg
14281 ataggtgtat ccttcattgt gcaaacttta atgtgttatt ttctactgtg tttccaccta
14341 caagttttgg accactagta agaaaaatat ttgtagatgg tgttcctttt gttgtttcaa
14401 ctggatacca ttttcgtgag ttaggagtcg tacataatca ggatgtaaac ttacatagct
14461 cgcgtctcag tttcaaggaa cttttagtgt atgctgctga tccagctatg catgcagctt
14521 ctggcaattt attgctagat aaacgcacta catgcttttc agtagctgca ctaacaaaca
14581 atgttgcttt tcaaactgtc aaacccggta attttaataa agacttttat gactttgctg
14641 tgtctaaagg tttctttaag gaaggaagtt ctgttgaact aaaacacttc ttctttgctc
14701 aggatggcaa cgctgctatc agtgattatg actattatcg ttataatctg ccaacaatgt
14761 gtgatatcag acaactccta ttcgtagttg aagttgttga taaatacttt gattgttacg
14821 atggtggctg tattaatgcc aaccaagtaa tcgttaacaa tctggataaa tcagctggtt
14881 tcccatttaa taaatggggt aaggctagac tttattatga ctcaatgagt tatgaggatc
14941 aagatgcact tttcgcgtat actaagcgta atgtcatccc tactataact caaatgaatc
15001 ttaagtatgc cattagtgca aagaatagag ctcgcaccgt agctggtgtc tctatctgta
15061 gtactatgac aaatagacag tttcatcaga aattattgaa gtcaatagcc gccactagag
15121 gagctactgt ggtaattgga acaagcaagt tttacggtgg ctggcataat atgttaaaaa
15181 ctgtttacag tgatgtagaa actccacacc ttatgggttg ggattatcca aaatgtgaca
15241 gagccatgcc taacatgctt aggataatgg cctctcttgt tcttgctcgc aaacataaca
15301 cttgctgtaa cttatcacac cgtttctaca ggttagctaa cgagtgtgcg caagtattaa
15361 gtgagatggt catgtgtggc ggctcactat atgttaaacc aggtggaaca tcatccggtg
15421 atgctacaac tgcttatgct aatagtgtct ttaacatttg tcaagctgtt acagccaatg
15481 taaatgcact tctttcaact gatggtaata agatagctga caagtatgtc cgcaatctac

FIGURE 8 F 15541 aacacaggct ctatgagtgt ctctatagaa atagggatgt tgatcatgaa ttcgtggatg
15601 agttttacgc ttacctgcgt aaacatttct ccatgatgat tctttctgat gatgccgttg
15661 tgtgctataa cagtaactat gcggctcaag gtttagtagc tagcattaag aactttaagg
15721 cagttcttta ttatcaaaat aatgtgttca tgtctgaggc aaaatgttgg actgagactg
15781 accttactaa aggacctcac gaattttgct cacagcatac aatgctagtt aaacaaggag
15841 atgattacgt gtacctgcct tacccagatc catcaagaat attaggcgca ggctgttttg
15901 tcgatgatat tgtcaaaaca gatggtacac ttatgattga aaggttcgtg tcactggcta
15961 ttgatgctta cccacttaca aaacatccta atcaggagta tgctgatgtc tttcacttgt
16021 atttacaata cattagaaag ttacatgatg agcttactgg ccacatgttg gacatgtatt
16081 ccgtaatgct aactaatgat aacacctcac ggtactggga acctgagttt tatgaggcta
16141 tgtacacacc acatacagtc ttgcaggctg taggtgcttg tgtattgtgc aattcacaga
16201 cttcacttcg ttgcggtgcc tgtattagga gaccattcct atgttgcaag tgctgctatg
16261 accatgtcat ttcaacatca cacaaattag tgttgtctgt taatccctat gtttgcaatg
16321 ccccaggttg tgatgtcact gatgtgacac aactgtatct aggaggtatg agctattatt
16381 gcaagtcaca taagcctccc attagttttc cattatgtgc taatggtcag gtttttggtt
16441 tatacaaaaa cacatgtgta ggcagtgaca atgtcactga cttcaatgcg atagcaacat
16501 gtgattggac taatgctggc gattacatac ttgccaacac ttgtactgag agactcaagc
16561 ttttcgcagc agaaacgctc aaagccactg aggaaacatt taagctgtca tatggtattg
16621 ccactgtacg cgaagtactc tctgacagag aattgcatct ttcatgggag gttggaaaac
16681 ctagaccacc attgaacaga aactatgtct ttactggtta ccgtgtaact aaaaatagta
16741 aagtacagat tggagagtac acctttgaaa aaggtgacta tggtgatgct gttgtgtaca
16801 gaggtactac gacatacaag ttgaatgttg gtgattactt tgtgttgaca tctcacactg
16861 taatgccact tagtgcacct actctagtgc cacaagagca ctatgtgaga attactggct
16921 tgtacccaac actcaacatc tcagatgagt tttctagcaa tgttgcaaat tatcaaaagg
16981 tcggcatgca aaagtactct acactccaag gaccacctgg tactggtaag agtcattttg
17041 ccatcggact tgctctctat tacccatctg ctcgcatagt gtatacggca tgctctcatg
17101 cagctgttga tgccctatgt gaaaaggcat taaaatattt gcccatagat aaatgtagta
17161 gaatcatacc tgcgcgtgcg cgcgtagagt gttttgataa attcaaagtg aattcaacac
17221 tagaacagta tgttttctgc actgtaaatg cattgccaga aacaactgct gacattgtag
17281 tctttgatga aatctctatg gctactaatt atgacttgag tgttgtcaat gctagacttc
17341 gtgcaaaaca ctacgtctat attggcgatc ctgctcaatt accagccccc cgcacattgc
17401 tgactaaagg cacactagaa ccagaatatt ttaattcagt gtgcagactt atgaaaacaa
17461 taggtccaga catgttcctt ggaacttgtc gccgttgtcc tgctgaaatt gttgacactg
17521 tgagtgcttt agtttatgac aataagctaa aagcacacaa ggataagtca gctcaatgct
17581 tcaaaatgtt ctacaaaggt gttattacac atgatgtttc atctgcaatc aacagacctc
17641 aaataggcgt tgtaagagaa tttcttacac gcaatcctgc ttggagaaaa gctgttttta
17701 tctcacctta taattcacag aacgctgtag cttcaaaaat cttaggattg cctacgcaga
17761 ctgttgattc atcacagggt tctgaatatg actatgtcat attcacacaa actactgaaa
17821 cagcacactc ttgtaatgtc aaccgcttca atgtggctat cacaagggca aaaattggca
17881 ttttgtgcat aatgtctgat agagatcttt atgacaaact gcaatttaca agtctagaaa
17941 taccacgtcg caatgtggct acattacaag cagaaaatgt aactggactt tttaaggact
18001 gtagtaagat cattactggt cttcatccta cacaggcacc tacacacctc agcgttgata
18061 taaagttcaa gactgaagga ttatgtgttg acataccagg cataccaaag gacatgacct
18121 accgtagact catctctatg atgggtttca aaatgaatta ccaagtcaat ggttacccta
18181 atatgtttat cacccgcgaa gaagctattc gtcacgttcg tgcgtggatt ggctttgatg
18241 tagagggctg tcatgcaact agagatgctg tgggtactaa cctacctctc cagctaggat
18301 tttctacagg tgttaactta gtagctgtac cgactggtta tgttgacact gaaaataaca
18361 cagaattcac cagagttaat gcaaaacctc caccaggtga ccagtttaaa catcttatac
18421 cactcatgta taaaggcttg ccctggaatg tagtgcgtat taagatagta caaatgctca
18481 gtgatacact gaaaggattg tcagacagag tcgtgttcgt cctttgggcg catggctttg
18541 agcttacatc aatgaagtac tttgtcaaga ttggacctga aagaacgtgt tgtctgtgtg
18601 acaaacgtgc aacttgcttt tctacttcat cagatactta tgcctgctgg aatcattctg

FIGURE 8 G 18661 tgggttttga ctatgtctat aacccattta tgattgatgt tcagcagtgg ggctttacgg
18721 gtaaccttca gagtaaccat gaccaacatt gccaggtaca tggaaatgca catgtggcta
18781 gttgtgatgc tatcatgact agatgtttag cagtccatga gtgctttgtt aagcgcgttg
18841 attggtctgt tgaataccct attataggag atgaactgag ggttaattct gcttgcagaa
18901 aagtacaaca catggttgtg aagtctgcat tgcttgctga taagtttcca gttcttcatg
18961 acattggaaa tccaaaggct atcaagtgtg tgcctcaggc tgaagtagaa tggaagttct
19021 acgatgctca gccatgtagt gacaaagctt acaaaataga ggaactcttc tattcttatg
19081 ctacacatca cgataaattc actgatggtg tttgtttgtt ttggaattgt aacgttgatc
19141 gttacccagc caatgcaatt gtgtgtaggt ttgacacaag agtcttgtca aacttgaact
19201 taccaggctg tgatggtggt agtttgtatg tgaataagca tgcattccac actccagctt
19261 tcgataaaag tgcatttact aatttaaagc aattgccttt cttttactat tctgatagtc
19321 cttgtgagtc tcatggcaaa caagtagtgt cggatattga ttatgttcca ctcaaatctg
19381 ctacgtgtat tacacgatgc aatttaggtg gtgctgtttg cagacaccat gcaaatgagt
19441 accgacagta cttggatgca tataatatga tgatttctgc tggatttagc ctatggattt
19501 acaaacaatt tgatacttat aacctgtgga atacatttac caggttacag agtttagaaa
19561 atgtggctta taatgttgtt aataaaggac actttgatgg acacgccggc gaagcacctg
19621 tttccatcat taataatgct gtttacacaa aggtagatgg tattgatgtg gagatctttg
19681 aaaataagac aacacttcct gttaatgttg catttgagct ttgggctaag cgtaacatta
19741 aaccagtgcc agagattaag atactcaata atttgggtgt tgatatcgct gctaatactg
19801 taatctggga ctacaaaaga gaagccccag cacatgtatc tacaataggt gtctgcacaa
19861 tgactgacat tgccaagaaa cctactgaga gtgcttgttc ttcacttact gtcttgtttg
19921 atggtagagt ggaaggacag gtagaccttt ttagaaacgc ccgtaatggt gttttaataa
19981 cagaaggttc agtcaaaggt ctaacacctt caaagggacc agcacaagct agcgtcaatg
20041 gagtcacatt aattggagaa tcagtaaaaa cacagtttaa ctactttaag aaagtagacg
20101 gcattattca acagttgcct gaaacctact ttactcagag cagagactta gaggatttta
20161 agcccagatc acaaatggaa actgactttc tcgagctcgc tatggatgaa ttcatacagc
20221 gatataagct cgagggctat gccttcgaac acatcgttta tggagatttc agtcatggac
20281 aacttggcgg tcttcattta atgataggct tagccaagcg ctcacaagat tcaccactta
20341 aattagagga ttttatccct atggacagca cagtgaaaaa ttacttcata acagatgcgc
20401 aaacaggttc atcaaaatgt gtgtgttctg tgattgatct tttacttgat gactttgtcg
20461 agataataaa gtcacaagat ttgtcagtga tttcaaaagt ggtcaaggtt acaattgact
20521 atgctgaaat ttcattcatg ctttggtgta aggatggaca tgttgaaacc ttctacccaa
20581 aactacaagc aagtcaagcg tggcaaccag gtgttgcgat gcctaacttg tacaagatgc
20641 aaagaatgct tcttgaaaag tgtgaccttc agaattatgg tgaaaatgct gttataccaa
20701 aaggaataat gatgaatgtc gcaaagtata ctcaactgtg tcaatactta aatacactta
20761 ctttagctgt accctacaac atgagagtta ttcactttgg tgctggctct gataaaggag
20821 ttgcaccagg tacagctgtg ctcagacaat ggttgccaac tggcacacta cttgtcgatt
20881 cagatcttaa tgacttcgtc tccgacgcag attctacttt aattggagac tgtgcaacag
20941 tacatacggc taataaatgg gaccttatta ttagcgatat gtatgaccct aggaccaaac
21001 atgtgacaaa agagaatgac tctaaagaag ggtttttcac ttatctgtgt ggatttataa
21061 agcaaaaact agccctgggt ggttctatag ctgtaaagat aacagagcat tcttggaatg
21121 ctgaccttta caagcttatg ggccatttct catggtggac agcttttgtt acaaatgtaa
21181 atgcatcatc atcggaagca tttttaattg gggctaacta tcttggcaag ccgaaggaac
21241 aaattgatgg ctataccatg catgctaact acattttctg gaggaacaca aatcctatcc
21301 agttgtcttc ctattcactc tttgacatga gcaaatttcc tcttaaatta agaggaactg
21361 ctgtaatgtc tcttaaggag aatcaaatca atgatatgat ttattctctt ctggaaaaag
21421 gtaggcttat cattagagaa aacaacagag ttgtggtttc aagtgatatt cttgttaaca
21481 actaaacgaa catgtttatt ttcttattat ttcttactct cactagtggt agtgaccttg
21541 accggtgcac cacttttgat gatgttcaag ctcctaatta cactcaacat acttcatcta
21601 tgaggggggt ttactatcct gatgaaattt ttagatcaga cactctttat ttaactcagg
21661 atttatttct tccattttat tctaatgtta cagggtttca tactattaat catacgtttg
21721 gcaaccctgt catacctttt aaggatggta tttattttgc tgccacagag aaatcaaatg

FIGURE 8 H 21781 ttgtccgtgg ttgggttttt ggttctacca tgaacaacaa gtcacagtcg gtgattatta
21841 ttaacaattc tactaatgtt gttatacgag catgtaactt tgaattgtgt gacaaccctt
21901 tctttgctgt ttctaaaccc atgggtacac agacacatac tatgatattc gataatgcat
21961 ttaattgcac tttcgagtac atatctgatg ccttttcgct tgatgtttca gaaaagtcag
22021 gtaattttaa acacttacga gagtttgtgt ttaaaaataa agatgggttt ctctatgttt
22081 ataagggcta tcaacctata gatgtagttc gtgatctacc ttctggtttt aacactttga
22141 aacctatttt taagttgcct cttggtatta acattacaaa ttttagagcc attcttacag
22201 ccttttcacc tgctcaagac atttggggca cgtcagctgc agcctatttt gttggctatt
22261 taaagccaac tacatttatg ctcaagtatg atgaaaatgg tacaatcaca gatgctgttg
22321 attgttctca aaatccactt gctgaactca aatgctctgt taagagcttt gagattgaca
22381 aaggaattta ccagacctct aatttcaggg ttgttccctc aggagatgtt gtgagattcc
22441 ctaatattac aaacttgtgt ccttttggag aggtttttaa tgctactaaa ttcccttctg
22501 tctatgcatg ggagagaaaa aaaatttcta attgtgttgc tgattactct gtgctctaca
22561 actcaacatt tttttcaacc tttaagtgct atggcgtttc tgccactaag ttgaatgatc
22621 tttgcttctc caatgtctat gcagattctt ttgtagtcaa gggagatgat gtaagacaaa
22681 tagcgccagg acaaactggt gttattgctg attataatta taaattgcca gatgatttca
22741 tgggttgtgt ccttgcttgg aatactagga acattgatgc tacttcaact ggtaattata
22801 attataaata taggtatctt agacatggca agcttaggcc ctttgagaga gacatatcta
22861 atgtgccttt ctcccctgat ggcaaacctt gcaccccacc tgctcttaat tgttattggc
22921 cattaaatga ttatggtttt tacaccacta ctggcattgg ctaccaacct tacagagttg
22981 tagtactttc ttttgaactt ttaaatgcac cggccacggt ttgtggacca aaattatcca
23041 ctgaccttat taagaaccag tgtgtcaatt ttaattttaa tggactcact ggtactggtg
23101 tgttaactcc ttcttcaaag agatttcaac catttcaaca atttggccgt gatgtttctg
23161 atttcactga ttccgttcga gatcctaaaa catctgaaat attagacatt tcaccttgcg
23221 cttttggggg tgtaagtgta attacacctg gaacaaatgc ttcatctgaa gttgctgttc
23281 tatatcaaga tgttaactgc actgatgttt ctacagcaat tcatgcagat caactcacac
23341 cagcttggcg catatattct actggaaaca atgtattcca gactcaagca ggctgtctta
23401 taggagctga gcatgtcgac acttcttatg agtgcgacat tcctattgga gctggcattt
23461 gtgctagtta ccatacagtt tctttattac gtagtactag ccaaaaatct attgtggctt
23521 atactatgtc tttaggtgct gatagttcaa ttgcttactc taataacacc attgctatac
23581 ctactaactt ttcaattagc attactacag aagtaatgcc tgtttctatg gctaaaacct
23641 ccgtagattg taatatgtac atctgcggag attctactga atgtgctaat ttgcttctcc
23701 aatatggtag cttttgcaca caactaaatc gtgcactctc aggtattgct gctgaacagg
23761 atcgcaacac acgtgaagtg ttcgctcaag tcaaacaaat gtacaaaacc ccaactttga
23821 aatattttgg tggttttaat ttttcacaaa tattacctga ccctctaaag ccaactaaga
23881 ggtcttttat tgaggacttg ctctttaata aggtgacact cgctgatgct ggcttcatga
23941 agcaatatgg cgaatgccta ggtgatatta atgctagaga tctcatttgt gcgcagaagt
24001 tcaatggact tacagtgttg ccacctctgc tcactgatga tatgattgct gcctacactg
24061 ctgctctagt tagtggtact gccactgctg gatggacatt tggtgctggc gctgctcttc
24121 aaatacctttt tgctatgcaa atggcatata ggttcaatgg cattggagtt acccaaaatg
24181 ttctctatga gaaccaaaaa caaatcgcca accaatttaa caaggcgatt agtcaaattc
24241 aagaatcact tacaacaaca tcaactgcat tgggcaagct gcaagacgtt gttaaccaga
24301 atgctcaagc attaaacaca cttgttaaac aacttagctc taattttggt gcaatttcaa
24361 gtgtgctaaa tgatatcctt tcgcgacttg ataaagtcga ggcggaggta caaattgaca
24421 ggttaattac aggcagactt caaagccttc aaacctatgt aacacaacaa ctaatcaggg
24481 ctgctgaaat cagggcttct gctaatcttg ctgctactaa aatgtctgag tgtgttcttg
24541 gacaatcaaa aagagttgac ttttgtggaa agggctacca ccttatgtcc ttcccacaag
24601 cagccccgca tggtgttgtc ttcctacatg tcacgtatgt gccatcccag gagaggaact
24661 tcaccacagc gccagcaatt tgtcatgaag gcaaagcata cttccctcgt gaaggtgttt
24721 ttgtgtttaa tggcacttct tggtttatta cacagaggaa cttcttttct ccacaaataa
24781 ttactacaga caatacattt gtctcaggaa attgtgatgt cgttattggc atcattaaca
24841 acacagttta tgatcctctg caacctgagc ttgactcatt caaagaagag ctggacaagt

FIGURE 8 I 24901 acttcaaaaa tcatacatca ccagatgttg atcttggcga catttcaggc attaacgctt
24961 ctgtcgtcaa cattcaaaaa gaaattgacc gcctcaatga ggtcgctaaa aatttaaatg
25021 aatcactcat tgaccttcaa gaattgggaa aatatgagca atatattaaa tggccttggt
25081 atgtttggct cggcttcatt gctggactaa ttgccatcgt catggttaca atcttgcttt
25141 gttgcatgac tagttgttgc agttgcctca agggtgcatg ctcttgtggt tcttgctgca
25201 agtttgatga ggatgactct gagccagttc tcaagggtgt caaattacat tacacataaa
25261 cgaacttatg gatttgttta tgagattttt tactcttaga tcaattactg cacagccagt
25321 aaaaattgac aatgcttctc ctgcaagtac tgttcatgct acagcaacga taccgctaca
25381 agcctcactc cctttcggat ggcttgttat tggcgttgca tttcttgctg tttttcagag
25441 cgctaccaaa ataattgcgc tcaataaaag atggcagcta gccctttata agggcttcca
25501 gttcatttgc aatttactgc tgctatttgt taccatctat tcacatcttt tgcttgtcgc
25561 tgcaggtatg gaggcgcaat ttttgtacct ctatgccttg atatattttc tacaatgcat
25621 caacgcatgt agaattatta tgagatgttg gctttgttgg aagtgcaaat ccaagaaccc
25681 attactttat gatgccaact actttgtttg ctggcacaca cataactatg actactgtat
25741 accatataac agtgtcacag atacaattgt cgttactgaa ggtgacggca tttcaacacc
25801 aaaactcaaa gaagactacc aaattggtgg ttattctgag gataggcact caggtgttaa
25861 agactatgtc gttgtacatg gctatttcac cgaagtttac taccagcttg agtctacaca
25921 aattactaca gacactggta ttgaaaatgc tacattcttc atctttaaca agcttgttaa
25981 agacccaccg aatgtgcaaa tacacacaat cgacggctct tcaggagttg ctaatccagc
26041 aatggatcca atttatgatg agccgacgac gactactagc gtgcctttgt aagcacaaga
26101 aagtgagtac gaacttatgt actcattcgt ttcggaagaa acaggtacgt taatagttaa
26161 tagcgtactt ctttttcttg ctttcgtggt attcttgcta gtcacactag ccatccttac
26221 tgcgcttcga ttgtgtgcgt actgctgcaa tattgttaac gtgagtttag taaaaccaac
26281 ggtttacgtc tactcgcgtg ttaaaaatct gaactcttct gaaggagttc ctgatcttct
26341 ggtctaaacg aactaactat tattattatt ctgtttggaa ctttaacatt gcttatcatg
26401 gcagacaacg gtactattac cgttgaggag cttaaacaac tcctggaaca atggaaccta
26461 gtaataggtt tcctattcct agcctggatt atgttactac aatttgccta ttctaatcgg
26521 aacaggtttt tgtacataat aaagcttgtt ttcctctggc tcttgtggcc agtaacactt
26581 gcttgttttg tgcttgctgc tgtctacaga attaattggg tgactggcgg gattgcgatt
26641 gcaatggctt gtattgtagg cttgatgtgg cttagctact tcgttgcttc cttcaggctg
26701 tttgctcgta cccgctcaat gtggtcattc aacccagaaa caaacattct tctcaatgtg
26761 cctctccggg ggacaattgt gaccagaccg ctcatggaaa gtgaacttgt cattggtgct
26821 gtgatcattc gtggtcactt gcgaatggcc ggacactccc tagggcgctg tgacattaag
26881 gacctgccaa aagagatcac tgtggctaca tcacgaacgc tttcttatta caaattagga
26941 gcgtcgcagc gtgtaggcac tgattcaggt tttgctgcat acaaccgcta ccgtattgga
27001 aactataaat taaatacaga ccacgccggt agcaacgaca atattgcttt gctagtacag
27061 taagtgacaa cagatgtttc atcttgttga cttccaggtt acaatagcag agatattgat
27121 tatcattatg aggactttca ggattgctat ttggaatctt gacgttataa taagttcaat
27181 agtgagacaa ttatttaagc ctctaactaa gaagaattat tcggagttag atgatgaaga
27241 acctatggag ttagattatc cataaaacga acatgaaaat tattctcttc ctgacattga
27301 ttgtatttac atcttgcgag ctatatcact atcaggagtg tgttagaggt acgactgtac
27361 tactaaaaga accttgccca tcaggaacat acgagggcaa ttcaccattt caccctcttg
27421 ctgacaataa atttgcacta acttgcacta gcacacactt tgcttttgct tgtgctgacg
27481 gtactcgaca tacctatcag ctgcgtgcaa gatcagtttc accaaaactt ttcatcagac
27541 aagaggaggt tcaacaagag ctctactcgc cactttttct cattgttgct gctctagtat
27601 ttttaatact ttgcttcacc attaagagaa agacagaatg aatgagctca ctttaattga
27661 cttctatttg tgctttttag cctttctgct attccttgtt ttaataatgc ttattatatt
27721 ttggttttca ctcgaaatcc aggatctaga agaaccttgt accaaagtct aaacgaacat
27781 gaaacttctc attgttttga cttgtatttc tctatgcagt tgcatatgca ctgtagtaca
27841 gcgctgtgca tctaataaac ctcatgtgct tgaagatcct tgtaaggtac aacactaggg
27901 gtaatactta tagcactgct tggctttgtg ctctaggaaa ggttttacct tttcatagat
27961 ggcacactat ggttcaaaca tgcacaccta atgttactat caactgtcaa gatccagctg

FIGURE 8 J 28021 gtggtgcgct tatagctagg tgttggtacc ttcatgaagg tcaccaaact gctgcattta
28081 gagacgtact tgttgtttta aataaacgaa caaattaaaa tgtctgataa tggaccccaa
28141 tcaaaccaac gtagtgcccc ccgcattaca tttggtggac ccacagattc aactgacaat
28201 aaccagaatg gaggacgcaa tggggcaagg ccaaaacagc gccgacccca aggtttaccc
28261 aataatactg cgtcttggtt cacagctctc actcagcatg gcaaggagga acttagattc
28321 cctcgaggcc agggcgttcc aatcaacacc aatagtggtc cagatgacca aattggctac
28381 taccgaagag ctacccgacg agttcgtggt ggtgacggca aaatgaaaga gctcagcccc
28441 agatggtact tctattacct aggaactggc ccagaagctt cacttcccta cggcgctaac
28501 aaagaaggca tcgtatgggt tgcaactgag ggagccttga atacacccaa agaccacatt
28561 ggcacccgca atcctaataa caatgctgcc accgtgctac aacttcctca aggaacaaca
28621 ttgccaaaag gcttctacgc agagggaagc agaggcggca gtcaagcctc ttctcgctcc
28681 tcatcacgta gtcgcggtaa ttcaagaaat tcaactcctg gcagcagtag gggaaattct
28741 cctgctcgaa tggctagcgg aggtggtgaa actgccctcg cgctattgct gctagacaga
28801 ttgaaccagc ttgagagcaa agtttctggt aaaggccaac aacaacaagg ccaaactgtc
28861 actaagaaat ctgctgctga ggcatctaaa aagcctcgcc aaaaacgtac tgccacaaaa
28921 cagtacaacg tcactcaagc atttgggaga cgtggtccag aacaaaccca aggaaatttc
28981 ggggaccaag acctaatcag acaaggaact gattacaaac attggccgca aattgcacaa
29041 tttgctccaa gtgcctctgc attctttgga atgtcacgca ttggcatgga agtcacacct
29101 tcgggaacat ggctgactta tcatggagcc attaaattgg atgacaaaga tccacaattc
29161 aaagacaacg tcatactgct gaacaagcac attgacgcat acaaaacatt cccaccaaca
29221 gagcctaaaa aggacaaaaa gaaaaagact gatgaagctc agcctttgcc gcagagacaa
29281 aagaagcagc ccactgtgac tcttcttcct gcggctgaca tggatgattt ctccagacaa
29341 cttcaaaatt ccatgagtgg agcttctgct gattcaactc aggcataaac actcatgatg
29401 accacacaag gcagatgggc tatgtaaacg ttttcgcaat tccgtttacg atacatagtc
29461 tactcttgtg cagaatgaat tctcgtaact aaacagcaca agtaggttta gttaacttta
29521 atctcacata gcaatcttta atcaatgtgt aacattaggg aggacttgaa agagccacca
29581 cattttcatc gaggccacgc ggagtacgat cgagggtaca gtgaataatg ctagggagag
29641 ctgcctatat ggaagagccc taatgtgtaa aattaatttt agtagtgcta tccccatgtg
29701 attttaatag cttcttagga gaatgacaaa aaaaaaaaaa aaaaaaaaaa a

FIGURE 9A

```
   1 ctacccagga aaagccaacc aacctcgatc tcttgtagat ctgttctcta aacgaacttt
  61 aaaatctgtg tagctgtcgc tcggctgcat gcctagtgca cctacgcagt ataaacaata
 121 ataaatttta ctgtcgttga caagaaacga gtaactcgtc cctcttctgc agactgctta
 181 cggtttcgtc cgtgttgcag tcgatcatca gcatacctag gtttcgtccg ggtgtgaccg
 241 aaaggtaaga tggagagcct tgttcttggt gtcaacgaga aaacacacgt ccaactcagt
 301 ttgcctgtcc ttcaggttag agacgtgcta gtgcgtggct tcggggactc tgtggaagag
 361 gccctatcgg aggcacgtga acacctcaaa aatggcactt gtggtctagt agagctggaa
 421 aaaggcgtac tgccccagct tgaacagccc tatgtgttca ttaaacgttc tgatgcctta
 481 agcaccaatc acggccacaa ggtcgttgag ctggttgcag aaatggacgg cattcagtac
 541 ggtcgtagcg gtataacact gggagtactc gtgccacatg tgggcgaaac cccaattgca
 601 taccgcaatg ttcttcttcg taagaacggt aataagggag ccggtggtca tagctatggc
 661 atcgatctaa agtcttatga cttaggtgac gagcttggca ctgatcccat tgaagattat
 721 gaacaaaact ggaacactaa gcatggcagt ggtgcactcc gtgaactcac tcgtgagctc
 781 aatggaggtg cagtcactcg ctatgtcgac aacaatttct gtggcccaga tgggtaccct
 841 cttgattgca tcaaagattt tctcgcacgc gcgggcaagt caatgtgcac tctttccgaa
 901 caacttgatt acatcgagtc gaagagaggt gtctactgct gccgtgacca tgagcatgaa
 961 attgcctggt tcactgagcg ctctgataag agctacgagc accagacacc cttcgaaatt
1021 aagagtgcca agaaatttga cactttcaaa ggggaatgcc caaagtttgt gtttcctctt
1081 aactcaaaag tcaaagtcat tcaaccacgt gttgaaaaga aaaagactga gggtttcatg
1141 gggcgtatac gctctgtgta ccctgttgca tctccacagg agtgtaacaa tatgcacttg
1201 tctaccttga tgaaatgtaa tcattgcgat gaagtttcat ggcagacgtg cgactttctg
1261 aaagccactt gtgaacattg tggcactgaa aatttagtta ttgaaggacc tactacatgt
1321 gggtacctac ctactaatgc tgtagtgaaa atgccatgtc ctgcctgtca agacccagag
1381 attggacctg agcatagtgt tgcagattat cacaaccact caaacattga aactcgactc
1441 cgcaagggag gtaggactag atgttttgga ggctgtgtgt ttgcctatgt tggctgctat
1501 aataagcgtg cctactgggt tcctcgtgct agtgctgata ttggctcagg ccatactggc
1561 attactggtg acaatgtgga gaccttgaat gaggatctcc ttgagatact gagtcgtgaa
1621 cgtgttaaca ttaacattgt tggcgatttt catttgaatg aagaggttgc catcattttg
1681 gcatctttct ctgcttctac aagtgccttt attgacacta taaagagtct tgattacaag
1741 tctttcaaaa ccattgttga gtcctgcggt aactataaag ttaccaaggg aaagcccgta
1801 aaaggtgctt ggaacattgg acaacagaga tcagttttaa caccactgtg tggtttttccc
1861 tcacaggctg ctggtgttat cagatcaatt tttgcgcgca cacttgatgc agcaaaccac
1921 tcaattcctg atttgcaaag agcagctgtc accatacttg atggtatttc tgaacagtca
1981 ttacgtcttg tcgacgccat ggtttatact tcagacctgc tcaccaacag tgtcattatt
2041 atggcatatg taactggtgg tcttgtacaa cagacttctc agtggttgtc taatcttttg
2101 ggcactactg ttgaaaaact caggcctatc tttgaatgga ttgaggcgaa acttagtgca
2161 ggagttgaat ttctcaagga tgcttgggag attctcaaat ttctcattac aggtgttttt
2221 gacatcgtca agggtcaaat acaggttgct tcagataaca tcaaggattg tgtaaaatgc
2281 ttcattgatg ttgttaacaa ggcactcgaa atgtgcattg atcaagtcac tatcgctggc
2341 gcaaagttgc gatcactcaa cttaggtgaa gtcttcatcg ctcaaagcaa gggactttac
2401 cgtcagtgta tacgtggcaa ggagcagctg caactactca tgcctcttaa ggcaccaaaa
2461 gaagtaacct ttcttgaagg tgattcacat gacacagtac ttacctctga ggaggttgtt
2521 ctcaagaacg gtgaactcga agcactcgag acgcccgttg atagcttcac aaatggagct
2581 atcgttggca caccagtctg tgtaaatggc ctcatgctct tagagattaa ggacaaagaa
2641 caatactgcg cattgtctcc tggtttactg gctacaaaca atgtctttcg cttaaaaggg
2701 ggtgcaccaa ttaaaggtgt aacctttgga gaagatactg tttgggaagt tcaaggttac
2761 aagaatgtga gaatcacatt tgagcttgat gaacgtgttg acaaagtgct taatgaaaag
2821 tgctctgtct acactgttga atccggtacc gaagttactg agtttgcatg tgttgtagca
2881 gaggctgttg tgaagacttt acaaccagtt tctgatctcc ttaccaacat gggtattgat
2941 cttgatgagt ggagtgtagc tacattctac ttatttgatg atgctggtga agaaaacttt
3001 tcatcacgta tgtattgttc cttttaccct ccagatgagg aagaagagga cgatgcagag
3061 tgtgaggaag aagaaattga tgaaacctgt gaacatgagt acggtacaga ggatgattat
3121 caaggtctcc ctctggaatt tggtgcctca gctgaaacag ttcgagttga ggaagaagaa
3181 gaggaagact ggctggatga tactactgag caatcagaga ttgagccaga accagaacct
3241 acacctgaag aaccagttaa tcagtttact ggttatttaa aacttactga caatgttgcc
3301 attaaatgtg ttgacatcgt taaggaggca caaagtgcta atcctatggt gattgtaaat
3361 gctgctaaca tacacctgaa acatggtggt ggtgtagcag gtgcactcaa caaggcaacc
3421 aatggtgcca tgcaaaagga gagtgatgat tacattaagc taaatggccc tcttacagta
3481 ggagggtctt gtttgctttc tggacataat cttgctaaga agtgtctgca tgttgttgga
3541 cctaacctaa atgcaggtga ggacatccag cttcttaagg cagcatatga aaatttcaat
3601 tcacaggaca tcttacttgc accattgttg tcagcaggca tatttggtgc taaaccactt
```

FIGURE 9B

```
3661 cagtctttac aagtgtgcgt gcagacggtt cgtacacagg tttatattgc agtcaatgac
3721 aaagctcttt atgagcaggt tgtcatggat tatcttgata acctgaagcc tagagtggaa
3781 gcacctaaac aagaggagcc accaaacaca gaagattcca aaactgagga gaaatctgtc
3841 gtacagaagc ctgtcgatgt gaagccaaaa attaaggcct gcattgatga ggttaccaca
3901 acactggaag aaactaagtt tcttaccaat aagttactct tgtttgctga tatcaatggt
3961 aagctttacc atgattctca gaacatgctt agaggtgaag atatgtcttt ccttgagaag
4021 gatgcacctt acatggtagg tgatgttatc actagtggtg atatcacttg tgttgtaata
4081 ccctccaaaa aggctggtgg cactactgag atgctctcaa gagctttgaa gaaagtgcca
4141 gttgatgagt atataaccac gtaccctgga caaggatgtg ctggttatac acttgaggaa
4201 gctaagactg ctcttaagaa atgcaaatct gcattttatg tactaccttc agaagcacct
4261 aatgctaagg aagagattct aggaactgta tcctggaatt tgagagaaat gcttgctcat
4321 gctgaagaga caagaaaatt aatgcctata tgcatggatg ttagagccat aatggcaacc
4381 atccaacgta agtataaagg aattaaaatt caagagggca tcgttgacta tggtgtccga
4441 ttcttctttt atactagtaa agagcctgta gcttctatta ttacgaagct gaactctcta
4501 aatgagccgc ttgtcacaat gccaattggt tatgtgacac atggttttaa tcttgaagag
4561 gctgcgcgct gtatgcgttc tcttaaagct cctgccgtag tgtcagtatc atcaccagat
4621 gctgttacta catataatgg atacctcact tcgtcatcaa agacatctga ggagcacttt
4681 gtagaaacag tttctttggc tggctcttac agagattggt cctattcagg acagcgtaca
4741 gagttaggtg ttgaatttct taagcgtggt gacaaaattg tgtaccacac tctggagagc
4801 cccgtcgagt ttcatcttga cggtgaggtt ctttcacttg acaaactaaa gagtctctta
4861 tccctgcggg aggttaagac tataaaagtg ttcacaactg tggacaacac taatctccac
4921 acacagcttg tggatatgtc tatgacatat ggacagcagt ttggtccaac atacttggat
4981 ggtgctgatg ttacaaaaat taaacctcat gtaaatcatg agggtaagac tttctttgta
5041 ctacctagtg atgacacact acgtagtgaa gctttcgagt actaccatac tcttgatgag
5101 agttttcttg gtaggtacat gtctgcttta aaccacacaa agaaatggaa atttcctcaa
5161 gttggtggtt taacttcaat taaatgggct gataacaatt gttatttgtc tagtgtttta
5221 ttagcacttc aacagcttga agtcaaattc aatgcaccag cacttcaaga ggcttattat
5281 agagcccgtg ctggtgatgc tgctaacttt tgtgcactca tactcgctta cagtaataaa
5341 actgttggcg agcttggtga tgtcagagaa actatgaccc atcttctaca gcatgctaat
5401 ttggaatctg caaagcgagt tcttaatgtg gtgtgtaaac attgtggtca gaaaactact
5461 accttaacgg gtgtagaagc tgtgatgtat atgggtactc tatcttatga taatcttaag
5521 acaggtgttt ccattccatg tgtgtgtggt cgtgatgcta cacaatatct agtacaacaa
5581 gagtcttctt ttgttatgat gtctgcacca cctgctgagt ataaattaca gcaaggtaca
5641 ttcttatgtg cgaatgagta cactggtaac tatcagtgtg gtcattacac tcatataact
5701 gctaaggaga ccctctatcg tattgacgga gctcacctta caaagatgtc agagtacaaa
5761 ggaccagtga ctgatgtttt ctacaaggaa acatcttaca ctacaaccat caagcctgtg
5821 tcgtataaac tcgatggagt tacttacaca gagattgaac caaaattgga tgggtattat
5881 aaaaaggata atgcttacta tacagagcag cctatagacc ttgtaccaac tcaaccatta
5941 ccaaatgcga gttttgataa tttcaaactc acatgttcta acacaaaatt tgctgatgat
6001 ttaaatcaaa tgacaggctt cacaaagcca gcttcacgag agctatctgt cacattcttc
6061 ccagacttga atggcgatgt agtggctatt gactatagac actattcagc gagtttcaag
6121 aaaggtgcta aattactgca taagccaatt gtttggcaca ttaaccaggc tacaaccaag
6181 acaacgttca aaccaaacac ttggtgttta cgttgtcttt ggagtacaaa gccagtagat
6241 acttcaaatt catttgaagt tctggcagta gaagacacac aaggaatgga caatcttgct
6301 tgtgaaagtc aacaacccac ctctgaagaa gtagtggaaa atcctaccat acagaaggaa
6361 gtcatagagt gtgacgtgaa aactaccgaa gttgtaggca atgtcatact taaaccatca
6421 gatgaaggtg ttaaagtaac acaagagtta ggtcatgagg atcttatggc tgcttatgtg
6481 gaaaacacaa gcattaccat taagaaacct aatgagcttt cactagcctt aggtttaaaa
6541 acaattgcca ctcatggtat tgctgcaatt aatagtgttc cttggagtaa aattttggct
6601 tatgtcaaac cattcttagg acaagcagca attacaacat caaattgcgc taagagatta
6661 gcacaacgtg tgtttaacaa ttatatgcct tatgtgttta cattattgtt ccaattgtgt
6721 acttttacta aaagtaccaa ttctagaatt agagcttcac tacctacaac tattgctaaa
6781 aatagtgtta agagtgttgc taaattatgt ttggatgccg gcattaatta tgtgaagtca
6841 cccaaatttt ctaaattgtt cacaatcgct atgtggctat tgttgttaag tatttgctta
6901 ggttctctaa tctgtgtaac tgctgctttt ggtgtactct tatctaattt tggtgctcct
6961 tcttattgta atggcgttag agaattgtat cttaattcgt ctaacgttac tactatggat
7021 ttctgtgaag gttcttttcc ttgcagcatt tgtttaagtg gattagactc ccttgattct
7081 tatccagctc ttgaaaccat tcaggtgacg atttcatcgt acaagctaga cttgacaatt
7141 ttaggtctgg ccgctgagtg ggttttggca tatatgttgt tcacaaaatt cttttattta
7201 ttaggtcttt cagctataat gcaggtgttc tttggctatt ttgctagtca tttcatcagc
7261 aattcttggc tcatgtggtt tatcattagt attgtacaaa tggcacccgt ttctgcaatg
7321 gttaggatgt acatcttctt tgcttctttc tactacatat ggaagagcta tgttcatatc
```

FIGURE 9C

```
 7381 atggatggtt gcacctcttc gacttgcatg atgtgctata agcgcaatcg tgccacacgc
 7441 gttgagtgta caactattgt taatggcatg aagagatctt tctatgtcta tgcaaatgga
 7501 ggccgtggct tctgcaagac tcacaattgg aattgtctca attgtgacac attttgcact
 7561 ggtagtacat tcattagtga tgaagttgct cgtgatttgt cactccagtt taaaagacca
 7621 atcaacccta ctgaccagtc atcgtatatt gttgatagtg ttgctgtgaa aaatggcgcg
 7681 cttcacctct actttgacaa ggctggtcaa aagacctatg agagacatcc tctctcccat
 7741 tttgtcaatt tagacaattt gagagctaac aacactaaag gttcactgcc tattaatgtc
 7801 atagtttttg atggcaagtc caaatgcgac gagtctgctt ctaagtctgc ttctgtgtac
 7861 tacagtcagc tgatgtgcca acctattctg ttgcttgacc aagctcttgt atcagacgtt
 7921 ggagatagta ctgaagtttc cgttaagatg tttgatgctt atgtcgacac cttttcagca
 7981 acttttagtg ttcctatgga aaaacttaag gcacttgttg ctacagctca cagcgagtta
 8041 gcaaagggtg tagctttaga tggtgtcctt tctacattcg tgtcagctgc ccgacaaggt
 8101 gttgttgata ccgatgttga cacaaaggat gttattgaat gtctcaaact ttcacatcac
 8161 tctgacttag aagtgacagg tgacagttgt aacaatttca tgctcaccta taataaggtt
 8221 gaaaacatga cgcccagaga tcttggcgca tgtattgact gtaatgcaag gcatatcaat
 8281 gcccaagtag caaaaagtca caatgtttca ctcatctgga atgtaaaaga ctacatgtct
 8341 ttatctgaac agctgcgtaa acaaattcgt agtgctgcca agaagaacaa cataccttttt
 8401 agactaactt gtgctacaac tagacaggtt gtcaatgtca taactactaa aatctcactc
 8461 aagggtggta agattgttag tacttgtttt aaacttatgc ttaaggccac attattgtgc
 8521 gttcttgctg cattggtttg ttatatcgtt atgccagtac atacattgtc aatccatgat
 8581 ggttacacaa atgaaatcat tggttacaaa gccattcagg atggtgtcac tcgtgacatc
 8641 atttctactg atgattgttt tgcaaataaa catgctggtt ttgacgcatg gtttagccag
 8701 cgtggtggtt catacaaaaa tgacaaaagc tgccctgtag tagctgctat cattacaaga
 8761 gagattggtt tcatagtgcc tggcttaccg ggtactgtgc tgagagcaat caatggtgac
 8821 ttcttgcatt ttctacctcg tgtttttagt gctgttggca acatttgcta cacaccttcc
 8881 aaactcattg agtatagtga ttttgctacc tctgcttgcg ttcttgctgc tgagtgtaca
 8941 atttttaagg atgctatggg caaacctgtg ccatattgtt atgacactaa tttgctagag
 9001 ggttctattt cttatagtga gcttcgtcca gacactcgtt atgtgcttat ggatggttcc
 9061 atcatacagt ttcctaacac ttacctggag ggttctgtta gagtagtaac aacttttgat
 9121 gctgagtact gtagacatgg tacatgcgaa aggtcagaag taggtatttg cctatctacc
 9181 agtggtagat gggttcttaa taatgagcat tacagagctc tatcaggagt tttctgtggt
 9241 gttgatgcga tgaatctcat agctaacatc tttactcctc ttgtgcaacc tgtgggtgct
 9301 ttagatgtgt ctgcttcagt agtggctggt ggtattattg ccatattggt gacttgtgct
 9361 gcctactact ttatgaaatt cagacgtgct tttggtgagt acaaccatgt tgttgctgct
 9421 aatgcacttt tgtttttgat gtctttcact atactctgtc tggcaccagc ttacagcttt
 9481 ctgccgggag tctactcagt cttttacttg tacttgacat tctatttcac caatgatgtt
 9541 tcattcttgg ctcaccttca atggtttgcc atgttttctc ctattgtgcc tttttggata
 9601 acagcaatct atgtattctg tatttctctg aagcactgcc attggttctt taacaactat
 9661 cttaggaaaa gagtcatgtt taatggagtt acatttagta ccttcgagga ggctgctttg
 9721 tgtacctttt tgctcaacaa ggaaatgtac ctaaaattgc gtagcgagac actgttgcca
 9781 cttacacagt ataacaggta tcttgctcta tataacaagt acaagtattt cagtggagcc
 9841 ttagatacta ccagctatcg tgaagcagct tgctgccact tagcaaaggc tctaaatgac
 9901 tttagcaact caggtgctga tgttctctac caaccaccac agacatcaat cacttctgct
 9961 gttctgcaga gtggttttag gaaaatggca ttcccgtcag gcaaagttga agggtgcatg
10021 gtacaagtaa cctgtggaac tacaactctt aatggattgt ggttggatga cacagtatac
10081 tgtccaagac atgtcatttg cacagcagaa gacatgctta atcctaacta tgaagatctg
10141 ctcattcgca aatccaacca tagctttctt gttcaggctg gcaatgttca acttcgtgtt
10201 attggccatt ctatgcaaaa ttgtctgctt aggcttaaag ttgatacttc taaccctaag
10261 acacccaagt ataaatttgt ccgtatccaa cctggtcaaa cattttcagt tctagcatgc
10321 tacaatggtt caccatctgg tgtttatcag tgtgccatga gacctaatca taccattaaa
10381 ggttctttcc ttaatggatc atgtggtagt gttggtttta acattgatta tgattgcgtg
10441 tctttctgct atatgcatca tatggagctt ccaacaggag tacacgctgg tactgactta
10501 gaaggtaaat tctatggtcc atttgttgac agacaaactg cacaggctgc aggtacagac
10561 acaaccataa cattaaatgt tttggcatgg ctgtatgctg ctgttatcaa tggtgatagg
10621 tggtttctta atagattcac cactactttg aatgacttta accttgtggc aatgaagtac
10681 aactatgaac ctttgacaca agatcatgtt gacatattgg gacctctttc tgctcaaaca
10741 ggaattgccg tcttagatat gtgtgctgct ttgaaagagc tgctgcagaa tggtatgaat
10801 ggtcgtacta tccttggtag cactatttta gaagatgagt ttacaccatt tgatgttgtt
10861 agacaatgct ctggtgttac cttccaaggt aagttcaaga aaattgttaa gggcactcat
10921 cattggatgc ttttaacttt cttgacatca ctattgattc ttgttcaaag tacacagtgg
10981 tcactgtttt tctttgttta cgagaatgct ttcttgccat ttactcttgg tattatggca
11041 attgctgcat gtgctatgct gcttgttaag cataagcacg cattcttgtg cttgtttctg
```

FIGURE 9D

```
11101 ttaccttctc ttgcaacagt tgcttacttt aatatggtct acatgcctgc tagctgggtg
11161 atgcgtatca tgacatggct tgaattggct gacactagct tgtctggtta taggcttaag
11221 gattgtgtta tgtatgcttc agctttagtt ttgcttattc tcatgacagc tcgcactgtt
11281 tatgatgatg ctgctagacg tgtttggaca ctgatgaatg tcattacact tgtttacaaa
11341 gtctactatg gtaatgcttt agatcaagct atttccatgt gggccttagt tatttctgta
11401 acctctaact attctggtgt cgttacgact atcatgtttt tagctagagc tatagtgttt
11461 gtgtgtgttg agtattaccc attgttattt attactggca acaccttaca gtgtatcatg
11521 cttgtttatt gtttcttagg ctattgttgc tgctgctact ttggcctttt ctgtttactc
11581 aaccgttact tcaggcttac tcttggtgtt tatgactact tggtctctac acaagaattt
11641 aggtatatga actcccaggg gcttttgcct cctaagagta gtattgatgc tttcaagctt
11701 aacattaagt tgttgggtat tggaggtaaa ccatgtatca aggttgctac tgtacagtct
11761 aaaatgtctg acgtaaagtg cacatctgtg gtactgctct cggttcttca acaacttaga
11821 gtagagtcat cttctaaatt gtgggcacaa tgtgtacaac tccacaatga tattcttctt
11881 gcaaaagaca caactgaagc tttcgagaag atggtttctc ttttgtctgt tttgctatcc
11941 atgcagggtg ctgtagacat taataggttg tgcgaggaaa tgctcgataa ccgtgctact
12001 cttcaggcta ttgcttcaga atttagttct ttaccatcat atgccgctta tgccactgcc
12061 caggaggcct atgagcaggc tgtagctaat ggtgattctg aagtcgttct caaaaagtta
12121 aagaaatctt tgaatgtggc taaatctgag tttgaccgtg atgctgccat gcaacgcaag
12181 ttggaaaaga tggcagatca ggctatgacc caaatgtaca aacaggcaag atctgaggac
12241 aagagggcaa aagtaactag tgctatgcaa acaatgctct tcactatgct taggaagctt
12301 gataatgatg cacttaacaa cattatcaac aatgcgcgtg atggttgtgt tccactcaac
12361 atcataccat tgactacagc agccaaactc atggttgttg tccctgatta tggtacctac
12421 aagaacactt gtgatggtaa cacctttaca tatgcatctg cactctggga aatccagcaa
12481 gttgttgatg cggatagcaa gattgttcaa cttagtgaaa ttaacatgga caattcacca
12541 aatttggctt ggcctcttat tgttacagct ctaagagcca actcagctgt taaactacag
12601 aataatgaac tgagtccagt agcactacga cagatgtcct gtgcggctgg taccacacaa
12661 acagcttgta ctgatgacaa tgcacttgcc tactataaca attcgaaggg aggtaggttt
12721 gtgctggcat tactatcaga ccaccaagat ctcaaatggg ctagattccc taagagtgat
12781 ggtacaggta caatttacac agaactggaa ccaccttgta ggtttgttac agacacacca
12841 aaagggccta aagtgaaata cttgtacttc atcaaaggct taaacaacct aaatagaggt
12901 atggtgctgg gcagtttagc tgctacagta cgtcttcagg ctggaaatgc tacagaagta
12961 cctgccaatt caactgtgct ttccttctgt gcttttgcag tagaccctgc taaagcatat
13021 aaggattacc tagcaagtgg aggacaacca atcaccaact gtgtgaagat gttgtgtaca
13081 cacactggta caggacaggc aattactgta acaccagaag ctaacatgga ccaagagtcc
13141 tttggtggtg cttcatgttg tctgtattgt agatgccaca ttgaccatcc aaatcctaaa
13201 ggattctgtg acttgaaagg taagtacgtc caaataccta ccacttgtgc taatgaccca
13261 gtgggtttta cacttagaaa cacagtctgt accgtctgcg gaatgtggaa aggttatggc
13321 tgtagttgtg accaactccg cgaacccttg atgcagtctg cggatgcatc aacgttttta
13381 aacgggtttg cggtgtaagt gcagcccgtc ttacaccgtg cggcacaggc actagtactg
13441 atgtcgtcta cagggctttt gatatttaca acgaaaaagt tgctggtttt gcaaagttcc
13501 taaaaactaa ttgctgtcgc ttccaggaga aggatgagga aggcaattta ttagactctt
13561 actttgtagt taagaggcat actatgtcta actaccaaca tgaagagact atttataact
13621 tggttaaaga ttgtccagcg gttgctgtcc atgacttttt caagtttaga gtagatggtg
13681 acatggtacc acatatatca cgtcagcgtc taactaaata cacaatggct gatttagtct
13741 atgctctacg tcattttgat gagggtaatt gtgatacatt aaaagaaata ctcgtcacat
13801 acaattgctg tgatgatgat tatttcaata agaaggattg gtatgacttc gtagagaatc
13861 ctgacatctt acgcgtatat gctaacttag gtgagcgtgt acgccaatca ttattaaaga
13921 ctgtacaatt ctgcgatgct atgcgtgatg caggcattgt aggcgtactg acattagata
13981 atcaggatct taatgggaac tggtacgatt tcggtgattt cgtacaagta gcaccaggct
14041 gcggagttcc tattgtggat tcatattact cattgctgat gcccatcctc actttgacta
14101 gggcattggc tgctgagtcc catatggatg ctgatctcgc aaaaccactt attaagtggg
14161 atttgctgaa atatgatttt acggaagaga gactttgtct cttcgaccgt tattttaaat
14221 attgggacca gacataccat cccaattgta ttaactgttt ggatgatagg tgtatccttc
14281 attgtgcaaa ctttaatgtg ttattttcta ctgtgtttcc acctacaagt tttggaccac
14341 tagtaagaaa aatatttgta gatggtgttc cttttgttgt ttcaactgga taccatttc
14401 gtgagttagg agtcgtacat aatcaggatg taaacttaca tagctcgcgt ctcagtttca
14461 aggaactttt agtgtatgct gctgatccag ctatgcatgc agcttctggc aatttattgc
14521 tagataaacg cactacatgc ttttcagtag ctgcactaac aaacaatgtt gcttttcaaa
14581 ctgtcaaacc cggtaatttt aataaagact tttatgactt tgctgtgtct aaaggtttct
14641 ttaaggaagg aagttctgtt gaactaaaac acttcttctt tgctcaggat ggcaacgctg
14701 ctatcagtga ttatgactat tatcgttata atctgccaac aatgtgtgat atcagacaac
14761 tcctattcgt agttgaagtt gttgataaat actttgattg ttacgatggt ggctgtatta
```

FIGURE 9E

```
14821 atgccaacca agtaatcgtt aacaatctgg ataaatcagc tggtttccca tttaataaat
14881 ggggtaaggc tagactttat tatgactcaa tgagttatga ggatcaagat gcacttttcg
14941 cgtatactaa gcgtaatgtc atccctacta taactcaaat gaatcttaag tatgccatta
15001 gtgcaaagaa tagagctcgc accgtagctg gtgtctctat ctgtagtact atgacaaata
15061 gacagtttca tcagaaatta ttgaagtcaa tagccgccac tagaggagct actgtggtaa
15121 ttggaacaag caagttttac ggtggctggc ataatatgtt aaaaactgtt tacagtgatg
15181 tagaaactcc acaccttatg ggttgggatt atccaaaatg tgacagagcc atgcctaaca
15241 tgcttaggat aatggcctct cttgttcttg ctcgcaaaca taacacttgc tgtaacttat
15301 cacaccgttt ctacaggtta gctaacgagt gtgcgcaagt attaagtgag atggtcatgt
15361 gtggcggctc actatatgtt aaaccaggtg gaacatcatc cggtgatgct acaactgctt
15421 atgctaatag tgtctttaac atttgtcaag ctgttacagc caatgtaaat gcacttcttt
15481 caactgatgg taataagata gctgacaagt atgtccgcaa tctacaacac aggctctatg
15541 agtgtctcta tagaaatagg gatgttgatc atgaattcgt ggatgagttt tacgcttacc
15601 tgcgtaaaca tttctccatg atgattcttt ctgatgatgc cgttgtgtgc tataacagta
15661 actatgcggc tcaaggttta gtagctagca ttaagaactt taaggcagtt ctttattatc
15721 aaaataatgt gttcatgtct gaggcaaaat gttggactga gactgacctt actaaaggac
15781 ctcacgaatt ttgctcacag catacaatgc tagttaaaca aggagatgat tacgtgtacc
15841 tgccttaccc agatccatca agaatattag gcgcaggctg ttttgtcgat gatattgtca
15901 aaacagatgg tacacttatg attgaaaggt tcgtgtcact ggctattgat gcttacccac
15961 ttacaaaaca tcctaatcag gagtatgctg atgtctttca cttgtattta caatacatta
16021 gaaagttaca tgatgagctt actggccaca tgttggacat gtattccgta atgctaacta
16081 atgataacac ctcacggtac tgggaacctg agttttatga ggctatgtac acaccacata
16141 cagtcttgca ggctgtaggt gcttgtgtat tgtgcaattc acagacttca cttcgttgcg
16201 gtgcctgtat taggagacca ttcctatgtt gcaagtgctg ctatgaccat gtcatttcaa
16261 catcacacaa attagtgttg tctgttaatc cctatgtttg caatgcccca ggttgtgatg
16321 tcactgatgt gacacaactg tatctaggag gtatgagcta ttattgcaag tcacataagc
16381 ctcccattag ttttccatta tgtgctaatg gtcaggtttt tggtttatac aaaaacacat
16441 gtgtaggcag tgacaatgtc actgacttca atgcgatagc aacatgtgat tggactaatg
16501 ctggcgatta catacttgcc aacacttgta ctgagagact caagcttttc gcagcagaaa
16561 cgctcaaagc cactgaggaa acatttaagc tgtcatatgg tattgccact gtacgcgaag
16621 tactctctga cagagaattg catctttcat gggaggttgg aaaacctaga ccaccattga
16681 acagaaacta tgtctttact ggttaccgtg taactaaaaa tagtaaagta cagattggag
16741 agtacacctt tgaaaaaggt gactatggtg atgctgttgt gtacagaggt actacgacat
16801 acaagttgaa tgttggtgat tactttgtgt tgacatctca cactgtaatg ccacttagtg
16861 cacctactct agtgccacaa gagcactatg tgagaattac tggcttgtac ccaacactca
16921 acatctcaga tgagttttct agcaatgttg caaattatca aaaggtcggc atgcaaaagt
16981 actctacact ccaaggacca cctggtactg gtaagagtca ttttgccatc ggacttgctc
17041 tctattaccc atctgctcgc atagtgtata cggcatgctc tcatgcagct gttgatgccc
17101 tatgtgaaaa ggcattaaaa tatttgccca tagataaatg tagtagaatc atacctgcgc
17161 gtgcgcgcgt agagtgtttt gataaattca aagtgaattc aacactagaa cagtatgttt
17221 tctgcactgt aaatgcattg ccagaaacaa ctgctgacat tgtagtcttt gatgaaatct
17281 ctatggctac taattatgac ttgagtgttg tcaatgctag acttcgtgca aaacactacg
17341 tctatattgg cgatcctgct caattaccag ccccccgcac attgctgact aaaggcacac
17401 tagaaccaga atattttaat tcagtgtgca gacttatgaa aacaataggt ccagacatgt
17461 tccttggaac ttgtcgccgt tgtcctgctg aaattgttga cactgtgagt gctttagttt
17521 atgacaataa gctaaaagca cacaaggaga agtcagctca atgcttcaaa atgttctaca
17581 aaggtgttat tacacatgat gtttcatctg caatcaacag acctcaaata ggcgttgtaa
17641 gagaatttct tacacgcaat cctgcttgga gaaaagctgt ttttatctca ccttataatt
17701 cacagaacgc tgtagcttca aaaatcttag gattgcctac gcagactgtt gattcatcac
17761 agggttctga atatgactat gtcatattca cacaaactac tgaaacagca cactcttgta
17821 atgtcaaccg tttcaatgtg gctatcacaa gggcaaaaat tggcattttg tgcataatgt
17881 ctgatagaga tctttatgac aaactgcaat ttacaagtct agaaatacca cgtcgcaatg
17941 tggctacatt acaagcagaa aatgtaactg gacttttaa ggactgtagt aagatcatta
18001 ctggtcttca tcctacacag gcacctacac acctcagcgt tgatataaag ttcaagactg
18061 aaggattatg tgttgacata ccaggcatac caaaggacat gacctaccgt agactcatct
18121 ctatgatggg tttcaaaatg aattaccaag tcaatggtta ccctaatatg tttatcaccc
18181 gcgaagaagc tattcgtcac gttcgtgcgt ggattggctt tgatgtagag ggctgtcatg
18241 caactagaga tgctgtgggt actaacctac ctctccagct aggattttct acaggtgtta
18301 acttagtagc tgtaccgact ggttatgttg acactgaaaa taacacagaa ttcaccagag
18361 ttaatgcaaa acctccacca ggtgaccagt ttaaacatct tataccactc atgtataaag
18421 gcttgccctg gaatgtagtg cgtattaaga tagtacaaat gctcagtgat acactgaaag
18481 gattgtcaga cagagtcgtg ttcgtccttt gggcgcatgg ctttgagctt acatcaatga
```

FIGURE 9F

```
18541 agtactttgt caagattgga cctgaaagaa cgtgttgtct gtgtgacaaa cgtgcaactt
18601 gcttttctac ttcatcagat acttatgcct gctggaatca ttctgtgggt tttgactatg
18661 tctataaccc atttatgatt gatgttcagc agtggggctt tacgggtaac cttcagagta
18721 accatgacca acattgccag gtacatggaa atgcacatgt ggctagttgt gatgctatca
18781 tgactagatg tttagcagtc catgagtgct ttgttaagcg cgttgattgg tctgttgaat
18841 accctattat aggagatgaa ctgagggtta attctgcttg cagaaaagta caacacatgg
18901 ttgtgaagtc tgcattgctt gctgataagt ttccagttct tcatgacatt ggaaatccaa
18961 aggctatcaa gtgtgtgcct caggctgaag tagaatggaa gttctacgat gctcagccat
19021 gtagtgacaa agcttacaaa atagaggagc tcttctattc ttatgctaca catcacgata
19081 aattcactga tggtgtttgt ttgttttgga attgtaacgt tgatcgttac ccagccaatg
19141 caattgtgtg taggtttgac acaagagtct tgtcaaactt gaacttacca ggctgtgatg
19201 gtggtagttt gtatgtgaat aagcatgcat tccacactcc agctttcgat aaaagtgcat
19261 ttactaattt aaagcaattg cctttctttt actattctga tagtccttgt gagtctcatg
19321 gcaaacaagt agtgtcggat attgattatg ttccactcaa atctgctacg tgtattacac
19381 gatgcaattt aggtggtgct gtttgcagac accatgcaaa tgagtaccga cagtacttgg
19441 atgcatataa tatgatgatt tctgctggat ttagcctatg gatttacaaa caatttgata
19501 cttataacct gtggaataca tttaccaggt tacagagttt agaaaatgtg gcttataatg
19561 ttgttaataa aggacacttt gatggacacg ccggcgaagc acctgtttcc atcattaata
19621 atgctgttta cacaaaggta gatggtattg atgtggagat ctttgaaaat aagacaacac
19681 ttcctgttaa tgttgcattt gagctttggg ctaagcgtaa cattaaacca gtgccagaga
19741 ttaagatact caataatttg ggtgttgata tcgctgctaa tactgtaatc tgggactaca
19801 aaagagaagc cccagcacat gtatctacaa taggtgtctg cacaatgact gacattgcca
19861 agaaacctac tgagagtgct tgttcttcac ttactgtctt gtttgatggt agagtggaag
19921 gacaggtaga cctttttaga aacgcccgta atggtgtttt aataacagaa ggttcagtca
19981 aaggtctaac accttcaaag ggaccagcac aagctagcgt caatggagtc acattaattg
20041 gagaatcagt aaaaacacag tttaactact ttaagaaagt agacggcatt attcaacagt
20101 tgcctgaaac ctactttact cagagcagag acttagagga ttttaagccc agatcacaaa
20161 tggaaactga ctttctcgag ctcgctatgg atgaattcat acagcgatat aagctcgagg
20221 gctatgcctt cgaacacatc gtttatggag atttcagtca tggacaactt ggcggtcttc
20281 atttaatgat aggcttagcc aagcgctcac aagattcacc acttaaatta gaggatttta
20341 tccctatgga cagcacagtg aaaaattact tcataacaga tgcgcaaaca ggttcatcaa
20401 aatgtgtgtg ttctgtgatt gatcttttac ttgatgactt tgtcgagata ataaagtcac
20461 aagatttgtc agtgatttca aaagtggtca aggttacaat tgactatgct gaaatttcat
20521 tcatgctttg gtgtaaggat ggacatgttg aaaccttcta cccaaaacta caagcaagtc
20581 aagcgtggca accaggtgtt gcgatgccta acttgtacaa gatgcaaaga atgcttcttg
20641 aaaagtgtga ccttcagaat tatggtgaaa atgctgttat accaaaagga ataatgatga
20701 atgtcgcaaa gtatactcaa ctgtgtcaat acttaaatac acttacttta gctgtaccct
20761 acaacatgag agttattcac tttggtgctg gctctgataa aggagttgca ccaggtacag
20821 ctgtgctcag acaatggttg ccaactggca cactacttgt cgattcagat cttaatgact
20881 tcgtctccga cgcagattct actttaattg gagactgtgc aacagtacat acggctaata
20941 aatgggacct tattattagc gatatgtatg accctaggac caaacatgtg acaaaagaga
21001 atgactctaa agaagggttt ttcacttatc tgtgtggatt tataaagcaa aaactagccc
21061 tgggtggttc tatagctgta aagataacag agcattcttg gaatgctgac ctttacaagc
21121 ttatgggcca tttctcatgg tggacagctt ttgttacaaa tgtaaatgca tcatcatcgg
21181 aagcattttt aattggggct aactatcttg gcaagccgaa ggaacaaatt gatggctata
21241 ccatgcatgc taactacatt ttctggagga acacaaatcc tatccagttg tcttcctatt
21301 cactctttga catgagcaaa tttcctctta aattaagagg aactgctgta atgtctctta
21361 aggagaatca aatcaatgat atgatttatt ctcttctgga aaaaggtagg cttatcatta
21421 gagaaaacaa cagagttgtg gtttcaagtg atattcttgt taacaactaa acgaacatgt
21481 ttattttctt attatttctt actctcacta gtggtagtga ccttgaccgg tgcaccactt
21541 ttgatgatgt tcaagctcct aattacactc aacatacttc atctatgagg ggggtttact
21601 atcctgatga aatttttaga tcagacactc tttatttaac tcaggattta tttcttccat
21661 tttattctaa tgttacaggg tttcatacta ttaatcatac gtttgacaac cctgtcatac
21721 cttttaagga tggtatttat tttgctgcca cagagaaatc aaatgttgtc cgtggttggg
21781 tttttggttc taccatgaac aacaagtcac agtcggtgat tattattaac aattctacta
21841 atgttgttat acgagcatgt aactttgaat tgtgtgacaa ccctttcttt gctgtttcta
21901 aacccatggg tacacagaca catactatga tattcgataa tgcatttaat tgcactttcg
21961 agtacatatc tgatgccttt tcgcttgatg tttcagaaaa gtcaggtaat tttaaacact
22021 tacgagagtt tgtgtttaaa aataaagatg ggtttctcta tgtttataag ggctatcaac
22081 ctatagatgt agttcgtgat ctaccttctg gttttaacac tttgaaacct atttttaagt
22141 tgcctcttgg tattaacatt acaaatttta gagccattct tacagccttt tcacctgctc
22201 aagacacttg gggcacgtca gctgcagcct attttgttgg ctatttaaag ccaactacat
```

FIGURE 9G

```
22261 ttatgctcaa gtatgatgaa aatggtacaa tcacagatgc tgttgattgt tctcaaaatc
22321 cacttgctga actcaaatgc tctgttaaga gctttgagat tgacaaagga atttaccaga
22381 cctctaattt cagggttgtt ccctcaggag atgttgtgag attccctaat attacaaact
22441 tgtgtccttt tggagaggtt tttaatgcta ctaaattccc ttctgtctat gcatgggaga
22501 gaaaaaaaat ttctaattgt gttgctgatt actctgtgct ctacaactca acattttttt
22561 caacctttaa gtgctatggc gtttctgcca ctaagttgaa tgatctttgc ttctccaatg
22621 tctatgcaga ttcttttgta gtcaagggag atgatgtaag acaaatagcg ccaggacaaa
22681 ctggtgttat tgctgattat aattataaat tgccagatga tttcatgggt tgtgtccttg
22741 cttggaatac taggaacatt gatgctactt caactggtaa ttataattat aaatataggt
22801 atcttagaca tggcaagctt aggccctttg agagagacat atctaatgtg cctttctccc
22861 ctgatggcaa accttgcacc ccacctgctc ttaattgtta ttggccatta aatgattatg
22921 gtttttacac cactactggc attggctacc aaccttacag agttgtagta ctttcttttg
22981 aacttttaaa tgcaccggcc acggtttgtg gaccaaaatt atccactgac cttattaaga
23041 accagtgtgt caattttaat tttaatggac tcactggtac tggtgtgtta actccttctt
23101 caaagagatt tcaaccattt caacaatttg gccgtgatgt ttctgatttc actgattccg
23161 ttcgagatcc taaaacatct gaaatattag acatttcacc ttgctctttt gggggtgtaa
23221 gtgtaattac acctggaaca aatgcttcat ctgaagttgc tgttctatat caagatgtta
23281 actgcactga tgtttctaca gcaattcatg cagatcaact cacaccagct tggcgcatat
23341 attctactgg aaacaatgta ttccagactc aagcaggctg tcttatagga gctgagcatg
23401 tcgacacttc ttatgagtgc gacattccta ttggagctgg catttgtgct agttaccata
23461 cagtttcttt attacgtagt actagccaaa aatctattgt ggcttatact atgtctttag
23521 gtgctgatag ttcaattgct tactctaata acaccattgc tatacctact aacttttcaa
23581 ttagcattac tacagaagta atgcctgttt ctatggctaa aacctccgta gattgtaata
23641 tgtacatctg cggagattct actgaatgtg ctaatttgct tctccaatat ggtagctttt
23701 gcacacaact aaatcgtgca ctctcaggta ttgctgctga acaggatcgc aacacacgtg
23761 aagtgttcgc tcaagtcaaa caaatgtaca aaaccccaac tttgaaatat tttggtggtt
23821 ttaatttttc acaaatatta cctgaccctc taaagccaac taagaggtct tttattgagg
23881 acttgctctt taataaggtg acactcgctg atgctggctt catgaagcaa tatggcgaat
23941 gcctaggtga tattaatgct agagatctca tttgtgcgca gaagttcaat ggacttacag
24001 tgttgccacc tctgctcact gatgatatga ttgctgccta cactgctgct ctagttagtg
24061 gtactgccac tgctggatgg acatttggtg ctggcgctgc tcttcaaata ccttttgcta
24121 tgcaaatggc atataggttc aatggcattg gagttaccca aaatgttctc tatgagaacc
24181 aaaaacaaat cgccaaccaa tttaacaagg cgattagtca aattcaagaa tcacttacaa
24241 caacatcaac tgcattgggc aagctgcaag acgttgttaa ccagaatgct caagcattaa
24301 acacacttgt taaacaactt agctctaatt ttggtgcaat ttcaagtgtg ctaaatgata
24361 tcctttcgcg acttgataaa gtcgaggcgg aggtacaaat tgacaggtta attacaggca
24421 gacttcaaag ccttcaaacc tatgtaacac aacaactaat cagggctgct gaaatcaggg
24481 cttctgctaa tcttgctgct actaaaatgt ctgagtgtgt tcttggacaa tcaaaaagag
24541 ttgacttttg tggaaagggc taccacctta tgtccttccc acaagcagcc ccgcatggtg
24601 ttgtcttcct acatgtcacg tatgtgccat cccaggagag gaacttcacc acagcgccag
24661 caatttgtca tgaaggcaaa gcatacttcc ctcgtgaagg tgtttttgtg tttaatggca
24721 cttcttggtt tattacacag aggaacttct tttctccaca aataattact acagacaata
24781 catttgtctc aggaaattgt gatgtcgtta ttggcatcat taacaacaca gtttatgatc
24841 ctctgcaacc tgagcttgac tcattcaaag aagagctgga caagtacttc aaaaatcata
24901 catcaccaga tgttgatctt ggcgacattt caggcattaa cgcttctgtc gtcaacattc
24961 aaaaagaaat tgaccgcctc aatgaggtcg ctaaaaattt aaatgaatca ctcattgacc
25021 ttcaagaatt gggaaaatat gagcaatata ttaaatggcc ttggtatgtt tggctcggct
25081 tcattgctgg actaattgcc atcgtcatgg ttacaatctt gctttgttgc atgactagtt
25141 gttgcagttg cctcaagggt gcatgctctt gtggttcttg ctgcaagttt gatgaggatg
25201 actctgagcc agttctcaag ggtgtcaaat tacattacac ataaacgaac ttatggattt
25261 gtttatgaga tttttttactc ttggatcaat tactgcacag ccagtaaaaa ttgacaatgc
25321 ttctcctgca agtactgttc atgctacagc aacgataccg ctacaagcct cactcccttt
25381 cggatggctt gttattggcg ttgcatttct tgctgttttt cagagcgcta ccaaaataat
25441 tgcgctcaat aaaagatggc agctagccct ttataagggc ttccagttca tttgcaattt
25501 actgctgcta tttgttacca tctattcaca tcttttgctt gtcgctgcag gtatggaggc
25561 gcaatttttg tacctctatg ccttgatata ttttctacaa tgcatcaacg catgtagaat
25621 tattatgaga tgttggcttt gttggaagtg caaatccaag aacccattac tttatgatgc
25681 caactacttt gtttgctggc acacacataa ctatgactac tgtatacat ataacagtgt
25741 cacagataca attgtcgtta ctgaaggtga cggcatttca acaccaaaac tcaaagaaga
25801 ctaccaaatt ggtggttatt ctgaggatag gcactcaggt gttaaagact atgtcgttgt
25861 acatggctat ttcaccgaag tttactacca gcttgagtct acacaaatta ctacagacac
25921 tggtattgaa aatgctacat tcttcatctt taacaagctt gttaaagacc caccgaatgt
```

FIGURE 9H

```
25981 gcaaatacac acaatcgacg gctcttcagg agttgctaat ccagcaatgg atccaattta
26041 tgatgagccg acgacgacta ctagcgtgcc tttgtaagca caagaaagtg agtacgaact
26101 tatgtactca ttcgtttcgg aagaaacagg tacgttaata gttaatagcg tacttctttt
26161 tcttgctttc gtggtattct tgctagtcac actagccatc cttactgcgc ttcgattgtg
26221 tgcgtactgc tgcaatattg ttaacgtgag tttagtaaaa ccaacggttt acgtctactc
26281 gcgtgttaaa aatctgaact cttctgaagg agttcctgat cttctggtct aaacgaacta
26341 actattatta ttattctgtt tggaacttta acattgctta tcatggcaga caacggtact
26401 attaccgttg aggagcttaa acaactcctg gaacaatgga acctagtaat aggtttccta
26461 ttcctagcct ggattatgtt actacaattt gcctattcta atcggaacag gtttttgtac
26521 ataataaagc ttgttttcct ctggctcttg tggccagtaa cacttgcttg ttttgtgctt
26581 gctgctgtct acagaattaa ttgggtgact ggcgggattg cgattgcaat ggcttgtatt
26641 gtaggcttga tgtggcttag ctacttcgtt gcttccttca ggctgtttgc tcgtacccgc
26701 tcaatgtggt cattcaaccc agaaacaaac attcttctca atgtgcctct ccgggggaca
26761 attgtgacca gaccgctcat ggaaagtgaa cttgtcattg gtgctgtgat cattcgtggt
26821 cacttgcgaa tggccggaca ctccctaggg cgctgtgaca ttaaggacct gccaaaagag
26881 atcactgtgg ctacatcacg aacgctttct tattacaaat taggagcgtc gcagcgtgta
26941 ggcactgatt caggttttgc tgcatacaac cgctaccgta ttggaaacta taaattaaat
27001 acagaccacg ccggtagcaa cgacaatatt gctttgctag tacagtaagt gacaacagat
27061 gtttcatctt gttgacttcc aggttacaat agcagagata ttgattatca ttatgaggac
27121 tttcaggatt gctatttgga atcttgacgt tataataagt tcaatagtga gacaattatt
27181 taagcctcta actaagaaga attattcgga gttagatgat gaagaaccta tggagttaga
27241 ttatccataa aacgaacatg aaaattattc tcttcctgac attgattgta tttacatctt
27301 gcgagctata tcactatcag gagtgtgtta gaggtacgac tgtactacta aaagaacctt
27361 gcccatcagg aacatacgag ggcaattcac catttcaccc tcttgctgac aataaatttg
27421 cactaacttg cactagcaca cactttgctt ttgcttgtgc tgacggtact cgacatacct
27481 atcagctgcg tgcaagatca gtttcaccaa aacttttcat cagacaagag gaggttcaac
27541 aagagctcta ctcgccactt tttctcattg ttgctgctct agtattttta atactttgct
27601 tcaccattaa gagaaagaca gaatgaatga gctcacttta attgacttct atttgtgctt
27661 tttagccttt ctgctattcc ttgttttaat aatgcttatt atattttggt tttcactcga
27721 aatccaggat ctagaagaac cttgtaccaa agtctaaacg aacatgaaac ttctcattgt
27781 tttgacttgt atttctctat gcagttgcat acgcactgta gtacagcgct gtgcatctaa
27841 taaacctcat gtgcttgaag atccttgtaa ggtacaacac taggggtaat acttatagca
27901 ctgcttggct ttgtgctcta ggaaaggttt tacctttta tagatggcac actatggttc
27961 aaacatgcac acctaatgtt actatcaact gtcaagatcc agctggtggt gcgcttatag
28021 ctaggtgttg gtaccttcat gaaggtcacc aaactgctgc atttagagac gtacttgttg
28081 ttttaaataa acgaacaaat taaaatgtct gataatggac cccaatcaaa ccaacgtagt
28141 gccccccgca ttacatttgg tggacccaca gattcaactg acaataacca gaatggagga
28201 cgcaatgggg caaggccaaa acagcgccga ccccaaggtt tacccaataa tactgcgtct
28261 tggttcacag ctctcactca gcatggcaag gaggaactta gattccctcg aggccagggc
28321 gttccaatca acaccaatag tggtccagat gaccaaattg gctactaccg aagagctacc
28381 cgacgagttc gtggtggtga cggcaaaatg aaagagctca gccccagatg gtacttctat
28441 tacctaggaa ctggcccaga agcttcactt ccctacggcg ctaacaaaga aggcatcgta
28501 tgggttgcaa ctgagggagc cttgaataca cccaaagacc acattggcac ccgcaatcct
28561 aataacaatg ctgccaccgt gctacaactt cctcaaggaa caacattgcc aaaaggcttc
28621 tacgcagagg gaagcagagg cggcagtcaa gcctcttctc gctcctcatc acgtagtcgc
28681 ggtaattcaa gaaattcaac tcctggcagc agtaggggaa attctcctgc tcgaatggct
28741 agcggaggtg gtgaaactgc cctcgcgcta ttgctgctag acagattgaa ccagcttgag
28801 agcaaagttt ctggtaaagg ccaacaacaa caaggccaaa ctgtcactaa gaaatctgct
28861 gctgaggcat ctaaaaagcc tcgccaaaaa cgtactgcca caaaacagta caacgtcact
28921 caagcatttg ggagacgtgg tccagaacaa acccaaggaa atttcgggga ccaagaccta
28981 atcagacaag gaactgatta caaacattgg ccgcaaattg cacaatttgc tccaagtgcc
29041 tctgcattct ttggaatgtc acgcattggc atggaagtca caccttcggg aacatggctg
29101 acttatcatg gagccattaa attggatgac aaagatccac aattcaaaga caacgtcata
29161 ctgctgaaca agcacattga cgcatacaaa acattcccac caacagagcc taaaaaggac
29221 aaaaagaaaa agactgatga agctcagcct ttgccgcaga gacaaaagaa gcagcccact
29281 gtgactcttc ttcctgcggc tgacatggat gatttctcca gacaacttca aaattccatg
29341 agtggagctt ctgctgattc aactcaggca taaacactca tgatgaccac acaaggcaga
29401 tgggctatgt aaacgttttc gcaattccgt ttacgataca tagtctactc ttgtgcagaa
29461 tgaattctcg taactaaaca gcacaagtag gtttagttaa ctttaatctc acatagcaat
29521 ctttaatcaa tgtgtaacat tagggaggac ttgaaagagc caccacattt tcatcgaggc
29581 cacgcggagt acgatcgagg gtacagtgaa taatgctagg gagagctgcc tatatggaag
```

FIGURE 9I

29641 agccctaatg tgtaaaatta attttagtag tgctatcccc atgtgatttt aatagcttct
29701 taggagaatg acaaaaaaaa aaaaaaaaaa aaaaaa

FIGURE 10

```
   1 tctgtgtagc tgtcgctcgg ctgcatgcct agtgcaccta cgcagtataa acaataataa
  61 attttactgt cgttgacaag aaacgagtaa ctcgtccctc ttctgcagac tgcttacggt
 121 ttcgtccgtg ttgcagtcga tcatcagcat acctaggttt cgtccgggtg tgaccgaaag
 181 gtaagatgga gagccttgtt cttggtgtca acgagaaaac acacgtccaa ctcagtttgc
 241 ctgtccttca ggttagagac gtgctagtgc gtggcttcgg ggactctgtg gaagaggccc
 301 tatcggaggc acgtgaacac ctcaaaaatg gcacttgtgg tctagtagag ctggaaaaag
 361 gcgtactgcc ccagcttgaa cagccctatg tgttcattaa acgttctgat gccttaagca
 421 ccaatcacgg ccacaaggtc gttgagctgg ttgcagaaat ggacggcatt cagtacggtc
 481 gtagcggtat aacactggga gtactcgtgc cacatgtggg cgaaacccca attgcatacc
 541 gcaatgttct tcttcgtaag aacggtaata agggagccgg tggtcatagc tatggcatcg
 601 atctaaagtc ttatgactta ggtgacgagc ttggcactga tcccattgaa gattatgaac
 661 aaaactggaa cactaagcat ggcagtggtg cactccgtga actcactcgt gagctcaatg
 721 gaggtgtagt cactcgctat gtcgacaaca atttctgtgg cccagatggg taccctcttg
 781 attgcatcaa agatttttcta gcacgcgcgg gcaagtcaat gtgcactctt tccgaacaac
 841 ttgattacat cgagtcgaag agaggtgtct actgctgccg tgaccatgag catgaaattg
 901 cctggttcac tgagcgctct gataagagct gcgagcacca gacacccttc gaaattaaga
 961 gtgccaagaa atttgacact ttcaaagggg aatgcccaaa gtttgtgttt cctcttaact
1021 caaaagtcaa agtcattcaa ccacgtgttg aaaagaaaaa gactgagggt ttcatggggc
1081 gtatacgctc tgtgtaccct gttgcatctc cacaggagtg taacaatatg cacttgtcta
1141 ccttgatgaa atgtaatcat tgcgatgaag tttcatggca gacgtgcgac tttctgaaag
1201 ccacttgtga acattgtggc actgaaaatt tagttattga aggacctact acatgtgggt
1261 acctacctac taatgctgta gtgaaaatgc catgtcctgc ctgtcaagac ccagagattg
1321 gacctgagca tagtgttgca gattatcaca accactcaaa cattgaaact cgactccgca
1381 agggaggtag gactagatgt tttggaggct gtgtgtttgc ctatgttggc tgctataata
1441 agcgtgccta ctgggttcct cgtgctagtg ctgatattgg ctcaggccat actggcatta
1501 ctggtgacaa tgtggagacc ttgaatgagg atctccttga gatactgagt cgtgaacgtg
1561 ttaacattaa cattgttggc gattttcatt tgaatgaaga ggttgccatc attttggcat
1621 ctttctctgc ttctacaagt gcctttattg acactataaa gagtcttgat tacaagtctt
1681 tcaaaaccat tgttgagtcc tgcggt
```

FIGURE 11A

```
   1 agtgttttat tagcacttca acagcttgaa gtcaaattca atgcaccagc acttcaagag
  61 gcttattata gagcccgtgc tggtgatgct gctaactttt gtgcactcat actcgcttac
 121 agtaataaaa ctgttggcga gcttggtgat gtcagagaaa ctatgaccca tcttctacag
 181 catgctaatt tggaatctgc aaagcgagtt cttaatgtgg tgtgtaaaca ttgtggtcag
 241 aaaactacta ccttaacggg tgtagaagct gtgatgtata tgggtactct atcttatgat
 301 aatcttaaga caggtgtttc cattccatgt gtgtgtggtc gtgatgctac acaatatcta
 361 gtacaacaag agtcttcttt tgttatgatg tctgcaccac ctgctgagta taaattacag
 421 caaggtacat tcttatgtgc gaatgagtac actggtaact atcagtgtgg tcattacact
 481 catataactg ctaaggagac cctctatcgt attgacggag ctcaccttac aaagatgtca
 541 gagtacaaag gaccagtgac tgatgtttc tacaaggaaa catcttacac tacaaccatc
 601 aagcctgtgt cgtataaact cgatggagtt acttacacag agattgaacc aaaattggat
 661 gggtattata aaaaggataa tgcttactat acagagcagc ctatagacct tgtaccaact
 721 caaccattac caaatgcgag ttttgataat ttcaaactca catgttctaa cacaaaattt
 781 gctgatgatt taaatcaaat gacaggcttc acaaagccag cttcacgaga gctatctgtc
 841 acattcttcc cagacttgaa tggcgatgta gtggctattg actatagaca ctattcagcg
 901 agtttcaaga aaggtgctaa attactgcat aagccaattg tttggcacat taaccaggct
 961 acaaccaaga caacgttcaa accaaacact tggtgtttac gttgtctttg gagtacaaag
1021 ccagtagata cttcaaattc atttgaagtt ctggcagtag aagacacaca aggaatggac
1081 aatcttgctt gtgaaagtca acaacccacc tctgaagaag tagtggaaaa tcctaccata
1141 cagaaggaag tcatagagtg tgacgtgaaa actaccgaag ttgtaggcaa tgtcatactt
1201 aaaccatcag atgaaggtgt taaagtaaca caagagttag gtcatgagga tcttatggct
1261 gcttatgtgg aaaacacaag cattaccatt aagaaaccta atgagctttc actagcctta
1321 ggtttaaaaa caattgccac tcatggtatt gctgcaatta atagtgttcc ttggagtaaa
1381 attttggctt atgtcaaacc attcttagga caagcagcaa ttacaacatc aaattgcgct
1441 aagagattag cacaacgtgt gtttaacaat tatatgcctt atgtgtttac attattgttc
1501 caattgtgta cttttactaa aagtaccaat tctagaatta gagcttcact acctacaact
1561 attgctaaaa atagtgttaa gagtgttgct aaattatgtt tggatgccgg cattaattat
1621 gtgaagtcac ccaaattttc taaattgttc acaatcgcta tgtggctatt gttgttaagt
1681 atttgcttag gttctctaat ctgtgtaact gctgcttttg gtgtactctt atctaatttt
1741 ggtgctcctt cttattgtaa tggcgttaga gaattgtatc ttaattcgtc taacgttact
1801 actatggatt tctgtgaagg ttcttttcct tgcagcattt gtttaagtgg attagactcc
1861 cttgattctt atccagctct tgaaaccatt caggtgacga tttcatcgta caagctagac
1921 ttgacaattt taggtctggc cgctgagtgg gttttggcat atatgttgtt cacaaaattc
1981 ttttatttat taggtctttc agctataatg caggtgttct ttggctattt tgctagtcat
2041 ttcatcagca attcttggct catgtggttt atcattagta ttgtacaaat ggcacccgtt
2101 tctgcaatgg ttaggatgta catcttcttt gcttctttct actacatatg gaagagctat
2161 gttcatatca tggatggttg cacctcttcg acttgcatga tgtgctataa gcgcaatcgt
2221 gccacacgcg ttgagtgtac aactattgtt aatggcatga agagatcttt ctatgtctat
2281 gcaaatggag gccgtggctt ctgcaagact cacaattgga attgtctcaa ttgtgacaca
2341 ttttgcactg gtagtacatt cattagtgat gaagttgctc gtgatttgtc actccagttt
2401 aaaagaccaa tcaaccctac tgaccagtca tcgtatattg ttgatagtgt tgctgtgaaa
2461 aatggcgcgc ttcacctcta ctttgacaag gctggtcaaa agacctatga gagacatccg
2521 ctctcccatt ttgtcaattt agacaatttg agagctaaca acactaaagg ttcactgcct
2581 attaatgtca tagtttttga tggcaagtcc aaatgcgacg agtctgcttc taagtctgct
2641 tctgtgtact acagtcagct gatgtgccaa cctattctgt tgcttgacca agctcttgta
2701 tcagacgttg gagatagtac tgaagtttcc gttaagatgt ttgatgctta tgtcgacacc
2761 ttttcagcaa cttttagtgt tcctatggaa aaacttaagg cacttgttgc tacagctcac
2821 agcgagttag caaagggtgt agctttagat ggtgtccttt ctacattcgt gtcagctgcc
2881 cgacaaggtg ttgttgatac cgatgttgac acaaaggatg ttattgaatg tctcaaactt
2941 tcacatcact ctgacttaga agtgacaggt gacagttgta acaatttcat gctcacctat
3001 aataaggttg aaaacatgac gcccagagat cttggcgcat gtattgactg taatgcaagg
3061 catatcaatg cccaagtagc aaaaagtcac aatgtttcac tcatctggaa tgtaaaagac
3121 tacatgtctt tatctgaaca gctgcgtaaa caaattcgta gtgctgccaa gaagaacaac
3181 ataccttta gactaacttg tgctacaact agacaggttg tcaatgtcat aactactaaa
3241 atctcactca agggtggtaa gattgttagt acttgtttta aacttatgct taaggccaca
3301 ttattgtgcg ttcttgctgc attggtttgt tatatcgtta tgccagtaca tacattgtca
3361 atccatgatg gttacacaaa tgaaatcatt ggttacaaag ccattcagga tggtgtcact
3421 cgtgacatca tttctactga tgattgtttt gcaaataaac atgctggttt tgacgcatgg
3481 tttagccagc gtggtggttc atacaaaaat gacaaaagct gccctgtagt agctgctatc
3541 attacaagag agattggttt catagtgcct ggcttaccgg gtactgtgct gagagcaatc
3601 aatggtgact tcttgcattt tctacctcgt gtttttagtg ctgttggcaa catttgctac
```

FIGURE 11B

```
3661 acaccttcca aactcattga gtatagtgat tttgctacct ctgcttgcgt tcttgctgct
3721 gagtgtacaa tttttaagga tgctatgggc aaacctgtgc catattgtta tgacactaat
3781 ttgctagagg gttctatttc ttatagtgag cttcgtccag acactcgtta tgtgcttatg
3841 gatggttcca tcatacagtt tcctaacact tacctggagg gttctgttag agtagtaaca
3901 acttttgatg ctgagtactg tagacatggt acatgcgaaa ggtcagaagt aggtatttgc
3961 ctatctacca gtggtagatg ggttcttaat aatgagcatt acagagctct atcaggagtt
4021 ttctgtggtg ttgatgcgat gaatctcata gctaacatct ttactcctct tgtgcaacct
4081 gtgggtgctt tagatgtgtc tgcttcagta gtggctggtg gtattattgc catattggtg
4141 acttgtgctg cctactactt tatgaaattc agacgtgttt ttggtgagta caaccatgtt
4201 gttgctgcta atgcactttt gtttttgatg tctttcacta tactctgtct ggtaccagct
4261 tacagctttc tgccgggagt ctactcagtc ttttacttgt acttgacatt ctatttcacc
4321 aatgatgttt cattcttggc tcaccttcaa tggtttgcca tgttttctcc tattgtgcct
4381 ttttggataa cagcaatcta tgtattctgt atttctctga agcactgcca ttggttcttt
4441 aacaactatc ttaggaaaag agtcatgttt aatggagtta catttagtac cttcgaggag
4501 gctgctttgt gtaccttttt gctcaacaag gaaatgtacc taaaattgcg tagcgagaca
4561 ctgttgccac ttacacagta taacaggtat cttgctctat ataacaagta caagtatttc
4621 agtggagcct tagatactac cagctatcgt gaagcagctt gctgccactt agcaaaggct
4681 ctaaatgact ttagcaactc aggtgctgat gttctctacc aaccaccaca gacatcaatc
4741 acttctgctg ttctgcagag tggttttagg aaaatggcat tcccgtcagg caaagttgaa
4801 gggtgcatgg tacaagtaac ctgtggaact acaactctta atggattgtg gttggatgac
4861 acagtatact gtccaagaca tgtcatttgc acagcagaag acatgcttaa tcctaactat
4921 gaagatctgc tcattcgcaa atccaaccat agctttcttg ttcaggctgg caatgttcaa
4981 cttcgtgtta ttggccattc tatgcaaaat tgtctgctta ggcttaaagt tgatacttct
5041 aaccctaaga cacccaagta taaatttgtc cgtatccaac ctggtcaaac attttcagtt
5101 ctagcatgct acaatggttc accatctggt gtttatcagt gtgccatgag acctaatcat
5161 accattaaag gttctttcct taatggatca tgtggtagtg ttggttttaa cattgattat
5221 gattgcgtgt ctttctgcta tatgcatcat atggagcttc caacaggagt acacgctggt
5281 accgacttag aaggtaaatt ctatggtcca tttgttgaca gacaaactgc acaggctgca
5341 ggtacagaca caaccataac attaaatgtt ttggcatggc tgtatgctgc tgttatcaat
5401 ggtgataggt ggtttcttaa tagattcacc actactttga atgactttaa ccttgtggca
5461 atgaagtaca actatgaacc tttgacacaa gatcatgttg acatattggg acctctttct
5521 gctcaaacag gaattgccgt cttagatatg tgtgctgctt tgaaagagct gctgcagaat
5581 ggtatgaatg gtcgtactat ccttggtagc actattttag aagatgagtt tacaccattt
5641 gatgttgtta gacaatgctc tggtgttacc ttccaaggta agttcaagaa aattgttaag
5701 ggcactcatc attggatgct tttaactttc ttgacatcac tattgattct tgttcaaagt
5761 acacagtggt cactgttttt ctttgtttac gagaatgctt tcttgccatt tactcttggt
5821 attatggcaa ttgctgcatg tgctatgctg cttgttaagc ataagcacgc attcttgtgc
5881 ttgtttctgt taccttctct tgcaacagtt gcttacttta atatggtcta catgcctgct
5941 agctgggtga tgcgtatcat gacatggctt gaattggctg acactagctt gtctggttat
6001 aggcttaagg attgtgttat gtatgcttca gctttagttt tgcttattct catgacagct
6061 cgcactgttt atgatgatgc tgctagacgt gtttggacac tgatgaatgt cattacactt
6121 gtttacaaag tctactatgg taatgcttta gatcaagcta tttccatgtg ggccttagtt
6181 atttctgtaa cctctaacta ttctggtgtc gttacgacta tcatgttttt agctagagct
6241 atagtgtttg tgtgtgttga gtattatcca ttgttattta ttactggcaa caccttacag
6301 tgtatcatgc ttgtttattg tttcttaggc tattgttgct gctgctactt tggccttttc
6361 tgtttactca accgttactt caggcttact cttggtgttt atgactactt ggtctctaca
6421 caagaattta ggtatatgaa ctcccagggg cttttgcctc ctaagagtag tattgatgct
6481 ttcaagctta acattaagtt gttgggtatt ggaggtaaac catgtatcaa ggttgctact
6541 gtacagtcta aaatgtctga cgtaaagtgc acatctgtgg tactgctctc ggttcttcaa
6601 caacttagag tagagtcatc ttctaaattg tgggcacaat gtgtacaact ccacaatgat
6661 attcttcttg caaaagacac aactgaagct ttcgagaaga tggtttctct tttgtctgtt
6721 ttgctatcca tgcagggtgc tgtagacatt aataggttgt gcgaggaaat gctcgataac
6781 cgtgctactc ttcaggctat tgcttcagaa tttagttctt taccatcata tgccgcttat
6841 gccactgccc aggaggccta tgagcaggct gtagctaatg gtgattctga agtcgttctc
6901 aaaaagttaa agaaatcttt gaatgtggct aaatctgagt ttgaccgtga tgctgccatg
6961 caacgcaagt tggaaaagat ggcagatcag gctatgaccc aaatgtacaa acaggcaaga
7021 tctgaggaca agagggccca agtcgcttct gctatgcaaa caatgctctt cactatgcta
7081 aggaagcttg ataatgatgc acttaacaac attatcaaca atgcgcgtga tggttgtgtt
7141 ccactcaaca tcataccatt gactacagca gccaaactca tggttgttgt ccctgattat
7201 ggtacctaca agaacacttg tgatggtaac acctttacat atgcatctgc actctgggaa
7261 atccagcaag ttgttgatgc ggatagcaag attgttcaac ttagtgaaat taacatggac
7321 aattcaccaa atttggcttg gcctcttatt gttacagctc taagagccaa ctcagctgtt
```

FIGURE 11C

```
 7381 aaactacaga ataatgaact gagtccagta gcactacgac agatgtcctg tgcggctggt
 7441 accacacaaa cagcttgtac tgatgacaat gcacttgcct actataacaa ttcgaaggga
 7501 ggtaggtttg tgctggcatt actatcagac caccaagatc tcaaatgggc tagattccct
 7561 aagagtgatg gtacaggtac aatttacaca gaactggaac caccttgtag gtttgttaca
 7621 gacacaccaa aagggcctaa agtgaaatac ttgtacttca tcaaaggctt aaacaaccta
 7681 aatagaggta tggtgctggg cagtttagct gctacagtac gtcttcaggc tggaaatgct
 7741 acagaagtac ctgccaattc aactgtgctt tccttctgtg cttttgcagt agaccctgct
 7801 aaagcatata aggattacct agcaagtgga ggacaaccaa tcaccaactg tgtgaagatg
 7861 ttgtgtacac acactggtac aggacaggca attactgtaa caccagaagc taacatggac
 7921 caagagtcct ttggtggtgc ttcatgttgt ctgtattgta gatgccacat tgaccatcca
 7981 aatcctaaag gattctgtga cttgaaaggt aagtacgtcc aaatacctac cacttgtgct
 8041 aatgacccag tgggttttac acttagaaac acagtctgta ccgtctgcgg aatgtggaaa
 8101 ggttatggct gtagttgtga ccaactccgc gaacccttga tgcagtctgc ggatgcatca
 8161 acgtttttaa acgggtttgc ggtgtaagtg cagcccgtct tacaccgtgc ggcacaggca
 8221 ctagtactga tgtcgtctac agggcttttg atatttacaa cgaaaaagtt gctggtttg
 8281 caaagttcct aaaaactaat tgctgtcgct tccaggagaa ggatgaggaa ggcaatttat
 8341 tagactctta ctttgtagtt aagaggcata ctatgtctaa ctaccaacat gaagagacta
 8401 tttataactt ggttaaagat tgtccagcgg ttgctgtcca tgactttttc aagtttagag
 8461 tagatggtga catggtacca catatatcac gtcagcgtct aactaaatac acaatggctg
 8521 atttagtcta tgctctacgt cattttgatg agggtaattg tgatacatta aaagaaatac
 8581 tcgtcacata caattgctgt gatgatgatt atttcaataa gaaggattgg tatgacttcg
 8641 tagagaatcc tgacatctta cgcgtatatg ctaacttagg tgagcgtgta cgccaatcat
 8701 tattaaagac tgtacaattc tgcgatgcta tgcgtgatgc aggcattgta ggcgtactga
 8761 cattagataa tcaggatctt aatgggaact ggtacgattt cggtgatttc gtacaagtag
 8821 caccaggctg cggagttcct attgtggatt catattactc attgctgatg cccatcctca
 8881 ctttgactag ggcattggct gctgagtccc atatggatgc tgatctcgca aaaccactta
 8941 ttaagtggga tttgctgaaa tatgatttta cggaagagag actttgtctc ttcgaccgtt
 9001 attttaaata ttgggaccag acataccatc ccaattgtat taactgtttg gatgataggt
 9061 gtatccttca ttgtgcaaac tttaatgtgt tattttctac tgtgtttcca cctacaagtt
 9121 ttggaccact agtaagaaaa atatttgtag atggtgttcc ttttgttgtt tcaactggat
 9181 accattttcg tgagttagga gtcgtacata atcaggatgt aaacttacat agctcgcgtc
 9241 tcagtttcaa ggaactttta gtgtatgctg ctgatccagc tatgcatgca gcttctggca
 9301 atttattgct agataaacgc actacatgct tttcagtagc tgcactaaca aacaatgttg
 9361 cttttcaaac tgtcaaaccc ggtaatttta ataaagactt ttatgacttt gctgtgtcta
 9421 aaggtttctt taaggaagga agttctgttg aactaaaaca cttcttcttt gctcaggatg
 9481 gcaacgctgc tatcagtgat tatgactatt atcgttataa tctgccaaca atgtgtgata
 9541 tcagacaact cctattcgta gttgaagttg ttgataaata ctttgattgt tacgatggtg
 9601 gctgtattaa tgccaaccaa gtaatcgtta acaatctgga taaatcagct ggtttcccat
 9661 ttaataaatg ggtaaggct agactttatt atgactcaat gagttatgag gatcaagatg
 9721 cacttttcgc gtatactaag cgtaatgtca tccctactat aactcaaatg aatcttaagt
 9781 atgccattag tgcaaagaat agagctcgca ccgtagctgg tgtctctatc tgtagtacta
 9841 tgacaaatag acagtttcat cagaaattat tgaagtcaat agccgccact agaggagcta
 9901 ctgtggtaat tggaacaagc aagttttacg gtggctggca taatatgtta aaaactgttt
 9961 acagtgatgt agaaactcca caccttatgg gttgggatta tccaaaatgt gacagagcca
10021 tgcctaacat gcttaggata atggcctctc ttgttcttgc tcgcaaacat aacacttgct
10081 gtaacttatc acaccgtttc tacaggttag ctaacgagtg tgcgcaagta ttaagtgaga
10141 tggtcatgtg tggcggctca ctatatgtta aaccaggtgg aacatcatcc ggtgatgcta
10201 caactgctta tgctaatagt gtctttaaca tttgtcaagc tgttacagcc aatgtaaatg
10261 cacttctttc aactgatggt aataagatag ctgacaagta tgtccgcaat ctacaacaca
10321 ggctctatga gtgtctctat agaaataggg atgttgatca tgaattcgtg gatgagtttt
10381 acgcttacct gcgtaaacat ttctccatga tgattctttc tgatgatgcc gttgtgtgct
10441 ataacagtaa ctatgcggct caaggtttag tagctagcat taagaacttt aaggcagttc
10501 tttattatca aaataatgtg ttcatgtctg aggcaaaatg ttggac
```

FIGURE 12A

| | | | | | | |
|---|---|---|---|---|---|---|
| 1 | attagcgata | tgtatgaccc | taggaccaaa | catgtgacaa | aagagaatga | ctctaaagaa |
| 61 | gggtttttca | cttatctgtg | tggatttata | aagcaaaaac | tagccctggg | tggttctata |
| 121 | gctgtaaaga | taacagagca | ttcttggaat | gctgaccttt | acaagcttat | gggccatttc |
| 181 | tcatggtgga | cagcttttgt | tacaaatgta | aatgcatcat | catcggaagc | atttttaatt |
| 241 | ggggctaact | atcttggcaa | gccgaaggaa | caaattgatg | gctataccat | gcatgctaac |
| 301 | tacattttct | ggaggaacac | aaatcctatc | cagttgtctt | cctattcact | ctttgacatg |
| 361 | agcaaatttc | ctcttaaatt | aaggggaact | gctgtaatgt | ctcttaagga | gaatcaaatc |
| 421 | aatgatatga | tttattctct | tctggaaaaa | ggtaggctta | tcattagaga | aaacaacaga |
| 481 | gttgtggttt | caagtgatat | tcttgttaac | aactaaacga | acatgtttat | tttcttatta |
| 541 | tttcttactc | tcactagtgg | tagtgacctt | gaccggtgca | ccacttttga | tgatgttcaa |
| 601 | gctcctaatt | acactcaaca | tacttcatct | atgagggggg | tttactatcc | tgatgaaatt |
| 661 | tttagatcag | acactcttta | tttaactcag | gatttatttc | ttccatttta | ttctaatgtt |
| 721 | acagggtttc | atactattaa | tcatacgttt | ggcaaccctg | tcataccttt | taaggatggt |
| 781 | atttattttg | ctgccacaga | gaaatcaaat | gttgtccgtg | gttgggtttt | tggttctacc |
| 841 | atgaacaaca | agtcacagtc | ggtgattatt | attagcaatt | ctactaatgt | tgttatacga |
| 901 | gcatgtaact | ttgaattgtg | tgacaaccct | ttctttgctg | tttctaaacc | catgggtaca |
| 961 | cagacacata | ctatgatatt | cgataatgca | tttaattgca | ctttcgagta | catatctgat |
| 1021 | gccttttcgc | ttgatgtttc | agaaaagtca | ggtaatttta | aacacttacg | agagtttgtg |
| 1081 | tttaaaaata | aagatgggtc | tctctatgtt | tataagggct | atcaacctat | agatgtagtt |
| 1141 | cgtgatctac | cttctggttt | taacactttg | aaacctattt | ttaagttgcc | tcttggtatt |
| 1201 | aacattacaa | attttagagc | cattcttaca | gccttttcac | ctgctcaaga | catttggggc |
| 1261 | acgtcagctg | cagcctattt | tgttggctat | ttaaagccaa | ctacatttat | gctcaagtat |
| 1321 | gatgaaaatg | gtacaatcac | agatgctgtt | gattgctctc | aaaatccact | tgctgaactc |
| 1381 | aaatgctctg | ttaagagctt | tgagattgac | aaaggaattt | accagacctc | taatttcagg |
| 1441 | gttgttccct | caggagatgt | tgtgagattc | cctaatatta | caaacttgtg | tcccttttgga |
| 1501 | gaggttttta | atgctactaa | attcccttct | gtctatgcat | gggagagaaa | aaaaatttct |
| 1561 | aattgtgttg | ctgattactc | tgtgctctac | aactcaacat | ttttttcaac | ctttaagtgc |
| 1621 | tatggcgttt | ctgccactaa | gttgaatgat | ctttgcttct | ccaatgtcta | tgcagattct |
| 1681 | tttgtagtca | agggagatga | tgtaagacaa | atagcgccag | gacaaactgg | tgttattgct |
| 1741 | gattataatt | ataaattgcc | agatgatttc | atgggttgtg | tccttgcttg | gaatactggg |
| 1801 | aacattgatg | ctacttcaac | tggtaattat | gattataaat | ataggtatct | tagacatggc |
| 1861 | aagcttaggc | cctttgagag | agacatatct | aatgtgcctt | tctcccctga | tggcaaacct |
| 1921 | tgcaccccac | ctgctcttaa | ttgttattgg | ccattaaatg | attatggttt | ttacaccact |
| 1981 | actggcattg | gctaccaacc | ttacagagtt | gtagtacttt | cttttgaact | tttaaatgca |
| 2041 | ccggccacgg | tttgtggacc | aaaattatcc | actgacctta | ttaagaacca | gtgtgtcaat |
| 2101 | tttaatttta | atggactcac | tggtactggt | gtgttaactc | cttcttcaaa | gagatttcaa |
| 2161 | ccatttcaac | aatttggccg | tgatgtttct | gatttcactg | attccgttcg | agatcctaaa |
| 2221 | acatctgaaa | tattagacat | ttcaccttgc | tcttttgggg | gtgtaagtgt | aattacacct |
| 2281 | ggaacaaatg | cttcatctga | agttgctgtt | ctatatcaag | atgttaactg | cactgatgtt |
| 2341 | tctacagcaa | ttcatgcaga | tcaactcaca | ccagcttggc | gcatatattc | tactggaaac |
| 2401 | aatgtattcc | agactcaagc | aggctgtctt | ataggagctg | agcatgtcga | cacttcttat |
| 2461 | gagtgcgaca | ttcctattgg | agctggcatt | tgtgctagtt | accatacagt | ttctttatta |
| 2521 | cgtagtacta | gccaaaaatc | tattgtggct | tatactatgt | ctttaggtgc | tgatagttca |
| 2581 | attgcttact | ctaataacac | cattgctata | cctactaact | tttcaattag | cattactaca |
| 2641 | gaagtaatgc | ctgtttctat | ggctaaaacc | tccgtagatt | gtaatatgta | catctgcgga |
| 2701 | gattctactg | aatgtgctaa | tttgcttctc | caatatggta | gcttttgcac | acaactaaat |
| 2761 | cgtgcactct | caggtattgc | tgctgaacag | gatcgcaaca | cacgtgaagt | gttcgctcaa |
| 2821 | gtcaaacaaa | tgtacaaaac | cccaactttg | aaatattttg | gtggttttaa | tttttcacaa |
| 2881 | atattacctg | accctctaaa | gccaactaag | aggtctttta | ttgaggactt | gccctttaat |
| 2941 | aaggtgacac | tcgctgatgc | tggcttcatg | aagcaatatg | gcgaatgcct | aggtgatatt |
| 3001 | aatgctagag | atctcatttg | tgcgcagaag | ttcaatggac | ttacagtgtt | gccacctctg |
| 3061 | ctcactgatg | atatgattgc | tgcctacact | gctgctctag | ttagtggtac | tgccactgct |
| 3121 | ggatggacat | ttggtgctgg | cgctgctctt | caaatacctt | ttgctatgca | aatggcatat |
| 3181 | aggttcaatg | gcattggagt | tacccaaaat | gttctctatg | agaaccaaaa | acaaatcgcc |
| 3241 | aaccaattta | acaaggcgat | tagtcaaatt | caagaatcac | ttacaacaac | atcaactgca |
| 3301 | ttgggcaagc | tgcaagacgt | tgttaaccag | aatgctcaag | cattaaacac | acttgttaaa |
| 3361 | caacttagct | ctaattttgg | tgcaatttca | agtgtgctaa | atgatatcct | ttcgcgactt |
| 3421 | gataaagtcg | aggcggaggt | acaaattgac | aggttaatta | caggcagact | tcaaagcctt |
| 3481 | caaacctatg | taacacaaca | actaatcagg | gctgctggaa | tcagggcttc | tgctaatctt |
| 3541 | gctgctacta | aaatgtctga | gtgtgttctt | ggacaatcaa | aaagagttga | cttttgtgga |
| 3601 | aagggctacc | accttatgtc | cttcccacaa | gcagccccgc | atggtgttgt | cttcctacat |

FIGURE 12B

```
3661 gtcacgtatg tgccatccca ggagaggaac ttcaccacag cgccagcaat ttgtcatgaa
3721 ggcaaagcat acttccctcg tgaaggtgtt tttgtgttta atggcacttc ttggtttatt
3781 acacagagga acttcttttc tccacaaata attactacag acaatacatt tgtctcagga
3841 aattgtgatg tcgttattgg catcattaac aacacagttt atgatcctct gcaacctgag
3901 cttgactcat tcaaagaaga gctggacaag tacttcaaaa atcatacatc accagatgtt
3961 gatcttggcg acatttcagg cattaacgct tctgtcgtca acattcaaaa agaaattgac
4021 cgcctcaatg aggtcgctaa aaatttaaat gaatcactca ttgaccttca agaattggga
4081 aaatatgagc aatatattaa atggccttgg tatgtttggc tcggcttcat tgctggacta
4141 attgccatcg tcatggttac aatcttgctt tgttgcatga ctagttgttg tagttgcctc
4201 aagggtgcat gctcttgtgg ttcttgctgc aagtttgatg aggatgactc tgagccagtt
4261 ctcaagggtg tcaaattaca ttacacataa acgaacttat ggatttgttt atgagatttt
4321 ttactcttgg atcaattact gcacagccag taaaaactga caatgcttct cctgcaagta
4381 ctgttcatgc tacagcaacg ataccgctac aagcctcact ccctttcgga tggcttgtta
4441 ttggcgttgc atttcttgct gtttttcaga gcgctaccaa aataattgcg ctcaataaaa
4501 gatggcagct agccctttat aagggcttcc agttcatttg caatttactg ctgctatttg
4561 ttaccatcta ttcacatctt ttgcttgtcg ctgcaggtat ggaggcgcaa tttttgtacc
4621 tctatgcctt gatatacttt ctacaatgca tcaacgcatg tagaattatt atg
```

FIGURE 13

```
   1 aaagaacctt gcccatcagc aacatacgag ggcaattcac catttcaccc tcttgctgac
  61 aataaatttg cactaacttg cactagcaca cactttgctt ttgcttgtgc tgacggtact
 121 cgacatacct atcagctgcg tgcaagatca gtttcaccaa aacttttcat cagacaagag
 181 gaggttcaac aagagctcta ctcgccactt tttctcattg ttgctgctct agtattttta
 241 atactttgct tcaccattaa gagaaagaca gaatgaatga gctcacttta attgacttct
 301 atttgtgctt tttagccttt ctgctattcc ttgttttaat aatgcttatt atatttggt
 361 tttcactcga aatccaggat ctagaagaac cttgtaccaa agtctaaacg aacatgaaac
 421 ttctcattgt tttgacttgt atttctctat gcagttgcat atgcactgta gtacagcgct
 481 gtgcatctaa taaacctcat gtgcttgaag atccttgtaa ggtacaacac taggggtaat
 541 acttatagca ctgcttggct ttgtgctcta ggaaaggttt tacctttca tagatggcac
 601 actatggttc aaacatgcac acctaatgtt actatcaact gtcaagatcc agctggtggt
 661 gcgcttatag ctaggtgttg gtaccttcat gaaggtcacc aaactgctgc atttagagac
 721 gtacttgttg ttttaaataa acgaacaaat taaaatgtct gataatggac cccaatcaaa
 781 ccaacgtagt gccccccgca ttacatttgg tggacccaca gattcaactg acaataacca
 841 gaatggagga cgcaatgggg caaggccaaa acagcgccga ccccaaggtt tacccaataa
 901 tactgcgtct tggttcacag ctctcactca gcatggcaag gaggaactta gattccctcg
 961 aggccagggc gttccaatca acaccaatag tggtccagat gaccaaattg gctactaccg
1021 aagagctacc cgacgagttc gtggtggtga cggcaaaatg aaagagctca gccccagatg
1081 gtacttctat tacctaggaa ctggcccaga agcttcactt ccctacggcg ctaacaaaga
1141 aggcatcgta tgggttgcaa ctgagggagc cttgaataca cccaaagacc acattggcac
1201 ccgcaatcct aataacaatg ctgccaccgt gctacaactt cctcaaggaa caacattgcc
1261 aaaaggcttc tacgcagagg gaagcagagg cggcagtcaa gcctcttctc gctcctcatc
1321 acgtagtcgc ggtaattcaa gaaattcaac tcctggcagc agtaggggaa attctcctgc
1381 tcgaatggct agcggaggtg gtgaaactgc cctcgcgcta ttgctgctag acagattgaa
1441 ccagcttgag agcaaagttt ctggtaaagg ccaacaacaa caaggccaaa ctgtcactaa
1501 gaaatctgct gctgaggcat ctaaaaagcc tcgccaaaaa cgtacagcca caaaacagta
1561 caacgtcact caagcatttg ggagacgtgg tccagaacaa acccaaggaa atttcgggga
1621 ccaagaccta atcagacaag gaactgatta caaacattgg ccgcaaattg cacaatttgc
1681 tccaagtgcc tctgcattct ttggaatgtc acgcattggc atggaagccg caccttcggg
1741 aacatggctg acttatcatg gagccattaa attggatgac aaagatccac aattcaaaga
1801 caacgtcata ctgctgaaca agcacattga cgcatacaaa acattcccac caacagagcc
1861 taaaaaggac aaaaagaaaa agactgatga agctcagcct ttgccgcaga gacaaaagaa
1921 gcagcccact gtgactcttc ttcctgcggc tgacatggat gatttctcca gacaacttca
1981 aaattccatg agtggagctt ctgctgattc aactcaggca taaacactca tgatgaccac
2041 acaaggcaga tgggctatgt aaacgttttc gcaattccgt ttacgataca tagtctactc
2101 ttgtgcagaa tgaattctcg taactaaaca gcacaagtag gtttagttaa ctttaatctc
2161 acatagcaat ctttaatcaa tgtgtaacat tagggaggac ttgaaagagc caccacattt
2221 tcatcgaggc cacgcggagt acgatcgagg gtacagtgaa taatgctagg gagagctgcc
2281 tatatggaag agccctaatg tgta
```

Figure 14A 1 caagtctttc aaaaccattg ttgagtcctg cggtaactat aaagttacca agggaaagcc
61 cgtaaaaggt gcttggaaca ttggacaaca gagatcagtt ttaacaccac tgtgtggttt
121 tccctcacag gctgctggtg ttatcagatc aatttttgcg cgcacacttg atgcagcaaa
181 ccactcaatt cctgatttgc aaagagcagc tgtcaccata cttgatggta tttctgaaca
241 gtcattacgt cttgtcgacg ccatggttta tacttcagac ctgctcacca acagtgtcat
301 tattatggca tatgtaactg gtggtcttgt acaacagact tctcagtggt tgtctaatct
361 tttgggcact actgttgaaa aactcaggcc tatctttgaa tggattgagg cgaaacttag
421 tgcaggagtt gaatttctca aggatgcttg ggagattctc aaatttctca ttacaggtgt
481 ttttgacatc gtcaagggtc aaatacaggt tgcttcagat aacatcaagg attgtgtaaa
541 atgcttcatt gatgttgtta acaaggcact cgaaatgtgc attgatcaag tcactatcgc
601 tggcgcaaag ttgcgatcac tcaacttagg tgaagtcttc atcgctcaaa gcaagggact
661 ttaccgtcag tgtatacgtg gcaaggagca gctgcaacta ctcatgcctc ttaaggcacc
721 aaaagaagta acctttcttg aaggtgattc acatgacaca gtacttacct ctgaggaggt
781 tgttctcaag aacggtgaac tcgaagcact cgagacgccc gttgatagct tcacaaatgg
841 agctatcgtt ggcacaccag tctgtgtaaa tggcctcatg ctcttagaga ttaaggacaa
901 agaacaatac tgcgcattgt ctcctggttt actggctaca aacaatgtct ttcgcttaaa
961 agggggtgca ccaattaaag gtgtaacctt tggagaagat actgtttggg aagttcaagg
1021 ttacaagaat gtgagaatca catttgagct tgatgaacgt gttgacaaag tgcttaatga
1081 aaagtgctct gtctacactg ttgaatccgg taccgaagtt actgagtttg catgtgttgt
1141 agcagaggct gttgtgaaga ctttacaacc agtttctgat ctccttacca acatgggtat
1201 tgatcttgat gagtggagtg tagctacatt ctacttattt gatgatgctg gtgaagaaaa
1261 cttttcatca cgtatgtatt gttcctttta ccctccagat gaggaagaag aggacgatgc
1321 agagtgtgag gaagaagaaa ttgatgaaac ctgtgaacat gagtacggta cagaggatga
1381 ttatcaaggt ctccctctgg aatttggtgc ctcagctgaa acagttcgag ttgaggaaga
1441 agaagaggaa gactggctgg atgatactac tgagcaatca gagattgagc cagaaccaga
1501 acctacacct gaagaaccag ttaatcagtt tactggttat ttaaaactta ctgacaatgt
1561 tgccattaaa tgtgttgaca ccgttaagga ggcacaaagt gctaatccta tggtgattgt
1621 aaatgctgct aacatacacc tgaaacatgg tggtggtgta gcaggtgcac tcaacaaggc
1681 aaccaatggt gccatgcaaa aggagagtga tgattacatt aagctaaatg gccctcttac
1741 agtaggaggg tcttgtttgc tttctggaca taatcttgct aagaagtgtc tgcatgttgt
1801 tggacctaac ctaaatgcag gtgaggacat ccagcttctt aaggcagcat atgaaaattt
1861 caattcacag gacatcttac ttgcaccatt gttgtcagca ggcatatttg gtgctaaacc
1921 acttcagtct ttacaagtgt gcgtgcagac ggttcgtaca caggtttata ttgcagtcaa
1981 tgacaaagct ctttatgagc aggttgtcat ggattatctt gataacctga agcctagagt
2041 ggaagcacct aaacaagagg agccaccaaa cacagaagat tccaaaactg aggagaaatc
2101 tgtcgtacag aagcctgtcg atgtgaagcc aaaaaattaag gcctgcattg atgaggttac
2161 cacaacactg gaagaaacta agtttcttac caataagtta ctcttgtttg ctgatatcaa
2221 tggtaagctt taccatgatt ctcagaacat gcttagaggt gaagatatgt ctttccttga
2281 ggaggatgca ccttacatgg taggtgatgt tatcactagt ggtgatatca cttgtgttgt
2341 aataccctcc aaaaaggctg gtggcactac tgagatgctc tcaagagctt tgaagaaagt
2401 gccagttgat gagtatataa ccacgtaccc tggacaagga tgtgctggtt atacacttga
2461 ggaagctaag actgctctta agaaatgcaa atctgcattt tatgtactac cttcagaagc
2521 acctaatgct aaggaagaga ttctaggaac tgtatcctgg aatttgagag aaatgcttgc
2581 tcatgctgaa gaggcaagaa aattaatgcc tatatgcatg gatgttagag ccataatggc
2641 aaccatccaa cgtaagtata aaggagttaa aattcaagag ggcatcgttg actatggtgt
2701 ccgattcttc ttttatacta gtaaagagcc tgtagcttct attattacga agctgaactc
2761 tctaaatgag ccgcttgtca caatgccaat tggttatgtg acacatggtt ttaatcttga
2821 agaggctgcg cgctgtatgc gttctcttaa agctcctgcc gtagtgtcag tatcatcacc
2881 agatgctgtt actacatata atggatacct cacttcgtca tcaaagacat ctgaggagca
2941 ctttgtagaa acagtttctt tggctggctc ttacagagat tggtcctatt caggacagcg
3001 tacagagtta ggtgttgaat ttcttaagcg tggtgacaaa attgtgtacc acaccctgga

Figure 14B

3061 gagccccgtc gagtttcatc ttgacggtga ggttctttca cttgacaaac taaagagtct
3121 cttatccctg cgggaggtta agactataaa agtgttcaca actgtggaca acactaatct
3181 ccacacacag cttgtggata tgtctatgac atatggacag cagtttggtc caacatactt
3241 ggatggtgct gatgttacaa aaattaaacc tcatgtaaat catgagggta agactttctt
3301 tgtactacct agtgatgaca cactacgtag tgaagctttc gagtactacc atactcttga
3361 tgagagtttt cttggtaggt acatgtctgc tttaaaccac acaaagaaat ggaaatttcc
3421 tcaagttggt ggtttaactt caattaaatg ggctgataac aattgttatt tgtctagtgt
3481 tttattagca cttcaacagc ttgaagtcaa attcaatgca ccagcacttc aagagg

FIGURE 15A 1 caaaataatg tgttcatgtc tgaggcaaaa tgttggactg agactgacct tactaaagga
61 cctcacgaat tttgctcaca gcatacaatg ctagttaaac aaggagatga ttacgtgtac
121 ctgccttacc cagatccatc aagaatatta ggcgcaggct gttttgtcga tgatattgtc
181 aaaacagatg gtacacttat gattgaaagg ttcgtgtcac tggctattga tgcttaccca
241 cttacaaaac atcctaatca ggagtatgct gatgtctttc acttgtattt acaatacatt
301 agaaagttac atgatgagct tactggccac atgttggaca tgtattccgt aatgctaact
361 aatgataaca cctcacggta ctgggaacct gagttttatg aggctatgta cacaccacat
421 acagtcttgc aggctgtagg tgcttgtgta ttgtgcaatt cacagacttc acttcgttgc
481 ggtgcctgta ttaggagacc actcctatgt tgcaagtgct gctatgacca tgtcatttca
541 acatcacaca aattagtgtt gtctgttaat ccctatgttt gcaatgcccc aggttgtgat
601 gtcactgatg tgacacaact gtatctagga ggtatgagct attattgcaa gtcacataag
661 cctcccatta gttttccatt atgtgctaat ggtcaggttt ttggtttata caaaaacaca
721 tgtgtaggca gtgacaatgt cactgacttc aatgcgatag caacatgtga ttggactaat
781 gctggcgatt acatacttgc caacacttgt actgagagac tcaagctttt cgcagcagaa
841 acgctcaaag ccactgagga aacatttaag ctgtcatatg gtattgccac tgtacgcgaa
901 gtactctctg acagagaatt gcatctttca tgggaggttg gaaaacctag accaccattg
961 aacagaaact atgtctttac tggttaccgt gtaactaaaa atagtaaagt acagattgga
1021 gagtacacct ttgaaaaagg tgactatggt gatgctgttg tgtacagagg tactacgaca
1081 tacaagttga atgttggtga ttactttgtg ttgacatctc acactgtaat gccacttagt
1141 gcacctactc tagtgccaca agagcactat gtgagaatta ctggcttgta cccaacactc
1201 aacatctcag atgagttttc tagcaatgtt gcaaattatc aaaaggtcgg catgcaaaag
1261 tactctacac tccaaggacc acctggtact ggtaagagtc attttgccat cggacttgct
1321 ctctattacc catctgctcg catagtgtat acggcatgct ctcatgcagc tgttgatgcc
1381 ctatgtgaaa aggcattaaa atatttgccc atagataaat gtagtagaat catacctgcg
1441 cgtgcgcgcg tagagtgttt tgataaattc aaagtgaatt caacactaga acagtatgtt
1501 ttctgcactg taaatgcatt gccagaaaca actgctgaca ttgtagtctt tgatgaaatc
1561 tctatggcta ctaattatga cttgagtgtt gtcaatgcta gacttcgtgc aaaacactac
1621 gtctatattg gcgatcctgc tcaattacca gccccccgca cattgctgac taaaggcaca
1681 ctagaaccag aatattttaa ttcagtgtgc agacttatga aaacaatagg tccagacatg
1741 ttccttggaa cttgtcgccg ttgtcctgct gaaattgttg acactgtgag tgctttagtt
1801 tatgacaata agctaaaagc acacaaggag aagtcagctc aatgcttcaa aatgttctac
1861 aaaggtgtta ttacacatga tgtttcatct gcaatcaaca gacctcaaat aggcgttgta
1921 agagaatttc ttacacgcaa tcctgcttgg agaaaagctg tttttatctc accttataat
1981 tcacagaacg ctgtagcttc aaaaatctta ggattgccta cgcagactgt tgattcatca
2041 cagggttctg aatatgacta tgtcatattc acacaaacta ctgaaacagc acactcttgt
2101 aatgtcaacc gcttcaatgt ggctatcaca agggcaaaaa ttggcatttt gtgcataatg
2161 tctgataggg atctttatga caaactgcaa tttacaagtc tagaaatacc acgtcgcaat
2221 gtggctacat tacaagcaga aaatgtaact ggacttttta aggactgtag taagatcatt
2281 actggtcttc atcctacaca ggcacctaca cacctcagcg ttgatataaa gttcaagact
2341 gaaggattat gtgttgacat accaggcata ccaaaggaca tgacctaccg tagactcatc
2401 tctatgatgg gtttcaaaat gaattaccaa gtcaatggtt accctaatat gtttatcacc
2461 cgcgaagaag ctattcgtca cgttcgtgcg tggattggct ttgatgtaga gggctgtcat
2521 gcaactagag atgctgtggg tactaaccta cctctccagc taggattttc tacaggtgtt
2581 aacttagtag ctgtaccgac tggttatgtt gacactgaaa ataacacaga attcaccaga
2641 gttaatgcaa aacctccacc aggtgaccag tttaaacatc ttataccact catgtataaa
2701 ggcttgccct ggaatgtagt gcgtattaag atagtacaaa tgctcagtga tacactgaaa
2761 ggattgtcag acagagtcgt gttcgtcctt tgggcgcatg gctttgagct tacatcaatg
2821 aagtactttg tcaagattgg acctgaaaga acgtgttgtc tgtgtgacaa acgtgcaact
2881 tgcttttcta cttcatcaga tacttatgcc tgctggaatc attctgtggg ttttgactat
2941 gtctataacc catttatgat tgatgttcag cagtggggct ttacgggtaa ccttcagagt
3001 aaccatgacc aacattgcca ggtacatgga aatgcacatg tggctagttg tgatgctatc

FIGURE 15B 3061 atgactagat gtttagcagt ccatgagtgc tttgttaagc gcgttgattg gtctgttgaa
3121 taccctatta taggagatga actgagggtt aattctgctt gcagaaaagt acaacacatg
3181 gttgtgaagt ctgcattgct tgctgataag tttccagttc ttcatgacat tggaaatcca
3241 aaggctatca agtgtgtgcc tcaggctgaa gtagaatgga agttctacga tgctcagcca
3301 tgtagtgaca aagcttacaa aatagaggaa ctcttctatt cttatgctac acatcacgat
3361 aaattcactg atggtgtttg tttgttttgg aattgtaacg ttgatcgtta cccagccaat
3421 gcaattgtgt gtaggtttga cacaagagtc ttgtcaaact tgaacttacc aggctgtgac
3481 ggtggtagtt tgtatgtgaa taagcatgca ttccacactc cagctttcga taaaagtgca
3541 tttactaatt taaagcaatt gcctttcttt tactattctg atagtccttg tgagtctcat
3601 ggcaaacaag tagtgtcgga tattgattat gttccactca aatctgctac gtgtattaca
3661 cgatgcaatt taggtggtgc tgtttgcaga caccatgcaa atgagtaccg acagtacttg
3721 gatgcatata atatgatgat ttctgctgga tttagcctat ggatttacaa acaatttgat
3781 acttataacc tgtggaatac atttaccagg ttacagagtt tagaaaatgt ggcttataat
3841 gttgttaata aaggacactt tgatggacac gccggcgaag cacctgtttc catcattaat
3901 aatgctgttt acacaaaggt agatggtatt gatgtggaga tctttgaaag taagacaaca
3961 cttcctgtta atgttgcatt tgagctttgg gctaagcgta acattaaacc agtgccagag
4021 attaagatac tcaataattt gggtgttgat atcgctgcta atactgtaat ctgggactac
4081 aaaagagaag ccccagcaca tgtgtctaca ataggtgtct gcacaatgac tgacattgcc
4141 aagaaaccta ctgagagtgc ttgttcttca cttactgtct tgtttgatgg tagagtggaa
4201 ggacaggtag acctttttag aaacgccccgt aatggtgttt taataacaga aggttcagtc
4261 aaaggtctaa caccttcaaa gggaccagca caagctagcg tcaatggagt cacattaatt
4321 ggagaatcag taaaaacaca gtttaactac tttaagaaag tagacggcat tattcaacag
4381 ttgcctgaaa cctactttac tcagagcaga gacttagagg attttaagcc cagatcacaa
4441 atggaaactg actttctcga gctcgctatg gatgaattca tacagcgata taagctcgag
4501 ggctatgcct tcgaacacat cgtttatgga gatttcagtc atggacaact tggcggtctt
4561 catttaatga taggcttagc caagcgctca caagattcac cacttaaatt agaggatttt
4621 atccctatgg acagcacagt gaaaaattac ttcataacag atgcgcaaac aggttcatca
4681 aaatgtgtgc gttctgtgat tgatctttta cttgatgact ttgtcgagat aataaagtca
4741 caagatttgt cagtgatttc aaaagtggtc aaggttacaa ttgactatgc tgaaatttca
4801 ttcatgcttt ggtgtaagga tggacatgtt gaaaccttct acccaaaact acaagcaagt
4861 caagcgtggc aaccaggtgt tgcgatgcct aacttgtaca agatgcaaag aatgcttctt
4921 gaaaagtgtg accttcagaa ttatggtgaa aatgctgtta taccaaaagg aataatgatg
4981 aatgtcgcaa agtatactca actgtgtcaa tacttaaata cacttacttt agctgtaccc
5041 tacaacatga gagttattca ctttggtgct ggctctgata aaggagttgc accaggtaca
5101 gctgtgctca gacaatggtt gccaactggc acactacttg tcgattcaga tcttaatgac
5161 ttcgtctccg acgcagattc tactttaatt ggagactgtg caacagtaca tacggctaat
5221 aaatgggacc ttattattag cgatatgtat gaccctagga cc

FIGURE 16

1 cattacttta tgatgccaac tactttgttt gctggcacac acataactat gactactgta
61 taccatataa cagtgtcaca gatacaattg tcgttactga aggtgacggc atttcaacac
121 caaaactcaa agaagactac caaattggtg gttattctga ggataggcac tcaggtgtta
181 aagactatgt cgttgtacat ggctatttca ccgaagttta ctaccagctt gagtctacac
241 aaattactac aaacactggt attgaaaatg ctacattctt catctttaac aagcttgtta
301 aagacccacc gaatgtgcaa atacacacaa tcgacggctc ttcaggagtt gctaatccag
361 caatggatcc aatttatgat gagccgacga cgactactag cgtgcctttg taagcacaag
421 aaagtgagta cgaacttatg tactcattcg tttcggaaga aacaggtacg ttaatagtta
481 atagcgtact tctttttctt gccttcgtgg tattcttgct agtcacacta gccatcctta
541 ctgcgcttcg attgtgtgcg tactgctgca atattgttaa cgtgagttta gtaaaaccaa
601 cggtttacgt ctactcgcgt gttaaaaatc tgaactctcc tgaaggagtt cctgatcttc
661 tggtctaaac gaactaacta ttattattat tctgtttgga actttaacat tgcttatcat
721 ggcagacaac ggtactatta ccgttgagga gcttaaacaa ctcctggaac aatggaacct
781 agtaataggt ttcctattcc tagcctggat tatgttacta caatttgcct attctaatcg
841 gaacaggttt ttgtacataa taaagcttgt tttcctctgg ctcttgtggc cagtaacact
901 tgcttgtttt gtgcttgctg ctgtctacag aattaattgg gtgactggcg ggattgcgat
961 tgcaatggct tgtattgtag gcttgatgtg gcttagctac ttcgttgctt ccttcaggct
1021 gtttgctcgt acccgctcaa tgtggtcatt caacccggaa acaaacattc ttcccaatgt
1081 gcctctccgg gggacaattg tgaccagacc gctcatggaa agtgaacttg tcattggtgc
1141 tgtgatcatt cgtggtcact tgcgaatggc cggacactcc ctagggcgct gtgacattaa
1201 ggacctgcca aaagagatca ctgtggctac atcacgaacg ctttcttatt acaaattagg
1261 agcgtcgcag cgtgtaggca ctgattcagg ttttgctgca tacaaccgct accgtattgg
1321 aaactataaa ttaaatacag accacgccgg tagcaacgac aatattgctt tgctagtaca
1381 gtaagtgaca acagatgttt catcttgttg acttccaggt tacaatagca gagatattga
1441 ttatcattat gaggactttc aggattgcta tttggaatct tgacgttata ataagttcaa
1501 tagtgagaca attatttaag cctctaacta agaagaatta ttcggagtta gatgatgaag
1561 aacctatgga gttagattat ccataaaacg aacatgaaaa ttattctctt cctgacattg
1621 attgtattta catcttgcga gctatatcac tatcaggagt gtgttagagg tacgactgta
1681 ctactaaaag aaccttgccc atcagcaaca tacgagggca attcaccatt tcaccctctt
1741 gctgacaata aatttgcact aacttgcact agcacacact ttgcttttgc ttgtgctgac
1801 g

FIGURE 17

1 aaagaacctt gcccatcagc aacatacgag ggcaattcac catttcaccc tcttgctgac
61 aataaatttg cactaacttg cactagcaca cactttgctt ttgcttgtgc tgacggtact
121 cgacatacct atcagctgcg tgcaagatca gtttcaccaa aacttttcat cagacaagag
181 gaggttcaac aagagctcta ctcgccactt tttctcattg ttgctgctct agtattttta
241 atactttgct tcaccattaa gagaaagaca gaatgaatga gctcacttta attgacttct
301 atttgtgctt tttagccttt ctgctattcc ttgttttaat aatgcttatt atattttggt
361 tttcactcga aatccaggat ctagaagaac cttgtaccaa agtctaaacg aacatgaaac
421 ttctcattgt tttgacttgt atttctctat gcagttgcat atgcactgta gtacagcgct
481 gtgcatctaa taaacctcat gtgcttgaag atccttgtaa ggtacaacac taggggtaat
541 acttatagca ctgcttggct ttgtgctcta ggaaaggttt taccttttca tagatggcac
601 actatggttc aaacatgcac acctaatgtt actatcaact gtcaagatcc agctggtggt
661 gcgcttatag ctaggtgttg gtaccttcat gaaggtcacc aaactgctgc atttagagac
721 gtacttgttg ttttaaataa acgaacaaat taaaatgtct gataatggac cccaatcaaa
781 ccaacgtagt gcccccgca ttacatttgg tggacccaca gattcaactg acaataacca
841 gaatggagga cgcaatgggg caaggccaaa acagcgccga ccccaaggtt tacccaataa
901 tactgcgtct tggttcacag ctctcactca gcatggcaag gaggaactta gattccctcg
961 aggccagggc gttccaatca acaccaatag tggtccagat gaccaaattg gctactaccg
1021 aagagctacc cgacgagttc gtggtggtga cggcaaaatg aaagagctca gccccagatg
1081 gtacttctat tacctaggaa ctggcccaga agcttcactt ccctacggcg ctaacaaaga
1141 aggcatcgta tgggttgcaa ctgagggagc cttgaataca cccaaagacc acattggcac
1201 ccgcaatcct aataacaatg ctgccaccgt gctacaactt cctcaaggaa caacattgcc
1261 aaaaggcttc tacgcagagg gaagcagagg cggcagtcaa gcctcttctc gctcctcatc
1321 acgtagtcgc ggtaattcaa gaaattcaac tcctggcagc agtaggggaa attctcctgc
1381 tcgaatggct agcggaggtg gtgaaactgc cctcgcgcta ttgctgctag acagattgaa
1441 ccagcttgag agcaaagttt ctggtaaagg ccaacaacaa caaggccaaa ctgtcactaa
1501 gaaatctgct gctgaggcat ctaaaaagcc tcgccaaaaa cgtacagcca caaaacagta
1561 caacgtcact caagcatttg ggagacgtgg tccagaacaa acccaaggaa atttcgggga
1621 ccaagaccta atcagacaag gaactgatta caaacattgg ccgcaaattg cacaatttgc
1681 tccaagtgcc tctgcattct ttggaatgtc acgcattggc atggaagccg caccttcggg
1741 aacatggctg acttatcatg gagccattaa attggatgac aaagatccac aattcaaaga
1801 caacgtcata ctgctgaaca agcacattga cgcatacaaa acattcccac caacagagcc
1861 taaaaaggac aaaaagaaaa agactgatga agctcagcct ttgccgcaga gacaaaagaa
1921 gcagcccact gtgactcttc ttcctgcggc tgacatggat gatttctcca gacaacttca
1981 aaattccatg agtggagctt ctgctgattc aactcaggca taaacactca tgatgaccac
2041 acaaggcaga tgggctatgt aaacgttttc gcaattccgt ttacgataca tagtctactc
2101 ttgtgcagaa tgaattctcg taactaaaca gcacaagtag gtttagttaa ctttaatctc
2161 acatagcaat ctttaatcaa tgtgtaacat tagggaggac ttgaaagagc caccacattt
2221 tcatcgaggc cacgcggagt acgatcgagg gtacagtgaa taatgctagg gagagctgcc
2281 tatatggaag agccctaatg tgta

FIGURE 18A 1 caagtctttc aaaaccattg ttgagtcctg cggtaactat aaagttacca agggaaagcc
61 cgtaaaaggt gcttggaaca ttggacaaca gagatcagtt ttaacaccac tgtgtggttt
121 tccctcacag gctgctggtg ttatcagatc aatttttgcg cgcacacttg atgcagcaaa
181 ccactcaatt cctgatttgc aaagagcagc tgtcaccata cttgatggta tttctgaaca
241 gtcattacgt cttgtcgacg ccatggttta tacttcagac ctgctcacca acagtgtcat
301 tattatggca tatgtaactg gtggtcttgt acaacagact tctcagtggt tgtctaatct
361 tttgggcact actgttgaaa aactcaggcc tatctttgaa tggattgagg cgaaacttag
421 tgcaggagtt gaatttctca aggatgcttg ggagattctc aaatttctca ttacaggtgt
481 ttttgacatc gtcaagggtc aaatacaggt tgcttcagat aacatcaagg attgtgtaaa
541 atgcttcatt gatgttgtta acaaggcact cgaaatgtgc attgatcaag tcactatcgc
601 tggcgcaaag ttgcgatcac tcaacttagg tgaagtcttc atcgctcaaa gcaagggact
661 ttaccgtcag tgtatacgtg gcaaggagca gctgcaacta ctcatgcctc ttaaggcacc
721 aaaagaagta acctttcttg aaggtgattc acatgacaca gtacttacct ctgaggaggt
781 tgttctcaag aacggtgaac tcgaagcact cgagacgccc gttgatagct tcacaaatgg
841 agctatcgtt ggcacaccag tctgtgtaaa tggcctcatg ctcttagaga ttaaggacaa
901 agaacaatac tgcgcattgt ctcctggttt actggctaca aacaatgtct ttcgcttaaa
961 agggggtgca ccaattaaag gtgtaacctt tggagaagat actgtttggg aagttcaagg
1021 ttacaagaat gtgagaatca catttgagct tgatgaacgt gttgacaaag tgcttaatga
1081 aaagtgctct gtctacactg ttgaatccgg taccgaagtt actgagtttg catgtgttgt
1141 agcagaggct gttgtgaaga ctttacaacc agtttctgat ctccttacca acatgggtat
1201 tgatcttgat gagtggagtg tagctacatt ctacttattt gatgatgctg gtgaagaaaa
1261 cttttcatca cgtatgtatt gttcctttta ccctccagat gaggaagaag aggacgatgc
1321 agagtgtgag gaagaagaaa ttgatgaaac ctgtgaacat gagtacggta cagaggatga
1381 ttatcaaggt ctccctctgg aatttggtgc ctcagctgaa acagttcgag ttgaggaaga
1441 agaagaggaa gactggctgg atgatactac tgagcaatca gagattgagc cagaaccaga
1501 acctacacct gaagaaccag ttaatcagtt tactggttat ttaaaactta ctgacaatgt
1561 tgccattaaa tgtgttgaca ccgttaagga ggcacaaagt gctaatccta tggtgattgt
1621 aaatgctgct aacatacacc tgaaacatgg tggtggtgta gcaggtgcac tcaacaaggc
1681 aaccaatggt gccatgcaaa aggagagtga tgattacatt aagctaaatg gccctcttac
1741 agtaggaggg tcttgtttgc tttctggaca taatcttgct aagaagtgtc tgcatgttgt
1801 tggacctaac ctaaatgcag gtgaggacat ccagcttctt aaggcagcat atgaaaattt
1861 caattcacag gacatcttac ttgcaccatt gttgtcagca ggcatatttg gtgctaaacc
1921 acttcagtct ttacaagtgt gcgtgcagac ggttcgtaca caggtttata ttgcagtcaa
1981 tgacaaagct ctttatgagc aggttgtcat ggattatctt gataacctga agcctagagt
2041 ggaagcacct aaacaagagg agccaccaaa cacagaagat tccaaaactg aggagaaatc
2101 tgtcgtacag aagcctgtcg atgtgaagcc aaaaattaag gcctgcattg atgaggttac
2161 cacaacactg gaagaaacta agtttcttac caataagtta ctcttgtttg ctgatatcaa
2221 tggtaagctt taccatgatt ctcagaacat gcttagaggt gaagatatgt ctttccttga
2281 ggaggatgca ccttacatgg taggtgatgt tatcactagt ggtgatatca cttgtgttgt
2341 aataccctcc aaaaaggctg gtggcactac tgagatgctc tcaagagctt tgaagaaagt
2401 gccagttgat gagtatataa ccacgtaccc tggacaagga tgtgctggtt atacacttga
2461 ggaagctaag actgctctta agaaatgcaa atctgcattt tatgtactac cttcagaagc
2521 acctaatgct aaggaagaga ttctaggaac tgtatcctgg aatttgagag aaatgcttgc
2581 tcatgctgaa gaggcaagaa aattaatgcc tatatgcatg gatgttagag ccataatggc

FIGURE 18B 2641 aaccatccaa cgtaagtata aaggagttaa aattcaagag ggcatcgttg actatggtgt
2701 ccgattcttc ttttatacta gtaaagagcc tgtagcttct attattacga agctgaactc
2761 tctaaatgag ccgcttgtca caatgccaat tggttatgtg acacatggtt ttaatcttga
2821 agaggctgcg cgctgtatgc gttctcttaa agctcctgcc gtagtgtcag tatcatcacc
2881 agatgctgtt actacatata atggatacct cacttcgtca tcaaagacat ctgaggagca
2941 ctttgtagaa acagtttctt tggctggctc ttacagagat tggtcctatt caggacagcg
3001 tacagagtta ggtgttgaat ttcttaagcg tggtgacaaa attgtgtacc acaccctgga
3061 gagccccgtc gagtttcatc ttgacggtga ggttctttca cttgacaaac taaagagtct
3121 cttatccctg cgggaggtta agactataaa agtgttcaca actgtggaca acactaatct
3181 ccacacacag cttgtggata tgtctatgac atatggacag cagtttggtc caacatactt
3241 ggatggtgct gatgttacaa aaattaaacc tcatgtaaat catgagggta agactttctt
3301 tgtactacct agtgatgaca cactacgtag tgaagctttc gagtactacc atactcttga
3361 tgagagtttt cttggtaggt acatgtctgc tttaaaccac acaaagaaat ggaaatttcc
3421 tcaagttggt ggtttaactt caattaaatg ggctgataac aattgttatt tgtctagtgt
3481 tttattagca cttcaacagc ttgaagtcaa attcaatgca ccagcacttc aagagg

FIGURE 19

1 cattacttta tgatgccaac tactttgttt gctggcacac acataactat gactactgta
61 taccatataa cagtgtcaca gatacaattg tcgttactga aggtgacggc atttcaacac
121 caaaactcaa agaagactac caaattggtg gttattctga ggataggcac tcaggtgtta
181 aagactatgt cgttgtacat ggctatttca ccgaagttta ctaccagctt gagtctacac
241 aaattactac aaacactggt attgaaaatg ctacattctt catctttaac aagcttgtta
301 aagacccacc gaatgtgcaa atacacacaa tcgacggctc ttcaggagtt gctaatccag
361 caatggatcc aatttatgat gagccgacga cgactactag cgtgcctttg taagcacaag
421 aaagtgagta cgaacttatg tactcattcg tttcggaaga aacaggtacg ttaatagtta
481 atagcgtact tctttttctt gccttcgtgg tattcttgct agtcacacta gccatcctta
541 ctgcgcttcg attgtgtgcg tactgctgca atattgttaa cgtgagttta gtaaaaccaa
601 cggtttacgt ctactcgcgt gttaaaaatc tgaactctcc tgaaggagtt cctgatcttc
661 tggtctaaac gaactaacta ttattattat tctgtttgga actttaacat tgcttatcat
721 ggcagacaac ggtactatta ccgttgagga gcttaaacaa ctcctggaac aatggaacct
781 agtaataggt ttcctattcc tagcctggat tatgttacta caatttgcct attctaatcg
841 gaacaggttt ttgtacataa taaagcttgt tttcctctgg ctcttgtggc cagtaacact
901 tgcttgtttt gtgcttgctg ctgtctacag aattaattgg gtgactggcg ggattgcgat
961 tgcaatggct tgtattgtag gcttgatgtg gcttagctac ttcgttgctt ccttcaggct
1021 gtttgctcgt acccgctcaa tgtggtcatt caacccggaa acaaacattc ttcccaatgt
1081 gcctctccgg gggacaattg tgaccagacc gctcatggaa agtgaacttg tcattggtgc
1141 tgtgatcatt cgtggtcact tgcgaatggc cggacactcc ctagggcgct gtgacattaa
1201 ggacctgcca aaagagatca ctgtggctac atcacgaacg ctttcttatt acaaattagg
1261 agcgtcgcag cgtgtaggca ctgattcagg ttttgctgca tacaaccgct accgtattgg
1321 aaactataaa ttaaatacag accacgccgg tagcaacgac aatattgctt tgctagtaca
1381 gtaagtgaca acagatgttt catcttgttg acttccaggt tacaatagca gagatattga
1441 ttatcattat gaggactttc aggattgcta tttggaatct tgacgttata ataagttcaa
1501 tagtgagaca attatttaag cctctaacta agaagaatta ttcggagtta gatgatgaag
1561 aacctatgga gttagattat ccataaaacg aacatgaaaa ttattctctt cctgacattg
1621 attgtattta catcttgcga gctatatcac tatcaggagt gtgttagagg tacgactgta
1681 ctactaaaag aaccttgccc atcagcaaca tacgagggca attcaccatt tcaccctctt
1741 gctgacaata aatttgcact aacttgcact agcacacact ttgcttttgc ttgtgctgac
1801 g

FIGURE 20

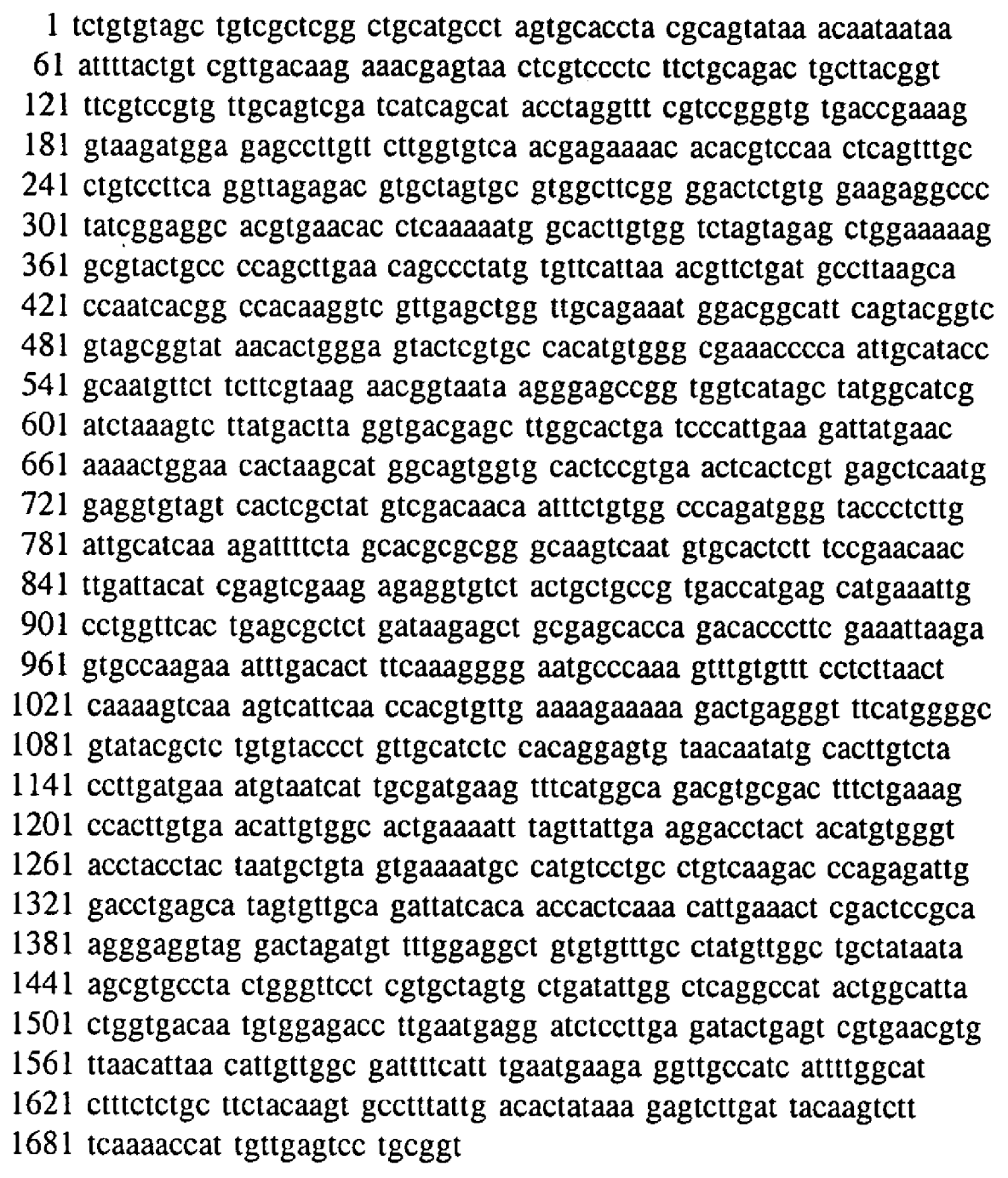

1 tctgtgtagc tgtcgctcgg ctgcatgcct agtgcaccta cgcagtataa acaataataa
61 attttactgt cgttgacaag aaacgagtaa ctcgtccctc ttctgcagac tgcttacggt
121 ttcgtccgtg ttgcagtcga tcatcagcat acctaggttt cgtccgggtg tgaccgaaag
181 gtaagatgga gagccttgtt cttggtgtca acgagaaaac acacgtccaa ctcagtttgc
241 ctgtccttca ggttagagac gtgctagtgc gtggcttcgg ggactctgtg gaagaggccc
301 tatcggaggc acgtgaacac ctcaaaaatg gcacttgtgg tctagtagag ctggaaaaag
361 gcgtactgcc ccagcttgaa cagccctatg tgttcattaa acgttctgat gccttaagca
421 ccaatcacgg ccacaaggtc gttgagctgg ttgcagaaat ggacggcatt cagtacggtc
481 gtagcggtat aacactggga gtactcgtgc cacatgtggg cgaaacccca attgcatacc
541 gcaatgttct tcttcgtaag aacggtaata agggagccgg tggtcatagc tatggcatcg
601 atctaaagtc ttatgactta ggtgacgagc ttggcactga tcccattgaa gattatgaac
661 aaaactggaa cactaagcat ggcagtggtg cactccgtga actcactcgt gagctcaatg
721 gaggtgtagt cactcgctat gtcgacaaca atttctgtgg cccagatggg taccctcttg
781 attgcatcaa agattttcta gcacgcgcgg gcaagtcaat gtgcactctt tccgaacaac
841 ttgattacat cgagtcgaag agaggtgtct actgctgccg tgaccatgag catgaaattg
901 cctggttcac tgagcgctct gataagagct gcgagcacca gacacccttc gaaattaaga
961 gtgccaagaa atttgacact ttcaaagggg aatgcccaaa gtttgtgttt cctcttaact
1021 caaaagtcaa agtcattcaa ccacgtgttg aaaagaaaaa gactgagggt ttcatggggc
1081 gtatacgctc tgtgtaccct gttgcatctc cacaggagtg taacaatatg cacttgtcta
1141 ccttgatgaa atgtaatcat tgcgatgaag tttcatggca gacgtgcgac tttctgaaag
1201 ccacttgtga acattgtggc actgaaaatt tagttattga aggacctact acatgtgggt
1261 acctacctac taatgctgta gtgaaaatgc catgtcctgc ctgtcaagac ccagagattg
1321 gacctgagca tagtgttgca gattatcaca accactcaaa cattgaaact cgactccgca
1381 agggaggtag gactagatgt tttggaggct gtgtgtttgc ctatgttggc tgctataata
1441 agcgtgccta ctgggttcct cgtgctagtg ctgatattgg ctcaggccat actggcatta
1501 ctggtgacaa tgtggagacc ttgaatgagg atctccttga gatactgagt cgtgaacgtg
1561 ttaacattaa cattgttggc gattttcatt tgaatgaaga ggttgccatc attttggcat
1621 ctttctctgc ttctacaagt gcctttattg acactataaa gagtcttgat tacaagtctt
1681 tcaaaaccat tgttgagtcc tgcggt

FIGURE 21 (A)

1 agtgttttat tagcacttca acagcttgaa gtcaaattca atgcaccagc acttcaagag
61 gcttattata gagcccgtgc tggtgatgct gctaactttt gtgcactcat actcgcttac
121 agtaataaaa ctgttggcga gcttggtgat gtcagagaaa ctatgaccca tcttctacag
181 catgctaatt tggaatctgc aaagcgagtt cttaatgtgg tgtgtaaaca ttgtggtcag
241 aaaactacta ccttaacggg tgtagaagct gtgatgtata tgggtactct atcttatgat
301 aatcttaaga caggtgtttc cattccatgt gtgtgtggtc gtgatgctac acaatatcta
361 gtacaacaag agtcttcttt tgttatgatg tctgcaccac ctgctgagta taaattacag
421 caaggtacat tcttatgtgc gaatgagtac actggtaact atcagtgtgg tcattacact
481 catataactg ctaaggagac cctctatcgt attgacggag ctcaccttac aaagatgtca
541 gagtacaaag gaccagtgac tgatgttttc tacaaggaaa catcttacac tacaaccatc
601 aagcctgtgt cgtataaact cgatggagtt acttacacag agattgaacc aaaattggat
661 gggtattata aaaggataa tgcttactat acagagcagc ctatagacct tgtaccaact
721 caaccattac caaatgcgag ttttgataat ttcaaactca catgttctaa cacaaaattt
781 gctgatgatt taaatcaaat gacaggcttc acaaagccag cttcacgaga gctatctgtc
841 acattcttcc cagacttgaa tggcgatgta gtggctattg actatagaca ctattcagcg
901 agtttcaaga aaggtgctaa attactgcat aagccaattg tttggcacat taaccaggct
961 acaaccaaga caacgttcaa accaaacact tggtgtttac gttgtctttg gagtacaaag
1021 ccagtagata cttcaaattc atttgaagtt ctggcagtag aagacacaca aggaatggac
1081 aatcttgctt gtgaaagtca acaacccacc tctgaagaag tagtggaaaa tcctaccata
1141 cagaaggaag tcatagagtg tgacgtgaaa actaccgaag ttgtaggcaa tgtcatactt
1201 aaaccatcag atgaaggtgt taaagtaaca caagagttag gtcatgagga tcttatggct
1261 gcttatgtgg aaaacacaag cattaccatt aagaaaccta atgagctttc actagcctta
1321 ggtttaaaaa caattgccac tcatggtatt gctgcaatta atagtgttcc ttggagtaaa
1381 attttggctt atgtcaaacc attcttagga caagcagcaa ttacaacatc aaattgcgct
1441 aagagattag cacaacgtgt gtttaacaat tatatgcctt atgtgtttac attattgttc
1501 caattgtgta cttttactaa aagtaccaat tctagaatta gagcttcact acctacaact
1561 attgctaaaa atagtgttaa gagtgttgct aaattatgtt tggatgccgg cattaattat
1621 gtgaagtcac ccaaattttc taaattgttc acaatcgcta tgtggctatt gttgttaagt
1681 atttgcttag gttctctaat ctgtgtaact gctgcttttg gtgtactctt atctaatttt
1741 ggtgctcctt cttattgtaa tggcgttaga gaattgtatc ttaattcgtc taacgttact
1801 actatggatt tctgtgaagg ttcttttcct tgcagcattt gtttaagtgg attagactcc
1861 cttgattctt atccagctct tgaaaccatt caggtgacga tttcatcgta caagctagac
1921 ttgacaattt taggtctggc cgctgagtgg gttttggcat atatgttgtt cacaaaattc
1981 ttttatttat taggtctttc agctataatg caggtgttct ttggctattt tgctagtcat
2041 ttcatcagca attcttggct catgtggttt atcattagta ttgtacaaat ggcacccgtt
2101 tctgcaatgg ttaggatgta catcttcttt gcttctttct actacatatg gaagagctat
2161 gttcatatca tggatggttg cacctcttcg acttgcatga tgtgctataa gcgcaatcgt
2221 gccacacgcg ttgagtgtac aactattgtt aatggcatga agagatcttt ctatgtctat
2281 gcaaatggag gccgtggctt ctgcaagact cacaattgga attgtctcaa ttgtgacaca
2341 ttttgcactg gtagtacatt cattagtgat gaagttgctc gtgatttgtc actccagttt
2401 aaaagaccaa tcaaccctac tgaccagtca tcgtatattg ttgatagtgt tgctgtgaaa
2461 aatggcgcgc ttcacctcta ctttgacaag gctggtcaaa agacctatga gagacatccg
2521 ctctcccatt ttgtcaattt agacaatttg agagctaaca acactaaagg ttcactgcct
2581 attaatgtca tagtttttga tggcaagtcc aaatgcgacg agtctgcttc taagtctgct
2641 tctgtgtact acagtcagct gatgtgccaa cctattctgt tgcttgacca agctcttgta
2701 tcagacgttg gagatagtac tgaagtttcc gttaagatgt ttgatgctta tgtcgacacc
2761 ttttcagcaa cttttagtgt tcctatggaa aaacttaagg cacttgttgc tacagctcac
2821 agcgagttag caaagggtgt agctttagat ggtgtccttt ctacattcgt gtcagctgcc
2881 cgacaaggtg ttgttgatac cgatgttgac acaaaggatg ttattgaatg tctcaaactt
2941 tcacatcact ctgacttaga agtgacaggt gacagttgta acaatttcat gctcacctat
3001 aataaggttg aaaacatgac gcccagagat cttggcgcat gtattgactg taatgcaagg

FIGURE 21 (B)

3061 catatcaatg cccaagtagc aaaaagtcac aatgtttcac tcatctggaa tgtaaaagac
3121 tacatgtctt tatctgaaca gctgcgtaaa caaattcgta gtgctgccaa gaagaacaac
3181 ataccttta gactaacttg tgctacaact agacaggttg tcaatgtcat aactactaaa
3241 atctcactca agggtggtaa gattgttagt acttgtttta aacttatgct taaggccaca
3301 ttattgtgcg ttcttgctgc attggtttgt tatatcgtta tgccagtaca tacattgtca
3361 atccatgatg gttacacaaa tgaaatcatt ggttacaaag ccattcagga tggtgtcact
3421 cgtgacatca tttctactga tgattgtttt gcaaataaac atgctggttt tgacgcatgg
3481 tttagccagc gtggtggttc atacaaaaat gacaaaagct gccctgtagt agctgctatc
3541 attacaagag agattggttt catagtgcct ggcttaccgg gtactgtgct gagagcaatc
3601 aatggtgact tcttgcattt tctacctcgt gtttttagtg ctgttggcaa catttgctac
3661 acaccttcca aactcattga gtatagtgat tttgctacct ctgcttgcgt tcttgctgct
3721 gagtgtacaa tttttaagga tgctatgggc aaacctgtgc catattgtta tgacactaat
3781 ttgctagagg gttctatttc ttatagtgag cttcgtccag acactcgtta tgtgcttatg
3841 gatggttcca tcatacagtt tcctaacact tacctggagg gttctgttag agtagtaaca
3901 acttttgatg ctgagtactg tagacatggt acatgcgaaa ggtcagaagt aggtatttgc
3961 ctatctacca gtggtagatg ggttcttaat aatgagcatt acagagctct atcaggagtt
4021 ttctgtggtg ttgatgcgat gaatctcata gctaacatct ttactcctct tgtgcaacct
4081 gtgggtgctt tagatgtgtc tgcttcagta gtggctggtg gtattattgc catattggtg
4141 acttgtgctg cctactactt tatgaaattc agacgtgttt ttggtgagta caaccatgtt
4201 gttgctgcta atgcactttt gtttttgatg tctttcacta tactctgtct ggtaccagct
4261 tacagctttc tgccgggagt ctactcagtc ttttacttgt acttgacatt ctatttcacc
4321 aatgatgttt cattcttggc tcaccttcaa tggtttgcca tgttttctcc tattgtgcct
4381 ttttggataa cagcaatcta tgtattctgt atttctctga agcactgcca ttggttcttt
4441 aacaactatc ttaggaaaag agtcatgttt aatggagtta catttagtac cttcgaggag
4501 gctgctttgt gtaccttttt gctcaacaag gaaatgtacc taaaattgcg tagcgagaca
4561 ctgttgccac ttacacagta taacaggtat cttgctctat ataacaagta caagtatttc
4621 agtggagcct tagatactac cagctatcgt gaagcagctt gctgccactt agcaaaggct
4681 ctaaatgact ttagcaactc aggtgctgat gttctctacc aaccaccaca gacatcaatc
4741 acttctgctg ttctgcagag tggttttagg aaaatggcat tcccgtcagg caaagttgaa
4801 gggtgcatgg tacaagtaac ctgtggaact acaactctta atggattgtg gttggatgac
4861 acagtatact gtccaagaca tgtcatttgc acagcagaag acatgcttaa tcctaactat
4921 gaagatctgc tcattcgcaa atccaaccat agctttcttg ttcaggctgg caatgttcaa
4981 cttcgtgtta ttggccattc tatgcaaaat tgtctgctta ggcttaaagt tgatacttct
5041 aaccctaaga cacccaagta taaatttgtc cgtatccaac ctggtcaaac attttcagtt
5101 ctagcatgct acaatggttc accatctggt gtttatcagt gtgccatgag acctaatcat
5161 accattaaag gttctttcct taatggatca tgtggtagtg ttggttttaa cattgattat
5221 gattgcgtgt ctttctgcta tatgcatcat atggagcttc caacaggagt acacgctggt
5281 accgacttag aaggtaaatt ctatggtcca tttgttgaca gacaaactgc acaggctgca
5341 ggtacagaca caaccataac attaaatgtt ttggcatggc tgtatgctgc tgttatcaat
5401 ggtgataggt ggtttcttaa tagattcacc actactttga atgactttaa ccttgtggca
5461 atgaagtaca actatgaacc tttgacacaa gatcatgttg acatattggg acctctttct
5521 gctcaaacag gaattgccgt cttagatatg tgtgctgctt tgaaagagct gctgcagaat
5581 ggtatgaatg gtcgtactat ccttggtagc actattttag aagatgagtt tacaccattt
5641 gatgttgtta gacaatgctc tggtgttacc ttccaaggta agttcaagaa aattgttaag
5701 ggcactcatc attggatgct tttaactttc ttgacatcac tattgattct tgttcaaagt
5761 acacagtggt cactgttttt ctttgtttac gagaatgctt tcttgccatt tactcttggt
5821 attatggcaa ttgctgcatg tgctatgctg cttgttaagc ataagcacgc attcttgtgc
5881 ttgtttctgt taccttctct tgcaacagtt gcttacttta atatggtcta catgcctgct
5941 agctgggtga tgcgtatcat gacatggctt gaattggctg acactagctt gtctggttat
6001 aggcttaagg attgtgttat gtatgcttca gctttagttt tgcttattct catgacagct
6061 cgcactgttt atgatgatgc tgctagacgt gtttggacac tgatgaatgt cattacactt

FIGURE 21 (C)

6121 gtttacaaag tctactatgg taatgcttta gatcaagcta tttccatgtg ggccttagtt
6181 atttctgtaa cctctaacta ttctggtgtc gttacgacta tcatgttttt agctagagct
6241 atagtgtttg tgtgtgttga gtattatcca ttgttattta ttactggcaa caccttacag
6301 tgtatcatgc ttgtttattg tttcttaggc tattgttgct gctgctactt tggccttttc
6361 tgtttactca accgttactt caggcttact cttggtgttt atgactactt ggtctctaca
6421 caagaattta ggtatatgaa ctcccagggg cttttgcctc ctaagagtag tattgatgct
6481 ttcaagctta acattaagtt gttgggtatt ggaggtaaac catgtatcaa ggttgctact
6541 gtacagtcta aaatgtctga cgtaaagtgc acatctgtgg tactgctctc ggttcttcaa
6601 caacttagag tagagtcatc ttctaaattg tgggcacaat gtgtacaact ccacaatgat
6661 attcttcttg caaaagacac aactgaagct ttcgagaaga tggtttctct tttgtctgtt
6721 ttgctatcca tgcagggtgc tgtagacatt aataggttgt gcgaggaaat gctcgataac
6781 cgtgctactc ttcaggctat tgcttcagaa tttagttctt taccatcata tgccgcttat
6841 gccactgccc aggaggccta tgagcaggct gtagctaatg gtgattctga agtcgttctc
6901 aaaaagttaa agaaatcttt gaatgtggct aaatctgagt ttgaccgtga tgctgccatg
6961 caacgcaagt tggaaaagat ggcagatcag gctatgaccc aaatgtacaa acaggcaaga
7021 tctgaggaca agagggccca agtcgcttct gctatgcaaa caatgctctt cactatgcta
7081 aggaagcttg ataatgatgc acttaacaac attatcaaca atgcgcgtga tggttgtgtt
7141 ccactcaaca tcataccatt gactacagca gccaaactca tggttgttgt ccctgattat
7201 ggtacctaca agaacacttg tgatggtaac acctttacat atgcatctgc actctgggaa
7261 atccagcaag ttgttgatgc ggatagcaag attgttcaac ttagtgaaat taacatggac
7321 aattcaccaa atttggcttg gcctcttatt gttacagctc taagagccaa ctcagctgtt
7381 aaactacaga ataatgaact gagtccagta gcactacgac agatgtcctg tgcggctggt
7441 accacacaaa cagcttgtac tgatgacaat gcacttgcct actataacaa ttcgaaggga
7501 ggtaggtttg tgctggcatt actatcagac caccaagatc tcaaatgggc tagattccct
7561 aagagtgatg gtacaggtac aatttacaca gaactggaac caccttgtag gtttgttaca
7621 gacacaccaa aagggcctaa agtgaaatac ttgtacttca tcaaaggctt aaacaaccta
7681 aatagaggta tggtgctggg cagtttagct gctacagtac gtcttcaggc tggaaatgct
7741 acagaagtac ctgccaattc aactgtgctt tccttctgtg cttttgcagt agaccctgct
7801 aaagcatata aggattacct agcaagtgga ggacaaccaa tcaccaactg tgtgaagatg
7861 ttgtgtacac acactggtac aggacaggca attactgtaa caccagaagc taacatggac
7921 caagagtcct ttggtggtgc ttcatgttgt ctgtattgta gatgccacat tgaccatcca
7981 aatcctaaag gattctgtga cttgaaaggt aagtacgtcc aaatacctac cacttgtgct
8041 aatgacccag tgggttttac acttagaaac acagtctgta ccgtctgcgg aatgtggaaa
8101 ggttatggct gtagttgtga ccaactccgc gaacccttga tgcagtctgc ggatgcatca
8161 acgtttttaa acgggtttgc ggtgtaagtg cagcccgtct tacaccgtgc ggcacaggca
8221 ctagtactga tgtcgtctac agggcttttg atatttacaa cgaaaaagtt gctggttttg
8281 caaagttcct aaaaactaat tgctgtcgct tccaggagaa ggatgaggaa ggcaatttat
8341 tagactctta ctttgtagtt aagaggcata ctatgtctaa ctaccaacat gaagagacta
8401 tttataactt ggttaaagat tgtccagcgg ttgctgtcca tgactttttc aagtttagag
8461 tagatggtga catggtacca catatatcac gtcagcgtct aactaaatac acaatggctg
8521 atttagtcta tgctctacgt cattttgatg agggtaattg tgatacatta aaagaaatac
8581 tcgtcacata caattgctgt gatgatgatt atttcaataa gaaggattgg tatgacttcg
8641 tagagaatcc tgacatctta cgcgtatatg ctaacttagg tgagcgtgta cgccaatcat
8701 tattaaagac tgtacaattc tgcgatgcta tgcgtgatgc aggcattgta ggcgtactga
8761 cattagataa tcaggatctt aatgggaact ggtacgattt cggtgatttc gtacaagtag
8821 caccaggctg cggagttcct attgtggatt catattactc attgctgatg cccatcctca
8881 ctttgactag ggcattggct gctgagtccc atatggatgc tgatctcgca aaaccactta
8941 ttaagtggga tttgctgaaa tatgatttta cggaagagag actttgtctc ttcgaccgtt
9001 attttaaata ttgggaccag acataccatc ccaattgtat taactgtttg gatgataggt
9061 gtatccttca ttgtgcaaac tttaatgtgt tattttctac tgtgtttcca cctacaagtt
9121 ttggaccact agtaagaaaa atatttgtag atggtgttcc ttttgttgtt tcaactggat
9181 accattttcg tgagttagga gtcgtacata atcaggatgt aaacttacat agctcgcgtc

FIGURE 21 (D)

9241 tcagtttcaa ggaactttta gtgtatgctg ctgatccagc tatgcatgca gcttctggca
9301 atttattgct agataaacgc actacatgct tttcagtagc tgcactaaca aacaatgttg
9361 cttttcaaac tgtcaaaccc ggtaatttta ataaagactt ttatgacttt gctgtgtcta
9421 aaggtttctt taaggaagga agttctgttg aactaaaaca cttcttcttt gctcaggatg
9481 gcaacgctgc tatcagtgat tatgactatt atcgttataa tctgccaaca atgtgtgata
9541 tcagacaact cctattcgta gttgaagttg ttgataaata ctttgattgt tacgatggtg
9601 gctgtattaa tgccaaccaa gtaatcgtta acaatctgga taaatcagct ggtttcccat
9661 ttaataaatg gggtaaggct agactttatt atgactcaat gagttatgag gatcaagatg
9721 cacttttcgc gtatactaag cgtaatgtca tccctactat aactcaaatg aatcttaagt
9781 atgccattag tgcaaagaat agagctcgca ccgtagctgg tgtctctatc tgtagtacta
9841 tgacaaatag acagtttcat cagaaattat tgaagtcaat agccgccact agaggagcta
9901 ctgtggtaat tggaacaagc aagttttacg gtggctggca taatatgtta aaaactgttt
9961 acagtgatgt agaaactcca caccttatgg gttgggatta tccaaaatgt gacagagcca
10021 tgcctaacat gcttaggata atggcctctc ttgttcttgc tcgcaaacat aacacttgct
10081 gtaacttatc acaccgtttc tacaggttag ctaacgagtg tgcgcaagta ttaagtgaga
10141 tggtcatgtg tggcggctca ctatatgtta aaccaggtgg aacatcatcc ggtgatgcta
10201 caactgctta tgctaatagt gtctttaaca tttgtcaagc tgttacagcc aatgtaaatg
10261 cacttctttc aactgatggt aataagatag ctgacaagta tgtccgcaat ctacaacaca
10321 ggctctatga gtgtctctat agaaataggg atgttgatca tgaattcgtg gatgagtttt
10381 acgcttacct gcgtaaacat ttctccatga tgattctttc tgatgatgcc gttgtgtgct
10441 ataacagtaa ctatgcggct caaggtttag tagctagcat taagaacttt aaggcagttc
10501 tttattatca aaataatgtg ttcatgtctg aggcaaaatg ttggac

FIGURE 22

1 gtaccttcat gaaggtcacc aaactgctgc atttagagac gtacttgttg ttttaaataa
61 acgaacaaat taaaatgtct gataatggac cccaatcaaa ccaacgtagt gccccccgca
121 ttacatttgg tggacccaca gattcaactg acaataacca gaatggagga cgcaatgggg
181 caaggccaaa acagcgccga ccccaaggtt tacccaataa tactgcgtct tggttcacag
241 ctctcactca gcatggcaag gaggaactta gattccctcg aggccagggc gttccaatca
301 acaccaatag tggtccagat gaccaaattg gctactaccg aagagctacc cgacgagttc
361 gtggtggtga cggcaaaatg aaagagctca gccccagatg gtacttctat tacctaggaa
421 ctggcccaga agcttcactt ccctacggcg ctaacaaaga aggcatcgta tgggttgcaa
481 ctgagggagc cttgaataca cccaaagacc acattggcac ccgcaatcct aataacaatg
541 ctgccaccgt gctacaactt cctcaaggaa caacattgcc aaaaggcttc tacgcagagg
601 gaagcagagg cggcagtcaa gcctcttctc gctcctcatc acgtagtcgc ggtaattcaa
661 gaaattcaac tcctggcagc agtaggggaa attctcctgc tcgaatggct agcggaggtg
721 gtgaaactgc cctcgcgcta ttgctgctag acagattgaa ccagcttgag agcaaagttt
781 ctggtaaagg ccaacaacaa caaggccaaa ctgtcactaa gaaatctgct gctgaggcat
841 ctaaaaagcc tcgccaaaaa cgtactgcca caaaacagta caacgtcact caagcatttg
901 ggagacgtgg tccagaacaa acccaaggaa atttcgggga ccaagaccta atcagacaag
961 gaactgatta caaacattgg ccgcaaattg cacaatttgc tccaagtgcc tctgcattct
1021 ttggaatgtc acgcattggc atggaagtca caccttcggg aacatggctg acttatcatg
1081 gagccattaa attggatgac aaagatccac aattcaaaga caacgtcata ctgctgaaca
1141 agcacattga cgcatacaaa acattcccac caacagagcc taaaaaggac aaaaagaaaa
1201 agactgatga agctcagcct ttgccgcaga gacaaaagaa gcagcccact gtgactcttc
1261 ttcctgcggc tgacatggat gatttctcca gacaacttca aaattccatg agtggagctt
1321 ctgctgattc aactcaggca taaacactca tgatgaccac acaaggcaga tgggctatgt
1381 aaacgttttc gcaattccgt ttacgataca tagtctactc ttgtgcagaa tgaattctcg
1441 taactaaaca gcacaagtag gtttagttaa ctttaatctc acatagcaat ctttaatcaa
1501 tgtgtaacat tagggaggac ttgaaagagc caccacattt tcatcgaggc cacgcggagt
1561 acgatcgagg gtacagtgaa taatgctagg gagagctgcc tatatggaag agccctaatg

FIGURE 23

MSDNGPQSNQRSAPRITFGGPTDSTDNNQNGGRNGARPKQRRPQGLPNNTASWFTALTQHGKEEL
RFPRGQGVPINTNSGPDDQIGYYRRATRRVRGGDGKMKELSPRWYFYYLGTGPEASLPYGANKEG
IVWVATEGALNTPKDHIGTRNPNNNAATVLQLPQGTTLPKGFYAEGSRGGSQASSRSSSRSRGNS
RNSTPGSSRGNSPARMASGGGETALALLLLDRLNQLESKVSGKGQQQQGQTVTKKSAAEASKKPR
QKRTATKQYNVTQAFGRRGPEQTQGNFGDQDLIRQGTDYKHWPQIAQFAPSASAFFGMSRIGMEV
TPSGTWLTYHGAIKLDDKDPQFKDNVILLNKHIDAYKTFPPTEPKKDKKKKTDEAQPLPQRQKKQ
PTVTLLPAADMDDFSRQLQNSMSGASADSTQA

Figure 24

MSDNGPQSNQRSAPRITFGGPTDSTDNNQNGGRNGARPKQRRPQ

GLPNNTASWFTALTQHGKEELRFPRGQGVPINTNSGPDDQIGYYRRATRRVRGGDGKM

KELSPRWYFYYLGTGPEASLPYGANKEGIVWVATEGALNTPKDHIGTRNPNNNAATVL

QLPQGTTLPKGFYAEGSRGGSQASSRSSSRSRGNSRNSTPGSSRGNSPARMASGGGET

ALALLLLDRLNQLESKVSGKGQQQQGQTVTKKSAAEASKKPRQKRTATKQYNVTQAFG

RRGPEQTQGNFGDQDLIRQGTDYKHWPQIAQFAPSASAFFGMSRIGMEVTPSGTWLTY

HGAIKLDDKDPQFKDNVILLNKHIDAYKTFPPTEPKKDKKKKTDEAQPLPQRQKKQPT

VTLLPAADMDDFSRQLQNSMSGASADSTQA

MSDNGPQSNQRSAPRITFGGPTDSTDNNQNGGRNGARPKQRRPQ

GLPNNTASWFTALTQHGKEELRFPRGQGVPINTNSGPDDQIGYYRRATRRVRGGDGKM

KELSPRWYFYYLGTGPEASLPYGANKEGIVWVATEGALNTPKDHIGTRNPNNNAATVL

QLPQGTTLPKGFYAEGSRGGSQASSRSSSRSRGNSRNSTPGSSRGNSPARMASGGGET

ALALLLLDRLNQLESKVSGKGQQQQGQTVTKKSAAEASKKPRQKRTATKQYNVTQAFG

RRGPEQTQGNFGDQDLIRQGTDYKHWPQIAQFAPSASAFFGMSRIGMEAAPSGTWLTY

HGAIKLDDKDPQFKDNVILLNKHIDAYKTFPPTEPKKDKKKKTDEAQPLPQRQKKQPT

VTLLPAADMDDFSRQLQNSMSGASADSTQA

(B)

MSDNGPQSNQRSAPRITFGGPTDSTDNNQNGGRNGARPKQRRPQ

GLPNNTASWFTALTQHGKEELRFPRGQGVPINTNSGPDDQIGYYRRATRRVRGGDGKM

KELSPRWYFYYLGTGPEASLPYGANKEGIVWVATEGALNTPKDHIGTRNPNNNAATVL

QLPQGTTLPKGFYAEGSRGGSQASSRSSSRSRGNSRNSTPGSSRGNSPARMASGGGET

ALALLLLDRLNQLESKVSGKGQQQQGQTVTKKSAAEASKKPRQKRTATKQYNVTQAFG

RRGPEQTQGNFGDQDLIRQGTDYKHWPQIAQFAPSASAFFGMSRIGMEAAPSGTWLTY

HGAIKLDDKDPQFKDNVILLNKHIDAYKTFPPTEPKKDKKKKTDEAQPLPQRQKKQPT

VTLLPAADMDDFSRQLQNSMSGASADSTQA

FIGURE 26

MSDNGPQSNQRSAPRITFGGPTDSTDNNQNGGRNGARPKQRRPQ

GLPNNTASWFTALTQHGKEELRFPRGQGVPINTNSGPDDQIGYYRRATRRVRGGDGKM

KELSPRWYFYYLGTGPEASLPYGANKEGIVWVATEGALNTPKDHIGTRNPNNNAATVL

QLPQGTTLPKGFYAEGSRGGSQASSRSSSRSRGNSRNSTPGSSRGNSPARMASGGGET

ALALLLLDRLNQLESKVSGKGQQQQGQTVTKKSAAEASKKPRQKRTATKQYNVTQAFG

RRGPEQTQGNFGDQDLIRQGTDYKHWPQIAQFAPSASAFFGMSRIGMEVTPSGTWLTY

HGAIKLDDKDPQFKDNVILLNKHIDAYKTFPPTEPKKDKKKKTDEAQPLPQRQKKQPT

VTLLPAADMDDFSRQLQNSMSGASADSTQA

FIGURE 27

MFIFLLFLTLTSGSDLDRCTTFDDVQAPNYTQHTSSMRGVYYPD

EIFRSDTLYLTQDLFLPFYSNVTGFHTINHTFGNPVIPFKDGIYFAATEKSNVVRGWV

FGSTMNNKSQSVIIINNSTNVVIRACNFELCDNPFFAVSKPMGTQTHTMIFDNAFNCT

FEYISDAFSLDVSEKSGNFKHLREFVFKNKDGFLYVYKGYQPIDVVRDLPSGFNTLKP

IFKLPLGINITNFRAILTAFSPAQDIWGTSAAAYFVGYLKPTTFMLKYDENGTITDAV

DCSQNPLAELKCSVKSFEIDKGIYQTSNFRVVPSGDVVRFPNITNLCPFGEVFNATKF

PSVYAWERKKISNCVADYSVLYNSTFFSTFKCYGVSATKLNDLCFSNVYADSFVVKGD

DVRQIAPGQTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLSFELLNAPA

TVCGPKLSTDLIKNQCVNFNFNGLTGTGVLTPSSKRFQPFQQFGRDVSDFTDSVRDPK

TSEILDISPCSFGGVSVITPGTNASSEVAVLYQDVNCTDVSTAIHADQLTPAWRIYST

GNNVFQTQAGCLIGAEHVDTSYECDIPIGAGICASYHTVSLLRSTSQKSIVAYTMSLG

ADSSIAYSNNTIAIPTNFSISITTEVMPVSMAKTSVDCNMYICGDSTECANLLLQYGS

FCTQLNRALSGIAAEQDRNTREVFAQVKQMYKTPTLKYFGGFNFSQILPDPLKPTKRS

FIEDLLFNKVTLADAGFMKQYGECLGDINARDLICAQKFNGLTVLPPLLTDDMIAAYT

AALVSGTATAGWTFGAGAALQIPFAMQMAYRFNGIGVTQNVLYENQKQIANQFNKAIS

QIQESLTTTSTALGKLQDVVNQNAQALNTLVKQLSSNFGAISSVLNDILSRLDKVEAE

VQIDRLITGRLQSLQTYVTQQLIRAAEIRASANLAATKMSECVLGQSKRVDFCGKGYH

LMSFPQAAPHGVVFLHVTYVPSQERNFTTAPAICHEGKAYFPREGVFVFNGTSWFITQ

RNFFSPQIITTDNTFVSGNCDVVIGIINNTVYDPLQPELDSFKEELDKYFKNHTSPDV

DLGDISGINASVVNIQKEIDRLNEVAKNLNESLIDLQELGKYEQYIKWPWYVWLGFIA

GLIAIVMVTILLCCMTSCCSCLKGACSCGSCCKFDEDDSEPVLKGVKLHYT

FIGURE 28

MFIFLLFLTLTSGSDLDRCTTFDDVQAPNYTQHTSSMRGVYYPD

EIFRSDTLYLTQDLFLPFYSNVTGFHTINHTFGNPVIPFKDGIYFAATEKSNVVRGWV

FGSTMNNKSQSVIIINNSTNVVIRACNFELCDNPFFAVSKPMGTQTHTMIFDNAFNCT

FEYISDAFSLDVSEKSGNFKHLREFVFKNKDGFLYVYKGYQPIDVVRDLPSGFNTLKP

IFKLPLGINITNFRAILTAFSPAQDIWGTSAAAYFVGYLKPTTFMLKYDENGTITDAV

DCSQNPLAELKCSVKSFEIDKGIYQTSNFRVVPSGDVVRFPNITNLCPFGEVFNATKF

PSVYAWERKKISNCVADYSVLYNSTFFSTFKCYGVSATKLNDLCFSNVYADSFVVKGD

DVRQIAPGQTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLSFELLNAPA

TVCGPKLSTDLIKNQCVNFNFNGLTGTGVLTPSSKRFQPFQQFGRDVSDFTDSVRDPK

TSEILDISPCAFGGVSVITPGTNASSEVAVLYQDVNCTDVSTAIHADQLTPAWRIYST

GNNVFQTQAGCLIGAEHVDTSYECDIPIGAGICASYHTVSLLRSTSQKSIVAYTMSLG

ADSSIAYSNNTIAIPTNFSISITTEVMPVSMAKTSVDCNMYICGDSTECANLLLQYGS

FCTQLNRALSGIAAEQDRNTREVFAQVKQMYKTPTLKYFGGFNFSQILPDPLKPTKRS

FIEDLLFNKVTLADAGFMKQYGECLGDINARDLICAQKFNGLTVLPPLLTDDMIAAYT

AALVSGTATAGWTFGAGAALQIPFAMQMAYRFNGIGVTQNVLYENQKQIANQFNKAIS

QIQESLTTTSTALGKLQDVVNQNAQALNTLVKQLSSNFGAISSVLNDILSRLDKVEAE

VQIDRLITGRLQSLQTYVTQQLIRAAEIRASANLAATKMSECVLGQSKRVDFCGKGYH

LMSFPQAAPHGVVFLHVTYVPSQERNFTTAPAICHEGKAYFPREGVFVFNGTSWFITQ

RNFFSPQIITTDNTFVSGNCDVVIGIINNTVYDPLQPELDSFKEELDKYFKNHTSPDV

DLGDISGINASVVNIQKEIDRLNEVAKNLNESLIDLQELGKYEQYIKWPWYVWLGFIA

GLIAIVMVTILLCCMTSCCSCLKGACSCGSCCKFDEDDSEPVLKGVKLHYT

FIGURE 29

MFIFLLFLTLTSGSDLDRCTTFDDVQAPNYTQHTSSMRGVYYPD

EIFRSDTLYLTQDLFLPFYSNVTGFHTINHTFGNPVIPFKDGIYFAATEKSNVVRGWV

FGSTMNNKSQSVIIISNSTNVVIRACNFELCDNPFFAVSKPMGTQTHTMIFDNAFNCT

FEYISDAFSLDVSEKSGNFKHLREFVFKNKDGSLYVYKGYQPIDVVRDLPSGFNTLKP

IFKLPLGINITNFRAILTAFSPAQDIWGTSAAAYFVGYLKPTTFMLKYDENGTITDAV

DCSQNPLAELKCSVKSFEIDKGIYQTSNFRVVPSGDVVRFPNITNLCPFGEVFNATKF

PSVYAWERKKISNCVADYSVLYNSTFFSTFKCYGVSATKLNDLCFSNVYADSFVVKGD

DVRQIAPGQTGVIADYNYKLPDDFMGCVLAWNTGNIDATSTGNYDYKYRYLRHGKLRP

FERDISNVPFSPDGKPCTPPALNCYWPLNDYGFYTTTGIGYQPYRVVVLSFELLNAPA

TVCGPKLSTDLIKNQCVNFNFNGLTGTGVLTPSSKRFQPFQQFGRDVSDFTDSVRDPK

TSEILDISPCSFGGVSVITPGTNASSEVAVLYQDVNCTDVSTAIHADQLTPAWRIYST

GNNVFQTQAGCLIGAEHVDTSYECDIPIGAGICASYHTVSLLRSTSQKSIVAYTMSLG

ADSSIAYSNNTIAIPTNFSISITTEVMPVSMAKTSVDCNMYICGDSTECANLLLQYGS

FCTQLNRALSGIAAEQDRNTREVFAQVKQMYKTPTLKYFGGFNFSQILPDPLKPTKRS

FIEDLPFNKVTLADAGFMKQYGECLGDINARDLICAQKFNGLTVLPPLLTDDMIAAYT

AALVSGTATAGWTFGAGAALQIPFAMQMAYRFNGIGVTQNVLYENQKQIANQFNKAIS

QIQESLTTTSTALGKLQDVVNQNAQALNTLVKQLSSNFGAISSVLNDILSRLDKVEAE

VQIDRLITGRLQSLQTYVTQQLIRAAGIRASANLAATKMSECVLGQSKRVDFCGKGYH

LMSFPQAAPHGVVFLHVTYVPSQERNFTTAPAICHEGKAYFPREGVFVFNGTSWFITQ

RNFFSPQIITTDNTFVSGNCDVVIGIINNTVYDPLQPELDSFKEELDKYFKNHTSPDV

DLGDISGINASVVNIQKEIDRLNEVAKNLNESLIDLQELGKYEQYIKWPWYVWLGFIA

GLIAIVMVTILLCCMTSCCSCLKGACSCGSCCKFDEDDSEPVLKGVKLHYT

MADNGTITVEELKQLLEQWNLVIGFLFLAWIMLLQFAYSNRNRF

LYIIKLVFLWLLWPVTLACFVLAAVYRINWVTGGIAIAMACIVGLMWLSYFVASFRLF

ARTRSMWSFNPETNILLNVPLRGTIVTRPLMESELVIGAVIIRGHLRMAGHPLGRCDI

KDLPKEITVATSRTLSYYKLGASQRVGTDSGFAAYNRYRIGNYKLNTDHAGSNDNIAL

LVQ (B)

MADNGTITVEELKQLLEQWNLVIGFLFLAWIMLLQFAYSNRNRF

LYIIKLVFLWLLWPVTLACFVLAAVYRINWVTGGIAIAMACIVGLMWLSYFVASFRLF

ARTRSMWSFNPETNILLNVPLRGTIVTRPLMESELVIGAVIIRGHLRMAGHSLGRCDI

KDLPKEITVATSRTLSYYKLGASQRVGTDSGFAAYNRYRIGNYKLNTDHAGSNDNIAL

LVQ (C)

MADNGTITVEELKQLLEQWNLVIGFLFLAWIMLLQFAYSNRNRF

LYIIKLVFLWLLWPVTLACFVLAAVYRINWVTGGIAIAMACIVGLMWLSYFVASFRLF

ARTRSMWSFNPETNILPNVPLRGTIVTRPLMESELVIGAVIIRGHLRMAGHSLGRCDI

KDLPKEITVATSRTLSYYKLGASQRVGTDSGFAAYNRYRIGNYKLNTDHAGSNDNIAL

LVQ (D)

MADNGTITVEELKQLLEQWNLVIGFLFLAWIMLLQFAYSNRNRF

LYIIKLVFLWLLWPVTLACFVLAAVYRINWVTGGIAIAMACIVGLMWLSYFVASFRLF

ARTRSMWSFNPETNILPNVPLRGTIVTRPLMESELVIGAVIIRGHLRMAGHSLGRCDI

KDLPKEITVATSRTLSYYKLGASQRVGTDSGFAAYNRYRIGNYKLNTDHAGSNDNIAL

LVQ

FIGURE 31

(A)
MYSFVSEETGTLIVNSVLLFLAFVVFLLVTLAILTALRLCAYCC
NIVNVSLVKPTVYVYSRVKNLNSSEGVPDLLV (B)
MYSFVSEETGTLIVNSVLLFLAFVVFLLVTLAILTALRLCAYCC
NIVNVSLVKPTVYVYSRVKNLNSSEGVPDLLV (C)
MYSFVSEETGTLIVNSVLLFLAFVVFLLVTLAILTALRLCAYCC
NIVNVSLVKPTVYVYSRVKNLNSPEGVPDLLV (D)
MYSFVSEETGTLIVNSVLLFLAFVVFLLVTLAILTALRLCAYCC
NIVNVSLVKPTVYVYSRVKNLNSPEGVPDLLV (E)
MYSFVSEETGTLIVNSVLLFLAFVVFLLVTLAILTALRLCAYCC
NIVNVSLVKPTVYVYSRVKNLNSSEGVPDLLV

FIGURE 32(A)

MESLVLGVNEKTHVQLSLPVLQVRDVLVRGFGDSVEEALSEARE

HLKNGTCGLVELEKGVLPQLEQPYVFIKRSDALSTNHGHKVVELVAEMDGIQYGRSGI

TLGVLVPHVGETPIAYRNVLLRKNGNKGAGGHSYGIDLKSYDLGDELGTDPIEDYEQN

WNTKHGSGALRELTRELNGGAVTRYVDNNFCGPDGYPLDCIKDFLARAGKSMCTLSEQ

LDYIESKRGVYCCRDHEHEIAWFTERSDKSYEHQTPFEIKSAKKFDTFKGECPKFVFP

LNSKVKVIQPRVEKKKTEGFMGRIRSVYPVASPQECNNMHLSTLMKCNHCDEVSWQTC

DFLKATCEHCGTENLVIEGPTTCGYLPTNAVVKMPCPACQDPEIGPEHSVADYHNHSN

IETRLRKGGRTRCFGGCVFAYVGCYNKRAYWVPRASADIGSGHTGITGDNVETLNEDL

LEILSRERVNINIVGDFHLNEEVAIILASFSASTSAFIDTIKSLDYKSFKTIVESCGN

YKVTKGKPVKGAWNIGQQRSVLTPLCGFPSQAAGVIRSIFARTLDAANHSIPDLQRAA

VTILDGISEQSLRLVDAMVYTSDLLTNSVIIMAYVTGGLVQQTSQWLSNLLGTTVEKL

RPIFEWIEAKLSAGVEFLKDAWEILKFLITGVFDIVKGQIQVASDNIKDCVKCFIDVV

NKALEMCIDQVTIAGAKLRSLNLGEVFIAQSKGLYRQCIRGKEQLQLLMPLKAPKEVT

FLEGDSHDTVLTSEEVVLKNGELEALETPVDSFTNGAIVGTPVCVNGLMLLEIKDKEQ

YCALSPGLLATNNVFRLKGGAPIKGVTFGEDTVWEVQGYKNVRITFELDERVDKVLNE

KCSVYTVESGTEVTEFACVVAEAVVKTLQPVSDLLTNMGIDLDEWSVATFYLFDDAGE

ENFSSRMYCSFYPPDEEEEDDAECEEEEIDETCEHEYGTEDDYQGLPLEFGASAETVR

VEEEEEEDWLDDTTEQSEIEPEPEPTPEEPVNQFTGYLKLTDNVAIKCVDIVKEAQSA

NPMVIVNAANIHLKHGGGVAGALNKATNGAMQKESDDYIKLNGPLTVGGSCLLSGHNL

AKKCLHVVGPNLNAGEDIQLLKAAYENFNSQDILLAPLLSAGIFGAKPLQSLQVCVQT

VRTQVYIAVNDKALYEQVVMDYLDNLKPRVEAPKQEEPPNTEDSKTEEKSVVQKPVDV

KPKIKACIDEVTTTLEETKFLTNKLLLFADINGKLYHDSQNMLRGEDMSFLEKDAPYM

VGDVITSGDITCVVIPSKKAGGTTEMLSRALKKVPVDEYITTYPGQGCAGYTLEEAKT

ALKKCKSAFYVLPSEAPNAKEEILGTVSWNLREMLAHAEETRKLMPICMDVRAIMATI

QRKYKGIKIQEGIVDYGVRFFFYTSKEPVASIITKLNSLNEPLVTMPIGYVTHGFNLE

EAARCMRSLKAPAVVSVSSPDAVTTYNGYLTSSSKTSEEHFVETVSLAGSYRDWSYSG

FIGURE 32(B)

QRTELGVEFLKRGDKIVYHTLESPVEFHLDGEVLSLDKLKSLLSLREVKTIKVFTTVD
NTNLHTQLVDMSMTYGQQFGPTYLDGADVTKIKPHVNHEGKTFFVLPSDDTLRSEAFE
YYHTLDESFLGRYMSALNHTKKWKFPQVGGLTSIKWADNNCYLSSVLLALQQLEVKFN
APALQEAYYRARAGDAANFCALILAYSNKTVGELGDVRETMTHLLQHANLESAKRVLN
VVCKHCGQKTTTLTGVEAVMYMGTLSYDNLKTGVSIPCVCGRDATQYLVQQESSFVMM
SAPPAEYKLQQGTFLCANEYTGNYQCGHYTHITAKETLYRIDGAHLTKMSEYKGPVTD
VFYKETSYTTTIKPVSYKLDGVTYTEIEPKLDGYYKKDNAYYTEQPIDLVPTQPLPNA
SFDNFKLTCSNTKFADDLNQMTGFTKPASRELSVTFFPDLNGDVVAIDYRHYSASFKK
GAKLLHKPIVWHINQATTKTTFKPNTWCLRCLWSTKPVDTSNSFEVLAVEDTQGMDNL
ACESQQPTSEEVVENPTIQKEVIECDVKTTEVVGNVILKPSDEGVKVTQELGHEDLMA
AYVENTSITIKKPNELSLALGLKTIATHGIAAINSVPWSKILAYVKPFLGQAAITTSN
CAKRLAQRVFNNYMPYVFTLLFQLCTFTKSTNSRIRASLPTTIAKNSVKSVAKLCLDA
GINYVKSPKFSKLFTIAMWLLLLSICLGSLICVTAAFGVLLSNFGAPSYCNGVRELYL
NSSNVTTMDFCEGSFPCSICLSGLDSLDSYPALETIQVTISSYKLDLTILGLAAEWVL
AYMLFTKFFYLLGLSAIMQVFFGYFASHFISNSWLMWFIISIVQMAPVSAMVRMYIFF
ASFYYIWKSYVHIMDGCTSSTCMMCYKRNRATRVECTTIVNGMKRSFYVYANGGRGFC
KTHNWNCLNCDTFCTGSTFISDEVARDLSLQFKRPINPTDQSSYIVDSVAVKNGALHL
YFDKAGQKTYERHPLSHFVNLDNLRANNTKGSLPINVIVFDGKSKCDESASKSASVYY
SQLMCQPILLLDQVLVSDVGDSTEVSVKMFDAYVDTFSATFSVPMEKLKALVATAHSE
LAKGVALDGVLSTFVSAARQGVVDTDVDTKDVIECLKLSHHSDLEVTGDSCNNFMLTY
NKVENMTPRDLGACIDCNARHINAQVAKSHNVSLIWNVKDYMSLSEQLRKQIRSAAKK
NNIPFRLTCATTRQVVNVITTKISLKGGKIVSTCFKLMLKATLLCVLAALVCYIVMPV
HTLSIHDGYTNEIIGYKAIQDGVTRDIISTDDCFANKHAGFDAWFSQRGGSYKNDKSC
PVVAAIITREIGFIVPGLPGTVLRAINGDFLHFLPRVFSAVGNICYTPSKLIEYSDFA
TSACVLAAECTIFKDAMGKPVPYCYDTNLLEGSISYSELRPDTRYVLMDGSIIQFPNT
YLEGSVRVVTTFDAEYCRHGTCERSEVGICLSTSGRWVLNNEHYRALSGVFCGVDAMN

FIGURE 32(C)

LIANIFTPLVQPVGALDVSASVVAGGIIAILVTCAAYYFMKFRRVFGEYNHVVAANAL
LFLMSFTILCLVPAYSFLPGVYSVFYLYLTFYFTNDVSFLAHLQWFAMFSPIVPFWIT
AIYVFCISLKHCHWFFNNYLRKRVMFNGVTFSTFEEAALCTFLLNKEMYLKLRSETLL
PLTQYNRYLALYNKYKYFSGALDTTSYREAACCHLAKALNDFSNSGADVLYQPPQTSI
TSAVLQSGFRKMAFPSGKVEGCMVQVTCGTTTLNGLWLDDTVYCPRHVICTAEDMLNP
NYEDLLIRKSNHSFLVQAGNVQLRVIGHSMQNCLLRLKVDTSNPKTPKYKFVRIQPGQ
TFSVLACYNGSPSGVYQCAMRPNHTIKGSFLNGSCGSVGFNIDYDCVSFCYMHHMELP
TGVHAGTDLEGKFYGPFVDRQTAQAAGTDTTITLNVLAWLYAAVINGDRWFLNRFTTT
LNDFNLVAMKYNYEPLTQDHVDILGPLSAQTGIAVLDMCAALKELLQNGMNGRTILGS
TILEDEFTPFDVVRQCSGVTFQGKFKKIVKGTHHWMLLTFLTSLLILVQSTQWSLFFF
VYENAFLPFTLGIMAIAACAMLLVKHKHAFLCLFLLPSLATVAYFNMVYMPASWVMRI
MTWLELADTSLSGYRLKDCVMYASALVLLILMTARTVYDDAARRVWTLMNVITLVYKV
YYGNALDQAISMWALVISVTSNYSGVVTTIMFLARAIVFVCVEYYPLLFITGNTLQCI
MLVYCFLGYCCCCYFGLFCLLNRYFRLTLGVYDYLVSTQEFRYMNSQGLLPPKSSIDA
FKLNIKLLGIGGKPCIKVATVQSKMSDVKCTSVVLLSVLQQLRVESSSKLWAQCVQLH
NDILLAKDTTEAFEKMVSLLSVLLSMQGAVDINRLCEEMLDNRATLQAIASEFSSLPS
YAAYATAQEAYEQAVANGDSEVVLKKLKKSLNVAKSEFDRDAAMQRKLEKMADQAMTQ
MYKQARSEDKRAKVTSAMQTMLFTMLRKLDNDALNNIINNARDGCVPLNIIPLTTAAK
LMVVVPDYGTYKNTCDGNTFTYASALWEIQQVVDADSKIVQLSEINMDNSPNLAWPLI
VTALRANSAVKLQNNELSPVALRQMSCAAGTTQTACTDDNALAYYNNSKGGRFVLALL
SDHQDLKWARFPKSDGTGTIYTELEPPCRFVTDTPKGPKVKYLYFIKGLNNLNRGMVL
GSLAATVRLQAGNATEVPANSTVLSFCAFAVDPAKAYKDYLASGGQPITNCVKMLCTH
TGTGQAITVTPEANMDQESFGGASCCLYCRCHIDHPNPKGFCDLKGKYVQIPTTCAND
PVGFTLRNTVCTVCGMWKGYGCSCDQLREPLMQSADASTFLNGFAV

FIGURE 33 (A)

MESLVLGVNEKTHVQLSLPVLQVRDVLVRGFGDSVEEALSEARE

HLKNGTCGLVELEKGVLPQLEQPYVFIKRSDALSTNHGHKVVELVAEMDGIQYGRSGI

TLGVLVPHVGETPIAYRNVLLRKNGNKGAGGHSYGIDLKSYDLGDELGTDPIEDYEQN

WNTKHGSGALRELTRELNGGAVTRYVDNNFCGPDGYPLDCIKDFLARAGKSMCTLSEQ

LDYIESKRGVYCCRDHEHEIAWFTERSDKSYEHQTPFEIKSAKKFDTFKGECPKFVFP

LNSKVKVIQPRVEKKKTEGFMGRIRSVYPVASPQECNNMHLSTLMKCNHCDEVSWQTC

DFLKATCEHCGTENLVIEGPTTCGYLPTNAVVKMPCPACQDPEIGPEHSVADYHNHSN

IETRLRKGGRTRCFGGCVFAYVGCYNKRAYWVPRASADIGSGHTGITGDNVETLNEDL

LEILSRERVNINIVGDFHLNEEVAIILASFSASTSAFIDTIKSLDYKSFKTIVESCGN

YKVTKGKPVKGAWNIGQQRSVLTPLCGFPSQAAGVIRSIFARTLDAANHSIPDLQRAA

VTILDGISEQSLRLVDAMVYTSDLLTNSVIIMAYVTGGLVQQTSQWLSNLLGTTVEKL

RPIFEWIEAKLSAGVEFLKDAWEILKFLITGVFDIVKGQIQVASDNIKDCVKCFIDVV

NKALEMCIDQVTIAGAKLRSLNLGEVFIAQSKGLYRQCIRGKEQLQLLMPLKAPKEVT

FLEGDSHDTVLTSEEVVLKNGELEALETPVDSFTNGAIVGTPVCVNGLMLLEIKDKEQ

YCALSPGLLATNNVFRLKGGAPIKGVTFGEDTVWEVQGYKNVRITFELDERVDKVLNE

KCSVYTVESGTEVTEFACVVAEAVVKTLQPVSDLLTNMGIDLDEWSVATFYLFDDAGE

ENFSSRMYCSFYPPDEEEEDDAECEEEEIDETCEHEYGTEDDYQGLPLEFGASAETVR

VEEEEEEDWLDDTTEQSEIEPEPEPTPEEPVNQFTGYLKLTDNVAIKCVDIVKEAQSA

NPMVIVNAANIHLKHGGGVAGALNKATNGAMQKESDDYIKLNGPLTVGGSCLLSGHNL

AKKCLHVVGPNLNAGEDIQLLKAAYENFNSQDILLAPLLSAGIFGAKPLQSLQVCVQT

VRTQVYIAVNDKALYEQVVMDYLDNLKPRVEAPKQEEPPNTEDSKTEEKSVVQKPVDV

KPKIKACIDEVTTTLEETKFLTNKLLLFADINGKLYHDSQNMLRGEDMSFLEKDAPYM

VGDVITSGDITCVVIPSKKAGGTTEMLSRALKKVPVDEYITTYPGQGCAGYTLEEAKT

ALKKCKSAFYVLPSEAPNAKEEILGTVSWNLREMLAHAEETRKLMPICMDVRAIMATI

QRKYKGIKIQEGIVDYGVRFFFYTSKEPVASIITKLNSLNEPLVTMPIGYVTHGFNLE

EAARCMRSLKAPAVVSVSSPDAVTTYNGYLTSSSKTSEEHFVETVSLAGSYRDWSYSG

FIGURE 33 (B)

QRTELGVEFLKRGDKIVYHTLESPVEFHLDGEVLSLDKLKSLLSLREVKTIKVFTTVD
NTNLHTQLVDMSMTYGQQFGPTYLDGADVTKIKPHVNHEGKTFFVLPSDDTLRSEAFE
YYHTLDESFLGRYMSALNHTKKWKFPQVGGLTSIKWADNNCYLSSVLLALQQLEVKFN
APALQEAYYRARAGDAANFCALILAYSNKTVGELGDVRETMTHLLQHANLESAKRVLN
VVCKHCGQKTTTLTGVEAVMYMGTLSYDNLKTGVSIPCVCGRDATQYLVQQESSFVMM
SAPPAEYKLQQGTFLCANEYTGNYQCGHYTHITAKETLYRIDGAHLTKMSEYKGPVTD
VFYKETSYTTTIKPVSYKLDGVTYTEIEPKLDGYYKKDNAYYTEQPIDLVPTQPLPNA
SFDNFKLTCSNTKFADDLNQMTGFTKPASRELSVTFFPDLNGDVVAIDYRHYSASFKK
GAKLLHKPIVWHINQATTKTTFKPNTWCLRCLWSTKPVDTSNSFEVLAVEDTQGMDNL
ACESQQPTSEEVVENPTIQKEVIECDVKTTEVVGNVILKPSDEGVKVTQELGHEDLMA
AYVENTSITIKKPNELSLALGLKTIATHGIAAINSVPWSKILAYVKPFLGQAAITTSN
CAKRLAQRVFNNYMPYVFTLLFQLCTFTKSTNSRIRASLPTTIAKNSVKSVAKLCLDA
GINYVKSPKFSKLFTIAMWLLLLSICLGSLICVTAAFGVLLSNFGAPSYCNGVRELYL
NSSNVTTMDFCEGSFPCSICLSGLDSLDSYPALETIQVTISSYKLDLTILGLAAEWVL
AYMLFTKFFYLLGLSAIMQVFFGYFASHFISNSWLMWFIISIVQMAPVSAMVRMYIFF
ASFYYIWKSYVHIMDGCTSSTCMMCYKRNRATRVECTTIVNGMKRSFYVYANGGRGFC
KTHNWNCLNCDTFCTGSTFISDEVARDLSLQFKRPINPTDQSSYIVDSVAVKNGALHL
YFDKAGQKTYERHPLSHFVNLDNLRANNTKGSLPINVIVFDGKSKCDESASKSASVYY
SQLMCQPILLLDQALVSDVGDSTEVSVKMFDAYVDTFSATFSVPMEKLKALVATAHSE
LAKGVALDGVLSTFVSAARQGVVDTDVDTKDVIECLKLSHHSDLEVTGDSCNNFMLTY
NKVENMTPRDLGACIDCNARHINAQVAKSHNVSLIWNVKDYMSLSEQLRKQIRSAAKK
NNIPFRLTCATTRQVVNVITTKISLKGGKIVSTCFKLMLKATLLCVLAALVCYIVMPV
HTLSIHDGYTNEIIGYKAIQDGVTRDIISTDDCFANKHAGFDAWFSQRGGSYKNDKSC
PVVAAIITREIGFIVPGLPGTVLRAINGDFLHFLPRVFSAVGNICYTPSKLIEYSDFA
TSACVLAAECTIFKDAMGKPVPYCYDTNLLEGSISYSELRPDTRYVLMDGSIIQFPNT
YLEGSVRVVTTFDAEYCRHGTCERSEVGICLSTSGRWVLNNEHYRALSGVFCGVDAMN

FIGURE 33 (C)

LIANIFTPLVQPVGALDVSASVVAGGIIAILVTCAAYYFMKFRRVFGEYNHVVAANAL
LFLMSFTILCLVPAYSFLPGVYSVFYLYLTFYFTNDVSFLAHLQWFAMFSPIVPFWIT
AIYVFCISLKHCHWFFNNYLRKRVMFNGVTFSTFEEAALCTFLLNKEMYLKLRSETLL
PLTQYNRYLALYNKYKYFSGALDTTSYREAACCHLAKALNDFSNSGADVLYQPPQTSI
TSAVLQSGFRKMAFPSGKVEGCMVQVTCGTTTLNGLWLDDTVYCPRHVICTAEDMLNP
NYEDLLIRKSNHSFLVQAGNVQLRVIGHSMQNCLLRLKVDTSNPKTPKYKFVRIQPGQ
TFSVLACYNGSPSGVYQCAMRPNHTIKGSFLNGSCGSVGFNIDYDCVSFCYMHHMELP
TGVHAGTDLEGKFYGPFVDRQTAQAAGTDTTITLNVLAWLYAAVINGDRWFLNRFTTT
LNDFNLVAMKYNYEPLTQDHVDILGPLSAQTGIAVLDMCAALKELLQNGMNGRTILGS
TILEDEFTPFDVVRQCSGVTFQGKFKKIVKGTHHWMLLTFLTSLLILVQSTQWSLFFF
VYENAFLPFTLGIMAIAACAMLLVKHKHAFLCLFLLPSLATVAYFNMVYMPASWVMRI
MTWLELADTSLSGYRLKDCVMYASALVLLILMTARTVYDDAARRVWTLMNVITLVYKV
YYGNALDQAISMWALVISVTSNYSGVVTTIMFLARAIVFVCVEYYPLLFITGNTLQCI
MLVYCFLGYCCCCYFGLFCLLNRYFRLTLGVYDYLVSTQEFRYMNSQGLLPPKSSIDA
FKLNIKLLGIGGKPCIKVATVQSKMSDVKCTSVVLLSVLQQLRVESSSKLWAQCVQLH
NDILLAKDTTEAFEKMVSLLSVLLSMQGAVDINRLCEEMLDNRATLQAIASEFSSLPS
YAAYATAQEAYEQAVANGDSEVVLKKLKKSLNVAKSEFDRDAAMQRKLEKMADQAMTQ
MYKQARSEDKRAKVTSAMQTMLFTMLRKLDNDALNNIINNARDGCVPLNIIPLTTAAK
LMVVVPDYGTYKNTCDGNTFTYASALWEIQQVVDADSKIVQLSEINMDNSPNLAWPLI
VTALRANSAVKLQNNELSPVALRQMSCAAGTTQTACTDDNALAYYNNSKGGRFVLALL
SDHQDLKWARFPKSDGTGTIYTELEPPCRFVTDTPKGPKVKYLYFIKGLNNLNRGMVL
GSLAATVRLQAGNATEVPANSTVLSFCAFAVDPAKAYKDYLASGGQPITNCVKMLCTH
TGTGQAITVTPEANMDQESFGGASCCLYCRCHIDHPNPKGFCDLKGKYVQIPTTCAND
PVGFTLRNTVCTVCGMWKGYGCSCDQLREPLMQSADASTFFKRVCGVSAARLTPCGTG
TSTDVVYRAFDIYNEKVAGFAKFLKTNCCRFQEKDEEGNLLDSYFVVKRHTMSNYQHE

FIGURE 33 (D)

ETIYNLVKDCPAVAVHDFFKFRVDGDMVPHISRQRLTKYTMADLVYALRHFDEGNCDT
LKEILVTYNCCDDDYFNKKDWYDFVENPDILRVYANLGERVRQSLLKTVQFCDAMRDA
GIVGVLTLDNQDLNGNWYDFGDFVQVAPGCGVPIVDSYYSLLMPILTLTRALAAESHM
DADLAKPLIKWDLLKYDFTEERLCLFDRYFKYWDQTYHPNCINCLDDRCILHCANFNV
LFSTVFPPTSFGPLVRKIFVDGVPFVVSTGYHFRELGVVHNQDVNLHSSRLSFKELLV
YAADPAMHAASGNLLLDKRTTCFSVAALTNNVAFQTVKPGNFNKDFYDFAVSKGFFKE
GSSVELKHFFFAQDGNAAISDYDYYRYNLPTMCDIRQLLFVVEVVDKYFDCYDGGCIN
ANQVIVNNLDKSAGFPFNKWGKARLYYDSMSYEDQDALFAYTKRNVIPTITQMNLKYA
ISAKNRARTVAGVSICSTMTNRQFHQKLLKSIAATRGATVVIGTSKFYGGWHNMLKTV
YSDVETPHLMGWDYPKCDRAMPNMLRIMASLVLARKHNTCCNLSHRFYRLANECAQVL
SEMVMCGGSLYVKPGGTSSGDATTAYANSVFNICQAVTANVNALLSTDGNKIADKYVR
NLQHRLYECLYRNRDVDHEFVDEFYAYLRKHFSMMILSDDAVVCYNSNYAAQGLVASI
KNFKAVLYYQNNVFMSEAKCWTETDLTKGPHEFCSQHTMLVKQGDDYVYLPYPDPSRI
LGAGCFVDDIVKTDGTLMIERFVSLAIDAYPLTKHPNQEYADVFHLYLQYIRKLHDEL
TGHMLDMYSVMLTNDNTSRYWEPEFYEAMYTPHTVLQAVGACVLCNSQTSLRCGACIR
RPFLCCKCCYDHVISTSHKLVLSVNPYVCNAPGCDVTDVTQLYLGGMSYYCKSHKPPI
SFPLCANGQVFGLYKNTCVGSDNVTDFNAIATCDWTNAGDYILANTCTERLKLFAAET
LKATEETFKLSYGIATVREVLSDRELHLSWEVGKPRPPLNRNYVFTGYRVTKNSKVQI
GEYTFEKGDYGDAVVYRGTTTYKLNVGDYFVLTSHTVMPLSAPTLVPQEHYVRITGLY
PTLNISDEFSSNVANYQKVGMQKYSTLQGPPGTGKSHFAIGLALYYPSARIVYTACSH
AAVDALCEKALKYLPIDKCSRIIPARARVECFDKFKVNSTLEQYVFCTVNALPETTAD
IVVFDEISMATNYDLSVVNARLRAKHYVYIGDPAQLPAPRTLLTKGTLEPEYFNSVCR
LMKTIGPDMFLGTCRRCPAEIVDTVSALVYDNKLKAHKDKSAQCFKMFYKGVITHDVS
SAINRPQIGVVREFLTRNPAWRKAVFISPYNSQNAVASKILGLPTQTVDSSQGSEYDY
VIFTQTTETAHSCNVNRFNVAITRAKIGILCIMSDRDLYDKLQFTSLEIPRRNVATLQ

FIGURE 33 (E)

AENVTGLFKDCSKIITGLHPTQAPTHLSVDIKFKTEGLCVDIPGIPKDMTYRRLISMM
GFKMNYQVNGYPNMFITREEAIRHVRAWIGFDVEGCHATRDAVGTNLPLQLGFSTGVN
LVAVPTGYVDTENNTEFTRVNAKPPPGDQFKHLIPLMYKGLPWNVVRIKIVQMLSDTL
KGLSDRVVFVLWAHGFELTSMKYFVKIGPERTCCLCDKRATCFSTSSDTYACWNHSVG
FDYVYNPFMIDVQQWGFTGNLQSNHDQHCQVHGNAHVASCDAIMTRCLAVHECFVKRV
DWSVEYPIIGDELRVNSACRKVQHMVVKSALLADKFPVLHDIGNPKAIKCVPQAEVEW
KFYDAQPCSDKAYKIEELFYSYATHHDKFTDGVCLFWNCNVDRYPANAIVCRFDTRVL
SNLNLPGCDGGSLYVNKHAFHTPAFDKSAFTNLKQLPFFYYSDSPCESHGKQVVSDID
YVPLKSATCITRCNLGGAVCRHHANEYRQYLDAYNMMISAGFSLWIYKQFDTYNLWNT
FTRLQSLENVAYNVVNKGHFDGHAGEAPVSIINNAVYTKVDGIDVEIFENKTTLPVNV
AFELWAKRNIKPVPEIKILNNLGVDIAANTVIWDYKREAPAHVSTIGVCTMTDIAKKP
TESACSSLTVLFDGRVEGQVDLFRNARNGVLITEGSVKGLTPSKGPAQASVNGVTLIG
ESVKTQFNYFKKVDGIIQQLPETYFTQSRDLEDFKPRSQMETDFLELAMDEFIQRYKL
EGYAFEHIVYGDFSHGQLGGLHLMIGLAKRSQDSPLKLEDFIPMDSTVKNYFITDAQT
GSSKCVCSVIDLLLDDFVEIIKSQDLSVISKVVKVTIDYAEISFMLWCKDGHVETFYP
KLQASQAWQPGVAMPNLYKMQRMLLEKCDLQNYGENAVIPKGIMMNVAKYTQLCQYLN
TLTLAVPYNMRVIHFGAGSDKGVAPGTAVLRQWLPTGTLLVDSDLNDFVSDADSTLIG
DCATVHTANKWDLIISDMYDPRTKHVTKENDSKEGFFTYLCGFIKQKLALGGSIAVKI
TEHSWNADLYKLMGHFSWWTAFVTNVNASSSEAFLIGANYLGKPKEQIDGYTMHANYI
FWRNTNPIQLSSYSLFDMSKFPLKLRGTAVMSLKENQINDMIYSLLEKGRLIIRENNR
VVVSSDILVNN

FIGURE 34 (A)

RVCGVSAARLTPCGTGTSTDVVYRAFDIYNEKVAGFAKFLKTNC

CRFQEKDEEGNLLDSYFVVKRHTMSNYQHEETIYNLVKDCPAVAVHDFFKFRVDGDMV

PHISRQRLTKYTMADLVYALRHFDEGNCDTLKEILVTYNCCDDDYFNKKDWYDFVENP

DILRVYANLGERVRQSLLKTVQFCDAMRDAGIVGVLTLDNQDLNGNWYDFGDFVQVAP

GCGVPIVDSYYSLLMPILTLTRALAAESHMDADLAKPLIKWDLLKYDFTEERLCLFDR

YFKYWDQTYHPNCINCLDDRCILHCANFNVLFSTVFPPTSFGPLVRKIFVDGVPFVVS

TGYHFRELGVVHNQDVNLHSSRLSFKELLVYAADPAMHAASGNLLLDKRTTCFSVAAL

TNNVAFQTVKPGNFNKDFYDFAVSKGFFKEGSSVELKHFFFAQDGNAAISDYDYYRYN

LPTMCDIRQLLFVVEVVDKYFDCYDGGCINANQVIVNNLDKSAGFPFNKWGKARLYYD

SMSYEDQDALFAYTKRNVIPTITQMNLKYAISAKNRARTVAGVSICSTMTNRQFHQKL

LKSIAATRGATVVIGTSKFYGGWHNMLKTVYSDVETPHLMGWDYPKCDRAMPNMLRIM

ASLVLARKHNTCCNLSHRFYRLANECAQVLSEMVMCGGSLYVKPGGTSSGDATTAYAN

SVFNICQAVTANVNALLSTDGNKIADKYVRNLQHRLYECLYRNRDVDHEFVDEFYAYL

RKHFSMMILSDDAVVCYNSNYAAQGLVASIKNFKAVLYYQNNVFMSEAKCWTETDLTK

GPHEFCSQHTMLVKQGDDYVYLPYPDPSRILGAGCFVDDIVKTDGTLMIERFVSLAID

AYPLTKHPNQEYADVFHLYLQYIRKLHDELTGHMLDMYSVMLTNDNTSRYWEPEFYEA

MYTPHTVLQAVGACVLCNSQTSLRCGACIRRPFLCCKCCYDHVISTSHKLVLSVNPYV

CNAPGCDVTDVTQLYLGGMSYYCKSHKPPISFPLCANGQVFGLYKNTCVGSDNVTDFN

AIATCDWTNAGDYILANTCTERLKLFAAETLKATEETFKLSYGIATVREVLSDRELHL

SWEVGKPRPPLNRNYVFTGYRVTKNSKVQIGEYTFEKGDYGDAVVYRGTTTYKLNVGD

YFVLTSHTVMPLSAPTLVPQEHYVRITGLYPTLNISDEFSSNVANYQKVGMQKYSTLQ

GPPGTGKSHFAIGLALYYPSARIVYTACSHAAVDALCEKALKYLPIDKCSRIIPARAR

VECFDKFKVNSTLEQYVFCTVNALPETTADIVVFDEISMATNYDLSVVNARLRAKHYV

YIGDPAQLPAPRTLLTKGTLEPEYFNSVCRLMKTIGPDMFLGTCRRCPAEIVDTVSAL

VYDNKLKAHKDKSAQCFKMFYKGVITHDVSSAINRPQIGVVREFLTRNPAWRKAVFIS

PYNSQNAVASKILGLPTQTVDSSQGSEYDYVIFTQTTETAHSCNVNRFNVAITRAKIG

FIGURE 34 (B)

ILCIMSDRDLYDKLQFTSLEIPRRNVATLQAENVTGLFKDCSKIITGLHPTQAPTHLS
VDIKFKTEGLCVDIPGIPKDMTYRRLISMMGFKMNYQVNGYPNMFITREEAIRHVRAW
IGFDVEGCHATRDAVGTNLPLQLGFSTGVNLVAVPTGYVDTENNTEFTRVNAKPPPGD
QFKHLIPLMYKGLPWNVVRIKIVQMLSDTLKGLSDRVVFVLWAHGFELTSMKYFVKIG
PERTCCLCDKRATCFSTSSDTYACWNHSVGFDYVYNPFMIDVQQWGFTGNLQSNHDQH
CQVHGNAHVASCDAIMTRCLAVHECFVKRVDWSVEYPIIGDELRVNSACRKVQHMVVK
SALLADKFPVLHDIGNPKAIKCVPQAEVEWKFYDAQPCSDKAYKIEELFYSYATHHDK
FTDGVCLFWNCNVDRYPANAIVCRFDTRVLSNLNLPGCDGGSLYVNKHAFHTPAFDKS
AFTNLKQLPFFYYSDSPCESHGKQVVSDIDYVPLKSATCITRCNLGGAVCRHHANEYR
QYLDAYNMMISAGFSLWIYKQFDTYNLWNTFTRLQSLENVAYNVVNKGHFDGHAGEAP
VSIINNAVYTKVDGIDVEIFENKTTLPVNVAFELWAKRNIKPVPEIKILNNLGVDIAA
NTVIWDYKREAPAHVSTIGVCTMTDIAKKPTESACSSLTVLFDGRVEGQVDLFRNARN
GVLITEGSVKGLTPSKGPAQASVNGVTLIGESVKTQFNYFKKVDGIIQQLPETYFTQS
RDLEDFKPRSQMETDFLELAMDEFIQRYKLEGYAFEHIVYGDFSHGQLGGLHLMIGLA
KRSQDSPLKLEDFIPMDSTVKNYFITDAQTGSSKCVCSVIDLLLDDFVEIIKSQDLSV
ISKVVKVTIDYAEISFMLWCKDGHVETFYPKLQASQAWQPGVAMPNLYKMQRMLLEKC
DLQNYGENAVIPKGIMMNVAKYTQLCQYLNTLTLAVPYNMRVIHFGAGSDKGVAPGTA
VLRQWLPTGTLLVDSDLNDFVSDADSTLIGDCATVHTANKWDLIISDMYDPRTKHVTK
ENDSKEGFFTYLCGFIKQKLALGGSIAVKITEHSWNADLYKLMGHFSWWTAFVTNVNA
SSSEAFLIGANYLGKPKEQIDGYTMHANYIFWRNTNPIQLSSYSLFDMSKFPLKLRGT
AVMSLKENQINDMIYSLLEKGRLIIRENNRVVVSSDILVNN

FIGURE 35 (A)

MESLVLGVNEKTHVQLSLPVLQVRDVLVRGFGDSVEEALSEARE

HLKNGTCGLVELEKGVLPQLEQPYVFIKRSDALSTNHGHKVVELVAEMDGIQYGRSGI

TLGVLVPHVGETPIAYRNVLLRKNGNKGAGGHSYGIDLKSYDLGDELGTDPIEDYEQN

WNTKHGSGALRELTRELNGGAVTRYVDNNFCGPDGYPLDCIKDFLARAGKSMCTLSEQ

LDYIESKRGVYCCRDHEHEIAWFTERSDKSYEHQTPFEIKSAKKFDTFKGECPKFVFP

LNSKVKVIQPRVEKKKTEGFMGRIRSVYPVASPQECNNMHLSTLMKCNHCDEVSWQTC

DFLKATCEHCGTENLVIEGPTTCGYLPTNAVVKMPCPACQDPEIGPEHSVADYHNHSN

IETRLRKGGRTRCFGGCVFAYVGCYNKRAYWVPRASADIGSGHTGITGDNVETLNEDL

LEILSRERVNINIVGDFHLNEEVAIILASFSASTSAFIDTIKSLDYKSFKTIVESCGN

YKVTKGKPVKGAWNIGQQRSVLTPLCGFPSQAAGVIRSIFARTLDAANHSIPDLQRAA

VTILDGISEQSLRLVDAMVYTSDLLTNSVIIMAYVTGGLVQQTSQWLSNLLGTTVEKL

RPIFEWIEAKLSAGVEFLKDAWEILKFLITGVFDIVKGQIQVASDNIKDCVKCFIDVV

NKALEMCIDQVTIAGAKLRSLNLGEVFIAQSKGLYRQCIRGKEQLQLLMPLKAPKEVT

FLEGDSHDTVLTSEEVVLKNGELEALETPVDSFTNGAIVGTPVCVNGLMLLEIKDKEQ

YCALSPGLLATNNVFRLKGGAPIKGVTFGEDTVWEVQGYKNVRITFELDERVDKVLNE

KCSVYTVESGTEVTEFACVVAEAVVKTLQPVSDLLTNMGIDLDEWSVATFYLFDDAGE

ENFSSRMYCSFYPPDEEEEDDAECEEEEIDETCEHEYGTEDDYQGLPLEFGASAETVR

VEEEEEEDWLDDTTEQSEIEPEPEPTPEEPVNQFTGYLKLTDNVAIKCVDIVKEAQSA

NPMVIVNAANIHLKHGGGVAGALNKATNGAMQKESDDYIKLNGPLTVGGSCLLSGHNL

AKKCLHVVGPNLNAGEDIQLLKAAYENFNSQDILLAPLLSAGIFGAKPLQSLQVCVQT

VRTQVYIAVNDKALYEQVVMDYLDNLKPRVEAPKQEEPPNTEDSKTEEKSVVQKPVDV

KPKIKACIDEVTTTLEETKFLTNKLLLFADINGKLYHDSQNMLRGEDMSFLEKDAPYM

VGDVITSGDITCVVIPSKKAGGTTEMLSRALKKVPVDEYITTYPGQGCAGYTLEEAKT

ALKKCKSAFYVLPSEAPNAKEEILGTVSWNLREMLAHAEETRKLMPICMDVRAIMATI

QRKYKGIKIQEGIVDYGVRFFFYTSKEPVASIITKLNSLNEPLVTMPIGYVTHGFNLE

EAARCMRSLKAPAVVSVSSPDAVTTYNGYLTSSSKTSEEHFVETVSLAGSYRDWSYSG

FIGURE 35 (B)

QRTELGVEFLKRGDKIVYHTLESPVEFHLDGEVLSLDKLKSLLSLREVKTIKVFTTVD
NTNLHTQLVDMSMTYGQQFGPTYLDGADVTKIKPHVNHEGKTFFVLPSDDTLRSEAFE
YYHTLDESFLGRYMSALNHTKKWKFPQVGGLTSIKWADNNCYLSSVLLALQQLEVKFN
APALQEAYYRARAGDAANFCALILAYSNKTVGELGDVRETMTHLLQHANLESAKRVLN
VVCKHCGQKTTTLTGVEAVMYMGTLSYDNLKTGVSIPCVCGRDATQYLVQQESSFVMM
SAPPAEYKLQQGTFLCANEYTGNYQCGHYTHITAKETLYRIDGAHLTKMSEYKGPVTD
VFYKETSYTTTIKPVSYKLDGVTYTEIEPKLDGYYKKDNAYYTEQPIDLVPTQPLPNA
SFDNFKLTCSNTKFADDLNQMTGFTKPASRELSVTFFPDLNGDVVAIDYRHYSASFKK
GAKLLHKPIVWHINQATTKTTFKPNTWCLRCLWSTKPVDTSNSFEVLAVEDTQGMDNL
ACESQQPTSEEVVENPTIQKEVIECDVKTTEVVGNVILKPSDEGVKVTQELGHEDLMA
AYVENTSITIKKPNELSLALGLKTIATHGIAAINSVPWSKILAYVKPFLGQAAITTSN
CAKRLAQRVFNNYMPYVFTLLFQLCTFTKSTNSRIRASLPTTIAKNSVKSVAKLCLDA
GINYVKSPKFSKLFTIAMWLLLLSICLGSLICVTAAFGVLLSNFGAPSYCNGVRELYL
NSSNVTTMDFCEGSFPCSICLSGLDSLDSYPALETIQVTISSYKLDLTILGLAAEWVL
AYMLFTKFFYLLGLSAIMQVFFGYFASHFISNSWLMWFIISIVQMAPVSAMVRMYIFF
ASFYYIWKSYVHIMDGCTSSTCMMCYKRNRATRVECTTIVNGMKRSFYVYANGGRGFC
KTHNWNCLNCDTFCTGSTFISDEVARDLSLQFKRPINPTDQSSYIVDSVAVKNGALHL
YFDKAGQKTYERHPLSHFVNLDNLRANNTKGSLPINVIVFDGKSKCDESASKSASVYY
SQLMCQPILLLDQALVSDVGDSTEVSVKMFDAYVDTFSATFSVPMEKLKALVATAHSE
LAKGVALDGVLSTFVSAARQGVVDTDVDTKDVIECLKLSHHSDLEVTGDSCNNFMLTY
NKVENMTPRDLGACIDCNARHINAQVAKSHNVSLIWNVKDYMSLSEQLRKQIRSAAKK
NNIPFRLTCATTRQVVNVITTKISLKGGKIVSTCFKLMLKATLLCVLAALVCYIVMPV
HTLSIHDGYTNEIIGYKAIQDGVTRDIISTDDCFANKHAGFDAWFSQRGGSYKNDKSC
PVVAAIITREIGFIVPGLPGTVLRAINGDFLHFLPRVFSAVGNICYTPSKLIEYSDFA
TSACVLAAECTIFKDAMGKPVPYCYDTNLLEGSISYSELRPDTRYVLMDGSIIQFPNT
YLEGSVRVVTTFDAEYCRHGTCERSEVGICLSTSGRWVLNNEHYRALSGVFCGVDAMN

FIGURE 35 (C)

LIANIFTPLVQPVGALDVSASVVAGGIIAILVTCAAYYFMKFRRAFGEYNHVVAANAL

LFLMSFTILCLAPAYSFLPGVYSVFYLYLTFYFTNDVSFLAHLQWFAMFSPIVPFWIT

AIYVFCISLKHCHWFFNNYLRKRVMFNGVTFSTFEEAALCTFLLNKEMYLKLRSETLL

PLTQYNRYLALYNKYKYFSGALDTTSYREAACCHLAKALNDFSNSGADVLYQPPQTSI

TSAVLQSGFRKMAFPSGKVEGCMVQVTCGTTTLNGLWLDDTVYCPRHVICTAEDMLNP

NYEDLLIRKSNHSFLVQAGNVQLRVIGHSMQNCLLRLKVDTSNPKTPKYKFVRIQPGQ

TFSVLACYNGSPSGVYQCAMRPNHTIKGSFLNGSCGSVGFNIDYDCVSFCYMHHMELP

TGVHAGTDLEGKFYGPFVDRQTAQAAGTDTTITLNVLAWLYAAVINGDRWFLNRFTTT

LNDFNLVAMKYNYEPLTQDHVDILGPLSAQTGIAVLDMCAALKELLQNGMNGRTILGS

TILEDEFTPFDVVRQCSGVTFQGKFKKIVKGTHHWMLLTFLTSLLILVQSTQWSLFFF

VYENAFLPFTLGIMAIAACAMLLVKHKHAFLCLFLLPSLATVAYFNMVYMPASWVMRI

MTWLELADTSLSGYRLKDCVMYASALVLLILMTARTVYDDAARRVWTLMNVITLVYKV

YYGNALDQAISMWALVISVTSNYSGVVTTIMFLARAIVFVCVEYYPLLFITGNTLQCI

MLVYCFLGYCCCCYFGLFCLLNRYFRLTLGVYDYLVSTQEFRYMNSQGLLPPKSSIDA

FKLNIKLLGIGGKPCIKVATVQSKMSDVKCTSVVLLSVLQQLRVESSSKLWAQCVQLH

NDILLAKDTTEAFEKMVSLLSVLLSMQGAVDINRLCEEMLDNRATLQAIASEFSSLPS

YAAYATAQEAYEQAVANGDSEVVLKKLKKSLNVAKSEFDRDAAMQRKLEKMADQAMTQ

MYKQARSEDKRAKVTSAMQTMLFTMLRKLDNDALNNIINNARDGCVPLNIIPLTTAAK

LMVVVPDYGTYKNTCDGNTFTYASALWEIQQVVDADSKIVQLSEINMDNSPNLAWPLI

VTALRANSAVKLQNNELSPVALRQMSCAAGTTQTACTDDNALAYYNNSKGGRFVLALL

SDHQDLKWARFPKSDGTGTIYTELEPPCRFVTDTPKGPKVKYLYFIKGLNNLNRGMVL

GSLAATVRLQAGNATEVPANSTVLSFCAFAVDPAKAYKDYLASGGQPITNCVKMLCTH

TGTGQAITVTPEANMDQESFGGASCCLYCRCHIDHPNPKGFCDLKGKYVQIPTTCAND

PVGFTLRNTVCTVCGMWKGYGCSCDQLREPLMQSADASTFLNRVCGVSAARLTPCGTG

TSTDVVYRAFDIYNEKVAGFAKFLKTNCCRFQEKDEEGNLLDSYFVVKRHTMSNYQHE

ETIYNLVKDCPAVAVHDFFKFRVDGDMVPHISRQRLTKYTMADLVYALRHFDEGNCDT

FIGURE 35 (D)

LKEILVTYNCCDDDYFNKKDWYDFVENPDILRVYANLGERVRQSLLKTVQFCDAMRDA
GIVGVLTLDNQDLNGNWYDFGDFVQVAPGCGVPIVDSYYSLLMPILTLTRALAAESHM
DADLAKPLIKWDLLKYDFTEERLCLFDRYFKYWDQTYHPNCINCLDDRCILHCANFNV
LFSTVFPPTSFGPLVRKIFVDGVPFVVSTGYHFRELGVVHNQDVNLHSSRLSFKELLV
YAADPAMHAASGNLLLDKRTTCFSVAALTNNVAFQTVKPGNFNKDFYDFAVSKGFFKE
GSSVELKHFFFAQDGNAAISDYDYYRYNLPTMCDIRQLLFVVEVVDKYFDCYDGGCIN
ANQVIVNNLDKSAGFPFNKWGKARLYYDSMSYEDQDALFAYTKRNVIPTITQMNLKYA
ISAKNRARTVAGVSICSTMTNRQFHQKLLKSIAATRGATVVIGTSKFYGGWHNMLKTV
YSDVETPHLMGWDYPKCDRAMPNMLRIMASLVLARKHNTCCNLSHRFYRLANECAQVL
SEMVMCGGSLYVKPGGTSSGDATTAYANSVFNICQAVTANVNALLSTDGNKIADKYVR
NLQHRLYECLYRNRDVDHEFVDEFYAYLRKHFSMMILSDDAVVCYNSNYAAQGLVASI
KNFKAVLYYQNNVFMSEAKCWTETDLTKGPHEFCSQHTMLVKQGDDYVYLPYPDPSRI
LGAGCFVDDIVKTDGTLMIERFVSLAIDAYPLTKHPNQEYADVFHLYLQYIRKLHDEL
TGHMLDMYSVMLTNDNTSRYWEPEFYEAMYTPHTVLQAVGACVLCNSQTSLRCGACIR
RPFLCCKCCYDHVISTSHKLVLSVNPYVCNAPGCDVTDVTQLYLGGMSYYCKSHKPPI
SFPLCANGQVFGLYKNTCVGSDNVTDFNAIATCDWTNAGDYILANTCTERLKLFAAET
LKATEETFKLSYGIATVREVLSDRELHLSWEVGKPRPPLNRNYVFTGYRVTKNSKVQI
GEYTFEKGDYGDAVVYRGTTTYKLNVGDYFVLTSHTVMPLSAPTLVPQEHYVRITGLY
PTLNISDEFSSNVANYQKVGMQKYSTLQGPPGTGKSHFAIGLALYYPSARIVYTACSH
AAVDALCEKALKYLPIDKCSRIIPARARVECFDKFKVNSTLEQYVFCTVNALPETTAD
IVVFDEISMATNYDLSVVNARLRAKHYVYIGDPAQLPAPRTLLTKGTLEPEYFNSVCR
LMKTIGPDMFLGTCRRCPAEIVDTVSALVYDNKLKAHKEKSAQCFKMFYKGVITHDVS
SAINRPQIGVVREFLTRNPAWRKAVFISPYNSQNAVASKILGLPTQTVDSSQGSEYDY
VIFTQTTETAHSCNVNRFNVAITRAKIGILCIMSDRDLYDKLQFTSLEIPRRNVATLQ
AENVTGLFKDCSKIITGLHPTQAPTHLSVDIKFKTEGLCVDIPGIPKDMTYRRLISMM
GFKMNYQVNGYPNMFITREEAIRHVRAWIGFDVEGCHATRDAVGTNLPLQLGFSTGVN

FIGURE 35 (E)

LVAVPTGYVDTENNTEFTRVNAKPPPGDQFKHLIPLMYKGLPWNVVRIKIVQMLSDTL
KGLSDRVVFVLWAHGFELTSMKYFVKIGPERTCCLCDKRATCFSTSSDTYACWNHSVG
FDYVYNPFMIDVQQWGFTGNLQSNHDQHCQVHGNAHVASCDAIMTRCLAVHECFVKRV
DWSVEYPIIGDELRVNSACRKVQHMVVKSALLADKFPVLHDIGNPKAIKCVPQAEVEW
KFYDAQPCSDKAYKIEELFYSYATHHDKFTDGVCLFWNCNVDRYPANAIVCRFDTRVL
SNLNLPGCDGGSLYVNKHAFHTPAFDKSAFTNLKQLPFFYYSDSPCESHGKQVVSDID
YVPLKSATCITRCNLGGAVCRHHANEYRQYLDAYNMMISAGFSLWIYKQFDTYNLWNT
FTRLQSLENVAYNVVNKGHFDGHAGEAPVSIINNAVYTKVDGIDVEIFENKTTLPVNV
AFELWAKRNIKPVPEIKILNNLGVDIAANTVIWDYKREAPAHVSTIGVCTMTDIAKKP
TESACSSLTVLFDGRVEGQVDLFRNARNGVLITEGSVKGLTPSKGPAQASVNGVTLIG
ESVKTQFNYFKKVDGIIQQLPETYFTQSRDLEDFKPRSQMETDFLELAMDEFIQRYKL
EGYAFEHIVYGDFSHGQLGGLHLMIGLAKRSQDSPLKLEDFIPMDSTVKNYFITDAQT
GSSKCVCSVIDLLLDDFVEIIKSQDLSVISKVVKVTIDYAEISFMLWCKDGHVETFYP
KLQASQAWQPGVAMPNLYKMQRMLLEKCDLQNYGENAVIPKGIMMNVAKYTQLCQYLN
TLTLAVPYNMRVIHFGAGSDKGVAPGTAVLRQWLPTGTLLVDSDLNDFVSDADSTLIG
DCATVHTANKWDLIISDMYDPRTKHVTKENDSKEGFFTYLCGFIKQKLALGGSIAVKI
TEHSWNADLYKLMGHFSWWTAFVTNVNASSSEAFLIGANYLGKPKEQIDGYTMHANYI
FWRNTNPIQLSSYSLFDMSKFPLKLRGTAVMSLKENQINDMIYSLLEKGRLIIRENNR
VVVSSDILVNN

FIGURE 36

KSFKTIVESCGNYKVTKGKPVKGAWNIGQQRSVLTPLCGFPSQA

AGVIRSIFARTLDAANHSIPDLQRAAVTILDGISEQSLRLVDAMVYTSDLLTNSVIIM

AYVTGGLVQQTSQWLSNLLGTTVEKLRPIFEWIEAKLSAGVEFLKDAWEILKFLITGV

FDIVKGQIQVASDNIKDCVKCFIDVVNKALEMCIDQVTIAGAKLRSLNLGEVFIAQSK

GLYRQCIRGKEQLQLLMPLKAPKEVTFLEGDSHDTVLTSEEVVLKNGELEALETPVDS

FTNGAIVGTPVCVNGLMLLEIKDKEQYCALSPGLLATNNVFRLKGGAPIKGVTFGEDT

VWEVQGYKNVRITFELDERVDKVLNEKCSVYTVESGTEVTEFACVVAEAVVKTLQPVS

DLLTNMGIDLDEWSVATFYLFDDAGEENFSSRMYCSFYPPDEEEEDDAECEEEEIDET

CEHEYGTEDDYQGLPLEFGASAETVRVEEEEEEDWLDDTTEQSEIEPEPEPTPEEPVN

QFTGYLKLTDNVAIKCVDTVKEAQSANPMVIVNAANIHLKHGGGVAGALNKATNGAMQ

KESDDYIKLNGPLTVGGSCLLSGHNLAKKCLHVVGPNLNAGEDIQLLKAAYENFNSQD

ILLAPLLSAGIFGAKPLQSLQVCVQTVRTQVYIAVNDKALYEQVVMDYLDNLKPRVEA

PKQEEPPNTEDSKTEEKSVVQKPVDVKPKIKACIDEVTTTLEETKFLTNKLLLFADIN

GKLYHDSQNMLRGEDMSFLEEDAPYMVGDVITSGDITCVVIPSKKAGGTTEMLSRALK

KVPVDEYITTYPGQGCAGYTLEEAKTALKKCKSAFYVLPSEAPNAKEEILGTVSWNLR

EMLAHAEEARKLMPICMDVRAIMATIQRKYKGVKIQEGIVDYGVRFFFYTSKEPVASI

ITKLNSLNEPLVTMPIGYVTHGFNLEEAARCMRSLKAPAVVSVSSPDAVTTYNGYLTS

SSKTSEEHFVETVSLAGSYRDWSYSGQRTELGVEFLKRGDKIVYHTLESPVEFHLDGE

VLSLDKLKSLLSLREVKTIKVFTTVDNTNLHTQLVDMSMTYGQQFGPTYLDGADVTKI

KPHVNHEGKTFFVLPSDDTLRSEAFEYYHTLDESFLGRYMSALNHTKKWKFPQVGGLT

SIKWADNNCYLSSVLLALQQLEVKFNAPALQE

FIGURE 37

KSFKTIVESCGNYKVTKGKPVKGAWNIGQQRSVLTPLCGFPSQA

AGVIRSIFARTLDAANHSIPDLQRAAVTILDGISEQSLRLVDAMVYTSDLLTNSVIIM

AYVTGGLVQQTSQWLSNLLGTTVEKLRPIFEWIEAKLSAGVEFLKDAWEILKFLITGV

FDIVKGQIQVASDNIKDCVKCFIDVVNKALEMCIDQVTIAGAKLRSLNLGEVFIAQSK

GLYRQCIRGKEQLQLLMPLKAPKEVTFLEGDSHDTVLTSEEVVLKNGELEALETPVDS

FTNGAIVGTPVCVNGLMLLEIKDKEQYCALSPGLLATNNVFRLKGGAPIKGVTFGEDT

VWEVQGYKNVRITFELDERVDKVLNEKCSVYTVESGTEVTEFACVVAEAVVKTLQPVS

DLLTNMGIDLDEWSVATFYLFDDAGEENFSSRMYCSFYPPDEEEEDDAECEEEEIDET

CEHEYGTEDDYQGLPLEFGASAETVRVEEEEEEDWLDDTTEQSEIEPEPEPTPEEPVN

QFTGYLKLTDNVAIKCVDTVKEAQSANPMVIVNAANIHLKHGGGVAGALNKATNGAMQ

KESDDYIKLNGPLTVGGSCLLSGHNLAKKCLHVVGPNLNAGEDIQLLKAAYENFNSQD

ILLAPLLSAGIFGAKPLQSLQVCVQTVRTQVYIAVNDKALYEQVVMDYLDNLKPRVEA

PKQEEPPNTEDSKTEEKSVVQKPVDVKPKIKACIDEVTTTLEETKFLTNKLLLFADIN

GKLYHDSQNMLRGEDMSFLEEDAPYMVGDVITSGDITCVVIPSKKAGGTTEMLSRALK

KVPVDEYITTYPGQGCAGYTLEEAKTALKKCKSAFYVLPSEAPNAKEEILGTVSWNLR

EMLAHAEEARKLMPICMDVRAIMATIQRKYKGVKIQEGIVDYGVRFFFYTSKEPVASI

ITKLNSLNEPLVTMPIGYVTHGFNLEEAARCMRSLKAPAVVSVSSPDAVTTYNGYLTS

SSKTSEEHFVETVSLAGSYRDWSYSGQRTELGVEFLKRGDKIVYHTLESPVEFHLDGE

VLSLDKLKSLLSLREVKTIKVFTTVDNTNLHTQLVDMSMTYGQQFGPTYLDGADVTKI

KPHVNHEGKTFFVLPSDDTLRSEAFEYYHTLDESFLGRYMSALNHTKKWKFPQVGGLT

SIKWADNNCYLSSVLLALQQLEVKFNAPALQE

FIGURE 38

MESLVLGVNEKTHVQLSLPVLQVRDVLVRGFGDSVEEALSEARE

HLKNGTCGLVELEKGVLPQLEQPYVFIKRSDALSTNHGHKVVELVAEMDGIQYGRSGI

TLGVLVPHVGETPIAYRNVLLRKNGNKGAGGHSYGIDLKSYDLGDELGTDPIEDYEQN

WNTKHGSGALRELTRELNGGVVTRYVDNNFCGPDGYPLDCIKDFLARAGKSMCTLSEQ

LDYIESKRGVYCCRDHEHEIAWFTERSDKSCEHQTPFEIKSAKKFDTFKGECPKFVFP

LNSKVKVIQPRVEKKKTEGFMGRIRSVYPVASPQECNNMHLSTLMKCNHCDEVSWQTC

DFLKATCEHCGTENLVIEGPTTCGYLPTNAVVKMPCPACQDPEIGPEHSVADYHNHSN

IETRLRKGGRTRCFGGCVFAYVGCYNKRAYWVPRASADIGSGHTGITGDNVETLNEDL

LEILSRERVNINIVGDFHLNEEVAIILASFSASTSAFIDTIKSLDYKSFKTIVESCG

FIGURE 39

MESLVLGVNEKTHVQLSLPVLQVRDVLVRGFGDSVEEALSEARE

HLKNGTCGLVELEKGVLPQLEQPYVFIKRSDALSTNHGHKVVELVAEMDGIQYGRSGI

TLGVLVPHVGETPIAYRNVLLRKNGNKGAGGHSYGIDLKSYDLGDELGTDPIEDYEQN

WNTKHGSGALRELTRELNGGVVTRYVDNNFCGPDGYPLDCIKDFLARAGKSMCTLSEQ

LDYIESKRGVYCCRDHEHEIAWFTERSDKSCEHQTPFEIKSAKKFDTFKGECPKFVFP

LNSKVKVIQPRVEKKKTEGFMGRIRSVYPVASPQECNNMHLSTLMKCNHCDEVSWQTC

DFLKATCEHCGTENLVIEGPTTCGYLPTNAVVKMPCPACQDPEIGPEHSVADYHNHSN

IETRLRKGGRTRCFGGCVFAYVGCYNKRAYWVPRASADIGSGHTGITGDNVETLNEDL

LEILSRERVNINIVGDFHLNEEVAIILASFSASTSAFIDTIKSLDYKSFKTIVESCG

FIGURE 40

MSDNGPQSNQRSAPRITFGGPTDSTDNNQNGGRNGARPKQRRPQ

GLPNNTASWFTALTQHGKEELRFPRGQGVPINTNSGPDDQIGYYRRATRRVRGGDGKM

KELSPRWYFYYLGTGPEASLPYGANKEGIVWVATEGALNTPKDHIGTRNPNNNAATVL

QLPQGTTLPKGFYAEGSRGGSQASSRSSSRSRGNSRNSTPGSSRGNSPARMASGGGET

ALALLLLDRLNQLESKVSGKGQQQQGQTVTKKSAAEASKKPRQKRTATKQYNVTQAFG

RRGPEQTQGNFGDQDLIRQGTDYKHWPQIAQFAPSASAFFGMSRIGMEVTPSGTWLTY

HGAIKLDDKDPQFKDNVILLNKHIDAYKTFPPTEPKKDKKKKTDEAQPLPQRQKKQPT

VTLLPAADMDDFSRQLQNSMSGASADSTQA

FIGURE 41

MFIFLLFLTLTSGSDLDRCTTFDDVQAPNYTQHTSSMRGVYYPD

EIFRSDTLYLTQDLFLPFYSNVTGFHTINHTFDNPVIPFKDGIYFAATEKSNVVRGWV

FGSTMNNKSQSVIIINNSTNVVIRACNFELCDNPFFAVSKPMGTQTHTMIFDNAFNCT

FEYISDAFSLDVSEKSGNFKHLREFVFKNKDGFLYVYKGYQPIDVVRDLPSGFNTLKP

IFKLPLGINITNFRAILTAFSPAQDTWGTSAAAYFVGYLKPTTFMLKYDENGTITDAV

DCSQNPLAELKCSVKSFEIDKGIYQTSNFRVVPSGDVVRFPNITNLCPFGEVFNATKF

PSVYAWERKKISNCVADYSVLYNSTFFSTFKCYGVSATKLNDLCFSNVYADSFVVKGD

DVRQIAPGQTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLSFELLNAPA

TVCGPKLSTDLIKNQCVNFNFNGLTGTGVLTPSSKRFQPFQQFGRDVSDFTDSVRDPK

TSEILDISPCSFGGVSVITPGTNASSEVAVLYQDVNCTDVSTAIHADQLTPAWRIYST

GNNVFQTQAGCLIGAEHVDTSYECDIPIGAGICASYHTVSLLRSTSQKSIVAYTMSLG

ADSSIAYSNNTIAIPTNFSISITTEVMPVSMAKTSVDCNMYICGDSTECANLLLQYGS

FCTQLNRALSGIAAEQDRNTREVFAQVKQMYKTPTLKYFGGFNFSQILPDPLKPTKRS

FIEDLLFNKVTLADAGFMKQYGECLGDINARDLICAQKFNGLTVLPPLLTDDMIAAYT

AALVSGTATAGWTFGAGAALQIPFAMQMAYRFNGIGVTQNVLYENQKQIANQFNKAIS

QIQESLTTTSTALGKLQDVVNQNAQALNTLVKQLSSNFGAISSVLNDILSRLDKVEAE

VQIDRLITGRLQSLQTYVTQQLIRAAEIRASANLAATKMSECVLGQSKRVDFCGKGYH

LMSFPQAAPHGVVFLHVTYVPSQERNFTTAPAICHEGKAYFPREGVFVFNGTSWFITQ

RNFFSPQIITTDNTFVSGNCDVVIGIINNTVYDPLQPELDSFKEELDKYFKNHTSPDV

DLGDISGINASVVNIQKEIDRLNEVAKNLNESLIDLQELGKYEQYIKWPWYVWLGFIA

GLIAIVMVTILLCCMTSCCSCLKGACSCGSCCKFDEDDSEPVLKGVKLHYT

COMPOSITIONS AND METHODS FOR DETECTING SEVERE ACUTE RESPIRATORY SYNDROME CORONAVIRUS

This invention was made, in part, with government support under grant number N01-A1-25490 awarded by the National Institutes of Health, and grant number 1N01-AI-25490 awarded by the Emerging Viral Diseases. The U.S. government has certain rights in the invention.

FIELD OF THE INVENTION

The invention relates to compositions and methods for detecting the presence of SARS-coronavirus, and for screening anti-SARS coronavirus agents and vaccines. The invention also relates to reducing infection with plus-strand RNA viruses such as SARS-coronavirus. These methods may be used for increasing the safety of cell cultures that are used in screening clinical samples for respiratory pathogens other than SARS-coronavirus.

BACKGROUND OF THE INVENTION

An outbreak of severe acute respiratory syndrome (SARS) emerged in Guangdong Province, People's Republic of China in November 2002. From China, SARS spread to 30 other countries and as of Aug. 7, 2003, this outbreak resulted in 8,422 reported cases, of which 918 were fatal. Through the coordinated efforts of laboratories around the world, a novel coronavirus, SARS-coronavirus (SARS-CoV), was identified as the causative agent of SARS (Drosten, et al., 2003, N. Engl. J. Med. 348:1967–1976; Fouchier, et al., 2003, Nature 423:240; Ksiazek, et al., 2003, N. Engl. J. Med. 348:1953–1966; Peiris, et al., 2003, Lancet 361: 1319–1325; Poutanen, et al., 2003, N. Engl. J. Med. 348: 1995–2005). This discovery was quickly followed by the publication of the complete genomic sequences of two SARS-CoV isolates and identification of specific subgenomic RNAs and proteins involved in replication (Marra, et al., 2003, Science 300:1399–1404; Rota, et al., 2003, Science 300:1394–1399; Thiel, et al., 2003, J. Gen. Virol. 84:2305–2315). Phylogenetic analysis of the SARS-CoV replicase gene demonstrated that despite a number of unique features, SARS-CoV is most closely related to group 2 coronaviruses, which include mouse hepatitis virus (MHV), bovine coronavirus (BCoV) and human coronavirus OC43 (HCoV-OC43) (Snijder, et al., 2003, J. Mol. Biol. 331: 991–1004).

SARS-CoV has been detected using the Vero E6 cell line and fetal rhesus monkey kidney cells, which are the only cell lines reported to be susceptible to SARS-CoV. Susceptibility of these cells to SARS-CoV was based on observing a cytopathic effect (CPE) post inoculation with SARS-CoV. However, many coronaviruses cause persistent infections in cell cultures and some show little evidence of CPE. Thus, using CPE to identify entry of SARS-CoV or abortive replication is insensitive, misleading, and does not correctly identify virus entry and/or replication.

SARS-CoV has also been detected using virus titration techniques, RT-PCR specific to SARS-CoV genomic RNA, and immunofluorescence assay. However, these methods are laborious, and do not distinguish between entry and replication of the virus.

Thus, there remains a need for compositions and methods for detecting the presence of SARS-coronavirus, for screening anti-SARS coronavirus agents and vaccines. There is also a need for increasing the safety of cell cultures that are routinely used in laboratories and that may support infection by plus-strand RNA viruses, such as SARS-coronavirus.

SUMMARY OF THE INVENTION

The invention provides compositions and methods for detecting the presence of SARS-coronavirus, and for screening anti-SARS coronavirus agents and vaccines. Also provided are compositions and methods for reducing infection with plus-strand RNA viruses such as SARS-coronavirus.

In one embodiment, the invention provides a method for detecting replication of severe acute respiratory syndrome coronavirus (SARS-coronavirus) in a sample, comprising detecting the presence SARS-coronavirus sgRNA in the sample. In one example, sgRNA comprises at least a portion of a leader sequence. In another example, the sgRNA comprises a gene encoding a SARS-coronavirus polypeptide. In another embodiment, the method further comprises detecting SARS-coronavirus gRNA. While not intending to limit the method of detection, in one embodiment, the detecting of gRNA and/or sgRNA is by reverse transcriptase PCR, ribonuclease protection assay, and/or by Northern blot. In another embodiment, the method further comprises quantitating sgRNA and/or gRNA. In yet a further embodiment, the method further comprises detecting one or more SARS-coronavirus polypeptide using, for example, immunofluorescence and/or Western blot. In an additional embodiment, the method further comprises detecting SARS-coronavirus particles.

The invention also provides a method for detecting the presence of severe acute respiratory syndrome coronavirus (SARS-coronavirus) in a sample, comprising: a) providing: (i) a sample; and (ii) cells chosen from HEK-293T, Huh-7, Mv1Lu, pRHMK and pCMK; b) inoculating the cells with the sample to produce inoculated cells; and c) detecting the presence of the SARS-coronavirus in the inoculated cells. In one embodiment, the detecting step comprises detecting the presence of a SARS-coronavirus polypeptide (such as Nucleocapsid (N), Spike Glycoprotein (S), Matrix (M), E protein, and Replicase proteins) by, for example, immunofluorescence and/or Western blot. Alternatively, or in addition, the detecting may comprise detecting the presence of SARS-coronavirus gRNA and/or sgRNA.

While not intending to limit the type or source of cell in any of the invention's methods, in one embodiment, the cells comprises a transgenic cell and/or wild type cell. In a preferred embodiment, the transgenic cell comprises Mv1Lu-hF deposited as ATCC accession number PTA-4737. Alternatively, the transgenic cell comprises a cell line established from a transgenic cell line designated Mv1Lu-hF, wherein the established cell line has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line. In another embodiment, the transgenic cell comprises a transgenic mink lung epithelial cell line expressing human furin, wherein the cell line has a property selected from the group consisting of (a) increased sensitivity to at least one virus selected from the group consisting of influenza A virus, influenza B virus and parainfluenza virus 3, as compared to Mv1Lu, and (b) enhanced productivity of infectious virions upon inoculation with at least one virus selected from the group one consisting of influenza A virus, influenza B virus and parainfluenza virus 3, as compared to Mv1Lu. In a further embodiment, the inoculating step comprises contacting the cells (whether wild type and/or transgenic) with a protease inhibitor.

While not intending to limit the type of culture in any of the invention's methods, the cells may be in single cell type culture, in mixed cell type culture with a second cell type, and/or are frozen in situ. Also without limiting the source or type of sample in any of the invention's methods, sample is isolated from a mammal, preferably from a human.

The invention further provides a method for detecting the presence of severe acute respiratory syndrome coronavirus (SARS-coronavirus) in a first sample and in a second sample, comprising: a) providing: (i) a first sample; (ii) a second sample; b) contacting test cells chosen from HEK-293T, Huh-7, Mv1Lu, pRHMK and pCMK with: (i) the first sample to produce a first treated sample; and (ii) the second sample to produce a second treated sample; wherein the exposing is under conditions such that the test cells are infected with SARS-coronavirus; c) detecting the presence of SARS-coronavirus gRNA and SARS-coronavirus sgRNA, wherein the detecting indicates the presence of the SARS-coronavirus. In one embodiment, the detecting step comprises detecting one or more of: i) absence of SARS-coronavirus gRNA in the first treated sample; ii) reduced level of SARS-coronavirus sgRNA in the first treated sample compared to the level of sgRNA in the second treated sample; and iii) reduced ratio of SARS-coronavirus sgRNA level to SARS-coronavirus gRNA level in the first treated sample compared to in the second treated sample; wherein the detecting indicates that the first sample contains a reduced level of SARS-coronavirus compared to the second sample. In one embodiment, the first sample is from a mammal treated with an agent identified according to any method, and the second sample is from the mammal that is not treated with the agent. In another embodiment, the first sample is from a mammal treated with a first concentration of an agent identified according to any method, and the second sample is from the mammal treated with a second concentration of the agent, wherein the first and second concentrations are different. In yet another embodiment, the first sample is from a mammal treated with a first agent identified according to any method, and the second sample is from the mammal treated with a second agent identified according to any method, wherein the first and second agent are different.

The invention also provides a method for identifying a test agent as altering (such as reducing or increasing) replication of severe acute respiratory syndrome coronavirus (SARS-coronavirus) in a cell, comprising: a) providing cells treated with a first test agent, wherein the cells are chosen from HEK-293T, Huh-7, Mv1Lu, pRHMK and pCMK; and b) detecting an altered level of replication of cells treated with the first test agent compared to a level of replication of the cells not treated with the first test agent, wherein the detecting identifies the first test agent as altering replication of severe acute respiratory syndrome coronavirus (SARS-coronavirus) in a cell. Without limiting the method of detection, in one embodiment, the detecting step may comprise detecting SARS-coronavirus sgRNA, gRNA, polypeptide and/or virus particle. In another embodiment, the detecting comprises detecting one or more of: i) absence of SARS-coronavirus gRNA in the treated cells; ii) reduced level of SARS-coronavirus sgRNA in the treated cells compared to the level of sgRNA in the cells that are not treated with the first test agent; and iii) reduced ratio of SARS-coronavirus sgRNA level relative to SARS-coronavirus gRNA level in the treated cells compared to in the cells that are not treated with the first test agent; wherein the detecting identifies the first test agent as reducing replication of severe acute respiratory syndrome coronavirus (SARS-coronavirus) in a cell. Without limiting the use or methodology, it may be desirable to compare the efficacy of two potential drugs, by comparing their effect on only sgRNA by detecting comprises detecting one or more of: i) reduced level of SARS-coronavirus sgRNA in the cells treated with a second test agent compared to the level of sgRNA in the cells treated with the first test agent; and ii) reduced ratio of SARS-coronavirus sgRNA level to SARS-coronavirus gRNA level in the cells treated with a second test agent compared to the ratio in the cells treated with the first test agent. In an exemplary embodiment, detecting one or more of: a) an increased reduction in the level of SARS-coronavirus sgRNA in the cells treated with the first test agent compared to the cells treated with the second test agent, and b) an increased reduction in the ratio of SARS-coronavirus sgRNA level to SARS-coronavirus gRNA level in the cells treated with the first test agent compared to the cells treated with the second test agent, wherein the detecting identifies the first test agent as more efficacious than the second test agent in reducing replication of severe acute respiratory syndrome coronavirus (SARS-coronavirus) in a cell.

Additionally provided herein is a method for reducing replication of severe acute respiratory syndrome coronavirus (SARS-coronavirus) in a mammal, comprising administering a therapeutic amount of a test agent to the mammal, wherein the test agent is identified according to the above method.

The invention also provides a method for producing one or more of severe acute respiratory syndrome coronavirus (SARS-coronavirus) particles and SARS-coronavirus polypeptide, comprising: a) providing: (i) SARS-coronavirus; and (ii) a cell type chosen from HEK-293T, Huh-7, Mv1Lu, pRHMK and pCMK; and b) inoculating the cell type with the virus under conditions such that the inoculated cell produces one or more of SARS-coronavirus and SARS-coronavirus polypeptide.

Moreover, provided by the invention is an antibody specific for one or more SARS-coronavirus antigen that is produced by a cell chosen from HEK-293T, Huh-7, Mv1Lu, pRHMK and pCMK. The antibody may comprises a polyclonal antibody, monoclonal antibody, and/or humanized antibody.

Also provided is a severe acute respiratory syndrome coronavirus (SARS-coronavirus) vaccine produced using cells chosen from HEK-293T, Huh-7, Mv1Lu, pRHMK and pCMK.

The invention additionally provides a method for immunizing a mammal against severe acute respiratory syndrome coronavirus (SARS-coronavirus), comprising administering to a mammal a vaccine produced according any method, wherein the administering generating an immune response in the mammal against severe acute respiratory syndrome coronavirus (SARS-coronavirus).

Also provided herein is a composition comprising (i) cells susceptible to a virus that is not a plus-strand RNA virus, and (ii) protease inhibitor. The plus-strand RNA virus is exemplified by Adenovirus, Arenaviridae, Baculoviridae, Birnaviridae, Bunyaviridae, Caliciviridae, Cardiovirus, Corticoviridae, Cystoviridae, Epstein-Barr virus, Enterovirus, Filoviridae, Foot-and-mouth disease virus, Hepadnviridae, Hepatitis virus, Herpesviridae, Immunodeficiency virus, Influenza virus, Inoviridae, Iridoviridae, Orthomyxoviridae, Papovaviru, Paramyxoviridae, Parvoviridae, Poliovirus, Polydnaviridae, Poxyviridae, Reoviridae, Retrovirus, Rhabdoviridae, Rhinoviridae, Semliki Forest virus, Tetraviridae, Toroviridae, Vaccinia virus, and Vesicular stomatitis virus.

Further provided herein is a method for detecting a virus that is not a plus-strand RNA virus in a sample, comprising: a) providing: i) a sample; ii) cells susceptible to the virus that is not a plus-strand RNA virus; and iii) one or more protease inhibitor; b) contacting the cells and the sample in the presence of the protease inhibitor to produce contacted cells, wherein replication of the virus that is not a plus-strand RNA virus in the contacted cells is not reduced relative to replication of the virus that is not a plus-strand RNA virus in cells not contacted with the protease inhibitor, and wherein replication of a plus-strand RNA virus in the cells contacted with the protease inhibitor is reduced relative to replication of the plus-strand RNA virus in cells not contacted with the protease inhibitor. In one embodiment, the plus-strand RNA virus is chosen from togavirus, flavivirus, coronavirus, and picornavirus.

The invention also provides a composition comprising (i) cells susceptible to a virus chosen from influenza virus, parainfluenza virus, adenovirus, and respiratory syncytial virus, and (ii) protease inhibitor.

Also provided herein, is method for detecting a virus chosen from influenza virus, parainfluenza virus, adenovirus, and respiratory syncytial virus in a sample, comprising: a) providing: i) a sample; ii) cells susceptible to the virus; and iii) one or more protease inhibitor; b) contacting the cells and the sample in the presence of the protease inhibitor to produce contacted cells, wherein replication of the contacted cells by the virus is not reduced relative to cells not contacted with the protease inhibitor, and wherein replication of the contacted cells by severe acute respiratory syndrome coronavirus (SARS-coronavirus) is reduced relative to cells not contacted with the protease inhibitor. In one embodiment, the influenza virus is chosen from influenza A, influenza B, and influenza C, the parainfluenza virus is chosen from parainfluenza 1, parainfluenza 2, and parainfluenza 3. Without limiting the cell type in this or any of the invention's methods, in one embodiment, the cells comprise a transgenic cell (such as Mv1Lu-hF) and/or wild type cell. Also without limiting the nature of the culture used in this and in any other of the invention's methods, the cells may be in single cell type culture, mixed cell type culture (comprising a wild type cell and/or a transgenic cell), and/or are frozen in situ. In one embodiment, the inoculated Mv1Lu cells are incubated with the sample for up to 24 hours and/or up to 48 hours. Without limiting the type of sample in any of the invention's methods, the sample is isolated from a mammal that has been treated with an agent that is suspected of reducing replication of SARS-coronavirus in a cell.

BRIEF DESCRIPTION OF THE DRAWINGS

FIG. 2 shows susceptibility of monkey kidney cells to SARS-CoV. (A) Amplification of G3PDH, SARS-CoV gRNA and sgRNA at 1, 24, 48 h post-inoculation (p.i.). African green monkey cells (Vero E6), primary rhesus monkey kidney cells (pRhMK), primary cynomologous monkey kidney cells (pCMK). Mock inoculated cells (M) and baby hamster kidney cells (BHK21) included as negative controls. Negative images are shown. Results are representative of 2 experiments performed in duplicate. (B) Titration of cell supernatants in Vero E6 cells ($TCID_{50}$). Graph depicts the average of two to three experiments each in triplicate.

FIG. 4 shows susceptibility of clinically relevant cells to SARS-CoV. (A) Amplification of G3PDH, SARS-CoV gRNA and sgRNA at 1, 24 and 48 h p.i. Mixed monolayer of mink lung cells and human lung cells (R-Mix), Mink lung cells (Mv1Lu), human lung cells (A549) and human embryonic lung cells (HEL). Mock inoculated cells included as negative control. Negative images are shown. Figure is representative of two experiments performed in duplicate. (B) Titration of cell supernatants in Vero E6 cells ($TCID_{50}$). Graph is average of 2 experiments performed in triplicate.

FIG. 5 shows susceptibility of human cell lines to SARS-CoV. (A) Amplification of G3PDH, SARS-CoV gRNA and sgRNA at 1, 24 and 48 h p.i. Human embryonic kidney (HEK-293T) and human liver carcinoma cells (Huh-7). Mock inoculated cells were included as a negative control (M). Negative images are shown. This Figure is representative of three experiments performed in duplicate.

FIG. 6 shows the effect of human APN on susceptibility of cells. (A) Amplification of G3PDH, SARS-CoV gRNA and sgRNA at 1, 24 and 48 h p.i. Murine epithelia cells (CMT-93), CMT-93 expressing human APN (hAPN) (CMT-93/hAPN), baby hamster kidney cells (BHK-21) and BHK-21 expressing hAPN (BHK-21/hAPN). Mock inoculated cells included as negative control; Huh-7 cells included as positive control. Negative images are shown. Figure is representative of three experiments performed in triplicate. (B) FACS analysis of APN expression. Cells transfected with hAPN are depicted by the solid line, cells without APN are depicted by the dashed line, staining with isotype control antibody is represented by the shaded curve.

FIG. 7A–I shows the genomic RNA sequence of SARS-CoV Urbani (GenBank accession # AY278741) (SEQ ID NO:1).

FIG. 8A–J shows the genomic RNA sequence of SARS-CoV Tor2 (GenBank accession # AY274119) (SEQ ID NO:2).

FIG. 9A–I shows the genomic RNA sequence of SARS-CoV CUHK-W1 (GenBank accession # AY278554) (SEQ ID NO:3).

FIG. 10 shows a partial genomic RNA sequence of SARS-CoV Shanghai LY (GenBank accession # H012999) (SEQ ID NO:4) orf1a polyprotein gene.

FIG. 11A–C shows a partial genomic RNA sequence of SARS-CoV Shanhgai LY (GenBank accession # H012999) (SEQ ID NO:5) orf1ab polyprotein and orf1a polyprotein genes.

FIG. 12A–B shows a partial genomic RNA sequence of SARS-CoV Shanhgai LY (GenBank accession # H012999) (SEQ ID NO:6) orf1ab polyprotein, Spike glycoprotein, and Orf3a genes.

FIG. 13 shows a partial genomic RNA sequence of SARS-CoV Shanhgai LY (GenBank accession # H012999) (SEQ ID NO:7) Orf7a, Orf7b, Orf8A, Orf8b, and Nucleocapsid protein genes.

FIG. 14A–B shows a partial genomic RNA sequence of SARS-CoV Shanghai QXC (GenBank accession # AH013000) (SEQ ID NO:8) orf1a polyprotein, and orf1ab polyprotein genes.

FIG. 15A–B shows a partial genomic RNA sequence of SARS-CoV Shanghai QXC (GenBank accession # AH013000) (SEQ ID NO:9) orf1ab polyprotein gene.

FIG. 16 shows a partial genomic RNA sequence of SARS-CoV Shanghai QXC (GenBank accession # AH013000) (SEQ ID NO:10) of the Orf3a, Orf4b, envelope protein E, membrane glycoprotein M, Orf6, and Orf7a genes.

FIG. 17 shows a partial genomic RNA sequence of SARS-CoV Shanhgai LY (GenBank accession # AY322208) (SEQ ID NO:11) of the Orf7a gene (partial cds); and Orf7b, Orf8A, Orf8b, and Nucleocapsid protein genes (complete cds).

FIG. 18A–B shows a genomic RNA sequence of SARS-CoV Shanghai QXC (GenBank accession # AY322197) (SEQ ID NO:12) orf1ab polyprotein and orf1a polyprotein genes.

FIG. 19 shows a genomic RNA sequence of SARS-CoV Shanghai QXC (GenBank accession # AY322199) (SEQ ID NO:13) Orf3a gene (partial cds), Orf4b, envelope protein E, membrane glycoprotein M, and Orf6 genes (complete cds), and Orf7a gene (partial cds).

FIG. 20 shows a genomic RNA sequence of SARS-CoV Shanghai LY (GenBank accession # AY322205) (SEQ ID NO:14) orf1ab polyprotein and orf1a polyprotein genes (partial cds).

FIG. 21A–D shows a genomic RNA sequence of SARS-CoV Shanghai LY (GenBank accession # AY322206) (SEQ ID NO:15) orf1a polyprotein and orf1ab polyprotein genes (partial cds).

FIG. 22 shows a genomic RNA sequence of SARS-CoV ZJ-HZ01 (GenBank accession # AY322206) (SEQ ID NO:16) Nucleocapsid protein, uncharacterized protein 9b, and uncharacterized protein 9c genes, (complete cds).

FIG. 23 shows the amino acid sequence (SEQ ID NO:17) of Nucleocapsid protein of SARS-CoV (Urbani) (Genbank Accession Number AY278741).

FIG. 24 shows the amino acid sequence (SEQ ID NO:18) of Nucleocapsid protein of SARS-CoV (Tor2) (Genbank Accession Number AY274119).

FIG. 25 shows the amino acid sequence of Nucleocapsid protein of SARS-CoV (Shanghai LY) (A) for Genbank Accession Number AY322205 (SEQ ID NO:19), and (B) for Genbank Accession Number AY322208 (SEQ ID NO:80).

FIG. 26 shows the amino acid sequence (SEQ ID NO:20) of Nucleocapsid protein of SARS-CoV (ZJ-HZ01) (Genbank Accession Number AY290752).

FIG. 27 shows the amino acid sequence (SEQ ID NO:21) of the Spike glycoprotein of SARS-CoV (Urbani) (Genbank Accession Number AY278741).

FIG. 28 shows the amino acid sequence (SEQ ID NO:22) of the Spike glycoprotein of SARS-CoV (Tor2) (Genbank Accession Number AY274119).

FIG. 29 shows the amino acid sequence (SEQ ID NO:23) of the Spike glycoprotein of SARS-CoV (Shanghai LY) (Genbank Accession Number AY322205).

FIG. 30 shows the amino acid sequence of the Matrix protein of SARS-CoV (A) Urbani (Genbank Accession Number AY278741) (SEQ ID NO:24), (B) Tor2 (Genbank Accession Number AY274119) (SEQ ID NO:81), (C and D) Shanghai QXC (Genbank Accession Numbers AY322199 (SEQ ID NO:82) and AH013000 (SEQ ID NO:83), respectively).

FIG. 31 shows the amino acid sequence of the E protein of SARS-CoV (A) Urbani (Genbank Accession Number AY278741) (SEQ ID NO:25), (B) Tor2 (Genbank Accession Number AY274119) (SEQ ID NO:84), (C and D) Shanghai QXC (Genbank Accession Numbers AY322199 (SEQ ID NO:85) and AH013000 (SEQ ID NO:86), respectively), and (E) UHK-W1 (Genbank Accession Number AY278554) (SEQ ID NO:87).

FIG. 32A–C shows the amino acid sequence (SEQ ID NO:26) of the polyprotein 1a of SARS-CoV Urbani (Genbank Accession Number AY278741).

FIG. 33A–E shows the amino acid sequence (SEQ ID NO:27) of the polyprotein lab of SARS-CoV (Tor2) (Genbank Accession Number AY274119).

FIG. 34A–B shows the amino acid sequence (SEQ ID NO:28) of the polyprotein 1b of SARS-CoV (Urbani) (Genbank Accession Number AY278741).

FIG. 35A–E shows the amino acid sequence (SEQ ID NO:29) of the polyprotein 1ab of SARS-CoV (CUHK-W1) (Genbank Accession Number AY278554).

FIG. 36 shows the amino acid sequence (SEQ ID NO:30) of the polyprotein 1a of SARS-CoV (Shanghai QXC) (Genbank Accession Number AY322197).

FIG. 37 shows the amino acid sequence (SEQ ID NO:31) of the polyprotein 1ab of SARS-CoV (Shanghai QXC) (Genbank Accession Number AY322197).

FIG. 38 shows the amino acid sequence (SEQ ID NO:32) of the polyprotein 1a of SARS-CoV (Shanghai LY) (Genbank Accession Number AY322197).

FIG. 39 shows the amino acid sequence (SEQ ID NO:33) of the polyprotein 1ab of SARS-CoV (Shanghai LY) (Genbank Accession Number AY322197).

FIG. 40 shows the amino acid sequence (SEQ ID NO:34) of Nucleocapsid protein of SARS-CoV (CUHK-W1) (Genbank Accession Number AY278554).

FIG. 41 shows the amino acid sequence (SEQ ID NO:35) of Spike protein of SARS-CoV (CUHK-W1) (Genbank Accession Number AY278554).

DEFINITIONS

Figure 1:
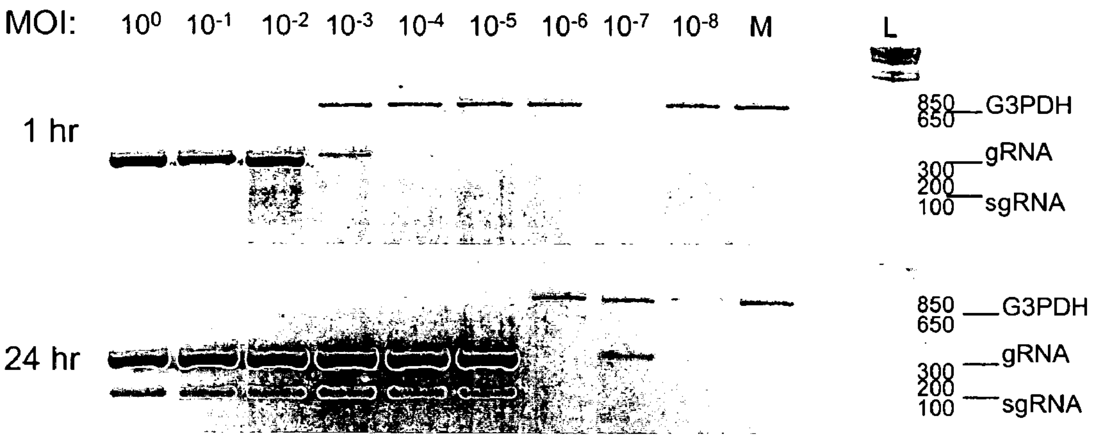
FIG. 1 shows an exemplary multiplex RT-PCR assay for the detection of SARS-CoV replication. Amplification of G3PDH, SARS-CoV genomic RNA (gRNA) and subgenomic RNA (sgRNA) from RNA at 1 and 24 hours post inoculation of Vero E6 cells inoculated with serial dilutions of SARS-CoV. Mock inoculation (M). Negative images are shown. Figure is representative of 3 experiments each performed in duplicate.

To facilitate understanding of the invention, a number of terms are defined below.

As used herein, the term “cell type,” refers to any cell, regardless of its source or characteristics. A cell type includes a “wild-type cell” (i.e., a cell whose genome has not been manipulated by man), and a “transgenic cell.”

As used herein, the term “microorganism” refers to any organism of microscopic or ultramicroscopic size including, but not limited to, viruses, bacteria, and protozoa.

As used herein, the term “culture” refers to a composition, whether liquid, gel, or solid, which contains one or more microorganisms and/or one or more cells. A culture of organisms and/or cells can be pure or mixed. For example, the terms “pure culture” of a microorganism as used herein refers to a culture in which the microorganisms present are of only one strain of a single species of a particular genus. This is in contrast to a “mixed culture” of microorganisms which refers to a culture in which more than one strain of a single genus and/or species of microorganism is present.

As used herein, the terms "culture media," and "cell culture media," refer to media that are suitable to support maintenance and/or growth of cells in vitro (i.e., cell cultures).

A "primary cell" is a cell which is directly obtained from a tissue or organ of an animal whether or not the cell is in culture.

A "cultured cell" is a cell which has been maintained and/or propagated in vitro. Cultured cells include primary cultured cells and cell lines.

"Primary cultured cells" are primary cells which are in in vitro culture and which preferably, though not necessarily, are capable of undergoing ten or fewer passages in in vitro culture before senescence and/or cessation of proliferation.

The terms "cell line" and "immortalized cell" refer to a cell which is capable of a greater number of cell divisions in vitro before cessation of proliferation and/or senescence as compared to a primary cell from the same source. A cell line includes, but does not require, that the cells be capable of an infinite number of cell divisions in culture. The number of cell divisions may be determined by the number of times a cell population may be passaged (i.e., subcultured) in in vitro culture. Passaging of cells is accomplished by methods known in the art. Briefly, a confluent or subconfluent population of cells which is adhered to a solid substrate (e.g., plastic Petri dish) is released from the substrate (e.g., by enzymatic digestion), and a proportion (e.g., 10%) of the released cells is seeded onto a fresh substrate. The cells are allowed to adhere to the substrate, and to proliferate in the presence of appropriate culture medium. The ability of adhered cells to proliferate may be determined visually by observing increased coverage of the solid substrate over a period of time by the adhered cells. Alternatively, proliferation of adhered cells may be determined by maintaining the initially adhered cells on the solid support over a period of time, removing and counting the adhered cells and observing an increase in the number of maintained adhered cells as compared to the number of initially adhered cells.

Cell lines may be generated spontaneously or by transformation. A "spontaneous cell line" is a cell line which arises during routine culture of cells. A "transformed cell line" refers to a cell line which is generated by the introduction of a "transgene" comprising nucleic acid (usually DNA) into a primary cell or into a finite cell line by way of human intervention.

Cell lines include, but are not limited to, finite cell lines and continuous cell lines. As used herein, the term "finite cell line" refers to a cell line which is capable of a limited number (from about 1 to about 50, more preferably from about 1 to about 40, and most preferably from about 1 to about 20) of cell divisions prior to senescence.

The term "continuous cell line" refers to a cell line which is capable of more than about 50 (and more preferably, an infinite number of) cell divisions. A continuous cell line generally, although not necessarily, also has the general characteristics of a reduced cell size, higher growth rate, higher cloning efficiency, increased tumorigenicity, and/or a variable chromosomal complement as compared to the finite cell line or primary cultured cells from which it is derived.

The term "transgene" as used herein refers to any nucleic acid sequence which is introduced into the cell by experimental manipulations. A transgene may be an "endogenous DNA sequence" or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "nucleotide sequence of interest" refers to any nucleotide sequence, the manipulation of which may be deemed desirable for any reason, by one of ordinary skill in the art. Nucleotide sequences of interest include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.).

As used herein, the singular forms "a," "an" and "the" include both singular and plural references unless the content clearly dictates otherwise.

As used herein, the term "or" when used in the expression "A or B," where A and B refer to a composition, disease, product, etc., means one, or the other, or both.

The terms "chosen from A, B and C" and "chosen from one or more of A, B and C" are equivalent terms that mean selecting any one of A, B, and C, or any combination of A, B, and C.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weight, reaction conditions, and so forth as used herein, are to be understood as being modified in all instances by the term "about." Accordingly, unless indicated to the contrary, the numerical parameters herein are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (e.g., nucleic acid sequence such as "gRNA," "sgRNA," amino acid sequence such as "Nucleocapsid," "Spike," "Matrix," "E protein," and "Replicase proteins," etc.), and/or phenomenon (e.g., susceptibility, permissivity, infection with a microorganism, binding to a molecule, expression of a nucleic acid sequence, transcription of a nucleic acid sequence, enzyme activity, etc.) means that only the particularly named molecule or phenomenon is excluded.

The term "altering" and grammatical equivalents as used herein in reference to the level of any molecule (e.g., nucleic acid sequence such as "gRNA," "sgRNA," amino acid sequence such as "Nucleocapsid," "Spike," "Matrix," "E protein," and "Replicase proteins," etc.), and/or phenomenon (e.g., susceptibility, permissivity, infection with a microorganism, binding to a molecule, expression of a nucleic acid sequence, transcription of a nucleic acid sequence, enzyme activity, etc.) refers to an increase and/or decrease in the quantity of the molecule and/or phenomenon, regardless of whether the quantity is determined objectively, and/or subjectively. For example, "altering replication" of a virus includes increasing and/or decreasing the quantity of any one or more of the steps of adsorption (e.g., receptor binding) to a cell, entry into a cell (such as by endocytosis), introducing the viral genome sequence into the cell, uncoating the viral genome, initiating transcription of genomic RNA, producing subgenomic RNA, directing expression of SARS-CoV encapsidation proteins, encapsidating the replicated viral nucleic acid sequence with the encapsidation proteins into a viral particle, release of the encapsidated virus from the cell, and infection of other cells by the released virus.

Unless defined otherwise in reference to the level of molecules and/or phenomena, the terms "increase," "elevate," "raise," and grammatical equivalents when in reference to the level of any molecule (e.g., nucleic acid sequence such as "gRNA," "sgRNA," amino acid sequence such as "Nucleocapsid," "Spike," "Matrix," "E protein," and "Replicase proteins," etc.), and/or phenomenon (e.g., susceptibility, permissivity, infection with a microorganism, binding to a molecule, expression of a nucleic acid sequence, transcription of a nucleic acid sequence, enzyme activity, etc.) in a first sample relative to a second sample, mean that the quantity of the molecule and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, difficulty in breathing, clarity of vision, nausea, tiredness, etc. In another embodiment, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

Unless defined otherwise in reference to the level of molecules and/or phenomena, the terms "reduce," "inhibit," "diminish," "suppress," "decrease," and grammatical equivalents when in reference to the level of any molecule (e.g., nucleic acid sequence such as "gRNA," "sgRNA," amino acid sequence such as "Nucleocapsid," "Spike," "Matrix," "E protein," and "Replicase proteins," etc.), and/or phenomenon (e.g., susceptibility, permissivity, infection with a microorganism, binding to a molecule, expression of a nucleic acid sequence, transcription of a nucleic acid sequence, enzyme activity, etc.) in a first sample relative to a second sample, mean that the quantity of molecule and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, difficulty in breathing, clarity of vision, nausea, tiredness, etc. In another embodiment, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample.

Reference herein to any specifically named protein (such as "Nucleocapsid," "Spike," "Matrix," "E protein," and "Replicase proteins," etc.) refers to any and all equivalent fragments, fusion proteins, and variants of the specifically named protein, having at least one of the biological activities (such as those disclosed herein and/or known in the art) of the specifically named protein, wherein the biological activity is detectable by any method.

The term "fragment" when in reference to a protein (such as "Nucleocapsid," "Spike," "Matrix," "E protein," and "Replicase proteins," etc.) refers to a portion of that protein that may range in size from four (4) contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

The term "fusion protein" refers to two or more polypeptides that are operably linked. The term "operably linked" when in reference to the relationship between nucleic acid sequences and/or amino acid sequences refers to linking the sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. The term also refers to the linkage of amino acid sequences in such a manner so that a functional protein is produced.

The term "variant" of a protein (such as "Nucleocapsid," "Spike," "Matrix," "E protein," and "Replicase proteins," etc.) as used herein is defined as an amino acid sequence which differs by insertion, deletion, and/or conservative substitution of one or more amino acids from the protein of which it is a variant. The term "conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) my be conservatively substituted for glutamic acid (glutamate) as both are acidic, charged (hydrophilic) amino acids. Also, lysine, arginine, and histidine my be conservatively substituted one for the other since each is a basic, charged (hydrophilic) amino acid. Guidance in determining which and how many amino acid residues may be substituted, inserted or deleted without abolishing biological and/or immunological activity may be found using computer programs well known in the art, for example, DNAStar™ software. In one embodiment, the sequence of the variant has at least 95% identity, at least 90% identity, at least 85% identity, at least 80% identity, at least 75% identity, at least 70% identity, and/or at least 65% identity with the sequence of the protein in issue.

Reference herein to any specifically named nucleotide sequence (such as a sequence encoding "Nucleocapsid," "Spike," "Matrix," "E protein," and "Replicase proteins," etc.) includes within its scope any and all equivalent fragments, homologs, and sequences that hybridize under highly stringent and/or medium stringent conditions to the specifically named nucleotide sequence, and that have at least one of the biological activities (such as those disclosed herein and/or known in the art) of the specifically named nucleotide sequence, wherein the biological activity is detectable by any method.

The "fragment" or "portion" may range in size from an exemplary 5, 10, 20, 50, or 100 contiguous nucleotide residues to the entire nucleic acid sequence minus one nucleic acid residue. Thus, a nucleic acid sequence comprising "at least a portion of" a nucleotide sequence comprises from five (5) contiguous nucleotide residues of the nucleotide sequence to the entire nucleotide sequence.

The term "homolog" of a specifically named nucleotide sequence refers to an oligonucleotide sequence which exhibits greater than 50% identity to the specifically named nucleotide sequence. Alternatively, or in addition, a homolog of a specifically named nucleotide sequence is defined as an oligonucleotide sequence which has at least 95% identity, at least 90% identity, at least 85% identity, at least 80% identity, at least 75% identity, at least 70% identity, and/or at least 65% identity to nucleotide sequence in issue.

With respect to sequences that hybridize under stringent conditions to the specifically named nucleotide sequence, high stringency conditions comprise conditions equivalent to binding or hybridization at 68° C. in a solution containing 5× SSPE, 1% SDS, 5× Denhardt's reagent and 100 μg/ml denatured salmon sperm DNA followed by washing in a solution containing 0.1× SSPE, and 0.1% SDS at 68° C. "Medium stringency conditions" when used in reference to nucleic acid hybridization comprise conditions equivalent to binding or hybridization at 42° C. in a solution of 5× SSPE (43.8 g/l NaCl, 6.9 g/l NaH2PO4-H2O and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

As will be understood by those of skill in the art, it may be advantageous to produce a nucleotide sequence encoding a protein of interest, wherein the nucleotide sequence possesses non-naturally occurring codons. Therefore, in some embodiments, codons preferred by a particular prokaryotic or eukaryotic host (Murray et al., Nucl. Acids Res., 17 (1989)) are selected, for example, to increase the rate of expression or to produce recombinant RNA transcripts having desirable properties, such as a longer half-life, than transcripts produced from naturally occurring sequence. The term "naturally occurring" as used herein when applied to an object (such as cell, tissue, etc.) and/or molecule (such as amino acid, amino acid sequence, nucleic acid, nucleic acid sequence, codon, etc.) means that the object and/or molecule can be found in nature. For example, a naturally occurring polypeptide sequence refers to a polypeptide sequence that is present in an organism (including viruses) that can be isolated from a source in nature, wherein the polypeptide sequence has not been intentionally modified by man in the laboratory.

A "composition" comprising a particular polynucleotide sequence and/or comprising a particular protein sequence as used herein refers broadly to any composition containing the recited polynucleotide sequence (and/or its equivalent fragments, homologs, and sequences that hybridize under highly stringent and/or medium stringent conditions to the specifically named nucleotide sequence) and/or the recited protein sequence (and/or its equivalent fragments, fusion proteins, and variants), respectively. The composition may comprise an aqueous solution containing, for example, salts (e.g., NaCl), detergents (e.g., SDS), and other components (e.g., Denhardt's solution, dry milk, salmon sperm DNA, etc.).

The terms nucleotide sequence "comprising a particular nucleic acid sequence" and protein "comprising a particular amino acid sequence" and equivalents of these terms, refer to any nucleotide sequence of interest and to any protein of interest, respectively, that contain the particularly named nucleic acid sequence (and/or its equivalent fragments, homologs, and sequences that hybridize under highly stringent and/or medium stringent conditions to the specifically named nucleotide sequence) and the particularly named amino acid sequence (and/or its equivalent fragments, fusion proteins, and variants), respectively. The invention does not limit the source (e.g., cell type, tissue, animal, etc.), nature (e.g., synthetic, recombinant, purified from cell extract, etc.), and/or sequence of the nucleotide sequence of interest and/or protein of interest. In one embodiment, the nucleotide sequence of interest and protein of interest include coding sequences of structural genes (e.g., probe genes, reporter genes, selection marker genes, oncogenes, drug resistance genes, growth factors, etc.).

DESCRIPTION OF THE INVENTION

The invention provides compositions and methods for detecting the presence of SARS-coronavirus, and screening anti-SARS-coronavirus drugs and vaccines. These compositions and methods were premised, at least in part, on the inventors' discovery of a sensitive assay for determining susceptibility and/or permissivity of cells to SARS-CoV. The invention's compositions and methods are useful for culturing SARS-CoV isolates, producing SARS-CoV virions and/or antigens that may be used in vaccine formulations, as antigen preparations for diagnostic applications, and for screening antiviral drugs. Additional uses of the invention's compositions and methods may be found in the elucidation of potential animal models and the identification of the SARS-CoV receptor(s).

Also provided are compositions and methods for reducing infection with plus-strand RNA viruses such as SARS-coronavirus. In one embodiment, the invention provides compositions and methods for reducing infection with SARS-coronavirus, without substantially reducing infection with other respiratory viruses. These methods are premised, at least in part, on the inventors' discovery that protease inhibitors do not substantially reduce infection of cells by the exemplary respiratory viruses influenza, parainfluenza, RSV, and adenovirus (Example 8). This is in contrast to the inhibition in replication of coronaviruses by the protease inhibitor E64 (Example 8) and the cysteine proteinase inhibitor (2S,3S)transepoxysuccinyl-L-leucylamido-3-methylbutane ethyl ester (Yount et al. PNAS 100:12995–13000 (2003). These methods are useful, where it is desirable to reduce exposure of personnel to SARS-coronavirus in clinical virology laboratories that routinely screen clinical specimen for respiratory pathogens (such as influenza, parainfluenza, RSV, and adenovirus) other than SARS-coronavirus.

In one embodiment, the invention's methods for detecting SARS-coronavirus are exemplified by a multiplex RT-PCR assay for detecting G3PDH, SARS-CoV genomic RNA (gRNA) and subgenomic RNA (sgRNA). In one embodiment, subgenomic RNA is indicative of virus entry and replication. The sensitivity of the PCR assay was determined by inoculation of Vero E6 cells with serial dilutions of SARS-CoV. Human, murine, canine, hamster, feline, mink and monkey cells were analyzed at various times post-inoculation and supernatants were titered to determine if cells produced infectious virus.

The invention is further premised on the discovery, using the exemplary multiplex RT-PCR assay, of mink, human, and monkey cells that are permissive to SARS-CoV infection. In particular, kidney cells derived from different species of monkey (primary Rhesus monkey kidney cells (pRhMK) and primary Cynomolgous monkey kidney cells (pCMK) were discovered by the inventors to be susceptible to, and to be productively infected by SARS-CoV. Data herein also shows that mink lung (Mv1Lu) epithelial cells are also susceptible to, and productively infected by SARS-CoV. In addition, the data shows that SARS-CoV does not use the receptor for serogroup 1 coronaviruses (APN/CD13) or the receptor for murine coronavirus (CEACAM 1a).

The invention is further described under (A) Coronaviruses, (B) Severe Acute Respiratory Syndrome Coronavirus (SARS-CoV), (C) Cytophathic Effect Does Not Always Correlate With SARS-CoV infection, (D) SARS-CoV Does Not Bind to The Group 1 Coronavirus Receptor aminopeptidase N (APN/CD13) and The Group 2 Coronavirus Receptor carcinoembryonic antigen (CEACAM1a), (E) Cells Permissive To SARS-CoV, (F) Exemplary Assays For Detecting Replication Of SARS-CoV, (G) Detecting Replication of SARS-CoV Using The Invention's Exemplary Cells, (H) Screening Anti-SARS-CoV Agents, (I) Administering Anti-SARS-CoV Agents, (J) Producing SARS-CoV And SARS-CoV polypeptides, and (K) Compositions And Methods For Using Protease Inhibitors To Reduce SARS-CoV Infection.

A. Coronaviruses

Coronaviruses (order Nidovirales, family Coronaviridae) are a diverse group of enveloped, positive-stranded RNA viruses. The coronavirus genome, approximately 27–32 Kb in length, is the largest found in any of the RNA viruses. Large Spike (S) glycoproteins protrude from the virus particle giving coronaviruses a distinctive corona-like appearance when visualized by electron microscopy. Coronaviruses infect a wide variety of species, including canine, feline, porcine, murine, bovine, avian and human (Holmes, et al., 1996. Coronaviridae: the viruses and their replication, p. 1075–1094. In D. M. K. a. P. M. H. B. N. Fields (ed.), Fields Virology. Lippincott-Raven, Philadelphia, Pa.). However, the natural host range of each coronavirus strain is narrow, typically consisting of a single species.

Coronaviruses typically bind to target cells through Spike-receptor interactions and enter cells by receptor mediated endocytosis or fusion with the plasma membrane (Holmes, et al., 1996, supra). The Spike-receptor interaction is a strong determinant of species specificity as demonstrated for both group 1 and group 2 coronaviruses. The receptor for group 1 coronaviruses, including human coronavirus 229E (HCoV-229E), feline coronavirus (FCoV) and porcine coronavirus (PCoV) has been identified as aminopeptidase N (APN/CD13) (Delmas, et al., 1992, Nature 357:417–420; Tresnan, et al., 1996, J. Virol. 70:8669–8674; Yeager, et al., 1992, Nature 357:420–422). APN/CD13 is a 150- to 160-kDa type II protein that is a membrane peptidase (Look, et al., 1989, J. Clin. Invest 83:1299–1307). Expression of cDNAs encoding APN in cells from species normally resistant to infection, renders them susceptible to infection (Delmas, et al., 1992, Nature 357:417–420; Yeager, et al., 1992, Nature 357:420–422). APN is typically used in a species specific manner (eg. PCoV binds porcine APN, HCoV-229E binds hAPN, etc.) (Benbacer, et al., J. Virol. 71:734–737; Kolb, et al., 1997. J. Gen. Virol. 78 (Pt 11): 2795–2802; Wentworth, et al., 2001, J. Virol. 75:9741–9752). However, feline APN acts as a universal receptor for group 1 coronaviruses (Tresnan, et al., 1996, J. Virol. 70:8669–8674).

The receptor used by MHV, a group 2 coronavirus, was identified as a biliary glycoprotein in the carcinoembryonic antigen (CEA) family of the immunoglobulin superfamily (CEACAM) (Williams, et al., 1991, Proc. Natl. Acad. Sci. U.S.A 88:5533–5536; Williams, et al., 1990, J. Virol. 64:3817–3823). MHV binds a mouse-specific epitope of CEACAM known as CEACAM1a, and it is this species specificity of virus binding that is believed to be a principal determinant of the restricted host range of MHV infection (Compton, et al., 1982, J. Virol. 66:7420–7428). CEACAM1a cDNA transfected into MHV resistant cell lines renders the cells susceptible to infection with MHV-A59 and MHV-JHM (Dveksler, et al., 1996, J. Virol. 70:4142–4145; Dveksler, et al., 1991, J. Virol. 65:6881–6891). Additionally, SL/J mice which express an allelic variant of CEACAM1a are resistant to MHV-A59 (Dveksler, et al., 1995, J. Virol. 69:543–546).

Upon entry into susceptible cells, the open reading frame (ORF) nearest the 5' terminus of the coronavirus genome is translated into a large polyprotein. This polyprotein is autocatalytically cleaved by viral-encoded proteases, to yield multiple proteins that together serve as a virus-specific, RNA-dependent RNA polymerase (RdRP). The RdRP replicates the viral genome and generates 3' coterminal nested subgenomic RNAs. Subgenomic RNAs include capped, polyadenylated RNAs that serve as mRNAs, and antisense subgenomic RNAs complementary to mRNAs. In one embodiment, each of the subgenomic RNA molecules shares the same short leader sequence fused to the body of each gene at conserved sequence elements known as intergenic sequences (IGS), transcriptional regulating sequences (TRS) or transcription activation sequences. It has been controversial as to whether the nested subgenomic RNAs are generated during positive or negative strand synthesis; however, recent work favors the model of discontinuous transcription during minus strand synthesis (Sawicki, et al., 1995, Adv. Exp. Med. Biol. 380:499–506; Sawicki and Sawicki Adv. Expt. Biol. 1998, 440:215).

B. Severe Acute Respiratory Syndrome Coronavirus (SARS-CoV)

The terms "SARS coronavirus," "SARS-CoV," and "severe acute respiratory syndrome coronavirus" are equivalent, and are used to refer to an RNA virus that is the causative agent of severe acute respiratory syndrome (Drosten, et al., 2003, supra; Fouchier, et al., 2003, supra; Ksiazek, et al., 2003, supra; Peiris, et al., 2003, supra; Poutanen, et al., 2003, supra). Exemplary strains of SARS coronavirus include, but are not limited to, Urbani, Tor2, CUHK-W1, Shanhgai LY, Shanghai QXC, ZJ-HZ01, TW1, HSR 1, WHU, TWY, TWS, TWK, TWJ, TWH, HKU-39849, FRA, TWC3, TWC2, TWC, ZMY 1, BJ03, ZJ01, CUHK-Su10, GZ50, SZ16, SZ3, CUHK-W1, BJ04, AS, Sin2774, GD01, Sin2500, Sin2677, Sin2679, Sin2748, ZJ-HZ01, and BJ01. While the invention is illustrated using SARS-CoV from humans, the term "SARS coronavirus" expressly includes within its scope equivalent coronaviruses that cause equivalent severe acute respiratory syndromes in other mammals (such as, without limitation, monkey, hamster, mink, ferret, pig, cat, and rabbit), insects (such as mosquito), etc.

The genome of SARS-CoV contains a single stranded (+)-sense RNA. Complete and partial genome sequences of several SARS coronavirus isolates have been reported, including SARS coronavirus Urbani (GenBank accession # AY278741, FIG. 7), SARS coronavirus Tor2 (GenBank accession # AY274119, FIG. 8), SARS coronavirus CUHK-W1 (GenBank accession # AY278554, FIG. 9), SARS-CoV Shanhgai LY (GenBank accession # H012999, FIGS. 10–13; GenBank accession # AY322205, FIG. 20; GenBank accession # AY322206, FIG. 21), SARS-CoV Shanghai QXC (GenBank accession # AH013000, FIGS. 14–16; GenBank accession # AY322208, FIG. 17; GenBank accession # AY322197, FIG. 18; GenBank accession # AY322199, FIG. 19), and SARS-CoV ZJ-HZ01 (GenBank accession # AY322206, FIG. 22), gi|31416292|gb|AY278487.3| SARS coronavirus BJ02,gi|30248028|gb|AY274119.3| SARS coronavirus TOR2, gi|30698326|gb|AY291451.1| SARS coronavirus TW1, gi|33115118|gb|AY323977.2|SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1| SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|AY278741.1| SARS coronavirus Urbani, gi|31873092|gb|AY321118.1|SARS coronavirus TWC, gi|33304219|gb|AY351680.1| SARS coronavirus ZMY 1, gi|31416305|gb|AY278490.3| SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2| SARS coronavirus BJ04, gi|37576845|gb|AY427439.1| SARS coronavirus AS, gi|37361915|gb|AY283798.2| SARS coronavirus Sin2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, gi|30275666|gb|AY278488.2| SARS coronavirus BJ01.

SARS-CoV may be productive or replication defective. A "productive" SARS-CoV refers to a SARS-CoV particle that is capable of replication. The term "replication" includes, but is not limited to, the steps of adsorbing (e.g., receptor binding) to a cell, entry into a cell (such as by endocytosis), introducing its genome sequence into the cell, uncoating the viral genome, initiating transcription of SARS-CoV genomic RNA to produce sgRNA, directing expression of SARS-CoV encapsidation proteins, encapsidating of the replicated viral nucleic acid sequence with the encapsidation proteins into a viral particle that is released from the cell to infect other cells that are of either a permissive or susceptible character. The terms "replication defective," "replication-incompetent," and "defective" SARS-Cov refer to a SARS-CoV particle which is substantially incapable of one or more of the steps of replication.

The origin of SARS-CoV has not been determined but its emergence may be the result of zoonotic transmission. The location and source of the SARS-CoV outbreak are reminiscent of influenza pandemics that have killed millions of people in the past.

SARS-CoV has been isolated from humans, civet cats and a raccoon-dog, and has been propagated in kidney cells derived from different species of monkey (Drosten, et al., 2003, N. Engl. J. Med. 348:1967–1976; Ksiazek, et al., 2003, N. Engl. J. Med. 348:1953–1966; Peiris, et al., 2003, Lancet 361:1319–1325; Poutanen, et al., 2003, N. Engl. J. Med. 348:1995–2005). Coronaviruses typically demonstrate a narrow host range and are species specific yet, SARS-CoV appears to have a broad host range. Furthermore, while disease caused by the known humans coronaviruses is mild, SARS-CoV, like some of the animal coronaviruses, causes fatal disease (Holmes, et al., 1996, supra).

C. Cytophathic Effect Does Not Always Correlate With SARS-CoV Infection

Cell lines are routinely utilized to screen clinical specimen for respiratory pathogens. At the beginning of the SARS-CoV outbreak, clinical specimen were inoculated onto panels of cells to identify the causative agent of SARS (Drosten, et al., 2003, N. Engl. J. Med. 348:1967–1976; Ksiazek, et al., 2003, N. Engl. J. Med. 348:1953–1966; Peiris, et al., 2003, Lancet 361:1319–1325). Based on CPE, Vero E6 and FRhMK cells were identified as susceptible to SARS-CoV infection (Drosten, et al., 2003, N. Engl. J. Med. 348:1967–1976; Ksiazek, et al., 2003, N. Engl. J. Med. 348:1953–1966; Peiris, et al., 2003, Lancet 361:1319–1325). Surprisingly, however, coronaviruses can establish persistent infection in cells without inducing CPE, suggesting that CPE may not be an accurate indicator of infection (Chaloner, et al., 1981, Arch. Virol. 69:117–129). Data herein confirmed this surprising observation by demonstrating replication of SARS-CoV in the absence of CPE. For example, significant CPE was not observed in pRhMK or pCMK 5 days p.i., although the inventors discovered that virus titers were actually increased within 24 hours p.i. (FIG. 2B, Table 1).

TABLE 1

Susceptibility of cells to SARS-CoV

| Cell | Species of Origin | SARS-CoV Replication | CPE | Viral Titer at 48 hr ($TCID_{50}$) |
|---|---|---|---|---|
| Vero E6 | African green monkey kidney | + | + | $2.4 \times 10^7$ |
| pRhMK | Primary rhesus monkey kidney | + | – | $5.6 \times 10^5$ |
| pCMK | Primary cynomologous monkey kidney | + | – | $7.8 \times 10^4$ |
| MRC-5 | Human lung fibroblast | – | – | 0 |
| MDCK | Canine kidney | – | – | N/D |
| AK-D | Feline lung epithelia | – | – | N/D |
| HRT-18 | Human rectal tumor | – | – | 0 |
| L2 | Murine fibroblast | – | – | N/D |
| R-Mix | Mink and Human lung | + | – | $7.8 \times 10^3$ |
| Mv1Lu | Mink lung | + | – | $2.5 \times 10^4$ |
| A549 | Human lung epithelia | – | – | N/D |
| HEL | Human embryonic lung | – | – | 0 |
| HEK-293T | Human embryonic kidney | + | – | $5.6 \times 10^3$ |
| Huh-7 | Human liver | + | – | $1.3 \times 10^5$ |
| CMT-93 | Murine epithelia | – | – | N/D |
| CMT-93/hAPN | Murine epithelia | – | – | N/D |
| BHK | Baby hamster kidney | – | – | N/D |
| BHK/hAPN | Baby hamster kidney | – | – | N/D |

D. SARS-CoV Does Not Bind to the Group 1 Coronavirus Receptor Aminopeptidase N (APN/CD13) and the Group 2 Coronavirus Receptor Carcinoembryonic Antigen (CEACAM1a)

Aminopeptidase N, the receptor for group 1 coronaviruses is expressed on the surface of epithelial cells of the kidney. The identification of monkey kidney cells susceptible to SARS-CoV, the culturing of SARS-CoV from the kidney of an infected patient, and sequence-based studies predicting that the SARS-CoV Spike glycoprotein contains APN binding domains, led to the proposal that APN is a potential receptor for SARS-CoV (Yu, et al., 2003, Acta Pharmacol. Sin. 24:481–488). Based on these assumptions, APN inhibitors were proposed for the treatment of SARS-CoV infection (Kontoyiannis, et al., 2003, Lancet 361:1558). However, data herein (such as Examples 4 and 7) show that cells expressing species specific APN molecules as well as feline APN, the universal group 1 receptor, were all non permissive to SARS-CoV. Even cells expressing high levels of hAPN, previously demonstrated to be susceptible to HCoV-229E, were non permissive to SARS-CoV, suggesting that SARS-CoV uses a receptor other than APN (Wentworth et al. 2001. J. Virol. 75:9741–9752.). Snijder et al. has suggested that SARS-CoV is most closely related to Group II coronaviruses, suggesting that it may use a receptor utilized by a group 2 coronavirus. However, cell lines permissive to group 2 coronaviruses were not susceptible to SARS-CoV. Murine cells expressing CEACAM1a, the receptor for MHV and HRT-18 cells which are susceptible to HCoV-0C43, were both non permissive to SARS-CoV infection. The inventors' findings suggest that SARS-CoV utilizes a yet unidentified receptor.

E. Cells Permissive to SARS-CoV

SARS-CoV was first isolated in African green monkey kidney cells (Vero E6) and fetal rhesus monkey kidney cells (FRhMK) inoculated with clinical specimen (Drosten, et al., 2003, N. Engl. J. Med. 348:1967–1976; Ksiazek, et al., 2003, N. Engl. J. Med. 348:1953–1966; Peiris, et al., 2003, Lancet 361:1319–1325; Poutanen, et al., 2003, N. Engl. J. Med. 348:1995–2005). Based on cytopathic effect (CPE), other cells routinely used for identification of respiratory pathogens were determined to be non-permissive to SARS-CoV infection, such as MDCK, A549, NCI-H292, HeLa, LLC-MK2, Hut-292, B95–8, MRC-5, RDE and Hep-2 (Drosten, et al., 2003, N. Engl. J. Med. 348:1967–1976; Ksiazek, et al., 2003, N. Engl. J. Med. 348:1953–1966; Peiris, et al., 2003, Lancet 361:1319–1325).

To identify cell lines permissive to SARS-CoV, a multiplex reverse transcriptase polymerase chain reaction (RT-PCR) assay for detection of SARS-CoV replication was developed by the inventors as described herein (Example 2). Primary cells and continuous cell lines derived from a number of species and tissues were analyzed for susceptibility to SARS-CoV. Additionally, cells routinely used by clinical virology laboratories for pathogen screening were analyzed for susceptibility to SARS-CoV. Data herein demonstrates the identification of identified both human and non-human (monkey and mink) cells that support SARS-CoV replication (Examples 3, 5, and 6, Table 1).

In particular, data herein (Example 3, Table 1) show that kidney cells derived from three different species of monkey (African green monkey, Rhesus macaque and Cynomolgous macaque) were susceptible to productive SARS-CoV infection. However, infection of pCMK and pRhMK cells resulted in lower viral titers than infection of Vero E6 cells. Without intending to limit the invention to any particular mechanism, and while an understanding of the mechanism of the invention is not required, it is the inventors' consideration that the discrepancy in virus production may be due to Vero E6 cells being a transformed cell line while pCMK and pRhMK are both primary cell populations. Furthermore, pCMK and pRhMK are both mixed cell populations; the cells susceptible to SARS-CoV may make up only a small percentage of the total cell population. Thus, in certain embodiments, it may be more advantageous to use cell lines such as HEK-293T, Huh-7 and Mv1Lu cells as compared to primary cells such as pCMK and pRhMK.

Kuiken et al. recently demonstrated that Cynomolgous Macaques inoculated with SARS-CoV develop clinical symptoms similar to those observed in infected humans. SARS-CoV was subsequently isolated from the inoculated monkeys (Fouchier, et al., 2003, Nature 423:240; Kuiken, et al., 2003, Lancet 362:263–270). However, SARS-CoV was not detected in kidney from these animals by immunohistochemical techniques. Surprisingly, therefore, and in contrast to Kuiken et al.'s report, the inventors' data suggest that kidney cells from monkeys supports SARS-CoV replication (Ksiazek, et al., 2003, N. Engl. J. Med. 348:1953–1966).

Data herein (Example 5, Table 1) also identifies mink lung cells (Mv1Lu) as susceptible to SARS-CoV productive infection. In contrast, all of the clinically relevant cells that were tested by the inventors were not susceptible to SARS-CoV infection. Mv1Lu cells are incorporated into respiratory panels, that are used to screen clinical specimen for respiratory pathogens including influenza A and B, adenovirus, RSV and parainfluenza. Additionally, Mv1Lu cells are a component of R-Mix, the cell mix which is also used for detection of RSV and parainfluenza viruses. Without intending to limit the invention to any mechanism, and while an understanding of the mechanism of the invention is not necessary, it is the inventors' view that the low level of virus replication detected in Mv1Lu cells by titration may be due to slower replication of SARS-CoV in mink-derived cells than in Vero E6 cells where the virus was passaged.

Data herein (Example 6, Table 1) further demonstrates that two human-derived cell lines are susceptible to SARS-CoV productive infection. A kidney cell line (HEK-293T) and a liver cell line (Huh-7) were both permissive to SARS-CoV infection. HEK-293T cells were susceptible to SARS-CoV infection but do not support production of high titers of virus, suggesting that these cells may contain a block to SARS-CoV replication. Conversely, Huh-7 cells produced higher titers of SARS-CoV although the titers were still lower then those produced from infected Vero E6 cells. Without intending to limit the invention to any mechanism, and while an understanding of the mechanism of the invention is not necessary, it is the inventors' opinion that the discrepancy in viral titers may be due to the passage of the virus in Vero E6 cells where it may have adapted.

In one embodiment, the cells used in any one of the invention's methods is chosen from one or more of HEK-293T, Huh-7, Mv1Lu, pRHMK and pCMK.

While the invention is illustrated using HEK-293T, Huh-7, Mv1Lu, pRHMK and pCMK cells, it should be understood that the invention is not limited to these particular cells, but rather includes equivalent cells that are established from these particular cells.

The term "established from" when made in reference to any cell disclosed herein (such as HEK-293T, Huh-7, Mv1Lu, pRHMK and/or pCMK cell, etc.) refers to a cell which has been obtained (e.g., isolated, purified, etc.) from the parent cell in issue using any manipulation, such as, without limitation, infection with virus, transfection with DNA sequences, treatment and/or mutagenesis using for example chemicals, radiation, etc., selection (such as by serial culture) of any cell that is contained in cultured parent cells. For example, the invention includes within its scope cell lines that may be established from any cell disclosed herein (such as HEK-293T, Huh-7, Mv1Lu, pRHMK and/or pCMK cell, etc.) by treatment with chemical compounds (e.g., N-ethyl-N-nitrosurea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6MP), mitomycin-C (MMC), procarbazine (PRC), N-methyl-N'-nitro-N-nitrosoguanidine (MNNG), $^3H_2O$, and urethane (UR)), and electromagnetic radiation (e.g., X-ray radiation, gamma-radiation, ultraviolet light).

In one embodiment, equivalent cells within the scope of the invention include cells that are established from the exemplary HEK-293T, Huh-7, Mv1Lu, pRHMK and/or pCMK cells, and that have substantially the same sensitivity, increased sensitivity, or reduced sensitivity to SARS-CoV as the cell from which it is established. The term "sensitivity" and "sensitive" when made in reference to a cell is a relative term which refers to the degree of permissiveness of the cell to a virus as compared to the degree of permissiveness of another cell to the same virus. For example, the term "increased sensitivity" to SARS-CoV when used in reference to the sensitivity of a first cell relative to a second cell refers to an increase in the first cell, preferably at least a 5%, more preferably from 5% to 10,000%, more preferably from 5% to 1,000%, yet more preferably from 10% to 200%, and even more preferably from 10% to 100%, increase in the quantity of SARS-CoV protein, SARS-CoV nucleic acid, and/or of CPE by progeny virus which is produced following infection of the first cell with SARS-CoV, as compared with the quantity of SARS-CoV protein, SARS-CoV nucleic acid, and/or of CPE by progeny virus (respectively) which is produced following infection of the second cell. For example, if 34 samples containing SARS-CoV were tested for the presence of progeny virus, with 25 and 13 samples showing the presence of CPE using a first cell and second cell, respectively, then the sensitivity is 74% and 38% for the first cell and second cell, respectively. This reflects an increase of 90% in the sensitivity of the first cell as compared to the sensitivity of the second cell.

In another embodiment, equivalent cells within the scope of the invention include cells that are established from the exemplary HEK-293T, Huh-7, Mv1Lu, pRHMK and/or pCMK cells, and that have substantially the same sensitivity to sARS-CoV as the cell from which it is established. This may be advantageous where, for example, the parent cell is made transgenic for a reporter gene.

In a further embodiment, equivalent cells within the scope of the invention include cells that are established from the exemplary HEK-293T, Huh-7, Mv1Lu, pRHMK and/or pCMK cells, and that have increased sensitivity or decreased sensitivity to SARS-CoV as compared to HEK-293T, Huh-7, Mv1Lu, pRHMK and/or pCMK cells from which they were established. This may be desirable where, for example, the parent cell is made transgenic for a receptor gene which alters the level of binding of SARS-CoV to the cell.

The invention's cells (such as the exemplary HEK-293T, Huh-7, Mv1Lu, pRHMK and/or pCMK cell, etc.) show the surprising property of being susceptible to, and permissive for, infection by SARS-CoV. The term "susceptible" as used herein in reference to a cell describes the ability of a permissive or non-permissive host cell to be infected by a virus. "Infection" refers to adsorption of the virus to the cell and penetration into the cell. A cell may be susceptible without being permissive in that it can be penetrated by a virus in the absence of viral replication and/or release of virions from the cell. A permissive cell line however must be susceptible. Susceptibility of a cell to a virus may be determined by methods known in the art such as detecting the presence of viral proteins using electrophoretic analysis (i.e., SDS-PAGE) of protein extracts prepared from the infected cell cultures. Susceptibility to SARS-CoV may also be determined by detecting the presence of SARS-CoV gRNA using the exemplary methods disclosed herein.

The terms "permissive" and "permissiveness" as used herein describe the sequence of interactive events between a virus and its putative host cell. The process begins with viral adsorption to the host cell surface and ends with release of infectious virions. A cell is "permissive" (i.e., shows "permissiveness") if it is capable of supporting viral replication as determined by, for example, production of viral nucleic acid sequences and/or of viral peptide sequences, regardless of whether the viral nucleic acid sequences and viral peptide sequences are assembled into a virion. While not required, in one embodiment, a cell is permissive if it generates virions and/or releases the virions contained therein. Many methods are available for the determination of the permissiveness of a given cell line. For example, the replication of a particular virus in a host cell line may be measured by the production of various viral markers including viral proteins, viral nucleic acid (including both RNA and DNA) and the progeny virus. The presence of viral proteins may be determined using electrophoretic analysis (i.e., SDS-PAGE) of protein extracts prepared from the infected cell cultures. Viral nucleic acid may be quantitated using nucleic acid hybridization assays. In a preferred embodiment, permissivity to SARS-CoV may also be determined by detecting the presence of SARS-CoV sgRNA using the exemplary methods disclosed herein. Susceptibility to SARS-CoV may also be determined by detecting the presence of SARS-CoV gRNA using the exemplary methods disclosed herein. Production of progeny virus may also be determined by observation of a cytopathic effect. However, this method is less preferred than detection of SARS-CoV sgRNA, since data herein shows that a cytopathic effect may not be observed even when viral replication is detectable by sgRNA (Table 1). The invention is not limited to the specific quantity of replication of virus.

The terms "not permissive" and "non-infections" encompasses, for example, a cell that is not capable of supporting viral replication as determined by, for example, production of viral nucleic acid sequences and/or of viral peptide sequences, and/or assembly of viral nucleic acid sequences and viral peptide sequences into a virion.

The terms "cytopathic effect" and "CPE" as used herein describe changes in cellular structure (i.e., a pathologic effect). Common cytopathic effects include cell destruction, syncytia (i.e., fused giant cells) formation, cell rounding, vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci are initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released from their anchorage points in the monolayer. When many cells reach the point of focal destruction, the area is called a viral plaque, which appears as a hole in the monolayer. The terms "plaque" and "focus of viral infection" refer to a defined area of CPE which is usually the result of infection of the cell monolayer with a single infectious virus which then replicates and spreads to adjacent cells of the monolayer. Cytopathic effects are readily discernable and distinguishable by those skilled in the art.

In another embodiment, the invention contemplates the use of transgenic cells such as transgenic HEK-293T, transgenic Huh-7, transgenic Mv1Lu, transgenic pRHMK and/or transgenic pCMK cells. The terms "transgenic" and "genetically engineered" when made in reference to a cell, refer to a cell that has been transformed to contain a transgene. The term "transformation" as used herein refers to the introduction of a transgene into a cell by way of human intervention, using standard methods in the art. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA) which detects the presence of a polypeptide encoded by one or more of the nucleotide sequences of interest. Alternatively, transient transformation may be detected by detecting the activity of the protein (e.g., β-glucuronidase) encoded by the nucleotide sequence of interest. The term "transient transformant" refer to a cell which has transiently incorporated one or more nucleotide sequences of interest. Transient transformation with the invention's vectors may be desirable in, for example, cell biology or cell cycle investigations which require efficient gene transfer.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more nucleotide sequences of interest, genomic DNA from the transient transformant does not contain the nucleotide sequence of interest. Stable transformation of a cell may be detected by Southern blot hybridization of genomic DNA of the cell with nucleic acid sequences which are capable of binding to one or more of the nucleotide sequences of interest. Alternatively, stable transformation of a cell may also be detected by the polymerase chain reaction of genomic DNA of the cell to amplify the nucleotide sequence of interest.

A transgene that is introduced into the cells of the invention may comprise nucleotide sequence that is "endogenous" or "heterologous" (i.e., "foreign"). The term "endogenous" refers to a sequence which is naturally found in the cell or virus into which it is introduced so long as it does not contain some modification relative to the naturally-occurring sequence. The term "heterologous" refers to a sequence which is not endogenous to the cell or virus into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell or virus into which it is introduced and which contains some modification relative to the naturally-occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc.

The term "wild-type" when made in reference to a peptide sequence and nucleotide sequence refers to a peptide sequence and nucleotide sequence, respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. In contrast, the term "modified" or "mutant" refers to a peptide sequence and nucleotide sequence which displays modifications in sequence and/or functional properties (i.e., altered characteristics) when compared to the wild-type peptide sequence and nucleotide sequence, respectively. It is noted that naturally-occurring mutants can be isolated; these are identified by the fact that they have altered characteristics when compared to the wild-type peptide sequence and nucleotide sequence. Nucleic acid sequences and/or proteins may be modified by chemical, biochemical, and/or molecular biological techniques. Modifications to nucleic acid sequences include introduction of one or more deletion, insertion, and substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides.

While not required, in one embodiment, it may be desirable that the transgene contains a sequence encoding a selectable marker. The term "selectable marker" as used herein refers to nucleotide sequence which encodes an enzymatic activity that confers resistance to a compound (e.g., antibiotic or drug) upon the cell in which the selectable marker is expressed. Selectable markers may be "positive"; i.e., genes which encode an enzymatic activity which can be detected in any cell or cell line. Examples of dominant selectable markers include, but are not limited to, (1) the bacterial aminoglycoside 3' phosphotransferase gene (also referred to as the neo gene) which confers resistance to the drug G418 in cells, (2) the bacterial hygromycin G phosphotransferase (hyg) gene which confers resistance to the antibiotic hygromycin, and (3) the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Selectable markers may be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin. In one embodiment, the selectable marker gene used is the neo gene in plasmid pcDNA3 (Invitrogen) and cells which incorporat this transgene may be selected by exposure to Geneticin (G418) (Gibco-BRL Inc.).

In another embodiment, it may be desirable that the transgene contains a sequence (e.g., the uid A gene) encoding a reporter protein. This may be desirable where, for example, the reporter protein is more readily detectable than another protein to which it is operably linked. The term "reporter gene" refers to a gene which encodes a reporter molecule (e.g., RNA, polypeptide, etc.) which is detectable in any detection system, including, but not limited to enzyme (e.g., ELISA, as well as enzyme-based histochemical assays), fluorescent, radioactive, and luminescent systems. Exemplary reporter genes include, for example, β-glucuronidase gene, green fluorescent protein gene, *E. coli* β-galactosidase (LacZ) gene, *Halobacterium* β-galactosidase gene, *E. coli* luciferase gene, *Neuropsora* tyrosinase gene, Aequorin (jellyfish bioluminescenece) gene, human placental alkaline phosphatase gene, and chloramphenicol acetyltransferase (CAT) gene. Reporter genes are commercially available, such as from Clontech, Invtrogen, and Promega. It is not intended that the present invention be limited to any particular detection system or label.

In a further embodiment, it may be desirable that the transgenic cell (such as transgenic cells of the exemplary HEK-293T, Huh-7, Mv1Lu, pRHMK and/or pCMK cell, etc.) expresses a probe gene. The term "probe" gene refers to a sequence useful in the detection, identification and/or isolation of particular polypeptide sequence. Exemplary probe genes encode ligand-binding systems useful for the isolation of polypeptides such as the staphylococcal protein A and its derivative ZZ (which binds to human polyclonal IgG), histidine tails (which bind to $Ni^{2+}$), biotin (which binds to streptavidin), maltose-binding protein (MBP) (which binds to amylose), glutathione S-transferase (which binds to glutathione), etc. Exemplary probe gene sequences include reporter genes, as discussed above.

In yet another embodiment, the transgenic cell (such as the transgenic cell of an exemplary HEK-293T, Huh-7, Mv1Lu, pRHMK and/or pCMK cell, etc.) may express a "fusion protein." Exemplary sequences that may be included in a fusion gene include those for adenosine deaminase (ADA) gene (GenBank Accession No. M13792); alpha-1-antitrypsin gene (GenBank Accession No. M11465); beta chain of hemoglobin gene (GenBank Accession No. NM_000518); receptor for low density lipoprotein gene (GenBank Accession No. D16494); lysosomal glucocerebrosidase gene (GenBank Accession No. K02920); hypoxanthine-guanine phosphoribosyltransferase (HPRT) gene (GenBank Accession No. M26434, J00205, M27558, M27559, M27560, M27561, M29753, M29754, M29755, M29756, M29757); lysosomal arylsulfatase A (ARSA) gene (GenBank Accession No. NM_000487); ornithine transcarbamylase (OTC) gene (GenBank Accession No. NM_000531); phenylalanine hydroxylase (PAH) gene (GenBank Accession No. NM_000277); purine nucleoside phosphorylase (NP) gene (GenBank Accession No. NM_000270); the dystrophin gene (GenBank Accession Nos. M18533, M17154, and M18026); the utrophin (also called the dystrophin related protein) gene (GenBank Accession No. NM_007124); and the human cystic fibrosis transmembrane conductance regulator (CFTR) gene (GenBank Accession No. M28668).

In another embodiment, the transgenic cell (such as the transgenic cell of the exemplary HEK-293T, Huh-7, Mv1Lu, pRHMK and/or pCMK cell, etc.) may be transfected with nucleotide sequences encoding a cytokine. "Cytokine" refers to a molecule, such a protein or glycoprotein, involved in the regulation of cellular proliferation and function. Cytokines are exemplified by lymphokines (e.g., tumor necrosis factor-α (TNF-α), tumor necrosis factor-β (TNF-β), tumor necrosis factor-γ (TNF-γ), etc.), interferons such as interferon-γ (IFN-γ), tumor necrosis factor (TNF), etc.), growth factors (e.g., erythropoietin, G-CSF, M-CSF, GM-CSF, epidermal growth factor (EGF), insulin, platelet-derived growth factor (PDGF), fibroblast growth factor (FGF), etc.), and interleukins (e.g., interleukin-2 (IL-2), interleukin-4 (IL-4), interleukin-5 (IL-5), interleukin-6 (IL-6), interleukin-9 (IL-9), interleukin-10 (IL-10), and interleukin-13 (IL-13)).

The transgenic cells may be useful where it is desirable to determine the effect of the transgenic polypeptide on the cell's susceptibility and/or permissivity to SARS-CoV. For example, increased permissivity of the transgenic cell compared to the cell into which the transgene was introduced may be useful in generating higher virus titers and/or higher viral proteins for use in vaccine production and/or generation of antibodies. Conversely, reduced permissivity of the transgenic cell compared to the cell into which the transgene was introduced may be useful in reducing the risk of infection with SARS-CoV. For example, Mv1Lu cells are routinely used in diagnostic assays for the detection of influenza and/or parainfluenza viruses. Thus, a transgenic Mv1Lu cell with reduced permissivity to SARS-CoV compared to a Mv1Lu cell into which the transgene was introduced is safer to use in small laboratories for detection of influenza and/or parainfluenza viruses without the need to resort to containment approaches that would otherwise be required for cells producing infectious SARS-CoV. Thus, in one embodiment, the Mv1Lu cells (whether or not they are transgenic) retain their susceptibility to one or more of influenza virus and parainfluenza virus.

In a further embodiment, the transgenic cell (such as the transgenic cell of the exemplary HEK-293T, Huh-7, Mv1Lu, pRHMK and/or pCMK cell, etc.) may be engineered to include other nucleotide sequences of interest, such as non-coding regulatory sequences which do not encode an mRNA or protein product, (e.g., promoter sequence, polyadenylation sequence, termination sequence, enhancer sequence, etc.). Exemplary "promoters" include, without limitation, single, double and triple promoters.

In a further embodiment, the transgenic cell (such as the transgenic cell of the exemplary HEK-293T, Huh-7, Mv1Lu, pRHMK and/or pCMK cell, etc.) expresses a receptor gene. The term "receptor" refers to a structure (generally, but not necessarily, a protein) located on or in a cell, which specifically recognizes a binding molecule (i.e., a ligand). In one embodiment, this binding initiates either a specific biological response or the transduction of a signal. However, it is not necessary that binding result is in a specific biological response or the transduction of a signal, as for example when a virus binds to a receptor on a cell.

In one embodiment, the transgenic cell is a Mv1Lu-hF cell (ATCC accession No. PTA-4737), i.e., a transgenic Mv1Lu that expresses human furin, as described in U.S. Pat. No. 6,610,474, which is incorporated by reference in its entirety.

In a further embodiment, the transgenic cell comprises a cell line established from a transgenic cell line designated Mv1Lu-hF, wherein the established cell line has a property selected from the group consisting of (a) increased sensitivity to at least one virus selected from the group consisting of influenza A virus, influenza B virus and parainfluenza virus 3, as compared to the Mv1Lu cell line, and (b) enhanced productivity of infectious virions upon inoculation with at least one virus selected from the group one consisting of influenza A virus, influenza B virus and parainfluenza virus 3, as compared to the Mv1Lu cell line. In a more preferred embodiment, the cell line has the sensitivity of the cell line designated Mv1Lu-hF, to at least one virus selected from the group consisting of influenza A virus, influenza B virus and parainfluenza virus 3. In an alternative embodiment, the transgenic cell comprises a transgenic mink lung epithelial cell line expressing human furin, wherein the cell line has a property selected from the group consisting of (a) increased sensitivity to at least one virus selected from the group consisting of influenza A virus, influenza B virus and parainfluenza virus 3, as compared to Mv1Lu, and (b) enhanced productivity of infectious virions upon inoculation with at least one virus selected from the group one consisting of influenza A virus, influenza B virus and parainfluenza virus 3, as compared to Mv1Lu. More preferably, transgenic mink lung epithelial cell line has the sensitivity of the cell line designated Mv1Lu-hF and deposited as ATCC accession number PTA-4737, to at least one virus selected from the group consisting of influenza A virus, influenza B virus and parainfluenza virus 3. Each of these transgenic cells is described in U.S. Pat. No. 6,610,474, which is incorporated by reference in its entirety F. Exemplary Assays for Detecting Replication of SARS-CoV The invention provides a method for detecting replication of SARS-coronavirus in a sample, comprising detecting the presence SARS-coronavirus sgRNA in the sample. These methods are useful in, for example, diagnosing the presence of SARS-CoV, identifying cells that are susceptible and/or permissive for SARS-CoV, screening agents that alter infection with SARS-CoV, and in determining the relative efficacy of agents and/or modalities of treatment in altering SARS infection.

One aspect that distinguishes the invention's methods from the prior art is that the invention's methods detect the presence of sgRNA, whereas prior art methods relied on detection of gRNA, which only detected virus input, but could not distinguish this from viral RNA replication and mRNA production (Drosten, et al., 2003, N. Engl. J. Med. 348:1967–1976; Poon, et al., 2003, Clin. Chem. 49:953–955; Poutanen, et al., 2003, N. Engl. J. Med. 348: 1995–2005). Thus, the invention's assay can differentiate non-replicating genomic SARS-CoV RNA from the replicative forms produced during an active infection. The assay could therefore be used to differentiate exposure (or mechanical transmission in an animal vector) from active infection and or viral replication.

Also, the invention's methods that utilize detection of sgRNA are distinguished from prior methods that use CPE for detection of virus in that data herein (Table 1) confirms that CPE is not an accurate indicator of SARS-CoV replication, whereas detection of sgRNA reproducibly detected such replication. The invention's use of sgRNA to identify an active SARS-CoV infection is not currently used to diagnose human and/or animal coronaviruses of veterinary importance.

The invention's methods are also distinguished from methods using RACE assay (Zeng et al. (2003) Exp. Biol. Med. 228(7):866–73).

The detection of sgRNA in accordance with the invention's methods detect early replication of SARS-CoV. One utility and advantage of this method is that, when coupled with titration of viral supernatants, cells permissive to SARS-CoV can be identified. As disclosed herein (Examples 3, 5 and 6), the invention's methods have successfully identified monkey, mink and human cells that are susceptible and permissive to SARS-CoV infection. The finding that SARS-CoV enters various cell types and initiates replication is useful as the basis for the development of diagnostic assays, especially when coupled with a SARS-CoV-specific nucleic acid and/or SARS-CoV-specific antigen detection methods. Where RNA replication results in the production of infectious virions, the permissive cell lines are also useful candidates for vaccine production. Identification of cell lines that result in abortive replication will lead to more sensitive and/or safer diagnostic cells that can be used as antigen sources and for identifying potential anti-SARS-CoV drug targets.

Additionally, cells that are susceptible to SARS-CoV binding and entry, but that have blocks between the initiation of replication and the production of new virus, can also be identified using the invention's methods. The use of molecular diagnostic methods such as nucleic acid probes and monoclonal antibodies has however, demonstrated that non-permissive cells may have the ability to provide a cell-based test for detecting the presence of a virus. In fact, when considering detection of viruses that require level III biological containment for cell culture amplification, e.g. SARS coronavirus, a cell line that does not produce and release infectious virus to a high level may have substantial advantages in safety. An example from the art of the diagnostic use of a non-permissive cell line is the use of mink lung cells (Mv1Lu) to detect cytomegalovirus (CMV) (Gleaves, et al., J Clin Microbiol, 1992. 30(4): p. 1045–8). Human embryonic lung cells (MRC-5) are considered the cell line of choice to produce infectious CMV virus, however mink lung cells have been shown to be useful in detecting the primary infection event of CMV by using a monoclonal antibody that targets the CMV immediate early (mIE Ag) protein that is produced in abundant amounts. Reported benefits of the non-permissive Mv1Lu cells over MRC-5 cells were higher detection sensitivity and lower toxicity from non-specific material present in the clinical specimen. Mink lung cells have also been shown to be commercially useful for influenza virus detection.

i. sgRNA

In one embodiment, the invention's methods detect sgRNA. The term "subgenomic RNA" and "sgRNA" are used interchangeably herein to refer to a nucleotide sequence comprising at least a portion of the leader sequence.

The term "leader sequence" refers to a sequence of about 40 to about 150, about 50 to about 80, and or about 55 to about 75, nucleotides that is located at the 5' terminus of the genome. This sequence is juxtaposed to the 5' terminus of each subgenomic RNA by transcriptional mechanisms during synthesis. There is very strong sequence conservation of the leader sequence across the strains of SARS (Drosten et al., N. Engl. J. Med. 2003;1967–76; Ksiazek et al., N. Engl. J. Med. 2003;1953–66; Marra et al., Science 2003;1399–404). The leader sequence plays a role in the generation of the subgenomic RNA transcripts (Holmes et al., In: Knipe D M, Howley P M, Griffin D E, Lamb R A, Martin M A, Roizman B, eds. Fields Virology. Philadelphia: Lippincott Williams & Wilkins, 2001;1187–1203; Holmes et al. "Coronaviridae: The viruses and their replication." In: Fields B N, Knipe D M, Howely P M, eds. Fields Virology. Philadelphia: Lippincott-Raven, 1996;1075–1094; Sawicki et al., J. Gen. Virol. 2001;385–96; Sawicki et al., Adv. Exp. Med. Biol. 1998;215–9; Wang et al., Adv. Exp. Med. Biol. 2001;491–7), transcription, replication, translation and/or packaging of viral RNA.

Sequence alignment by the inventors showed conservation of at least a portion of the leader sequence in the following exemplary strains of SARS-CoV: gi|31416292|gb|AY278487.3| SARS coronavirus BJ02, gi|30248028|gb|AY274119.3| SARS coronavirus TOR2, gi|30698326|gb|AY291451.1| SARS coronavirus TW1, gi|33115118|gb|AY323977.2| SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1|SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|AY278741.1| SARS coronavirus Urbani, gi|31873092|gb|AY321118.1| SARS coronavirus TWC, gi|33304219|gb|AY351680.1| SARS coronavirus ZMY 1, gi|31416305|gb|AY278490.3|SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2| SARS coronavirus BJ04, gi|37576845|gb|AY427439.1| SARS coronavirus AS, gi|37361915|gb|AY283798.2| SARS coronavirus Sin2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, gi|30275666|gb|AY278488.2| SARS coronavirus BJ01.

In one embodiment, the leader sequence is exemplified by the sequence from nucleotide 1 to nucleotide 72 for SARS-CoV (Urbani) (FIG. 7): 5'-atattaggtttttac ctacccaggaaaagccaaccaacctcgatctcttgtagatctgttctctaaacgaac-3' (SEQ ID NO:36); 5'-tattaggtttttacctacccaggaaaagccaaccaacctcgatctcttgtagatctgttctctaaacgaac-3' (SEQ ID NO:37) of gi|33304219|gb|AY351680.1| SARS coronavirus ZMY 1,5'-taggtttttacctacccaggaaaagccaaccaacctcgatctcttgtagatctgttctctaaacgaac-3' (SEQ ID NO:38) of gi|31416305|gb|AY278490.3| SARS coronavirus BJ03,5'-ctacccaggaaaagccaaccaacctcgatctcttgtagatctgttctctaaacgaac-3' (SEQ ID NO:77) of gi|30421451|gb|AY282752.1| SARS coronavirus CUHK-Su10, 5'-tacccaggaaaagccaaccaacctcgatctcttgtagatctgttctctaaacgaac-3' (SEQ ID NO:78) of gi|31416306|gb|AY279354.2| SARS coronavirus BJ04, and 5'-ccaggaaaagccaaccaacctcgatctcttgtagatctgttctctaaacgaac-3' (SEQ ID NO:79) of gi|30275666|gb|AY278488.2| SARS coronavirus BJ01.

As disclosed herein, portions of the leader sequence are expressly contemplated as equivalents to the full length leader sequence for the detection of sgRNA and/or SARS-CoV replication. Exemplary portions of the SARS-CoV (Urbani) leader sequence include, without limitation, 5'-

```
5'-atattaggtttttacctacccaggaaaagccaaccaacctcgatctcttgtagatctgttct-3',        (SEQ ID NO:39)

5'-atattaggtttttacctacccaggaaaagccaaccaacctcgatctcttgtagatct-3',             (SEQ ID NO:40)
```

-continued

5'-atattaggtttttacctacccaggaaaagccaaccaacctcgatctcttgtag3', (SEQ ID NO:41)

5'-atattaggtttttacctacccaggaaaagccaaccaacctcgatc-3', (SEQ ID NO:42)

5'-atattaggtttttacctacccaggaaaagccaaccaacc-3', (SEQ ID NO:43)

5'-atattaggtttttacctacccaggaaaagccaac-3', (SEQ ID NO:44)

5'-atattaggtttttacctacccaggaaaagc-3', (SEQ ID NO:45)

5'-atattaggtttttacctacccagg-3', (SEQ ID NO:46)

5'-atattaggtttttacctac-3', (SEQ ID NO:47)

5'-atattagg-3', (SEQ ID NO:48)

5'-ttacctacccaggaaaagccaaccaacctcgatctcttgtagatctgttctctaaacgaac-3', (SEQ ID NO:49)

5'-aaaagccaaccaacctcgatctcttgtagatctgttctctaaacgaac-3', (SEQ ID NO:50)

5'-gccaaccaacctcgatctcttgtagatctgttctctaaacgaac-3', (SEQ ID NO:51)

5'-ccaacctcgatctcttgtagatctgttctctaaacgaac-3', (SEQ ID NO:52)

5'-ctcgatctcttgtagatctgttctctaaacgaac-3', (SEQ ID NO:53)

5'-tcttgtagatctgttctctaaacgaac-3', (SEQ ID NO:54)

5'-gatctgttctctaaacgaac-3', (SEQ ID NO:55)
and

5'-taaacgaac-3', (SEQ ID NO:56)

5'- atattaggtt tttacctacc caggaaaagc caaccaacct cgatctcttg tagatctgtt -3', (SEQ ID NO:57)

5'- atattaggtt tttacctacc caggaaaagc caaccaacct cgatctcttg -3', (SEQ ID NO:58)

5'- atattaggtt tttacctacc caggaaaagc caaccaacct -3', (SEQ ID NO:59)

5'- atattaggtt tttacctacc caggaaaagc -3', (SEQ ID NO:60)

5'- atattaggtt tttacctacc -3', (SEQ ID NO:61)

5'- atattaggtt -3', (SEQ ID NO:62)

5'- tttacctacc caggaaaagc caaccaacct cgatctcttg tagatctgtt ctctaaacga ac-3', (SEQ ID NO:63)

5'- caggaaaagc caaccaacct cgatctcttg tagatctgtt ctctaaacga ac-3', (SEQ ID NO:64)

5'- caaccaacct cgatctcttg tagatctgtt ctctaaacga ac-3', (SEQ ID NO:65)

5'- cgatctcttg tagatctgtt ctctaaacga ac-3', (SEQ ID NO:66)

5'- tagatctgtt ctctaaacga ac-3', (SEQ ID NO:67)
and

5'- ctctaaacga ac-3'. (SEQ ID NO:68)

In one embodiment, the sgRNA comprises at least a portion of a leader sequence operably linked to at least a portion of a gene encoding a SARS-CoV polypeptide. The term "polypeptide," "protein," "peptide," "peptide sequence," "amino acid sequence," and "polypeptide sequence" are used interchangeably herein to refer to at least two amino acids or amino acid analogs which are covalently linked by a peptide bond or an analog of a peptide bond. The term peptide includes oligomers and polymers of amino acids or amino acid analogs. The term peptide also includes molecules which are commonly referred to as peptides, which generally contain from about two (2) to about twenty (20) amino acids. The term peptide also includes molecules which are commonly referred to as polypeptides, which generally contain from about twenty (20) to about fifty amino acids (50). The term peptide also includes molecules which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide which is produced by artificial means in vitro (e.g., was not produced in vivo).

The term "SARS-CoV polypeptide" refers to any polypeptide that is encoded by the SARS-CoV genome (regardless of whether the genome is "wild type" or "modified"), including, for example, antigenic polypeptides. SARS-CoV polypeptides are exemplified by, but not limited to, Nucleocapsid (N), Spike glycoprotein (S), Matrix (M), E protein, and Replicase proteins (Pol 1a/b).

The "Nucleocapsid" protein (also referred to as "N") refers to a protein that is produced early in infection and at very high abundance. The N of other CoVs is highly immunogenic, eliciting antibodies and T-cell responses in natural infections. The Nucleocapsid protein is exemplified, but not limited to, the sequences in FIGS. 23–26 and 40, and those encoded by the genomic sequences in gi|31416292|gb|AY278487.3| SARS coronavirus BJ02, gi|30248028|gb|AY274119.3| SARS coronavirus TOR2, gi|30698326|gb|AY291451.1| SARS coronavirus TW1, gi|33115118|gb|AY323977.2| SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1| SARS coronavirus TWK, gi|33411414|dbj|AP006558.1| SARS coronavirus TWJ, gi|33411399|dbj|AP006557.1| SARS coronavirus TWH, gi|30023963|gb|AY278491.2° SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|278741.1| SARS coronavirus Urbani, gi|31873092|gb|AY321118.1| SARS coronavirus TWC, gi|33304219|gb|AY351680.1| SARS coronavirus ZMY 1, gi|31416305|gb|AY278490.3| SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2|SARS coronavirus BJ04, gi|37576845|gb|AY427439.1| SARS coronavirus AS, gi|37361915|gb|AY283798.2|SARS coronavirus SIN2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, and gi|30275666|gb|AY278488.2| SARS coronavirus BJ01.

The "Spike glycoprotein" (also referred to as "S") refers to a viral attachment protein that protrudes from the viron and that is a major antigenic determinant. Antibodies to this protein may neutralize the virus rendering it non infectious. The Spike glyocoprotein is exemplified, but not limited to, the sequences in FIGS. 27–29 and 41, and by those encoded by the genomic sequences in gi|31416292|gb|AY278487.3| SARS coronavirus BJ02,gi|30248028|gb|AY274119.3| SARS coronavirus TOR2, gi|30698326|gb|AY291451.1| SARS coronavirus TW1, gi|33115118|gb|AY323977.2| SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1| SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1 | SARS coronavirus TWC3, gi|33518724|gb|AY362698| SARS coronavirus TWC2, gi|30027617|gb|AY278741.1| SARS coronavirus Urbani, gi|31873092|gb|AY321118.1| SARS coronavirus TWC, gi|33304219|gb|AY351680.1| SARS coronavirus ZMY 1, gi|31416305|gb|AY278490.3° SARS coronavirus BJ03, gi|30910859|gb|AY297028.1| SARS coronavirus ZJ01, gi|30421451|gb|AY282752.1| SARS coronavirus CUHK-Su10, SARS coronavirus SZ16, gi|34482137|gb|AY304486.1| SARS coronavirus SZ3 gi|30027610|gb|AY278554.2| SARS coronavirus CUHK-W1, gi|31416306|gb|AY279354.2| SARS coronavirus BJ04, gi|37576845|gb|AY427439.1|SARS coronavirus AS, gi|37361915|gb|AY283798.2| SARS coronavirus Sin2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, and gi|30275666|gb|AY278488.2| SARS coronavirus BJ01.

The terms "Matrix protein," "Membrane protein," "membrane glycoprotein," and "M protein" refer to a protein that makes the shell of the virus and is closely associated with the lipid membrane that is acquired from the host cell. This protein is also made in abundance in an infected cell and there is typically a strong immune response (particularly, antibody response) to M in CoV infections. The Matrix protein is exemplified, but not limited to, the sequences in FIG. 30, and by those encoded by the genomic sequences in gi|31416292|gb|AY278487.3| SARS coronavirus BJ02, gi|30248028|gb|AY274119.3| SARS coronavirus TOR2, gi|30698326|gb|AY291451.1| SARS coronavirus TW1, gi|33115118|gb|AY323977.2| SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1 SARS coronavirus TWS, gi|33411429|dbj|AP006559.1, SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|AY278741.1| SARS coronavirus Urbani, gi|31873092|gb|AY321118.1| SARS coronavirus TWC, gi|33304219|gb|AY351680.1| SARS coronavirus ZMY 1, gi|31416305|gb|AY278490.3| SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2| SARS coronavirus BJ04, gi|37576845|gb|AY427439.1| SARS coronavirus AS, gi|37361915|gb|AY283798.2| SARS coronavirus Sin2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, and gi|30275666|gb|AY278488.2| SARS coronavirus BJ01.

The terms "E protein," "envelope protein," and "small envelope E protein" refer to a protein that interacts with the M protein, and that it is believed to aid in particle formation. It is present at low levels in the virus particle and at higher levels in an infected cell. The E protein is exemplified, but not limited to, the sequences in FIG. 31, and by those encoded by the genomic sequences in gi|31416292|gb|AY278487.3| SARS coronavirus BJ02, gi|30248028|gb|AY274119.3| SARS coronavirus TOR2, gi|30698326|gb|AY291451.1| SARS coronavirus TW1, gi|33115118|gb|AY323977.2| SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1| SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|AY278741.1| SARS coronavirus Urbani, gi|31873092|gb|AY321118| SARS coronavirus TWC, gi|33304219|gb|AY351680.1| SARS coronavirus ZMY 1, gi|31416305|gb|AY278490.3| SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2| SARS coronavirus BJ04, gi|37576845|gb|AY427439.1| SARS coronavirus AS, gi|37361915|gb|AY283798.2| SARS coronavirus Sin2774, gi|31416290|gb|AY278489.2° SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, and gi|30275666|gb|AY278488.2| SARS coronavirus BJ01.

The terms "Replicase protein," "polyprotein 1a," "polypeptide 1a," "polypeptide 1b," "polyprotein 1b," "polyprotein 1ab" and "Pol 1a/b" refer to a relatively large polyprotein that is produced upon infection of a cell by coronaviruses, and that encodes proteins required for genome replication. The polyprotein is encoded by about the 5' two thirds of the genome and it is produced very early during a CoV infection. The polyprotein is autocatalytically cleaved by encoded proteases (e.g., 3C-like protease) into many proteins that are present in an infected cell but are not packaged in the virus particle. These include, without limitation, the RNA dependent RNA polymerase, a helicase and proteases (e.g., 3C-like, P11 and P12). The polyprotein 1a, 1b and 1ab are exemplified, but not limited to, the sequences in FIGS. 32–39, and by those encoded by the genomic sequences in gi|31416292|gb|AY278487.3| SARS coronavirus BJ02, gi|30248028|gb|AY274119.3| SARS coronavirus TOR2, gi|30698326|gb|AY291451.1| SARS coronavirus TW1, gi|33115118|gb|AY323977.2| SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1| SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|AY278741.1° SARS coronavirus Urbani, gi|31873092|gb|AY321118.1| SARS coronavirus TWC, gi|33304219|gb|AY351680.1| SARS coronavirus ZMY 1, gi|31416305|gb|AY278490.3| SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2| SARS coronavirus BJ04, gi|37576845|gb|AY427439.1| SARS coronavirus AS, gi|37361915|gb|AY283798.2| SARS coronavirus Sin2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, and gi|30275666|gb|AY278488.2| SARS coronavirus BJ01.

As disclosed herein, in one preferred embodiment, the sgRNA comprises a leader sequence operably linked to the amino terminal region of the Spike protein. This sequence may be amplified by RT-PCR using the primers SARS-1 (5'-ATATTAGGTTTTTACCTACCCAGG-3') (SEQ ID NO:69) which binds to the leader sequence from nucleotides 1–24 and primer SARS-21,593R (5'-AGTATGTTGAGTGTAATTAGGAG-3') (SEQ ID NO:70) which binds to nucleotides encoding the Spike glycoprotein.

ii. gRNA

The invention's methods may further comprises detecting SARS-coronavirus gRNA. The terms "genomic RNA" and "gRNA" are used interchangeably to refer to at least a portion of the genomic sequence such as that exemplified in by the genome sequences of SARS coronavirus Urbani (GenBank accession # AY278741, FIG. 7), SARS coronavirus Tor2 (GenBank accession # AY274119, FIG. 8), SARS coronavirus CUHK-W1 (GenBank accession # AY278554, FIG. 9), SARS-CoV Shanhgai LY (GenBank accession # H012999, FIGS. 10–13; GenBank accession # AY322205, FIG. 20; GenBank accession # AY322206, FIG. 21), SARS-CoV Shanghai QXC (GenBank accession # AH013000, FIGS. 14–16; GenBank accession # AY322208, FIG. 17; GenBank accession # AY322197, FIG. 18; GenBank accession # AY322199, FIG. 19), and SARS-CoV ZJ-HZ01 (GenBank accession # AY322206, FIG. 22), gi|31416292|gb|AY278487.3| SARS coronavirus BJ02, gi|30248028|gb|AY274119.3| SARS coronavirus TOR2, gi|30698326|gb|AY291451.1| SARS coronavirus TW1, gi|33115118|gb|AY323977.2| SARS coronavirus HSR 1, gi|35396382|gb|AY394850.1| SARS coronavirus WHU, gi|33411459|dbj|AP006561.1| SARS coronavirus TWY, gi|33411444|dbj|AP006560.1| SARS coronavirus TWS, gi|33411429|dbj|AP006559.1| SARS coronavirus TWK, gi|33411414|dbj|AP006558.1| SARS coronavirus TWJ, gi|33411399|dbj|AP006557.1| SARS coronavirus TWH, gi|30023963|gb|AY278491.2| SARS coronavirus HKU-39849, gi|33578015|gb|AY310120.1| SARS coronavirus FRA, gi|33518725|gb|AY362699.1| SARS coronavirus TWC3, gi|33518724|gb|AY362698.1| SARS coronavirus TWC2, gi|30027617|gb|AY278741.1| SARS coronavirus Urbani, gi|31873092|gb|AY321118.1| SARS coronavirus TWC, gi|33304219|gb|AY351680.1| SARS coronavirus ZMY 1, gi|31416305|gb|AY278490.3| SARS coronavirus BJ03, gi|30910859|gb|AY297028.1| SARS coronavirus ZJ01, gi|30421451|gb|AY282752.1| SARS coronavirus CUHK-Su10, gi|34482146|gb|AY304495.1| SARS coronavirus GZ50, gi|34482139|gb|AY304488.1| SARS coronavirus SZ16, gi|34482137|gb|AY304486.1| SARS coronavirus SZ3, gi|30027610|gb|AY278554.2| SARS coronavirus CUHK-W1, gi|31416306|gb|AY279354.2| SARS coronavirus BJ04, gi|37576845|gb|AY427439.1|

SARS coronavirus AS, gi|37361915|gb|AY283798.2| SARS coronavirus Sin2774, gi|31416290|gb|AY278489.2| SARS coronavirus GD01, gi|30468042|gb|AY283794.1| SARS coronavirus Sin2500, gi|30468043|gb|AY283795.1| SARS coronavirus Sin2677, gi|30468044|gb|AY283796.1| SARS coronavirus Sin2679, gi|30468045|gb|AY283797.1| SARS coronavirus Sin2748, gi|31982987|gb|AY286320.2| SARS coronavirus isolate ZJ-HZ01, and gi|30275666|gb|AY278488.2| SARS coronavirus BJ01.

Exemplary genomic RNA includes, without limitation, at least a portion of orf1ab polyprotein, orf1a polyprotein, Spike glycoprotein, Orf3a, Orf3a, Orf4b, Orf6, Orf7a, Orf7b, Orf8A, Orf8b, Nucleocapsid protein, Envelope protein E, and Membrane glycoprotein M.

In one preferred embodiment, the gRNA is at least a portion of the Polyprotein lab (also referred to as Polypeptide lab) gene. In one embodiment, detection of at least a portion of this gene distinguishes between sgRNA and gRNA, while detection 3' to the polyprotein lab gene detects both gRNa and sgRNA, without distinguishing between them. In one embodiment, the gRNA is of the polyprotein lab gene nucleotides from about 1 to about 21,485 of the Urbani strain (FIG. 7, GenBank accession # AY278741). In another embodiment, the gRNA is of the polyprotein lab gene nucleotides from about 250 to about 21470 of the CUHK strain (FIG. 9, GenBank accession # AY278554). In a further embodiment, the gRNA is of the polyprotein lab gene nucleotides from about 186 to about 1706 (GenBank accession # AH012999, FIG. 11) from about 1 to about 10,546 (GenBank accession # AH012999, FIG. 12), from about 186 to about 1,706 (GenBank accession # AY322205, FIG. 20), and from about 1 to about 10,546 (GenBank accession # AY322206, FIG. 21) of the Shanghai LY strain. In an alternative embodiment, the gRNA is of the polyprotein lab gene nucleotides from about 1 to about 3536 (GenBank accession # AH013000, FIG. 14), from about 1 to about 5262 (GenBank accession # AH013000, FIG. 15), and from about 1 to about 3,536 (GenBank accession # AY322197, FIG. 18) of the Shanghai QXC strain.

In another embodiment, the gRNA is at least a portion of the Polyprotein 1b (also referred to as Polyprotein 1b) gene. As disclosed herein, the inventors selected an exemplary sequence (tgctaactacattttctggagg) (SEQ ID NO:71) in Polypeptide-1b to favor conditions for the exemplary multiplex RT-PCR reaction.

iii. Detecting Nucleic Acids, Proteins, and Virions

Methods for detecting RNA (such as gRNA and sgRNA) are known in the art, and include, but are not limited to, Northern blot, ribonuclease protection assay, and polymerase chain reaction.

In one embodiment, RNA (such as gRNA and sgRNA) is detected by Northern blot. The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots provide information on both size and abundance of target RNA species. Northern blots are a standard tool of molecular biologists (J. Sambrook, et al. "Molecular Cloning: A Laboratory Manual," Third Edition, Publ. Cold Spring Harbor Laboratory Press, Cold Spring Harbor, N.Y.).

In another embodiment, RNA (such as gRNA and sgRNA) is detected by ribonuclease protection assay. Ribonuclease protection assays are used to measure the abundance of specific RNAs and to map their topological features. The method involves hybridization of test samples to complementary radiolabeled RNA probes (riboprobes), followed by digestion of non-hybridized sequences with one or more single-strand-specific ribonucleases. At the end of the digestion, the ribonucleases are inactivated, and the protected fragments of radiolabeled RNA are analyzed by polyacrylamide gel electrophoresis and autoradiography. The ribonuclease protection assay is more sensitive than the northern blot. The method can detect several target species simultaneously, and because the intensity of the signal is directly proportional to the concentration of target RNA, comparisons of the level of expression of the target gene in different tissues can be accomplished. Methods for ribonuclease protection assay are standard in the art (J. Sambrook, et al., supra).

In a further embodiment, RNA (such as gRNA and sgRNA) is detected by amplification of a target RNA sequence using reverse transcriptase polymerase chain reaction. The term "amplification" is defined as the production of additional copies of a nucleic acid sequence. The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a one or two primers prior to PCR amplification of the desired segment of the transcribed DNA using two primers.

Polymerase chain reaction technologies are well known in the art (Dieffenbach C W and G S Dveksler (1995) *PCR Primer, a Laboratory Manual*, Cold Spring Harbor Press, Plainview N.Y.). PCR describes a method for increasing the concentration of a segment of a target sequence in a mixture of DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment).

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer is selected such that it is sufficiently long to prime the synthesis of extension products in the presence of the inducing agent. Suitable lengths of the primers may be empirically determined and depend on factors such as temperature, source of primer and the use of the method. In one embodiment, the primers may be from 3 to 100, preferably from 3 to 50, more preferably from 3 to 25 nucleotide bases in length.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

In one embodiment of the invention using RT-PCR, the inventors designed oligonucleotide RT-PCR primers that will amplify genomic RNA or the sgRNA that is specific to the leader-body junction and virus replication. The inventors probed for sgRNA since the presence of genomic RNA alone could result from residual input virus, while the presence of newly synthesized subgenomic RNA is indicative of virus entry and replication initiation. Genomic RNA was detected by amplifying a region between the 1b coding region and the sequence encoding the Spike (S) glycoprotein. Subgenomic RNA was detected using a primer specific to the leader sequence in conjunction with the reverse primer in S that is used for the genomic RNA detection. This procedure could be modified for any sgRNA and sensitivity could be increased by utilizing 3' genes (e.g. Nucleocapsid). However, the inventors decided to use primers specific for S because it was their opinion that this gene clearly differentiates genomic and subgenomic RNA molecules and it decreases false positives that result from viral sgRNA packaging. The SARS-CoV primer sets were multiplexed with primers for glyceraldehyde 3' phosphate dehydrogenase (G3PDH). These primers were designed to amplify G3PDH from multiple species to serve as a positive control for RNA integrity and cDNA production. A one step RT-PCR procedure (Qiagen) was chosen to increase sensitivity over two step procedures because both "forward" and "reverse" primers can serve as reverse transcription primers of antisense and sense coronavirus RNAs, respectively. The reaction conditions (temperatures, MgCl concentrations etc.) for the multiplexed assay were optimized using SARS-CoV infected Vero E6 cells.

The sensitivity of an exemplary RT-PCR assay of SARS-CoV sgRNA was determined by analyzing RNA isolated from Vero E6 cells inoculated with serial 10-fold dilutions of SARS-CoV. Vero E6 cells were inoculated with input multiplicities of infection (MOI) ranging from $10^{-1}$ to $10^{-9}$ or were mock inoculated. Total RNA was isolated and subjected to multiplex RT-PCR at 1 h and 24 h post inoculation (FIG. 2). Input genomic RNA was detected at 1 PFU per 10,000 cells (FIG. 2, 1 hour panel). Newly synthesized gRNA and sgRNA was detectable at 1 PFU/million cells (FIG. 2, 24 hour panel).

Figure 3:
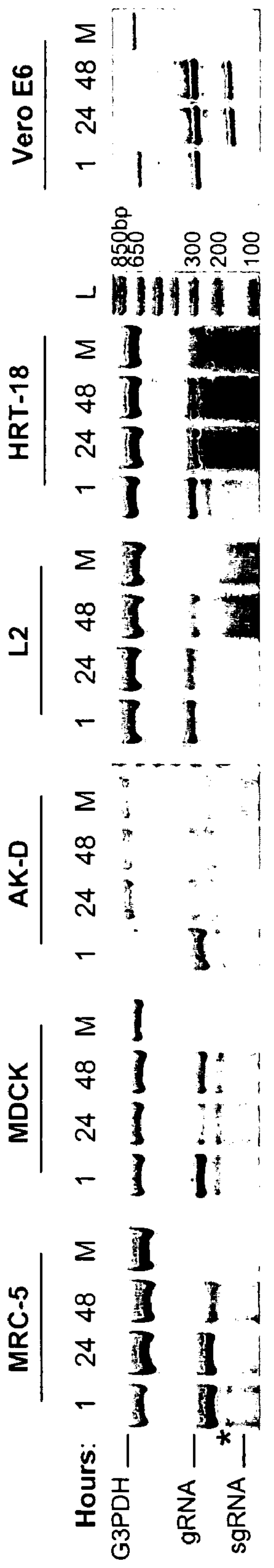
FIG. 3 shows susceptibility of cells expressing known coronavirus receptors. Amplification of G3PDH, SARS-CoV gRNA and sgRNA at 1, 24 and 48 h p.i. Human lung fibroblasts (MRC-5), canine kidney (MDCK), feline lung epithelia (AK-D), murine fibroblast (L2), and human rectal tumor (HRT-18). Vero E6 included as a positive control, mock infected as negative control (M). * denotes non-specific amplification product. Negative images are shown. Figure is representative of 2 experiments performed in duplicate.

In any of the methods of the invention that employ detection of SARS-CoV gRNA and/or sgRNA, it may be desirable to use a negative control. Data herein shows that exemplarynegative control cells include baby hamster kidney cells (BHK-21) (FIG. 2A), MRC-5, MDCK, AK-D, L2, and HRT-18 cells (FIG. 3) which did not produce either gRNA or sgRNA following infection with SARS-CoV.

In another embodiment, the invention's methods may employ detecting one or more SARS-coronavirus polypeptide (such as an antigen). The polypeptides may be detected by methods known in the art, such as Western blot. The terms "Western blot," "Western immunoblot," "immunoblot," and "Western" refer to the immunological analysis of protein(s), polypeptides or peptides that have been immobilized onto a membrane support. The proteins are first resolved by acrylamide gel electrophoresis to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody which specifically binds the primary antibody. The secondary antibody is typically conjugated to an enzyme which permits visualization by the production of a colored reaction product or catalyzes a luminescent enzymatic reaction (e.g., ECL reagent, Amersham). The SARS-CoV polypeptides (such as antigens) may also be detected using enzyme-linked immunosorbent assay (ELISA), enzyme-based histochemical assays, using fluorescent, radioactive, and/or luminescent systems.

In yet another embodiment, the invention's methods employ detecting the production of SARS-coronavirus virions directly or indirectly by using, for example, electron microscopy, CPE, and infection of cells (as disclosed herein).

G. Detecting Replication of SARS-CoV Using the Invention's Exemplary Cells

The invention provides methods for detecting the presence of SARS-coronavirus in a sample, comprising: a) providing: (i) a sample; and (ii) cells chosen from one or more of the exemplary HEK-293T, Huh-7, Mv1Lu, pRHMK and pCMK; b) inoculating the cells with the sample to produce inoculated cells; and c) detecting the presence of the SARS-coronavirus in the inoculated cells. These methods are useful in, for example, diagnosing the presence of SARS-CoV in samples, screening agents for their activity in reducing SARS-CoV infection, determining the relative efficacy of agents and/or modalities of treatment in altering (e.g., increasing or reducing) the levels SARS infection.

i. Cultures Containing the Invention's Cells

In one embodiment, any of the invention's methods may be performed using single cell type culture. The term "single-cell type culture" refers to a composition, whether liquid, gel, or solid, which contains one cell type (for example, HEK-293T alone, Huh-7 alone, Mv1Lu alone, pRHMK alone, or pCMK alone).

The invention further employs mixed cell type cultures. As used herein, the term "mixed-cell type culture" refers to a composition, whether liquid, gel, or solid, which contains a mixture of two or more types of cells wherein the cell types are mingled together. For example, a mixed-cell type culture may contain cells from different tissues or organs from the same species and same genus. Alternatively, a mixed-cell type culture may contain cells from different species in the same genus. Yet another alternative is that a mixed-cell type culture contain cells from a different genus. The present invention encompasses any combination of cell types. Such combinations may be suitable in, for example, the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

The term "cell type different from a specifically identified cell type" as used herein means any cell type that differs in any way from the specifically identified cell type. This term includes, without limitation, the parental cells from which the specifically identified cell type has been established (e.g., by serial culture, transfection with one or more nucleotide sequences of interest, immortalization, etc.).

An advantage of using one or more of the invention's cells (such as the exemplary HEK-293T, Huh-7, Mv1Lu, pRHMK and/or pCMK cell, etc.) in mixed-cell-type culture with each other is that they may provide different SARS-CoV antigens that may be used for vaccine and/or antibody production. An advantage of using one or more of the invention's cells (such as the exemplary HEK-293T, Huh-7, Mv1Lu, pRHMK and/or pCMK cell, etc.) in mixed-cell-type culture with other cell types, is that such cultures provide rapid and sensitive assay systems in a single unit for the detection of multiple viruses, and they also eliminate the need for multiple cell lines cultured in individual containers.

In one embodiment, the mixed cell type culture contains one or more of the exemplary HEK-293T, Huh-7, Mv1Lu, pRHMK and pCMK cell together. In another embodiment, the mixed cell type culture contains one or more of the exemplary HEK-293T, Huh-7, Mv1Lu, pRHMK and pCMK cell together, as well as other cell types. These mixed cell type cultures are useful in, for example, detecting the presence of viruses other than SARS-CoV. For example, mixed cell type cultures containing Mv1Lu cells and A549 cells (ATCC No. CCL185) may be used for detection of SARS-CoV, parainfluenza viruses, and influenza viruses by Mv1Lu cells, as well as detection of Herpes viruses, enteroviruses, adenoviruses, myxoviruses, and paramyviruses by A549 cells. Mixed cell cultures of Mv1Lu and A549 are known in the art (sold as "R-MIX™" By Diagnostic Hybrids Inc., Ohio) (U.S. Pat. No. 6,376,172, incorporated by reference in its entirety).

While not limiting the invention to any particular cell type, exemplary cell lines which may be used in mixed-cell type cultures with each other and/or with any one or more of the invention's cells (such as the exemplary HEK-293T, Huh-7, Mv1Lu, pRHMK and/or pCMK cell, etc.) are listed in Table 2.

TABLE 2

Exemplary Cell Lines For Mixed-Cell Type Cultures With The Invention's Cells

| Cell Line | ATCC No. | Source | Virus[a] |
|---|---|---|---|
| primary monkey | none[b] | Kidney, rhesus monkey | Herpes, entero, adeno, myxo, paramy |
| BS-C-1 | CCL26 | Kidney, African green monkey | Herpes, entero, adeno, myxo, paramy |
| CV-1 | CCL70 | Kidney, African green monkey | Herpes, entero, adeno, myxo, paramy |
| Vero | CCL81 | Kidney, African green monkey | Herpes, entero, adeno, myxo, paramy |
| Vero 76 | CRL1587 | Kidney, African green monkey | Herpes, entero, adeno, myxo, paramy |
| Vero C1008 | CRL1586 | Kidney, African green monkey | Herpes, entero, adeno, myxo, paramy |
| Vero 76 | CCL81 | Kidney, African green monkey | Herpes, entero, adeno, myxo, paramy |
| Cos-1 | CRL1650 | Kidney, African green monkey, transformed | Herpes, entero, adeno, myxo, paramy |
| Cos-7 | CRL1651 | Kidney, African green monkey, transformed | Herpes, entero, adeno, myxo, paramy |
| FRhK-4 | CRL1688 | Kidney, fetal rhesus monkey | Herpes, entero, adeno, myxo, paramy |
| LLC-MK2 original | CCL7 | Kidney, rhesus monkey | Herpes, entero, adeno, myxo, paramy |
| LLC-MK2 derivative | CCL7.1 | Kidney, rhesus monkey | Herpes, entero, adeno, myxo, paramy |
| MDCK | CCL34 | Kidney, canine | Herpes, entero, adeno, myxo, paramy |
| CCD-13 Lu | CCL200 | Lung, human | Herpes, entero, adeno, paramy |
| CCD-8 Lu | CCL201 | Lung, human | Herpes, entero, adeno, paramy |
| CCD-14 Br | CCL203 | Bronchiole, human | Herpes, entero, adeno, myxo, paramy |
| CCD-16 Lu | CCL204 | Lung, human | Herpes, entero, adeno, paramy |
| CCD-18 Lu | CCL205 | Lung, human | Herpes, entero, adeno, paramy |
| CCD-19 Lu | CCL210 | Lung, human | Herpes, entero, adeno, paramy |

TABLE 2-continued

Exemplary Cell Lines For Mixed-Cell Type Cultures With The Invention's Cells

| Cell Line | ATCC No. | Source | Virus[a] |
|---|---|---|---|
| Hs888 Lu | CCL211 | Lung, human | Herpes, entero, adeno, paramy |
| MRC-9 | CCL212 | Lung, human | Herpes, entero, adeno, paramy |
| CCD-25 Lu | CCL215 | Lung, human | Herpes, entero, adeno, paramy |
| WiDr | CCL218 | Colon, adenocarcinoma, human | Herpes, entero, adeno |
| DLD-1 | CCL221 | Colon, adenocarcinoma, human | Herpes, entero, adeno |
| COLO205 | CCL222 | Colon, adenocarcinoma, human | Herpes, entero, adeno |
| HCT-15 | CCL222 | Colon, adenocarcinoma, human | Herpes, entero, adeno |
| SW 480 | CCL228 | Colon, adenocarcinoma, human | Herpes, entero, adeno |
| LOVO | CCL229 | Colon, adenocarcinoma, human | Herpes, entero, adeno |
| SW403 | CCL230 | Colon, adenocarcinoma, human | Herpes, entero, adeno |
| SW48 | CCL231 | Colon, adenocarcinoma, human | Herpes, entero, adeno |
| SW116 | CCL233 | Colon, adenocarcinoma, human | Herpes, entero, adeno |
| SW1463 | CCL234 | Colon, adenocarcinoma, human | Herpes, entero, adeno |
| SW837 | CCL235 | Rectum, adenocarcinoma, human | Herpes, entero, adeno |
| SW948 | CCL237 | Colon, adenocarcinoma, human | Herpes, entero, adeno |
| SW1417 | CCL238 | Colon, adenocarcinoma, human | Herpes, entero, adeno |
| FHs74 Int | CCL241 | Small intestine, adenocarcinoma, human | Herpes, entero, adeno |
| HCT-8 | CCL244 | Adenocarcinoma, ileococal | Herpes, entero, adeno |
| HCT-116 | CCL247 | Colon carcinoma, human | Herpes, entero, adeno |
| T84 | CCL248 | Colon carcinoma, human | Herpes, entero, adeno |
| NCI-H747 | CCL252 | Cecum, adenocarcinoma, human | Herpes, entero, adeno |
| NCI-H508 | CCL253 | Cecum, adenocarcinoma, human | Herpes, entero, adeno |
| LS123 | CCL255 | Colon, human, adenocarcinoma | Herpes, entero, adeno |
| CaCo-2 | HTB37 | Colon, adenocarcinoma, human | Herpes, entero, adeno |
| HT-29 | HTB38 | Colon, adenocarcinoma, human | Herpes, entero, adeno |
| SK-CO-1 | HTB39 | Colon, adenocarcinoma, human | Herpes, entero, adeno |
| HuTu 80 | HTB40 | Duodenum, adenocarcinoma, human | Herpes, entero, adeno |
| A253 | HTB41 | Epidemoid carcinoma | Herpes, entero, adeno, paramyo |
| A704 | HTB45 | Kidney adenocarcinoma, human | Herpes, entero, adeno, paramyo |
| Hela | CCL2 | Epitheloid carcinoma, cervix, human | Herpes, entero, adeno, myxo, paramy |
| Hela | CCL2.1 | Epitheloid carcinoma, cervix, human | Herpes, entero, adeno, myxo, paramy |
| Hela53 | CCL2.2 | Epitheloid carcinoma, cervix, human | Herpes, entero, adeno, myxo, paramy |
| L-132 | CCL5 | Embryonic lung, human, Hela marker | Herpes, entero, adeno, myxo, paramy |
| Intestine | CCL6 | Embryonic intestine, human, Hela marker | Herpes, entero, adeno |
| BHK-21 | CCL10 | Kidney, synister or golden hamster | Herpes, entero, adeno, myxo, paramy |
| Hak | CCL15 | Kidney, syn hamster | Herpes, entero, adeno, myxo, paramy |
| KB | CCL17 | Epidermoid carcinoma oral, human | Herpes, entero, adeno, paramy |
| Hep-2 | CCL23 | Epidermoid carcinoma larynx, human | Herpes, entero, adeno, paramy |
| Wish | CCL25 | Ammion, human | Herpes, entero, adeno |
| Detroit 532 | CCL54 | Skin, human | Herpes, entero, adeno |
| FL | CCL62 | Ammion, human | Herpes, entero |
| Detroit 525 | CCL65 | Skin, human | Herpes, entero, adeno |
| Detroit 529 | CCL66 | Skin, human | Herpes, entero, adeno |
| Detroit 510 | CCL72 | Skin, human | Herpes, entero, adeno |
| WI-38 | CCL75 | Lung, diploid human | Herpes, entero, adeno, paramy |
| WI-38 VA13 | CCL75.1 | Lung, diploid human, SV-40 transformed | Herpes, entero, adeno, paramy |
| Citrullinemia | CCL76 | Skin, human | Herpes, entero, adeno, paramy |
| Spik (NBL-10) | CCL78 | Kidney, dolphin | Herpes, entero, adeno |
| Detroit 539 | CCL84 | Skin, human | Herpes, entero, adeno |
| Cridu Chat | CCL90 | Skin, human | Herpes, entero, adeno |
| WI26 VA4 | CCL95.1 | Lung, human | Herpes, entero, adeno, paramy |
| BeWo | CCL98 | Choriocarcinoma, human | Herpes, entero, adeno |
| SW-13 | CCL105 | Adenocarcinoma, human, adrenal cortex | Herpes, entero, adeno |
| Detroit 548 | CCL116 | Skin | Herpes, entero, adeno |
| Detroit 573 | CCL117 | Skin | Herpes, entero, adeno |

TABLE 2-continued

Exemplary Cell Lines For Mixed-Cell Type Cultures With The Invention's Cells

| Cell Line | ATCC No. | Source | Virus[a] |
|---|---|---|---|
| HT-1080 | CCL121 | Fibrocarcinoma, human | Herpes, entero, adeno |
| HG 261 | CCL122 | Skin, human | Herpes, entero, adeno |
| C211 | CCL123 | Skin, human | Herpes, entero, adeno |
| Amdur II | CCL124 | Skin, human | Herpes, entero, adeno |
| CHP 3 (M.W.) | CCL132 | Skin, human, fibroid like | Herpes, entero, adeno |
| CHP 4 (W.W.) | CCL133 | Skin, human, fibroid like | Herpes, entero, adeno |
| RD | CCL136 | Rhabdomyosarcoma | Herpes, entero, adeno |
| HEL 299 | CCL137 | Lung, diploid | Herpes, entero, adeno, paramy |
| Detroit 562 | CCL138 | Carcinoma, pharynx | Herpes, entero, adeno, myxo, paramy |
| MRC-5 | CCL171 | Lung, diploid, human | Herpes, entero, adeno, paramy |
| A-549 | CCL185 | Lung, carcinoma, human | Herpes, entero, adeno, myxo, paramy |
| IMR-90 | CCL186 | Lung, carcinoma, human | Herpes, entero, adeno, myxo, paramy |
| LS180 | CCL187 | Colon, adenocarcinoma, human | Herpes, entero, adeno |
| LS174T | CCL188 | Colon, adenocarcinoma, human | Herpes, entero, adeno |
| NCI-H292 | CCL-1848 | Mucoepidermoid, human | Respir. syncytial virus |
| BHK/ICP6La cZ-5 | CCL-12072 | | |
| CV-1 | CCL-70 | | |
| hs27 | HFF; CRL-1634 | | |
| Mv1Lu | CCL-64 | | |
| McCoy | CCL-1696 | | |
| MRC-5 | CCL-171 | | |
| Vero | CCL-81 | | |
| MDCK (NBL-2) | CCL-34 | | |
| BHK21 | CCL-10 | | |
| Mv1Lu-hF | PTA-4737 | Lung, epithelial, mink | Influenza, parainfluenza |

[a]Herpes = Herpes viruses
Entero = Enteroviruses
Adeno = Adenoviruses
Myxo = Myxoviruses
Paramy = Paramyxoviruses
[b]Primary monkey kidney cells may be obtained from Diagnostic Hybrids (catalog numbers 490102A for shell format and 49-0600A for tube format)

In one embodiment, it may be desirable use Mv1Lu cells for the replication and/or detection of parainfluenza and influenza viruses without replication and/or detection of SARS-CoV. This is advantageous in laboratories that diagnose infection with parainfluenza and influenza viruses, and that do not have access to containment facilities that are required for manipulation of SARS-CoV. In one embodiment, this goal may be achieved by incubating a test sample with Mv1Lu cells for up to 24 hours. This is based on data herein (FIG. 4B) which shows that SARS-CoV was not produced by Mv1Lu cells within 24 hours p.i. In another embodiment, this goal may be achieved by contacting one or more of the Mv1Lu cells and the sample with antibody specific for one or more SARS-coronavirus antigen.

In a further embodiment, the goal of reducing infection of Mv1Lu cells by SARS-coronavirus, while not substantially reducing susceptibility of Mv1Lu cells to parainfluenza and/or influenza viruses, may be attained by contacting the Mv1Lu cells and/or sample that is being tested with a protease inhibitor, as further described below.

In another embodiment, it may be desirable to use Mv1Lu cells for the detection and/or proliferating of parainfluenza and influenza viruses in addition to detection and/or replication of SARS-CoV, such as where the specificity of action of certain reagents on different viruses is being investigated. This may be achieved by incubating Mv1Lu cells with a test sample for more than 24 hours (FIG. 4B).

ii. Cells Frozen In Situ

In one embodiment, the invention's cells (such as the exemplary HEK-293T, Huh-7, Mv1Lu, pRHMK and/or pCMK cell, etc.) are frozen in situ. Methods for the in situ growth, freezing and testing of cultured cells are know in the art (U.S. Pat. No. 6,472,206, incorporated by reference in its entirety). In one embodiment, the in situ frozen cells are in single cell type culture. In another embodiment, the in situ frozen cells are in mixed cell type culture.

iii. Samples

The invention contemplates contacting the invention's cells (such as the exemplary HEK-293T, Huh-7, Mv1Lu, pRHMK and/or pCMK cell, etc.) with a sample for the purpose of, for example and without limitation, detecting and/or quantitating SARS-CoV polypeptides, proteins, and/or virus particles in a sample. The terms "sample" and "specimen" as used herein are used in their broadest sense to include any composition that is obtained and/or derived from biological or environmental source, as well as sampling devices (e.g., swabs) which are brought into contact with biological or environmental samples. "Biological samples" include those obtained from an animal (including humans, domestic animals, as well as feral or wild animals, such as ungulates, bear, fish, lagamorphs, rodents, etc.), body fluids such as urine, blood, plasma, fecal matter, cerebrospinal fluid (CSF), semen, sputum, and saliva, as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like. Also included are materials obtained from food products and food ingredients such as dairy items, vegetables, meat, meat by-products, and waste. Environmental samples" include environmental material such as surface matter, soil, water, and industrial materials, as well as material obtained from food and dairy processing instruments, apparatus, equipment, disposable, and non-disposable items. In one embodiment, the biological sample is a cell, tissue, and or fluid obtained from a mammal, including from the upper respiratory tissues (such as nasopharyngeal wash, nasopharyngeal aspirate, nasopharyngeal swab, and oropharyngeal swab), from the lower respiratory tissues (such as bronchiolar lavage, tracheal aspirate, pleural tap, sputum), blood, plasma, serum, stool, and tissue from any organ such as, without limitation, lung, heart, spleen, liver, brain, kidney, and adrenal glands. These examples are illustrative, and are not to be construed as limiting the sample types applicable to the present invention.

While not intending to limit the source of the sample, in one embodiment, the sample is isolated from a mammal. In one embodiment, the "mammal" is rodent (such as mouse and rat, such as cotton rat), primate (including simian and human) ovine, bovine, ruminant, lagomorph, porcine, caprine, equine, canine, feline, avian, etc. Expressly included are hamster, mink, ferret, pig, cat, and rabbit.

The invention also provides methods for detecting the presence of SARS-CoV in one or more samples, such as in samples from mammals that have been treated with anti-SARS-CoV agents. These methods may be used in, for example, determining the efficacy of a therapeutic modality (such as a chemical drug) in reducing SARS-coronavirus infection in a mammal, including a model animal and human. These methods are also useful in determining the relative efficacy of different therapeutic modalities, such as different concentrations of the same drug, the same concentration of different drugs, and different combinations of drugs.

Thus, in one embodiment, the invention provides a method for detecting the presence of SARS-coronavirus in a first sample and in a second sample, comprising: a) providing: (i) a first sample; (ii) a second sample; b) contacting test cells chosen from one or more of the invention's cells (such as the exemplary HEK-293T, Huh-7, Mv1Lu, pRHMK and/or pCMK cell, etc.) with: (i) the first sample to produce a first treated sample; and (ii) the second sample to produce a second treated sample; wherein the exposing is under conditions such that the test cells are infected with SARS-coronavirus; c) detecting the presence of one or more of SARS-coronavirus gRNA and SARS-coronavirus sgRNA, wherein the detecting indicates the presence of the SARS-coronavirus. In a preferred embodiment, the detecting step comprises detecting one or more of: i) absence of SARS-coronavirus gRNA in the first treated sample; ii) reduced level of SARS-coronavirus sgRNA in the first treated sample compared to the level of sgRNA in the second treated sample; and iii) reduced ratio of SARS-coronavirus sgRNA level to SARS-coronavirus gRNA level in the first treated sample compared to in the second treated sample. Detection of any one or more of these phenomena indicates that the first sample contains a reduced level of SARS-coronavirus compared to the second sample.

In one embodiment, the method comprises detecting an absence of SARS-coronavirus gRNA in the first treated sample. Without limiting the invention to any particular mechanism, such detection indicates that SARS-coronavirus has not adsorbed to cells from which the first sample was obtained.

In another embodiment, the method comprises detecting an absence of SARS-coronavirus sgRNA in the first treated sample. Without limiting the invention to any particular mechanism, such detection indicates that SARS-coronavirus has not replicated in cells from which the first sample was obtained.

In a preferred embodiment, the method comprises detecting an absence of SARS-coronavirus gRNA and SARS-coronavirus sgRNA in the first treated sample. Without limiting the invention to any particular mechanism, such detection indicates that SARS-coronavirus has neither adsorbed to nor replicated in cells from which the first sample was obtained.

In one embodiment, the first sample and the second sample are from a mammal. In a preferred embodiment, the first sample is from a mammal treated with an agent and the second sample is from the mammal that is not treated with the agent. These steps may be used in, for example, identifying an agent as reducing infection with SARS-CoV in a model animal or in human clinical trials.

In another embodiment, the first sample is from a mammal treated with a first concentration of an agent and the second sample is from the mammal treated with a second concentration of the agent, wherein the first and second concentrations are different. These steps may be used in, for example, comparing the relative efficacy of different concentrations of the same agent in reducing infection with SARS-CoV in a model animal or in human clinical trials.

In a further embodiment, the first sample is from a mammal treated with a first agent and the second sample is from the mammal treated with a second agent wherein the first and second agents are different. These steps may be used in, for example, comparing the relative efficacy of different agents in reducing infection with SARS-CoV in a model animal or in human clinical trials.

H. Screening Anti-SARS-CoV Agents

In one embodiment, the invention provides a method for identifying a test agent as altering infection of a cell by SARS-coronavirus, comprising: a) providing cells treated with a test agent, wherein the cells are chosen from one or more of HEK-293T, Huh-7, Mv1Lu, pRHMK and pCMK; and b) detecting an altered level of infection of cells treated with the test agent compared to a level of infection of the cells not treated with the test agent, wherein the detecting identifies the test agent as altering infection of a cell by SARS-coronavirus. The altered level of infection may be a reduced level or an increased level.

This method may be used in, for example, screening anti-SARS-coronavirus drugs. Anti-SARS-coronavirus drugs may be used as prophylactic agents and/or therapeutic agents in the treatment of SARS-coronavirus. Anti-SARS-coronavirus drugs may also be used to increase the safety of handling cells, such as Mv1Lu cells that are used in clinical laboratories for and that may be susceptible and/or permissive to SARS-coronavirus. For example, with respect to Mv1Lu cells, which are routinely used in clinical laboratories for screening infection with influenza and parainfluenza viruses, and which show low permissivity to SARS-CoV, particularly useful are anti-SARS CoV drugs that reduce permissivity of Mv1Lu cells to SARS, while not substantially reducing susceptibility and/or permissivity of Mv1Lu cells to influenza virus and/or parainfluenza virus. The invention's methods are also useful in determining the efficacy of a drug in reducing infection in a model mammal and in human clinical trials.

In one embodiment, the detecting step may comprise detecting SARS-coronavirus sgRNA, gRNA, polypeptide and/or virion. In another embodiment, the detecting step comprises detecting one or more of: i) absence of SARS-coronavirus gRNA in the treated cells; ii) reduced level of SARS-coronavirus sgRNA in the treated cells compared to the level of sgRNA in the cells that are not treated with the test agent; and (iii) reduced ratio of SARS-coronavirus sgRNA level to SARS-coronavirus gRNA level in the treated cells compared to in the cells that are not treated with the test agent; wherein the detecting identifies the test agent as reducing infection of a cell by SARS-coronavirus.

In another embodiment, it may be desirable to compare the efficacy of two agents in reducing infection with SARS-coronavirus. This may be achieved by detecting one or more of: i) reduced level of SARS-coronavirus sgRNA in the cells treated with a second test agent compared to the level of sgRNA in the cells treated with the test agent; and ii) reduced ratio of SARS-coronavirus sgRNA level to SARS-coronavirus gRNA level in the cells treated with a second test agent compared to the ratio in the cells treated with the test agent, wherein detecting an increased reduction in one or more of the level of SARS-coronavirus sgRNA and of the ratio of SARS-coronavirus sgRNA level to SARS-coronavirus gRNA level in the cells treated with the test agent compared to the cells treated with the second test agent identifies the test agent as more efficacious than the second test agent in reducing infection of a cell by SARS-coronavirus.

The "agent" identified by, and/or used by, the invention's methods refers to any type of molecule (for example, a peptide, nucleic acid, carbohydrate, lipid, organic, and inorganic molecule, etc.) obtained from any source (for example, plant, animal, and environmental source, etc.), or prepared by any method (for example, purification of naturally occurring molecules, chemical synthesis, and genetic engineering methods, etc.). The terms "test compound," "compound," "agent," "test agent," "molecule," and "test molecule," as used herein, refer to any chemical entity, pharmaceutical, drug, and the like that can be used to treat or prevent a disease, illness, sickness, or disorder of bodily function. Agents comprise both known and potential therapeutic compounds. An agent can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of SARS-coronavirus infection. Agents are exemplified by, but not limited to, vaccines, antibodies, nucleic acid sequences such as ribozyme sequences, and other agents as further described herein.

In one embodiment, the agent is an antibody that is specific for one or more SARS-coronavirus antigens. The terms "antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term "antibody" includes polyclonal antibodies, monoclonal antibodies, naturally occurring antibodies as well as non-naturally occurring antibodies, including, for example, single chain antibodies, chimeric, bifunctional and humanized antibodies, as well as antigen-binding fragments thereof, including, for example, Fab, F(ab')$_2$, Fab fragments, Fd fragments, and Ev fragments of an antibody, as well as a Fab expression library. It is intended that the term "antibody" encompass any immunoglobulin (e.g., IgG, IgM, IgA, IgE, IgD, etc.) obtained from any source (e.g., humans, rodents, non-human primates, caprines, bovines, equines, ovines, etc.). The term "polyclonal antibody" refers to an immunoglobulin produced from more than a single clone of plasma cells; in contrast "monoclonal antibody" refers to an immunoglobulin produced from a single clone of plasma cells. Monoclonal and polyclonal antibodies may or may not be purified. For example, polyclonal antibodies contained in crude antiserum may be used in this unpurified state.

Naturally occurring antibodies may be generated in any species including, for example, murine, rat, rabbit, hamster, human, and simian species using methods known in the art. Non-naturally occurring antibodies can be constructed using solid phase peptide synthesis, can be produced recombinantly or can be obtained, for example, by screening combinatorial libraries consisting of variable heavy chains and variable light chains as previously described (Huse et al., Science 246:1275–1281 (1989)). These and other methods of making, for example, chimeric, humanized, CDR-grafted, single chain, and bifunctional antibodies are well known to those skilled in the art (Winter and Harris, Immunol. Today 14:243–246 (1993); Ward et al., Nature 341:544–546 (1989); Hilyard et al., Protein Engineering: A practical approach (IRL Press 1992); and Borrabeck, Antibody Engineering, 2d ed. (Oxford University Press 1995).

Those skilled in the art know how to make polyclonal and monoclonal antibodies which are specific to a desirable polypeptide. For the production of monoclonal and polyclonal antibodies, various host animals can be immunized by injection with the peptide corresponding to any molecule of interest in the present invention, including but not limited to rabbits, mice, rats, sheep, goats, etc. In one embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels such as aluminum hydroxide, surface active molecules such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

For preparation of monoclonal antibodies directed toward molecules of interest in the present invention, any technique that provides for the production of antibody molecules by continuous cell lines in culture may be used (See, e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495–497 (1975)), as well as the trioma technique, the human B-cell hybridoma technique (See e.g., Kozbor et al. Immunol. Today 4:72 (1983)), and the EBV-hybridoma technique to produce human monoclonal antibodies (Cole et al., in *Monoclonal Antibodies and Cancer Therapy*, Alan R. Liss, Inc., pp. 77–96 (1985)). In one embodiment of the monoclonal antibodies are of the IgG class.

In additional embodiments of the invention, monoclonal antibodies can be produced in germ-free animals utilizing technology such as that described in PCT/U.S. Ser. No. 90/02545. In addition, human antibodies may be used and can be obtained by using human hybridomas (Cote et al., Proc. Natl. Acad. Sci. U.S.A. 80:2026–2030 (1983)) or by transforming human B cells with EBV virus in vitro (Cole et al., in *Monoclonal Antibodies and Cancer Therapy*, Alan R. Liss, pp. 77–96 (1985)).

Furthermore, techniques described for the production of single chain antibodies (See e.g., U.S. Pat. No. 4,946,778; herein incorporated by reference) can be adapted to produce single chain antibodies that specifically recognize one or more SARS antigens. An additional embodiment of the invention utilizes the techniques described for the construction of Fab expression libraries (Huse et al., Science 246: 1275–1281 (1989)) to allow rapid and easy identification of monoclonal Fab fragments with the desired specificity for a particular protein or epitope of interest (e.g., at least a portion of an AUBP or mammalian exosome).

The invention also contemplates humanized antibodies. Humanized antibodies may be generated using methods known in the art, including those described in U.S. Pat. Nos. 5,545,806; 5,569,825 and 5,625,126, the entire contents of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

According to the invention, techniques described for the production of single chain antibodies (U.S. Pat. No. 4,946, 778; herein incorporated by reference) can be adapted to produce specific single chain antibodies as desired. An additional embodiment of the invention utilizes the techniques known in the art for the construction of Fab expression libraries (Huse et al., Science, 246:1275–1281 (1989)) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

In the production of antibodies, screening for the desired antibody can be accomplished by techniques known in the art (e.g., radioimmunoassay, ELISA (enzyme-linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In an alternative embodiment, the agent is a nucleic acid sequence. The terms "nucleic acid sequence" and "nucleotide sequence" as used herein refer to two or more nucleotides which are covalently linked to each other. Included within this definition are oligonucleotides, polynucleotide, and fragments or portions thereof, DNA or RNA of genomic or synthetic origin which may be single- or double-stranded, and represent the sense or antisense strand. Nucleic acid sequences which are particularly useful in the instant invention include, without limitation, antisense sequences and ribozymes.

In one embodiment, the agent that alters the infection by SARS-coronavirus is an antisense nucleic acid sequence which hybridizes with at least a portion of SARS-coronavirus genomic RNA and/or subgenomic RNA. Antisense sequences have been successfully used to inhibit the expression of several genes (Markus-Sekura (1988) Anal. Biochem. 172:289–295; Hambor et al. (1988) J. Exp. Med. 168:1237–1245; and patent EP 140 308), including the gene encoding VCAM1, one of the integrin $\alpha4\beta1$ ligands (U.S. Pat. No. 6,252,043, incorporated in its entirety by reference). The terms "antisense DNA sequence" and "antisense sequence" as used herein interchangeably refer to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Sense mRNA generally is ultimately translated into a polypeptide. Thus, an "antisense DNA sequence" is a sequence which has the same sequence as the non-coding strand in a DNA duplex, and which encodes an "antisense RNA" (i.e., a ribonucleotide sequence whose sequence is complementary to a "sense mRNA" sequence). The designation (−) (i.e., "negative") is sometimes used in reference to the antisense strand, with the designation (+) sometimes used in reference to the sense (i.e., "positive") strand. Antisense RNA may be produced by any method, including synthesis by splicing an antisense DNA sequence to a promoter which permits the synthesis of antisense RNA. The transcribed antisense RNA strand combines with natural mRNA produced by the cell to form duplexes. These duplexes then block either the further transcription of the mRNA or its translation, or promote its degradation.

Antisense oligonucleotide sequences may be synthesized using any of a number of methods known in the art (such as solid support and commercially available DNA synthesizers, standard phosphoramidate chemistry techniques, and commercially available services, e.g., Genta, Inc.).

Other molecules which find use as agents for altering infection by SARS-coronavirus include organic molecules, inorganic molecules, and libraries of any type of molecule, which can be screened using a method of the invention, and which may be prepared using methods known in the art. These agents are made by methods for preparing oligonucleotide libraries (Gold et al., U.S. Pat. No. 5,270,163, incorporated by reference); peptide libraries (Koivunen et al. J. Cell Biol., 124: 373–380 (1994)); peptidomimetic libraries (Blondelle et al., Trends Anal. Chem. 14:83–92 (1995)) oligosaccharide libraries (York et al., Carb. Res. 285:99–128 (1996); Liang et al., Science 274:1520–1522 (1996); and Ding et al., Adv. Expt. Med. Biol. 376:261–269 (1995)); lipoprotein libraries (de Kruif et al., FEBS Lett., 399: 232–236 (1996)); glycoprotein or glycolipid libraries (Karaoglu et al., J. Cell Biol. 130:567–577 (1995)); or chemical libraries containing, for example, drugs or other pharmaceutical agents (Gordon et al., J. Med. Chem. 37:1385–1401 (1994); Ecker and Crook, Bio/Technology 13:351–360 (1995), U.S. Pat. No. 5,760,029, incorporated by reference). Libraries of diverse molecules also can be obtained from commercial sources.

I. Administering Anti-SARS-CoV Agents

The invention provides a method for reducing infection by SARS-coronavirus comprising administering a therapeutic amount of an agent to a mammal. The terms "therapeutic amount," "pharmaceutically effective amount," "therapeutically effective amount," "biologically effective amount," and are used interchangeably herein to refer to an amount which is sufficient to achieve a desired result, whether quantitative or qualitative. In particular, a pharmaceutically effective amount is that amount that results in the reduction, delay, and/or elimination of undesirable effects (such as pathological, clinical, biochemical and the like) in the subject that are associated with infection with SARS-coronavirus. As used herein, the actual amount encompassed by the term "therapeutic amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors which those skilled in the art will recognize.

In one embodiment, the agent is administered for a "therapeutically effective time" refers to the period of time during which a pharmaceutically effective amount of a compound is administered, and that is sufficient to reduce one or more symptoms associated with SARS-coronavirus infection.

The agent may be administered before, concomitantly with, and/or after detection of symptoms of infection with SARS-coronavirus. The term "concomitant" when in reference to the relationship between administration of a compound and disease symptoms means that administration occurs at the same time as, or during, manifestation of symptom associated with SARS-coronavirus infection. Also, the invention's agents may be administered before, concomitantly with, and/or after administration of another type of drug or therapeutic procedure.

As used herein, the actual amount encompassed by the term "therapeutic amount" will depend on the nature of agent, route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors which those skilled in the art will recognize. The dosage amount and frequency are selected to create an effective level of the compound without substantially harmful effects. The agent may be administered by, for example, oral, parenteral (e.g., subcutaneous, intravenous, intramuscular, intrastemal injection, and infusion), intranasal, and/or inhalation routes. A therapeutic amount of the agent may be determined using in vitro and in vivo assays known in the art.

The agents may be administered with one or more pharmaceutically acceptable carrier, diluent or excipient. Pharmaceutically acceptable carriers are known in the art such as those described in, for example, Remingtons Pharmaceutical Sciences, Mack Publishing Co. (A. R. Gennaro edit. 1985). The pharmaceutically acceptable carriers may be liquid, with the compositions being, for example, an oral syrup or injectable liquid. Compositions in solid or liquid form may include an agent which binds to the active component(s) and thereby assists in the delivery of the active components. Suitable agents which may act in this capacity include a monoclonal or polyclonal antibody, a protein or a liposome. Alternatively, the pharmaceutical composition of the present invention may consist of gaseous dosage units, e.g., it may be in the form of an aerosol useful in, for example, inhalatory administration. The term "aerosol" is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

J. Producing SARS-CoV and SARS-CoV Polypeptides

The invention also provides a method for producing one or more of SARS-coronavirus particles and SARS-coronavirus polypeptide, comprising: a) providing: (i) SARS-coronavirus; and (ii) a cell type chosen from one or more of HEK-293T, Huh-7, Mv1Lu, pRHMK and pCMK; and b) inoculating the cell type with the virus under conditions such that the inoculated cell produces one or more of SARS-coronavirus and SARS-coronavirus polypeptide. One advantage in using a combination of cells that are infected with SARS-CoV to generate antibodies and/or vaccines is that each cell in the combination may differently process the viral proteins. Thus, a combination of cells infected with SARS-CoV would enable the generation of antibodies and/or vaccines that are specific to different viral proteins, thereby increasing the sensitivity and/or specificity of the antibodies and/or vaccines in SARS-CoV detection and/or treatment.

In one embodiment, the invention's methods may be used to produce one or more SARS-coronavirus antigens. The terms "antigen," "immunogen," "antigenic," "immunogenic," "antigenically active," and "immunologically active" refer to any molecule that is capable of inducing a specific humoral or cell-mediated immune response. An immunogen generally contains at least one epitope. Immunogens are exemplified by, but not restricted to molecules which contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

The terms "epitope" and "antigenic determinant" refer to a structure on an antigen which interacts with the binding site of an antibody and/or T cell receptor as a result of molecular complementarity. An epitope may compete with the intact antigen, from which it is derived, for binding to an antibody. Generally, secreted antibodies and their corresponding membrane-bound forms are capable of recognizing a wide variety of molecules as antigens, whereas T cell receptors are capable of recognizing only fragments of proteins which are complexed with MHC molecules on cell surfaces. Antigens recognized by immunoglobulin receptors on B cells are subdivided into three categories: T-cell dependent antigens, type 1 T cell-independent antigens; and type 2 T cell-independent antigens. Also, for example, when a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

Exemplary SARS-coronavirus antigens include, without limitation, at least a portion of a SARS-CoV polypeptide chosen from one or more of Nucleocapsid (N), Spike glycoprotein (S), Matrix (M), E protein, and Replicase proteins (Pol 1a/b) described supra.

SARS-CoV polypeptides and antigens may be made using methods known in the art. In one embodiment, SARS-CoV antigens may be obtained by purifying them using routine methods, from cells (such as the exemplary HEK-293T, Huh-7, Mv1Lu, pRHMK and/or pCMK cell, etc.) that are infected with SARS-CoV.

In another embodiment, SARS-CoV polypeptides (such as antigens) may be synthesized by chemical synthesis. Synthetic chemistry techniques, such as solid phase Merrifield synthesis are advantageous for reasons of purity, freedom from undesired side products, ease of production, etc. A summary of the techniques available are found in several articles, including Steward et al., Solid Phase Peptide Synthesis, W. H. Freeman, Co., San Francisco (1969); Bodanszky, et al., Peptide Synthesis, John Wiley and Sons, Second Edition (1976); J. Meienhofer, Hormonal Proteins and Peptides, 2:46, Academic Press (1983); Merrifield, Adv. Enzymol. 32:221–96 (1969); Fields, et al., Intl. Peptide Protein Res., 35:161–214 (1990), and U.S. Pat. No. 4,244,946 for solid phase peptide synthesis; and Schroder et al., The Peptides, Vol 1, Academic Press (New York) (1965) for classical solution synthesis. Protecting groups usable in synthesis are described as well in Protective Groups in Organic Chemistry, Plenum Press, New York (1973). Solid phase synthesis methods consist of the sequential addition of one or more amino acid residues or suitably protected amino acid residues to a growing peptide chain. Either the amino or carboxyl group of the first amino acid residue is protected by a suitable selectively removable protecting group. A different, selectively removable protecting group is utilized for amino acids containing a reactive side group such as lysine.

In a further embodiment, SARS-CoV polypeptides (such as antigens) may be produced by expression of recombinant DNA constructs prepared in accordance with well-known methods. Such production can be desirable to provide large quantities or alternative embodiments of such compounds. In one embodiment, DNA sequences of open reading frames (ORFs) encoding the desired peptide sequence is prepared using commercially available nucleic acid synthesis methods. The chemically synthesized DNA is isolated in a purified form, and inserted into an expression vector, as exemplified by, but not limited to, plasmid, phagemid, shuttle vector, cosmid, and virus.

Expression can be effected in procaryotic, eukaryotic and/or viral hosts. Prokaryotes most frequently are represented by various strains of *E. coli*. However, other microbial strains may also be used, such as bacilli, for example *Bacillus subtilis*, various species of *Pseudomonas*, or other bacterial strains. In such procaryotic systems, plasmid vectors which contain replication sites and control sequences derived from a species compatible with the host are used. For example, a workhorse vector for *E. coli* is pBR322 and its derivatives. Commonly used procaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived PL promoter and N-gene ribosome binding site. However, any available promoter system compatible with procaryote expression can be used.

Expression in eukaryotic cells (such as yeast, insect, and mammalian cells) is expressly contemplated. This method is particularly suited for glycoproteins, such as S.

Expression by viral vectors may be achieved using, for example, vaccinia viruses, retroviral vectors, alpha viruses, influenza virus, adenoviruses, and baculoviruses, which may be engineered to express the SARS-CoV polypeptides and/or antigens upon infection/transduction of various cell types. These systems can be used to infect a variety of cell types from mammalian to insect cells. This approach may be very efficient resulting in very high level protein expression.

In one embodiment, the SARS-CoV polypeptide (such as antigen) may be isolated following recombinant expression. The terms "isolated," "to isolate," "isolation," "purified," "to purify," "purification," and grammatical equivalents thereof as used herein, refer to the reduction in the amount of at least one contaminant (such as protein and/or nucleic acid sequence) from a sample. Thus purification results in an "enrichment," i.e., an increase in the amount of a desirable protein and/or nucleic acid sequence in the sample. For example, the SARS-CoV polypeptide (such as antigen) may be fused to another molecule capable of binding to a ligand. The ligand may be immobilized to a solid support to facilitate isolation of the fused polypeptide. Ligand-binding systems useful for the isolation of polypeptides are commercially available and include, for example, the staphylococcal protein A and its derivative ZZ (which binds to human polyclonal IgG), histidine tails (which bind to $Ni^{2+}$), biotin (which binds to streptavidin), maltose-binding protein (MBP) (which binds to amylose), glutathione S-transferase (which binds to glutathione), etc. It is not intended that the polypeptide probes of the present invention be limited to any particular isolation system. The use of 6–8 Histidine tags in combination with $Ni^{2+}$ chromatography has been successfully used for the production of N and E proteins of other CoVs (e.g., MHV).

In one embodiment, the SARS-CoV particles and/or antigens find use in antibody generation. These antibodies may be used in diagnostic assays for the detection of SARS-CoV, as described supra. The antibodies may also be used in the prophylaxis and/or treatment of SARS-CoV infection.

In another embodiment, the cells and methods of the invention are useful for the production of SARS-CoV particles and/or antigens for use in vaccine formulations. The term "vaccine" as used herein refers to a preparation of a pathogenic organism (such as virus as exemplified by SARS-CoV and human immunodeficiency virus, bacterium, fungus, protist such as the malaria agent *Plasmodium*, multicellular parasite such as *Schistosoma*, etc.) and/or an antigen isolated from the organism, which can be administered prophylactially to an animal to induce immunity. Vaccines include, but are not limited to, live attenuated vaccines, inactivated vaccines, and subunit vaccines. Methods for making and using vaccines are known in the art (Murphy and Chanock, "Immunization against viral diseases" Chapter 16 pp. 435–467, Eds. Knipe and Howley, Publ. Lippincott Williams and Wilkins, Philadelphia, Field's Virology Fourth Edition, 2001).

In one embodiment, the vaccine is a live attenuated vaccine. The term "live attenuated vaccine" refers to a strain (preferably an avirulent strain) of a pathogenic organism that is nonpathogenic and which still induces specific immunity against the pathogenic organism. Methods for producing live attenuated vaccines are know in the art such as those which use vaccinia virus to vaccinate against smallpox. In one embodiment, passage of the virulent virus in cell culture can be used to produce a live attenuated vaccine strain. Such vaccines are exemplified by those for measles, mumps and rubella. In another embodiment, live attenuated vaccines may be produced by introducing site specific mutations into virulence genes to produce an attenuated virus strain for vaccine.

The term "inactivated vaccine" refers to a preparation of a killed and/or inactivated pathogenic organism. Methods for making inactivated vaccines are known in the art such as by chemical inactivation of virus that has been grown in eggs or in cell culture. Successful inactivated vaccines have been produced for rabies and influenza. In one embodiment, inactivated SARS-CoV vaccine may be prepared from virus produced by the invention's cells (such as the exemplary HEK-293T, Huh-7, Mv1Lu, pRHMK and/or pCMK cell, etc.). The virus is isolated from the culture medium by affinity chromatography using cellufine sulphate (Palache et al., J. Infect. Dis. 176(suppl. 1):S20–S23 (1997)). The intact live virus is inactivated after purification by any one of a number of methods known in the art, such as formalin and/or propiolactone treatment to produce an inactivated viral vaccine. Virus inactivation may be achieved by incubation of the virus suspension in 0.1% formaldehyde for 10 to 14 days at 4° C. The inactivated viral preparation is then tested in a model mammal using standard protocols, before use in human clinical trials.

The term "subunit vaccine" refers to an antigenic polypeptide of the pathogenic organism that has been recombinantly expressed in vitro. Methods for making subunit vaccines are known in the art such as for the hepatitis B virus vaccine which was generated using hepatitis B surface antigen expressed in yeast cells. A "subunit vaccine" also refers to a recombinant viral or bacterial vectors that expresses genes encoding an antigenic polypeptide of the pathogenic organism. Exemplary recombinant viral vectors include vaccinia virus, adenovirus, paramyxoviruses, avian poxviruses, yellow fever virus and vesicular stomatitis virus. A "subunit vaccine" further includes DNA sequences, such as a plasmid containing the coding sequence for an antigen that is linked to a strong promoter sequence that is active in mammalian cells. Such plasmids are inoculated directly into the host, the viral gene is expressed in the host and antibody and cell-mediated immunity can then be induced to the recombinant antigen.

Vaccines and/or antibodies against SARS-CoV may be used for immunizing a mammal against SARS-coronavirus, by administering these compositions to generating an immune response in the mammal against SARS-coronavirus. In one embodiment, vaccines and/or antibodies are used therapeutically in a mammal that is already infected with SARS-coronavirus. In another embodiment, vaccines and/or antibodies are used prophylactically in a mammal that is not known to be infected with SARS-coronavirus.

K. Compositions and Methods for Using Protease Inhibitors to Reduce Infection With Plus-Strand RNA Viruses The invention provides compositions and methods for reducing infection with plus-strand RNA viruses. In one embodiment, the invention provides a composition comprising (i) cells susceptible to a virus that is not a plus-strand RNA virus, and (ii) protease inhibitor. The terms "positive-strand RNA virus "plus-strand RNA virus," and "+-strand RNA virus," are equivalent terms that refer to a virus whose genome contains a plus-strand RNA.

Without intending to limit the type of the virus, in one embodiment, the "virus that is not a plus-strand RNA virus" contains a genome of single stranded DNA, double stranded DNA, double stranded RNA, or negative-strand RNA. Also without limiting the source of the virus, the virus that is not a plus-strand RNA virus may be an animal virus, plant virus, and bacteriophage. More particularly, the animal virus that is not a plus-strand RNA virus is exemplified by, but not limited to, Arenaviridae, Baculoviridae, Birnaviridae, Bunyaviridae, Cardiovirus, Corticoviridae, Cystoviridae, Epstein-Barr virus, Filoviridae, Hepadnviridae, Hepatitis virus, Herpesviridae, Influenza virus, Inoviridae, Iridoviridae, Metapneumovirus, Orthomyxoviridae, Papovaviru, Paramyxoviridae, Parvoviridae, Polydnaviridae, Poxyviridae, Reoviridae, Rhabdoviridae, Semliki Forest virus, Tetraviridae, Toroviridae, Vaccinia virus, Vesicular stomatitis virus.

Cells that are susceptible to viruses are known in the art and are exemplified, but not limited to, cells susceptible to metapneumovirus, cells susceptible to cells susceptible to Arbovirus (such as BHK-21 cells), cells susceptible to BK polyomavirus (such as NCI-H292 cells), cells susceptible to BVDV (such as BT, and EBTr cells), cells susceptible to CMV (such as H&V-Mix, HEL, HEL-299, HFL-Chang, Hs27 (HFF), Human Fetal Tonsil, MRC-5, MRHF, Mv1Lu, and WI-38 cells), cells susceptible to Coxsackie A (such as MRC-5, RD, HeLa, HEp-2, pMK, MDCK, and E-Mix cells), cells susceptible to Echovirus (such as HEL-299, HFL-Chang, and pMK cells), cells susceptible to Encephalitis (such as CV1 cells), cells susceptible to Herpesviruses (such as Human Fetal Tonsil, L-929, CHO-K1 cells), cells susceptible to HSV (such as A549, BGMK, CV1, Duck Embryo, EBTr, ELVIS-HSV, H&V-Mix, HEL, HEL-299, HeLa, HEp-2, Hs27 (HFF), LLC-MK2, MDCK, MRC-5, MRHF, Mv1Lu, NCI-H292, pAGMK, pCMK, pRK, RD, RK, RK1, R-Mix, Vero, WI 38 cells), cells susceptible to Influenza (such as A549, Chicken embryo, HEp-2, LLC-MK2, MDCK, MRC-5, pAGMK, pCMK, pRhMK, R-Mix, WI 38, NCI-H292, and Mv1Lu cells), cells susceptible to Measles (such as A549, Chicken embryo, CV1, HEp-2, LLC-MK2, NCI-H292, pMK, and Vero cells), cells susceptible to Mumps (such as A549, BGMK, CV1, HEp-2, Hs27 (HFF), LLC-MK2, MRC-5, pCMK, pMK, pRK, RK1, Vero, and WI 38 cells), cells susceptible to Myxovirus (such as LLC-MK2 cells), cells susceptible to Newcastle disease (such as Chicken embryo cells), cells susceptible to Panleukopenia (such as CHO-K1 cells), cells susceptible to Parainfluenza (such as A549, BGMK, HEp-2, Hs27 (HFF), L-929, LLC-MK2, MDCK, MRC-5, MRHF, pAGMK, pCMK, pRhMK, R-Mix, Vero, WI 38, BT, EBTr cells), cells susceptible to canine Parvovirus (such as CHO-K1 cells), cells susceptible to feline Picornavirus (such as CHO-K1 cells), most fibroblast and heteroploid cell lines, MRC-5, pCMK, WI 38, HeLa, HeLa S-3, BS-C-2, CV1, Vero, LLC-MK2 cells), cells susceptible to Poxvirus (such as LLC-MK2 cells), cells susceptible to Rabies (such as CHO-K1 and L-929 cells), cells susceptible to Reovirus (such as MDCK, EBTr, CHO-K1, L-929, NCI-H292 cells), cells susceptible to Rhinovirus (such as HEL, HEL-299, HFL-Chang, Hs27 (HFF), LLC-MK2, MRC-5, WI 38, NCI-H292 cells), cells susceptible to Rotavirus (such as A549, CV1, Vero cells), cells susceptible to RSV (such as A549, BGMK, HeLa, HEp-2, Hs27 (HFF), Human Fetal Tonsil, MDCK, MRC-5, MRHF, NCI-H292, pRhMK, R-Mix, Vero, WI 38 cells), cells susceptible to Rubella (such as BHK-21, BS-C-1, HEp-2, LLC-MK2, pMK, RK13, SIRC, Vero cells), cells susceptible to SV40 (such as BS-C-3, CV1 cells), cells susceptible to Vaccinia (such as Chicken embryo, EBTr, L-929, NCI-H292 cells), cells susceptible to Vesicular stomatitis (such as BS-C-4, Duck Embryo, HEL-299, HeLa S-5, EBTr cells), and cells susceptible to VZV (such as A549, CV1, H&V-Mix, HEL, HEL-299, HFL-Chang, HNK, Hs27 (HFF), MRC-5, MRHF, SF, Vero, WI 38, M7, pGuinea Pig Embryo cells).

Also without intending to limit the source or type of virus, the "plus-strand RNA virus" is exemplified by togavirus, flavivirus, coronavirus, and picornavirus (including Adenovirus, Enterovirus, Immunodeficiency virus, Poliovirus, and Retrovirus).

More particularly, Togaviruses are exemplified by eastern equine encephalitis virus, western equine encephalitis virus, rubella virus. A variety of infectious agents comprise the alphaviruses (a subgroup of togaviridae), including Chikungunya, Mayaro, Igbo Ora, Ross River virus, Venezuelan equine encephalitis, Eastern equine encephalitis, and Western equine encephalitis. While the encephalitides have been discussed previously (Small Group 3, Neurotropic Viruses, Nov. 13–15, 2001), this group of "emerging viruses" causes a range of diseases (from acute arthropathy to systemic febrile illness) in various parts of the world including the United States. A wide range of animals host these viruses, including birds, rodents, primates, wallabies, equines, and bats. However, all alphaviruses pathogenic for humans replicate in and are transmitted by mosquitoes.

Flaviviruses are exemplified by Dengue fever virus, Yellow fever virus, St. Louis encephalitis virus, Japanese B encephalitis virus, West Nile virus, and Hepatitis C virus.

The term "coronavirus" refers to a virus whose genome is plus-stranded RNA of about 27 kb to about 33 kb in length depending on the particular virus. The virion RNA has a cap at the 5' end and a poly A tail at the 3' end. The length of the RNA makes coronaviruses the largest of the RNA virus genomes. In one embodiment, coronavirus RNAs encode: (1) an RNA-dependent RNA polymerase; (2) N-protein; (3) three envelope glycoproteins; plus (4) three non-structural proteins. These coronaviruses infect a variety of mammals & birds. They cause respiratory infections (common), enteric infections (mostly in infants >12 mo.), and possibly neurological syndromes. Coronaviruses are transmitted by aerosols of respiratory secretions. Coronaviruses are exemplified by, but not limited to, human enteric coV (ATCC accession # VR-1475), human coV 229E (ATCC accession # VR-740), human coV OC43 (ATCC accession # VR-920), and SARS-coronavirus (Center for Disease Control).

Picornavirus comprises several genuses such as Enterovirus (exemplified by human enterovirus A, B, C, and D, porcine enterovirus A and B, Poliovirus, Coxsackie A and B virus, and Echo virus), Rhinovirus (exemplified by Human rhinovirus), Hepatovirus (exemplified by Hepatitis A virus), Cardiovirus (exemplified by Encephalomyocarditis virus), Aphthovirus (exemplified by Foot-and-mouth disease virus), Parechovirus (exemplified by Human parechovirus), Erbovirus (exemplified by Equine rhinitis B virus), Kobuvirus (exemplified by Aichi virus), Hepatovirus, and Teschovirus (exemplified by Porcine teschovirus).

Cells susceptible to plus-sense RNA viruses are exemplified by, but not limited to, cells susceptible to Adenovirus (such as 293, A549, HEL, HEL-299, HEp-2, HFL-Chang, HNK, Hs27, KB, LC-MK2, MDCK, MRC-5, MRHF, NCI-H292, pRK, RK1, R-Mix, Vero, WI 38, HeLa, and HeLa S-4 cells), cells susceptible to Bovine adenovirus (such as BT cells), cells susceptible to Bovine enterovirus (such as BT cells), cells susceptible to Enterovirus (such as A549, BGMK, Caco-2, HEL, HEp-2, HNK, Hs27 (HFF), LLC-MK2, MRC-5, MRHF, NCI-H292, pAGMK, pCMK, pRhMK, RD, Vero, and WI 38 cells), cells susceptible to feline Calicivirus (such as CHO-K1 cells), cells susceptible to *Poliovirus* (such as A549, BGMK, FL Amnion, HEL-299, HEp-2, HFL-Chang, Hs27 (HFF), and cells susceptible to bovine Infectious rhinotracheitis virus (such as BT and EBTr cells).

The invention further provides a method for detecting a virus that is not a plus-strand RNA virus in a sample, comprising: a) providing: i) a sample; ii) cells susceptible to the virus that is not a plus-strand RNA virus; and iii) one or more protease inhibitor; b) contacting the cells and the sample in the presence of the protease inhibitor to produce contacted cells, wherein replication of the plus-strand RNA virus in the contacted cells is not reduced relative to replication of the virus that is not a plus-strand RNA virus in cells not contacted with the protease inhibitor, and wherein replication of a plus-strand RNA virus in the cells contacted with the protease inhibitor is reduced relative to replication of the plus-strand RNA virus in cells not contacted with the protease inhibitor.

In one embodiment, the invention provides, compositions and methods for reducing infection with SARS-coronavirus, without substantially reducing infection with other respiratory viruses. Thus, the invention provides a composition comprising (i) cells susceptible to a virus chosen from influenza virus, parainfluenza virus, adenovirus, metapneumovirus, and respiratory syncytial virus, and (ii) protease inhibitor. The invention also provides a method for detecting a virus chosen from influenza virus, parainfluenza virus, adenovirus, and respiratory syncytial virus in a sample, comprising: a) providing: i) a sample; ii) cells susceptible to the virus; and iii) one or more protease inhibitor; b) contacting the cells and the sample in the presence of the protease inhibitor to produce contacted cells, wherein infection of the contacted cells by the virus is not reduced relative to cells not contacted with the protease inhibitor, and wherein infection of the contacted cells by severe acute respiratory syndrome coronavirus (SARS-coronavirus) is reduced relative to cells not contacted with the protease inhibitor.

These methods are premised, at least in part, on the inventors' discovery that protease inhibitors do not substantially reduce infection of cells by the exemplary respiratory viruses influenza, parainfluenza, RSV, and adenovirus (Example 8). This is in contrast to the inhibition in replication of SARS-coronavirus by the cysteine proteinase inhibitor (2S,3S)transepoxysuccinyl-L-leucylamido-3-methylbutane ethyl ester (Yount et al. PNAS 100:12995–13000 (2003).

The invention's methods are useful, where it is desirable to reduce infectivity by SARS-coronavirus of cells that are routinely used in diagnostic assays of respiratory viruses such as influenza, parainfluenza, RSV, and adenovirus.

As used herein the term "influenza virus" refers to members of the orthomyxoviridae family of enveloped viruses with a segmented antisense RNA genome (Knipe and Howley (eds.) Fields Virology, 4th edition, Lippincott Williams and Wilkins, Philadelphia, Pa. [2001]). Two types of influenza virus (A and B) are human pathogens causing respiratory pathology. While not intending to limit the type of influenza virus, in one embodiment, the influenza virus is chosen from influenza A, influenza B, and influenza C. Also while not intending to limit the cell type, the cells susceptible to influenza virus comprise cells chosen from A549 (Influenza), Chicken embryo (Influenza), HEp-2 (Influenza), LLC-MK2 (Influenza), MDCK (Influenza), MRC-5 (Influenza), pAGMK (Influenza), pCMK (Influenza), pRhMK (Influenza), R-Mix (Influenza), WI 38 (Influenza A), NCI-H292 (Influenza A), Mv1Lu (Influenza A,B), and Mv1Lu-hF (Influenza A,B). These cells are available from Diagnostic Hybrids, Inc., Athens, Ohio.

As used herein, the term "parainfluenza virus" refers to certain members of the paramyxoviridae genus of enveloped viruses with a single-stranded antisense RNA genome (Knipe and Howley (eds.) Fields Virology, 4th edition, Lippincott Williams and Wilkins, Philadelphia, Pa. [2001]). Four types of parainfluenza virus (1 to 4) are human respiratory pathogens. While not intending to limit the type of parainfluenza virus, in one embodiment, the parainfluenza virus is chosen from parainfluenza 1, parainfluenza 2, and parainfluenza 3. In another embodiment, the cells susceptible to parainfluenza virus comprise cells chosen from A549 (Parainfluenza), BGMK (Parainfluenza), HEp-2 (Parainfluenza), Hs27 (HFF) (Parainfluenza), L-929 (Parainfluenza), LLC-MK2 (Parainfluenza), MDCK (Parainfluenza), MRC-5 (Parainfluenza), MRHF (Parainfluenza), pAGMK (Parainfluenza), pCMK (Parainfluenza), pRhMK (Parainfluenza), R-Mix (Parainfluenza), Vero (Parainfluenza), WI 38 (Parainfluenza), BT (Parainfluenza 3), and EBTr (Parainfluenza 3). These cells are available from Diagnostic Hybrids, Inc., Athens, Ohio.

As used herein, the term "adenovirus" refers to a double-stranded DNA adenovirus of animal origin, such as avian, bovine, ovine, murine, porcine, canine, simian, and human origin. Avian adenoviruses are exemplified by serotypes 1 to 10 which are available from the ATCC, such as, for example, the Phelps (ATCC VR-432), Fontes (ATCC VR-280), P7-A (ATCC VR-827), IBH-2A (ATCC VR-828), J2-A (ATCC VR-829), T8-A (ATCC VR-830), and K-1¦ (ATCC VR-921) strains, or else the strains designated as ATCC VR-831 to 835. Bovine adenoviruses are illustrated by those available from the ATCC (types 1 to 8) under reference numbers ATCC VR-313, 314, 639–642, 768 and 769. Ovine adenoviruses include the type 5 (ATCC VR-1343) or type 6 (ATCC VR-1340). Murine adenoviruses are exemplified by FL (ATCC VR-550) and E20308 (ATCC VR-528). Porcine adenovirus (5359) may also be used. Adenoviruses of canine origin include all the strains of the CAVI and CAV2 adenoviruses [for example, Manhattan strain or A26/61 (ATCC VR-800) strain]. Simian adenoviruses are also contemplated, and they include the adenoviruses with the ATCC reference numbers VR-591–594, 941–943, and 195–203. Human adenoviruses, of which there greater than fifty (50) serotypes are known in the art, are also contemplated, including the Ad2, Ad3, Ad4, Ad5, Ad7, Ad9, Ad12, Ad17, and Ad40 adenoviruses.

Without limiting the type of cell, the cells susceptible to adenovirus comprise cells chosen from 293 (Adenovirus), A549 (Adenovirus), HEL (Adenovirus), HEL-299 (Adenovirus), HEp-2 (Adenovirus), HFL-Chang (Adenovirus), HNK (Adenovirus), Hs27 (HFF) (Adenovirus), KB (Adenovirus), LLC-MK2 (Adenovirus), MDCK (Adenovirus), MRC-5 (Adenovirus), MRHF (Adenovirus), NCI-H292 (Adenovirus), pRK (Adenovirus), RK1 (Adenovirus), R-Mix (Adenovirus), Vero (Adenovirus), WI 38 (Adenovirus), HeLa (Adenovirus 3), and HeLa S-4 (Adenovirus 5). These cells are available from Diagnostic Hybrids, Inc., Athens, Ohio.

In another embodiment, the cells susceptible to respiratory syncytial virus comprise cells chosen from A549, BGMK, HeLa, HEp-2, Hs27 (HFF), Human Fetal Tonsil, MDCK, MRC-5, MRHF, NCI-H292, pRhMK, R-Mix, Vero, and WI 38. These cells are available from Diagnostic Hybrids, Inc., Athens, Ohio.

In one embodiment, the goal of reducing infection of cells by SARS-coronavirus while not substantially reducing susceptibility of the cells to influenza, parainfluenza, RSV, and/or adenovirus viruses may be attained by contacting the cells and/or sample that is being tested with a "protease inhibitor," i.e., an agent that reduces the activity of an enzyme that degrades proteins by hydrolysing peptide bonds between amino acid residues. Exemplary protease inhibitors include, but are not limited to, those obtained from Sigma, and listed in catalog 2000–20001, page 845, including AMASTATIN (page 1046), (2S, 3R)-3-Amino-2-hydroxy-4-(4-nitrophenyl)-butanoyl-L-leucine (NITROBESTATIN) (page 1046), 4-Amidinophenylmethanesulfonyl Fluoride (AMPSF) (page 84), Antipain (page 1046), $\alpha_1$-Antitrypsin (page 125), Aprotinin (page 128), BESTATIN (page 160), CHYMOSTATIN (page 1046), CYSTATIN (page 299), 3,4-Dichlorolsocoumarin (page 336), EBELACTONE A (page 382), EBELACTONE B (page 382), ELASTATINAL (page 1047), trans-Epoxysuccinyl-L-leucylamido-(4-guanidino) butane (E-64) (page 393), ethylene diamine tetra-acetic acid (EDTA) (page 1768), EGTA (page 408), Leupeptin (page 1047), $\alpha_2$-Macroglobulin (page 626), Nle-Sta-Ala-Sta (page 1047), Pepstatin A (page 1048), phenylmethylsulfonylfluoride (PMSF) (page 772), N-($\alpha$-Rhamnopyranosyloxy)hydroxy-phosphinyl-Leu-Trp (PHOSPHORAMIDON) (page 1048), TLCK (page 964), TPCK (page 964), Trypsin Inhibitor (Soybean) (page 1735), Trypsin Inhibitor (Egg) (page 992), Actinonin (page 128), and Glycyrrhizio Acid (page 489).

In one embodiment the protease inhibitor is a drug that has been approved by the FDA. These are exemplified by protease inhibitors approved for reducing infection with human immunodeficiency virus (HIV), such as, without limitation AGENERASE (AMPRENAVIR), CRIXIVAN (INDINAVIR), FORTOVASE (SAQUINAVIR), INVIRASE (SAQUINAVIR), KALETRA (LOPINAVIR), LEXIVA (FOSAMPRENAVIR) which is formerly know as GW-433908 and VX-175 and is an improved formulation of AGENERASE (AMPRENAVIR), NORVIR (RITONAVIR), REYATAZ (ATAZANAVIR; BMS-232632), and VIRACEPT (NELFINAVIR).

In one embodiment, the cells used in the invention's methods may comprise a transgenic cell, such as Mv1Lu-hF. In a further embodiment, the contacting further comprises contacting the cells with antibody specific for one or more SARS-coronavirus antigen.

The cells may be in single cell type culture or in mixed cell type culture with a second cell type. The second cell type may comprise a wild type cell and/or a transgenic cell. In one embodiment, the mixed cell types comprise mink lung cells such as Mv1Lu cells, and the second cell type comprises A549 cells (R-mix). In a further embodiment, the cells are frozen in situ, regardless of whether they are in single cell culture or in mixed cell culture.

Where mink lung cells such as Mv1Lu cells are used, the inoculated cells may be incubated with the sample for up to 24 hours to reduce the chance of detecting SARS, while maximizing detection of influenza virus and/or parainfluenza. Data herein (FIG. 4B) shows that SARS was not produced by Mv1Lu cells within 24 hours p.i.

The samples that may be used in the invention's methods may be isolated from a mammal such as human, non-human primate, canine, feline, porcine, murine, bovine, avian, hamster, mink.

EXPERIMENTAL

The following examples serve to illustrate certain preferred embodiments and aspects of the present invention and are not to be construed as limiting the scope thereof.

EXAMPLE 1

Materials and Methods

The following is a brief description of the exemplary materials and methods used in the subsequent Examples.

A. Virus

A seed stock of SARS-CoV Urbani that was passaged twice in Vero E6 cells provided by the Centers for Disease Control and Prevention, Atlanta, Ga. This virus was amplified by two passages in Vero E6 cells to establish a high titer stock (passage 4) that was utilized for all experiments. SARS-CoV was titered in Vero E6 cells by $TCID_{50}$. Briefly, cells were plated in 96-well plates (Falcon, Becton Dickson) at a density of $4\times10^5$ cells/well in 150 μl of medium. Virus was serially diluted by half logs from $10^0$–$10^{-7}$ in culture medium containing 2% antibiotic-antimycotic (Invitrogen Corporation, Carlsbad, Calif.). 100 μl of each dilution was added per well and cells were incubated 3–4 days at 37° C.

B. Cell Lines

The following Table lists exemplary cell lines that were used and/or equivalent cells that may be used in the invention's methods, and that are publically available (e.g., from the American Type Culture Collection (ATCC), Rockville, Md., and Diagnostic Hybrids, Inc. (DHI), Athens, Ohio; Cell Bank, Ministry of Health and Welfare, Japan):

TABLE 3

Exemplary Cells Useful In The Invention

| Cells | Source |
|---|---|
| Vero E6 | ATCC # CRL-1586<br>DHI # 67-0102 |
| MRC-5 | ATCC # CCL-171<br>DHI # 51-0102 |
| BHK-21 | ATCC # CCL-10<br>DHI # 89-0102 |
| MDCK | ATCC # CCL-34<br>DHI # 83-0102 |
| HRT-18 (HCT-18) | ATCC # CCL-244 |
| Mv1Lu | ATCC # CCL-64<br>DHI # 58-0102 |
| CMT-93 | ATCC # CCL-223 |
| AK-D | ATCC # CCL-150 |
| A549 | ATCC # CCL-185<br>DHI # 56-0102 |
| HEL | DHI # 88-0102 |
| pRHMK | DHI # 49-T025<br>DHI # 49-0102 |
| pCMK | DHI # 47-T025<br>DHI # 47-0102 |
| L2 | ATCC # CCL-149 |
| R-Mix | DHI # 96-T025 |
| HEK-293 | ATCC # CRL-1573; |
| HEK-293T | Pear, et al., PNAS USA, 90:8392–8396(1993)<br>DuBridge et al., Mol. Cell. Bio. 7:379–387(1987) |
| Huh-7 (JTC-39) | Japanese Collection of Research Bioresources CellBank # JCRB0403<br>Nakabayashi et al., Cancer Res, 42:3858–63(1982) |

R-Mix (R-Mix FreshCells™, Diagnostic Hybrids, Inc., Ohio) is a mixed monolayer of mink lung cells (strain Mv1Lu) and human Adenocarcinoma cells (strain A549). the hAPN expression construct used to create BHK21/hAPN and CMT-93/hAPN was previously described (Wentworth, et al., 2001). Further description of Huh-7 cells is in Nakabayashi et al., Cancer Res., 42: 3858–3863, 1982; Nakabayashi et al., Gann, 75: 151–158, 1984; and Nakabayashi et al., Cancer Res., 45:6379–6383, 1985.

Vero E6, 293T, L2, AK-D, A549, pCMK, pRhMK, Mv1Lu, CMT-93, and R-mix were maintained in Dulbecco's modified Eagle Medium (DMEM) (Invitrogen Corp.) supplemented with 10% fetal bovine serum (FBS) (Hyclone, Logan, Utah) and 2% antibiotic-antimycotic. MDCK cells were maintained in DMEM high glucose (Invitrogen Corp.) supplemented with 5% FBS and 2% antibiotic-antimycotic. HEL cells were maintained in Modified Eagle's Medium (MEM) supplemented with 10% FBS and 2% antibiotic-antimycotic. HRT-18 cells were maintained in RPMI 1640 (Invitrogen Corp.) supplemented with 10% horse serum (Hyclone), 1 mM MEM sodium pyruvate (Invitrogen Corp.) and 2% antibiotic-antimycotic. Huh-7 cells were maintained in DMEM supplemented with 20% FBS and 2% antibiotic-antimycotic. MRC-5 cells were maintained in MEM supplemented with 10% FBS, 1 mM sodium pyruvate, 0.1 mM MEM nonessential amino acids (Invitrogen Corp.) and 2% antibiotic-antimycotic. BHK-21 cells were maintained in DMEM supplemented with 10% FBS and 5% tris phosphate buffer (Invitrogen Corp.).

C. PCR Assay

G3PDH, genomic SARS-CoV RNA (gRNA) and subgenomic RNA (sgRNA) were detected using multiplex one-step RT-PCR. Oligonucleotide primers used to amplify the different targets were as follows: G3P-279 (sense) 5' CATCACCATCTTCCAGGAGC-3' (SEQ ID NO:72) binds at nt 279–299; G3P-1069R (antisense) 5'-CTTACTCCTTGGAGGCCATG-3' (SEQ ID NO:73) binds at nt 1069–1049; SARS-21,263 (sense) 5'-TGCTAACTACATTTTCTGGAGG-3' (SEQ ID NO:74) binds at nt 21,263–21,284 of SARS-Urbani; SARS-21,593R (antisense) 5'-AGTATGTTGAGTGTAATTAGGAG-3' (SEQ ID NO:75) binds at nt 21,593–21,571 of SARS-Urbani; and SARS-1 (sense) 5'-ATATTAGGTTTTTACCTACCCAGG-3' (SEQ ID NO:76) binds at nt 1–24 of SARS-Urbani. Amplification was carried out using the Qiagen® OneStep RT-PCR kit (Qiagen) according to the manufacturer's protocol. Briefly, each reaction consisted of 2 μg of total RNA isolated using TRIZOL® Reagent (Invitrogen), 400 μM dNTPs, 200 nM of each G3PDH primer, 400 nM SARS-1, 400 nM SARS-21,263, 600 nM SARS-21,593R and 2 μl Qiagen enzyme mix. The cycling parameters were: 50° C. for 30 min, 95° C. for 15 min, 35 cycles of 94° C. for 30 s, 57–58° C. for 30 s, 72° C. for 1 min, followed by 10 min at 72° C. in an Eppendorf Mastercycler gradient (eppendorf). Amplification products were analyzed by electrophoresis through a 1.5% agarose gel and visualized by ethidium bromide staining. All primers were synthesized by the Molecular Genetics Core (David Axelrod Institute, Wadsworth Center, Albany, N.Y.).

D. Cell Infection

Cells seeded at a density of $2\times10^6$ in T25 flasks (Falcon, Becton Dickson) were inoculated with virus at an MOI of 0.001 in a final volume of 1 ml and were incubated 1 h at 37° C. Virus was removed and 5 ml fresh medium added to each flask. Cells were maintained at 37° C. throughout the experiment. At 1, 24 and 48 h post-inoculation (p.i.), cells were observed for CPE, supernatants were collected for subsequent titration and total RNA was extracted using TRIZOL® Reagent (Invitrogen Corp.). RNA was quantitated by spectrophotometer (Eppendorf).

EXAMPLE 2

Exemplary Multiplex RT-PCR Assay for the Detection of SARS-CoV Replication

A RT-PCR assay for the detection of SARS-CoV replication was developed. Replication of corona- and arterivirus RNA occurs through discontinuous synthesis, thought to occur during negative strand synthesis, generating 3' co-terminal nested subgenomic RNAs (sgRNA). The inventors identified targets within the genome for amplification. Oligonucleotide RT-PCR primers were designed that amplify genomic SARS-CoV RNA (gRNA) or the sgRNA that is specific to the leader-body junction. Because genomic RNA is present in input virus, the inventors probed for sgRNA, which is indicative of virus entry and/or replication initiation. Genomic RNA was detected by amplifying a region between the 1b coding region of the polymerase gene and the sequence encoding the Spike (S) glycoprotein. Subgenomic RNA was detected using a primer specific to the leader sequence in conjunction with the reverse primer in S that was used for the gRNA detection. G3PDH primers, designed to amplify G3PDH from multiple species, served as a positive control for RNA integrity and cDNA production.

To evaluate the RT-PCR assay, Vero E6 cells were inoculated with serial dilutions of SARS-CoV ranging from an MOI of $10^0$ to $10^{-8}$ $TCID_{50}$/cell. Total RNA was extracted at 1 and 24 h post-inoculation (p.i.). At 1 h p.i. gRNA was detected in cells inoculated with virus at an MOI of $10^0$ to $10^{-2}$, as indicated by a band at 300 bp (FIG. 1). Subgenomic RNA was not detected (180 bp). However, at 24 h p.i. both gRNA and sgRNA, 300 bp and 180 bp respectively, were detected in cells inoculated with an MOI of $10^0$ to $10^{-5}$. The sgRNA amplicon was confirmed to correspond to the S leader-body junction sgRNA by sequence analysis (Thiel, et al., 2003, J. Gen. Virol. 84:2305–2315). Genomic RNA was visible at 24 h p.i. in cells inoculated with an MOI of $10^{-7}$, however this was not seen in repeated experiments. The decrease in amplified G3PDH (~800 bp) as seen in lanes 1–6 at 24 h p.i. was consistent between repeated experiments. The decrease in G3PDH may be a result of the RT-PCR conditions, which were optimized to favor amplification of SARS-CoV gRNA and sgRNA. Individual amplicon were amplified by PCR of cDNAs from the same samples and G3PDH was consistently detected. Additionally, the decrease in G3PDH may be due to cell death, which is seen in Vero E6 cells. G3PDH was included as a control for template concentration and RNA integrity, and was always detected in the absence of viral RNA.

This data demonstrates that the exemplary multiplex RT-PCR assays is sensitive for detection of SARS-CoV infection.

EXAMPLE 3

Primary Monkey Kidney Cells pRhMK and pCMK are Susceptible and Permissive to SARS-CoV To test the specificity of the RT-PCR assay and to identify cells susceptible to SARS-CoV, kidney cells derived from two species of monkey were inoculated with SARS-CoV at an MOI of approximately 0.001. Vero E6 cells were included in all experiments as a positive control. Entry and early replication of SARS-CoV was detected in primary Rhesus monkey kidney cells (pRhMK) and primary Cynomolgous monkey kidney cells (pCMK) at 24 and 48 h p.i. (FIG. 2A). SARS-CoV genomic RNA was detected at 1 h p.i. and increased by 24 and 48 h p.i. In both cell types, sgRNA, absent from input virus (1 h) was detected at 24 and 48 h p.i. Once again, G3PDH amplification decreased as the amplification of viral RNA increased. Subgenomic RNA was not detected in inoculated baby hamster kidney cells (BHK-21), included as a negative control. In these cells, gRNA was detected only in the viral inoculum (1 h). Both pRhMK and pCMK support productive SARS-CoV infection as demonstrated by virus titration (FIG. 2B). Inoculated cells demonstrated an increase in viral titer by 48 h p.i. over input virus (2.5 log and 1.5 log increases respectively). At 48 h p.i. supernatants from pRhMK contained virus titers of $5.6\times10^5$ $TCID_{50}$ and supernatants from pCMK contained virus at titers of $7.8\times10^4$ $TCID_{50}$. The rise in titer was different between the two cell types; pCMK demonstrated a slower rise in titer from 1 to 24 h p.i. than both pRhMK and Vero E6. Supernatants collected from Vero E6 cells at 48 h p.i. contained viral titers of $3.9\times10^7$ $TCID_{50}$. Consistent with reports by Ksiazek et al., cytopathic effect (CPE) was observed in Vero E6 cells as early as 24 h p.i. (Ksiazek, et al., 2003, N. Engl. J. Med. 348:1953–1966). Surprisingly, however, significant CPE was not observed in pRhMK or pCMK 5 days p.i.

This data suggest that CPE may not be an accurate indicator of SARS-CoV replication. Furthermore, this is the first report of the susceptibility and permissivity of primary monkey kidney cells pRhMK and pCMK to SARS-CoV.

EXAMPLE 4

Cells Expressing Known Coronavirus Receptors are not Susceptible to SARS-CoV

Cell lines known to be susceptible to other coronaviruses were assayed for their susceptibility to SARS-CoV. Human, feline, canine and murine cells expressing known coronavirus receptors were inoculated with SARS-CoV and assayed for viral replication. Cells expressing the receptor for serogroup 1 coronaviruses (APN) tested included human lung fibroblast-derived cells (MRC-5), canine kidney-derived cells (MDCK), and feline lung epithelia (AK-D). These cells are susceptible to human coronavirus 229E (HCoV-229E), canine coronavirus (CCoV), and feline coronavirus (FcoV), respectively. Cells permissive to group 2 coronaviruses were also analyzed, including mouse fibroblast derived cells (L2), that expresses CEACAM 1a, the receptor utilized by MHV-A59 and MHV-JHM and a human rectal tumor cell line (HRT-18), known to be susceptible to HCoV-OC43. SARS-CoV gRNA was amplified in all four cell lines at 1, 24 and 48 h p.i. (FIG. 3); however, sgRNA was not detectable at any time points post inoculation. A non-specific band (~220 bp) was amplified in MRC-5, MDCK and AK-D cells, in all samples including mock. Subgenomic RNA was detected in Vero E6 cells included as a positive control. This data suggest that SARS-CoV utilizes a different receptor than both group 1 and group 2 coronaviruses.

EXAMPLE 5

Mv1Lu Cells are Susceptible and Permissive to SARS-CoV

Virology laboratories routinely inoculate cells with clinical specimen to identify potential respiratory pathogens. Because little is known about the cell types susceptible to SARS-CoV, cells utilized by clinical laboratories were assayed. R-Mix, a mixed monolayer of mink lung-derived cells (Mv1Lu) and human lung-derived cells (A549) are used to detect a range of respiratory pathogens. Influenza A and B, adenovirus, RSV and parainfluenza can be detected in Mv1Lu cells while influenza and adenovirus can be detected in A549 cells. Human embryonic lung cells (HEL) are often used to detect rhinovirus and RSV. R-Mix, Mv1Lu, A549 and HEL were inoculated with SARS-CoV at an MOI of 0.001. SARS-CoV genomic RNA was detected in all four cell lines at 1, 24 and 48 h p.i. (FIG. 4A); however, while the gRNA increased from 1 to 48 h p.i. in R-Mix and Mv1Lu cells, it decreased in A549 and HEL cells (FIG. 4). Subgenomic RNA was amplified in R-Mix and Mv1Lu cells at 24 and 48 h p.i. but was not detectable in A549 and HEL cells at any time points post inoculation. These results suggest that Mv1Lu cells support productive SARS-CoV infection. A non-specific band (~220 bp) was amplified in all four cell lines but was present in all samples including the mock infection. Supernatants from R-Mix and Mv1Lu cells were titered on Vero E6 cells (FIG. 4B). Viral titers decreased approximately 0.5 log from 1 h to 24 h p.i. and then increased 1.5 logs by 48 h p.i. Viral titers from Vero E6 cells increased sharply by 4 logs from 1 to 24 h p.i. and leveled off. Data herein shows that while SARS-CoV can productively infect Mv1Lu cells, viral replication occurs at much lower levels than that observed in Vero E6 cells.

This is the first report of the susceptibility and permissivity of Mv1Lu cells to SARS-CoV.

EXAMPLE 6

Human Cell Lines HEK-293T and Huh-7 are Susceptible and Permissive to SARS-CoV Although humans have been infected by SARS-CoV, human-derived cells susceptible to SARS-CoV infection have not been reported. Human embryonic kidney-derived cells (HEK-293T) and human liver-derived cells (Huh-7) were inoculated with SARS-CoV at an MOI of 0.001. SARS-CoV gRNA was detected at 1, 24 and 48 h p.i. in both cell lines, and increased from 1 to 24 h p.i. (FIG. 5A). Subgenomic RNA was amplified at 24 and 48 h p.i. in both HEK-293T and Huh-7 cells, indicating that they were permissive to SARS-CoV infection. MDCK cell, included as a negative control, were negative for sgRNA at all time points. Supernatants collected at all time points were titered on Vero E6 cells (FIG. 5B). A 2-log increase in viral titer ($TCID_{50}$) was seen at 48 h p.i. in Huh-7 cells while an increase of less than 1 log was seen in 293T cells, compared to a 4 log increase in Vero E6 cells. CPE was apparent by 24 h p.i. in Vero E6 cells inoculated at the same time however, no CPE was observed in Huh-7 or HEK-293T cells out to 48 h p.i. Surprisingly, these results again suggest that CPE is not an accurate indicator of viral replication in all cell lines.

This is the first report of human cell lines that are susceptible and permissive to SARS-CoV.

EXAMPLE 7

Transgenic Cells Expressing Aminopeptidase N are Not Permissive to SARS-CoV

As demonstrated above, MRC-5 cells did not support SARS-CoV RNA replication suggesting that APN is not sufficient to render cells permissive to SARS-CoV. However, the human cell lines HEK-293T and Huh-7, shown to be permissive to SARS-CoV replication, express hAPN, the host cell receptor utilized by HCoV-229E. To further test the role of APN in SARS-CoV entry, cells expressing relatively high levels of hAPN on their surface were tested for susceptibility to infection with SARS-CoV. The murine epithelia-derived cell line (CMT-93) and the baby hamster kidney cell line (BHK-21) were transfected with constructs expressing hAPN to yield CMT-93/hAPN and BHK-21/hAPN (Wentworth et al. 2001. J. Virol. 75:9741–9752). These cells, normally non permissive to HcoV-229E infection and replication, were rendered permissive to infection by expression of hAPN. SARS-CoV genomic RNA was detected in CMT-93, CMT-93/hAPN, BHK-21 and BHK-21/hAPN cells inoculated with SARS-CoV, at 1 to 24 h p.i. (FIG. 6A). The presence of genomic RNA at time points post inoculation varied between experiments. SARS-CoV subgenomic RNA was not detected at any time points demonstrating that all four cell lines were non permissive for SARS-CoV replication. Human APN was expressed at high levels on both CMT-93/hAPN and BHK-21/hAPN cells as demonstrated by FACS (FIG. 6B). Additionally, Huh-7 cells, included as a positive control for SARS-CoV replication, also express high levels of hAPN as demonstrated by FACS analysis.

EXAMPLE 8

Protease Inhibitors do not Reduce Infection of Cells by the Respiratory Viruses Influenza, Parainfluenza, and Adenovirus This Example describes the effect of exemplary protease inhibitors on the detection of influenza A & B, RSV, adenovirus, and parainfluenza 1, 2, and 3 in R-Mix cells.

A. Materials and Methods

Viruses used were influenza A, influenza B, RSV, adenovirus, parainfluenza 1, 2, and 3, all contained in the respiratory virus proficiency panel (Diagnostic Hybrids, Inc., Athens, Ohio). Protease inhibitors tested were Actinonin, a leucine aminopeptidase inhibitor (Sigma), Glycyrrhizin, a biologically active derivative of licorice root (Sigma), and E-64, a cysteine protease inhibitor (Sigma). Cells were R-Mix (Diagnostic Hybrids, Inc., Athens, Ohio) in 48 well plates. Medium was RM03T (Diagnostic Hybrids, Inc., Athens, Ohio). Viral detection was by monoclonal antibody specific for the viruses tested, using a "D3" antibody kit (Diagnostic Hybrids, Inc., Athens, Ohio).

B. Procedure

All inhibitors were dissolved it RM03T to give final concentrations of: Actinonin, 40, 20, and 10 mcg/ml, Glycycrrhizin, 6.08, 1.216, and 0.152 mcg/ml, and E-64, 10, 5, 0.5 mcg/ml. Viral stocks were diluted in RM03T. R-Mix 48 well plates containing the appropriate concentration of inhibitor and additional no-inhibitor control wells were inoculated with the seven individual viruses separately. The inhibitor wells were in duplicate and the control wells were six replicates for each virus. Following inoculation, all plates were centrifuged at 700 g for one hour at room temperature, then incubated in a humidified, $CO_2$ incubator at 37° C. for 24 hours. The cell monolayers were then fixed and stained according to the D3 detection kit instructions. Infected foci were counted using fluorescent microscopy. The data is shown in Table 4.

TABLE 4

Number of infected foci in R-Mix cells treated with respiratory virus and protease inhibitors

| | No inhibitor | | Inhibitor micrograms/ml | | | | | | | |
|---|---|---|---|---|---|---|---|---|---|---|
| | | | Actinonin | | Glycycrrhizin | | | E-64 | | |
| | Control* | 40** | 20 | 10 | 6.08 | 1.216 | 0.152 | 10 | 5 | 0.5 |
| FluA | 189 ± 12 | 118 | 122 | 171 | 163 | 175 | 218 | 176 | 179 | 174 |
| FluB | 455 ± 22 | 190 | 260 | 317 | 273 | 402 | 426 | 323 | 328 | 398 |
| Adeno | 863 ± 100 | 147 | 383 | 781 | 1061 | 938 | 766 | 865 | 868 | 904 |
| RSV | 116 ± 12 | 41 | 64 | 103 | 53 | 103 | 130 | 103 | 115 | 107 |
| Para 1 | 245 ± 18 | 160 | 191 | 222 | 295 | 233 | 268 | 207 | 243 | 251 |
| Para 2 | 243 ± 12 | 151 | 196 | 220 | 281 | 257 | 265 | 205 | 221 | 223 |
| Para 3 | 142 ± 14 | 75 | 104 | 115 | 138 | 149 | 138 | 107 | 99 | 127 |

*mean of 6 samples
**Evidence of cell toxicity
Actinonin—a leucine aminopeptidase inhibitor
Glycyrrhizin—biologically active plant derivative
E-64—cysteine protease inhibitor
R-Mix lot 960925

The above results demonstrate that protease inhibitors are not inhibitory to infection by any of the seven exemplary viruses that are detected by Mv1Lu cells and/or R-Mix cells. This is in contrast to the inventors' data demonstrating inhibition in replication of human coronavirus 229E by the protease inhibitor E64.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiment, it should be understood that the invention as claimed should not be unduly limited to such specific embodiment. Indeed, various modifications of the described modes for carrying out the invention which are obvious to those skilled in the art and in fields related thereto are intended to be within the scope of the following claims.

The invention claimed is:

1. A method for detecting the presence of severe acute respiratory syndrome coronavirus (SARS-coronavirus) in a sample, comprising:

a) providing:

(i) a sample; and (ii) cells chosen from human embryonic kidney (HEK)-293, HEK-293T, Huh-7, Mv1Lu, Mv1Lu-hf and primary rhesus monkey kidney (pRHMK) cells;

b) inoculating said cells with said sample to produce inoculated cells; and c) detecting the presence of said SARS-coronavirus in said inoculated cells, wherein said detecting comprises detecting the presence of SARS-coronavirus subgenomic RNA.

2. The method of claim 1, wherein said detecting further comprises detecting the presence of SARS-coronavirus genomic RNA.

3. The method of claim 1, wherein said detecting further comprises detecting the presence of a SARS-coronavirus polypeptide.

4. The method of claim 1, wherein said cells comprise HEK-293 cells.

5. The method of claim 1, wherein said cells comprise HEK-293T cells.

6. The method of claim 1, wherein said cells are in single cell type culture.

7. The method of claim 1, wherein said cells are in mixed cell type culture with a second cell type.

8. The method of claim 1, wherein said sample is isolated from a mammal.

9. The method of claim 1, wherein said mammal is human.

10. A method for detecting the presence of severe acute respiratory syndrome coronavirus (SARS-coronavirus) in a first sample and in a second sample, comprising:

a) providing:

(i) a first sample;

(ii) a second sample;

b) contacting test cells chosen from human embryonic kidney (HEK)-293, HEK-293T, Huh-7, Mv1Lu, Mv1Lu-hf and primary rhesus monkey kidney (pRHMK) cells with:

(i) said first sample to produce a first treated sample; and (ii) said second sample to produce a second treated sample; wherein said contacting is such that said test cells are infected with SARS-coronavirus if present in one or both of said first sample and said second sample;

c) detecting the presence of one or both of SARS-coronavirus genomic RNA and SARS-coronavirus subgenomic RNA in said first treated sample and said second treated sample, wherein said detecting indicates the presence of said SARS-coronavirus in one or both of said first treated sample and said second treated sample.

11. The method of claim 10, wherein said detecting comprises detecting an absence of SARS-coronavirus subgenomic RNA in said first treated sample.

12. The method of claim 10, wherein said detecting comprises detecting a reduced level of SARS-coronavirus subgenomic RNA in said first treated sample compared to the level of subgenomic RNA in said second treated sample.

13. The method of claim 10, wherein said detecting comprises detecting a reduced ratio of SARS-coronavirus sub genomic RNA level to SARS-coronavirus genomic RNA level in said first treated sample compared to said ratio in said second treated sample.

14. The method of claim 10, wherein said first sample and said second sample are isolated from a mammal.

15. The method of claim 10, wherein said mammal is human.

16. A method for identifying a test agent as altering replication of severe acute respiratory syndrome coronavirus (SARS-coronavirus) in a cell, comprising:

a) providing cells chosen from human embryonic kidney (HEK)-293, HEK-293T, Huh-7, Mv1Lu, Mv1Lu-hf and primary rhesus monkey kidney (pRHMK) cells;

b) treating said cells with a sample comprising SARS-coronavirus before or after incubating said cells in the presence and absence of a first test agent; and c) detecting an altered level of replication of SARS-coronavirus in cells treated with said first test agent compared to a level of replication of SARS-coronavirus in cells not treated with said first test agent, wherein said detecting identifies said first test agent as altering replication of SALRS-coronavirus in a cell, and said detecting comprises detecting SARS-coronavirus subgenomic RNA in one or both of said cells treated with a first test agent and said cells not treated with said first test agent.

17. The method of claim 16, wherein said altered level is a reduced level.

18. The method of claim 16, wherein said altered level is an increased level.

19. The method of claim 16, wherein said detecting further comprises detecting SARS-coronavirus genomic RNA.

20. The method of claim 16, wherein said detecting further comprises detecting SARS-coronavirus polypeptide.

21. The method of claim 16, further comprising detecting SARS-coronavirus particles.

22. The method of claim 16, wherein said detecting further comprises detecting an absence of SARS-coronavirus genomic RNA in said cells treated with said first test agent.

23. The method of claim 16, wherein said detecting comprises detecting a reduced level of SARS-coronavirus subgenomic RNA in said cells treated with said first test agent compared to the level of SARS-coronavirus subgenomic RNA in said cells that are not treated with said first test agent.

24. The method of claim 23, wherein detecting an increased reduction in the level of SARS-coronavirus subgenomic RNA in said cells treated with said first test agent compared to said cells treated with a second test agent identifies said first test agent as more efficacious than said second test agent in reducing replication of SARS-coronavirus in a cell.

25. The method of claim 16, wherein said detecting comprises detecting a reduced ratio of SARS-coronavirus subgenomic RNA level relative to SARS-coronavirus genomic RNA level in said cells treated with said first test agent compared to said ratio in said cells that are not treated with said first test agent.

26. The method of claim 25, wherein detecting an increased reduction in said ratio of SARS-coronavirus subgenomic RNA level to SARS-coronavirus genomic RNA level in said cells treated with said first test agent compared to said ratio in said cells treated with a second test agent identifies said first test agent as more efficacious than said second test agent in reducing replication of SARS-coronavirus in a cell.

27. The method of claim 1, wherein said cells comprise Huh-7 cells.

28. The method of claim 1, wherein said cells comprise Mv1Lu cells.

29. The method of claim 1, wherein said cells comprise Mv1Lu-hF cells.

30. The method of claim 1, wherein said cells comprise pRHMK cells.

* * * * *

UNITED STATES PATENT AND TRADEMARK OFFICE

CERTIFICATE OF CORRECTION

PATENT NO. : 7,129,042 B2
APPLICATION NO. : 10/699936
DATED : October 31, 2006
INVENTOR(S) : Gilliam-Ross et al.

It is certified that error appears in the above-identified patent and that said Letters Patent is hereby corrected as shown below:

Col. 1, Lines 5-9 should read:

This invention was made with government support under N01-AI025490 awarded by the National Institutes of Health and U90 CCU216988 awarded by the Centers for Disease Control. The government has certain rights in the invention.

Signed and Sealed this
Twenty-third Day of October, 2012

David J. Kappos
*Director of the United States Patent and Trademark Office*

SEQUENCE LISTING

```
<160> NUMBER OF SEQ ID NOS: 87

<210> SEQ ID NO 1
<211> LENGTH: 29727
<212> TYPE: DNA
<213> ORGANISM: SARS coronavirus Urbani

<400> SEQUENCE: 1

atattaggtt tttacctacc caggaaaagc caaccaacct cgatctcttg tagatctgtt     60

ctctaaacga actttaaaat ctgtgtagct gtcgctcggc tgcatgccta gtgcacctac    120

gcagtataaa caataataaa ttttactgtc gttgacaaga aacgagtaac tcgtccctct    180

tctgcagact gcttacggtt tcgtccgtgt tgcagtcgat catcagcata cctaggtttc    240

gtccgggtgt gaccgaaagg taagatggag agccttgttc ttggtgtcaa cgagaaaaca    300

cacgtccaac tcagtttgcc tgtccttcag gttagagacg tgctagtgcg tggcttcggg    360

gactctgtgg aagaggccct atcggaggca cgtgaacacc tcaaaaatgg cacttgtggt    420

ctagtagagc tggaaaaagg cgtactgccc cagcttgaac agccctatgt gttcattaaa    480

cgttctgatg ccttaagcac caatcacggc cacaaggtcg ttgagctggt tgcagaaatg    540

gacggcattc agtacggtcg tagcggtata acactgggag tactcgtgcc acatgtgggc    600

gaaaccccaa ttgcataccg caatgttctt cttcgtaaga acggtaataa gggagccggt    660

ggtcatagct atggcatcga tctaaagtct tatgacttag gtgacgagct tggcactgat    720

cccattgaag attatgaaca aaactggaac actaagcatg gcagtggtgc actccgtgaa    780
```

-continued

```
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaagggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct tgaatgagga tctccttgag   1620
atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taaagttacc   1800
aagggaaagc ccgtaaaagg tgcttggaac attggacaac agagatcagt tttaacacca   1860
ctgtgtggtt ttccctcaca ggctgctggt gttatcagat caatttttgc gcgcacactt   1920
gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca aagaacaata ctgcgcattg tctcctggtt tactggctac aaacaatgtc   2700
tttcgcttaa aaggggggtgc accaattaaa ggtgtaacct ttggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat tctacttatt tgatgatgct   3000
ggtgaagaaa acttttcatc acgtatgtat tgttcctttt accctccaga tgaggaagaa   3060
gaggacgatg cagagtgtga ggaagaagaa attgatgaaa cctgtgaaca tgagtacggt   3120
```

-continued

```
acagaggatg attatcaagg tctccctctg gaatttggtg cctcagctga aacagttcga   3180
gttgaggaag aagaagagga agactggctg gatgatacta ctgagcaatc agagattgag   3240
ccagaaccag aacctacacc tgaagaacca gttaatcagt ttactggtta tttaaaactt   3300
actgacaatg ttgccattaa atgtgttgac atcgttaagg aggcacaaag tgctaatcct   3360
atggtgattg taaatgctgc taacatacac ctgaaacatg gtggtggtgt agcaggtgca   3420
ctcaacaagg caaccaatgg tgccatgcaa aaggagagtg atgattacat taagctaaat   3480
ggccctctta cagtaggagg gtcttgtttg ctttctggac ataatcttgc taagaagtgt   3540
ctgcatgttg ttggacctaa cctaaatgca ggtgaggaca tccagcttct taaggcagca   3600
tatgaaaatt tcaattcaca ggacatctta cttgcaccat tgttgtcagc aggcatattt   3660
ggtgctaaac cacttcagtc tttacaagtg tgcgtgcaga cggttcgtac acaggtttat   3720
attgcagtca atgacaaagc tctttatgag caggttgtca tggattatct tgataacctg   3780
aagcctagag tggaagcacc taaacaagag gagccaccaa acacagaaga ttccaaaact   3840
gaggagaaat ctgtcgtaca gaagcctgtc gatgtgaagc caaaaattaa ggcctgcatt   3900
gatgaggtta ccacaacact ggaagaaact aagtttctta ccaataagtt actcttgttt   3960
gctgatatca atggtaagct ttaccatgat tctcagaaca tgcttagagg tgaagatatg   4020
tctttccttg agaaggatgc accttacatg gtaggtgatg ttatcactag tggtgatatc   4080
acttgtgttg taataccctc caaaaaggct ggtggcacta ctgagatgct ctcaagagct   4140
ttgaagaaag tgccagttga tgagtatata accacgtacc ctggacaagg atgtgctggt   4200
tatacacttg aggaagctaa gactgctctt aagaaatgca aatctgcatt ttatgtacta   4260
ccttcagaag cacctaatgc taaggaagag attctaggaa ctgtatcctg gaatttgaga   4320
gaaatgcttg ctcatgctga agagacaaga aaattaatgc ctatatgcat ggatgttaga   4380
gccataatgg caaccatcca acgtaagtat aaaggaatta aaattcaaga gggcatcgtt   4440
gactatggtg tccgattctt cttttatact agtaaagagc ctgtagcttc tattattacg   4500
aagctgaact ctctaaatga gccgcttgtc acaatgccaa ttggttatgt gacacatggt   4560
tttaatcttg aagaggctgc gcgctgtatg cgttctctta aagctcctgc cgtagtgtca   4620
gtatcatcac cagatgctgt tactacatat aatggatacc tcacttcgtc atcaaagaca   4680
tctgaggagc actttgtaga aacagtttct ttggctggct cttacagaga ttggtcctat   4740
tcaggacagc gtacagagtt aggtgttgaa tttcttaagc gtggtgacaa aattgtgtac   4800
cacactctgg agagccccgt cgagtttcat cttgacggtg aggttctttc acttgacaaa   4860
ctaaagagtc tcttatccct gcgggaggtt aagactataa aagtgttcac aactgtggac   4920
aacactaatc tccacacaca gcttgtggat atgtctatga catatggaca gcagtttggt   4980
ccaacatact tggatggtgc tgatgttaca aaaattaaac ctcatgtaaa tcatgagggt   5040
aagactttct ttgtactacc tagtgatgac acactacgta gtgaagcttt cgagtactac   5100
catactcttg atgagagttt tcttggtagg tacatgtctg ctttaaacca cacaaagaaa   5160
tggaaatttc ctcaagttgg tggtttaact tcaattaaat gggctgataa caattgttat   5220
ttgtctagtg ttttattagc acttcaacag cttgaagtca aattcaatgc accagcactt   5280
caagaggctt attatagagc ccgtgctggt gatgctgcta acttttgtgc actcatactc   5340
gcttacagta ataaaactgt tggcgagctt ggtgatgtca gagaaactat gacccatctt   5400
ctacagcatg ctaatttgga atctgcaaag cgagttctta atgtggtgtg taaacattgt   5460
ggtcagaaaa ctactacctt aacgggtgta gaagctgtga tgtatatggg tactctatct   5520
```

-continued

```
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtacattctt atgtgcgaat gagtacactg gtaactatca gtgtggtcat   5700
tacactcata taactgctaa ggagaccctc tatcgtattg acggagctca ccttacaaag   5760
atgtcagagt acaaaggacc agtgactgat gttttctaca aggaaacatc ttacactaca   5820
accatcaagc ctgtgtcgta taaactcgat ggagttactt acacagagat tgaaccaaaa   5880
ttggatgggt attataaaaa ggataatgct tactatacag agcagcctat agaccttgta   5940
ccaactcaac cattaccaaa tgcgagtttt gataatttca aactcacatg ttctaacaca   6000
aaatttgctg atgatttaaa tcaaatgaca ggcttcacaa agccagcttc acgagagcta   6060
tctgtcacat tcttcccaga cttgaatggc gatgtagtgg ctattgacta tagacactat   6120
tcagcgagtt tcaagaaagg tgctaaatta ctgcataagc caattgtttg gcacattaac   6180
caggctacaa ccaagacaac gttcaaacca aacacttggt gtttacgttg tctttggagt   6240
acaaagccag tagatacttc aaattcattt gaagttctgg cagtagaaga cacacaagga   6300
atggacaatc ttgcttgtga aagtcaacaa cccacctctg aagaagtagt ggaaaatcct   6360
accatacaga aggaagtcat agagtgtgac gtgaaaacta ccgaagttgt aggcaatgtc   6420
atacttaaac catcagatga aggtgttaaa gtaacacaag agttaggtca tgaggatctt   6480
atggctgctt atgtggaaaa cacaagcatt accattaaga aacctaatga gctttcacta   6540
gccttaggtt taaaaacaat tgccactcat ggtattgctg caattaatag tgttccttgg   6600
agtaaaattt tggcttatgt caaaccattc ttaggacaag cagcaattac aacatcaaat   6660
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa attttctaaa ttgttcacaa tcgctatgtg gctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
gttactacta tggatttctg tgaaggttct tttccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttctttgg ctattttgct   7260
agtcatttca tcagcaattc ttggctcatg tggtttatca ttagtattgt acaaatggca   7320
cccgtttctg caatggttag gatgtacatc ttctttgctt ctttctacta catatggaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg gcgcgcttca cctctacttt gacaaggctg gtcaaaagac ctatgagaga   7740
catccgctct cccattttgt caatttagac aatttgagag ctaacaacac taaaggttca   7800
ctgcctatta atgtcatagt ttttgatggc aagtccaaat gcgacgagtc tgcttctaag   7860
```

-continued

```
tctgcttctg tgtactacag tcagctgatg tgccaaccta ttctgttgct tgaccaagtt   7920
cttgtatcag acgttggaga tagtactgaa gtttccgtta agatgtttga tgcttatgtc   7980
gacacctttt cagcaacttt tagtgttcct atggaaaaac ttaaggcact tgttgctaca   8040
gctcacagcg agttagcaaa gggtgtagct ttagatggtg tcctttctac attcgtgtca   8100
gctgcccgac aaggtgttgt tgataccgat gttgacacaa aggatgttat tgaatgtctc   8160
aaactttcac atcactctga cttagaagtg acaggtgaca gttgtaacaa tttcatgctc   8220
acctataata aggttgaaaa catgacgccc agagatcttg gcgcatgtat tgactgtaat   8280
gcaaggcata tcaatgccca agtagcaaaa agtcacaatg tttcactcat ctggaatgta   8340
aaagactaca tgtctttatc tgaacagctg cgtaaacaaa ttcgtagtgc tgccaagaag   8400
aacaacatac cttttagact aacttgtgct acaactagac aggttgtcaa tgtcataact   8460
actaaaatct cactcaaggg tggtaagatt gttagtactt gttttaaact tatgcttaag   8520
gccacattat tgtgcgttct tgctgcattg gtttgttata tcgttatgcc agtacataca   8580
ttgtcaatcc atgatggtta cacaaatgaa atcattggtt acaaagccat tcaggatggt   8640
gtcactcgtg acatcatttc tactgatgat tgttttgcaa ataaacatgc tggttttgac   8700
gcatggttta gccagcgtgg tggttcatac aaaaatgaca aaagctgccc tgtagtagct   8760
gctatcatta caagagagat tggtttcata gtgcctggct taccgggtac tgtgctgaga   8820
gcaatcaatg gtgacttctt gcattttcta cctcgtgttt ttagtgctgt tggcaacatt   8880
tgctacacac cttccaaact cattgagtat agtgattttg ctacctctgc ttgcgttctt   8940
gctgctgagt gtacaatttt taaggatgct atgggcaaac ctgtgccata ttgttatgac   9000
actaatttgc tagagggttc tatttcttat agtgagcttc gtccagacac tcgttatgtg   9060
cttatggatg gttccatcat acagtttcct aacacttacc tggagggttc tgttagagta   9120
gtaacaactt ttgatgctga gtactgtaga catggtacat gcgaaaggtc agaagtaggt   9180
atttgcctat ctaccagtgg tagatgggtt cttaataatg agcattacag agctctatca   9240
ggagttttct gtggtgttga tgcgatgaat ctcatagcta acatctttac tcctcttgtg   9300
caacctgtgg gtgctttaga tgtgtctgct tcagtagtgg ctggtggtat tattgccata   9360
ttggtgactt gtgctgccta ctactttatg aaattcagac gtgtttttgg tgagtacaac   9420
catgttgttg ctgctaatgc acttttgttt ttgatgtctt tcactatact ctgtctggta   9480
ccagcttaca gctttctgcc gggagtctac tcagtctttt acttgtactt gacattctat   9540
ttcaccaatg atgtttcatt cttggctcac cttcaatggt ttgccatgtt ttctcctatt   9600
gtgccttttt ggataacagc aatctatgta ttctgtattt ctctgaagca ctgccattgg   9660
ttctttaaca actatcttag gaaaagagtc atgtttaatg gagttacatt tagtaccttc   9720
gaggaggctg ctttgtgtac ctttttgctc aacaaggaaa tgtacctaaa attgcgtagc   9780
gagacactgt tgccacttac acagtataac aggtatcttg ctctatataa caagtacaag   9840
tatttcagtg gagccttaga tactaccagc tatcgtgaag cagcttgctg ccacttagca   9900
aaggctctaa atgactttag caactcaggt gctgatgttc tctaccaacc accacagaca   9960
tcaatcactt ctgctgttct gcagagtggt tttaggaaaa tggcattccc gtcaggcaaa  10020
gttgaagggt gcatggtaca agtaacctgt ggaactacaa ctcttaatgg attgtggttg  10080
gatgacacag tatactgtcc aagacatgtc atttgcacag cagaagacat gcttaatcct  10140
aactatgaag atctgctcat tcgcaaatcc aaccatagct ttcttgttca ggctggcaat  10200
gttcaacttc gtgttattgg ccattctatg caaaattgtc tgcttaggct taaagttgat  10260
```

-continued

```
acttctaacc ctaagacacc caagtataaa tttgtccgta tccaacctgg tcaaacattt  10320
tcagttctag catgctacaa tggttcacca tctggtgttt atcagtgtgc catgagacct  10380
aatcatacca ttaaaggttc tttccttaat ggatcatgtg gtagtgttgg ttttaacatt  10440
gattatgatt gcgtgtcttt ctgctatatg catcatatgg agcttccaac aggagtacac  10500
gctggtactg acttagaagg taaattctat ggtccatttg ttgacagaca aactgcacag  10560
gctgcaggta cagacacaac cataacatta aatgttttgg catggctgta tgctgctgtt  10620
atcaatggtg ataggtggtt tcttaataga ttcaccacta ctttgaatga ctttaacctt  10680
gtggcaatga agtacaacta tgaacctttg acacaagatc atgttgacat attgggacct  10740
ctttctgctc aaacaggaat tgccgtctta gatatgtgtg ctgctttgaa agagctgctg  10800
cagaatggta tgaatggtcg tactatcctt ggtagcacta ttttagaaga tgagtttaca  10860
ccatttgatg ttgttagaca atgctctggt gttaccttcc aaggtaagtt caagaaaatt  10920
gttaagggca ctcatcattg gatgctttta actttcttga catcactatt gattcttgtt  10980
caaagtacac agtggtcact gtttttcttt gtttacgaga atgctttctt gccatttact  11040
cttggtatta tggcaattgc tgcatgtgct atgctgcttg ttaagcataa gcacgcattc  11100
ttgtgcttgt ttctgttacc ttctcttgca acagttgctt actttaatat ggtctacatg  11160
cctgctagct gggtgatgcg tatcatgaca tggcttgaat tggctgacac tagcttgtct  11220
ggttataggc ttaaggattg tgttatgtat gcttcagctt tagttttgct tattctcatg  11280
acagctcgca ctgtttatga tgatgctgct agacgtgttt ggacactgat gaatgtcatt  11340
acacttgttt acaaagtcta ctatggtaat gctttagatc aagctatttc catgtgggcc  11400
ttagttattt ctgtaacctc taactattct ggtgtcgtta cgactatcat gtttttagct  11460
agagctatag tgtttgtgtg tgttgagtat tacccattgt tatttattac tggcaacacc  11520
ttacagtgta tcatgcttgt ttattgtttc ttaggctatt gttgctgctg ctactttggc  11580
cttttctgtt tactcaaccg ttacttcagg cttactcttg gtgtttatga ctacttggtc  11640
tctacacaag aatttaggta tatgaactcc caggggcttt tgcctcctaa gagtagtatt  11700
gatgctttca agcttaacat taagttgttg ggtattggag gtaaaccatg tatcaaggtt  11760
gctactgtac agtctaaaat gtctgacgta aagtgcacat ctgtggtact gctctcggtt  11820
cttcaacaac ttagagtaga gtcatcttct aaattgtggg cacaatgtgt acaactccac  11880
aatgatattc ttcttgcaaa agacacaact gaagctttcg agaagatggt ttctcttttg  11940
tctgttttgc tatccatgca gggtgctgta gacattaata ggttgtgcga ggaaatgctc  12000
gataaccgtg ctactcttca ggctattgct tcagaattta gttctttacc atcatatgcc  12060
gcttatgcca ctgcccagga ggcctatgag caggctgtag ctaatggtga ttctgaagtc  12120
gttctcaaaa agttaaagaa atctttgaat gtggctaaat ctgagtttga ccgtgatgct  12180
gccatgcaac gcaagttgga aaagatggca gatcaggcta tgacccaaat gtacaaacag  12240
gcaagatctg aggacaagag ggcaaaagta actagtgcta tgcaaacaat gctcttcact  12300
atgcttagga agcttgataa tgatgcactt aacaacatta tcaacaatgc gcgtgatggt  12360
tgtgttccac tcaacatcat accattgact acagcagcca aactcatggt tgttgtccct  12420
gattatggta cctacaagaa cacttgtgat ggtaacacct ttacatatgc atctgcactc  12480
tgggaaatcc agcaagttgt tgatgcggat agcaagattg ttcaacttag tgaaattaac  12540
atggacaatt caccaaattt ggcttggcct cttattgtta cagctctaag agccaactca  12600
```

-continued

```
gctgttaaac tacagaataa tgaactgagt ccagtagcac tacgacagat gtcctgtgcg  12660
gctggtacca cacaaacagc ttgtactgat gacaatgcac ttgcctacta taacaattcg  12720
aagggaggta ggtttgtgct ggcattacta tcagaccacc aagatctcaa atgggctaga  12780
ttccctaaga gtgatggtac aggtacaatt tacacagaac tggaaccacc ttgtaggttt  12840
gttacagaca caccaaaagg gcctaaagtg aaatacttgt acttcatcaa aggcttaaac  12900
aacctaaata gaggtatggt gctgggcagt ttagctgcta cagtacgtct tcaggctgga  12960
aatgctacag aagtacctgc caattcaact gtgctttcct tctgtgcttt tgcagtagac  13020
cctgctaaag catataagga ttacctagca agtggaggac aaccaatcac caactgtgtg  13080
aagatgttgt gtacacacac tggtacagga caggcaatta ctgtaacacc agaagctaac  13140
atggaccaag agtcctttgg tggtgcttca tgttgtctgt attgtagatg ccacattgac  13200
catccaaatc ctaaaggatt ctgtgacttg aaaggtaagt acgtccaaat acctaccact  13260
tgtgctaatg acccagtggg ttttacactt agaaacacag tctgtaccgt ctgcggaatg  13320
tggaaaggtt atggctgtag ttgtgaccaa ctccgcgaac ccttgatgca gtctgcggat  13380
gcatcaacgt ttttaaacgg gtttgcggtg taagtgcagc ccgtcttaca ccgtgcggca  13440
caggcactag tactgatgtc gtctacaggg cttttgatat ttacaacgaa aaagttgctg  13500
gttttgcaaa gttcctaaaa actaattgct gtcgcttcca ggagaaggat gaggaaggca  13560
atttattaga ctcttacttt gtagttaaga ggcatactat gtctaactac caacatgaag  13620
agactattta taacttggtt aaagattgtc cagcggttgc tgtccatgac tttttcaagt  13680
ttagagtaga tggtgacatg gtaccacata tatcacgtca gcgtctaact aaatacacaa  13740
tggctgattt agtctatgct ctacgtcatt ttgatgaggg taattgtgat acattaaaag  13800
aaatactcgt cacatacaat tgctgtgatg atgattattt caataagaag gattggtatg  13860
acttcgtaga gaatcctgac atcttacgcg tatatgctaa cttaggtgag cgtgtacgcc  13920
aatcattatt aaagactgta caattctgcg atgctatgcg tgatgcaggc attgtaggcg  13980
tactgacatt agataatcag gatcttaatg ggaactggta cgatttcggt gatttcgtac  14040
aagtagcacc aggctgcgga gttcctattg tggattcata ttactcattg ctgatgccca  14100
tcctcacttt gactagggca ttggctgctg agtcccatat ggatgctgat ctcgcaaaac  14160
cacttattaa gtgggatttg ctgaaatatg attttacgga agagagactt tgtctcttcg  14220
accgttattt taaatattgg gaccagacat accatcccaa ttgtattaac tgtttggatg  14280
ataggtgtat ccttcattgt gcaaacttta atgtgttatt ttctactgtg tttccaccta  14340
caagttttgg accactagta agaaaaatat ttgtagatgg tgttcctttt gttgtttcaa  14400
ctggatacca ttttcgtgag ttaggagtcg tacataatca ggatgtaaac ttacatagct  14460
cgcgtctcag tttcaaggaa cttttagtgt atgctgctga tccagctatg catgcagctt  14520
ctggcaattt attgctagat aaacgcacta catgcttttc agtagctgca ctaacaaaca  14580
atgttgcttt tcaaactgtc aaacccggta attttaataa agacttttat gactttgctg  14640
tgtctaaagg tttctttaag gaaggaagtt ctgttgaact aaaacacttc ttctttgctc  14700
aggatggcaa cgctgctatc agtgattatg actattatcg ttataatctg ccaacaatgt  14760
gtgatatcag acaactccta ttcgtagttg aagttgttga taaatacttt gattgttacg  14820
atggtggctg tattaatgcc aaccaagtaa tcgttaacaa tctggataaa tcagctggtt  14880
tcccatttaa taaatggggt aaggctagac tttattatga ctcaatgagt tatgaggatc  14940
aagatgcact tttcgcgtat actaagcgta atgtcatccc tactataact caaatgaatc  15000
```

-continued

```
ttaagtatgc cattagtgca aagaatagag ctcgcaccgt agctggtgtc tctatctgta  15060
gtactatgac aaatagacag tttcatcaga aattattgaa gtcaatagcc gccactagag  15120
gagctactgt ggtaattgga acaagcaagt tttacggtgg ctggcataat atgttaaaaa  15180
ctgtttacag tgatgtagaa actccacacc ttatgggttg ggattatcca aaatgtgaca  15240
gagccatgcc taacatgctt aggataatgg cctctcttgt tcttgctcgc aaacataaca  15300
cttgctgtaa cttatcacac cgtttctaca ggttagctaa cgagtgtgcg caagtattaa  15360
gtgagatggt catgtgtggc ggctcactat atgttaaacc aggtggaaca tcatccggtg  15420
atgctacaac tgcttatgct aatagtgtct ttaacatttg tcaagctgtt acagccaatg  15480
taaatgcact tctttcaact gatggtaata agatagctga caagtatgtc cgcaatctac  15540
aacacaggct ctatgagtgt ctctatagaa atagggatgt tgatcatgaa ttcgtggatg  15600
agttttacgc ttacctgcgt aaacatttct ccatgatgat tctttctgat gatgccgttg  15660
tgtgctataa cagtaactat gcggctcaag gtttagtagc tagcattaag aactttaagg  15720
cagttcttta ttatcaaaat aatgtgttca tgtctgaggc aaaatgttgg actgagactg  15780
accttactaa aggacctcac gaattttgct cacagcatac aatgctagtt aaacaaggag  15840
atgattacgt gtacctgcct tacccagatc catcaagaat attaggcgca ggctgttttg  15900
tcgatgatat tgtcaaaaca gatggtacac ttatgattga aaggttcgtg tcactggcta  15960
ttgatgctta cccacttaca aaacatccta atcaggagta tgctgatgtc tttcacttgt  16020
atttacaata cattagaaag ttacatgatg agcttactgg ccacatgttg gacatgtatt  16080
ccgtaatgct aactaatgat aacacctcac ggtactggga acctgagttt tatgaggcta  16140
tgtacacacc acatacagtc ttgcaggctg taggtgcttg tgtattgtgc aattcacaga  16200
cttcacttcg ttgcggtgcc tgtattagga gaccattcct atgttgcaag tgctgctatg  16260
accatgtcat ttcaacatca cacaaattag tgttgtctgt taatccctat gtttgcaatg  16320
ccccaggttg tgatgtcact gatgtgacac aactgtatct aggaggtatg agctattatt  16380
gcaagtcaca taagcctccc attagttttc cattatgtgc taatggtcag gtttttggtt  16440
tatacaaaaa cacatgtgta ggcagtgaca atgtcactga cttcaatgcg atagcaacat  16500
gtgattggac taatgctggc gattacatac ttgccaacac ttgtactgag agactcaagc  16560
ttttcgcagc agaaacgctc aaagccactg aggaaacatt taagctgtca tatggtattg  16620
ctactgtacg cgaagtactc tctgacagag aattgcatct ttcatgggag gttggaaaac  16680
ctagaccacc attgaacaga aactatgtct ttactggtta ccgtgtaact aaaaatagta  16740
aagtacagat tggagagtac acctttgaaa aaggtgacta tggtgatgct gttgtgtaca  16800
gaggtactac gacatacaag ttgaatgttg gtgattactt tgtgttgaca tctcacactg  16860
taatgccact tagtgcacct actctagtgc cacaagagca ctatgtgaga attactggct  16920
tgtacccaac actcaacatc tcagatgagt tttctagcaa tgttgcaaat tatcaaaagg  16980
tcggcatgca aaagtactct acactccaag gaccacctgg tactggtaag agtcattttg  17040
ccatcggact tgctctctat tacccatctg ctcgcatagt gtatacggca tgctctcatg  17100
cagctgttga tgccctatgt gaaaaggcat taaaatattt gcccatagat aaatgtagta  17160
gaatcatacc tgcgcgtgcg cgcgtagagt gttttgataa attcaaagtg aattcaacac  17220
tagaacagta tgttttctgc actgtaaatg cattgccaga aacaactgct gacattgtag  17280
tctttgatga aatctctatg gctactaatt atgacttgag tgttgtcaat gctagacttc  17340
```

-continued

```
gtgcaaaaca ctacgtctat attggcgatc ctgctcaatt accagccccc cgcacattgc  17400
tgactaaagg cacactagaa ccagaatatt ttaattcagt gtgcagactt atgaaaacaa  17460
taggtccaga catgttcctt ggaacttgtc gccgttgtcc tgctgaaatt gttgacactg  17520
tgagtgcttt agtttatgac aataagctaa aagcacacaa ggataagtca gctcaatgct  17580
tcaaaatgtt ctacaaaggt gttattacac atgatgtttc atctgcaatc aacagacctc  17640
aaataggcgt tgtaagagaa tttcttacac gcaatcctgc ttggagaaaa gctgttttta  17700
tctcacctta taattcacag aacgctgtag cttcaaaaat cttaggattg cctacgcaga  17760
ctgttgattc atcacagggt tctgaatatg actatgtcat attcacacaa actactgaaa  17820
cagcacactc ttgtaatgtc aaccgcttca atgtggctat cacaagggca aaaattggca  17880
ttttgtgcat aatgtctgat agagatcttt atgacaaact gcaatttaca agtctagaaa  17940
taccacgtcg caatgtggct acattacaag cagaaaatgt aactggactt tttaaggact  18000
gtagtaagat cattactggt cttcatccta cacaggcacc tacacacctc agcgttgata  18060
taaagttcaa gactgaagga ttatgtgttg acataccagg cataccaaag gacatgacct  18120
accgtagact catctctatg atgggtttca aaatgaatta ccaagtcaat ggttacccta  18180
atatgtttat cacccgcgaa gaagctattc gtcacgttcg tgcgtggatt ggctttgatg  18240
tagagggctg tcatgcaact agagatgctg tgggtactaa cctacctctc cagctaggat  18300
tttctacagg tgttaactta gtagctgtac cgactggtta tgttgacact gaaaataaca  18360
cagaattcac cagagttaat gcaaaacctc caccaggtga ccagtttaaa catcttatac  18420
cactcatgta taaaggcttg ccctggaatg tagtgcgtat taagatagta caaatgctca  18480
gtgatacact gaaaggattg tcagacagag tcgtgttcgt cctttgggcg catggctttg  18540
agcttacatc aatgaagtac tttgtcaaga ttggacctga aagaacgtgt tgtctgtgtg  18600
acaaacgtgc aacttgcttt tctacttcat cagatactta tgcctgctgg aatcattctg  18660
tgggttttga ctatgtctat aacccattta tgattgatgt tcagcagtgg ggctttacgg  18720
gtaaccttca gagtaaccat gaccaacatt gccaggtaca tggaaatgca catgtggcta  18780
gttgtgatgc tatcatgact agatgtttag cagtccatga gtgctttgtt aagcgcgttg  18840
attggtctgt tgaataccct attataggag atgaactgag ggttaattct gcttgcagaa  18900
aagtacaaca catggttgtg aagtctgcat tgcttgctga taagtttcca gttcttcatg  18960
acattggaaa tccaaaggct atcaagtgtg tgcctcaggc tgaagtagaa tggaagttct  19020
acgatgctca gccatgtagt gacaaagctt acaaaataga ggagctcttc tattcttatg  19080
ctacacatca cgataaattc actgatggtg tttgtttgtt ttggaattgt aacgttgatc  19140
gttacccagc caatgcaatt gtgtgtaggt ttgacacaag agtcttgtca aacttgaact  19200
taccaggctg tgatggtggt agtttgtatg tgaataagca tgcattccac actccagctt  19260
tcgataaaag tgcatttact aatttaaagc aattgccttt cttttactat tctgatagtc  19320
cttgtgagtc tcatggcaaa caagtagtgt cggatattga ttatgttcca ctcaaatctg  19380
ctacgtgtat tacacgatgc aatttaggtg gtgctgtttg cagacaccat gcaaatgagt  19440
accgacagta cttggatgca tataatatga tgatttctgc tggatttagc ctatggattt  19500
acaaacaatt tgatacttat aacctgtgga atacatttac caggttacag agtttagaaa  19560
atgtggctta taatgttgtt aataaaggac actttgatgg acacgccggc gaagcacctg  19620
tttccatcat taataatgct gtttacacaa aggtagatgg tattgatgtg gagatctttg  19680
aaaataagac aacacttcct gttaatgttg catttgagct ttgggctaag cgtaacatta  19740
```

-continued

```
aaccagtgcc agagattaag atactcaata atttgggtgt tgatatcgct gctaatactg  19800
taatctggga ctacaaaaga gaagccccag cacatgtatc tacaataggt gtctgcacaa  19860
tgactgacat tgccaagaaa cctactgaga gtgcttgttc ttcacttact gtcttgtttg  19920
atggtagagt ggaaggacag gtagaccttt ttagaaacgc ccgtaatggt gttttaataa  19980
cagaaggttc agtcaaaggt ctaacacctt caaagggacc agcacaagct agcgtcaatg  20040
gagtcacatt aattggagaa tcagtaaaaa cacagtttaa ctactttaag aaagtagacg  20100
gcattattca acagttgcct gaaacctact ttactcagag cagagactta gaggatttta  20160
agcccagatc acaaatggaa actgactttc tcgagctcgc tatggatgaa ttcatacagc  20220
gatataagct cgagggctat gccttcgaac acatcgttta tggagatttc agtcatggac  20280
aacttggcgg tcttcattta atgataggct tagccaagcg ctcacaagat tcaccactta  20340
aattagagga ttttatccct atggacagca cagtgaaaaa ttacttcata acagatgcgc  20400
aaacaggttc atcaaaatgt gtgtgttctg tgattgatct tttacttgat gactttgtcg  20460
agataataaa gtcacaagat ttgtcagtga tttcaaaagt ggtcaaggtt acaattgact  20520
atgctgaaat ttcattcatg ctttggtgta aggatggaca tgttgaaacc ttctacccaa  20580
aactacaagc aagtcaagcg tggcaaccag gtgttgcgat gcctaacttg tacaagatgc  20640
aaagaatgct tcttgaaaag tgtgaccttc agaattatgg tgaaaatgct gttataccaa  20700
aaggaataat gatgaatgtc gcaaagtata ctcaactgtg tcaatactta aatacactta  20760
ctttagctgt accctacaac atgagagtta ttcactttgg tgctggctct gataaaggag  20820
ttgcaccagg tacagctgtg ctcagacaat ggttgccaac tggcacacta cttgtcgatt  20880
cagatcttaa tgacttcgtc tccgacgcag attctacttt aattggagac tgtgcaacag  20940
tacatacggc taataaatgg gaccttatta ttagcgatat gtatgaccct aggaccaaac  21000
atgtgacaaa agagaatgac tctaaagaag ggtttttcac ttatctgtgt ggatttataa  21060
agcaaaaact agccctgggt ggttctatag ctgtaaagat aacagagcat tcttggaatg  21120
ctgaccttta caagcttatg ggccatttct catggtggac agcttttgtt acaaatgtaa  21180
atgcatcatc atcggaagca tttttaattg ggctaacta tcttggcaag ccgaaggaac  21240
aaattgatgg ctataccatg catgctaact acattttctg gaggaacaca aatcctatcc  21300
agttgtcttc ctattcactc tttgacatga gcaaatttcc tcttaaatta agaggaactg  21360
ctgtaatgtc tcttaaggag aatcaaatca atgatatgat ttattctctt ctggaaaaag  21420
gtaggcttat cattagagaa aacaacagag ttgtggtttc aagtgatatt cttgttaaca  21480
actaaacgaa catgtttatt ttcttattat ttcttactct cactagtggt agtgaccttg  21540
accggtgcac cacttttgat gatgttcaag ctcctaatta cactcaacat acttcatcta  21600
tgaggggggt ttactatcct gatgaaattt ttagatcaga cactctttat ttaactcagg  21660
atttatttct tccattttat tctaatgtta cagggtttca tactattaat catacgtttg  21720
gcaaccctgt catacctttt aaggatggta tttattttgc tgccacagag aaatcaaatg  21780
ttgtccgtgg ttgggttttt ggttctacca tgaacaacaa gtcacagtcg gtgattatta  21840
ttaacaattc tactaatgtt gttatacgag catgtaactt tgaattgtgt gacaaccctt  21900
tctttgctgt ttctaaaccc atgggtacac agacacatac tatgatattc gataatgcat  21960
ttaattgcac tttcgagtac atatctgatg ccttttcgct tgatgtttca gaaaagtcag  22020
gtaattttaa acacttacga gagtttgtgt ttaaaaataa agatgggttt ctctatgttt  22080
```

-continued

```
ataagggcta tcaacctata gatgtagttc gtgatctacc ttctggtttt aacactttga  22140
aacctatttt taagttgcct cttggtatta acattacaaa ttttagagcc attcttacag  22200
ccttttcacc tgctcaagac atttggggca cgtcagctgc agcctatttt gttggctatt  22260
taaagccaac tacatttatg ctcaagtatg atgaaaatgg tacaatcaca gatgctgttg  22320
attgttctca aaatccactt gctgaactca aatgctctgt taagagcttt gagattgaca  22380
aaggaattta ccagacctct aatttcaggg ttgttccctc aggagatgtt gtgagattcc  22440
ctaatattac aaacttgtgt ccttttggag aggtttttaa tgctactaaa ttcccttctg  22500
tctatgcatg ggagagaaaa aaaatttcta attgtgttgc tgattactct gtgctctaca  22560
actcaacatt tttttcaacc tttaagtgct atggcgtttc tgccactaag ttgaatgatc  22620
tttgcttctc caatgtctat gcagattctt ttgtagtcaa gggagatgat gtaagacaaa  22680
tagcgccagg acaaactggt gttattgctg attataatta taaattgcca gatgatttca  22740
tgggttgtgt ccttgcttgg aatactagga acattgatgc tacttcaact ggtaattata  22800
attataaata taggtatctt agacatggca agcttaggcc ctttgagaga gacatatcta  22860
atgtgccttt ctcccctgat ggcaaacctt gcaccccacc tgctcttaat tgttattggc  22920
cattaaatga ttatggtttt tacaccacta ctggcattgg ctaccaacct tacagagttg  22980
tagtactttc ttttgaactt ttaaatgcac cggccacggt ttgtggacca aaattatcca  23040
ctgaccttat taagaaccag tgtgtcaatt ttaattttaa tggactcact ggtactggtg  23100
tgttaactcc ttcttcaaag agatttcaac catttcaaca atttggccgt gatgtttctg  23160
atttcactga ttccgttcga gatcctaaaa catctgaaat attagacatt tcaccttgct  23220
cttttggggg tgtaagtgta attacacctg gaacaaatgc ttcatctgaa gttgctgttc  23280
tatatcaaga tgttaactgc actgatgttt ctacagcaat tcatgcagat caactcacac  23340
cagcttggcg catatattct actggaaaca atgtattcca gactcaagca ggctgtctta  23400
taggagctga gcatgtcgac acttcttatg agtgcgacat tcctattgga gctggcattt  23460
gtgctagtta ccatacagtt tctttattac gtagtactag ccaaaaatct attgtggctt  23520
atactatgtc tttaggtgct gatagttcaa ttgcttactc taataacacc attgctatac  23580
ctactaactt ttcaattagc attactacag aagtaatgcc tgtttctatg gctaaaacct  23640
ccgtagattg taatatgtac atctgcggag attctactga atgtgctaat ttgcttctcc  23700
aatatggtag cttttgcaca caactaaatc gtgcactctc aggtattgct gctgaacagg  23760
atcgcaacac acgtgaagtg ttcgctcaag tcaaacaaat gtacaaaacc ccaactttga  23820
aatattttgg tggttttaat ttttcacaaa tattacctga ccctctaaag ccaactaaga  23880
ggtcttttat tgaggacttg ctctttaata aggtgacact cgctgatgct ggcttcatga  23940
agcaatatgg cgaatgccta ggtgatatta atgctagaga tctcatttgt gcgcagaagt  24000
tcaatggact tacagtgttg ccacctctgc tcactgatga tatgattgct gcctacactg  24060
ctgctctagt tagtggtact gccactgctg gatggacatt tggtgctggc gctgctcttc  24120
aaataccttt tgctatgcaa atggcatata ggttcaatgg cattggagtt acccaaaatg  24180
ttctctatga gaaccaaaaa caaatcgcca accaatttaa caaggcgatt agtcaaattc  24240
aagaatcact tacaacaaca tcaactgcat tgggcaagct gcaagacgtt gttaaccaga  24300
atgctcaagc attaaacaca cttgttaaac aacttagctc taattttggt gcaatttcaa  24360
gtgtgctaaa tgatatcctt tcgcgacttg ataaagtcga ggcggaggta caaattgaca  24420
ggttaattac aggcagactt caaagccttc aaacctatgt aacacaacaa ctaatcaggg  24480
```

-continued

```
ctgctgaaat cagggcttct gctaatcttg ctgctactaa aatgtctgag tgtgttcttg  24540
gacaatcaaa aagagttgac ttttgtggaa agggctacca ccttatgtcc ttcccacaag  24600
cagccccgca tggtgttgtc ttcctacatg tcacgtatgt gccatcccag gagaggaact  24660
tcaccacagc gccagcaatt tgtcatgaag gcaaagcata cttccctcgt gaaggtgttt  24720
ttgtgtttaa tggcacttct tggtttatta cacagaggaa cttcttttct ccacaaataa  24780
ttactacaga caatacattt gtctcaggaa attgtgatgt cgttattggc atcattaaca  24840
acacagttta tgatcctctg caacctgagc tcgactcatt caaagaagag ctggacaagt  24900
acttcaaaaa tcatacatca ccagatgttg atcttggcga catttcaggc attaacgctt  24960
ctgtcgtcaa cattcaaaaa gaaattgacc gcctcaatga ggtcgctaaa aatttaaatg  25020
aatcactcat tgaccttcaa gaattgggaa aatatgagca atatattaaa tggccttggt  25080
atgtttggct cggcttcatt gctggactaa ttgccatcgt catggttaca atcttgcttt  25140
gttgcatgac tagttgttgc agttgcctca agggtgcatg ctcttgtggt tcttgctgca  25200
agtttgatga ggatgactct gagccagttc tcaagggtgt caaattacat tacacataaa  25260
cgaacttatg gatttgttta tgagattttt tactcttgga tcaattactg cacagccagt  25320
aaaaattgac aatgcttctc ctgcaagtac tgttcatgct acagcaacga taccgctaca  25380
agcctcactc cctttcggat ggcttgttat tggcgttgca tttcttgctg tttttcagag  25440
cgctaccaaa ataattgcgc tcaataaaag atggcagcta gccctttata agggcttcca  25500
gttcatttgc aatttactgc tgctatttgt taccatctat tcacatcttt tgcttgtcgc  25560
tgcaggtatg gaggcgcaat tttgtacct ctatgccttg atatattttc tacaatgcat  25620
caacgcatgt agaattatta tgagatgttg gctttgttgg aagtgcaaat ccaagaaccc  25680
attactttat gatgccaact actttgtttg ctggcacaca cataactatg actactgtat  25740
accatataac agtgtcacag atacaattgt cgttactgaa ggtgacggca tttcaacacc  25800
aaaactcaaa gaagactacc aaattggtgg ttattctgag gataggcact caggtgttaa  25860
agactatgtc gttgtacatg gctatttcac cgaagtttac taccagcttg agtctacaca  25920
aattactaca gacactggta ttgaaaatgc tacattcttc atctttaaca agcttgttaa  25980
agacccaccg aatgtgcaaa tacacacaat cgacggctct tcaggagttg ctaatccagc  26040
aatggatcca atttatgatg agccgacgac gactactagc gtgcctttgt aagcacaaga  26100
aagtgagtac gaacttatgt actcattcgt ttcggaagaa acaggtacgt taatagttaa  26160
tagcgtactt ctttttcttg ctttcgtggt attcttgcta gtcacactag ccatccttac  26220
tgcgcttcga ttgtgtgcgt actgctgcaa tattgttaac gtgagtttag taaaaccaac  26280
ggtttacgtc tactcgcgtg ttaaaaatct gaactcttct gaaggagttc ctgatcttct  26340
ggtctaaacg aactaactat tattattatt ctgtttggaa ctttaacatt gcttatcatg  26400
gcagacaacg gtactattac cgttgaggag cttaaacaac tcctggaaca atggaaccta  26460
gtaataggtt tcctattcct agcctggatt atgttactac aatttgccta ttctaatcgg  26520
aacaggtttt tgtacataat aaagcttgtt ttcctctggc tcttgtggcc agtaacactt  26580
gcttgttttg tgcttgctgc tgtctacaga attaattggg tgactggcgg gattgcgatt  26640
gcaatggctt gtattgtagg cttgatgtgg cttagctact tcgttgcttc cttcaggctg  26700
tttgctcgta cccgctcaat gtggtcattc aacccagaaa caaacattct tctcaatgtg  26760
cctctccggg ggacaattgt gaccagaccg ctcatggaaa gtgaacttgt cattggtgct  26820
```

-continued

```
gtgatcattc gtggtcactt gcgaatggcc ggacaccccc tagggcgctg tgacattaag  26880
gacctgccaa aagagatcac tgtggctaca tcacgaacgc tttcttatta caaattagga  26940
gcgtcgcagc gtgtaggcac tgattcaggt tttgctgcat acaaccgcta ccgtattgga  27000
aactataaat taaatacaga ccacgccggt agcaacgaca atattgcttt gctagtacag  27060
taagtgacaa cagatgtttc atcttgttga cttccaggtt acaatagcag agatattgat  27120
tatcattatg aggactttca ggattgctat ttggaatctt gacgttataa taagttcaat  27180
agtgagacaa ttatttaagc ctctaactaa gaagaattat tcggagttag atgatgaaga  27240
acctatggag ttagattatc cataaaacga acatgaaaat tattctcttc ctgacattga  27300
ttgtatttac atcttgcgag ctatatcact atcaggagtg tgttagaggt acgactgtac  27360
tactaaaaga accttgccca tcaggaacat acgagggcaa ttcaccattt caccctcttg  27420
ctgacaataa atttgcacta acttgcacta gcacacactt tgcttttgct tgtgctgacg  27480
gtactcgaca tacctatcag ctgcgtgcaa gatcagtttc accaaaactt ttcatcagac  27540
aagaggaggt tcaacaagag ctctactcgc cactttttct cattgttgct gctctagtat  27600
ttttaatact ttgcttcacc attaagagaa agacagaatg aatgagctca ctttaattga  27660
cttctatttg tgctttttag cctttctgct attccttgtt ttaataatgc ttattatatt  27720
ttggttttca ctcgaaatcc aggatctaga agaaccttgt accaaagtct aaacgaacat  27780
gaaacttctc attgttttga cttgtatttc tctatgcagt tgcatatgca ctgtagtaca  27840
gcgctgtgca tctaataaac ctcatgtgct tgaagatcct tgtaaggtac aacactaggg  27900
gtaatactta tagcactgct tggctttgtg ctctaggaaa ggttttacct tttcatagat  27960
ggcacactat ggttcaaaca tgcacaccta atgttactat caactgtcaa gatccagctg  28020
gtggtgcgct tatagctagg tgttggtacc ttcatgaagg tcaccaaact gctgcattta  28080
gagacgtact tgttgtttta aataaacgaa caaattaaaa tgtctgataa tggaccccaa  28140
tcaaaccaac gtagtgcccc ccgcattaca tttggtggac ccacagattc aactgacaat  28200
aaccagaatg gaggacgcaa tggggcaagg ccaaaacagc gccgacccca aggtttaccc  28260
aataatactg cgtcttggtt cacagctctc actcagcatg gcaaggagga acttagattc  28320
cctcgaggcc agggcgttcc aatcaacacc aatagtggtc cagatgacca aattggctac  28380
taccgaagag ctacccgacg agttcgtggt ggtgacggca aaatgaaaga gctcagcccc  28440
agatggtact tctattacct aggaactggc ccagaagctt cacttcccta cggcgctaac  28500
aaagaaggca tcgtatgggt tgcaactgag ggagccttga atacacccaa agaccacatt  28560
ggcacccgca atcctaataa caatgctgcc accgtgctac aacttcctca aggaacaaca  28620
ttgccaaaag gcttctacgc agagggaagc agaggcggca gtcaagcctc ttctcgctcc  28680
tcatcacgta gtcgcggtaa ttcaagaaat tcaactcctg gcagcagtag gggaaattct  28740
cctgctcgaa tggctagcgg aggtggtgaa actgccctcg cgctattgct gctagacaga  28800
ttgaaccagc ttgagagcaa agtttctggt aaaggccaac aacaacaagg ccaaactgtc  28860
actaagaaat ctgctgctga ggcatctaaa aagcctcgcc aaaaacgtac tgccacaaaa  28920
cagtacaacg tcactcaagc atttgggaga cgtggtccag aacaaaccca aggaaatttc  28980
ggggaccaag acctaatcag acaaggaact gattacaaac attggccgca aattgcacaa  29040
tttgctccaa gtgcctctgc attctttgga atgtcacgca ttggcatgga agtcacacct  29100
tcgggaacat ggctgactta tcatggagcc attaaattgg atgacaaaga tccacaattc  29160
aaagacaacg tcatactgct gaacaagcac attgacgcat acaaaacatt cccaccaaca  29220
```

-continued

```
gagcctaaaa aggacaaaaa gaaaaagact gatgaagctc agcctttgcc gcagagacaa  29280
aagaagcagc ccactgtgac tcttcttcct gcggctgaca tggatgattt ctccagacaa  29340
cttcaaaatt ccatgagtgg agcttctgct gattcaactc aggcataaac actcatgatg  29400
accacacaag gcagatgggc tatgtaaacg ttttcgcaat tccgtttacg atacatagtc  29460
tactcttgtg cagaatgaat tctcgtaact aaacagcaca agtaggttta gttaacttta  29520
atctcacata gcaatcttta atcaatgtgt aacattaggg aggacttgaa agagccacca  29580
cattttcatc gaggccacgc ggagtacgat cgagggtaca gtgaataatg ctagggagag  29640
ctgcctatat ggaagagccc taatgtgtaa aattaatttt agtagtgcta tccccatgtg  29700
attttaatag cttcttagga gaatgac                                     29727
```

<210> SEQ ID NO 2
<211> LENGTH: 29751
<212> TYPE: DNA
<213> ORGANISM: SARS coronavirus Tor2

<400> SEQUENCE: 2

```
atattaggtt tttacctacc caggaaaagc caaccaacct cgatctcttg tagatctgtt     60
ctctaaacga actttaaaat ctgtgtagct gtcgctcggc tgcatgccta gtgcacctac    120
gcagtataaa caataataaa ttttactgtc gttgacaaga aacgagtaac tcgtccctct    180
tctgcagact gcttacggtt tcgtccgtgt tgcagtcgat catcagcata cctaggtttc    240
gtccgggtgt gaccgaaagg taagatggag agccttgttc ttggtgtcaa cgagaaaaca    300
cacgtccaac tcagtttgcc tgtccttcag gttagagacg tgctagtgcg tggcttcggg    360
gactctgtgg aagaggccct atcggaggca cgtgaacacc tcaaaaatgg cacttgtggt    420
ctagtagagc tggaaaaagg cgtactgccc cagcttgaac agccctatgt gttcattaaa    480
cgttctgatg ccttaagcac caatcacggc cacaaggtcg ttgagctggt tgcagaaatg    540
gacggcattc agtacggtcg tagcggtata acactgggag tactcgtgcc acatgtgggc    600
gaaaccccaa ttgcataccg caatgttctt cttcgtaaga acggtaataa gggagccggt    660
ggtcatagct atggcatcga tctaaagtct tatgacttag gtgacgagct tggcactgat    720
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaagggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
```

-continued

```
tcaggccata ctggcattac tggtgacaat gtggagacct tgaatgagga tctccttgag   1620
atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taaagttacc   1800
aagggaaagc ccgtaaaagg tgcttggaac attggacaac agagatcagt tttaacacca   1860
ctgtgtggtt ttccctcaca ggctgctggt gttatcagat caatttttgc gcgcacactt   1920
gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca aagaacaata ctgcgcattg tctcctggtt tactggctac aaacaatgtc   2700
tttcgcttaa aagggggtgc accaattaaa ggtgtaacct ttggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat tctacttatt tgatgatgct   3000
ggtgaagaaa acttttcatc acgtatgtat tgttcctttt accctccaga tgaggaagaa   3060
gaggacgatg cagagtgtga ggaagaagaa attgatgaaa cctgtgaaca tgagtacggt   3120
acagaggatg attatcaagg tctccctctg gaatttggtg cctcagctga aacagttcga   3180
gttgaggaag aagaagagga agactggctg gatgatacta ctgagcaatc agagattgag   3240
ccagaaccag aacctacacc tgaagaacca gttaatcagt ttactggtta tttaaaactt   3300
actgacaatg ttgccattaa atgtgttgac atcgttaagg aggcacaaag tgctaatcct   3360
atggtgattg taaatgctgc taacatacac ctgaaacatg gtggtggtgt agcaggtgca   3420
ctcaacaagg caaccaatgg tgccatgcaa aaggagagtg atgattacat taagctaaat   3480
ggccctctta cagtaggagg gtcttgtttg ctttctggac ataatcttgc taagaagtgt   3540
ctgcatgttg ttggacctaa cctaaatgca ggtgaggaca tccagcttct taaggcagca   3600
tatgaaaatt tcaattcaca ggacatctta cttgcaccat tgttgtcagc aggcatattt   3660
ggtgctaaac cacttcagtc tttacaagtg tgcgtgcaga cggttcgtac acaggtttat   3720
attgcagtca atgacaaagc tctttatgag caggttgtca tggattatct tgataacctg   3780
aagcctagag tggaagcacc taaacaagag gagccaccaa acacagaaga ttccaaaact   3840
gaggagaaat ctgtcgtaca gaagcctgtc gatgtgaagc caaaaattaa ggcctgcatt   3900
gatgaggtta ccacaacact ggaagaaact aagtttctta ccaataagtt actcttgttt   3960
```

-continued

```
gctgatatca atggtaagct ttaccatgat tctcagaaca tgcttagagg tgaagatatg   4020
tctttccttg agaaggatgc accttacatg gtaggtgatg ttatcactag tggtgatatc   4080
acttgtgttg taataccctc caaaaaggct ggtggcacta ctgagatgct ctcaagagct   4140
ttgaagaaag tgccagttga tgagtatata accacgtacc ctggacaagg atgtgctggt   4200
tatacacttg aggaagctaa gactgctctt aagaaatgca aatctgcatt ttatgtacta   4260
ccttcagaag cacctaatgc taaggaagag attctaggaa ctgtatcctg gaatttgaga   4320
gaaatgcttg ctcatgctga agagacaaga aaattaatgc ctatatgcat ggatgttaga   4380
gccataatgg caaccatcca acgtaagtat aaaggaatta aaattcaaga gggcatcgtt   4440
gactatggtg tccgattctt cttttatact agtaaagagc ctgtagcttc tattattacg   4500
aagctgaact ctctaaatga gccgcttgtc acaatgccaa ttggttatgt gacacatggt   4560
tttaatcttg aagaggctgc gcgctgtatg cgttctctta aagctcctgc cgtagtgtca   4620
gtatcatcac cagatgctgt tactacatat aatggatacc tcacttcgtc atcaaagaca   4680
tctgaggagc actttgtaga aacagtttct ttggctggct cttacagaga ttggtcctat   4740
tcaggacagc gtacagagtt aggtgttgaa tttcttaagc gtggtgacaa aattgtgtac   4800
cacactctgg agagccccgt cgagtttcat cttgacggtg aggttctttc acttgacaaa   4860
ctaaagagtc tcttatccct gcgggaggtt aagactataa aagtgttcac aactgtggac   4920
aacactaatc tccacacaca gcttgtggat atgtctatga catatggaca gcagtttggt   4980
ccaacatact tggatggtgc tgatgttaca aaaattaaac ctcatgtaaa tcatgagggt   5040
aagactttct ttgtactacc tagtgatgac acactacgta gtgaagcttt cgagtactac   5100
catactcttg atgagagttt tcttggtagg tacatgtctg ctttaaacca cacaaagaaa   5160
tggaaatttc ctcaagttgg tggtttaact tcaattaaat gggctgataa caattgttat   5220
ttgtctagtg ttttattagc acttcaacag cttgaagtca aattcaatgc accagcactt   5280
caagaggctt attatagagc ccgtgctggt gatgctgcta acttttgtgc actcatactc   5340
gcttacagta ataaaactgt tggcgagctt ggtgatgtca gagaaactat gacccatctt   5400
ctacagcatg ctaatttgga atctgcaaag cgagttctta atgtggtgtg taaacattgt   5460
ggtcagaaaa ctactacctt aacgggtgta gaagctgtga tgtatatggg tactctatct   5520
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtacattctt atgtgcgaat gagtacactg gtaactatca gtgtggtcat   5700
tacactcata taactgctaa ggagaccctc tatcgtattg acggagctca ccttacaaag   5760
atgtcagagt acaaaggacc agtgactgat gttttctaca aggaaacatc ttacactaca   5820
accatcaagc ctgtgtcgta taaactcgat ggagttactt acacagagat tgaaccaaaa   5880
ttggatgggt attataaaaa ggataatgct tactatacag agcagcctat agaccttgta   5940
ccaactcaac cattaccaaa tgcgagtttt gataatttca aactcacatg ttctaacaca   6000
aaatttgctg atgatttaaa tcaaatgaca ggcttcacaa agccagcttc acgagagcta   6060
tctgtcacat tcttcccaga cttgaatggc gatgtagtgg ctattgacta tagacactat   6120
tcagcgagtt tcaagaaagg tgctaaatta ctgcataagc caattgtttg gcacattaac   6180
caggctacaa ccaagacaac gttcaaacca aacacttggt gtttacgttg tctttggagt   6240
acaaagccag tagatacttc aaattcattt gaagttctgg cagtagaaga cacacaagga   6300
```

-continued

```
atggacaatc ttgcttgtga aagtcaacaa cccacctctg aagaagtagt ggaaaatcct   6360
accatacaga aggaagtcat agagtgtgac gtgaaaacta ccgaagttgt aggcaatgtc   6420
atacttaaac catcagatga aggtgttaaa gtaacacaag agttaggtca tgaggatctt   6480
atggctgctt atgtggaaaa cacaagcatt accattaaga aacctaatga gctttcacta   6540
gccttaggtt taaaaacaat tgccactcat ggtattgctg caattaatag tgttccttgg   6600
agtaaaattt tggcttatgt caaaccattc ttaggacaag cagcaattac aacatcaaat   6660
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa atttctaaa ttgttcacaa tcgctatgtg gctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
gttactacta tggatttctg tgaaggttct tttccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttctttgg ctattttgct   7260
agtcatttca tcagcaattc ttggctcatg tggtttatca ttagtattgt acaaatggca   7320
cccgtttctg caatggttag gatgtacatc ttctttgctt ctttctacta catatggaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg gcgcgcttca cctctacttt gacaaggctg gtcaaaagac ctatgagaga   7740
catccgctct cccattttgt caatttagac aatttgagag ctaacaacac taaaggttca   7800
ctgcctatta atgtcatagt ttttgatggc aagtccaaat gcgacgagtc tgcttctaag   7860
tctgcttctg tgtactacag tcagctgatg tgccaaccta ttctgttgct tgaccaagct   7920
cttgtatcag acgttggaga tagtactgaa gtttccgtta agatgtttga tgcttatgtc   7980
gacacctttt cagcaacttt tagtgttcct atggaaaaac ttaaggcact tgttgctaca   8040
gctcacagcg agttagcaaa gggtgtagct ttagatggtg tcctttctac attcgtgtca   8100
gctgcccgac aaggtgttgt tgataccgat gttgacacaa aggatgttat tgaatgtctc   8160
aaactttcac atcactctga cttagaagtg acaggtgaca gttgtaacaa tttcatgctc   8220
acctataata aggttgaaaa catgacgccc agagatcttg gcgcatgtat tgactgtaat   8280
gcaaggcata tcaatgccca agtagcaaaa agtcacaatg tttcactcat ctggaatgta   8340
aaagactaca tgtctttatc tgaacagctg cgtaaacaaa ttcgtagtgc tgccaagaag   8400
aacaacatac cttttagact aacttgtgct acaactagac aggttgtcaa tgtcataact   8460
actaaaatct cactcaaggg tggtaagatt gttagtactt gttttaaact tatgcttaag   8520
gccacattat tgtgcgttct tgctgcattg gtttgttata tcgttatgcc agtacataca   8580
ttgtcaatcc atgatggtta cacaaatgaa atcattggtt acaaagccat tcaggatggt   8640
gtcactcgtg acatcatttc tactgatgat tgttttgcaa ataaacatgc tggttttgac   8700
```

-continued

```
gcatggttta gccagcgtgg tggttcatac aaaaatgaca aaagctgccc tgtagtagct   8760
gctatcatta caagagagat tggtttcata gtgcctggct taccgggtac tgtgctgaga   8820
gcaatcaatg gtgacttctt gcattttcta cctcgtgttt ttagtgctgt tggcaacatt   8880
tgctacacac cttccaaact cattgagtat agtgattttg ctacctctgc ttgcgttctt   8940
gctgctgagt gtacaatttt taaggatgct atgggcaaac ctgtgccata ttgttatgac   9000
actaatttgc tagagggttc tatttcttat agtgagcttc gtccagacac tcgttatgtg   9060
cttatggatg gttccatcat acagtttcct aacacttacc tggagggttc tgttagagta   9120
gtaacaactt ttgatgctga gtactgtaga catggtacat gcgaaaggtc agaagtaggt   9180
atttgcctat ctaccagtgg tagatgggtt cttaataatg agcattacag agctctatca   9240
ggagttttct gtggtgttga tgcgatgaat ctcatagcta acatctttac tcctcttgtg   9300
caacctgtgg gtgctttaga tgtgtctgct tcagtagtgg ctggtggtat tattgccata   9360
ttggtgactt gtgctgccta ctactttatg aaattcagac gtgtttttgg tgagtacaac   9420
catgttgttg ctgctaatgc acttttgttt ttgatgtctt tcactatact ctgtctggta   9480
ccagcttaca gctttctgcc gggagtctac tcagtctttt acttgtactt gacattctat   9540
ttcaccaatg atgtttcatt cttggctcac cttcaatggt ttgccatgtt ttctcctatt   9600
gtgccttttt ggataacagc aatctatgta ttctgtattt ctctgaagca ctgccattgg   9660
ttctttaaca actatcttag gaaaagagtc atgtttaatg gagttacatt tagtaccttc   9720
gaggaggctg ctttgtgtac ctttttgctc aacaaggaaa tgtacctaaa attgcgtagc   9780
gagacactgt tgccacttac acagtataac aggtatcttg ctctatataa caagtacaag   9840
tatttcagtg gagccttaga tactaccagc tatcgtgaag cagcttgctg ccacttagca   9900
aaggctctaa atgactttag caactcaggt gctgatgttc tctaccaacc accacagaca   9960
tcaatcactt ctgctgttct gcagagtggt tttaggaaaa tggcattccc gtcaggcaaa  10020
gttgaagggt gcatggtaca agtaacctgt ggaactacaa ctcttaatgg attgtggttg  10080
gatgacacag tatactgtcc aagacatgtc atttgcacag cagaagacat gcttaatcct  10140
aactatgaag atctgctcat tcgcaaatcc aaccatagct ttcttgttca ggctggcaat  10200
gttcaacttc gtgttattgg ccattctatg caaaattgtc tgcttaggct taaagttgat  10260
acttctaacc ctaagacacc caagtataaa tttgtccgta tccaacctgg tcaaacattt  10320
tcagttctag catgctacaa tggttcacca tctggtgttt atcagtgtgc catgagacct  10380
aatcatacca ttaaaggttc tttccttaat ggatcatgtg gtagtgttgg ttttaacatt  10440
gattatgatt gcgtgtcttt ctgctatatg catcatatgg agcttccaac aggagtacac  10500
gctggtactg acttagaagg taaattctat ggtccatttg ttgacagaca aactgcacag  10560
gctgcaggta cagacacaac cataacatta aatgttttgg catggctgta tgctgctgtt  10620
atcaatggtg ataggtggtt tcttaataga ttcaccacta ctttgaatga ctttaacctt  10680
gtggcaatga agtacaacta tgaacctttg acacaagatc atgttgacat attgggacct  10740
ctttctgctc aaacaggaat tgccgtctta gatatgtgtg ctgctttgaa agagctgctg  10800
cagaatggta tgaatggtcg tactatcctt ggtagcacta ttttagaaga tgagtttaca  10860
ccatttgatg ttgttagaca atgctctggt gttaccttcc aaggtaagtt caagaaaatt  10920
gttaagggca ctcatcattg gatgctttta actttcttga catcactatt gattcttgtt  10980
caaagtacac agtggtcact gtttttcttt gtttacgaga atgctttctt gccatttact  11040
```

-continued

```
cttggtatta tggcaattgc tgcatgtgct atgctgcttg ttaagcataa gcacgcattc  11100
ttgtgcttgt ttctgttacc ttctcttgca acagttgctt actttaatat ggtctacatg  11160
cctgctagct gggtgatgcg tatcatgaca tggcttgaat tggctgacac tagcttgtct  11220
ggttataggc ttaaggattg tgttatgtat gcttcagctt tagttttgct tattctcatg  11280
acagctcgca ctgtttatga tgatgctgct agacgtgttt ggacactgat gaatgtcatt  11340
acacttgttt acaaagtcta ctatggtaat gctttagatc aagctatttc catgtgggcc  11400
ttagttattt ctgtaacctc taactattct ggtgtcgtta cgactatcat gtttttagct  11460
agagctatag tgtttgtgtg tgttgagtat tacccattgt tatttattac tggcaacacc  11520
ttacagtgta tcatgcttgt ttattgtttc ttaggctatt gttgctgctg ctactttggc  11580
cttttctgtt tactcaaccg ttacttcagg cttactcttg gtgtttatga ctacttggtc  11640
tctacacaag aatttaggta tatgaactcc caggggcttt tgcctcctaa gagtagtatt  11700
gatgctttca agcttaacat taagttgttg ggtattggag gtaaaccatg tatcaaggtt  11760
gctactgtac agtctaaaat gtctgacgta aagtgcacat ctgtggtact gctctcggtt  11820
cttcaacaac ttagagtaga gtcatcttct aaattgtggg cacaatgtgt acaactccac  11880
aatgatattc ttcttgcaaa agacacaact gaagctttcg agaagatggt ttctcttttg  11940
tctgttttgc tatccatgca gggtgctgta gacattaata ggttgtgcga ggaaatgctc  12000
gataaccgtg ctactcttca ggctattgct tcagaattta gttctttacc atcatatgcc  12060
gcttatgcca ctgcccagga ggcctatgag caggctgtag ctaatggtga ttctgaagtc  12120
gttctcaaaa agttaaagaa atctttgaat gtggctaaat ctgagtttga ccgtgatgct  12180
gccatgcaac gcaagttgga aaagatggca gatcaggcta tgacccaaat gtacaaacag  12240
gcaagatctg aggacaagag ggcaaaagta actagtgcta tgcaaacaat gctcttcact  12300
atgcttagga agcttgataa tgatgcactt aacaacatta tcaacaatgc gcgtgatggt  12360
tgtgttccac tcaacatcat accattgact acagcagcca aactcatggt tgttgtccct  12420
gattatggta cctacaagaa cacttgtgat ggtaacacct ttacatatgc atctgcactc  12480
tgggaaatcc agcaagttgt tgatgcggat agcaagattg ttcaacttag tgaaattaac  12540
atggacaatt caccaaattt ggcttggcct cttattgtta cagctctaag agccaactca  12600
gctgttaaac tacagaataa tgaactgagt ccagtagcac tacgacagat gtcctgtgcg  12660
gctggtacca cacaaacagc ttgtactgat gacaatgcac ttgcctacta taacaattcg  12720
aagggaggta ggtttgtgct ggcattacta tcagaccacc aagatctcaa atgggctaga  12780
ttccctaaga gtgatggtac aggtacaatt tacacagaac tggaaccacc ttgtaggttt  12840
gttacagaca caccaaaagg gcctaaagtg aaatacttgt acttcatcaa aggcttaaac  12900
aacctaaata gaggtatggt gctgggcagt ttagctgcta cagtacgtct tcaggctgga  12960
aatgctacag aagtacctgc caattcaact gtgctttcct tctgtgcttt tgcagtagac  13020
cctgctaaag catataagga ttacctagca agtggaggac aaccaatcac caactgtgtg  13080
aagatgttgt gtacacacac tggtacagga caggcaatta ctgtaacacc agaagctaac  13140
atggaccaag agtcctttgg tggtgcttca tgttgtctgt attgtagatg ccacattgac  13200
catccaaatc ctaaaggatt ctgtgacttg aaaggtaagt acgtccaaat acctaccact  13260
tgtgctaatg acccagtggg ttttacactt agaaacacag tctgtaccgt ctgcggaatg  13320
tggaaaggtt atggctgtag ttgtgaccaa ctccgcgaac ccttgatgca gtctgcggat  13380
gcatcaacgt tttttaaacgg gtttgcggtg taagtgcagc ccgtcttaca ccgtgcggca  13440
```

-continued caggcactag tactgatgtc gtctacaggg cttttgatat ttacaacgaa aaagttgctg 13500
gttttgcaaa gttcctaaaa actaattgct gtcgcttcca ggagaaggat gaggaaggca 13560
atttattaga ctcttacttt gtagttaaga ggcatactat gtctaactac caacatgaag 13620
agactattta taacttggtt aaagattgtc cagcggttgc tgtccatgac tttttcaagt 13680
ttagagtaga tggtgacatg gtaccacata tatcacgtca gcgtctaact aaatacacaa 13740
tggctgattt agtctatgct ctacgtcatt ttgatgaggg taattgtgat acattaaaag 13800
aaatactcgt cacatacaat tgctgtgatg atgattattt caataagaag gattggtatg 13860
acttcgtaga gaatcctgac atcttacgcg tatatgctaa cttaggtgag cgtgtacgcc 13920
aatcattatt aaagactgta caattctgcg atgctatgcg tgatgcaggc attgtaggcg 13980
tactgacatt agataatcag gatcttaatg ggaactggta cgatttcggt gatttcgtac 14040
aagtagcacc aggctgcgga gttcctattg tggattcata ttactcattg ctgatgccca 14100
tcctcacttt gactagggca ttggctgctg agtcccatat ggatgctgat ctcgcaaaac 14160
cacttattaa gtgggatttg ctgaaatatg attttacgga agagagactt tgtctcttcg 14220
accgttattt taaatattgg gaccagacat accatcccaa ttgtattaac tgtttggatg 14280
ataggtgtat ccttcattgt gcaaacttta atgtgttatt ttctactgtg tttccaccta 14340
caagttttgg accactagta agaaaaatat ttgtagatgg tgttcctttt gttgtttcaa 14400
ctggatacca ttttcgtgag ttaggagtcg tacataatca ggatgtaaac ttacatagct 14460
cgcgtctcag tttcaaggaa cttttagtgt atgctgctga tccagctatg catgcagctt 14520
ctggcaattt attgctagat aaacgcacta catgcttttc agtagctgca ctaacaaaca 14580
atgttgcttt tcaaactgtc aaacccggta attttaataa agacttttat gactttgctg 14640
tgtctaaagg tttctttaag gaaggaagtt ctgttgaact aaaacacttc ttctttgctc 14700
aggatggcaa cgctgctatc agtgattatg actattatcg ttataatctg ccaacaatgt 14760
gtgatatcag acaactccta ttcgtagttg aagttgttga taaatacttt gattgttacg 14820
atggtggctg tattaatgcc aaccaagtaa tcgttaacaa tctggataaa tcagctggtt 14880
tcccatttaa taaatggggt aaggctagac tttattatga ctcaatgagt tatgaggatc 14940
aagatgcact tttcgcgtat actaagcgta atgtcatccc tactataact caaatgaatc 15000
ttaagtatgc cattagtgca aagaatagag ctcgcaccgt agctggtgtc tctatctgta 15060
gtactatgac aaatagacag tttcatcaga aattattgaa gtcaatagcc gccactagag 15120
gagctactgt ggtaattgga acaagcaagt tttacggtgg ctggcataat atgttaaaaa 15180
ctgtttacag tgatgtagaa actccacacc ttatgggttg ggattatcca aaatgtgaca 15240
gagccatgcc taacatgctt aggataatgg cctctcttgt tcttgctcgc aaacataaca 15300
cttgctgtaa cttatcacac cgtttctaca ggttagctaa cgagtgtgcg caagtattaa 15360
gtgagatggt catgtgtggc ggctcactat atgttaaacc aggtggaaca tcatccggtg 15420
atgctacaac tgcttatgct aatagtgtct ttaacatttg tcaagctgtt acagccaatg 15480
taaatgcact tctttcaact gatggtaata agatagctga caagtatgtc cgcaatctac 15540
aacacaggct ctatgagtgt ctctatagaa atagggatgt tgatcatgaa ttcgtggatg 15600
agttttacgc ttacctgcgt aaacatttct ccatgatgat tctttctgat gatgccgttg 15660
tgtgctataa cagtaactat gcggctcaag gtttagtagc tagcattaag aactttaagg 15720
cagttcttta ttatcaaaat aatgtgttca tgtctgaggc aaaatgttgg actgagactg 15780

-continued

```
accttactaa aggacctcac gaattttgct cacagcatac aatgctagtt aaacaaggag  15840
atgattacgt gtacctgcct tacccagatc catcaagaat attaggcgca ggctgttttg  15900
tcgatgatat tgtcaaaaca gatggtacac ttatgattga aaggttcgtg tcactggcta  15960
ttgatgctta cccacttaca aaacatccta atcaggagta tgctgatgtc tttcacttgt  16020
atttacaata cattagaaag ttacatgatg agcttactgg ccacatgttg gacatgtatt  16080
ccgtaatgct aactaatgat aacacctcac ggtactggga acctgagttt tatgaggcta  16140
tgtacacacc acatacagtc ttgcaggctg taggtgcttg tgtattgtgc aattcacaga  16200
cttcacttcg ttgcggtgcc tgtattagga gaccattcct atgttgcaag tgctgctatg  16260
accatgtcat ttcaacatca cacaaattag tgttgtctgt taatccctat gtttgcaatg  16320
ccccaggttg tgatgtcact gatgtgacac aactgtatct aggaggtatg agctattatt  16380
gcaagtcaca taagcctccc attagttttc cattatgtgc taatggtcag gtttttggtt  16440
tatacaaaaa cacatgtgta ggcagtgaca atgtcactga cttcaatgcg atagcaacat  16500
gtgattggac taatgctggc gattacatac ttgccaacac ttgtactgag agactcaagc  16560
ttttcgcagc agaaacgctc aaagccactg aggaaacatt taagctgtca tatggtattg  16620
ccactgtacg cgaagtactc tctgacagag aattgcatct ttcatgggag gttggaaaac  16680
ctagaccacc attgaacaga aactatgtct ttactggtta ccgtgtaact aaaaatagta  16740
aagtacagat tggagagtac acctttgaaa aaggtgacta tggtgatgct gttgtgtaca  16800
gaggtactac gacatacaag ttgaatgttg gtgattactt tgtgttgaca tctcacactg  16860
taatgccact tagtgcacct actctagtgc cacaagagca ctatgtgaga attactggct  16920
tgtacccaac actcaacatc tcagatgagt tttctagcaa tgttgcaaat tatcaaaagg  16980
tcggcatgca aaagtactct acactccaag gaccacctgg tactggtaag agtcattttg  17040
ccatcggact tgctctctat tacccatctg ctcgcatagt gtatacggca tgctctcatg  17100
cagctgttga tgccctatgt gaaaaggcat taaaatattt gcccatagat aaatgtagta  17160
gaatcatacc tgcgcgtgcg cgcgtagagt gttttgataa attcaaagtg aattcaacac  17220
tagaacagta tgttttctgc actgtaaatg cattgccaga aacaactgct gacattgtag  17280
tctttgatga aatctctatg gctactaatt atgacttgag tgttgtcaat gctagacttc  17340
gtgcaaaaca ctacgtctat attggcgatc ctgctcaatt accagccccc cgcacattgc  17400
tgactaaagg cacactagaa ccagaatatt ttaattcagt gtgcagactt atgaaaacaa  17460
taggtccaga catgttcctt ggaacttgtc gccgttgtcc tgctgaaatt gttgacactg  17520
tgagtgcttt agtttatgac aataagctaa aagcacacaa ggataagtca gctcaatgct  17580
tcaaaatgtt ctacaaaggt gttattacac atgatgtttc atctgcaatc aacagacctc  17640
aaataggcgt tgtaagagaa tttcttacac gcaatcctgc ttggagaaaa gctgttttta  17700
tctcacctta taattcacag aacgctgtag cttcaaaaat cttaggattg cctacgcaga  17760
ctgttgattc atcacagggt tctgaatatg actatgtcat attcacacaa actactgaaa  17820
cagcacactc ttgtaatgtc aaccgcttca atgtggctat cacaagggca aaaattggca  17880
ttttgtgcat aatgtctgat agagatcttt atgacaaact gcaatttaca agtctagaaa  17940
taccacgtcg caatgtggct acattacaag cagaaaatgt aactggactt tttaaggact  18000
gtagtaagat cattactggt cttcatccta cacaggcacc tacacacctc agcgttgata  18060
taaagttcaa gactgaagga ttatgtgttg acataccagg cataccaaag gacatgacct  18120
accgtagact catctctatg atgggtttca aaatgaatta ccaagtcaat ggttacccta  18180
```

-continued

```
atatgtttat cacccgcgaa gaagctattc gtcacgttcg tgcgtggatt ggctttgatg  18240
tagagggctg tcatgcaact agagatgctg tgggtactaa cctacctctc cagctaggat  18300
tttctacagg tgttaactta gtagctgtac cgactggtta tgttgacact gaaaataaca  18360
cagaattcac cagagttaat gcaaaacctc caccaggtga ccagtttaaa catcttatac  18420
cactcatgta taaaggcttg ccctggaatg tagtgcgtat taagatagta caaatgctca  18480
gtgatacact gaaaggattg tcagacagag tcgtgttcgt cctttgggcg catggctttg  18540
agcttacatc aatgaagtac tttgtcaaga ttggacctga aagaacgtgt tgtctgtgtg  18600
acaaacgtgc aacttgcttt tctacttcat cagatactta tgcctgctgg aatcattctg  18660
tgggttttga ctatgtctat aacccattta tgattgatgt tcagcagtgg ggctttacgg  18720
gtaaccttca gagtaaccat gaccaacatt gccaggtaca tggaaatgca catgtggcta  18780
gttgtgatgc tatcatgact agatgtttag cagtccatga gtgctttgtt aagcgcgttg  18840
attggtctgt tgaataccct attataggag atgaactgag ggttaattct gcttgcagaa  18900
aagtacaaca catggttgtg aagtctgcat tgcttgctga taagtttcca gttcttcatg  18960
acattggaaa tccaaaggct atcaagtgtg tgcctcaggc tgaagtagaa tggaagttct  19020
acgatgctca gccatgtagt gacaaagctt acaaaataga ggaactcttc tattcttatg  19080
ctacacatca cgataaattc actgatggtg tttgtttgtt ttggaattgt aacgttgatc  19140
gttacccagc caatgcaatt gtgtgtaggt ttgacacaag agtcttgtca aacttgaact  19200
taccaggctg tgatggtggt agtttgtatg tgaataagca tgcattccac actccagctt  19260
tcgataaaag tgcatttact aatttaaagc aattgccttt cttttactat tctgatagtc  19320
cttgtgagtc tcatggcaaa caagtagtgt cggatattga ttatgttcca ctcaaatctg  19380
ctacgtgtat tacacgatgc aatttaggtg gtgctgtttg cagacaccat gcaaatgagt  19440
accgacagta cttggatgca tataatatga tgatttctgc tggatttagc ctatggattt  19500
acaaacaatt tgatacttat aacctgtgga atacatttac caggttacag agtttagaaa  19560
atgtggctta taatgttgtt aataaaggac actttgatgg acacgccggc gaagcacctg  19620
tttccatcat taataatgct gtttacacaa aggtagatgg tattgatgtg gagatctttg  19680
aaaataagac aacacttcct gttaatgttg catttgagct ttgggctaag cgtaacatta  19740
aaccagtgcc agagattaag atactcaata atttgggtgt tgatatcgct gctaatactg  19800
taatctggga ctacaaaaga gaagccccag cacatgtatc tacaataggt gtctgcacaa  19860
tgactgacat tgccaagaaa cctactgaga gtgcttgttc ttcacttact gtcttgtttg  19920
atggtagagt ggaaggacag gtagaccttt ttagaaacgc ccgtaatggt gttttaataa  19980
cagaaggttc agtcaaaggt ctaacacctt caaagggacc agcacaagct agcgtcaatg  20040
gagtcacatt aattggagaa tcagtaaaaa cacagtttaa ctactttaag aaagtagacg  20100
gcattattca acagttgcct gaaacctact ttactcagag cagagactta gaggatttta  20160
agcccagatc acaaatggaa actgactttc tcgagctcgc tatggatgaa ttcatacagc  20220
gatataagct cgagggctat gccttcgaac acatcgttta tggagatttc agtcatggac  20280
aacttggcgg tcttcattta atgataggct tagccaagcg ctcacaagat tcaccactta  20340
aattagagga ttttatccct atggacagca cagtgaaaaa ttacttcata acagatgcgc  20400
aaacaggttc atcaaaatgt gtgtgttctg tgattgatct tttacttgat gactttgtcg  20460
agataataaa gtcacaagat ttgtcagtga tttcaaaagt ggtcaaggtt acaattgact  20520
```

-continued atgctgaaat ttcattcatg ctttggtgta aggatggaca tgttgaaacc ttctacccaa 20580
aactacaagc aagtcaagcg tggcaaccag gtgttgcgat gcctaacttg tacaagatgc 20640
aaagaatgct tcttgaaaag tgtgaccttc agaattatgg tgaaaatgct gttataccaa 20700
aaggaataat gatgaatgtc gcaaagtata ctcaactgtg tcaatactta aatacactta 20760
ctttagctgt accctacaac atgagagtta ttcactttgg tgctggctct gataaaggag 20820
ttgcaccagg tacagctgtg ctcagacaat ggttgccaac tggcacacta cttgtcgatt 20880
cagatcttaa tgacttcgtc tccgacgcag attctacttt aattggagac tgtgcaacag 20940
tacatacggc taataaatgg gaccttatta ttagcgatat gtatgaccct aggaccaaac 21000
atgtgacaaa agagaatgac tctaaagaag ggtttttcac ttatctgtgt ggatttataa 21060
agcaaaaact agccctgggt ggttctatag ctgtaaagat aacagagcat tcttggaatg 21120
ctgaccttta caagcttatg ggccatttct catggtggac agcttttgtt acaaatgtaa 21180
atgcatcatc atcggaagca tttttaattg gggctaacta tcttggcaag ccgaaggaac 21240
aaattgatgg ctataccatg catgctaact acattttctg gaggaacaca aatcctatcc 21300
agttgtcttc ctattcactc tttgacatga gcaaatttcc tcttaaatta agaggaactg 21360
ctgtaatgtc tcttaaggag aatcaaatca atgatatgat ttattctctt ctggaaaaag 21420
gtaggcttat cattagagaa aacaacagag ttgtggtttc aagtgatatt cttgttaaca 21480
actaaacgaa catgtttatt ttcttattat ttcttactct cactagtggt agtgaccttg 21540
accggtgcac cacttttgat gatgttcaag ctcctaatta cactcaacat acttcatcta 21600
tgaggggggt ttactatcct gatgaaattt ttagatcaga cactctttat ttaactcagg 21660
atttatttct tccattttat tctaatgtta cagggtttca tactattaat catacgtttg 21720
gcaaccctgt catacctttt aaggatggta tttattttgc tgccacagag aaatcaaatg 21780
ttgtccgtgg ttgggttttt ggttctacca tgaacaacaa gtcacagtcg gtgattatta 21840
ttaacaattc tactaatgtt gttatacgag catgtaactt tgaattgtgt gacaaccctt 21900
tctttgctgt ttctaaaccc atgggtacac agacacatac tatgatattc gataatgcat 21960
ttaattgcac tttcgagtac atatctgatg ccttttcgct tgatgtttca gaaaagtcag 22020
gtaattttaa acacttacga gagtttgtgt ttaaaaataa agatgggttt ctctatgttt 22080
ataagggcta tcaacctata gatgtagttc gtgatctacc ttctggtttt aacactttga 22140
aacctatttt taagttgcct cttggtatta acattacaaa ttttagagcc attcttacag 22200
ccttttcacc tgctcaagac atttggggca cgtcagctgc agcctatttt gttggctatt 22260
taaagccaac tacatttatg ctcaagtatg atgaaaatgg tacaatcaca gatgctgttg 22320
attgttctca aaatccactt gctgaactca aatgctctgt taagagcttt gagattgaca 22380
aaggaattta ccagacctct aatttcaggg ttgttccctc aggagatgtt gtgagattcc 22440
ctaatattac aaacttgtgt ccttttggag aggtttttaa tgctactaaa ttcccttctg 22500
tctatgcatg ggagagaaaa aaaatttcta attgtgttgc tgattactct gtgctctaca 22560
actcaacatt tttttcaacc tttaagtgct atggcgtttc tgccactaag ttgaatgatc 22620
tttgcttctc caatgtctat gcagattctt ttgtagtcaa gggagatgat gtaagacaaa 22680
tagcgccagg acaaactggt gttattgctg attataatta taaattgcca gatgatttca 22740
tgggttgtgt ccttgcttgg aatactagga acattgatgc tacttcaact ggtaattata 22800
attataaata taggtatctt agacatggca agcttaggcc ctttgagaga gacatatcta 22860
atgtgccttt ctcccctgat ggcaaacctt gcaccccacc tgctcttaat tgttattggc 22920

-continued

```
cattaaatga ttatggtttt tacaccacta ctggcattgg ctaccaacct tacagagttg  22980
tagtactttc ttttgaactt ttaaatgcac cggccacggt ttgtggacca aaattatcca  23040
ctgaccttat taagaaccag tgtgtcaatt ttaattttaa tggactcact ggtactggtg  23100
tgttaactcc ttcttcaaag agatttcaac catttcaaca atttggccgt gatgtttctg  23160
atttcactga ttccgttcga gatcctaaaa catctgaaat attagacatt tcaccttgcg  23220
cttttggggg tgtaagtgta attacacctg gaacaaatgc ttcatctgaa gttgctgttc  23280
tatatcaaga tgttaactgc actgatgttt ctacagcaat tcatgcagat caactcacac  23340
cagcttggcg catatattct actggaaaca atgtattcca gactcaagca ggctgtctta  23400
taggagctga gcatgtcgac acttcttatg agtgcgacat tcctattgga gctggcattt  23460
gtgctagtta ccatacagtt tctttattac gtagtactag ccaaaaatct attgtggctt  23520
atactatgtc tttaggtgct gatagttcaa ttgcttactc taataacacc attgctatac  23580
ctactaactt ttcaattagc attactacag aagtaatgcc tgtttctatg gctaaaacct  23640
ccgtagattg taatatgtac atctgcggag attctactga atgtgctaat ttgcttctcc  23700
aatatggtag cttttgcaca caactaaatc gtgcactctc aggtattgct gctgaacagg  23760
atcgcaacac acgtgaagtg ttcgctcaag tcaaacaaat gtacaaaacc ccaactttga  23820
aatattttgg tggttttaat ttttcacaaa tattacctga ccctctaaag ccaactaaga  23880
ggtcttttat tgaggacttg ctctttaata aggtgacact cgctgatgct ggcttcatga  23940
agcaatatgg cgaatgccta ggtgatatta atgctagaga tctcatttgt gcgcagaagt  24000
tcaatggact tacagtgttg ccacctctgc tcactgatga tatgattgct gcctacactg  24060
ctgctctagt tagtggtact gccactgctg gatggacatt tggtgctggc gctgctcttc  24120
aaatacottt tgctatgcaa atggcatata ggttcaatgg cattggagtt acccaaaatg  24180
ttctctatga gaaccaaaaa caaatcgcca accaatttaa caaggcgatt agtcaaattc  24240
aagaatcact tacaacaaca tcaactgcat tgggcaagct gcaagacgtt gttaaccaga  24300
atgctcaagc attaaacaca cttgttaaac aacttagctc taattttggt gcaatttcaa  24360
gtgtgctaaa tgatatcctt tcgcgacttg ataaagtcga ggcggaggta caaattgaca  24420
ggttaattac aggcagactt caaagccttc aaacctatgt aacacaacaa ctaatcaggg  24480
ctgctgaaat cagggcttct gctaatcttg ctgctactaa aatgtctgag tgtgttcttg  24540
gacaatcaaa aagagttgac ttttgtggaa agggctacca ccttatgtcc ttcccacaag  24600
cagccccgca tggtgttgtc ttcctacatg tcacgtatgt gccatcccag gagaggaact  24660
tcaccacagc gccagcaatt tgtcatgaag gcaaagcata cttccctcgt gaaggtgttt  24720
ttgtgtttaa tggcacttct tggtttatta cacagaggaa cttcttttct ccacaaataa  24780
ttactacaga caatacattt gtctcaggaa attgtgatgt cgttattggc atcattaaca  24840
acacagttta tgatcctctg caacctgagc ttgactcatt caaagaagag ctggacaagt  24900
acttcaaaaa tcatacatca ccagatgttg atcttggcga catttcaggc attaacgctt  24960
ctgtcgtcaa cattcaaaaa gaaattgacc gcctcaatga ggtcgctaaa aatttaaatg  25020
aatcactcat tgaccttcaa gaattgggaa aatatgagca atatattaaa tggccttggt  25080
atgtttggct cggcttcatt gctggactaa ttgccatcgt catggttaca atcttgcttt  25140
gttgcatgac tagttgttgc agttgcctca agggtgcatg ctcttgtggt tcttgctgca  25200
agtttgatga ggatgactct gagccagttc tcaagggtgt caaattacat tacacataaa  25260
```

-continued

```
cgaacttatg gatttgttta tgagattttt tactcttaga tcaattactg cacagccagt  25320
aaaaattgac aatgcttctc ctgcaagtac tgttcatgct acagcaacga taccgctaca  25380
agcctcactc cctttcggat ggcttgttat tggcgttgca tttcttgctg tttttcagag  25440
cgctaccaaa ataattgcgc tcaataaaag atggcagcta gccctttata agggcttcca  25500
gttcatttgc aatttactgc tgctatttgt taccatctat tcacatcttt tgcttgtcgc  25560
tgcaggtatg gaggcgcaat tttgtacct ctatgccttg atatattttc tacaatgcat  25620
caacgcatgt agaattatta tgagatgttg gctttgttgg aagtgcaaat ccaagaaccc  25680
attactttat gatgccaact actttgtttg ctggcacaca cataactatg actactgtat  25740
accatataac agtgtcacag atacaattgt cgttactgaa ggtgacggca tttcaacacc  25800
aaaactcaaa gaagactacc aaattggtgg ttattctgag gataggcact caggtgttaa  25860
agactatgtc gttgtacatg gctatttcac cgaagtttac taccagcttg agtctacaca  25920
aattactaca gacactggta ttgaaaatgc tacattcttc atctttaaca agcttgttaa  25980
agacccaccg aatgtgcaaa tacacacaat cgacggctct tcaggagttg ctaatccagc  26040
aatggatcca atttatgatg agccgacgac gactactagc gtgcctttgt aagcacaaga  26100
aagtgagtac gaacttatgt actcattcgt ttcggaagaa acaggtacgt taatagttaa  26160
tagcgtactt ctttttcttg ctttcgtggt attcttgcta gtcacactag ccatccttac  26220
tgcgcttcga ttgtgtgcgt actgctgcaa tattgttaac gtgagtttag taaaaccaac  26280
ggtttacgtc tactcgcgtg ttaaaaatct gaactcttct gaaggagttc ctgatcttct  26340
ggtctaaacg aactaactat tattattatt ctgtttggaa ctttaacatt gcttatcatg  26400
gcagacaacg gtactattac cgttgaggag cttaaacaac tcctggaaca atggaaccta  26460
gtaataggtt tcctattcct agcctggatt atgttactac aatttgccta ttctaatcgg  26520
aacaggtttt tgtacataat aaagcttgtt ttcctctggc tcttgtggcc agtaacactt  26580
gcttgttttg tgcttgctgc tgtctacaga attaattggg tgactggcgg gattgcgatt  26640
gcaatggctt gtattgtagg cttgatgtgg cttagctact tcgttgcttc cttcaggctg  26700
tttgctcgta cccgctcaat gtggtcattc aacccagaaa caaacattct tctcaatgtg  26760
cctctccggg ggacaattgt gaccagaccg ctcatggaaa gtgaacttgt cattggtgct  26820
gtgatcattc gtggtcactt gcgaatggcc ggacactccc tagggcgctg tgacattaag  26880
gacctgccaa aagagatcac tgtggctaca tcacgaacgc tttcttatta caaattagga  26940
gcgtcgcagc gtgtaggcac tgattcaggt tttgctgcat acaaccgcta ccgtattgga  27000
aactataaat taaatacaga ccacgccggt agcaacgaca atattgcttt gctagtacag  27060
taagtgacaa cagatgtttc atcttgttga cttccaggtt acaatagcag agatattgat  27120
tatcattatg aggactttca ggattgctat ttggaatctt gacgttataa taagttcaat  27180
agtgagacaa ttatttaagc ctctaactaa gaagaattat tcggagttag atgatgaaga  27240
acctatggag ttagattatc cataaaacga acatgaaaat tattctcttc ctgacattga  27300
ttgtatttac atcttgcgag ctatatcact atcaggagtg tgttagaggt acgactgtac  27360
tactaaaaga accttgccca tcaggaacat acgagggcaa ttcaccattt caccctcttg  27420
ctgacaataa atttgcacta acttgcacta gcacacactt tgcttttgct tgtgctgacg  27480
gtactcgaca tacctatcag ctgcgtgcaa gatcagtttc accaaaactt ttcatcagac  27540
aagaggaggt tcaacaagag ctctactcgc cactttttct cattgttgct gctctagtat  27600
ttttaatact ttgcttcacc attaagagaa agacagaatg aatgagctca ctttaattga  27660
```

-continued

```
cttctatttg tgctttttag cctttctgct attccttgtt ttaataatgc ttattatatt  27720
ttggttttca ctcgaaatcc aggatctaga agaaccttgt accaaagtct aaacgaacat  27780
gaaacttctc attgttttga cttgtatttc tctatgcagt tgcatatgca ctgtagtaca  27840
gcgctgtgca tctaataaac ctcatgtgct tgaagatcct tgtaaggtac aacactaggg  27900
gtaatactta tagcactgct tggctttgtg ctctaggaaa ggttttacct tttcatagat  27960
ggcacactat ggttcaaaca tgcacaccta atgttactat caactgtcaa gatccagctg  28020
gtggtgcgct tatagctagg tgttggtacc ttcatgaagg tcaccaaact gctgcattta  28080
gagacgtact tgttgtttta aataaacgaa caaattaaaa tgtctgataa tggaccccaa  28140
tcaaaccaac gtagtgcccc ccgcattaca tttggtggac ccacagattc aactgacaat  28200
aaccagaatg gaggacgcaa tggggcaagg ccaaaacagc gccgacccca aggtttaccc  28260
aataatactg cgtcttggtt cacagctctc actcagcatg gcaaggagga acttagattc  28320
cctcgaggcc agggcgttcc aatcaacacc aatagtggtc cagatgacca aattggctac  28380
taccgaagag ctacccgacg agttcgtggt ggtgacggca aaatgaaaga gctcagcccc  28440
agatggtact tctattacct aggaactggc ccagaagctt cacttcccta cggcgctaac  28500
aaagaaggca tcgtatgggt tgcaactgag ggagccttga atacacccaa agaccacatt  28560
ggcacccgca atcctaataa caatgctgcc accgtgctac aacttcctca aggaacaaca  28620
ttgccaaaag gcttctacgc agagggaagc agaggcggca gtcaagcctc ttctcgctcc  28680
tcatcacgta gtcgcggtaa ttcaagaaat tcaactcctg gcagcagtag gggaaattct  28740
cctgctcgaa tggctagcgg aggtggtgaa actgccctcg cgctattgct gctagacaga  28800
ttgaaccagc ttgagagcaa agtttctggt aaaggccaac aacaacaagg ccaaactgtc  28860
actaagaaat ctgctgctga ggcatctaaa aagcctcgcc aaaaacgtac tgccacaaaa  28920
cagtacaacg tcactcaagc atttgggaga cgtggtccag aacaaaccca aggaaatttc  28980
ggggaccaag acctaatcag acaaggaact gattacaaac attggccgca aattgcacaa  29040
tttgctccaa gtgcctctgc attctttgga atgtcacgca ttggcatgga agtcacacct  29100
tcgggaacat ggctgactta tcatggagcc attaaattgg atgacaaaga tccacaattc  29160
aaagacaacg tcatactgct gaacaagcac attgacgcat acaaaacatt cccaccaaca  29220
gagcctaaaa aggacaaaaa gaaaaagact gatgaagctc agcctttgcc gcagagacaa  29280
aagaagcagc ccactgtgac tcttcttcct gcggctgaca tggatgattt ctccagacaa  29340
cttcaaaatt ccatgagtgg agcttctgct gattcaactc aggcataaac actcatgatg  29400
accacacaag gcagatgggc tatgtaaacg ttttcgcaat tccgtttacg atacatagtc  29460
tactcttgtg cagaatgaat tctcgtaact aaacagcaca agtaggttta gttaacttta  29520
atctcacata gcaatcttta atcaatgtgt aacattaggg aggacttgaa agagccacca  29580
cattttcatc gaggccacgc ggagtacgat cgagggtaca gtgaataatg ctagggagag  29640
ctgcctatat ggaagagccc taatgtgtaa aattaatttt agtagtgcta tccccatgtg  29700
attttaatag cttcttagga gaatgacaaa aaaaaaaaaa aaaaaaaaaa a           29751
```

<210> SEQ ID NO 3
<211> LENGTH: 29736
<212> TYPE: DNA
<213> ORGANISM: SARS coronavirus CUHK-W1

<400> SEQUENCE: 3

-continued

```
ctacccagga aaagccaacc aacctcgatc tcttgtagat ctgttctcta aacgaacttt      60
aaaatctgtg tagctgtcgc tcggctgcat gcctagtgca cctacgcagt ataaacaata     120
ataaatttta ctgtcgttga caagaaacga gtaactcgtc cctcttctgc agactgctta     180
cggtttcgtc cgtgttgcag tcgatcatca gcatacctag gtttcgtccg ggtgtgaccg     240
aaaggtaaga tggagagcct tgttcttggt gtcaacgaga aacacacgt ccaactcagt      300
ttgcctgtcc ttcaggttag agacgtgcta gtgcgtggct tcggggactc tgtggaagag     360
gccctatcgg aggcacgtga acacctcaaa aatggcactt gtggtctagt agagctggaa     420
aaaggcgtac tgccccagct tgaacagccc tatgtgttca ttaaacgttc tgatgcctta     480
agcaccaatc acggccacaa ggtcgttgag ctggttgcag aaatggacgg cattcagtac     540
ggtcgtagcg gtataacact gggagtactc gtgccacatg tgggcgaaac cccaattgca     600
taccgcaatg ttcttcttcg taagaacggt aataagggag ccggtggtca tagctatggc     660
atcgatctaa agtcttatga cttaggtgac gagcttggca ctgatcccat tgaagattat     720
gaacaaaact ggaacactaa gcatggcagt ggtgcactcc gtgaactcac tcgtgagctc     780
aatggaggtg cagtcactcg ctatgtcgac aacaatttct gtggcccaga tgggtaccct     840
cttgattgca tcaaagattt tctcgcacgc gcgggcaagt caatgtgcac tctttccgaa     900
caacttgatt acatcgagtc gaagagaggt gtctactgct gccgtgacca tgagcatgaa     960
attgcctggt tcactgagcg ctctgataag agctacgagc accagacacc cttcgaaatt    1020
aagagtgcca agaaatttga cactttcaaa ggggaatgcc caaagtttgt gtttcctctt    1080
aactcaaaag tcaaagtcat tcaaccacgt gttgaaaaga aaaagactga gggtttcatg    1140
gggcgtatac gctctgtgta ccctgttgca tctccacagg agtgtaacaa tatgcacttg    1200
tctaccttga tgaaatgtaa tcattgcgat gaagtttcat ggcagacgtg cgactttctg    1260
aaagccactt gtgaacattg tggcactgaa aatttagtta ttgaaggacc tactacatgt    1320
gggtacctac ctactaatgc tgtagtgaaa atgccatgtc ctgcctgtca agacccagag    1380
attggacctg agcatagtgt tgcagattat cacaaccact caaacattga aactcgactc    1440
cgcaagggag gtaggactag atgttttgga ggctgtgtgt ttgcctatgt tggctgctat    1500
aataagcgtg cctactgggt tcctcgtgct agtgctgata ttggctcagg ccatactggc    1560
attactggtg acaatgtgga gaccttgaat gaggatctcc ttgagatact gagtcgtgaa    1620
cgtgttaaca ttaacattgt tggcgatttt catttgaatg aagaggttgc catcattttg    1680
gcatctttct ctgcttctac aagtgccttt attgacacta taaagagtct tgattacaag    1740
tctttcaaaa ccattgttga gtcctgcggt aactataaag ttaccaaggg aaagcccgta    1800
aaaggtgctt ggaacattgg acaacagaga tcagttttaa caccactgtg tggttttccc    1860
tcacaggctg ctggtgttat cagatcaatt tttgcgcgca cacttgatgc agcaaaccac    1920
tcaattcctg atttgcaaag agcagctgtc accatacttg atggtatttc tgaacagtca    1980
ttacgtcttg tcgacgccat ggtttatact tcagacctgc tcaccaacag tgtcattatt    2040
atggcatatg taactggtgg tcttgtacaa cagacttctc agtggttgtc taatcttttg    2100
ggcactactg ttgaaaaact caggcctatc tttgaatgga ttgaggcgaa acttagtgca    2160
ggagttgaat ttctcaagga tgcttgggag attctcaaat ttctcattac aggtgttttt    2220
gacatcgtca agggtcaaat acaggttgct tcagataaca tcaaggattg tgtaaaatgc    2280
ttcattgatg ttgttaacaa ggcactcgaa atgtgcattg atcaagtcac tatcgctggc    2340
gcaaagttgc gatcactcaa cttaggtgaa gtcttcatcg ctcaaagcaa gggactttac    2400
```

-continued

```
cgtcagtgta tacgtggcaa ggagcagctg caactactca tgcctcttaa ggcaccaaaa   2460
gaagtaacct ttcttgaagg tgattcacat gacacagtac ttacctctga ggaggttgtt   2520
ctcaagaacg gtgaactcga agcactcgag acgcccgttg atagcttcac aaatggagct   2580
atcgttggca caccagtctg tgtaaatggc ctcatgctct tagagattaa ggacaaagaa   2640
caatactgcg cattgtctcc tggtttactg gctacaaaca atgtctttcg cttaaaaggg   2700
ggtgcaccaa ttaaaggtgt aacctttgga gaagatactg tttgggaagt tcaaggttac   2760
aagaatgtga gaatcacatt tgagcttgat gaacgtgttg acaaagtgct taatgaaaag   2820
tgctctgtct acactgttga atccggtacc gaagttactg agtttgcatg tgttgtagca   2880
gaggctgttg tgaagacttt acaaccagtt tctgatctcc ttaccaacat gggtattgat   2940
cttgatgagt ggagtgtagc tacattctac ttatttgatg atgctggtga agaaaacttt   3000
tcatcacgta tgtattgttc cttttaccct ccagatgagg aagaagagga cgatgcagag   3060
tgtgaggaag aagaaattga tgaaacctgt gaacatgagt acggtacaga ggatgattat   3120
caaggtctcc ctctggaatt tggtgcctca gctgaaacag ttcgagttga ggaagaagaa   3180
gaggaagact ggctggatga tactactgag caatcagaga ttgagccaga accagaacct   3240
acacctgaag aaccagttaa tcagtttact ggttatttaa aacttactga caatgttgcc   3300
attaaatgtg ttgacatcgt taaggaggca caaagtgcta atcctatggt gattgtaaat   3360
gctgctaaca tacacctgaa acatggtggt ggtgtagcag gtgcactcaa caaggcaacc   3420
aatggtgcca tgcaaaagga gagtgatgat tacattaagc taaatggccc tcttacagta   3480
ggagggtctt gtttgctttc tggacataat cttgctaaga agtgtctgca tgttgttgga   3540
cctaacctaa atgcaggtga ggacatccag cttcttaagg cagcatatga aaatttcaat   3600
tcacaggaca tcttacttgc accattgttg tcagcaggca tatttggtgc taaaccactt   3660
cagtctttac aagtgtgcgt gcagacggtt cgtacacagg tttatattgc agtcaatgac   3720
aaagctcttt atgagcaggt tgtcatggat tatcttgata acctgaagcc tagagtggaa   3780
gcacctaaac aagaggagcc accaaacaca gaagattcca aaactgagga gaaatctgtc   3840
gtacagaagc ctgtcgatgt gaagccaaaa attaaggcct gcattgatga ggttaccaca   3900
acactggaag aaactaagtt tcttaccaat aagttactct tgtttgctga tatcaatggt   3960
aagctttacc atgattctca gaacatgctt agaggtgaag atatgtcttt ccttgagaag   4020
gatgcacctt acatggtagg tgatgttatc actagtggtg atatcacttg tgttgtaata   4080
ccctccaaaa aggctggtgg cactactgag atgctctcaa gagctttgaa gaaagtgcca   4140
gttgatgagt atataaccac gtaccctgga caaggatgtg ctggttatac acttgaggaa   4200
gctaagactg ctcttaagaa atgcaaatct gcattttatg tactaccttc agaagcacct   4260
aatgctaagg aagagattct aggaactgta tcctggaatt tgagagaaat gcttgctcat   4320
gctgaagaga caagaaaatt aatgcctata tgcatggatg ttagagccat aatggcaacc   4380
atccaacgta agtataaagg aattaaaatt caagagggca tcgttgacta tggtgtccga   4440
ttcttctttt atactagtaa agagcctgta gcttctatta ttacgaagct gaactctcta   4500
aatgagccgc ttgtcacaat gccaattggt tatgtgacac atggttttaa tcttgaagag   4560
gctgcgcgct gtatgcgttc tcttaaagct cctgccgtag tgtcagtatc atcaccagat   4620
gctgttacta catataatgg atacctcact tcgtcatcaa agacatctga ggagcacttt   4680
gtagaaacag tttctttggc tggctcttac agagattggt cctattcagg acagcgtaca   4740
```

-continued

```
gagttaggtg ttgaatttct taagcgtggt gacaaaattg tgtaccacac tctggagagc   4800
cccgtcgagt ttcatcttga cggtgaggtt ctttcacttg acaaactaaa gagtctctta   4860
tccctgcggg aggttaagac tataaaagtg ttcacaactg tggacaacac taatctccac   4920
acacagcttg tggatatgtc tatgacatat ggacagcagt ttggtccaac atacttggat   4980
ggtgctgatg ttacaaaaat taaacctcat gtaaatcatg agggtaagac tttctttgta   5040
ctacctagtg atgacacact acgtagtgaa gctttcgagt actaccatac tcttgatgag   5100
agttttcttg gtaggtacat gtctgcttta aaccacacaa agaaatggaa atttcctcaa   5160
gttggtggtt taacttcaat taaatgggct gataacaatt gttatttgtc tagtgtttta   5220
ttagcacttc aacagcttga agtcaaattc aatgcaccag cacttcaaga ggcttattat   5280
agagcccgtg ctggtgatgc tgctaacttt tgtgcactca tactcgctta cagtaataaa   5340
actgttggcg agcttggtga tgtcagagaa actatgaccc atcttctaca gcatgctaat   5400
ttggaatctg caaagcgagt tcttaatgtg gtgtgtaaac attgtggtca gaaaactact   5460
accttaacgg gtgtagaagc tgtgatgtat atgggtactc tatcttatga taatcttaag   5520
acaggtgttt ccattccatg tgtgtgtggt cgtgatgcta cacaatatct agtacaacaa   5580
gagtcttctt ttgttatgat gtctgcacca cctgctgagt ataaattaca gcaaggtaca   5640
ttcttatgtg cgaatgagta cactggtaac tatcagtgtg gtcattacac tcatataact   5700
gctaaggaga ccctctatcg tattgacgga gctcacctta caaagatgtc agagtacaaa   5760
ggaccagtga ctgatgtttt ctacaaggaa acatcttaca ctacaaccat caagcctgtg   5820
tcgtataaac tcgatggagt tacttacaca gagattgaac caaaattgga tgggtattat   5880
aaaaaggata atgcttacta tacagagcag cctatagacc ttgtaccaac tcaaccatta   5940
ccaaatgcga gttttgataa tttcaaactc acatgttcta acacaaaatt tgctgatgat   6000
ttaaatcaaa tgacaggctt cacaaagcca gcttcacgag agctatctgt cacattcttc   6060
ccagacttga atggcgatgt agtggctatt gactatagac actattcagc gagtttcaag   6120
aaaggtgcta aattactgca taagccaatt gtttggcaca ttaaccaggc tacaaccaag   6180
acaacgttca aaccaaacac ttggtgttta cgttgtcttt ggagtacaaa gccagtagat   6240
acttcaaatt catttgaagt tctggcagta gaagacacac aaggaatgga caatcttgct   6300
tgtgaaagtc aacaacccac ctctgaagaa gtagtggaaa atcctaccat acagaaggaa   6360
gtcatagagt gtgacgtgaa aactaccgaa gttgtaggca atgtcatact taaaccatca   6420
gatgaaggtg ttaaagtaac acaagagtta ggtcatgagg atcttatggc tgcttatgtg   6480
gaaaacacaa gcattaccat taagaaacct aatgagcttt cactagcctt aggtttaaaa   6540
acaattgcca ctcatggtat tgctgcaatt aatagtgttc cttggagtaa aattttggct   6600
tatgtcaaac cattcttagg acaagcagca attacaacat caaattgcgc taagagatta   6660
gcacaacgtg tgtttaacaa ttatatgcct tatgtgttta cattattgtt ccaattgtgt   6720
acttttacta aaagtaccaa ttctagaatt agagcttcac tacctacaac tattgctaaa   6780
aatagtgtta agagtgttgc taaattatgt ttggatgccg gcattaatta tgtgaagtca   6840
cccaaatttt ctaaattgtt cacaatcgct atgtggctat tgttgttaag tatttgctta   6900
ggttctctaa tctgtgtaac tgctgctttt ggtgtactct tatctaattt tggtgctcct   6960
tcttattgta atggcgttag agaattgtat cttaattcgt ctaacgttac tactatggat   7020
ttctgtgaag gttcttttcc ttgcagcatt tgtttaagtg gattagactc ccttgattct   7080
tatccagctc ttgaaaccat tcaggtgacg atttcatcgt acaagctaga cttgacaatt   7140
```

-continued

```
ttaggtctgg ccgctgagtg ggttttggca tatatgttgt tcacaaaatt cttttattta   7200
ttaggtcttt cagctataat gcaggtgttc tttggctatt ttgctagtca tttcatcagc   7260
aattcttggc tcatgtggtt tatcattagt attgtacaaa tggcacccgt ttctgcaatg   7320
gttaggatgt acatcttctt tgcttctttc tactacatat ggaagagcta tgttcatatc   7380
atggatggtt gcacctcttc gacttgcatg atgtgctata agcgcaatcg tgccacacgc   7440
gttgagtgta caactattgt taatggcatg aagagatctt tctatgtcta tgcaaatgga   7500
ggccgtggct tctgcaagac tcacaattgg aattgtctca attgtgacac attttgcact   7560
ggtagtacat tcattagtga tgaagttgct cgtgatttgt cactccagtt taaaagacca   7620
atcaacccta ctgaccagtc atcgtatatt gttgatagtg ttgctgtgaa aaatggcgcg   7680
cttcacctct actttgacaa ggctggtcaa aagacctatg agagacatcc tctctcccat   7740
tttgtcaatt tagacaattt gagagctaac aacactaaag gttcactgcc tattaatgtc   7800
atagtttttg atggcaagtc caaatgcgac gagtctgctt ctaagtctgc ttctgtgtac   7860
tacagtcagc tgatgtgcca acctattctg ttgcttgacc aagctcttgt atcagacgtt   7920
ggagatagta ctgaagtttc cgttaagatg tttgatgctt atgtcgacac cttttcagca   7980
acttttagtg ttcctatgga aaaacttaag gcacttgttg ctacagctca cagcgagtta   8040
gcaaagggtg tagctttaga tggtgtcctt tctacattcg tgtcagctgc ccgacaaggt   8100
gttgttgata ccgatgttga cacaaaggat gttattgaat gtctcaaact ttcacatcac   8160
tctgacttag aagtgacagg tgacagttgt aacaatttca tgctcaccta taataaggtt   8220
gaaaacatga cgcccagaga tcttggcgca tgtattgact gtaatgcaag gcatatcaat   8280
gcccaagtag caaaaagtca caatgtttca ctcatctgga atgtaaaaga ctacatgtct   8340
ttatctgaac agctgcgtaa acaaattcgt agtgctgcca agaagaacaa catacctttt   8400
agactaactt gtgctacaac tagacaggtt gtcaatgtca taactactaa aatctcactc   8460
aagggtggta agattgttag tacttgtttt aaacttatgc ttaaggccac attattgtgc   8520
gttcttgctg cattggtttg ttatatcgtt atgccagtac atacattgtc aatccatgat   8580
ggttacacaa atgaaatcat tggttacaaa gccattcagg atggtgtcac tcgtgacatc   8640
atttctactg atgattgttt tgcaaataaa catgctggtt ttgacgcatg gtttagccag   8700
cgtggtggtt catacaaaaa tgacaaaagc tgccctgtag tagctgctat cattacaaga   8760
gagattggtt tcatagtgcc tggcttaccg ggtactgtgc tgagagcaat caatggtgac   8820
ttcttgcatt ttctacctcg tgtttttagt gctgttggca acatttgcta cacaccttcc   8880
aaactcattg agtatagtga ttttgctacc tctgcttgcg ttcttgctgc tgagtgtaca   8940
atttttaagg atgctatggg caaacctgtg ccatattgtt atgacactaa tttgctagag   9000
ggttctattt cttatagtga gcttcgtcca gacactcgtt atgtgcttat ggatggttcc   9060
atcatacagt ttcctaacac ttacctggag ggttctgtta gagtagtaac aacttttgat   9120
gctgagtact gtagacatgg tacatgcgaa aggtcagaag taggtatttg cctatctacc   9180
agtggtagat gggttcttaa taatgagcat tacagagctc tatcaggagt tttctgtggt   9240
gttgatgcga tgaatctcat agctaacatc tttactcctc ttgtgcaacc tgtgggtgct   9300
ttagatgtgt ctgcttcagt agtggctggt ggtattattg ccatattggt gacttgtgct   9360
gcctactact ttatgaaatt cagacgtgct tttggtgagt acaaccatgt tgttgctgct   9420
aatgcacttt tgtttttgat gtctttcact atactctgtc tggcaccagc ttacagcttt   9480
```

-continued

```
ctgccgggag tctactcagt cttttacttg tacttgacat tctatttcac caatgatgtt   9540
tcattcttgg ctcaccttca atggtttgcc atgttttctc ctattgtgcc tttttggata   9600
acagcaatct atgtattctg tatttctctg aagcactgcc attggttctt taacaactat   9660
cttaggaaaa gagtcatgtt taatggagtt acatttagta ccttcgagga ggctgctttg   9720
tgtacctttt tgctcaacaa ggaaatgtac ctaaaattgc gtagcgagac actgttgcca   9780
cttacacagt ataacaggta tcttgctcta tataacaagt acaagtattt cagtggagcc   9840
ttagatacta ccagctatcg tgaagcagct tgctgccact tagcaaaggc tctaaatgac   9900
tttagcaact caggtgctga tgttctctac caaccaccac agacatcaat cacttctgct   9960
gttctgcaga gtggttttag gaaaatggca ttcccgtcag gcaaagttga agggtgcatg  10020
gtacaagtaa cctgtggaac tacaactctt aatggattgt ggttggatga cacagtatac  10080
tgtccaagac atgtcatttg cacagcagaa gacatgctta atcctaacta tgaagatctg  10140
ctcattcgca aatccaacca tagctttctt gttcaggctg gcaatgttca acttcgtgtt  10200
attggccatt ctatgcaaaa ttgtctgctt aggcttaaag ttgatacttc taaccctaag  10260
acacccaagt ataaatttgt ccgtatccaa cctggtcaaa cattttcagt tctagcatgc  10320
tacaatggtt caccatctgg tgtttatcag tgtgccatga gacctaatca taccattaaa  10380
ggttctttcc ttaatggatc atgtggtagt gttggtttta acattgatta tgattgcgtg  10440
tctttctgct atatgcatca tatggagctt ccaacaggag tacacgctgg tactgactta  10500
gaaggtaaat tctatggtcc atttgttgac agacaaactg cacaggctgc aggtacagac  10560
acaaccataa cattaaatgt tttggcatgg ctgtatgctg ctgttatcaa tggtgatagg  10620
tggtttctta atagattcac cactactttg aatgacttta accttgtggc aatgaagtac  10680
aactatgaac ctttgacaca agatcatgtt gacatattgg gacctctttc tgctcaaaca  10740
ggaattgccg tcttagatat gtgtgctgct ttgaaagagc tgctgcagaa tggtatgaat  10800
ggtcgtacta tccttggtag cactatttta gaagatgagt ttacaccatt tgatgttgtt  10860
agacaatgct ctggtgttac cttccaaggt aagttcaaga aaattgttaa gggcactcat  10920
cattggatgc ttttaacttt cttgacatca ctattgattc ttgttcaaag tacacagtgg  10980
tcactgtttt tctttgttta cgagaatgct ttcttgccat ttactcttgg tattatggca  11040
attgctgcat gtgctatgct gcttgttaag cataagcacg cattcttgtg cttgtttctg  11100
ttaccttctc ttgcaacagt tgcttacttt aatatggtct acatgcctgc tagctgggtg  11160
atgcgtatca tgacatggct tgaattggct gacactagct tgtctggtta taggcttaag  11220
gattgtgtta tgtatgcttc agctttagtt ttgcttattc tcatgacagc tcgcactgtt  11280
tatgatgatg ctgctagacg tgtttggaca ctgatgaatg tcattacact tgtttacaaa  11340
gtctactatg gtaatgcttt agatcaagct atttccatgt gggccttagt tatttctgta  11400
acctctaact attctggtgt cgttacgact atcatgtttt tagctagagc tatagtgttt  11460
gtgtgtgttg agtattaccc attgttattt attactggca acaccttaca gtgtatcatg  11520
cttgtttatt gtttcttagg ctattgttgc tgctgctact ttggcctttt ctgtttactc  11580
aaccgttact tcaggcttac tcttggtgtt tatgactact tggtctctac acaagaattt  11640
aggtatatga actcccaggg gcttttgcct cctaagagta gtattgatgc tttcaagctt  11700
aacattaagt tgttgggtat tggaggtaaa ccatgtatca aggttgctac tgtacagtct  11760
aaaatgtctg acgtaaagtg cacatctgtg gtactgctct cggttcttca acaacttaga  11820
gtagagtcat cttctaaatt gtgggcacaa tgtgtacaac tccacaatga tattcttctt  11880
```

-continued

```
gcaaaagaca caactgaagc tttcgagaag atggtttctc ttttgtctgt tttgctatcc  11940
atgcagggtg ctgtagacat taataggttg tgcgaggaaa tgctcgataa ccgtgctact  12000
cttcaggcta ttgcttcaga atttagttct ttaccatcat atgccgctta tgccactgcc  12060
caggaggcct atgagcaggc tgtagctaat ggtgattctg aagtcgttct caaaaagtta  12120
aagaaatctt tgaatgtggc taaatctgag tttgaccgtg atgctgccat gcaacgcaag  12180
ttggaaaaga tggcagatca ggctatgacc caaatgtaca aacaggcaag atctgaggac  12240
aagagggcaa aagtaactag tgctatgcaa acaatgctct tcactatgct taggaagctt  12300
gataatgatg cacttaacaa cattatcaac aatgcgcgtg atggttgtgt tccactcaac  12360
atcataccat tgactacagc agccaaactc atggttgttg tccctgatta tggtacctac  12420
aagaacactt gtgatggtaa cacctttaca tatgcatctg cactctggga aatccagcaa  12480
gttgttgatg cggatagcaa gattgttcaa cttagtgaaa ttaacatgga caattcacca  12540
aatttggctt ggcctcttat tgttacagct ctaagagcca actcagctgt taaactacag  12600
aataatgaac tgagtccagt agcactacga cagatgtcct gtgcggctgg taccacacaa  12660
acagcttgta ctgatgacaa tgcacttgcc tactataaca attcgaaggg aggtaggttt  12720
gtgctggcat tactatcaga ccaccaagat ctcaaatggg ctagattccc taagagtgat  12780
ggtacaggta caatttacac agaactggaa ccaccttgta ggtttgttac agacacacca  12840
aaagggccta aagtgaaata cttgtacttc atcaaaggct taaacaacct aaatagaggt  12900
atggtgctgg gcagtttagc tgctacagta cgtcttcagg ctggaaatgc tacagaagta  12960
cctgccaatt caactgtgct ttccttctgt gcttttgcag tagaccctgc taaagcatat  13020
aaggattacc tagcaagtgg aggacaacca atcaccaact gtgtgaagat gttgtgtaca  13080
cacactggta caggacaggc aattactgta acaccagaag ctaacatgga ccaagagtcc  13140
tttggtggtg cttcatgttg tctgtattgt agatgccaca ttgaccatcc aaatcctaaa  13200
ggattctgtg acttgaaagg taagtacgtc caaataccta ccacttgtgc taatgaccca  13260
gtgggtttta cacttagaaa cacagtctgt accgtctgcg gaatgtggaa aggttatggc  13320
tgtagttgtg accaactccg cgaacccttg atgcagtctg cggatgcatc aacgtttta  13380
aacgggtttg cggtgtaagt gcagcccgtc ttacaccgtg cggcacaggc actagtactg  13440
atgtcgtcta cagggctttt gatatttaca acgaaaaagt tgctggtttt gcaaagttcc  13500
taaaaactaa ttgctgtcgc ttccaggaga aggatgagga aggcaattta ttagactctt  13560
actttgtagt taagaggcat actatgtcta actaccaaca tgaagagact atttataact  13620
tggttaaaga ttgtccagcg gttgctgtcc atgacttttt caagtttaga gtagatggtg  13680
acatggtacc acatatatca cgtcagcgtc taactaaata cacaatggct gatttagtct  13740
atgctctacg tcattttgat gagggtaatt gtgatacatt aaaagaaata ctcgtcacat  13800
acaattgctg tgatgatgat tatttcaata agaaggattg gtatgacttc gtagagaatc  13860
ctgacatctt acgcgtatat gctaacttag gtgagcgtgt acgccaatca ttattaaaga  13920
ctgtacaatt ctgcgatgct atgcgtgatg caggcattgt aggcgtactg acattagata  13980
atcaggatct taatgggaac tggtacgatt tcggtgattt cgtacaagta gcaccaggct  14040
gcggagttcc tattgtggat tcatattact cattgctgat gcccatcctc actttgacta  14100
gggcattggc tgctgagtcc catatggatg ctgatctcgc aaaaccactt attaagtggg  14160
atttgctgaa atatgatttt acggaagaga gactttgtct cttcgaccgt tattttaaat  14220
```

-continued

```
attgggacca gacataccat cccaattgta ttaactgttt ggatgatagg tgtatccttc  14280
attgtgcaaa ctttaatgtg ttattttcta ctgtgtttcc acctacaagt tttggaccac  14340
tagtaagaaa aatatttgta gatggtgttc cttttgttgt ttcaactgga taccattttc  14400
gtgagttagg agtcgtacat aatcaggatg taaacttaca tagctcgcgt ctcagtttca  14460
aggaactttt agtgtatgct gctgatccag ctatgcatgc agcttctggc aatttattgc  14520
tagataaacg cactacatgc ttttcagtag ctgcactaac aaacaatgtt gcttttcaaa  14580
ctgtcaaacc cggtaatttt aataaagact tttatgactt tgctgtgtct aaaggtttct  14640
ttaaggaagg aagttctgtt gaactaaaac acttcttctt tgctcaggat ggcaacgctg  14700
ctatcagtga ttatgactat tatcgttata atctgccaac aatgtgtgat atcagacaac  14760
tcctattcgt agttgaagtt gttgataaat actttgattg ttacgatggt ggctgtatta  14820
atgccaacca agtaatcgtt aacaatctgg ataaatcagc tggtttccca tttaataaat  14880
ggggtaaggc tagactttat tatgactcaa tgagttatga ggatcaagat gcacttttcg  14940
cgtatactaa gcgtaatgtc atccctacta taactcaaat gaatcttaag tatgccatta  15000
gtgcaaagaa tagagctcgc accgtagctg gtgtctctat ctgtagtact atgacaaata  15060
gacagtttca tcagaaatta ttgaagtcaa tagccgccac tagaggagct actgtggtaa  15120
ttggaacaag caagttttac ggtggctggc ataatatgtt aaaaactgtt tacagtgatg  15180
tagaaactcc acaccttatg ggttgggatt atccaaaatg tgacagagcc atgcctaaca  15240
tgcttaggat aatggcctct cttgttcttg ctcgcaaaca taacacttgc tgtaacttat  15300
cacaccgttt ctacaggtta gctaacgagt gtgcgcaagt attaagtgag atggtcatgt  15360
gtggcggctc actatatgtt aaaccaggtg gaacatcatc cggtgatgct acaactgctt  15420
atgctaatag tgtctttaac atttgtcaag ctgttacagc caatgtaaat gcacttcttt  15480
caactgatgg taataagata gctgacaagt atgtccgcaa tctacaacac aggctctatg  15540
agtgtctcta tagaaatagg gatgttgatc atgaattcgt ggatgagttt tacgcttacc  15600
tgcgtaaaca tttctccatg atgattcttt ctgatgatgc cgttgtgtgc tataacagta  15660
actatgcggc tcaaggttta gtagctagca ttaagaactt taaggcagtt ctttattatc  15720
aaaataatgt gttcatgtct gaggcaaaat gttggactga gactgacctt actaaaggac  15780
ctcacgaatt ttgctcacag catacaatgc tagttaaaca aggagatgat tacgtgtacc  15840
tgccttaccc agatccatca agaatattag gcgcaggctg ttttgtcgat gatattgtca  15900
aaacagatgg tacacttatg attgaaaggt tcgtgtcact ggctattgat gcttacccac  15960
ttacaaaaca tcctaatcag gagtatgctg atgtctttca cttgtattta caatacatta  16020
gaaagttaca tgatgagctt actggccaca tgttggacat gtattccgta atgctaacta  16080
atgataacac ctcacggtac tgggaacctg agttttatga ggctatgtac acaccacata  16140
cagtcttgca ggctgtaggt gcttgtgtat tgtgcaattc acagacttca cttcgttgcg  16200
gtgcctgtat taggagacca ttcctatgtt gcaagtgctg ctatgaccat gtcatttcaa  16260
catcacacaa attagtgttg tctgttaatc cctatgtttg caatgcccca ggttgtgatg  16320
tcactgatgt gacacaactg tatctaggag gtatgagcta ttattgcaag tcacataagc  16380
ctcccattag ttttccatta tgtgctaatg gtcaggtttt tggtttatac aaaaacacat  16440
gtgtaggcag tgacaatgtc actgacttca atgcgatagc aacatgtgat tggactaatg  16500
ctggcgatta catacttgcc aacacttgta ctgagagact caagcttttc gcagcagaaa  16560
cgctcaaagc cactgaggaa acatttaagc tgtcatatgg tattgccact gtacgcgaag  16620
```

-continued

```
tactctctga cagagaattg catctttcat gggaggttgg aaaacctaga ccaccattga  16680
acagaaacta tgtctttact ggttaccgtg taactaaaaa tagtaaagta cagattggag  16740
agtacacctt tgaaaaaggt gactatggtg atgctgttgt gtacagaggt actacgacat  16800
acaagttgaa tgttggtgat tactttgtgt tgacatctca cactgtaatg ccacttagtg  16860
cacctactct agtgccacaa gagcactatg tgagaattac tggcttgtac ccaacactca  16920
acatctcaga tgagttttct agcaatgttg caaattatca aaaggtcggc atgcaaaagt  16980
actctacact ccaaggacca cctggtactg gtaagagtca ttttgccatc ggacttgctc  17040
tctattaccc atctgctcgc atagtgtata cggcatgctc tcatgcagct gttgatgccc  17100
tatgtgaaaa ggcattaaaa tatttgccca tagataaatg tagtagaatc atacctgcgc  17160
gtgcgcgcgt agagtgtttt gataaattca aagtgaattc aacactagaa cagtatgttt  17220
tctgcactgt aaatgcattg ccagaaacaa ctgctgacat tgtagtcttt gatgaaatct  17280
ctatggctac taattatgac ttgagtgttg tcaatgctag acttcgtgca aaacactacg  17340
tctatattgg cgatcctgct caattaccag ccccccgcac attgctgact aaaggcacac  17400
tagaaccaga atattttaat tcagtgtgca gacttatgaa aacaataggt ccagacatgt  17460
tccttggaac ttgtcgccgt tgtcctgctg aaattgttga cactgtgagt gctttagttt  17520
atgacaataa gctaaaagca cacaaggaga agtcagctca atgcttcaaa atgttctaca  17580
aaggtgttat tacacatgat gtttcatctg caatcaacag acctcaaata ggcgttgtaa  17640
gagaatttct tacacgcaat cctgcttgga gaaaagctgt ttttatctca ccttataatt  17700
cacagaacgc tgtagcttca aaaatcttag gattgcctac gcagactgtt gattcatcac  17760
agggttctga atatgactat gtcatattca cacaaactac tgaaacagca cactcttgta  17820
atgtcaaccg tttcaatgtg gctatcacaa gggcaaaaat tggcattttg tgcataatgt  17880
ctgatagaga tctttatgac aaactgcaat ttacaagtct agaaatacca cgtcgcaatg  17940
tggctacatt acaagcagaa aatgtaactg gactttttaa ggactgtagt aagatcatta  18000
ctggtcttca tcctacacag gcacctacac acctcagcgt tgatataaag ttcaagactg  18060
aaggattatg tgttgacata ccaggcatac caaaggacat gacctaccgt agactcatct  18120
ctatgatggg tttcaaaatg aattaccaag tcaatggtta ccctaatatg tttatcaccc  18180
gcgaagaagc tattcgtcac gttcgtgcgt ggattggctt tgatgtagag ggctgtcatg  18240
caactagaga tgctgtgggt actaacctac ctctccagct aggattttct acaggtgtta  18300
acttagtagc tgtaccgact ggttatgttg acactgaaaa taacacagaa ttcaccagag  18360
ttaatgcaaa acctccacca ggtgaccagt ttaaacatct tataccactc atgtataaag  18420
gcttgccctg gaatgtagtg cgtattaaga tagtacaaat gctcagtgat acactgaaag  18480
gattgtcaga cagagtcgtg ttcgtccttt gggcgcatgg ctttgagctt acatcaatga  18540
agtactttgt caagattgga cctgaaagaa cgtgttgtct gtgtgacaaa cgtgcaactt  18600
gcttttctac ttcatcagat acttatgcct gctggaatca ttctgtgggt tttgactatg  18660
tctataaccc atttatgatt gatgttcagc agtggggctt tacgggtaac cttcagagta  18720
accatgacca acattgccag gtacatggaa atgcacatgt ggctagttgt gatgctatca  18780
tgactagatg tttagcagtc catgagtgct ttgttaagcg cgttgattgg tctgttgaat  18840
accctattat aggagatgaa ctgagggtta attctgcttg cagaaaagta caacacatgg  18900
ttgtgaagtc tgcattgctt gctgataagt ttccagttct tcatgacatt ggaaatccaa  18960
```

-continued

```
aggctatcaa gtgtgtgcct caggctgaag tagaatggaa gttctacgat gctcagccat  19020
gtagtgacaa agcttacaaa atagaggagc tcttctattc ttatgctaca catcacgata  19080
aattcactga tggtgtttgt ttgttttgga attgtaacgt tgatcgttac ccagccaatg  19140
caattgtgtg taggtttgac acaagagtct tgtcaaactt gaacttacca ggctgtgatg  19200
gtggtagttt gtatgtgaat aagcatgcat tccacactcc agctttcgat aaaagtgcat  19260
ttactaattt aaagcaattg cctttctttt actattctga tagtccttgt gagtctcatg  19320
gcaaacaagt agtgtcggat attgattatg ttccactcaa atctgctacg tgtattacac  19380
gatgcaattt aggtggtgct gtttgcagac accatgcaaa tgagtaccga cagtacttgg  19440
atgcatataa tatgatgatt tctgctggat ttagcctatg gatttacaaa caatttgata  19500
cttataacct gtggaataca tttaccaggt tacagagttt agaaaatgtg gcttataatg  19560
ttgttaataa aggacacttt gatggacacg ccggcgaagc acctgtttcc atcattaata  19620
atgctgttta cacaaaggta gatggtattg atgtggagat ctttgaaaat aagacaacac  19680
ttcctgttaa tgttgcattt gagctttggg ctaagcgtaa cattaaacca gtgccagaga  19740
ttaagatact caataatttg ggtgttgata tcgctgctaa tactgtaatc tgggactaca  19800
aaagagaagc cccagcacat gtatctacaa taggtgtctg cacaatgact gacattgcca  19860
agaaacctac tgagagtgct tgttcttcac ttactgtctt gtttgatggt agagtggaag  19920
gacaggtaga cctttttaga aacgcccgta atggtgtttt aataacagaa ggttcagtca  19980
aaggtctaac accttcaaag ggaccagcac aagctagcgt caatggagtc acattaattg  20040
gagaatcagt aaaaacacag tttaactact ttaagaaagt agacggcatt attcaacagt  20100
tgcctgaaac ctactttact cagagcagag acttagagga ttttaagccc agatcacaaa  20160
tggaaactga ctttctcgag ctcgctatgg atgaattcat acagcgatat aagctcgagg  20220
gctatgcctt cgaacacatc gtttatggag atttcagtca tggacaactt ggcggtcttc  20280
atttaatgat aggcttagcc aagcgctcac aagattcacc acttaaatta gaggatttta  20340
tccctatgga cagcacagtg aaaaattact tcataacaga tgcgcaaaca ggttcatcaa  20400
aatgtgtgtg ttctgtgatt gatcttttac ttgatgactt tgtcgagata ataaagtcac  20460
aagatttgtc agtgatttca aaagtggtca aggttacaat tgactatgct gaaatttcat  20520
tcatgctttg gtgtaaggat ggacatgttg aaaccttcta cccaaaacta caagcaagtc  20580
aagcgtggca accaggtgtt gcgatgccta acttgtacaa gatgcaaaga atgcttcttg  20640
aaaagtgtga ccttcagaat tatggtgaaa atgctgttat accaaaagga ataatgatga  20700
atgtcgcaaa gtatactcaa ctgtgtcaat acttaaatac acttacttta gctgtaccct  20760
acaacatgag agttattcac tttggtgctg gctctgataa aggagttgca ccaggtacag  20820
ctgtgctcag acaatggttg ccaactggca cactacttgt cgattcagat cttaatgact  20880
tcgtctccga cgcagattct actttaattg gagactgtgc aacagtacat acggctaata  20940
aatgggacct tattattagc gatatgtatg accctaggac caaacatgtg acaaaagaga  21000
atgactctaa agaagggttt ttcacttatc tgtgtggatt tataaagcaa aaactagccc  21060
tgggtggttc tatagctgta aagataacag agcattcttg gaatgctgac ctttacaagc  21120
ttatgggcca tttctcatgg tggacagctt ttgttacaaa tgtaaatgca tcatcatcgg  21180
aagcattttt aattggggct aactatcttg gcaagccgaa ggaacaaatt gatggctata  21240
ccatgcatgc taactacatt ttctggagga acacaaatcc tatccagttg tcttcctatt  21300
cactctttga catgagcaaa tttcctctta aattaagagg aactgctgta atgtctctta  21360
```

-continued

```
aggagaatca aatcaatgat atgatttatt ctcttctgga aaaaggtagg cttatcatta  21420
gagaaaacaa cagagttgtg gtttcaagtg atattcttgt taacaactaa acgaacatgt  21480
ttattttctt attatttctt actctcacta gtggtagtga ccttgaccgg tgcaccactt  21540
ttgatgatgt tcaagctcct aattacactc aacatacttc atctatgagg ggggtttact  21600
atcctgatga aatttttaga tcagacactc tttatttaac tcaggattta tttcttccat  21660
tttattctaa tgttacaggg tttcatacta ttaatcatac gtttgacaac cctgtcatac  21720
cttttaagga tggtatttat tttgctgcca cagagaaatc aaatgttgtc cgtggttggg  21780
tttttggttc taccatgaac aacaagtcac agtcggtgat tattattaac aattctacta  21840
atgttgttat acgagcatgt aactttgaat tgtgtgacaa ccctttcttt gctgtttcta  21900
aacccatggg tacacagaca catactatga tattcgataa tgcatttaat tgcactttcg  21960
agtacatatc tgatgccttt tcgcttgatg tttcagaaaa gtcaggtaat tttaaacact  22020
tacgagagtt tgtgtttaaa aataaagatg ggtttctcta tgtttataag ggctatcaac  22080
ctatagatgt agttcgtgat ctaccttctg gttttaacac tttgaaacct atttttaagt  22140
tgcctcttgg tattaacatt acaaatttta gagccattct tacagccttt tcacctgctc  22200
aagacacttg gggcacgtca gctgcagcct attttgttgg ctatttaaag ccaactacat  22260
ttatgctcaa gtatgatgaa aatggtacaa tcacagatgc tgttgattgt tctcaaaatc  22320
cacttgctga actcaaatgc tctgttaaga gctttgagat tgacaaagga atttaccaga  22380
cctctaattt cagggttgtt ccctcaggag atgttgtgag attccctaat attacaaact  22440
tgtgtccttt tggagaggtt tttaatgcta ctaaattccc ttctgtctat gcatgggaga  22500
gaaaaaaaat ttctaattgt gttgctgatt actctgtgct ctacaactca acattttttt  22560
caacctttaa gtgctatggc gtttctgcca ctaagttgaa tgatctttgc ttctccaatg  22620
tctatgcaga ttcttttgta gtcaagggag atgatgtaag acaaatagcg ccaggacaaa  22680
ctggtgttat tgctgattat aattataaat tgccagatga tttcatgggt tgtgtccttg  22740
cttggaatac taggaacatt gatgctactt caactggtaa ttataattat aaatataggt  22800
atcttagaca tggcaagctt aggccctttg agagagacat atctaatgtg cctttctccc  22860
ctgatggcaa accttgcacc ccacctgctc ttaattgtta ttggccatta aatgattatg  22920
gtttttacac cactactggc attggctacc aaccttacag agttgtagta ctttcttttg  22980
aacttttaaa tgcaccggcc acggtttgtg gaccaaaatt atccactgac cttattaaga  23040
accagtgtgt caattttaat tttaatggac tcactggtac tggtgtgtta actccttctt  23100
caaagagatt tcaaccattt caacaatttg gccgtgatgt ttctgatttc actgattccg  23160
ttcgagatcc taaaacatct gaaatattag acatttcacc ttgctctttt gggggtgtaa  23220
gtgtaattac acctggaaca aatgcttcat ctgaagttgc tgttctatat caagatgtta  23280
actgcactga tgtttctaca gcaattcatg cagatcaact cacaccagct tggcgcatat  23340
attctactgg aaacaatgta ttccagactc aagcaggctg tcttatagga gctgagcatg  23400
tcgacacttc ttatgagtgc gacattccta ttggagctgg catttgtgct agttaccata  23460
cagtttcttt attacgtagt actagccaaa aatctattgt ggcttatact atgtctttag  23520
gtgctgatag ttcaattgct tactctaata acaccattgc tatacctact aacttttcaa  23580
ttagcattac tacagaagta atgcctgttt ctatggctaa aacctccgta gattgtaata  23640
tgtacatctg cggagattct actgaatgtg ctaatttgct tctccaatat ggtagctttt  23700
```

-continued

```
gcacacaact aaatcgtgca ctctcaggta ttgctgctga acaggatcgc aacacacgtg  23760
aagtgttcgc tcaagtcaaa caaatgtaca aaaccccaac tttgaaatat tttggtggtt  23820
ttaatttttc acaaatatta cctgaccctc taaagccaac taagaggtct tttattgagg  23880
acttgctctt taataaggtg acactcgctg atgctggctt catgaagcaa tatggcgaat  23940
gcctaggtga tattaatgct agagatctca tttgtgcgca gaagttcaat ggacttacag  24000
tgttgccacc tctgctcact gatgatatga ttgctgccta cactgctgct ctagttagtg  24060
gtactgccac tgctggatgg acatttggtg ctggcgctgc tcttcaaata ccttttgcta  24120
tgcaaatggc atataggttc aatggcattg gagttaccca aaatgttctc tatgagaacc  24180
aaaaacaaat cgccaaccaa tttaacaagg cgattagtca aattcaagaa tcacttacaa  24240
caacatcaac tgcattgggc aagctgcaag acgttgttaa ccagaatgct caagcattaa  24300
acacacttgt taaacaactt agctctaatt ttggtgcaat ttcaagtgtg ctaaatgata  24360
tcctttcgcg acttgataaa gtcgaggcgg aggtacaaat tgacaggtta attacaggca  24420
gacttcaaag ccttcaaacc tatgtaacac aacaactaat cagggctgct gaaatcaggg  24480
cttctgctaa tcttgctgct actaaaatgt ctgagtgtgt tcttggacaa tcaaaaagag  24540
ttgacttttg tggaaagggc taccacctta tgtccttccc acaagcagcc ccgcatggtg  24600
ttgtcttcct acatgtcacg tatgtgccat cccaggagag gaacttcacc acagcgccag  24660
caatttgtca tgaaggcaaa gcatacttcc ctcgtgaagg tgtttttgtg tttaatggca  24720
cttcttggtt tattacacag aggaacttct tttctccaca aataattact acagacaata  24780
catttgtctc aggaaattgt gatgtcgtta ttggcatcat taacaacaca gtttatgatc  24840
ctctgcaacc tgagcttgac tcattcaaag aagagctgga caagtacttc aaaaatcata  24900
catcaccaga tgttgatctt ggcgacattt caggcattaa cgcttctgtc gtcaacattc  24960
aaaaagaaat tgaccgcctc aatgaggtcg ctaaaaattt aaatgaatca ctcattgacc  25020
ttcaagaatt gggaaaatat gagcaatata ttaaatggcc ttggtatgtt tggctcggct  25080
tcattgctgg actaattgcc atcgtcatgg ttacaatctt gctttgttgc atgactagtt  25140
gttgcagttg cctcaagggt gcatgctctt gtggttcttg ctgcaagttt gatgaggatg  25200
actctgagcc agttctcaag ggtgtcaaat tacattacac ataaacgaac ttatggattt  25260
gtttatgaga tttttttactc ttggatcaat tactgcacag ccagtaaaaa ttgacaatgc  25320
ttctcctgca agtactgttc atgctacagc aacgataccg ctacaagcct cactcccttt  25380
cggatggctt gttattggcg ttgcatttct tgctgttttt cagagcgcta ccaaaataat  25440
tgcgctcaat aaaagatggc agctagccct ttataagggc ttccagttca tttgcaattt  25500
actgctgcta tttgttacca tctattcaca tcttttgctt gtcgctgcag gtatggaggc  25560
gcaatttttg tacctctatg ccttgatata ttttctacaa tgcatcaacg catgtagaat  25620
tattatgaga tgttggcttt gttggaagtg caaatccaag aacccattac tttatgatgc  25680
caactacttt gtttgctggc acacacataa ctatgactac tgtataccat ataacagtgt  25740
cacagataca attgtcgtta ctgaaggtga cggcatttca acaccaaaac tcaaagaaga  25800
ctaccaaatt ggtggttatt ctgaggatag gcactcaggt gttaaagact atgtcgttgt  25860
acatggctat ttcaccgaag tttactacca gcttgagtct acacaaatta ctacagacac  25920
tggtattgaa aatgctacat tcttcatctt taacaagctt gttaaagacc caccgaatgt  25980
gcaaatacac acaatcgacg gctcttcagg agttgctaat ccagcaatgg atccaattta  26040
tgatgagccg acgacgacta ctagcgtgcc tttgtaagca caagaaagtg agtacgaact  26100
```

-continued

```
tatgtactca ttcgtttcgg aagaaacagg tacgttaata gttaatagcg tacttctttt  26160
tcttgctttc gtggtattct tgctagtcac actagccatc cttactgcgc ttcgattgtg  26220
tgcgtactgc tgcaatattg ttaacgtgag tttagtaaaa ccaacggttt acgtctactc  26280
gcgtgttaaa aatctgaact cttctgaagg agttcctgat cttctggtct aaacgaacta  26340
actattatta ttattctgtt tggaacttta acattgctta tcatggcaga caacggtact  26400
attaccgttg aggagcttaa acaactcctg gaacaatgga acctagtaat aggtttccta  26460
ttcctagcct ggattatgtt actacaattt gcctattcta atcggaacag gtttttgtac  26520
ataataaagc ttgttttcct ctggctcttg tggccagtaa cacttgcttg ttttgtgctt  26580
gctgctgtct acagaattaa ttgggtgact ggcgggattg cgattgcaat ggcttgtatt  26640
gtaggcttga tgtggcttag ctacttcgtt gcttccttca ggctgtttgc tcgtacccgc  26700
tcaatgtggt cattcaaccc agaaacaaac attcttctca atgtgcctct ccgggggaca  26760
attgtgacca gaccgctcat ggaaagtgaa cttgtcattg gtgctgtgat cattcgtggt  26820
cacttgcgaa tggccggaca ctccctaggg cgctgtgaca ttaaggacct gccaaaagag  26880
atcactgtgg ctacatcacg aacgctttct tattacaaat taggagcgtc gcagcgtgta  26940
ggcactgatt caggttttgc tgcatacaac cgctaccgta ttggaaacta taaattaaat  27000
acagaccacg ccggtagcaa cgacaatatt gctttgctag tacagtaagt gacaacagat  27060
gtttcatctt gttgacttcc aggttacaat agcagagata ttgattatca ttatgaggac  27120
tttcaggatt gctatttgga atcttgacgt tataataagt tcaatagtga gacaattatt  27180
taagcctcta actaagaaga attattcgga gttagatgat gaagaaccta tggagttaga  27240
ttatccataa aacgaacatg aaaattattc tcttcctgac attgattgta tttacatctt  27300
gcgagctata tcactatcag gagtgtgtta gaggtacgac tgtactacta aaagaacctt  27360
gcccatcagg aacatacgag ggcaattcac catttcaccc tcttgctgac aataaatttg  27420
cactaacttg cactagcaca cactttgctt ttgcttgtgc tgacggtact cgacatacct  27480
atcagctgcg tgcaagatca gtttcaccaa aacttttcat cagacaagag gaggttcaac  27540
aagagctcta ctcgccactt tttctcattg ttgctgctct agtattttta atactttgct  27600
tcaccattaa gagaaagaca gaatgaatga gctcacttta attgacttct atttgtgctt  27660
tttagccttt ctgctattcc ttgttttaat aatgcttatt atattttggt tttcactcga  27720
aatccaggat ctagaagaac cttgtaccaa agtctaaacg aacatgaaac ttctcattgt  27780
tttgacttgt atttctctat gcagttgcat acgcactgta gtacagcgct gtgcatctaa  27840
taaacctcat gtgcttgaag atccttgtaa ggtacaacac taggggtaat acttatagca  27900
ctgcttggct ttgtgctcta ggaaaggttt taccttttca tagatggcac actatggttc  27960
aaacatgcac acctaatgtt actatcaact gtcaagatcc agctggtggt gcgcttatag  28020
ctaggtgttg gtaccttcat gaaggtcacc aaactgctgc atttagagac gtacttgttg  28080
ttttaaataa acgaacaaat taaaatgtct gataatggac cccaatcaaa ccaacgtagt  28140
gccccccgca ttacatttgg tggacccaca gattcaactg acaataacca gaatggagga  28200
cgcaatgggg caaggccaaa acagcgccga ccccaaggtt tacccaataa tactgcgtct  28260
tggttcacag ctctcactca gcatggcaag gaggaactta gattccctcg aggccagggc  28320
gttccaatca acaccaatag tggtccagat gaccaaattg gctactaccg aagagctacc  28380
cgacgagttc gtggtggtga cggcaaaatg aaagagctca gccccagatg gtacttctat  28440
```

-continued

```
tacctaggaa ctggcccaga agcttcactt ccctacggcg ctaacaaaga aggcatcgta  28500
tgggttgcaa ctgagggagc cttgaataca cccaaagacc acattggcac ccgcaatcct  28560
aataacaatg ctgccaccgt gctacaactt cctcaaggaa caacattgcc aaaaggcttc  28620
tacgcagagg gaagcagagg cggcagtcaa gcctcttctc gctcctcatc acgtagtcgc  28680
ggtaattcaa gaaattcaac tcctggcagc agtaggggaa attctcctgc tcgaatggct  28740
agcggaggtg gtgaaactgc cctcgcgcta ttgctgctag acagattgaa ccagcttgag  28800
agcaaagttt ctggtaaagg ccaacaacaa caaggccaaa ctgtcactaa gaaatctgct  28860
gctgaggcat ctaaaaagcc tcgccaaaaa cgtactgcca caaaacagta caacgtcact  28920
caagcatttg ggagacgtgg tccagaacaa acccaaggaa atttcgggga ccaagaccta  28980
atcagacaag gaactgatta caaacattgg ccgcaaattg cacaatttgc tccaagtgcc  29040
tctgcattct ttggaatgtc acgcattggc atggaagtca caccttcggg aacatggctg  29100
acttatcatg gagccattaa attggatgac aaagatccac aattcaaaga caacgtcata  29160
ctgctgaaca agcacattga cgcatacaaa acattcccac caacagagcc taaaaaggac  29220
aaaaagaaaa agactgatga agctcagcct ttgccgcaga gacaaaagaa gcagcccact  29280
gtgactcttc ttcctgcggc tgacatggat gatttctcca gacaacttca aaattccatg  29340
agtggagctt ctgctgattc aactcaggca taaacactca tgatgaccac acaaggcaga  29400
tgggctatgt aaacgttttc gcaattccgt ttacgataca tagtctactc ttgtgcagaa  29460
tgaattctcg taactaaaca gcacaagtag gtttagttaa ctttaatctc acatagcaat  29520
ctttaatcaa tgtgtaacat tagggaggac ttgaaagagc caccacattt tcatcgaggc  29580
cacgcggagt acgatcgagg gtacagtgaa taatgctagg gagagctgcc tatatggaag  29640
agccctaatg tgtaaaatta attttagtag tgctatcccc atgtgatttt aatagcttct  29700
taggagaatg acaaaaaaaa aaaaaaaaaa aaaaaa                            29736
```

<210> SEQ ID NO 4
<211> LENGTH: 1706
<212> TYPE: DNA
<213> ORGANISM: SARS-CoV Shanghai LY

<400> SEQUENCE: 4

```
tctgtgtagc tgtcgctcgg ctgcatgcct agtgcaccta cgcagtataa acaataataa     60
attttactgt cgttgacaag aaacgagtaa ctcgtccctc ttctgcagac tgcttacggt    120
ttcgtccgtg ttgcagtcga tcatcagcat acctaggttt cgtccgggtg tgaccgaaag    180
gtaagatgga gagccttgtt cttggtgtca acgagaaaac acacgtccaa ctcagtttgc    240
ctgtccttca ggttagagac gtgctagtgc gtggcttcgg ggactctgtg gaagaggccc    300
tatcggaggc acgtgaacac ctcaaaaatg gcacttgtgg tctagtagag ctggaaaaag    360
gcgtactgcc ccagcttgaa cagccctatg tgttcattaa acgttctgat gccttaagca    420
ccaatcacgg ccacaaggtc gttgagctgg ttgcagaaat ggacggcatt cagtacggtc    480
gtagcggtat aacactggga gtactcgtgc cacatgtggg cgaaacccca attgcatacc    540
gcaatgttct tcttcgtaag aacggtaata agggagccgg tggtcatagc tatggcatcg    600
atctaaagtc ttatgactta ggtgacgagc ttggcactga tcccattgaa gattatgaac    660
aaaactggaa cactaagcat ggcagtggtg cactccgtga actcactcgt gagctcaatg    720
gaggtgtagt cactcgctat gtcgacaaca atttctgtgg cccagatggg taccctcttg    780
attgcatcaa agattttcta gcacgcgcgg gcaagtcaat gtgcactctt tccgaacaac    840
```

-continued

```
ttgattacat cgagtcgaag agaggtgtct actgctgccg tgaccatgag catgaaattg    900
cctggttcac tgagcgctct gataagagct gcgagcacca gacacccttc gaaattaaga    960
gtgccaagaa atttgacact ttcaaagggg aatgcccaaa gtttgtgttt cctcttaact   1020
caaaagtcaa agtcattcaa ccacgtgttg aaaagaaaaa gactgagggt ttcatggggc   1080
gtatacgctc tgtgtaccct gttgcatctc cacaggagtg taacaatatg cacttgtcta   1140
ccttgatgaa atgtaatcat tgcgatgaag tttcatggca gacgtgcgac tttctgaaag   1200
ccacttgtga acattgtggc actgaaaatt tagttattga aggacctact acatgtgggt   1260
acctacctac taatgctgta gtgaaaatgc catgtcctgc ctgtcaagac ccagagattg   1320
gacctgagca tagtgttgca gattatcaca accactcaaa cattgaaact cgactccgca   1380
agggaggtag gactagatgt tttggaggct gtgtgtttgc ctatgttggc tgctataata   1440
agcgtgccta ctgggttcct cgtgctagtg ctgatattgg ctcaggccat actggcatta   1500
ctggtgacaa tgtggagacc ttgaatgagg atctccttga gatactgagt cgtgaacgtg   1560
ttaacattaa cattgttggc gattttcatt tgaatgaaga ggttgccatc attttggcat   1620
ctttctctgc ttctacaagt gcctttattg acactataaa gagtcttgat tacaagtctt   1680
tcaaaaccat tgttgagtcc tgcggt                                        1706
```

<210> SEQ ID NO 5
<211> LENGTH: 10546
<212> TYPE: DNA
<213> ORGANISM: SARS-CoV Shanghai LY

<400> SEQUENCE: 5

```
agtgttttat tagcacttca acagcttgaa gtcaaattca atgcaccagc acttcaagag     60
gcttattata gagcccgtgc tggtgatgct gctaactttt gtgcactcat actcgcttac    120
agtaataaaa ctgttggcga gcttggtgat gtcagagaaa ctatgaccca tcttctacag    180
catgctaatt tggaatctgc aaagcgagtt cttaatgtgg tgtgtaaaca ttgtggtcag    240
aaaactacta ccttaacggg tgtagaagct gtgatgtata tgggtactct atcttatgat    300
aatcttaaga caggtgtttc cattccatgt gtgtgtggtc gtgatgctac acaatatcta    360
gtacaacaag agtcttcttt tgttatgatg tctgcaccac ctgctgagta taaattacag    420
caaggtacat tcttatgtgc gaatgagtac actggtaact atcagtgtgg tcattacact    480
catataactg ctaaggagac cctctatcgt attgacggag ctcaccttac aaagatgtca    540
gagtacaaag gaccagtgac tgatgttttc tacaaggaaa catcttacac tacaaccatc    600
aagcctgtgt cgtataaact cgatggagtt acttacacag agattgaacc aaaattggat    660
gggtattata aaaaggataa tgcttactat acagagcagc ctatagacct tgtaccaact    720
caaccattac caaatgcgag ttttgataat ttcaaactca catgttctaa cacaaaattt    780
gctgatgatt taaatcaaat gacaggcttc acaaagccag cttcacgaga gctatctgtc    840
acattcttcc cagacttgaa tggcgatgta gtggctattg actatagaca ctattcagcg    900
agtttcaaga aaggtgctaa attactgcat aagccaattg tttggcacat taaccaggct    960
acaaccaaga caacgttcaa accaaacact tggtgtttac gttgtctttg gagtacaaag   1020
ccagtagata cttcaaattc atttgaagtt ctggcagtag aagacacaca aggaatggac   1080
aatcttgctt gtgaaagtca acaacccacc tctgaagaag tagtggaaaa tcctaccata   1140
cagaaggaag tcatagagtg tgacgtgaaa actaccgaag ttgtaggcaa tgtcatactt   1200
```

-continued

```
aaaccatcag atgaaggtgt taaagtaaca caagagttag gtcatgagga tcttatggct   1260
gcttatgtgg aaaacacaag cattaccatt aagaaaccta atgagctttc actagcctta   1320
ggtttaaaaa caattgccac tcatggtatt gctgcaatta atagtgttcc ttggagtaaa   1380
attttggctt atgtcaaacc attcttagga caagcagcaa ttacaacatc aaattgcgct   1440
aagagattag cacaacgtgt gtttaacaat tatatgcctt atgtgtttac attattgttc   1500
caattgtgta cttttactaa aagtaccaat tctagaatta gagcttcact acctacaact   1560
attgctaaaa atagtgttaa gagtgttgct aaattatgtt tggatgccgg cattaattat   1620
gtgaagtcac ccaaattttc taaattgttc acaatcgcta tgtggctatt gttgttaagt   1680
atttgcttag gttctctaat ctgtgtaact gctgcttttg gtgtactctt atctaatttt   1740
ggtgctcctt cttattgtaa tggcgttaga gaattgtatc ttaattcgtc taacgttact   1800
actatggatt tctgtgaagg ttcttttcct tgcagcattt gtttaagtgg attagactcc   1860
cttgattctt atccagctct tgaaaccatt caggtgacga tttcatcgta caagctagac   1920
ttgacaattt taggtctggc cgctgagtgg gttttggcat atatgttgtt cacaaaattc   1980
ttttatttat taggtctttc agctataatg caggtgttct ttggctattt tgctagtcat   2040
ttcatcagca attcttggct catgtggttt atcattagta ttgtacaaat ggcacccgtt   2100
tctgcaatgg ttaggatgta catcttcttt gcttctttct actacatatg gaagagctat   2160
gttcatatca tggatggttg cacctcttcg acttgcatga tgtgctataa gcgcaatcgt   2220
gccacacgcg ttgagtgtac aactattgtt aatggcatga agagatcttt ctatgtctat   2280
gcaaatggag gccgtggctt ctgcaagact cacaattgga attgtctcaa ttgtgacaca   2340
ttttgcactg gtagtacatt cattagtgat gaagttgctc gtgatttgtc actccagttt   2400
aaaagaccaa tcaaccctac tgaccagtca tcgtatattg ttgatagtgt tgctgtgaaa   2460
aatggcgcgc ttcacctcta ctttgacaag gctggtcaaa agacctatga gagacatccg   2520
ctctcccatt ttgtcaattt agacaatttg agagctaaca acactaaagg ttcactgcct   2580
attaatgtca tagtttttga tggcaagtcc aaatgcgacg agtctgcttc taagtctgct   2640
tctgtgtact acagtcagct gatgtgccaa cctattctgt tgcttgacca agctcttgta   2700
tcagacgttg gagatagtac tgaagtttcc gttaagatgt ttgatgctta tgtcgacacc   2760
ttttcagcaa cttttagtgt tcctatggaa aaacttaagg cacttgttgc tacagctcac   2820
agcgagttag caaagggtgt agctttagat ggtgtccttt ctacattcgt gtcagctgcc   2880
cgacaaggtg ttgttgatac cgatgttgac acaaaggatg ttattgaatg tctcaaactt   2940
tcacatcact ctgacttaga agtgacaggt gacagttgta acaatttcat gctcacctat   3000
aataaggttg aaaacatgac gcccagagat cttggcgcat gtattgactg taatgcaagg   3060
catatcaatg cccaagtagc aaaaagtcac aatgtttcac tcatctggaa tgtaaaagac   3120
tacatgtctt tatctgaaca gctgcgtaaa caaattcgta gtgctgccaa gaagaacaac   3180
ataccttta gactaacttg tgctacaact agacaggttg tcaatgtcat aactactaaa   3240
atctcactca agggtggtaa gattgttagt acttgtttta aacttatgct taaggccaca   3300
ttattgtgcg ttcttgctgc attggtttgt tatatcgtta tgccagtaca tacattgtca   3360
atccatgatg gttacacaaa tgaaatcatt ggttacaaag ccattcagga tggtgtcact   3420
cgtgacatca tttctactga tgattgtttt gcaaataaac atgctggttt tgacgcatgg   3480
tttagccagc gtggtggttc atacaaaaat gacaaaagct gccctgtagt agctgctatc   3540
attacaagag agattggttt catagtgcct ggcttaccgg gtactgtgct gagagcaatc   3600
```

-continued

```
aatggtgact tcttgcattt tctacctcgt gtttttagtg ctgttggcaa catttgctac   3660
acaccttcca aactcattga gtatagtgat tttgctacct ctgcttgcgt tcttgctgct   3720
gagtgtacaa tttttaagga tgctatgggc aaacctgtgc catattgtta tgacactaat   3780
ttgctagagg gttctatttc ttatagtgag cttcgtccag acactcgtta tgtgcttatg   3840
gatggttcca tcatacagtt tcctaacact tacctggagg gttctgttag agtagtaaca   3900
acttttgatg ctgagtactg tagacatggt acatgcgaaa ggtcagaagt aggtatttgc   3960
ctatctacca gtggtagatg ggttcttaat aatgagcatt acagagctct atcaggagtt   4020
ttctgtggtg ttgatgcgat gaatctcata gctaacatct ttactcctct tgtgcaacct   4080
gtgggtgctt tagatgtgtc tgcttcagta gtggctggtg gtattattgc catattggtg   4140
acttgtgctg cctactactt tatgaaattc agacgtgttt ttggtgagta caaccatgtt   4200
gttgctgcta atgcactttt gtttttgatg tctttcacta tactctgtct ggtaccagct   4260
tacagctttc tgccgggagt ctactcagtc ttttacttgt acttgacatt ctatttcacc   4320
aatgatgttt cattcttggc tcaccttcaa tggtttgcca tgttttctcc tattgtgcct   4380
ttttggataa cagcaatcta tgtattctgt atttctctga agcactgcca ttggttcttt   4440
aacaactatc ttaggaaaag agtcatgttt aatggagtta catttagtac cttcgaggag   4500
gctgctttgt gtaccttttt gctcaacaag gaaatgtacc taaaattgcg tagcgagaca   4560
ctgttgccac ttacacagta taacaggtat cttgctctat ataacaagta caagtatttc   4620
agtggagcct tagatactac cagctatcgt gaagcagctt gctgccactt agcaaaggct   4680
ctaaatgact ttagcaactc aggtgctgat gttctctacc aaccaccaca gacatcaatc   4740
acttctgctg ttctgcagag tggttttagg aaaatggcat tcccgtcagg caaagttgaa   4800
gggtgcatgg tacaagtaac ctgtggaact acaactctta atggattgtg gttggatgac   4860
acagtatact gtccaagaca tgtcatttgc acagcagaag acatgcttaa tcctaactat   4920
gaagatctgc tcattcgcaa atccaaccat agctttcttg ttcaggctgg caatgttcaa   4980
cttcgtgtta ttggccattc tatgcaaaat tgtctgctta ggcttaaagt tgatacttct   5040
aaccctaaga cacccaagta taaatttgtc cgtatccaac ctggtcaaac attttcagtt   5100
ctagcatgct acaatggttc accatctggt gtttatcagt gtgccatgag acctaatcat   5160
accattaaag gttctttcct taatggatca tgtggtagtg ttggttttaa cattgattat   5220
gattgcgtgt ctttctgcta tatgcatcat atggagcttc caacaggagt acacgctggt   5280
accgacttag aaggtaaatt ctatggtcca tttgttgaca gacaaactgc acaggctgca   5340
ggtacagaca caaccataac attaaatgtt ttggcatggc tgtatgctgc tgttatcaat   5400
ggtgataggt ggtttcttaa tagattcacc actactttga atgactttaa ccttgtggca   5460
atgaagtaca actatgaacc tttgacacaa gatcatgttg acatattggg acctctttct   5520
gctcaaacag gaattgccgt cttagatatg tgtgctgctt tgaaagagct gctgcagaat   5580
ggtatgaatg gtcgtactat ccttggtagc actattttag aagatgagtt tacaccattt   5640
gatgttgtta gacaatgctc tggtgttacc ttccaaggta agttcaagaa aattgttaag   5700
ggcactcatc attggatgct tttaactttc ttgacatcac tattgattct tgttcaaagt   5760
acacagtggt cactgttttt ctttgtttac gagaatgctt tcttgccatt tactcttggt   5820
attatggcaa ttgctgcatg tgctatgctg cttgttaagc ataagcacgc attcttgtgc   5880
ttgtttctgt taccttctct tgcaacagtt gcttacttta atatggtcta catgcctgct   5940
```

-continued

```
agctgggtga tgcgtatcat gacatggctt gaattggctg acactagctt gtctggttat   6000
aggcttaagg attgtgttat gtatgcttca gctttagttt tgcttattct catgacagct   6060
cgcactgttt atgatgatgc tgctagacgt gtttggacac tgatgaatgt cattacactt   6120
gtttacaaag tctactatgg taatgcttta gatcaagcta tttccatgtg ggccttagtt   6180
atttctgtaa cctctaacta ttctggtgtc gttacgacta tcatgttttt agctagagct   6240
atagtgtttg tgtgtgttga gtattatcca ttgttattta ttactggcaa caccttacag   6300
tgtatcatgc ttgtttattg tttcttaggc tattgttgct gctgctactt tggccttttc   6360
tgtttactca accgttactt caggcttact cttggtgttt atgactactt ggtctctaca   6420
caagaattta ggtatatgaa ctcccagggg cttttgcctc ctaagagtag tattgatgct   6480
ttcaagctta acattaagtt gttgggtatt ggaggtaaac catgtatcaa ggttgctact   6540
gtacagtcta aaatgtctga cgtaaagtgc acatctgtgg tactgctctc ggttcttcaa   6600
caacttagag tagagtcatc ttctaaattg tgggcacaat gtgtacaact ccacaatgat   6660
attcttcttg caaaagacac aactgaagct ttcgagaaga tggtttctct tttgtctgtt   6720
ttgctatcca tgcagggtgc tgtagacatt aataggttgt gcgaggaaat gctcgataac   6780
cgtgctactc ttcaggctat tgcttcagaa tttagttctt taccatcata tgccgcttat   6840
gccactgccc aggaggccta tgagcaggct gtagctaatg gtgattctga agtcgttctc   6900
aaaaagttaa agaaatcttt gaatgtggct aaatctgagt ttgaccgtga tgctgccatg   6960
caacgcaagt tggaaaagat ggcagatcag gctatgaccc aaatgtacaa acaggcaaga   7020
tctgaggaca agagggccca agtcgcttct gctatgcaaa caatgctctt cactatgcta   7080
aggaagcttg ataatgatgc acttaacaac attatcaaca atgcgcgtga tggttgtgtt   7140
ccactcaaca tcataccatt gactacagca gccaaactca tggttgttgt ccctgattat   7200
ggtacctaca agaacacttg tgatggtaac acctttacat atgcatctgc actctgggaa   7260
atccagcaag ttgttgatgc ggatagcaag attgttcaac ttagtgaaat taacatggac   7320
aattcaccaa atttggcttg gcctcttatt gttacagctc taagagccaa ctcagctgtt   7380
aaactacaga ataatgaact gagtccagta gcactacgac agatgtcctg tgcggctggt   7440
accacacaaa cagcttgtac tgatgacaat gcacttgcct actataacaa ttcgaaggga   7500
ggtaggtttg tgctggcatt actatcagac caccaagatc tcaaatgggc tagattccct   7560
aagagtgatg gtacaggtac aatttacaca gaactggaac caccttgtag gtttgttaca   7620
gacacaccaa aagggcctaa agtgaaatac ttgtacttca tcaaaggctt aaacaaccta   7680
aatagaggta tggtgctggg cagtttagct gctacagtac gtcttcaggc tggaaatgct   7740
acagaagtac ctgccaattc aactgtgctt tccttctgtg cttttgcagt agaccctgct   7800
aaagcatata aggattacct agcaagtgga ggacaaccaa tcaccaactg tgtgaagatg   7860
ttgtgtacac acactggtac aggacaggca attactgtaa caccagaagc taacatggac   7920
caagagtcct ttggtggtgc ttcatgttgt ctgtattgta gatgccacat tgaccatcca   7980
aatcctaaag gattctgtga cttgaaaggt aagtacgtcc aaatacctac cacttgtgct   8040
aatgacccag tgggttttac acttagaaac acagtctgta ccgtctgcgg aatgtggaaa   8100
ggttatggct gtagttgtga ccaactccgc gaacccttga tgcagtctgc ggatgcatca   8160
acgtttttaa acgggtttgc ggtgtaagtg cagcccgtct tacaccgtgc ggcacaggca   8220
ctagtactga tgtcgtctac agggcttttg atatttacaa cgaaaaagtt gctggttttg   8280
caaagttcct aaaaactaat tgctgtcgct tccaggagaa ggatgaggaa ggcaatttat   8340
```

-continued

```
tagactctta ctttgtagtt aagaggcata ctatgtctaa ctaccaacat gaagagacta   8400
tttataactt ggttaaagat tgtccagcgg ttgctgtcca tgactttttc aagtttagag   8460
tagatggtga catggtacca catatatcac gtcagcgtct aactaaatac acaatggctg   8520
atttagtcta tgctctacgt cattttgatg agggtaattg tgatacatta aaagaaatac   8580
tcgtcacata caattgctgt gatgatgatt atttcaataa gaaggattgg tatgacttcg   8640
tagagaatcc tgacatctta cgcgtatatg ctaacttagg tgagcgtgta cgccaatcat   8700
tattaaagac tgtacaattc tgcgatgcta tgcgtgatgc aggcattgta ggcgtactga   8760
cattagataa tcaggatctt aatgggaact ggtacgattt cggtgatttc gtacaagtag   8820
caccaggctg cggagttcct attgtggatt catattactc attgctgatg cccatcctca   8880
ctttgactag ggcattggct gctgagtccc atatggatgc tgatctcgca aaaccactta   8940
ttaagtggga tttgctgaaa tatgatttta cggaagagag actttgtctc ttcgaccgtt   9000
attttaaata ttgggaccag acataccatc ccaattgtat taactgtttg gatgataggt   9060
gtatccttca ttgtgcaaac tttaatgtgt tattttctac tgtgtttcca cctacaagtt   9120
ttggaccact agtaagaaaa atatttgtag atggtgttcc ttttgttgtt tcaactggat   9180
accattttcg tgagttagga gtcgtacata atcaggatgt aaacttacat agctcgcgtc   9240
tcagtttcaa ggaactttta gtgtatgctg ctgatccagc tatgcatgca gcttctggca   9300
atttattgct agataaacgc actacatgct tttcagtagc tgcactaaca aacaatgttg   9360
cttttcaaac tgtcaaaccc ggtaatttta ataaagactt ttatgacttt gctgtgtcta   9420
aaggtttctt taaggaagga agttctgttg aactaaaaca cttcttcttt gctcaggatg   9480
gcaacgctgc tatcagtgat tatgactatt atcgttataa tctgccaaca atgtgtgata   9540
tcagacaact cctattcgta gttgaagttg ttgataaata ctttgattgt tacgatggtg   9600
gctgtattaa tgccaaccaa gtaatcgtta acaatctgga taaatcagct ggtttcccat   9660
ttaataaatg ggctaaggct agactttatt atgactcaat gagttatgag gatcaagatg   9720
cacttttcgc gtatactaag cgtaatgtca tccctactat aactcaaatg aatcttaagt   9780
atgccattag tgcaaagaat agagctcgca ccgtagctgg tgtctctatc tgtagtacta   9840
tgacaaatag acagtttcat cagaaattat tgaagtcaat agccgccact agaggagcta   9900
ctgtggtaat tggaacaagc aagttttacg gtggctggca taatatgtta aaaactgttt   9960
acagtgatgt agaaactcca caccttatgg gttgggatta tccaaaatgt gacagagcca  10020
tgcctaacat gcttaggata atggcctctc ttgttcttgc tcgcaaacat aacacttgct  10080
gtaacttatc acaccgtttc tacaggttag ctaacgagtg tgcgcaagta ttaagtgaga  10140
tggtcatgtg tggcggctca ctatatgtta aaccaggtgg aacatcatcc ggtgatgcta  10200
caactgctta tgctaatagt gtctttaaca tttgtcaagc tgttacagcc aatgtaaatg  10260
cacttctttc aactgatggt aataagatag ctgacaagta tgtccgcaat ctacaacaca  10320
ggctctatga gtgtctctat agaaataggg atgttgatca tgaattcgtg gatgagtttt  10380
acgcttacct gcgtaaacat ttctccatga tgattctttc tgatgatgcc gttgtgtgct  10440
ataacagtaa ctatgcggct caaggtttag tagctagcat taagaacttt aaggcagttc  10500
tttattatca aaataatgtg ttcatgtctg aggcaaaatg ttggac                 10546
```

<210> SEQ ID NO 6
<211> LENGTH: 4673
<212> TYPE: DNA

-continued

<213> ORGANISM: SARS-CoV Shanghai LY

<400> SEQUENCE: 6
attagcgata tgtatgaccc taggaccaaa catgtgacaa aagagaatga ctctaaagaa 60
gggtttttca cttatctgtg tggatttata aagcaaaaac tagccctggg tggttctata 120
gctgtaaaga taacagagca ttcttggaat gctgaccttt acaagcttat gggccatttc 180
tcatggtgga cagcttttgt tacaaatgta aatgcatcat catcggaagc atttttaatt 240
ggggctaact atcttggcaa gccgaaggaa caaattgatg gctataccat gcatgctaac 300
tacattttct ggaggaacac aaatcctatc cagttgtctt cctattcact ctttgacatg 360
agcaaatttc ctcttaaatt aaggggaact gctgtaatgt ctcttaagga gaatcaaatc 420
aatgatatga tttattctct tctggaaaaa ggtaggctta tcattagaga aaacaacaga 480
gttgtggttt caagtgatat tcttgttaac aactaaacga acatgtttat tttcttatta 540
tttcttactc tcactagtgg tagtgacctt gaccggtgca ccacttttga tgatgttcaa 600
gctcctaatt acactcaaca tacttcatct atgagggggg tttactatcc tgatgaaatt 660
tttagatcag acactcttta tttaactcag gatttatttc ttccatttta ttctaatgtt 720
acagggtttc atactattaa tcatacgttt ggcaaccctg tcataccttt taaggatggt 780
atttattttg ctgccacaga gaaatcaaat gttgtccgtg gttgggtttt tggttctacc 840
atgaacaaca agtcacagtc ggtgattatt attagcaatt ctactaatgt tgttatacga 900
gcatgtaact ttgaattgtg tgacaaccct ttctttgctg tttctaaacc catgggtaca 960
cagacacata ctatgatatt cgataatgca tttaattgca ctttcgagta catatctgat 1020
gccttttcgc ttgatgtttc agaaaagtca ggtaatttta aacacttacg agagtttgtg 1080
tttaaaaata aagatgggtc tctctatgtt tataagggct atcaacctat agatgtagtt 1140
cgtgatctac cttctggttt taacactttg aaacctattt ttaagttgcc tcttggtatt 1200
aacattacaa attttagagc cattcttaca gccttttcac ctgctcaaga catttggggc 1260
acgtcagctg cagcctattt tgttggctat ttaaagccaa ctacatttat gctcaagtat 1320
gatgaaaatg gtacaatcac agatgctgtt gattgctctc aaaatccact tgctgaactc 1380
aaatgctctg ttaagagctt tgagattgac aaaggaattt accagacctc taatttcagg 1440
gttgttccct caggagatgt tgtgagattc cctaatatta caaacttgtg tccttttgga 1500
gaggttttta atgctactaa attcccttct gtctatgcat gggagagaaa aaaaatttct 1560
aattgtgttg ctgattactc tgtgctctac aactcaacat ttttttcaac ctttaagtgc 1620
tatggcgttt ctgccactaa gttgaatgat ctttgcttct ccaatgtcta tgcagattct 1680
tttgtagtca agggagatga tgtaagacaa atagcgccag gacaaactgg tgttattgct 1740
gattataatt ataaattgcc agatgatttc atgggttgtg tccttgcttg gaatactggg 1800
aacattgatg ctacttcaac tggtaattat gattataaat ataggtatct tagacatggc 1860
aagcttaggc cctttgagag agacatatct aatgtgcctt tctcccctga tggcaaacct 1920
tgcaccccac ctgctcttaa ttgttattgg ccattaaatg attatggttt ttacaccact 1980
actggcattg gctaccaacc ttacagagtt gtagtacttt cttttgaact tttaaatgca 2040
ccggccacgg tttgtggacc aaaattatcc actgacctta ttaagaacca gtgtgtcaat 2100
tttaatttta atggactcac tggtactggt gtgttaactc cttcttcaaa gagatttcaa 2160
ccatttcaac aatttggccg tgatgtttct gatttcactg attccgttcg agatcctaaa 2220
acatctgaaa tattagacat ttcaccttgc tcttttgggg gtgtaagtgt aattacacct 2280

-continued

```
ggaacaaatg cttcatctga agttgctgtt ctatatcaag atgttaactg cactgatgtt   2340
tctacagcaa ttcatgcaga tcaactcaca ccagcttggc gcatatattc tactggaaac   2400
aatgtattcc agactcaagc aggctgtctt ataggagctg agcatgtcga cacttcttat   2460
gagtgcgaca ttcctattgg agctggcatt tgtgctagtt accatacagt ttctttatta   2520
cgtagtacta gccaaaaatc tattgtggct tatactatgt ctttaggtgc tgatagttca   2580
attgcttact ctaataacac cattgctata cctactaact tttcaattag cattactaca   2640
gaagtaatgc ctgtttctat ggctaaaacc tccgtagatt gtaatatgta catctgcgga   2700
gattctactg aatgtgctaa tttgcttctc caatatggta gcttttgcac acaactaaat   2760
cgtgcactct caggtattgc tgctgaacag gatcgcaaca cacgtgaagt gttcgctcaa   2820
gtcaaacaaa tgtacaaaac cccaactttg aaatattttg gtggttttaa tttttcacaa   2880
atattacctg accctctaaa gccaactaag aggtctttta ttgaggactt gccctttaat   2940
aaggtgacac tcgctgatgc tggcttcatg aagcaatatg gcgaatgcct aggtgatatt   3000
aatgctagag atctcatttg tgcgcagaag ttcaatggac ttacagtgtt gccacctctg   3060
ctcactgatg atatgattgc tgcctacact gctgctctag ttagtggtac tgccactgct   3120
ggatggacat ttggtgctgg cgctgctctt caaatacctt ttgctatgca aatggcatat   3180
aggttcaatg gcattggagt tacccaaaat gttctctatg agaaccaaaa acaaatcgcc   3240
aaccaattta acaaggcgat tagtcaaatt caagaatcac ttacaacaac atcaactgca   3300
ttgggcaagc tgcaagacgt tgttaaccag aatgctcaag cattaaacac acttgttaaa   3360
caacttagct ctaattttgg tgcaatttca agtgtgctaa atgatatcct ttcgcgactt   3420
gataaagtcg aggcggaggt acaaattgac aggttaatta caggcagact tcaaagcctt   3480
caaacctatg taacacaaca actaatcagg gctgctggaa tcagggcttc tgctaatctt   3540
gctgctacta aaatgtctga gtgtgttctt ggacaatcaa aaagagttga cttttgtgga   3600
aagggctacc accttatgtc cttcccacaa gcagccccgc atggtgttgt cttcctacat   3660
gtcacgtatg tgccatccca ggagaggaac ttcaccacag cgccagcaat ttgtcatgaa   3720
ggcaaagcat acttccctcg tgaaggtgtt tttgtgttta atggcacttc ttggtttatt   3780
acacagagga acttcttttc tccacaaata attactacag acaatacatt tgtctcagga   3840
aattgtgatg tcgttattgg catcattaac aacacagttt atgatcctct gcaacctgag   3900
cttgactcat tcaaagaaga gctggacaag tacttcaaaa atcatacatc accagatgtt   3960
gatcttggcg acatttcagg cattaacgct tctgtcgtca acattcaaaa agaaattgac   4020
cgcctcaatg aggtcgctaa aaatttaaat gaatcactca ttgaccttca agaattggga   4080
aaatatgagc aatatattaa atggccttgg tatgtttggc tcggcttcat tgctggacta   4140
attgccatcg tcatggttac aatcttgctt tgttgcatga ctagttgttg tagttgcctc   4200
aagggtgcat gctcttgtgg ttcttgctgc aagtttgatg aggatgactc tgagccagtt   4260
ctcaagggtg tcaaattaca ttacacataa acgaacttat ggatttgttt atgagatttt   4320
ttactcttgg atcaattact gcacagccag taaaaactga caatgcttct cctgcaagta   4380
ctgttcatgc tacagcaacg ataccgctac aagcctcact ccctttcgga tggcttgtta   4440
ttggcgttgc atttcttgct gtttttcaga gcgctaccaa aataattgcg ctcaataaaa   4500
gatggcagct agccctttat aagggcttcc agttcatttg caatttactg ctgctatttg   4560
ttaccatcta ttcacatctt ttgcttgtcg ctgcaggtat ggaggcgcaa tttttgtacc   4620
```

-continued tctatgcctt gatatacttt ctacaatgca tcaacgcatg tagaattatt atg 4673

<210> SEQ ID NO 7
<211> LENGTH: 2304
<212> TYPE: DNA
<213> ORGANISM: SARS-CoV Shanghai LY

<400> SEQUENCE: 7
aaagaacctt gcccatcagc aacatacgag ggcaattcac catttcaccc tcttgctgac 60
aataaatttg cactaacttg cactagcaca cactttgctt ttgcttgtgc tgacggtact 120
cgacatacct atcagctgcg tgcaagatca gtttcaccaa aacttttcat cagacaagag 180
gaggttcaac aagagctcta ctcgccactt tttctcattg ttgctgctct agtattttta 240
atactttgct tcaccattaa gagaaagaca gaatgaatga gctcacttta attgacttct 300
atttgtgctt tttagccttt ctgctattcc ttgttttaat aatgcttatt atattttggt 360
tttcactcga aatccaggat ctagaagaac cttgtaccaa agtctaaacg aacatgaaac 420
ttctcattgt tttgacttgt atttctctat gcagttgcat atgcactgta gtacagcgct 480
gtgcatctaa taaacctcat gtgcttgaag atccttgtaa ggtacaacac taggggtaat 540
acttatagca ctgcttggct ttgtgctcta ggaaaggttt taccttttca tagatggcac 600
actatggttc aaacatgcac acctaatgtt actatcaact gtcaagatcc agctggtggt 660
gcgcttatag ctaggtgttg gtaccttcat gaaggtcacc aaactgctgc atttagagac 720
gtacttgttg ttttaaataa acgaacaaat taaaatgtct gataatggac cccaatcaaa 780
ccaacgtagt gccccccgca ttacatttgg tggacccaca gattcaactg acaataacca 840
gaatggagga cgcaatgggg caaggccaaa acagcgccga ccccaaggtt tacccaataa 900
tactgcgtct tggttcacag ctctcactca gcatggcaag gaggaactta gattccctcg 960
aggccagggc gttccaatca acaccaatag tggtccagat gaccaaattg gctactaccg 1020
aagagctacc cgacgagttc gtggtggtga cggcaaaatg aaagagctca gccccagatg 1080
gtacttctat tacctaggaa ctggcccaga agcttcactt ccctacggcg ctaacaaaga 1140
aggcatcgta tgggttgcaa ctgagggagc cttgaataca cccaaagacc acattggcac 1200
ccgcaatcct aataacaatg ctgccaccgt gctacaactt cctcaaggaa caacattgcc 1260
aaaaggcttc tacgcagagg gaagcagagg cggcagtcaa gcctcttctc gctcctcatc 1320
acgtagtcgc ggtaattcaa gaaattcaac tcctggcagc agtaggggaa attctcctgc 1380
tcgaatggct agcggaggtg gtgaaactgc cctcgcgcta ttgctgctag acagattgaa 1440
ccagcttgag agcaaagttt ctggtaaagg ccaacaacaa caaggccaaa ctgtcactaa 1500
gaaatctgct gctgaggcat ctaaaaagcc tcgccaaaaa cgtacagcca caaaacagta 1560
caacgtcact caagcatttg ggagacgtgg tccagaacaa acccaaggaa atttcgggga 1620
ccaagaccta atcagacaag gaactgatta caaacattgg ccgcaaattg cacaatttgc 1680
tccaagtgcc tctgcattct ttggaatgtc acgcattggc atggaagccg caccttcggg 1740
aacatggctg acttatcatg gagccattaa attggatgac aaagatccac aattcaaaga 1800
caacgtcata ctgctgaaca agcacattga cgcatacaaa acattcccac caacagagcc 1860
taaaaaggac aaaaagaaaa agactgatga agctcagcct ttgccgcaga gacaaaagaa 1920
gcagcccact gtgactcttc ttcctgcggc tgacatggat gatttctcca gacaacttca 1980
aaattccatg agtggagctt ctgctgattc aactcaggca taaacactca tgatgaccac 2040
acaaggcaga tgggctatgt aaacgttttc gcaattccgt ttacgataca tagtctactc 2100

-continued ttgtgcagaa tgaattctcg taactaaaca gcacaagtag gtttagttaa ctttaatctc 2160
acatagcaat ctttaatcaa tgtgtaacat tagggaggac ttgaaagagc caccacattt 2220
tcatcgaggc cacgcggagt acgatcgagg gtacagtgaa taatgctagg gagagctgcc 2280
tatatggaag agccctaatg tgta 2304

<210> SEQ ID NO 8
<211> LENGTH: 3536
<212> TYPE: DNA
<213> ORGANISM: SARS coronavirus Shanghai QXC

<400> SEQUENCE: 8
caagtctttc aaaaccattg ttgagtcctg cggtaactat aaagttacca agggaaagcc 60
cgtaaaaggt gcttggaaca ttggacaaca gagatcagtt ttaacaccac tgtgtggttt 120
tccctcacag gctgctggtg ttatcagatc aatttttgcg cgcacacttg atgcagcaaa 180
ccactcaatt cctgatttgc aaagagcagc tgtcaccata cttgatggta tttctgaaca 240
gtcattacgt cttgtcgacg ccatggttta tacttcagac ctgctcacca acagtgtcat 300
tattatggca tatgtaactg gtggtcttgt acaacagact tctcagtggt tgtctaatct 360
tttgggcact actgttgaaa aactcaggcc tatctttgaa tggattgagg cgaaacttag 420
tgcaggagtt gaatttctca aggatgcttg ggagattctc aaatttctca ttacaggtgt 480
ttttgacatc gtcaagggtc aaatacaggt tgcttcagat aacatcaagg attgtgtaaa 540
atgcttcatt gatgttgtta acaaggcact cgaaatgtgc attgatcaag tcactatcgc 600
tggcgcaaag ttgcgatcac tcaacttagg tgaagtcttc atcgctcaaa gcaagggact 660
ttaccgtcag tgtatacgtg gcaaggagca gctgcaacta ctcatgcctc ttaaggcacc 720
aaaagaagta acctttcttg aaggtgattc acatgacaca gtacttacct ctgaggaggt 780
tgttctcaag aacggtgaac tcgaagcact cgagacgccc gttgatagct tcacaaatgg 840
agctatcgtt ggcacaccag tctgtgtaaa tggcctcatg ctcttagaga ttaaggacaa 900
agaacaatac tgcgcattgt ctcctggttt actggctaca aacaatgtct ttcgcttaaa 960
agggggtgca ccaattaaag gtgtaacctt tggagaagat actgtttggg aagttcaagg 1020
ttacaagaat gtgagaatca catttgagct tgatgaacgt gttgacaaag tgcttaatga 1080
aaagtgctct gtctacactg ttgaatccgg taccgaagtt actgagtttg catgtgttgt 1140
agcagaggct gttgtgaaga ctttacaacc agtttctgat ctccttacca acatgggtat 1200
tgatcttgat gagtggagtg tagctacatt ctacttattt gatgatgctg gtgaagaaaa 1260
cttttcatca cgtatgtatt gttcctttta ccctccagat gaggaagaag aggacgatgc 1320
agagtgtgag gaagaagaaa ttgatgaaac ctgtgaacat gagtacggta cagaggatga 1380
ttatcaaggt ctccctctgg aatttggtgc ctcagctgaa acagttcgag ttgaggaaga 1440
agaagaggaa gactggctgg atgatactac tgagcaatca gagattgagc cagaaccaga 1500
acctacacct gaagaaccag ttaatcagtt tactggttat ttaaaactta ctgacaatgt 1560
tgccattaaa tgtgttgaca ccgttaagga ggcacaaagt gctaatccta tggtgattgt 1620
aaatgctgct aacatacacc tgaaacatgg tggtggtgta gcaggtgcac tcaacaaggc 1680
aaccaatggt gccatgcaaa aggagagtga tgattacatt aagctaaatg gccctcttac 1740
agtaggaggg tcttgtttgc tttctggaca taatcttgct aagaagtgtc tgcatgttgt 1800
tggacctaac ctaaatgcag gtgaggacat ccagcttctt aaggcagcat atgaaaattt 1860

-continued

```
caattcacag gacatcttac ttgcaccatt gttgtcagca ggcatatttg gtgctaaacc   1920

acttcagtct ttacaagtgt gcgtgcagac ggttcgtaca caggtttata ttgcagtcaa   1980

tgacaaagct ctttatgagc aggttgtcat ggattatctt gataacctga agcctagagt   2040

ggaagcacct aaacaagagg agccaccaaa cacagaagat tccaaaactg aggagaaatc   2100

tgtcgtacag aagcctgtcg atgtgaagcc aaaaattaag gcctgcattg atgaggttac   2160

cacaacactg gaagaaacta agtttcttac caataagtta ctcttgtttg ctgatatcaa   2220

tggtaagctt taccatgatt ctcagaacat gcttagaggt gaagatatgt ctttccttga   2280

ggaggatgca ccttacatgg taggtgatgt tatcactagt ggtgatatca cttgtgttgt   2340

aataccctcc aaaaaggctg gtggcactac tgagatgctc tcaagagctt tgaagaaagt   2400

gccagttgat gagtatataa ccacgtaccc tggacaagga tgtgctggtt atacacttga   2460

ggaagctaag actgctctta agaaatgcaa atctgcattt tatgtactac cttcagaagc   2520

acctaatgct aaggaagaga ttctaggaac tgtatcctgg aatttgagag aaatgcttgc   2580

tcatgctgaa gaggcaagaa aattaatgcc tatatgcatg gatgttagag ccataatggc   2640

aaccatccaa cgtaagtata aaggagttaa aattcaagag ggcatcgttg actatggtgt   2700

ccgattcttc ttttatacta gtaaagagcc tgtagcttct attattacga agctgaactc   2760

tctaaatgag ccgcttgtca caatgccaat tggttatgtg acacatggtt ttaatcttga   2820

agaggctgcg cgctgtatgc gttctcttaa agctcctgcc gtagtgtcag tatcatcacc   2880

agatgctgtt actacatata atggatacct cacttcgtca tcaaagacat ctgaggagca   2940

ctttgtagaa acagtttctt tggctggctc ttacagagat tggtcctatt caggacagcg   3000

tacagagtta ggtgttgaat ttcttaagcg tggtgacaaa attgtgtacc acaccctgga   3060

gagccccgtc gagtttcatc ttgacggtga ggttctttca cttgacaaac taaagagtct   3120

cttatccctg cgggaggtta agactataaa agtgttcaca actgtggaca acactaatct   3180

ccacacacag cttgtggata tgtctatgac atatggacag cagtttggtc caacatactt   3240

ggatggtgct gatgttacaa aaattaaacc tcatgtaaat catgagggta agactttctt   3300

tgtactacct agtgatgaca cactacgtag tgaagctttc gagtactacc atactcttga   3360

tgagagtttt cttggtaggt acatgtctgc tttaaaccac acaaagaaat ggaaatttcc   3420

tcaagttggt ggtttaactt caattaaatg ggctgataac aattgttatt tgtctagtgt   3480

tttattagca cttcaacagc ttgaagtcaa attcaatgca ccagcacttc aagagg       3536
```

<210> SEQ ID NO 9
<211> LENGTH: 5262
<212> TYPE: DNA
<213> ORGANISM: SARS coronavirus Shanghai QXC

<400> SEQUENCE: 9

```
caaaataatg tgttcatgtc tgaggcaaaa tgttggactg agactgacct tactaaagga     60

cctcacgaat tttgctcaca gcatacaatg ctagttaaac aaggagatga ttacgtgtac    120

ctgccttacc cagatccatc aagaatatta ggcgcaggct gttttgtcga tgatattgtc    180

aaaacagatg gtacacttat gattgaaagg ttcgtgtcac tggctattga tgcttaccca    240

cttacaaaac atcctaatca ggagtatgct gatgtctttc acttgtattt acaatacatt    300

agaaagttac atgatgagct tactggccac atgttggaca tgtattccgt aatgctaact    360

aatgataaca cctcacggta ctgggaacct gagttttatg aggctatgta cacaccacat    420

acagtcttgc aggctgtagg tgcttgtgta ttgtgcaatt cacagacttc acttcgttgc    480
```

-continued

```
ggtgcctgta ttaggagacc actcctatgt tgcaagtgct gctatgacca tgtcatttca    540
acatcacaca aattagtgtt gtctgttaat ccctatgttt gcaatgcccc aggttgtgat    600
gtcactgatg tgacacaact gtatctagga ggtatgagct attattgcaa gtcacataag    660
cctcccatta gttttccatt atgtgctaat ggtcaggttt ttggtttata caaaaacaca    720
tgtgtaggca gtgacaatgt cactgacttc aatgcgatag caacatgtga ttggactaat    780
gctggcgatt acatacttgc caacacttgt actgagagac tcaagctttt cgcagcagaa    840
acgctcaaag ccactgagga aacatttaag ctgtcatatg gtattgccac tgtacgcgaa    900
gtactctctg acagagaatt gcatctttca tgggaggttg gaaaacctag accaccattg    960
aacagaaact atgtctttac tggttaccgt gtaactaaaa atagtaaagt acagattgga   1020
gagtacacct ttgaaaaagg tgactatggt gatgctgttg tgtacagagg tactacgaca   1080
tacaagttga atgttggtga ttactttgtg ttgacatctc acactgtaat gccacttagt   1140
gcacctactc tagtgccaca agagcactat gtgagaatta ctggcttgta cccaacactc   1200
aacatctcag atgagttttc tagcaatgtt gcaaattatc aaaaggtcgg catgcaaaag   1260
tactctacac tccaaggacc acctggtact ggtaagagtc attttgccat cggacttgct   1320
ctctattacc catctgctcg catagtgtat acggcatgct ctcatgcagc tgttgatgcc   1380
ctatgtgaaa aggcattaaa atatttgccc atagataaat gtagtagaat catacctgcg   1440
cgtgcgcgcg tagagtgttt tgataaattc aaagtgaatt caacactaga acagtatgtt   1500
ttctgcactg taaatgcatt gccagaaaca actgctgaca ttgtagtctt tgatgaaatc   1560
tctatggcta ctaattatga cttgagtgtt gtcaatgcta gacttcgtgc aaaacactac   1620
gtctatattg gcgatcctgc tcaattacca gccccccgca cattgctgac taaaggcaca   1680
ctagaaccag aatattttaa ttcagtgtgc agacttatga aaacaatagg tccagacatg   1740
ttccttggaa cttgtcgccg ttgtcctgct gaaattgttg acactgtgag tgctttagtt   1800
tatgacaata agctaaaagc acacaaggag aagtcagctc aatgcttcaa aatgttctac   1860
aaaggtgtta ttacacatga tgtttcatct gcaatcaaca gacctcaaat aggcgttgta   1920
agagaatttc ttacacgcaa tcctgcttgg agaaaagctg tttttatctc accttataat   1980
tcacagaacg ctgtagcttc aaaaatctta ggattgccta cgcagactgt tgattcatca   2040
cagggttctg aatatgacta tgtcatattc acacaaacta ctgaaacagc acactcttgt   2100
aatgtcaacc gcttcaatgt ggctatcaca agggcaaaaa ttggcatttt gtgcataatg   2160
tctgataggg atctttatga caaactgcaa tttacaagtc tagaaatacc acgtcgcaat   2220
gtggctacat tacaagcaga aaatgtaact ggacttttta aggactgtag taagatcatt   2280
actggtcttc atcctacaca ggcacctaca cacctcagcg ttgatataaa gttcaagact   2340
gaaggattat gtgttgacat accaggcata ccaaaggaca tgacctaccg tagactcatc   2400
tctatgatgg gtttcaaaat gaattaccaa gtcaatggtt accctaatat gtttatcacc   2460
cgcgaagaag ctattcgtca cgttcgtgcg tggattggct ttgatgtaga gggctgtcat   2520
gcaactagag atgctgtggg tactaaccta cctctccagc taggattttc tacaggtgtt   2580
aacttagtag ctgtaccgac tggttatgtt gacactgaaa ataacacaga attcaccaga   2640
gttaatgcaa aacctccacc aggtgaccag tttaaacatc ttataccact catgtataaa   2700
ggcttgccct ggaatgtagt gcgtattaag atagtacaaa tgctcagtga tacactgaaa   2760
ggattgtcag acagagtcgt gttcgtcctt tgggcgcatg gctttgagct tacatcaatg   2820
```

-continued

```
aagtactttg tcaagattgg acctgaaaga acgtgttgtc tgtgtgacaa acgtgcaact   2880
tgcttttcta cttcatcaga tacttatgcc tgctggaatc attctgtggg ttttgactat   2940
gtctataacc catttatgat tgatgttcag cagtggggct ttacgggtaa ccttcagagt   3000
aaccatgacc aacattgcca ggtacatgga aatgcacatg tggctagttg tgatgctatc   3060
atgactagat gtttagcagt ccatgagtgc tttgttaagc gcgttgattg gtctgttgaa   3120
taccctatta taggagatga actgagggtt aattctgctt gcagaaaagt acaacacatg   3180
gttgtgaagt ctgcattgct tgctgataag tttccagttc ttcatgacat tggaaatcca   3240
aaggctatca agtgtgtgcc tcaggctgaa gtagaatgga agttctacga tgctcagcca   3300
tgtagtgaca aagcttacaa aatagaggaa ctcttctatt cttatgctac acatcacgat   3360
aaattcactg atggtgtttg tttgttttgg aattgtaacg ttgatcgtta cccagccaat   3420
gcaattgtgt gtaggtttga cacaagagtc ttgtcaaact tgaacttacc aggctgtgac   3480
ggtggtagtt tgtatgtgaa taagcatgca ttccacactc cagctttcga taaaagtgca   3540
tttactaatt taaagcaatt gcctttcttt tactattctg atagtccttg tgagtctcat   3600
ggcaaacaag tagtgtcgga tattgattat gttccactca aatctgctac gtgtattaca   3660
cgatgcaatt taggtggtgc tgtttgcaga caccatgcaa atgagtaccg acagtacttg   3720
gatgcatata atatgatgat ttctgctgga tttagcctat ggatttacaa acaatttgat   3780
acttataacc tgtggaatac atttaccagg ttacagagtt tagaaaatgt ggcttataat   3840
gttgttaata aaggacactt tgatggacac gccggcgaag cacctgtttc catcattaat   3900
aatgctgttt acacaaaggt agatggtatt gatgtggaga tctttgaaag taagacaaca   3960
cttcctgtta atgttgcatt tgagctttgg gctaagcgta acattaaacc agtgccagag   4020
attaagatac tcaataattt gggtgttgat atcgctgcta atactgtaat ctgggactac   4080
aaaagagaag ccccagcaca tgtgtctaca ataggtgtct gcacaatgac tgacattgcc   4140
aagaaaccta ctgagagtgc ttgttcttca cttactgtct tgtttgatgg tagagtggaa   4200
ggacaggtag accttttag aaacgcccgt aatggtgttt taataacaga aggttcagtc   4260
aaaggtctaa caccttcaaa gggaccagca caagctagcg tcaatggagt cacattaatt   4320
ggagaatcag taaaaacaca gtttaactac tttaagaaag tagacggcat tattcaacag   4380
ttgcctgaaa cctactttac tcagagcaga gacttagagg attttaagcc cagatcacaa   4440
atggaaactg actttctcga gctcgctatg gatgaattca tacagcgata taagctcgag   4500
ggctatgcct tcgaacacat cgtttatgga gatttcagtc atggacaact tggcggtctt   4560
catttaatga taggcttagc caagcgctca caagattcac cacttaaatt agaggatttt   4620
atccctatgg acagcacagt gaaaaattac ttcataacag atgcgcaaac aggttcatca   4680
aaatgtgtgc gttctgtgat tgatctttta cttgatgact ttgtcgagat aataaagtca   4740
caagatttgt cagtgatttc aaaagtggtc aaggttacaa ttgactatgc tgaaatttca   4800
ttcatgcttt ggtgtaagga tggacatgtt gaaaccttct acccaaaact acaagcaagt   4860
caagcgtggc aaccaggtgt tgcgatgcct aacttgtaca agatgcaaag aatgcttctt   4920
gaaaagtgtg accttcagaa ttatggtgaa aatgctgtta taccaaaagg aataatgatg   4980
aatgtcgcaa agtatactca actgtgtcaa tacttaaata cacttacttt agctgtaccc   5040
tacaacatga gagttattca ctttggtgct ggctctgata aaggagttgc accaggtaca   5100
gctgtgctca gacaatggtt gccaactggc acactacttg tcgattcaga tcttaatgac   5160
ttcgtctccg acgcagattc tactttaatt ggagactgtg caacagtaca tacggctaat   5220
```

-continued aaatgggacc ttattattag cgatatgtat gaccctagga cc 5262

<210> SEQ ID NO 10
<211> LENGTH: 1801
<212> TYPE: DNA
<213> ORGANISM: SARS coronavirus Shanghai QXC

<400> SEQUENCE: 10
cattacttta tgatgccaac tactttgttt gctggcacac acataactat gactactgta 60
taccatataa cagtgtcaca gatacaattg tcgttactga aggtgacggc atttcaacac 120
caaaactcaa agaagactac caaattggtg gttattctga ggataggcac tcaggtgtta 180
aagactatgt cgttgtacat ggctatttca ccgaagttta ctaccagctt gagtctacac 240
aaattactac aaacactggt attgaaaatg ctacattctt catctttaac aagcttgtta 300
aagacccacc gaatgtgcaa atacacacaa tcgacggctc ttcaggagtt gctaatccag 360
caatggatcc aatttatgat gagccgacga cgactactag cgtgcctttg taagcacaag 420
aaagtgagta cgaacttatg tactcattcg tttcggaaga aacaggtacg ttaatagtta 480
atagcgtact tctttttctt gccttcgtgg tattcttgct agtcacacta gccatcctta 540
ctgcgcttcg attgtgtgcg tactgctgca atattgttaa cgtgagttta gtaaaaccaa 600
cggtttacgt ctactcgcgt gttaaaaatc tgaactctcc tgaaggagtt cctgatcttc 660
tggtctaaac gaactaacta ttattattat tctgtttgga actttaacat tgcttatcat 720
ggcagacaac ggtactatta ccgttgagga gcttaaacaa ctcctggaac aatggaacct 780
agtaataggt ttcctattcc tagcctggat tatgttacta caatttgcct attctaatcg 840
gaacaggttt ttgtacataa taaagcttgt tttcctctgg ctcttgtggc cagtaacact 900
tgcttgtttt gtgcttgctg ctgtctacag aattaattgg gtgactggcg ggattgcgat 960
tgcaatggct tgtattgtag gcttgatgtg gcttagctac ttcgttgctt ccttcaggct 1020
gtttgctcgt acccgctcaa tgtggtcatt caacccggaa acaaacattc ttcccaatgt 1080
gcctctccgg gggacaattg tgaccagacc gctcatggaa agtgaacttg tcattggtgc 1140
tgtgatcatt cgtggtcact tgcgaatggc cggacactcc ctagggcgct gtgacattaa 1200
ggacctgcca aaagagatca ctgtggctac atcacgaacg ctttcttatt acaaattagg 1260
agcgtcgcag cgtgtaggca ctgattcagg ttttgctgca tacaaccgct accgtattgg 1320
aaactataaa ttaaatacag accacgccgg tagcaacgac aatattgctt tgctagtaca 1380
gtaagtgaca acagatgttt catcttgttg acttccaggt tacaatagca gagatattga 1440
ttatcattat gaggactttc aggattgcta tttggaatct tgacgttata ataagttcaa 1500
tagtgagaca attatttaag cctctaacta agaagaatta ttcggagtta gatgatgaag 1560
aacctatgga gttagattat ccataaaacg aacatgaaaa ttattctctt cctgacattg 1620
attgtattta catcttgcga gctatatcac tatcaggagt gtgttagagg tacgactgta 1680
ctactaaaag aaccttgccc atcagcaaca tacgagggca attcaccatt tcaccctctt 1740
gctgacaata aatttgcact aacttgcact agcacacact ttgcttttgc ttgtgctgac 1800
g 1801

<210> SEQ ID NO 11
<211> LENGTH: 2304
<212> TYPE: DNA
<213> ORGANISM: SARS coronavirus Shanhgai LY -continued

<400> SEQUENCE: 11

```
aaagaacctt gcccatcagc aacatacgag ggcaattcac catttcaccc tcttgctgac      60
aataaatttg cactaacttg cactagcaca cactttgctt ttgcttgtgc tgacggtact     120
cgacatacct atcagctgcg tgcaagatca gtttcaccaa aacttttcat cagacaagag     180
gaggttcaac aagagctcta ctcgccactt tttctcattg ttgctgctct agtattttta     240
atactttgct tcaccattaa gagaaagaca gaatgaatga gctcacttta attgacttct     300
atttgtgctt tttagccttt ctgctattcc ttgttttaat aatgcttatt atattttggt     360
tttcactcga aatccaggat ctagaagaac cttgtaccaa agtctaaacg aacatgaaac     420
ttctcattgt tttgacttgt atttctctat gcagttgcat atgcactgta gtacagcgct     480
gtgcatctaa taaacctcat gtgcttgaag atccttgtaa ggtacaacac taggggtaat     540
acttatagca ctgcttggct ttgtgctcta ggaaaggttt taccttttca tagatggcac     600
actatggttc aaacatgcac acctaatgtt actatcaact gtcaagatcc agctggtggt     660
gcgcttatag ctaggtgttg gtaccttcat gaaggtcacc aaactgctgc atttagagac     720
gtacttgttg ttttaaataa acgaacaaat taaaatgtct gataatggac cccaatcaaa     780
ccaacgtagt gccccccgca ttacatttgg tggacccaca gattcaactg acaataacca     840
gaatggagga cgcaatgggg caaggccaaa acagcgccga ccccaaggtt tacccaataa     900
tactgcgtct tggttcacag ctctcactca gcatggcaag gaggaactta gattccctcg     960
aggccagggc gttccaatca acaccaatag tggtccagat gaccaaattg gctactaccg    1020
aagagctacc cgacgagttc gtggtggtga cggcaaaatg aaagagctca gccccagatg    1080
gtacttctat tacctaggaa ctggcccaga agcttcactt ccctacggcg ctaacaaaga    1140
aggcatcgta tgggttgcaa ctgagggagc cttgaataca cccaaagacc acattggcac    1200
ccgcaatcct aataacaatg ctgccaccgt gctacaactt cctcaaggaa caacattgcc    1260
aaaaggcttc tacgcagagg gaagcagagg cggcagtcaa gcctcttctc gctcctcatc    1320
acgtagtcgc ggtaattcaa gaaattcaac tcctggcagc agtaggggaa attctcctgc    1380
tcgaatggct agcggaggtg gtgaaactgc cctcgcgcta ttgctgctag acagattgaa    1440
ccagcttgag agcaaagttt ctggtaaagg ccaacaacaa caaggccaaa ctgtcactaa    1500
gaaatctgct gctgaggcat ctaaaaagcc tcgccaaaaa cgtacagcca caaaacagta    1560
caacgtcact caagcatttg ggagacgtgg tccagaacaa acccaaggaa atttcgggga    1620
ccaagaccta atcagacaag gaactgatta caaacattgg ccgcaaattg cacaatttgc    1680
tccaagtgcc tctgcattct ttggaatgtc acgcattggc atggaagccg caccttcggg    1740
aacatggctg acttatcatg gagccattaa attggatgac aaagatccac aattcaaaga    1800
caacgtcata ctgctgaaca agcacattga cgcatacaaa acattcccac caacagagcc    1860
taaaaaggac aaaaagaaaa agactgatga agctcagcct ttgccgcaga gacaaaagaa    1920
gcagcccact gtgactcttc ttcctgcggc tgacatggat gatttctcca gacaacttca    1980
aaattccatg agtggagctt ctgctgattc aactcaggca taaacactca tgatgaccac    2040
acaaggcaga tgggctatgt aaacgttttc gcaattccgt ttacgataca tagtctactc    2100
ttgtgcagaa tgaattctcg taactaaaca gcacaagtag gtttagttaa ctttaatctc    2160
acatagcaat ctttaatcaa tgtgtaacat tagggaggac ttgaaagagc caccacattt    2220
tcatcgaggc cacgcggagt acgatcgagg gtacagtgaa taatgctagg gagagctgcc    2280
tatatggaag agccctaatg tgta                                           2304
```

-continued

<210> SEQ ID NO 12
<211> LENGTH: 3536
<212> TYPE: DNA
<213> ORGANISM: SARS coronavirus Shanghai QXC

<400> SEQUENCE: 12
caagtctttc aaaaccattg ttgagtcctg cggtaactat aaagttacca agggaaagcc 60
cgtaaaaggt gcttggaaca ttggacaaca gagatcagtt ttaacaccac tgtgtggttt 120
tccctcacag gctgctggtg ttatcagatc aatttttgcg cgcacacttg atgcagcaaa 180
ccactcaatt cctgatttgc aaagagcagc tgtcaccata cttgatggta tttctgaaca 240
gtcattacgt cttgtcgacg ccatggttta tacttcagac ctgctcacca acagtgtcat 300
tattatggca tatgtaactg gtggtcttgt acaacagact tctcagtggt tgtctaatct 360
tttgggcact actgttgaaa aactcaggcc tatctttgaa tggattgagg cgaaacttag 420
tgcaggagtt gaatttctca aggatgcttg ggagattctc aaatttctca ttacaggtgt 480
ttttgacatc gtcaagggtc aaatacaggt tgcttcagat aacatcaagg attgtgtaaa 540
atgcttcatt gatgttgtta acaaggcact cgaaatgtgc attgatcaag tcactatcgc 600
tggcgcaaag ttgcgatcac tcaacttagg tgaagtcttc atcgctcaaa gcaagggact 660
ttaccgtcag tgtatacgtg gcaaggagca gctgcaacta ctcatgcctc ttaaggcacc 720
aaaagaagta acctttcttg aaggtgattc acatgacaca gtacttacct ctgaggaggt 780
tgttctcaag aacggtgaac tcgaagcact cgagacgccc gttgatagct tcacaaatgg 840
agctatcgtt ggcacaccag tctgtgtaaa tggcctcatg ctcttagaga ttaaggacaa 900
agaacaatac tgcgcattgt ctcctggttt actggctaca aacaatgtct ttcgcttaaa 960
agggggtgca ccaattaaag gtgtaacctt tggagaagat actgtttggg aagttcaagg 1020
ttacaagaat gtgagaatca catttgagct tgatgaacgt gttgacaaag tgcttaatga 1080
aaagtgctct gtctacactg ttgaatccgg taccgaagtt actgagtttg catgtgttgt 1140
agcagaggct gttgtgaaga ctttacaacc agtttctgat ctccttacca acatgggtat 1200
tgatcttgat gagtggagtg tagctacatt ctacttattt gatgatgctg gtgaagaaaa 1260
cttttcatca cgtatgtatt gttcctttta ccctccagat gaggaagaag aggacgatgc 1320
agagtgtgag gaagaagaaa ttgatgaaac ctgtgaacat gagtacggta cagaggatga 1380
ttatcaaggt ctccctctgg aatttggtgc ctcagctgaa acagttcgag ttgaggaaga 1440
agaagaggaa gactggctgg atgatactac tgagcaatca gagattgagc cagaaccaga 1500
acctacacct gaagaaccag ttaatcagtt tactggttat ttaaaactta ctgacaatgt 1560
tgccattaaa tgtgttgaca ccgttaagga ggcacaaagt gctaatccta tggtgattgt 1620
aaatgctgct aacatacacc tgaaacatgg tggtggtgta gcaggtgcac tcaacaaggc 1680
aaccaatggt gccatgcaaa aggagagtga tgattacatt aagctaaatg gccctcttac 1740
agtaggaggg tcttgtttgc tttctggaca taatcttgct aagaagtgtc tgcatgttgt 1800
tggacctaac ctaaatgcag gtgaggacat ccagcttctt aaggcagcat atgaaaattt 1860
caattcacag gacatcttac ttgcaccatt gttgtcagca ggcatatttg gtgctaaacc 1920
acttcagtct ttacaagtgt gcgtgcagac ggttcgtaca caggtttata ttgcagtcaa 1980
tgacaaagct ctttatgagc aggttgtcat ggattatctt gataacctga agcctagagt 2040
ggaagcacct aaacaagagg agccaccaaa cacagaagat tccaaaactg aggagaaatc 2100

-continued

```
tgtcgtacag aagcctgtcg atgtgaagcc aaaaattaag gcctgcattg atgaggttac   2160

cacaacactg gaagaaacta agtttcttac caataagtta ctcttgtttg ctgatatcaa   2220

tggtaagctt taccatgatt ctcagaacat gcttagaggt gaagatatgt ctttccttga   2280

ggaggatgca ccttacatgg taggtgatgt tatcactagt ggtgatatca cttgtgttgt   2340

aataccctcc aaaaaggctg gtggcactac tgagatgctc tcaagagctt tgaagaaagt   2400

gccagttgat gagtatataa ccacgtaccc tggacaagga tgtgctggtt atacacttga   2460

ggaagctaag actgctctta agaaatgcaa atctgcattt tatgtactac cttcagaagc   2520

acctaatgct aaggaagaga ttctaggaac tgtatcctgg aatttgagag aaatgcttgc   2580

tcatgctgaa gaggcaagaa aattaatgcc tatatgcatg gatgttagag ccataatggc   2640

aaccatccaa cgtaagtata aaggagttaa aattcaagag ggcatcgttg actatggtgt   2700

ccgattcttc ttttatacta gtaaagagcc tgtagcttct attattacga agctgaactc   2760

tctaaatgag ccgcttgtca caatgccaat tggttatgtg acacatggtt ttaatcttga   2820

agaggctgcg cgctgtatgc gttctcttaa agctcctgcc gtagtgtcag tatcatcacc   2880

agatgctgtt actacatata atggatacct cacttcgtca tcaaagacat ctgaggagca   2940

ctttgtagaa acagtttctt tggctggctc ttacagagat tggtcctatt caggacagcg   3000

tacagagtta ggtgttgaat ttcttaagcg tggtgacaaa attgtgtacc acaccctgga   3060

gagccccgtc gagtttcatc ttgacggtga ggttctttca cttgacaaac taaagagtct   3120

cttatccctg cgggaggtta agactataaa agtgttcaca actgtggaca acactaatct   3180

ccacacacag cttgtggata tgtctatgac atatggacag cagtttggtc caacatactt   3240

ggatggtgct gatgttacaa aaattaaacc tcatgtaaat catgagggta agactttctt   3300

tgtactacct agtgatgaca cactacgtag tgaagctttc gagtactacc atactcttga   3360

tgagagtttt cttggtaggt acatgtctgc tttaaaccac acaaagaaat ggaaatttcc   3420

tcaagttggt ggtttaactt caattaaatg ggctgataac aattgttatt tgtctagtgt   3480

tttattagca cttcaacagc ttgaagtcaa attcaatgca ccagcacttc aagagg       3536
```

<210> SEQ ID NO 13
<211> LENGTH: 1801
<212> TYPE: DNA
<213> ORGANISM: SARS coronavirus Shanghai QXC

<400> SEQUENCE: 13

```
cattacttta tgatgccaac tactttgttt gctggcacac acataactat gactactgta     60

taccatataa cagtgtcaca gatacaattg tcgttactga aggtgacggc atttcaacac    120

caaaactcaa agaagactac caaattggtg gttattctga ggataggcac tcaggtgtta    180

aagactatgt cgttgtacat ggctatttca ccgaagttta ctaccagctt gagtctacac    240

aaattactac aaacactggt attgaaaatg ctacattctt catctttaac aagcttgtta    300

aagacccacc gaatgtgcaa atacacacaa tcgacggctc ttcaggagtt gctaatccag    360

caatggatcc aatttatgat gagccgacga cgactactag cgtgcctttg taagcacaag    420

aaagtgagta cgaacttatg tactcattcg tttcggaaga aacaggtacg ttaatagtta    480

atagcgtact tctttttctt gccttcgtgg tattcttgct agtcacacta gccatcctta    540

ctgcgcttcg attgtgtgcg tactgctgca atattgttaa cgtgagttta gtaaaaccaa    600

cggtttacgt ctactcgcgt gttaaaaatc tgaactctcc tgaaggagtt cctgatcttc    660

tggtctaaac gaactaacta ttattattat tctgtttgga actttaacat tgcttatcat    720
```

-continued

```
ggcagacaac ggtactatta ccgttgagga gcttaaacaa ctcctggaac aatggaacct    780
agtaataggt ttcctattcc tagcctggat tatgttacta caatttgcct attctaatcg    840
gaacaggttt ttgtacataa taaagcttgt tttcctctgg ctcttgtggc cagtaacact    900
tgcttgtttt gtgcttgctg ctgtctacag aattaattgg gtgactggcg ggattgcgat    960
tgcaatggct tgtattgtag gcttgatgtg gcttagctac ttcgttgctt ccttcaggct   1020
gtttgctcgt acccgctcaa tgtggtcatt caacccggaa acaaacattc ttcccaatgt   1080
gcctctccgg gggacaattg tgaccagacc gctcatggaa agtgaacttg tcattggtgc   1140
tgtgatcatt cgtggtcact tgcgaatggc cggacactcc ctagggcgct gtgacattaa   1200
ggacctgcca aaagagatca ctgtggctac atcacgaacg ctttcttatt acaaattagg   1260
agcgtcgcag cgtgtaggca ctgattcagg ttttgctgca tacaaccgct accgtattgg   1320
aaactataaa ttaaatacag accacgccgg tagcaacgac aatattgctt tgctagtaca   1380
gtaagtgaca acagatgttt catcttgttg acttccaggt tacaatagca gagatattga   1440
ttatcattat gaggactttc aggattgcta tttggaatct tgacgttata ataagttcaa   1500
tagtgagaca attatttaag cctctaacta agaagaatta ttcggagtta gatgatgaag   1560
aacctatgga gttagattat ccataaaacg aacatgaaaa ttattctctt cctgacattg   1620
attgtattta catcttgcga gctatatcac tatcaggagt gtgttagagg tacgactgta   1680
ctactaaaag aaccttgccc atcagcaaca tacgagggca attcaccatt tcaccctctt   1740
gctgacaata aatttgcact aacttgcact agcacacact ttgcttttgc ttgtgctgac   1800
g                                                                   1801
```

<210> SEQ ID NO 14
<211> LENGTH: 1706
<212> TYPE: DNA
<213> ORGANISM: SARS coronavirus Shanghai LY

<400> SEQUENCE: 14

```
tctgtgtagc tgtcgctcgg ctgcatgcct agtgcaccta cgcagtataa acaataataa     60
attttactgt cgttgacaag aaacgagtaa ctcgtccctc ttctgcagac tgcttacggt    120
ttcgtccgtg ttgcagtcga tcatcagcat acctaggttt cgtccgggtg tgaccgaaag    180
gtaagatgga gagccttgtt cttggtgtca acgagaaaac acacgtccaa ctcagtttgc    240
ctgtccttca ggttagagac gtgctagtgc gtggcttcgg ggactctgtg gaagaggccc    300
tatcggaggc acgtgaacac ctcaaaaatg gcacttgtgg tctagtagag ctggaaaaag    360
gcgtactgcc ccagcttgaa cagccctatg tgttcattaa acgttctgat gccttaagca    420
ccaatcacgg ccacaaggtc gttgagctgg ttgcagaaat ggacggcatt cagtacggtc    480
gtagcggtat aacactggga gtactcgtgc cacatgtggg cgaaacccca attgcatacc    540
gcaatgttct tcttcgtaag aacggtaata agggagccgg tggtcatagc tatggcatcg    600
atctaaagtc ttatgactta ggtgacgagc ttggcactga tcccattgaa gattatgaac    660
aaaactggaa cactaagcat ggcagtggtg cactccgtga actcactcgt gagctcaatg    720
gaggtgtagt cactcgctat gtcgacaaca atttctgtgg cccagatggg taccctcttg    780
attgcatcaa agattttcta gcacgcgcgg gcaagtcaat gtgcactctt tccgaacaac    840
ttgattacat cgagtcgaag agaggtgtct actgctgccg tgaccatgag catgaaattg    900
cctggttcac tgagcgctct gataagagct gcgagcacca gacacccttc gaaattaaga    960
```

-continued

```
gtgccaagaa atttgacact ttcaaagggg aatgcccaaa gtttgtgttt cctcttaact   1020

caaaagtcaa agtcattcaa ccacgtgttg aaaagaaaaa gactgagggt ttcatggggc   1080

gtatacgctc tgtgtaccct gttgcatctc cacaggagtg taacaatatg cacttgtcta   1140

ccttgatgaa atgtaatcat tgcgatgaag tttcatggca gacgtgcgac tttctgaaag   1200

ccacttgtga acattgtggc actgaaaatt tagttattga aggacctact acatgtgggt   1260

acctacctac taatgctgta gtgaaaatgc catgtcctgc ctgtcaagac ccagagattg   1320

gacctgagca tagtgttgca gattatcaca accactcaaa cattgaaact cgactccgca   1380

agggaggtag gactagatgt tttggaggct gtgtgtttgc ctatgttggc tgctataata   1440

agcgtgccta ctgggttcct cgtgctagtg ctgatattgg ctcaggccat actggcatta   1500

ctggtgacaa tgtggagacc ttgaatgagg atctccttga gatactgagt cgtgaacgtg   1560

ttaacattaa cattgttggc gattttcatt tgaatgaaga ggttgccatc attttggcat   1620

ctttctctgc ttctacaagt gcctttattg acactataaa gagtcttgat tacaagtctt   1680

tcaaaaccat tgttgagtcc tgcggt                                        1706
```

<210> SEQ ID NO 15
<211> LENGTH: 10546
<212> TYPE: DNA
<213> ORGANISM: SARS coronavirus Shanghai LY

<400> SEQUENCE: 15

```
agtgttttat tagcacttca acagcttgaa gtcaaattca atgcaccagc acttcaagag     60

gcttattata gagcccgtgc tggtgatgct gctaactttt gtgcactcat actcgcttac    120

agtaataaaa ctgttggcga gcttggtgat gtcagagaaa ctatgaccca tcttctacag    180

catgctaatt tggaatctgc aaagcgagtt cttaatgtgg tgtgtaaaca ttgtggtcag    240

aaaactacta ccttaacggg tgtagaagct gtgatgtata tgggtactct atcttatgat    300

aatcttaaga caggtgtttc cattccatgt gtgtgtggtc gtgatgctac acaatatcta    360

gtacaacaag agtcttcttt tgttatgatg tctgcaccac ctgctgagta taaattacag    420

caaggtacat tcttatgtgc gaatgagtac actggtaact atcagtgtgg tcattacact    480

catataactg ctaaggagac cctctatcgt attgacggag ctcaccttac aaagatgtca    540

gagtacaaag gaccagtgac tgatgttttc tacaaggaaa catcttacac tacaaccatc    600

aagcctgtgt cgtataaact cgatggagtt acttacacag agattgaacc aaaattggat    660

gggtattata aaaaggataa tgcttactat acagagcagc ctatagacct tgtaccaact    720

caaccattac caaatgcgag ttttgataat ttcaaactca catgttctaa cacaaaattt    780

gctgatgatt taaatcaaat gacaggcttc acaaagccag cttcacgaga gctatctgtc    840

acattcttcc cagacttgaa tggcgatgta gtggctattg actatagaca ctattcagcg    900

agtttcaaga aaggtgctaa attactgcat aagccaattg tttggcacat taaccaggct    960

acaaccaaga caacgttcaa accaaacact tggtgtttac gttgtctttg gagtacaaag   1020

ccagtagata cttcaaattc atttgaagtt ctggcagtag aagacacaca aggaatggac   1080

aatcttgctt gtgaaagtca acaacccacc tctgaagaag tagtggaaaa tcctaccata   1140

cagaaggaag tcatagagtg tgacgtgaaa actaccgaag ttgtaggcaa tgtcatactt   1200

aaaccatcag atgaaggtgt taaagtaaca caagagttag gtcatgagga tcttatggct   1260

gcttatgtgg aaaacacaag cattaccatt aagaaaccta atgagctttc actagcctta   1320

ggtttaaaaa caattgccac tcatggtatt gctgcaatta atagtgttcc ttggagtaaa   1380
```

-continued

```
attttggctt atgtcaaacc attcttagga caagcagcaa ttacaacatc aaattgcgct   1440
aagagattag cacaacgtgt gtttaacaat tatatgcctt atgtgtttac attattgttc   1500
caattgtgta cttttactaa aagtaccaat tctagaatta gagcttcact acctacaact   1560
attgctaaaa atagtgttaa gagtgttgct aaattatgtt tggatgccgg cattaattat   1620
gtgaagtcac ccaaattttc taaattgttc acaatcgcta tgtggctatt gttgttaagt   1680
atttgcttag gttctctaat ctgtgtaact gctgcttttg gtgtactctt atctaatttt   1740
ggtgctcctt cttattgtaa tggcgttaga gaattgtatc ttaattcgtc taacgttact   1800
actatggatt tctgtgaagg ttcttttcct tgcagcattt gtttaagtgg attagactcc   1860
cttgattctt atccagctct tgaaaccatt caggtgacga tttcatcgta caagctagac   1920
ttgacaattt taggtctggc cgctgagtgg gttttggcat atatgttgtt cacaaaattc   1980
ttttatttat taggtctttc agctataatg caggtgttct ttggctattt tgctagtcat   2040
ttcatcagca attcttggct catgtggttt atcattagta ttgtacaaat ggcacccgtt   2100
tctgcaatgg ttaggatgta catcttcttt gcttctttct actacatatg gaagagctat   2160
gttcatatca tggatggttg cacctcttcg acttgcatga tgtgctataa gcgcaatcgt   2220
gccacacgcg ttgagtgtac aactattgtt aatggcatga agagatcttt ctatgtctat   2280
gcaaatggag gccgtggctt ctgcaagact cacaattgga attgtctcaa ttgtgacaca   2340
ttttgcactg gtagtacatt cattagtgat gaagttgctc gtgatttgtc actccagttt   2400
aaaagaccaa tcaaccctac tgaccagtca tcgtatattg ttgatagtgt tgctgtgaaa   2460
aatggcgcgc ttcacctcta ctttgacaag gctggtcaaa agacctatga gagacatccg   2520
ctctcccatt ttgtcaattt agacaatttg agagctaaca acactaaagg ttcactgcct   2580
attaatgtca tagtttttga tggcaagtcc aaatgcgacg agtctgcttc taagtctgct   2640
tctgtgtact acagtcagct gatgtgccaa cctattctgt tgcttgacca agctcttgta   2700
tcagacgttg gagatagtac tgaagtttcc gttaagatgt ttgatgctta tgtcgacacc   2760
ttttcagcaa cttttagtgt tcctatggaa aaacttaagg cacttgttgc tacagctcac   2820
agcgagttag caaagggtgt agctttagat ggtgtccttt ctacattcgt gtcagctgcc   2880
cgacaaggtg ttgttgatac cgatgttgac acaaaggatg ttattgaatg tctcaaactt   2940
tcacatcact ctgacttaga agtgacaggt gacagttgta acaatttcat gctcacctat   3000
aataaggttg aaaacatgac gcccagagat cttggcgcat gtattgactg taatgcaagg   3060
catatcaatg cccaagtagc aaaaagtcac aatgtttcac tcatctggaa tgtaaaagac   3120
tacatgtctt tatctgaaca gctgcgtaaa caaattcgta gtgctgccaa gaagaacaac   3180
ataccttta gactaacttg tgctacaact agacaggttg tcaatgtcat aactactaaa   3240
atctcactca agggtggtaa gattgttagt acttgtttta aacttatgct taaggccaca   3300
ttattgtgcg ttcttgctgc attggtttgt tatatcgtta tgccagtaca tacattgtca   3360
atccatgatg gttacacaaa tgaaatcatt ggttacaaag ccattcagga tggtgtcact   3420
cgtgacatca tttctactga tgattgtttt gcaaataaac atgctggttt tgacgcatgg   3480
tttagccagc gtggtggttc atacaaaaat gacaaaagct gccctgtagt agctgctatc   3540
attacaagag agattggttt catagtgcct ggcttaccgg gtactgtgct gagagcaatc   3600
aatggtgact tcttgcattt tctacctcgt gtttttagtg ctgttggcaa catttgctac   3660
acaccttcca aactcattga gtatagtgat tttgctacct ctgcttgcgt tcttgctgct   3720
```

-continued

```
gagtgtacaa tttttaagga tgctatgggc aaacctgtgc catattgtta tgacactaat   3780
ttgctagagg gttctatttc ttatagtgag cttcgtccag acactcgtta tgtgcttatg   3840
gatggttcca tcatacagtt tcctaacact tacctggagg gttctgttag agtagtaaca   3900
acttttgatg ctgagtactg tagacatggt acatgcgaaa ggtcagaagt aggtatttgc   3960
ctatctacca gtggtagatg ggttcttaat aatgagcatt acagagctct atcaggagtt   4020
ttctgtggtg ttgatgcgat gaatctcata gctaacatct ttactcctct tgtgcaacct   4080
gtgggtgctt tagatgtgtc tgcttcagta gtggctggtg gtattattgc catattggtg   4140
acttgtgctg cctactactt tatgaaattc agacgtgttt ttggtgagta caaccatgtt   4200
gttgctgcta atgcactttt gtttttgatg tctttcacta tactctgtct ggtaccagct   4260
tacagctttc tgccgggagt ctactcagtc ttttacttgt acttgacatt ctatttcacc   4320
aatgatgttt cattcttggc tcaccttcaa tggtttgcca tgttttctcc tattgtgcct   4380
ttttggataa cagcaatcta tgtattctgt atttctctga agcactgcca ttggttcttt   4440
aacaactatc ttaggaaaag agtcatgttt aatggagtta catttagtac cttcgaggag   4500
gctgctttgt gtaccttttt gctcaacaag gaaatgtacc taaaattgcg tagcgagaca   4560
ctgttgccac ttacacagta taacaggtat cttgctctat ataacaagta caagtatttc   4620
agtggagcct tagatactac cagctatcgt gaagcagctt gctgccactt agcaaaggct   4680
ctaaatgact ttagcaactc aggtgctgat gttctctacc aaccaccaca gacatcaatc   4740
acttctgctg ttctgcagag tggttttagg aaaatggcat tcccgtcagg caaagttgaa   4800
gggtgcatgg tacaagtaac ctgtggaact acaactctta atggattgtg gttggatgac   4860
acagtatact gtccaagaca tgtcatttgc acagcagaag acatgcttaa tcctaactat   4920
gaagatctgc tcattcgcaa atccaaccat agctttcttg ttcaggctgg caatgttcaa   4980
cttcgtgtta ttggccattc tatgcaaaat tgtctgctta ggcttaaagt tgatacttct   5040
aaccctaaga cacccaagta taaatttgtc cgtatccaac ctggtcaaac attttcagtt   5100
ctagcatgct acaatggttc accatctggt gtttatcagt gtgccatgag acctaatcat   5160
accattaaag gttctttcct taatggatca tgtggtagtg ttggttttaa cattgattat   5220
gattgcgtgt ctttctgcta tatgcatcat atggagcttc caacaggagt acacgctggt   5280
accgacttag aaggtaaatt ctatggtcca tttgttgaca gacaaactgc acaggctgca   5340
ggtacagaca caaccataac attaaatgtt ttggcatggc tgtatgctgc tgttatcaat   5400
ggtgataggt ggtttcttaa tagattcacc actactttga atgactttaa ccttgtggca   5460
atgaagtaca actatgaacc tttgacacaa gatcatgttg acatattggg acctctttct   5520
gctcaaacag gaattgccgt cttagatatg tgtgctgctt tgaaagagct gctgcagaat   5580
ggtatgaatg gtcgtactat ccttggtagc actattttag aagatgagtt tacaccattt   5640
gatgttgtta gacaatgctc tggtgttacc ttccaaggta agttcaagaa aattgttaag   5700
ggcactcatc attggatgct tttaactttc ttgacatcac tattgattct tgttcaaagt   5760
acacagtggt cactgttttt ctttgtttac gagaatgctt tcttgccatt tactcttggt   5820
attatggcaa ttgctgcatg tgctatgctg cttgttaagc ataagcacgc attcttgtgc   5880
ttgtttctgt taccttctct tgcaacagtt gcttacttta atatggtcta catgcctgct   5940
agctgggtga tgcgtatcat gacatggctt gaattggctg acactagctt gtctggttat   6000
aggcttaagg attgtgttat gtatgcttca gctttagttt tgcttattct catgacagct   6060
cgcactgttt atgatgatgc tgctagacgt gtttggacac tgatgaatgt cattacactt   6120
```

-continued

```
gtttacaaag tctactatgg taatgcttta gatcaagcta tttccatgtg ggccttagtt   6180
atttctgtaa cctctaacta ttctggtgtc gttacgacta tcatgttttt agctagagct   6240
atagtgtttg tgtgtgttga gtattatcca ttgttattta ttactggcaa caccttacag   6300
tgtatcatgc ttgtttattg tttcttaggc tattgttgct gctgctactt tggccttttc   6360
tgtttactca accgttactt caggcttact cttggtgttt atgactactt ggtctctaca   6420
caagaattta ggtatatgaa ctcccagggg cttttgcctc ctaagagtag tattgatgct   6480
ttcaagctta acattaagtt gttgggtatt ggaggtaaac catgtatcaa ggttgctact   6540
gtacagtcta aaatgtctga cgtaaagtgc acatctgtgg tactgctctc ggttcttcaa   6600
caacttagag tagagtcatc ttctaaattg tgggcacaat gtgtacaact ccacaatgat   6660
attcttcttg caaaagacac aactgaagct ttcgagaaga tggtttctct tttgtctgtt   6720
ttgctatcca tgcagggtgc tgtagacatt aataggttgt gcgaggaaat gctcgataac   6780
cgtgctactc ttcaggctat tgcttcagaa tttagttctt taccatcata tgccgcttat   6840
gccactgccc aggaggccta tgagcaggct gtagctaatg gtgattctga agtcgttctc   6900
aaaaagttaa agaaatcttt gaatgtggct aaatctgagt ttgaccgtga tgctgccatg   6960
caacgcaagt tggaaaagat ggcagatcag gctatgaccc aaatgtacaa acaggcaaga   7020
tctgaggaca agagggccca agtcgcttct gctatgcaaa caatgctctt cactatgcta   7080
aggaagcttg ataatgatgc acttaacaac attatcaaca atgcgcgtga tggttgtgtt   7140
ccactcaaca tcataccatt gactacagca gccaaactca tggttgttgt ccctgattat   7200
ggtacctaca agaacacttg tgatggtaac acctttacat atgcatctgc actctgggaa   7260
atccagcaag ttgttgatgc ggatagcaag attgttcaac ttagtgaaat taacatggac   7320
aattcaccaa atttggcttg gcctcttatt gttacagctc taagagccaa ctcagctgtt   7380
aaactacaga ataatgaact gagtccagta gcactacgac agatgtcctg tgcggctggt   7440
accacacaaa cagcttgtac tgatgacaat gcacttgcct actataacaa ttcgaaggga   7500
ggtaggtttg tgctggcatt actatcagac caccaagatc tcaaatgggc tagattccct   7560
aagagtgatg gtacaggtac aatttacaca gaactggaac caccttgtag gtttgttaca   7620
gacacaccaa aagggcctaa agtgaaatac ttgtacttca tcaaaggctt aaacaaccta   7680
aatagaggta tggtgctggg cagtttagct gctacagtac gtcttcaggc tggaaatgct   7740
acagaagtac ctgccaattc aactgtgctt tccttctgtg cttttgcagt agaccctgct   7800
aaagcatata aggattacct agcaagtgga ggacaaccaa tcaccaactg tgtgaagatg   7860
ttgtgtacac acactggtac aggacaggca attactgtaa caccagaagc taacatggac   7920
caagagtcct ttggtggtgc ttcatgttgt ctgtattgta gatgccacat tgaccatcca   7980
aatcctaaag gattctgtga cttgaaaggt aagtacgtcc aaatacctac cacttgtgct   8040
aatgacccag tgggttttac acttagaaac acagtctgta ccgtctgcgg aatgtggaaa   8100
ggttatggct gtagttgtga ccaactccgc gaacccttga tgcagtctgc ggatgcatca   8160
acgtttttaa acgggtttgc ggtgtaagtg cagcccgtct tacaccgtgc ggcacaggca   8220
ctagtactga tgtcgtctac agggcttttg atatttacaa cgaaaaagtt gctggttttg   8280
caaagttcct aaaaactaat tgctgtcgct tccaggagaa ggatgaggaa ggcaatttat   8340
tagactctta ctttgtagtt aagaggcata ctatgtctaa ctaccaacat gaagagacta   8400
tttataactt ggttaaagat tgtccagcgg ttgctgtcca tgactttttc aagtttagag   8460
```

-continued

```
tagatggtga catggtacca catatatcac gtcagcgtct aactaaatac acaatggctg   8520

atttagtcta tgctctacgt cattttgatg agggtaattg tgatacatta aaagaaatac   8580

tcgtcacata caattgctgt gatgatgatt atttcaataa gaaggattgg tatgacttcg   8640

tagagaatcc tgacatctta cgcgtatatg ctaacttagg tgagcgtgta cgccaatcat   8700

tattaaagac tgtacaattc tgcgatgcta tgcgtgatgc aggcattgta ggcgtactga   8760

cattagataa tcaggatctt aatgggaact ggtacgattt cggtgatttc gtacaagtag   8820

caccaggctg cggagttcct attgtggatt catattactc attgctgatg cccatcctca   8880

ctttgactag ggcattggct gctgagtccc atatggatgc tgatctcgca aaaccactta   8940

ttaagtggga tttgctgaaa tatgatttta cggaagagag actttgtctc ttcgaccgtt   9000

attttaaata ttgggaccag acataccatc ccaattgtat taactgtttg gatgataggt   9060

gtatccttca ttgtgcaaac tttaatgtgt tattttctac tgtgtttcca cctacaagtt   9120

ttggaccact agtaagaaaa atatttgtag atggtgttcc ttttgttgtt tcaactggat   9180

accattttcg tgagttagga gtcgtacata atcaggatgt aaacttacat agctcgcgtc   9240

tcagtttcaa ggaactttta gtgtatgctg ctgatccagc tatgcatgca gcttctggca   9300

atttattgct agataaacgc actacatgct tttcagtagc tgcactaaca aacaatgttg   9360

cttttcaaac tgtcaaaccc ggtaatttta ataaagactt ttatgacttt gctgtgtcta   9420

aaggtttctt taaggaagga agttctgttg aactaaaaca cttcttcttt gctcaggatg   9480

gcaacgctgc tatcagtgat tatgactatt atcgttataa tctgccaaca atgtgtgata   9540

tcagacaact cctattcgta gttgaagttg ttgataaata ctttgattgt tacgatggtg   9600

gctgtattaa tgccaaccaa gtaatcgtta acaatctgga taaatcagct ggtttcccat   9660

ttaataaatg ggtaaggct agactttatt atgactcaat gagttatgag gatcaagatg   9720

cacttttcgc gtatactaag cgtaatgtca tccctactat aactcaaatg aatcttaagt   9780

atgccattag tgcaaagaat agagctcgca ccgtagctgg tgtctctatc tgtagtacta   9840

tgacaaatag acagtttcat cagaaattat tgaagtcaat agccgccact agaggagcta   9900

ctgtggtaat tggaacaagc aagttttacg gtggctggca taatatgtta aaaactgttt   9960

acagtgatgt agaaactcca caccttatgg gttgggatta tccaaaatgt gacagagcca  10020

tgcctaacat gcttaggata atggcctctc ttgttcttgc tcgcaaacat aacacttgct  10080

gtaacttatc acaccgtttc tacaggttag ctaacgagtg tgcgcaagta ttaagtgaga  10140

tggtcatgtg tggcggctca ctatatgtta aaccaggtgg aacatcatcc ggtgatgcta  10200

caactgctta tgctaatagt gtctttaaca tttgtcaagc tgttacagcc aatgtaaatg  10260

cacttctttc aactgatggt aataagatag ctgacaagta tgtccgcaat ctacaacaca  10320

ggctctatga gtgtctctat agaaataggg atgttgatca tgaattcgtg gatgagtttt  10380

acgcttacct gcgtaaacat ttctccatga tgattctttc tgatgatgcc gttgtgtgct  10440

ataacagtaa ctatgcggct caaggtttag tagctagcat taagaacttt aaggcagttc  10500

tttattatca aaataatgtg ttcatgtctg aggcaaaatg ttggac                10546
```

<210> SEQ ID NO 16
<211> LENGTH: 1620
<212> TYPE: DNA
<213> ORGANISM: SARS-CoV ZJ-HZ01

<400> SEQUENCE: 16

```
gtaccttcat gaaggtcacc aaactgctgc atttagagac gtacttgttg ttttaaataa      60
```

-continued

```
acgaacaaat taaaatgtct gataatggac cccaatcaaa ccaacgtagt gccccccgca    120

ttacatttgg tggacccaca gattcaactg acaataacca gaatggagga cgcaatgggg    180

caaggccaaa acagcgccga ccccaaggtt tacccaataa tactgcgtct tggttcacag    240

ctctcactca gcatggcaag gaggaactta gattccctcg aggccagggc gttccaatca    300

acaccaatag tggtccagat gaccaaattg gctactaccg aagagctacc cgacgagttc    360

gtggtggtga cggcaaaatg aaagagctca gccccagatg gtacttctat tacctaggaa    420

ctggcccaga agcttcactt ccctacggcg ctaacaaaga aggcatcgta tgggttgcaa    480

ctgagggagc cttgaataca cccaaagacc acattggcac ccgcaatcct aataacaatg    540

ctgccaccgt gctacaactt cctcaaggaa caacattgcc aaaaggcttc tacgcagagg    600

gaagcagagg cggcagtcaa gcctcttctc gctcctcatc acgtagtcgc ggtaattcaa    660

gaaattcaac tcctggcagc agtaggggaa attctcctgc tcgaatggct agcggaggtg    720

gtgaaactgc cctcgcgcta ttgctgctag acagattgaa ccagcttgag agcaaagttt    780

ctggtaaagg ccaacaacaa caaggccaaa ctgtcactaa gaaatctgct gctgaggcat    840

ctaaaaagcc tcgccaaaaa cgtactgcca caaaacagta caacgtcact caagcatttg    900

ggagacgtgg tccagaacaa acccaaggaa atttcgggga ccaagaccta atcagacaag    960

gaactgatta caaacattgg ccgcaaattg cacaatttgc tccaagtgcc tctgcattct   1020

ttggaatgtc acgcattggc atggaagtca caccttcggg aacatggctg acttatcatg   1080

gagccattaa attggatgac aaagatccac aattcaaaga caacgtcata ctgctgaaca   1140

agcacattga cgcatacaaa acattcccac caacagagcc taaaaaggac aaaaagaaaa   1200

agactgatga agctcagcct ttgccgcaga gacaaaagaa gcagcccact gtgactcttc   1260

ttcctgcggc tgacatggat gatttctcca gacaacttca aaattccatg agtggagctt   1320

ctgctgattc aactcaggca taaacactca tgatgaccac acaaggcaga tgggctatgt   1380

aaacgttttc gcaattccgt ttacgataca tagtctactc ttgtgcagaa tgaattctcg   1440

taactaaaca gcacaagtag gtttagttaa ctttaatctc acatagcaat ctttaatcaa   1500

tgtgtaacat tagggaggac ttgaaagagc caccacattt tcatcgaggc cacgcggagt   1560

acgatcgagg gtacagtgaa taatgctagg gagagctgcc tatatggaag agccctaatg   1620
```

```
<210> SEQ ID NO 17
<211> LENGTH: 422
<212> TYPE: PRT
<213> ORGANISM: SARS-CoV Urbani

<400> SEQUENCE: 17

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95
```

-continued

```
Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420


<210> SEQ ID NO 18
<211> LENGTH: 422
<212> TYPE: PRT
<213> ORGANISM: SARS-CoV Tor2

<400> SEQUENCE: 18

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45
```

-continued

```
Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420
```

<210> SEQ ID NO 19
<211> LENGTH: 422
<212> TYPE: PRT
<213> ORGANISM: SARS-CoV Shanghai LY -continued

<400> SEQUENCE: 19

```
Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Ala Ala Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415
```

-continued

```
Ala Asp Ser Thr Gln Ala
            420


<210> SEQ ID NO 20
<211> LENGTH: 422
<212> TYPE: PRT
<213> ORGANISM: SARS-CoV ZJ-HZ01

<400> SEQUENCE: 20

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
```

-continued

```
        355                 360                 365

Pro Lys Lys Asp Lys Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420


<210> SEQ ID NO 21
<211> LENGTH: 1255
<212> TYPE: PRT
<213> ORGANISM: SARS-CoV Urbani

<400> SEQUENCE: 21

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300
```

-continued

```
Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
```

-continued

```
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140
```

-continued

```
Pro Asp  Val Asp Leu Gly Asp  Ile Ser Gly Ile Asn  Ala Ser Val
    1145                 1150                 1155

Val Asn  Ile Gln Lys Glu Ile  Asp Arg Leu Asn Glu  Val Ala Lys
    1160                 1165                 1170

Asn Leu  Asn Glu Ser Leu Ile  Asp Leu Gln Glu Leu  Gly Lys Tyr
    1175                 1180                 1185

Glu Gln  Tyr Ile Lys Trp Pro  Trp Tyr Val Trp Leu  Gly Phe Ile
    1190                 1195                 1200

Ala Gly  Leu Ile Ala Ile Val  Met Val Thr Ile Leu  Leu Cys Cys
    1205                 1210                 1215

Met Thr  Ser Cys Cys Ser Cys  Leu Lys Gly Ala Cys  Ser Cys Gly
    1220                 1225                 1230

Ser Cys  Cys Lys Phe Asp Glu  Asp Asp Ser Glu Pro  Val Leu Lys
    1235                 1240                 1245

Gly Val  Lys Leu His Tyr Thr
    1250                 1255


<210> SEQ ID NO 22
<211> LENGTH: 1255
<212> TYPE: PRT
<213> ORGANISM: SARS-CoV Tor2

<400> SEQUENCE: 22

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
```

-continued

```
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670
```

-continued

```
Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                 1005

Thr Lys  Met Ser Glu Cys Val  Leu Gly Gln Ser Lys  Arg Val Asp
    1010                 1015                 1020

Phe Cys  Gly Lys Gly Tyr His  Leu Met Ser Phe Pro  Gln Ala Ala
    1025                 1030                 1035

Pro His  Gly Val Val Phe Leu  His Val Thr Tyr Val  Pro Ser Gln
    1040                 1045                 1050

Glu Arg  Asn Phe Thr Thr Ala  Pro Ala Ile Cys His  Glu Gly Lys
    1055                 1060                 1065

Ala Tyr  Phe Pro Arg Glu Gly  Val Phe Val Phe Asn  Gly Thr Ser
    1070                 1075                 1080
```

-continued

Trp Phe Ile Thr Gln Arg Asn Phe Phe Ser Pro Gln Ile Ile Thr
    1085 1090 1095

Thr Asp Asn Thr Phe Val Ser Gly Asn Cys Asp Val Val Ile Gly
    1100 1105 1110

Ile Ile Asn Asn Thr Val Tyr Asp Pro Leu Gln Pro Glu Leu Asp
    1115 1120 1125

Ser Phe Lys Glu Glu Leu Asp Lys Tyr Phe Lys Asn His Thr Ser
    1130 1135 1140

Pro Asp Val Asp Leu Gly Asp Ile Ser Gly Ile Asn Ala Ser Val
    1145 1150 1155

Val Asn Ile Gln Lys Glu Ile Asp Arg Leu Asn Glu Val Ala Lys
    1160 1165 1170

Asn Leu Asn Glu Ser Leu Ile Asp Leu Gln Glu Leu Gly Lys Tyr
    1175 1180 1185

Glu Gln Tyr Ile Lys Trp Pro Trp Tyr Val Trp Leu Gly Phe Ile
    1190 1195 1200

Ala Gly Leu Ile Ala Ile Val Met Val Thr Ile Leu Leu Cys Cys
    1205 1210 1215

Met Thr Ser Cys Cys Ser Cys Leu Lys Gly Ala Cys Ser Cys Gly
    1220 1225 1230

Ser Cys Cys Lys Phe Asp Glu Asp Asp Ser Glu Pro Val Leu Lys
    1235 1240 1245

Gly Val Lys Leu His Tyr Thr
    1250 1255

<210> SEQ ID NO 23
<211> LENGTH: 1255
<212> TYPE: PRT
<213> ORGANISM: SARS-CoV Shanghai LY

<400> SEQUENCE: 23

Met Phe Ile Phe Leu Leu Phe Leu Thr Leu Thr Ser Gly Ser Asp Leu
1 5 10 15

Asp Arg Cys Thr Thr Phe Asp Asp Val Gln Ala Pro Asn Tyr Thr Gln
20 25 30

His Thr Ser Ser Met Arg Gly Val Tyr Tyr Pro Asp Glu Ile Phe Arg
35 40 45

Ser Asp Thr Leu Tyr Leu Thr Gln Asp Leu Phe Leu Pro Phe Tyr Ser
50 55 60

Asn Val Thr Gly Phe His Thr Ile Asn His Thr Phe Gly Asn Pro Val
65 70 75 80

Ile Pro Phe Lys Asp Gly Ile Tyr Phe Ala Ala Thr Glu Lys Ser Asn
85 90 95

Val Val Arg Gly Trp Val Phe Gly Ser Thr Met Asn Asn Lys Ser Gln
100 105 110

Ser Val Ile Ile Ile Ser Asn Ser Thr Asn Val Val Ile Arg Ala Cys
115 120 125

Asn Phe Glu Leu Cys Asp Asn Pro Phe Phe Ala Val Ser Lys Pro Met
130 135 140

Gly Thr Gln Thr His Thr Met Ile Phe Asp Asn Ala Phe Asn Cys Thr
145 150 155 160

Phe Glu Tyr Ile Ser Asp Ala Phe Ser Leu Asp Val Ser Glu Lys Ser
165 170 175

Gly Asn Phe Lys His Leu Arg Glu Phe Val Phe Lys Asn Lys Asp Gly
180 185 190

-continued

```
Ser Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Gly Asn Ile Asp Ala Thr Ser
            420                 425                 430

Thr Gly Asn Tyr Asp Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605
```

-continued

```
Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Pro Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Gly Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
```

-continued

```
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255


<210> SEQ ID NO 24
<211> LENGTH: 221
<212> TYPE: PRT
<213> ORGANISM: SARS-CoV Urbani

<400> SEQUENCE: 24

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe
    50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110

Pro Glu Thr Asn Ile Leu Leu Asn Val Pro Leu Arg Gly Thr Ile Val
        115                 120                 125
```

-continued

```
Thr Arg Pro Leu Met Glu Ser Glu Leu Val Ile Gly Ala Val Ile Ile
    130                 135                 140

Arg Gly His Leu Arg Met Ala Gly His Pro Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220


<210> SEQ ID NO 25
<211> LENGTH: 76
<212> TYPE: PRT
<213> ORGANISM: SARS-CoV Urbani

<400> SEQUENCE: 25

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75


<210> SEQ ID NO 26
<211> LENGTH: 4382
<212> TYPE: PRT
<213> ORGANISM: SARS-CoV Urbani

<400> SEQUENCE: 26

Met Glu Ser Leu Val Leu Gly Val Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Ala Leu Ser Glu Ala Arg Glu His Leu Lys Asn
        35                  40                  45

Gly Thr Cys Gly Leu Val Glu Leu Glu Lys Gly Val Leu Pro Gln Leu
    50                  55                  60

Glu Gln Pro Tyr Val Phe Ile Lys Arg Ser Asp Ala Leu Ser Thr Asn
65                  70                  75                  80

His Gly His Lys Val Val Glu Leu Val Ala Glu Met Asp Gly Ile Gln
                85                  90                  95

Tyr Gly Arg Ser Gly Ile Thr Leu Gly Val Leu Val Pro His Val Gly
            100                 105                 110

Glu Thr Pro Ile Ala Tyr Arg Asn Val Leu Leu Arg Lys Asn Gly Asn
        115                 120                 125

Lys Gly Ala Gly Gly His Ser Tyr Gly Ile Asp Leu Lys Ser Tyr Asp
    130                 135                 140

Leu Gly Asp Glu Leu Gly Thr Asp Pro Ile Glu Asp Tyr Glu Gln Asn
145                 150                 155                 160
```

-continued

```
Trp Asn Thr Lys His Gly Ser Gly Ala Leu Arg Glu Leu Thr Arg Glu
                165                 170                 175

Leu Asn Gly Gly Ala Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Tyr Glu His Gln Thr Pro Phe Glu
                245                 250                 255

Ile Lys Ser Ala Lys Lys Phe Asp Thr Phe Lys Gly Glu Cys Pro Lys
            260                 265                 270

Phe Val Phe Pro Leu Asn Ser Lys Val Lys Val Ile Gln Pro Arg Val
        275                 280                 285

Glu Lys Lys Lys Thr Glu Gly Phe Met Gly Arg Ile Arg Ser Val Tyr
    290                 295                 300

Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
                325                 330                 335

Leu Lys Ala Thr Cys Glu His Cys Gly Thr Glu Asn Leu Val Ile Glu
            340                 345                 350

Gly Pro Thr Thr Cys Gly Tyr Leu Pro Thr Asn Ala Val Val Lys Met
        355                 360                 365

Pro Cys Pro Ala Cys Gln Asp Pro Glu Ile Gly Pro Glu His Ser Val
    370                 375                 380

Ala Asp Tyr His Asn His Ser Asn Ile Glu Thr Arg Leu Arg Lys Gly
385                 390                 395                 400

Gly Arg Thr Arg Cys Phe Gly Gly Cys Val Phe Ala Tyr Val Gly Cys
                405                 410                 415

Tyr Asn Lys Arg Ala Tyr Trp Val Pro Arg Ala Ser Ala Asp Ile Gly
            420                 425                 430

Ser Gly His Thr Gly Ile Thr Gly Asp Asn Val Glu Thr Leu Asn Glu
        435                 440                 445

Asp Leu Leu Glu Ile Leu Ser Arg Glu Arg Val Asn Ile Asn Ile Val
    450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
                485                 490                 495

Lys Ser Phe Lys Thr Ile Val Glu Ser Cys Gly Asn Tyr Lys Val Thr
            500                 505                 510

Lys Gly Lys Pro Val Lys Gly Ala Trp Asn Ile Gly Gln Gln Arg Ser
        515                 520                 525

Val Leu Thr Pro Leu Cys Gly Phe Pro Ser Gln Ala Ala Gly Val Ile
    530                 535                 540

Arg Ser Ile Phe Ala Arg Thr Leu Asp Ala Ala Asn His Ser Ile Pro
545                 550                 555                 560

Asp Leu Gln Arg Ala Ala Val Thr Ile Leu Asp Gly Ile Ser Glu Gln
                565                 570                 575

Ser Leu Arg Leu Val Asp Ala Met Val Tyr Thr Ser Asp Leu Leu Thr
```

-continued

```
        580                 585                 590

Asn Ser Val Ile Ile Met Ala Tyr Val Thr Gly Gly Leu Val Gln Gln
    595                 600                 605

Thr Ser Gln Trp Leu Ser Asn Leu Leu Gly Thr Thr Val Glu Lys Leu
    610                 615                 620

Arg Pro Ile Phe Glu Trp Ile Glu Ala Lys Leu Ser Ala Gly Val Glu
625                 630                 635                 640

Phe Leu Lys Asp Ala Trp Glu Ile Leu Lys Phe Leu Ile Thr Gly Val
                645                 650                 655

Phe Asp Ile Val Lys Gly Gln Ile Gln Val Ala Ser Asp Asn Ile Lys
            660                 665                 670

Asp Cys Val Lys Cys Phe Ile Asp Val Val Asn Lys Ala Leu Glu Met
        675                 680                 685

Cys Ile Asp Gln Val Thr Ile Ala Gly Ala Lys Leu Arg Ser Leu Asn
    690                 695                 700

Leu Gly Glu Val Phe Ile Ala Gln Ser Lys Gly Leu Tyr Arg Gln Cys
705                 710                 715                 720

Ile Arg Gly Lys Glu Gln Leu Gln Leu Leu Met Pro Leu Lys Ala Pro
                725                 730                 735

Lys Glu Val Thr Phe Leu Glu Gly Asp Ser His Asp Thr Val Leu Thr
            740                 745                 750

Ser Glu Glu Val Val Leu Lys Asn Gly Glu Leu Glu Ala Leu Glu Thr
        755                 760                 765

Pro Val Asp Ser Phe Thr Asn Gly Ala Ile Val Gly Thr Pro Val Cys
    770                 775                 780

Val Asn Gly Leu Met Leu Leu Glu Ile Lys Asp Lys Glu Gln Tyr Cys
785                 790                 795                 800

Ala Leu Ser Pro Gly Leu Leu Ala Thr Asn Asn Val Phe Arg Leu Lys
                805                 810                 815

Gly Gly Ala Pro Ile Lys Gly Val Thr Phe Gly Glu Asp Thr Val Trp
            820                 825                 830

Glu Val Gln Gly Tyr Lys Asn Val Arg Ile Thr Phe Glu Leu Asp Glu
        835                 840                 845

Arg Val Asp Lys Val Leu Asn Glu Lys Cys Ser Val Tyr Thr Val Glu
    850                 855                 860

Ser Gly Thr Glu Val Thr Glu Phe Ala Cys Val Val Ala Glu Ala Val
865                 870                 875                 880

Val Lys Thr Leu Gln Pro Val Ser Asp Leu Leu Thr Asn Met Gly Ile
                885                 890                 895

Asp Leu Asp Glu Trp Ser Val Ala Thr Phe Tyr Leu Phe Asp Asp Ala
            900                 905                 910

Gly Glu Glu Asn Phe Ser Ser Arg Met Tyr Cys Ser Phe Tyr Pro Pro
        915                 920                 925

Asp Glu Glu Glu Glu Asp Asp Ala Glu Cys Glu Glu Glu Glu Ile Asp
    930                 935                 940

Glu Thr Cys Glu His Glu Tyr Gly Thr Glu Asp Asp Tyr Gln Gly Leu
945                 950                 955                 960

Pro Leu Glu Phe Gly Ala Ser Ala Glu Thr Val Arg Val Glu Glu Glu
                965                 970                 975

Glu Glu Glu Asp Trp Leu Asp Asp Thr Thr Glu Gln Ser Glu Ile Glu
            980                 985                 990

Pro Glu Pro Glu Pro Thr Pro Glu  Glu Pro Val Asn Gln  Phe Thr Gly
        995                 1000                1005
```

-continued

```
Tyr Leu  Lys Leu Thr Asp Asn  Val Ala Ile Lys Cys  Val Asp Ile
    1010                 1015                 1020

Val Lys  Glu Ala Gln Ser Ala  Asn Pro Met Val Ile  Val Asn Ala
    1025                 1030                 1035

Ala Asn  Ile His Leu Lys His  Gly Gly Gly Val Ala  Gly Ala Leu
    1040                 1045                 1050

Asn Lys  Ala Thr Asn Gly Ala  Met Gln Lys Glu Ser  Asp Asp Tyr
    1055                 1060                 1065

Ile Lys  Leu Asn Gly Pro Leu  Thr Val Gly Gly Ser  Cys Leu Leu
    1070                 1075                 1080

Ser Gly  His Asn Leu Ala Lys  Lys Cys Leu His Val  Val Gly Pro
    1085                 1090                 1095

Asn Leu  Asn Ala Gly Glu Asp  Ile Gln Leu Leu Lys  Ala Ala Tyr
    1100                 1105                 1110

Glu Asn  Phe Asn Ser Gln Asp  Ile Leu Leu Ala Pro  Leu Leu Ser
    1115                 1120                 1125

Ala Gly  Ile Phe Gly Ala Lys  Pro Leu Gln Ser Leu  Gln Val Cys
    1130                 1135                 1140

Val Gln  Thr Val Arg Thr Gln  Val Tyr Ile Ala Val  Asn Asp Lys
    1145                 1150                 1155

Ala Leu  Tyr Glu Gln Val Val  Met Asp Tyr Leu Asp  Asn Leu Lys
    1160                 1165                 1170

Pro Arg  Val Glu Ala Pro Lys  Gln Glu Glu Pro Pro  Asn Thr Glu
    1175                 1180                 1185

Asp Ser  Lys Thr Glu Glu Lys  Ser Val Val Gln Lys  Pro Val Asp
    1190                 1195                 1200

Val Lys  Pro Lys Ile Lys Ala  Cys Ile Asp Glu Val  Thr Thr Thr
    1205                 1210                 1215

Leu Glu  Glu Thr Lys Phe Leu  Thr Asn Lys Leu Leu  Leu Phe Ala
    1220                 1225                 1230

Asp Ile  Asn Gly Lys Leu Tyr  His Asp Ser Gln Asn  Met Leu Arg
    1235                 1240                 1245

Gly Glu  Asp Met Ser Phe Leu  Glu Lys Asp Ala Pro  Tyr Met Val
    1250                 1255                 1260

Gly Asp  Val Ile Thr Ser Gly  Asp Ile Thr Cys Val  Val Ile Pro
    1265                 1270                 1275

Ser Lys  Lys Ala Gly Gly Thr  Thr Glu Met Leu Ser  Arg Ala Leu
    1280                 1285                 1290

Lys Lys  Val Pro Val Asp Glu  Tyr Ile Thr Thr Tyr  Pro Gly Gln
    1295                 1300                 1305

Gly Cys  Ala Gly Tyr Thr Leu  Glu Glu Ala Lys Thr  Ala Leu Lys
    1310                 1315                 1320

Lys Cys  Lys Ser Ala Phe Tyr  Val Leu Pro Ser Glu  Ala Pro Asn
    1325                 1330                 1335

Ala Lys  Glu Glu Ile Leu Gly  Thr Val Ser Trp Asn  Leu Arg Glu
    1340                 1345                 1350

Met Leu  Ala His Ala Glu Glu  Thr Arg Lys Leu Met  Pro Ile Cys
    1355                 1360                 1365

Met Asp  Val Arg Ala Ile Met  Ala Thr Ile Gln Arg  Lys Tyr Lys
    1370                 1375                 1380

Gly Ile  Lys Ile Gln Glu Gly  Ile Val Asp Tyr Gly  Val Arg Phe
    1385                 1390                 1395
```

-continued

```
Phe Phe  Tyr Thr Ser Lys Glu  Pro Val Ala Ser Ile  Ile Thr Lys
    1400                 1405                 1410

Leu Asn  Ser Leu Asn Glu Pro  Leu Val Thr Met Pro  Ile Gly Tyr
    1415                 1420                 1425

Val Thr  His Gly Phe Asn Leu  Glu Glu Ala Ala Arg  Cys Met Arg
    1430                 1435                 1440

Ser Leu  Lys Ala Pro Ala Val  Val Ser Val Ser Ser  Pro Asp Ala
    1445                 1450                 1455

Val Thr  Thr Tyr Asn Gly Tyr  Leu Thr Ser Ser Ser  Lys Thr Ser
    1460                 1465                 1470

Glu Glu  His Phe Val Glu Thr  Val Ser Leu Ala Gly  Ser Tyr Arg
    1475                 1480                 1485

Asp Trp  Ser Tyr Ser Gly Gln  Arg Thr Glu Leu Gly  Val Glu Phe
    1490                 1495                 1500

Leu Lys  Arg Gly Asp Lys Ile  Val Tyr His Thr Leu  Glu Ser Pro
    1505                 1510                 1515

Val Glu  Phe His Leu Asp Gly  Glu Val Leu Ser Leu  Asp Lys Leu
    1520                 1525                 1530

Lys Ser  Leu Leu Ser Leu Arg  Glu Val Lys Thr Ile  Lys Val Phe
    1535                 1540                 1545

Thr Thr  Val Asp Asn Thr Asn  Leu His Thr Gln Leu  Val Asp Met
    1550                 1555                 1560

Ser Met  Thr Tyr Gly Gln Gln  Phe Gly Pro Thr Tyr  Leu Asp Gly
    1565                 1570                 1575

Ala Asp  Val Thr Lys Ile Lys  Pro His Val Asn His  Glu Gly Lys
    1580                 1585                 1590

Thr Phe  Phe Val Leu Pro Ser  Asp Asp Thr Leu Arg  Ser Glu Ala
    1595                 1600                 1605

Phe Glu  Tyr Tyr His Thr Leu  Asp Glu Ser Phe Leu  Gly Arg Tyr
    1610                 1615                 1620

Met Ser  Ala Leu Asn His Thr  Lys Lys Trp Lys Phe  Pro Gln Val
    1625                 1630                 1635

Gly Gly  Leu Thr Ser Ile Lys  Trp Ala Asp Asn Asn  Cys Tyr Leu
    1640                 1645                 1650

Ser Ser  Val Leu Leu Ala Leu  Gln Gln Leu Glu Val  Lys Phe Asn
    1655                 1660                 1665

Ala Pro  Ala Leu Gln Glu Ala  Tyr Tyr Arg Ala Arg  Ala Gly Asp
    1670                 1675                 1680

Ala Ala  Asn Phe Cys Ala Leu  Ile Leu Ala Tyr Ser  Asn Lys Thr
    1685                 1690                 1695

Val Gly  Glu Leu Gly Asp Val  Arg Glu Thr Met Thr  His Leu Leu
    1700                 1705                 1710

Gln His  Ala Asn Leu Glu Ser  Ala Lys Arg Val Leu  Asn Val Val
    1715                 1720                 1725

Cys Lys  His Cys Gly Gln Lys  Thr Thr Thr Leu Thr  Gly Val Glu
    1730                 1735                 1740

Ala Val  Met Tyr Met Gly Thr  Leu Ser Tyr Asp Asn  Leu Lys Thr
    1745                 1750                 1755

Gly Val  Ser Ile Pro Cys Val  Cys Gly Arg Asp Ala  Thr Gln Tyr
    1760                 1765                 1770

Leu Val  Gln Gln Glu Ser Ser  Phe Val Met Met Ser  Ala Pro Pro
    1775                 1780                 1785

Ala Glu  Tyr Lys Leu Gln Gln  Gly Thr Phe Leu Cys  Ala Asn Glu
```

-continued

```
    1790                1795                1800

Tyr Thr  Gly Asn Tyr Gln Cys  Gly His Tyr Thr His  Ile Thr Ala
    1805                1810                1815

Lys Glu  Thr Leu Tyr Arg Ile  Asp Gly Ala His Leu  Thr Lys Met
    1820                1825                1830

Ser Glu  Tyr Lys Gly Pro Val  Thr Asp Val Phe Tyr  Lys Glu Thr
    1835                1840                1845

Ser Tyr  Thr Thr Thr Ile Lys  Pro Val Ser Tyr Lys  Leu Asp Gly
    1850                1855                1860

Val Thr  Tyr Thr Glu Ile Glu  Pro Lys Leu Asp Gly  Tyr Tyr Lys
    1865                1870                1875

Lys Asp  Asn Ala Tyr Tyr Thr  Glu Gln Pro Ile Asp  Leu Val Pro
    1880                1885                1890

Thr Gln  Pro Leu Pro Asn Ala  Ser Phe Asp Asn Phe  Lys Leu Thr
    1895                1900                1905

Cys Ser  Asn Thr Lys Phe Ala  Asp Asp Leu Asn Gln  Met Thr Gly
    1910                1915                1920

Phe Thr  Lys Pro Ala Ser Arg  Glu Leu Ser Val Thr  Phe Phe Pro
    1925                1930                1935

Asp Leu  Asn Gly Asp Val Val  Ala Ile Asp Tyr Arg  His Tyr Ser
    1940                1945                1950

Ala Ser  Phe Lys Lys Gly Ala  Lys Leu Leu His Lys  Pro Ile Val
    1955                1960                1965

Trp His  Ile Asn Gln Ala Thr  Thr Lys Thr Thr Phe  Lys Pro Asn
    1970                1975                1980

Thr Trp  Cys Leu Arg Cys Leu  Trp Ser Thr Lys Pro  Val Asp Thr
    1985                1990                1995

Ser Asn  Ser Phe Glu Val Leu  Ala Val Glu Asp Thr  Gln Gly Met
    2000                2005                2010

Asp Asn  Leu Ala Cys Glu Ser  Gln Gln Pro Thr Ser  Glu Glu Val
    2015                2020                2025

Val Glu  Asn Pro Thr Ile Gln  Lys Glu Val Ile Glu  Cys Asp Val
    2030                2035                2040

Lys Thr  Thr Glu Val Val Gly  Asn Val Ile Leu Lys  Pro Ser Asp
    2045                2050                2055

Glu Gly  Val Lys Val Thr Gln  Glu Leu Gly His Glu  Asp Leu Met
    2060                2065                2070

Ala Ala  Tyr Val Glu Asn Thr  Ser Ile Thr Ile Lys  Lys Pro Asn
    2075                2080                2085

Glu Leu  Ser Leu Ala Leu Gly  Leu Lys Thr Ile Ala  Thr His Gly
    2090                2095                2100

Ile Ala  Ala Ile Asn Ser Val  Pro Trp Ser Lys Ile  Leu Ala Tyr
    2105                2110                2115

Val Lys  Pro Phe Leu Gly Gln  Ala Ala Ile Thr Thr  Ser Asn Cys
    2120                2125                2130

Ala Lys  Arg Leu Ala Gln Arg  Val Phe Asn Asn Tyr  Met Pro Tyr
    2135                2140                2145

Val Phe  Thr Leu Leu Phe Gln  Leu Cys Thr Phe Thr  Lys Ser Thr
    2150                2155                2160

Asn Ser  Arg Ile Arg Ala Ser  Leu Pro Thr Thr Ile  Ala Lys Asn
    2165                2170                2175

Ser Val  Lys Ser Val Ala Lys  Leu Cys Leu Asp Ala  Gly Ile Asn
    2180                2185                2190
```

-continued

```
Tyr Val  Lys Ser Pro Lys Phe  Ser Lys Leu Phe Thr  Ile Ala Met
    2195                 2200                 2205

Trp Leu  Leu Leu Leu Ser Ile  Cys Leu Gly Ser Leu  Ile Cys Val
    2210                 2215                 2220

Thr Ala  Ala Phe Gly Val Leu  Leu Ser Asn Phe Gly  Ala Pro Ser
    2225                 2230                 2235

Tyr Cys  Asn Gly Val Arg Glu  Leu Tyr Leu Asn Ser  Ser Asn Val
    2240                 2245                 2250

Thr Thr  Met Asp Phe Cys Glu  Gly Ser Phe Pro Cys  Ser Ile Cys
    2255                 2260                 2265

Leu Ser  Gly Leu Asp Ser Leu  Asp Ser Tyr Pro Ala  Leu Glu Thr
    2270                 2275                 2280

Ile Gln  Val Thr Ile Ser Ser  Tyr Lys Leu Asp Leu  Thr Ile Leu
    2285                 2290                 2295

Gly Leu  Ala Ala Glu Trp Val  Leu Ala Tyr Met Leu  Phe Thr Lys
    2300                 2305                 2310

Phe Phe  Tyr Leu Leu Gly Leu  Ser Ala Ile Met Gln  Val Phe Phe
    2315                 2320                 2325

Gly Tyr  Phe Ala Ser His Phe  Ile Ser Asn Ser Trp  Leu Met Trp
    2330                 2335                 2340

Phe Ile  Ile Ser Ile Val Gln  Met Ala Pro Val Ser  Ala Met Val
    2345                 2350                 2355

Arg Met  Tyr Ile Phe Phe Ala  Ser Phe Tyr Tyr Ile  Trp Lys Ser
    2360                 2365                 2370

Tyr Val  His Ile Met Asp Gly  Cys Thr Ser Ser Thr  Cys Met Met
    2375                 2380                 2385

Cys Tyr  Lys Arg Asn Arg Ala  Thr Arg Val Glu Cys  Thr Thr Ile
    2390                 2395                 2400

Val Asn  Gly Met Lys Arg Ser  Phe Tyr Val Tyr Ala  Asn Gly Gly
    2405                 2410                 2415

Arg Gly  Phe Cys Lys Thr His  Asn Trp Asn Cys Leu  Asn Cys Asp
    2420                 2425                 2430

Thr Phe  Cys Thr Gly Ser Thr  Phe Ile Ser Asp Glu  Val Ala Arg
    2435                 2440                 2445

Asp Leu  Ser Leu Gln Phe Lys  Arg Pro Ile Asn Pro  Thr Asp Gln
    2450                 2455                 2460

Ser Ser  Tyr Ile Val Asp Ser  Val Ala Val Lys Asn  Gly Ala Leu
    2465                 2470                 2475

His Leu  Tyr Phe Asp Lys Ala  Gly Gln Lys Thr Tyr  Glu Arg His
    2480                 2485                 2490

Pro Leu  Ser His Phe Val Asn  Leu Asp Asn Leu Arg  Ala Asn Asn
    2495                 2500                 2505

Thr Lys  Gly Ser Leu Pro Ile  Asn Val Ile Val Phe  Asp Gly Lys
    2510                 2515                 2520

Ser Lys  Cys Asp Glu Ser Ala  Ser Lys Ser Ala Ser  Val Tyr Tyr
    2525                 2530                 2535

Ser Gln  Leu Met Cys Gln Pro  Ile Leu Leu Leu Asp  Gln Val Leu
    2540                 2545                 2550

Val Ser  Asp Val Gly Asp Ser  Thr Glu Val Ser Val  Lys Met Phe
    2555                 2560                 2565

Asp Ala  Tyr Val Asp Thr Phe  Ser Ala Thr Phe Ser  Val Pro Met
    2570                 2575                 2580
```

-continued

```
Glu Lys  Leu Lys Ala Leu Val  Ala Thr Ala His Ser  Glu Leu Ala
    2585                 2590                 2595

Lys Gly  Val Ala Leu Asp Gly  Val Leu Ser Thr Phe  Val Ser Ala
    2600                 2605                 2610

Ala Arg  Gln Gly Val Val Asp  Thr Asp Val Asp Thr  Lys Asp Val
    2615                 2620                 2625

Ile Glu  Cys Leu Lys Leu Ser  His His Ser Asp Leu  Glu Val Thr
    2630                 2635                 2640

Gly Asp  Ser Cys Asn Asn Phe  Met Leu Thr Tyr Asn  Lys Val Glu
    2645                 2650                 2655

Asn Met  Thr Pro Arg Asp Leu  Gly Ala Cys Ile Asp  Cys Asn Ala
    2660                 2665                 2670

Arg His  Ile Asn Ala Gln Val  Ala Lys Ser His Asn  Val Ser Leu
    2675                 2680                 2685

Ile Trp  Asn Val Lys Asp Tyr  Met Ser Leu Ser Glu  Gln Leu Arg
    2690                 2695                 2700

Lys Gln  Ile Arg Ser Ala Ala  Lys Lys Asn Asn Ile  Pro Phe Arg
    2705                 2710                 2715

Leu Thr  Cys Ala Thr Thr Arg  Gln Val Val Asn Val  Ile Thr Thr
    2720                 2725                 2730

Lys Ile  Ser Leu Lys Gly Gly  Lys Ile Val Ser Thr  Cys Phe Lys
    2735                 2740                 2745

Leu Met  Leu Lys Ala Thr Leu  Leu Cys Val Leu Ala  Ala Leu Val
    2750                 2755                 2760

Cys Tyr  Ile Val Met Pro Val  His Thr Leu Ser Ile  His Asp Gly
    2765                 2770                 2775

Tyr Thr  Asn Glu Ile Ile Gly  Tyr Lys Ala Ile Gln  Asp Gly Val
    2780                 2785                 2790

Thr Arg  Asp Ile Ile Ser Thr  Asp Asp Cys Phe Ala  Asn Lys His
    2795                 2800                 2805

Ala Gly  Phe Asp Ala Trp Phe  Ser Gln Arg Gly Gly  Ser Tyr Lys
    2810                 2815                 2820

Asn Asp  Lys Ser Cys Pro Val  Val Ala Ala Ile Ile  Thr Arg Glu
    2825                 2830                 2835

Ile Gly  Phe Ile Val Pro Gly  Leu Pro Gly Thr Val  Leu Arg Ala
    2840                 2845                 2850

Ile Asn  Gly Asp Phe Leu His  Phe Leu Pro Arg Val  Phe Ser Ala
    2855                 2860                 2865

Val Gly  Asn Ile Cys Tyr Thr  Pro Ser Lys Leu Ile  Glu Tyr Ser
    2870                 2875                 2880

Asp Phe  Ala Thr Ser Ala Cys  Val Leu Ala Ala Glu  Cys Thr Ile
    2885                 2890                 2895

Phe Lys  Asp Ala Met Gly Lys  Pro Val Pro Tyr Cys  Tyr Asp Thr
    2900                 2905                 2910

Asn Leu  Leu Glu Gly Ser Ile  Ser Tyr Ser Glu Leu  Arg Pro Asp
    2915                 2920                 2925

Thr Arg  Tyr Val Leu Met Asp  Gly Ser Ile Ile Gln  Phe Pro Asn
    2930                 2935                 2940

Thr Tyr  Leu Glu Gly Ser Val  Arg Val Val Thr Thr  Phe Asp Ala
    2945                 2950                 2955

Glu Tyr  Cys Arg His Gly Thr  Cys Glu Arg Ser Glu  Val Gly Ile
    2960                 2965                 2970

Cys Leu  Ser Thr Ser Gly Arg  Trp Val Leu Asn Asn  Glu His Tyr
```

-continued

```
    2975                2980                2985

Arg Ala Leu Ser Gly Val Phe Cys Gly Val Asp Ala Met Asn Leu
    2990                2995                3000

Ile Ala Asn Ile Phe Thr Pro Leu Val Gln Pro Val Gly Ala Leu
    3005                3010                3015

Asp Val Ser Ala Ser Val Val Ala Gly Gly Ile Ile Ala Ile Leu
    3020                3025                3030

Val Thr Cys Ala Ala Tyr Tyr Phe Met Lys Phe Arg Arg Val Phe
    3035                3040                3045

Gly Glu Tyr Asn His Val Val Ala Ala Asn Ala Leu Leu Phe Leu
    3050                3055                3060

Met Ser Phe Thr Ile Leu Cys Leu Val Pro Ala Tyr Ser Phe Leu
    3065                3070                3075

Pro Gly Val Tyr Ser Val Phe Tyr Leu Tyr Leu Thr Phe Tyr Phe
    3080                3085                3090

Thr Asn Asp Val Ser Phe Leu Ala His Leu Gln Trp Phe Ala Met
    3095                3100                3105

Phe Ser Pro Ile Val Pro Phe Trp Ile Thr Ala Ile Tyr Val Phe
    3110                3115                3120

Cys Ile Ser Leu Lys His Cys His Trp Phe Phe Asn Asn Tyr Leu
    3125                3130                3135

Arg Lys Arg Val Met Phe Asn Gly Val Thr Phe Ser Thr Phe Glu
    3140                3145                3150

Glu Ala Ala Leu Cys Thr Phe Leu Leu Asn Lys Glu Met Tyr Leu
    3155                3160                3165

Lys Leu Arg Ser Glu Thr Leu Leu Pro Leu Thr Gln Tyr Asn Arg
    3170                3175                3180

Tyr Leu Ala Leu Tyr Asn Lys Tyr Lys Tyr Phe Ser Gly Ala Leu
    3185                3190                3195

Asp Thr Thr Ser Tyr Arg Glu Ala Ala Cys Cys His Leu Ala Lys
    3200                3205                3210

Ala Leu Asn Asp Phe Ser Asn Ser Gly Ala Asp Val Leu Tyr Gln
    3215                3220                3225

Pro Pro Gln Thr Ser Ile Thr Ser Ala Val Leu Gln Ser Gly Phe
    3230                3235                3240

Arg Lys Met Ala Phe Pro Ser Gly Lys Val Glu Gly Cys Met Val
    3245                3250                3255

Gln Val Thr Cys Gly Thr Thr Thr Leu Asn Gly Leu Trp Leu Asp
    3260                3265                3270

Asp Thr Val Tyr Cys Pro Arg His Val Ile Cys Thr Ala Glu Asp
    3275                3280                3285

Met Leu Asn Pro Asn Tyr Glu Asp Leu Leu Ile Arg Lys Ser Asn
    3290                3295                3300

His Ser Phe Leu Val Gln Ala Gly Asn Val Gln Leu Arg Val Ile
    3305                3310                3315

Gly His Ser Met Gln Asn Cys Leu Leu Arg Leu Lys Val Asp Thr
    3320                3325                3330

Ser Asn Pro Lys Thr Pro Lys Tyr Lys Phe Val Arg Ile Gln Pro
    3335                3340                3345

Gly Gln Thr Phe Ser Val Leu Ala Cys Tyr Asn Gly Ser Pro Ser
    3350                3355                3360

Gly Val Tyr Gln Cys Ala Met Arg Pro Asn His Thr Ile Lys Gly
    3365                3370                3375
```

-continued

```
Ser Phe Leu Asn Gly Ser Cys Gly Ser Val Gly Phe Asn Ile Asp
    3380                3385                3390

Tyr Asp Cys Val Ser Phe Cys Tyr Met His His Met Glu Leu Pro
    3395                3400                3405

Thr Gly Val His Ala Gly Thr Asp Leu Glu Gly Lys Phe Tyr Gly
    3410                3415                3420

Pro Phe Val Asp Arg Gln Thr Ala Gln Ala Ala Gly Thr Asp Thr
    3425                3430                3435

Thr Ile Thr Leu Asn Val Leu Ala Trp Leu Tyr Ala Ala Val Ile
    3440                3445                3450

Asn Gly Asp Arg Trp Phe Leu Asn Arg Phe Thr Thr Thr Leu Asn
    3455                3460                3465

Asp Phe Asn Leu Val Ala Met Lys Tyr Asn Tyr Glu Pro Leu Thr
    3470                3475                3480

Gln Asp His Val Asp Ile Leu Gly Pro Leu Ser Ala Gln Thr Gly
    3485                3490                3495

Ile Ala Val Leu Asp Met Cys Ala Ala Leu Lys Glu Leu Leu Gln
    3500                3505                3510

Asn Gly Met Asn Gly Arg Thr Ile Leu Gly Ser Thr Ile Leu Glu
    3515                3520                3525

Asp Glu Phe Thr Pro Phe Asp Val Val Arg Gln Cys Ser Gly Val
    3530                3535                3540

Thr Phe Gln Gly Lys Phe Lys Lys Ile Val Lys Gly Thr His His
    3545                3550                3555

Trp Met Leu Leu Thr Phe Leu Thr Ser Leu Leu Ile Leu Val Gln
    3560                3565                3570

Ser Thr Gln Trp Ser Leu Phe Phe Phe Val Tyr Glu Asn Ala Phe
    3575                3580                3585

Leu Pro Phe Thr Leu Gly Ile Met Ala Ile Ala Ala Cys Ala Met
    3590                3595                3600

Leu Leu Val Lys His Lys His Ala Phe Leu Cys Leu Phe Leu Leu
    3605                3610                3615

Pro Ser Leu Ala Thr Val Ala Tyr Phe Asn Met Val Tyr Met Pro
    3620                3625                3630

Ala Ser Trp Val Met Arg Ile Met Thr Trp Leu Glu Leu Ala Asp
    3635                3640                3645

Thr Ser Leu Ser Gly Tyr Arg Leu Lys Asp Cys Val Met Tyr Ala
    3650                3655                3660

Ser Ala Leu Val Leu Leu Ile Leu Met Thr Ala Arg Thr Val Tyr
    3665                3670                3675

Asp Asp Ala Ala Arg Arg Val Trp Thr Leu Met Asn Val Ile Thr
    3680                3685                3690

Leu Val Tyr Lys Val Tyr Tyr Gly Asn Ala Leu Asp Gln Ala Ile
    3695                3700                3705

Ser Met Trp Ala Leu Val Ile Ser Val Thr Ser Asn Tyr Ser Gly
    3710                3715                3720

Val Val Thr Thr Ile Met Phe Leu Ala Arg Ala Ile Val Phe Val
    3725                3730                3735

Cys Val Glu Tyr Tyr Pro Leu Leu Phe Ile Thr Gly Asn Thr Leu
    3740                3745                3750

Gln Cys Ile Met Leu Val Tyr Cys Phe Leu Gly Tyr Cys Cys Cys
    3755                3760                3765
```

-continued

```
Cys Tyr  Phe Gly Leu Phe Cys  Leu Leu Asn Arg Tyr  Phe Arg Leu
    3770                 3775                 3780

Thr Leu  Gly Val Tyr Asp Tyr  Leu Val Ser Thr Gln  Glu Phe Arg
    3785                 3790                 3795

Tyr Met  Asn Ser Gln Gly Leu  Leu Pro Pro Lys Ser  Ser Ile Asp
    3800                 3805                 3810

Ala Phe  Lys Leu Asn Ile Lys  Leu Leu Gly Ile Gly  Gly Lys Pro
    3815                 3820                 3825

Cys Ile  Lys Val Ala Thr Val  Gln Ser Lys Met Ser  Asp Val Lys
    3830                 3835                 3840

Cys Thr  Ser Val Val Leu Leu  Ser Val Leu Gln Gln  Leu Arg Val
    3845                 3850                 3855

Glu Ser  Ser Ser Lys Leu Trp  Ala Gln Cys Val Gln  Leu His Asn
    3860                 3865                 3870

Asp Ile  Leu Leu Ala Lys Asp  Thr Thr Glu Ala Phe  Glu Lys Met
    3875                 3880                 3885

Val Ser  Leu Leu Ser Val Leu  Leu Ser Met Gln Gly  Ala Val Asp
    3890                 3895                 3900

Ile Asn  Arg Leu Cys Glu Glu  Met Leu Asp Asn Arg  Ala Thr Leu
    3905                 3910                 3915

Gln Ala  Ile Ala Ser Glu Phe  Ser Ser Leu Pro Ser  Tyr Ala Ala
    3920                 3925                 3930

Tyr Ala  Thr Ala Gln Glu Ala  Tyr Glu Gln Ala Val  Ala Asn Gly
    3935                 3940                 3945

Asp Ser  Glu Val Val Leu Lys  Lys Leu Lys Lys Ser  Leu Asn Val
    3950                 3955                 3960

Ala Lys  Ser Glu Phe Asp Arg  Asp Ala Ala Met Gln  Arg Lys Leu
    3965                 3970                 3975

Glu Lys  Met Ala Asp Gln Ala  Met Thr Gln Met Tyr  Lys Gln Ala
    3980                 3985                 3990

Arg Ser  Glu Asp Lys Arg Ala  Lys Val Thr Ser Ala  Met Gln Thr
    3995                 4000                 4005

Met Leu  Phe Thr Met Leu Arg  Lys Leu Asp Asn Asp  Ala Leu Asn
    4010                 4015                 4020

Asn Ile  Ile Asn Asn Ala Arg  Asp Gly Cys Val Pro  Leu Asn Ile
    4025                 4030                 4035

Ile Pro  Leu Thr Thr Ala Ala  Lys Leu Met Val Val  Val Pro Asp
    4040                 4045                 4050

Tyr Gly  Thr Tyr Lys Asn Thr  Cys Asp Gly Asn Thr  Phe Thr Tyr
    4055                 4060                 4065

Ala Ser  Ala Leu Trp Glu Ile  Gln Gln Val Val Asp  Ala Asp Ser
    4070                 4075                 4080

Lys Ile  Val Gln Leu Ser Glu  Ile Asn Met Asp Asn  Ser Pro Asn
    4085                 4090                 4095

Leu Ala  Trp Pro Leu Ile Val  Thr Ala Leu Arg Ala  Asn Ser Ala
    4100                 4105                 4110

Val Lys  Leu Gln Asn Asn Glu  Leu Ser Pro Val Ala  Leu Arg Gln
    4115                 4120                 4125

Met Ser  Cys Ala Ala Gly Thr  Thr Gln Thr Ala Cys  Thr Asp Asp
    4130                 4135                 4140

Asn Ala  Leu Ala Tyr Tyr Asn  Asn Ser Lys Gly Gly  Arg Phe Val
    4145                 4150                 4155

Leu Ala  Leu Leu Ser Asp His  Gln Asp Leu Lys Trp  Ala Arg Phe
```

-continued 4160 4165 4170

Pro Lys Ser Asp Gly Thr Gly Thr Ile Tyr Thr Glu Leu Glu Pro
4175 4180 4185

Pro Cys Arg Phe Val Thr Asp Thr Pro Lys Gly Pro Lys Val Lys
4190 4195 4200

Tyr Leu Tyr Phe Ile Lys Gly Leu Asn Asn Leu Asn Arg Gly Met
4205 4210 4215

Val Leu Gly Ser Leu Ala Ala Thr Val Arg Leu Gln Ala Gly Asn
4220 4225 4230

Ala Thr Glu Val Pro Ala Asn Ser Thr Val Leu Ser Phe Cys Ala
4235 4240 4245

Phe Ala Val Asp Pro Ala Lys Ala Tyr Lys Asp Tyr Leu Ala Ser
4250 4255 4260

Gly Gly Gln Pro Ile Thr Asn Cys Val Lys Met Leu Cys Thr His
4265 4270 4275

Thr Gly Thr Gly Gln Ala Ile Thr Val Thr Pro Glu Ala Asn Met
4280 4285 4290

Asp Gln Glu Ser Phe Gly Gly Ala Ser Cys Cys Leu Tyr Cys Arg
4295 4300 4305

Cys His Ile Asp His Pro Asn Pro Lys Gly Phe Cys Asp Leu Lys
4310 4315 4320

Gly Lys Tyr Val Gln Ile Pro Thr Thr Cys Ala Asn Asp Pro Val
4325 4330 4335

Gly Phe Thr Leu Arg Asn Thr Val Cys Thr Val Cys Gly Met Trp
4340 4345 4350

Lys Gly Tyr Gly Cys Ser Cys Asp Gln Leu Arg Glu Pro Leu Met
4355 4360 4365

Gln Ser Ala Asp Ala Ser Thr Phe Leu Asn Gly Phe Ala Val
4370 4375 4380

<210> SEQ ID NO 27
<211> LENGTH: 7073
<212> TYPE: PRT
<213> ORGANISM: SARS-CoV Tor2

<400> SEQUENCE: 27

Met Glu Ser Leu Val Leu Gly Val Asn Glu Lys Thr His Val Gln Leu
1 5 10 15

Ser Leu Pro Val Leu Gln Val Arg Asp Val Leu Val Arg Gly Phe Gly
20 25 30

Asp Ser Val Glu Glu Ala Leu Ser Glu Ala Arg Glu His Leu Lys Asn
35 40 45

Gly Thr Cys Gly Leu Val Glu Leu Glu Lys Gly Val Leu Pro Gln Leu
50 55 60

Glu Gln Pro Tyr Val Phe Ile Lys Arg Ser Asp Ala Leu Ser Thr Asn
65 70 75 80

His Gly His Lys Val Val Glu Leu Val Ala Glu Met Asp Gly Ile Gln
85 90 95

Tyr Gly Arg Ser Gly Ile Thr Leu Gly Val Leu Val Pro His Val Gly
100 105 110

Glu Thr Pro Ile Ala Tyr Arg Asn Val Leu Leu Arg Lys Asn Gly Asn
115 120 125

Lys Gly Ala Gly Gly His Ser Tyr Gly Ile Asp Leu Lys Ser Tyr Asp
130 135 140

-continued

```
Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Ala Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Tyr Glu His Gln Thr Pro Phe Glu
                245                 250                 255

Ile Lys Ser Ala Lys Lys Phe Asp Thr Phe Lys Gly Glu Cys Pro Lys
            260                 265                 270

Phe Val Phe Pro Leu Asn Ser Lys Val Lys Val Ile Gln Pro Arg Val
        275                 280                 285

Glu Lys Lys Lys Thr Glu Gly Phe Met Gly Arg Ile Arg Ser Val Tyr
    290                 295                 300

Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
                325                 330                 335

Leu Lys Ala Thr Cys Glu His Cys Gly Thr Glu Asn Leu Val Ile Glu
            340                 345                 350

Gly Pro Thr Thr Cys Gly Tyr Leu Pro Thr Asn Ala Val Val Lys Met
        355                 360                 365

Pro Cys Pro Ala Cys Gln Asp Pro Glu Ile Gly Pro Glu His Ser Val
    370                 375                 380

Ala Asp Tyr His Asn His Ser Asn Ile Glu Thr Arg Leu Arg Lys Gly
385                 390                 395                 400

Gly Arg Thr Arg Cys Phe Gly Gly Cys Val Phe Ala Tyr Val Gly Cys
                405                 410                 415

Tyr Asn Lys Arg Ala Tyr Trp Val Pro Arg Ala Ser Ala Asp Ile Gly
            420                 425                 430

Ser Gly His Thr Gly Ile Thr Gly Asp Asn Val Glu Thr Leu Asn Glu
        435                 440                 445

Asp Leu Leu Glu Ile Leu Ser Arg Glu Arg Val Asn Ile Asn Ile Val
    450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
                485                 490                 495

Lys Ser Phe Lys Thr Ile Val Glu Ser Cys Gly Asn Tyr Lys Val Thr
            500                 505                 510

Lys Gly Lys Pro Val Lys Gly Ala Trp Asn Ile Gly Gln Gln Arg Ser
        515                 520                 525

Val Leu Thr Pro Leu Cys Gly Phe Pro Ser Gln Ala Ala Gly Val Ile
    530                 535                 540

Arg Ser Ile Phe Ala Arg Thr Leu Asp Ala Ala Asn His Ser Ile Pro
545                 550                 555                 560

Asp Leu Gln Arg Ala Ala Val Thr Ile Leu Asp Gly Ile Ser Glu Gln
```

-continued

```
                565                 570                 575

Ser Leu Arg Leu Val Asp Ala Met Val Tyr Thr Ser Asp Leu Leu Thr
            580                 585                 590

Asn Ser Val Ile Ile Met Ala Tyr Val Thr Gly Gly Leu Val Gln Gln
        595                 600                 605

Thr Ser Gln Trp Leu Ser Asn Leu Leu Gly Thr Thr Val Glu Lys Leu
    610                 615                 620

Arg Pro Ile Phe Glu Trp Ile Glu Ala Lys Leu Ser Ala Gly Val Glu
625                 630                 635                 640

Phe Leu Lys Asp Ala Trp Glu Ile Leu Lys Phe Leu Ile Thr Gly Val
                645                 650                 655

Phe Asp Ile Val Lys Gly Gln Ile Gln Val Ala Ser Asp Asn Ile Lys
            660                 665                 670

Asp Cys Val Lys Cys Phe Ile Asp Val Val Asn Lys Ala Leu Glu Met
        675                 680                 685

Cys Ile Asp Gln Val Thr Ile Ala Gly Ala Lys Leu Arg Ser Leu Asn
    690                 695                 700

Leu Gly Glu Val Phe Ile Ala Gln Ser Lys Gly Leu Tyr Arg Gln Cys
705                 710                 715                 720

Ile Arg Gly Lys Glu Gln Leu Gln Leu Leu Met Pro Leu Lys Ala Pro
                725                 730                 735

Lys Glu Val Thr Phe Leu Glu Gly Asp Ser His Asp Thr Val Leu Thr
            740                 745                 750

Ser Glu Glu Val Val Leu Lys Asn Gly Glu Leu Glu Ala Leu Glu Thr
        755                 760                 765

Pro Val Asp Ser Phe Thr Asn Gly Ala Ile Val Gly Thr Pro Val Cys
    770                 775                 780

Val Asn Gly Leu Met Leu Leu Glu Ile Lys Asp Lys Glu Gln Tyr Cys
785                 790                 795                 800

Ala Leu Ser Pro Gly Leu Leu Ala Thr Asn Asn Val Phe Arg Leu Lys
                805                 810                 815

Gly Gly Ala Pro Ile Lys Gly Val Thr Phe Gly Glu Asp Thr Val Trp
            820                 825                 830

Glu Val Gln Gly Tyr Lys Asn Val Arg Ile Thr Phe Glu Leu Asp Glu
        835                 840                 845

Arg Val Asp Lys Val Leu Asn Glu Lys Cys Ser Val Tyr Thr Val Glu
    850                 855                 860

Ser Gly Thr Glu Val Thr Glu Phe Ala Cys Val Val Ala Glu Ala Val
865                 870                 875                 880

Val Lys Thr Leu Gln Pro Val Ser Asp Leu Leu Thr Asn Met Gly Ile
                885                 890                 895

Asp Leu Asp Glu Trp Ser Val Ala Thr Phe Tyr Leu Phe Asp Asp Ala
            900                 905                 910

Gly Glu Glu Asn Phe Ser Ser Arg Met Tyr Cys Ser Phe Tyr Pro Pro
        915                 920                 925

Asp Glu Glu Glu Glu Asp Asp Ala Glu Cys Glu Glu Glu Glu Ile Asp
    930                 935                 940

Glu Thr Cys Glu His Glu Tyr Gly Thr Glu Asp Asp Tyr Gln Gly Leu
945                 950                 955                 960

Pro Leu Glu Phe Gly Ala Ser Ala Glu Thr Val Arg Val Glu Glu Glu
                965                 970                 975

Glu Glu Glu Asp Trp Leu Asp Asp Thr Thr Glu Gln Ser Glu Ile Glu
            980                 985                 990
```

-continued

```
Pro Glu Pro Glu Pro Thr Pro Glu  Glu Pro Val Asn Gln  Phe Thr Gly
      995                 1000                 1005

Tyr Leu  Lys Leu Thr Asp Asn  Val Ala Ile Lys Cys  Val Asp Ile
    1010                 1015                 1020

Val Lys  Glu Ala Gln Ser Ala  Asn Pro Met Val Ile  Val Asn Ala
    1025                 1030                 1035

Ala Asn  Ile His Leu Lys His  Gly Gly Gly Val Ala  Gly Ala Leu
    1040                 1045                 1050

Asn Lys  Ala Thr Asn Gly Ala  Met Gln Lys Glu Ser  Asp Asp Tyr
    1055                 1060                 1065

Ile Lys  Leu Asn Gly Pro Leu  Thr Val Gly Gly Ser  Cys Leu Leu
    1070                 1075                 1080

Ser Gly  His Asn Leu Ala Lys  Lys Cys Leu His Val  Val Gly Pro
    1085                 1090                 1095

Asn Leu  Asn Ala Gly Glu Asp  Ile Gln Leu Leu Lys  Ala Ala Tyr
    1100                 1105                 1110

Glu Asn  Phe Asn Ser Gln Asp  Ile Leu Leu Ala Pro  Leu Leu Ser
    1115                 1120                 1125

Ala Gly  Ile Phe Gly Ala Lys  Pro Leu Gln Ser Leu  Gln Val Cys
    1130                 1135                 1140

Val Gln  Thr Val Arg Thr Gln  Val Tyr Ile Ala Val  Asn Asp Lys
    1145                 1150                 1155

Ala Leu  Tyr Glu Gln Val Val  Met Asp Tyr Leu Asp  Asn Leu Lys
    1160                 1165                 1170

Pro Arg  Val Glu Ala Pro Lys  Gln Glu Glu Pro Pro  Asn Thr Glu
    1175                 1180                 1185

Asp Ser  Lys Thr Glu Glu Lys  Ser Val Val Gln Lys  Pro Val Asp
    1190                 1195                 1200

Val Lys  Pro Lys Ile Lys Ala  Cys Ile Asp Glu Val  Thr Thr Thr
    1205                 1210                 1215

Leu Glu  Glu Thr Lys Phe Leu  Thr Asn Lys Leu Leu  Leu Phe Ala
    1220                 1225                 1230

Asp Ile  Asn Gly Lys Leu Tyr  His Asp Ser Gln Asn  Met Leu Arg
    1235                 1240                 1245

Gly Glu  Asp Met Ser Phe Leu  Glu Lys Asp Ala Pro  Tyr Met Val
    1250                 1255                 1260

Gly Asp  Val Ile Thr Ser Gly  Asp Ile Thr Cys Val  Val Ile Pro
    1265                 1270                 1275

Ser Lys  Lys Ala Gly Gly Thr  Thr Glu Met Leu Ser  Arg Ala Leu
    1280                 1285                 1290

Lys Lys  Val Pro Val Asp Glu  Tyr Ile Thr Thr Tyr  Pro Gly Gln
    1295                 1300                 1305

Gly Cys  Ala Gly Tyr Thr Leu  Glu Glu Ala Lys Thr  Ala Leu Lys
    1310                 1315                 1320

Lys Cys  Lys Ser Ala Phe Tyr  Val Leu Pro Ser Glu  Ala Pro Asn
    1325                 1330                 1335

Ala Lys  Glu Glu Ile Leu Gly  Thr Val Ser Trp Asn  Leu Arg Glu
    1340                 1345                 1350

Met Leu  Ala His Ala Glu Glu  Thr Arg Lys Leu Met  Pro Ile Cys
    1355                 1360                 1365

Met Asp  Val Arg Ala Ile Met  Ala Thr Ile Gln Arg  Lys Tyr Lys
    1370                 1375                 1380
```

-continued

```
Gly Ile  Lys Ile Gln Glu Gly  Ile Val Asp Tyr Gly  Val Arg Phe
    1385                 1390                 1395

Phe Phe  Tyr Thr Ser Lys Glu  Pro Val Ala Ser Ile  Ile Thr Lys
    1400                 1405                 1410

Leu Asn  Ser Leu Asn Glu Pro  Leu Val Thr Met Pro  Ile Gly Tyr
    1415                 1420                 1425

Val Thr  His Gly Phe Asn Leu  Glu Glu Ala Ala Arg  Cys Met Arg
    1430                 1435                 1440

Ser Leu  Lys Ala Pro Ala Val  Val Ser Val Ser Ser  Pro Asp Ala
    1445                 1450                 1455

Val Thr  Thr Tyr Asn Gly Tyr  Leu Thr Ser Ser Ser  Lys Thr Ser
    1460                 1465                 1470

Glu Glu  His Phe Val Glu Thr  Val Ser Leu Ala Gly  Ser Tyr Arg
    1475                 1480                 1485

Asp Trp  Ser Tyr Ser Gly Gln  Arg Thr Glu Leu Gly  Val Glu Phe
    1490                 1495                 1500

Leu Lys  Arg Gly Asp Lys Ile  Val Tyr His Thr Leu  Glu Ser Pro
    1505                 1510                 1515

Val Glu  Phe His Leu Asp Gly  Glu Val Leu Ser Leu  Asp Lys Leu
    1520                 1525                 1530

Lys Ser  Leu Leu Ser Leu Arg  Glu Val Lys Thr Ile  Lys Val Phe
    1535                 1540                 1545

Thr Thr  Val Asp Asn Thr Asn  Leu His Thr Gln Leu  Val Asp Met
    1550                 1555                 1560

Ser Met  Thr Tyr Gly Gln Gln  Phe Gly Pro Thr Tyr  Leu Asp Gly
    1565                 1570                 1575

Ala Asp  Val Thr Lys Ile Lys  Pro His Val Asn His  Glu Gly Lys
    1580                 1585                 1590

Thr Phe  Phe Val Leu Pro Ser  Asp Asp Thr Leu Arg  Ser Glu Ala
    1595                 1600                 1605

Phe Glu  Tyr Tyr His Thr Leu  Asp Glu Ser Phe Leu  Gly Arg Tyr
    1610                 1615                 1620

Met Ser  Ala Leu Asn His Thr  Lys Lys Trp Lys Phe  Pro Gln Val
    1625                 1630                 1635

Gly Gly  Leu Thr Ser Ile Lys  Trp Ala Asp Asn Asn  Cys Tyr Leu
    1640                 1645                 1650

Ser Ser  Val Leu Leu Ala Leu  Gln Gln Leu Glu Val  Lys Phe Asn
    1655                 1660                 1665

Ala Pro  Ala Leu Gln Glu Ala  Tyr Tyr Arg Ala Arg  Ala Gly Asp
    1670                 1675                 1680

Ala Ala  Asn Phe Cys Ala Leu  Ile Leu Ala Tyr Ser  Asn Lys Thr
    1685                 1690                 1695

Val Gly  Glu Leu Gly Asp Val  Arg Glu Thr Met Thr  His Leu Leu
    1700                 1705                 1710

Gln His  Ala Asn Leu Glu Ser  Ala Lys Arg Val Leu  Asn Val Val
    1715                 1720                 1725

Cys Lys  His Cys Gly Gln Lys  Thr Thr Thr Leu Thr  Gly Val Glu
    1730                 1735                 1740

Ala Val  Met Tyr Met Gly Thr  Leu Ser Tyr Asp Asn  Leu Lys Thr
    1745                 1750                 1755

Gly Val  Ser Ile Pro Cys Val  Cys Gly Arg Asp Ala  Thr Gln Tyr
    1760                 1765                 1770

Leu Val  Gln Gln Glu Ser Ser  Phe Val Met Met Ser  Ala Pro Pro
```

-continued

```
    1775                1780                1785

Ala Glu  Tyr Lys Leu Gln Gln  Gly Thr Phe Leu Cys  Ala Asn Glu
    1790                1795                1800

Tyr Thr  Gly Asn Tyr Gln Cys  Gly His Tyr Thr His  Ile Thr Ala
    1805                1810                1815

Lys Glu  Thr Leu Tyr Arg Ile  Asp Gly Ala His Leu  Thr Lys Met
    1820                1825                1830

Ser Glu  Tyr Lys Gly Pro Val  Thr Asp Val Phe Tyr  Lys Glu Thr
    1835                1840                1845

Ser Tyr  Thr Thr Thr Ile Lys  Pro Val Ser Tyr Lys  Leu Asp Gly
    1850                1855                1860

Val Thr  Tyr Thr Glu Ile Glu  Pro Lys Leu Asp Gly  Tyr Tyr Lys
    1865                1870                1875

Lys Asp  Asn Ala Tyr Tyr Thr  Glu Gln Pro Ile Asp  Leu Val Pro
    1880                1885                1890

Thr Gln  Pro Leu Pro Asn Ala  Ser Phe Asp Asn Phe  Lys Leu Thr
    1895                1900                1905

Cys Ser  Asn Thr Lys Phe Ala  Asp Asp Leu Asn Gln  Met Thr Gly
    1910                1915                1920

Phe Thr  Lys Pro Ala Ser Arg  Glu Leu Ser Val Thr  Phe Phe Pro
    1925                1930                1935

Asp Leu  Asn Gly Asp Val Val  Ala Ile Asp Tyr Arg  His Tyr Ser
    1940                1945                1950

Ala Ser  Phe Lys Lys Gly Ala  Lys Leu Leu His Lys  Pro Ile Val
    1955                1960                1965

Trp His  Ile Asn Gln Ala Thr  Thr Lys Thr Thr Phe  Lys Pro Asn
    1970                1975                1980

Thr Trp  Cys Leu Arg Cys Leu  Trp Ser Thr Lys Pro  Val Asp Thr
    1985                1990                1995

Ser Asn  Ser Phe Glu Val Leu  Ala Val Glu Asp Thr  Gln Gly Met
    2000                2005                2010

Asp Asn  Leu Ala Cys Glu Ser  Gln Gln Pro Thr Ser  Glu Glu Val
    2015                2020                2025

Val Glu  Asn Pro Thr Ile Gln  Lys Glu Val Ile Glu  Cys Asp Val
    2030                2035                2040

Lys Thr  Thr Glu Val Val Gly  Asn Val Ile Leu Lys  Pro Ser Asp
    2045                2050                2055

Glu Gly  Val Lys Val Thr Gln  Glu Leu Gly His Glu  Asp Leu Met
    2060                2065                2070

Ala Ala  Tyr Val Glu Asn Thr  Ser Ile Thr Ile Lys  Lys Pro Asn
    2075                2080                2085

Glu Leu  Ser Leu Ala Leu Gly  Leu Lys Thr Ile Ala  Thr His Gly
    2090                2095                2100

Ile Ala  Ala Ile Asn Ser Val  Pro Trp Ser Lys Ile  Leu Ala Tyr
    2105                2110                2115

Val Lys  Pro Phe Leu Gly Gln  Ala Ala Ile Thr Thr  Ser Asn Cys
    2120                2125                2130

Ala Lys  Arg Leu Ala Gln Arg  Val Phe Asn Asn Tyr  Met Pro Tyr
    2135                2140                2145

Val Phe  Thr Leu Leu Phe Gln  Leu Cys Thr Phe Thr  Lys Ser Thr
    2150                2155                2160

Asn Ser  Arg Ile Arg Ala Ser  Leu Pro Thr Thr Ile  Ala Lys Asn
    2165                2170                2175
```

-continued

```
Ser Val  Lys Ser Val Ala Lys  Leu Cys Leu Asp Ala  Gly Ile Asn
    2180                 2185                 2190

Tyr Val  Lys Ser Pro Lys Phe  Ser Lys Leu Phe Thr  Ile Ala Met
    2195                 2200                 2205

Trp Leu  Leu Leu Leu Ser Ile  Cys Leu Gly Ser Leu  Ile Cys Val
    2210                 2215                 2220

Thr Ala  Ala Phe Gly Val Leu  Leu Ser Asn Phe Gly  Ala Pro Ser
    2225                 2230                 2235

Tyr Cys  Asn Gly Val Arg Glu  Leu Tyr Leu Asn Ser  Ser Asn Val
    2240                 2245                 2250

Thr Thr  Met Asp Phe Cys Glu  Gly Ser Phe Pro Cys  Ser Ile Cys
    2255                 2260                 2265

Leu Ser  Gly Leu Asp Ser Leu  Asp Ser Tyr Pro Ala  Leu Glu Thr
    2270                 2275                 2280

Ile Gln  Val Thr Ile Ser Ser  Tyr Lys Leu Asp Leu  Thr Ile Leu
    2285                 2290                 2295

Gly Leu  Ala Ala Glu Trp Val  Leu Ala Tyr Met Leu  Phe Thr Lys
    2300                 2305                 2310

Phe Phe  Tyr Leu Leu Gly Leu  Ser Ala Ile Met Gln  Val Phe Phe
    2315                 2320                 2325

Gly Tyr  Phe Ala Ser His Phe  Ile Ser Asn Ser Trp  Leu Met Trp
    2330                 2335                 2340

Phe Ile  Ile Ser Ile Val Gln  Met Ala Pro Val Ser  Ala Met Val
    2345                 2350                 2355

Arg Met  Tyr Ile Phe Phe Ala  Ser Phe Tyr Tyr Ile  Trp Lys Ser
    2360                 2365                 2370

Tyr Val  His Ile Met Asp Gly  Cys Thr Ser Ser Thr  Cys Met Met
    2375                 2380                 2385

Cys Tyr  Lys Arg Asn Arg Ala  Thr Arg Val Glu Cys  Thr Thr Ile
    2390                 2395                 2400

Val Asn  Gly Met Lys Arg Ser  Phe Tyr Val Tyr Ala  Asn Gly Gly
    2405                 2410                 2415

Arg Gly  Phe Cys Lys Thr His  Asn Trp Asn Cys Leu  Asn Cys Asp
    2420                 2425                 2430

Thr Phe  Cys Thr Gly Ser Thr  Phe Ile Ser Asp Glu  Val Ala Arg
    2435                 2440                 2445

Asp Leu  Ser Leu Gln Phe Lys  Arg Pro Ile Asn Pro  Thr Asp Gln
    2450                 2455                 2460

Ser Ser  Tyr Ile Val Asp Ser  Val Ala Val Lys Asn  Gly Ala Leu
    2465                 2470                 2475

His Leu  Tyr Phe Asp Lys Ala  Gly Gln Lys Thr Tyr  Glu Arg His
    2480                 2485                 2490

Pro Leu  Ser His Phe Val Asn  Leu Asp Asn Leu Arg  Ala Asn Asn
    2495                 2500                 2505

Thr Lys  Gly Ser Leu Pro Ile  Asn Val Ile Val Phe  Asp Gly Lys
    2510                 2515                 2520

Ser Lys  Cys Asp Glu Ser Ala  Ser Lys Ser Ala Ser  Val Tyr Tyr
    2525                 2530                 2535

Ser Gln  Leu Met Cys Gln Pro  Ile Leu Leu Leu Asp  Gln Ala Leu
    2540                 2545                 2550

Val Ser  Asp Val Gly Asp Ser  Thr Glu Val Ser Val  Lys Met Phe
    2555                 2560                 2565
```

-continued

```
Asp Ala Tyr Val Asp Thr Phe Ser Ala Thr Phe Ser Val Pro Met
    2570                2575                2580

Glu Lys Leu Lys Ala Leu Val Ala Thr Ala His Ser Glu Leu Ala
    2585                2590                2595

Lys Gly Val Ala Leu Asp Gly Val Leu Ser Thr Phe Val Ser Ala
    2600                2605                2610

Ala Arg Gln Gly Val Val Asp Thr Asp Val Asp Thr Lys Asp Val
    2615                2620                2625

Ile Glu Cys Leu Lys Leu Ser His His Ser Asp Leu Glu Val Thr
    2630                2635                2640

Gly Asp Ser Cys Asn Asn Phe Met Leu Thr Tyr Asn Lys Val Glu
    2645                2650                2655

Asn Met Thr Pro Arg Asp Leu Gly Ala Cys Ile Asp Cys Asn Ala
    2660                2665                2670

Arg His Ile Asn Ala Gln Val Ala Lys Ser His Asn Val Ser Leu
    2675                2680                2685

Ile Trp Asn Val Lys Asp Tyr Met Ser Leu Ser Glu Gln Leu Arg
    2690                2695                2700

Lys Gln Ile Arg Ser Ala Ala Lys Lys Asn Asn Ile Pro Phe Arg
    2705                2710                2715

Leu Thr Cys Ala Thr Thr Arg Gln Val Val Asn Val Ile Thr Thr
    2720                2725                2730

Lys Ile Ser Leu Lys Gly Gly Lys Ile Val Ser Thr Cys Phe Lys
    2735                2740                2745

Leu Met Leu Lys Ala Thr Leu Leu Cys Val Leu Ala Ala Leu Val
    2750                2755                2760

Cys Tyr Ile Val Met Pro Val His Thr Leu Ser Ile His Asp Gly
    2765                2770                2775

Tyr Thr Asn Glu Ile Ile Gly Tyr Lys Ala Ile Gln Asp Gly Val
    2780                2785                2790

Thr Arg Asp Ile Ile Ser Thr Asp Asp Cys Phe Ala Asn Lys His
    2795                2800                2805

Ala Gly Phe Asp Ala Trp Phe Ser Gln Arg Gly Gly Ser Tyr Lys
    2810                2815                2820

Asn Asp Lys Ser Cys Pro Val Val Ala Ala Ile Ile Thr Arg Glu
    2825                2830                2835

Ile Gly Phe Ile Val Pro Gly Leu Pro Gly Thr Val Leu Arg Ala
    2840                2845                2850

Ile Asn Gly Asp Phe Leu His Phe Leu Pro Arg Val Phe Ser Ala
    2855                2860                2865

Val Gly Asn Ile Cys Tyr Thr Pro Ser Lys Leu Ile Glu Tyr Ser
    2870                2875                2880

Asp Phe Ala Thr Ser Ala Cys Val Leu Ala Ala Glu Cys Thr Ile
    2885                2890                2895

Phe Lys Asp Ala Met Gly Lys Pro Val Pro Tyr Cys Tyr Asp Thr
    2900                2905                2910

Asn Leu Leu Glu Gly Ser Ile Ser Tyr Ser Glu Leu Arg Pro Asp
    2915                2920                2925

Thr Arg Tyr Val Leu Met Asp Gly Ser Ile Ile Gln Phe Pro Asn
    2930                2935                2940

Thr Tyr Leu Glu Gly Ser Val Arg Val Val Thr Thr Phe Asp Ala
    2945                2950                2955

Glu Tyr Cys Arg His Gly Thr Cys Glu Arg Ser Glu Val Gly Ile
```

-continued

```
    2960                2965                2970

Cys Leu  Ser Thr Ser Gly Arg  Trp Val Leu Asn Asn  Glu His Tyr
    2975                2980                2985

Arg Ala  Leu Ser Gly Val Phe  Cys Gly Val Asp Ala  Met Asn Leu
    2990                2995                3000

Ile Ala  Asn Ile Phe Thr Pro  Leu Val Gln Pro Val  Gly Ala Leu
    3005                3010                3015

Asp Val  Ser Ala Ser Val Val  Ala Gly Gly Ile Ile  Ala Ile Leu
    3020                3025                3030

Val Thr  Cys Ala Ala Tyr Tyr  Phe Met Lys Phe Arg  Arg Val Phe
    3035                3040                3045

Gly Glu  Tyr Asn His Val Val  Ala Ala Asn Ala Leu  Leu Phe Leu
    3050                3055                3060

Met Ser  Phe Thr Ile Leu Cys  Leu Val Pro Ala Tyr  Ser Phe Leu
    3065                3070                3075

Pro Gly  Val Tyr Ser Val Phe  Tyr Leu Tyr Leu Thr  Phe Tyr Phe
    3080                3085                3090

Thr Asn  Asp Val Ser Phe Leu  Ala His Leu Gln Trp  Phe Ala Met
    3095                3100                3105

Phe Ser  Pro Ile Val Pro Phe  Trp Ile Thr Ala Ile  Tyr Val Phe
    3110                3115                3120

Cys Ile  Ser Leu Lys His Cys  His Trp Phe Phe Asn  Asn Tyr Leu
    3125                3130                3135

Arg Lys  Arg Val Met Phe Asn  Gly Val Thr Phe Ser  Thr Phe Glu
    3140                3145                3150

Glu Ala  Ala Leu Cys Thr Phe  Leu Leu Asn Lys Glu  Met Tyr Leu
    3155                3160                3165

Lys Leu  Arg Ser Glu Thr Leu  Leu Pro Leu Thr Gln  Tyr Asn Arg
    3170                3175                3180

Tyr Leu  Ala Leu Tyr Asn Lys  Tyr Lys Tyr Phe Ser  Gly Ala Leu
    3185                3190                3195

Asp Thr  Thr Ser Tyr Arg Glu  Ala Ala Cys Cys His  Leu Ala Lys
    3200                3205                3210

Ala Leu  Asn Asp Phe Ser Asn  Ser Gly Ala Asp Val  Leu Tyr Gln
    3215                3220                3225

Pro Pro  Gln Thr Ser Ile Thr  Ser Ala Val Leu Gln  Ser Gly Phe
    3230                3235                3240

Arg Lys  Met Ala Phe Pro Ser  Gly Lys Val Glu Gly  Cys Met Val
    3245                3250                3255

Gln Val  Thr Cys Gly Thr Thr  Thr Leu Asn Gly Leu  Trp Leu Asp
    3260                3265                3270

Asp Thr  Val Tyr Cys Pro Arg  His Val Ile Cys Thr  Ala Glu Asp
    3275                3280                3285

Met Leu  Asn Pro Asn Tyr Glu  Asp Leu Leu Ile Arg  Lys Ser Asn
    3290                3295                3300

His Ser  Phe Leu Val Gln Ala  Gly Asn Val Gln Leu  Arg Val Ile
    3305                3310                3315

Gly His  Ser Met Gln Asn Cys  Leu Leu Arg Leu Lys  Val Asp Thr
    3320                3325                3330

Ser Asn  Pro Lys Thr Pro Lys  Tyr Lys Phe Val Arg  Ile Gln Pro
    3335                3340                3345

Gly Gln  Thr Phe Ser Val Leu  Ala Cys Tyr Asn Gly  Ser Pro Ser
    3350                3355                3360
```

-continued

```
Gly Val  Tyr Gln Cys Ala Met  Arg Pro Asn His Thr  Ile Lys Gly
    3365                 3370                 3375

Ser Phe  Leu Asn Gly Ser Cys  Gly Ser Val Gly Phe  Asn Ile Asp
    3380                 3385                 3390

Tyr Asp  Cys Val Ser Phe Cys  Tyr Met His His Met  Glu Leu Pro
    3395                 3400                 3405

Thr Gly  Val His Ala Gly Thr  Asp Leu Glu Gly Lys  Phe Tyr Gly
    3410                 3415                 3420

Pro Phe  Val Asp Arg Gln Thr  Ala Gln Ala Ala Gly  Thr Asp Thr
    3425                 3430                 3435

Thr Ile  Thr Leu Asn Val Leu  Ala Trp Leu Tyr Ala  Ala Val Ile
    3440                 3445                 3450

Asn Gly  Asp Arg Trp Phe Leu  Asn Arg Phe Thr Thr  Thr Leu Asn
    3455                 3460                 3465

Asp Phe  Asn Leu Val Ala Met  Lys Tyr Asn Tyr Glu  Pro Leu Thr
    3470                 3475                 3480

Gln Asp  His Val Asp Ile Leu  Gly Pro Leu Ser Ala  Gln Thr Gly
    3485                 3490                 3495

Ile Ala  Val Leu Asp Met Cys  Ala Ala Leu Lys Glu  Leu Leu Gln
    3500                 3505                 3510

Asn Gly  Met Asn Gly Arg Thr  Ile Leu Gly Ser Thr  Ile Leu Glu
    3515                 3520                 3525

Asp Glu  Phe Thr Pro Phe Asp  Val Val Arg Gln Cys  Ser Gly Val
    3530                 3535                 3540

Thr Phe  Gln Gly Lys Phe Lys  Lys Ile Val Lys Gly  Thr His His
    3545                 3550                 3555

Trp Met  Leu Leu Thr Phe Leu  Thr Ser Leu Leu Ile  Leu Val Gln
    3560                 3565                 3570

Ser Thr  Gln Trp Ser Leu Phe  Phe Phe Val Tyr Glu  Asn Ala Phe
    3575                 3580                 3585

Leu Pro  Phe Thr Leu Gly Ile  Met Ala Ile Ala Ala  Cys Ala Met
    3590                 3595                 3600

Leu Leu  Val Lys His Lys His  Ala Phe Leu Cys Leu  Phe Leu Leu
    3605                 3610                 3615

Pro Ser  Leu Ala Thr Val Ala  Tyr Phe Asn Met Val  Tyr Met Pro
    3620                 3625                 3630

Ala Ser  Trp Val Met Arg Ile  Met Thr Trp Leu Glu  Leu Ala Asp
    3635                 3640                 3645

Thr Ser  Leu Ser Gly Tyr Arg  Leu Lys Asp Cys Val  Met Tyr Ala
    3650                 3655                 3660

Ser Ala  Leu Val Leu Leu Ile  Leu Met Thr Ala Arg  Thr Val Tyr
    3665                 3670                 3675

Asp Asp  Ala Ala Arg Arg Val  Trp Thr Leu Met Asn  Val Ile Thr
    3680                 3685                 3690

Leu Val  Tyr Lys Val Tyr Tyr  Gly Asn Ala Leu Asp  Gln Ala Ile
    3695                 3700                 3705

Ser Met  Trp Ala Leu Val Ile  Ser Val Thr Ser Asn  Tyr Ser Gly
    3710                 3715                 3720

Val Val  Thr Thr Ile Met Phe  Leu Ala Arg Ala Ile  Val Phe Val
    3725                 3730                 3735

Cys Val  Glu Tyr Tyr Pro Leu  Leu Phe Ile Thr Gly  Asn Thr Leu
    3740                 3745                 3750
```

-continued

```
Gln Cys  Ile Met Leu Val Tyr  Cys Phe Leu Gly Tyr  Cys Cys Cys
    3755                 3760                 3765

Cys Tyr  Phe Gly Leu Phe Cys  Leu Leu Asn Arg Tyr  Phe Arg Leu
    3770                 3775                 3780

Thr Leu  Gly Val Tyr Asp Tyr  Leu Val Ser Thr Gln  Glu Phe Arg
    3785                 3790                 3795

Tyr Met  Asn Ser Gln Gly Leu  Leu Pro Pro Lys Ser  Ser Ile Asp
    3800                 3805                 3810

Ala Phe  Lys Leu Asn Ile Lys  Leu Leu Gly Ile Gly  Gly Lys Pro
    3815                 3820                 3825

Cys Ile  Lys Val Ala Thr Val  Gln Ser Lys Met Ser  Asp Val Lys
    3830                 3835                 3840

Cys Thr  Ser Val Val Leu Leu  Ser Val Leu Gln Gln  Leu Arg Val
    3845                 3850                 3855

Glu Ser  Ser Ser Lys Leu Trp  Ala Gln Cys Val Gln  Leu His Asn
    3860                 3865                 3870

Asp Ile  Leu Leu Ala Lys Asp  Thr Thr Glu Ala Phe  Glu Lys Met
    3875                 3880                 3885

Val Ser  Leu Leu Ser Val Leu  Leu Ser Met Gln Gly  Ala Val Asp
    3890                 3895                 3900

Ile Asn  Arg Leu Cys Glu Glu  Met Leu Asp Asn Arg  Ala Thr Leu
    3905                 3910                 3915

Gln Ala  Ile Ala Ser Glu Phe  Ser Ser Leu Pro Ser  Tyr Ala Ala
    3920                 3925                 3930

Tyr Ala  Thr Ala Gln Glu Ala  Tyr Glu Gln Ala Val  Ala Asn Gly
    3935                 3940                 3945

Asp Ser  Glu Val Val Leu Lys  Lys Leu Lys Lys Ser  Leu Asn Val
    3950                 3955                 3960

Ala Lys  Ser Glu Phe Asp Arg  Asp Ala Ala Met Gln  Arg Lys Leu
    3965                 3970                 3975

Glu Lys  Met Ala Asp Gln Ala  Met Thr Gln Met Tyr  Lys Gln Ala
    3980                 3985                 3990

Arg Ser  Glu Asp Lys Arg Ala  Lys Val Thr Ser Ala  Met Gln Thr
    3995                 4000                 4005

Met Leu  Phe Thr Met Leu Arg  Lys Leu Asp Asn Asp  Ala Leu Asn
    4010                 4015                 4020

Asn Ile  Ile Asn Asn Ala Arg  Asp Gly Cys Val Pro  Leu Asn Ile
    4025                 4030                 4035

Ile Pro  Leu Thr Thr Ala Ala  Lys Leu Met Val Val  Val Pro Asp
    4040                 4045                 4050

Tyr Gly  Thr Tyr Lys Asn Thr  Cys Asp Gly Asn Thr  Phe Thr Tyr
    4055                 4060                 4065

Ala Ser  Ala Leu Trp Glu Ile  Gln Gln Val Val Asp  Ala Asp Ser
    4070                 4075                 4080

Lys Ile  Val Gln Leu Ser Glu  Ile Asn Met Asp Asn  Ser Pro Asn
    4085                 4090                 4095

Leu Ala  Trp Pro Leu Ile Val  Thr Ala Leu Arg Ala  Asn Ser Ala
    4100                 4105                 4110

Val Lys  Leu Gln Asn Asn Glu  Leu Ser Pro Val Ala  Leu Arg Gln
    4115                 4120                 4125

Met Ser  Cys Ala Ala Gly Thr  Thr Gln Thr Ala Cys  Thr Asp Asp
    4130                 4135                 4140

Asn Ala  Leu Ala Tyr Tyr Asn  Asn Ser Lys Gly Gly  Arg Phe Val
```

-continued

```
    4145                4150                4155

Leu Ala Leu Leu Ser Asp His Gln Asp Leu Lys Trp Ala Arg Phe
    4160                4165                4170

Pro Lys Ser Asp Gly Thr Gly Thr Ile Tyr Thr Glu Leu Glu Pro
    4175                4180                4185

Pro Cys Arg Phe Val Thr Asp Thr Pro Lys Gly Pro Lys Val Lys
    4190                4195                4200

Tyr Leu Tyr Phe Ile Lys Gly Leu Asn Asn Leu Asn Arg Gly Met
    4205                4210                4215

Val Leu Gly Ser Leu Ala Ala Thr Val Arg Leu Gln Ala Gly Asn
    4220                4225                4230

Ala Thr Glu Val Pro Ala Asn Ser Thr Val Leu Ser Phe Cys Ala
    4235                4240                4245

Phe Ala Val Asp Pro Ala Lys Ala Tyr Lys Asp Tyr Leu Ala Ser
    4250                4255                4260

Gly Gly Gln Pro Ile Thr Asn Cys Val Lys Met Leu Cys Thr His
    4265                4270                4275

Thr Gly Thr Gly Gln Ala Ile Thr Val Thr Pro Glu Ala Asn Met
    4280                4285                4290

Asp Gln Glu Ser Phe Gly Gly Ala Ser Cys Cys Leu Tyr Cys Arg
    4295                4300                4305

Cys His Ile Asp His Pro Asn Pro Lys Gly Phe Cys Asp Leu Lys
    4310                4315                4320

Gly Lys Tyr Val Gln Ile Pro Thr Thr Cys Ala Asn Asp Pro Val
    4325                4330                4335

Gly Phe Thr Leu Arg Asn Thr Val Cys Thr Val Cys Gly Met Trp
    4340                4345                4350

Lys Gly Tyr Gly Cys Ser Cys Asp Gln Leu Arg Glu Pro Leu Met
    4355                4360                4365

Gln Ser Ala Asp Ala Ser Thr Phe Phe Lys Arg Val Cys Gly Val
    4370                4375                4380

Ser Ala Ala Arg Leu Thr Pro Cys Gly Thr Gly Thr Ser Thr Asp
    4385                4390                4395

Val Val Tyr Arg Ala Phe Asp Ile Tyr Asn Glu Lys Val Ala Gly
    4400                4405                4410

Phe Ala Lys Phe Leu Lys Thr Asn Cys Cys Arg Phe Gln Glu Lys
    4415                4420                4425

Asp Glu Glu Gly Asn Leu Leu Asp Ser Tyr Phe Val Val Lys Arg
    4430                4435                4440

His Thr Met Ser Asn Tyr Gln His Glu Glu Thr Ile Tyr Asn Leu
    4445                4450                4455

Val Lys Asp Cys Pro Ala Val Ala Val His Asp Phe Phe Lys Phe
    4460                4465                4470

Arg Val Asp Gly Asp Met Val Pro His Ile Ser Arg Gln Arg Leu
    4475                4480                4485

Thr Lys Tyr Thr Met Ala Asp Leu Val Tyr Ala Leu Arg His Phe
    4490                4495                4500

Asp Glu Gly Asn Cys Asp Thr Leu Lys Glu Ile Leu Val Thr Tyr
    4505                4510                4515

Asn Cys Cys Asp Asp Asp Tyr Phe Asn Lys Lys Asp Trp Tyr Asp
    4520                4525                4530

Phe Val Glu Asn Pro Asp Ile Leu Arg Val Tyr Ala Asn Leu Gly
    4535                4540                4545
```

-continued

Glu Arg Val Arg Gln Ser Leu Leu Lys Thr Val Gln Phe Cys Asp
4550 4555 4560

Ala Met Arg Asp Ala Gly Ile Val Gly Val Leu Thr Leu Asp Asn
4565 4570 4575

Gln Asp Leu Asn Gly Asn Trp Tyr Asp Phe Gly Asp Phe Val Gln
4580 4585 4590

Val Ala Pro Gly Cys Gly Val Pro Ile Val Asp Ser Tyr Tyr Ser
4595 4600 4605

Leu Leu Met Pro Ile Leu Thr Leu Thr Arg Ala Leu Ala Ala Glu
4610 4615 4620

Ser His Met Asp Ala Asp Leu Ala Lys Pro Leu Ile Lys Trp Asp
4625 4630 4635

Leu Leu Lys Tyr Asp Phe Thr Glu Glu Arg Leu Cys Leu Phe Asp
4640 4645 4650

Arg Tyr Phe Lys Tyr Trp Asp Gln Thr Tyr His Pro Asn Cys Ile
4655 4660 4665

Asn Cys Leu Asp Asp Arg Cys Ile Leu His Cys Ala Asn Phe Asn
4670 4675 4680

Val Leu Phe Ser Thr Val Phe Pro Pro Thr Ser Phe Gly Pro Leu
4685 4690 4695

Val Arg Lys Ile Phe Val Asp Gly Val Pro Phe Val Val Ser Thr
4700 4705 4710

Gly Tyr His Phe Arg Glu Leu Gly Val Val His Asn Gln Asp Val
4715 4720 4725

Asn Leu His Ser Ser Arg Leu Ser Phe Lys Glu Leu Leu Val Tyr
4730 4735 4740

Ala Ala Asp Pro Ala Met His Ala Ala Ser Gly Asn Leu Leu Leu
4745 4750 4755

Asp Lys Arg Thr Thr Cys Phe Ser Val Ala Ala Leu Thr Asn Asn
4760 4765 4770

Val Ala Phe Gln Thr Val Lys Pro Gly Asn Phe Asn Lys Asp Phe
4775 4780 4785

Tyr Asp Phe Ala Val Ser Lys Gly Phe Phe Lys Glu Gly Ser Ser
4790 4795 4800

Val Glu Leu Lys His Phe Phe Phe Ala Gln Asp Gly Asn Ala Ala
4805 4810 4815

Ile Ser Asp Tyr Asp Tyr Tyr Arg Tyr Asn Leu Pro Thr Met Cys
4820 4825 4830

Asp Ile Arg Gln Leu Leu Phe Val Val Glu Val Val Asp Lys Tyr
4835 4840 4845

Phe Asp Cys Tyr Asp Gly Gly Cys Ile Asn Ala Asn Gln Val Ile
4850 4855 4860

Val Asn Asn Leu Asp Lys Ser Ala Gly Phe Pro Phe Asn Lys Trp
4865 4870 4875

Gly Lys Ala Arg Leu Tyr Tyr Asp Ser Met Ser Tyr Glu Asp Gln
4880 4885 4890

Asp Ala Leu Phe Ala Tyr Thr Lys Arg Asn Val Ile Pro Thr Ile
4895 4900 4905

Thr Gln Met Asn Leu Lys Tyr Ala Ile Ser Ala Lys Asn Arg Ala
4910 4915 4920

Arg Thr Val Ala Gly Val Ser Ile Cys Ser Thr Met Thr Asn Arg
4925 4930 4935

-continued

```
Gln Phe His Gln Lys Leu Leu Lys Ser Ile Ala Ala Thr Arg Gly
    4940                4945                4950

Ala Thr Val Val Ile Gly Thr Ser Lys Phe Tyr Gly Gly Trp His
    4955                4960                4965

Asn Met Leu Lys Thr Val Tyr Ser Asp Val Glu Thr Pro His Leu
    4970                4975                4980

Met Gly Trp Asp Tyr Pro Lys Cys Asp Arg Ala Met Pro Asn Met
    4985                4990                4995

Leu Arg Ile Met Ala Ser Leu Val Leu Ala Arg Lys His Asn Thr
    5000                5005                5010

Cys Cys Asn Leu Ser His Arg Phe Tyr Arg Leu Ala Asn Glu Cys
    5015                5020                5025

Ala Gln Val Leu Ser Glu Met Val Met Cys Gly Gly Ser Leu Tyr
    5030                5035                5040

Val Lys Pro Gly Gly Thr Ser Ser Gly Asp Ala Thr Thr Ala Tyr
    5045                5050                5055

Ala Asn Ser Val Phe Asn Ile Cys Gln Ala Val Thr Ala Asn Val
    5060                5065                5070

Asn Ala Leu Leu Ser Thr Asp Gly Asn Lys Ile Ala Asp Lys Tyr
    5075                5080                5085

Val Arg Asn Leu Gln His Arg Leu Tyr Glu Cys Leu Tyr Arg Asn
    5090                5095                5100

Arg Asp Val Asp His Glu Phe Val Asp Glu Phe Tyr Ala Tyr Leu
    5105                5110                5115

Arg Lys His Phe Ser Met Met Ile Leu Ser Asp Asp Ala Val Val
    5120                5125                5130

Cys Tyr Asn Ser Asn Tyr Ala Ala Gln Gly Leu Val Ala Ser Ile
    5135                5140                5145

Lys Asn Phe Lys Ala Val Leu Tyr Tyr Gln Asn Asn Val Phe Met
    5150                5155                5160

Ser Glu Ala Lys Cys Trp Thr Glu Thr Asp Leu Thr Lys Gly Pro
    5165                5170                5175

His Glu Phe Cys Ser Gln His Thr Met Leu Val Lys Gln Gly Asp
    5180                5185                5190

Asp Tyr Val Tyr Leu Pro Tyr Pro Asp Pro Ser Arg Ile Leu Gly
    5195                5200                5205

Ala Gly Cys Phe Val Asp Asp Ile Val Lys Thr Asp Gly Thr Leu
    5210                5215                5220

Met Ile Glu Arg Phe Val Ser Leu Ala Ile Asp Ala Tyr Pro Leu
    5225                5230                5235

Thr Lys His Pro Asn Gln Glu Tyr Ala Asp Val Phe His Leu Tyr
    5240                5245                5250

Leu Gln Tyr Ile Arg Lys Leu His Asp Glu Leu Thr Gly His Met
    5255                5260                5265

Leu Asp Met Tyr Ser Val Met Leu Thr Asn Asp Asn Thr Ser Arg
    5270                5275                5280

Tyr Trp Glu Pro Glu Phe Tyr Glu Ala Met Tyr Thr Pro His Thr
    5285                5290                5295

Val Leu Gln Ala Val Gly Ala Cys Val Leu Cys Asn Ser Gln Thr
    5300                5305                5310

Ser Leu Arg Cys Gly Ala Cys Ile Arg Arg Pro Phe Leu Cys Cys
    5315                5320                5325

Lys Cys Cys Tyr Asp His Val Ile Ser Thr Ser His Lys Leu Val
```

-continued

```
    5330                5335                5340

Leu Ser Val Asn Pro Tyr Val Cys Asn Ala Pro Gly Cys Asp Val
    5345                5350                5355

Thr Asp Val Thr Gln Leu Tyr Leu Gly Gly Met Ser Tyr Tyr Cys
    5360                5365                5370

Lys Ser His Lys Pro Pro Ile Ser Phe Pro Leu Cys Ala Asn Gly
    5375                5380                5385

Gln Val Phe Gly Leu Tyr Lys Asn Thr Cys Val Gly Ser Asp Asn
    5390                5395                5400

Val Thr Asp Phe Asn Ala Ile Ala Thr Cys Asp Trp Thr Asn Ala
    5405                5410                5415

Gly Asp Tyr Ile Leu Ala Asn Thr Cys Thr Glu Arg Leu Lys Leu
    5420                5425                5430

Phe Ala Ala Glu Thr Leu Lys Ala Thr Glu Glu Thr Phe Lys Leu
    5435                5440                5445

Ser Tyr Gly Ile Ala Thr Val Arg Glu Val Leu Ser Asp Arg Glu
    5450                5455                5460

Leu His Leu Ser Trp Glu Val Gly Lys Pro Arg Pro Pro Leu Asn
    5465                5470                5475

Arg Asn Tyr Val Phe Thr Gly Tyr Arg Val Thr Lys Asn Ser Lys
    5480                5485                5490

Val Gln Ile Gly Glu Tyr Thr Phe Glu Lys Gly Asp Tyr Gly Asp
    5495                5500                5505

Ala Val Val Tyr Arg Gly Thr Thr Thr Tyr Lys Leu Asn Val Gly
    5510                5515                5520

Asp Tyr Phe Val Leu Thr Ser His Thr Val Met Pro Leu Ser Ala
    5525                5530                5535

Pro Thr Leu Val Pro Gln Glu His Tyr Val Arg Ile Thr Gly Leu
    5540                5545                5550

Tyr Pro Thr Leu Asn Ile Ser Asp Glu Phe Ser Ser Asn Val Ala
    5555                5560                5565

Asn Tyr Gln Lys Val Gly Met Gln Lys Tyr Ser Thr Leu Gln Gly
    5570                5575                5580

Pro Pro Gly Thr Gly Lys Ser His Phe Ala Ile Gly Leu Ala Leu
    5585                5590                5595

Tyr Tyr Pro Ser Ala Arg Ile Val Tyr Thr Ala Cys Ser His Ala
    5600                5605                5610

Ala Val Asp Ala Leu Cys Glu Lys Ala Leu Lys Tyr Leu Pro Ile
    5615                5620                5625

Asp Lys Cys Ser Arg Ile Ile Pro Ala Arg Ala Arg Val Glu Cys
    5630                5635                5640

Phe Asp Lys Phe Lys Val Asn Ser Thr Leu Glu Gln Tyr Val Phe
    5645                5650                5655

Cys Thr Val Asn Ala Leu Pro Glu Thr Thr Ala Asp Ile Val Val
    5660                5665                5670

Phe Asp Glu Ile Ser Met Ala Thr Asn Tyr Asp Leu Ser Val Val
    5675                5680                5685

Asn Ala Arg Leu Arg Ala Lys His Tyr Val Tyr Ile Gly Asp Pro
    5690                5695                5700

Ala Gln Leu Pro Ala Pro Arg Thr Leu Leu Thr Lys Gly Thr Leu
    5705                5710                5715

Glu Pro Glu Tyr Phe Asn Ser Val Cys Arg Leu Met Lys Thr Ile
    5720                5725                5730
```

-continued

```
Gly Pro  Asp Met Phe Leu Gly  Thr Cys Arg Arg Cys  Pro Ala Glu
    5735                 5740                 5745

Ile Val  Asp Thr Val Ser Ala  Leu Val Tyr Asp Asn  Lys Leu Lys
    5750                 5755                 5760

Ala His  Lys Asp Lys Ser Ala  Gln Cys Phe Lys Met  Phe Tyr Lys
    5765                 5770                 5775

Gly Val  Ile Thr His Asp Val  Ser Ser Ala Ile Asn  Arg Pro Gln
    5780                 5785                 5790

Ile Gly  Val Val Arg Glu Phe  Leu Thr Arg Asn Pro  Ala Trp Arg
    5795                 5800                 5805

Lys Ala  Val Phe Ile Ser Pro  Tyr Asn Ser Gln Asn  Ala Val Ala
    5810                 5815                 5820

Ser Lys  Ile Leu Gly Leu Pro  Thr Gln Thr Val Asp  Ser Ser Gln
    5825                 5830                 5835

Gly Ser  Glu Tyr Asp Tyr Val  Ile Phe Thr Gln Thr  Thr Glu Thr
    5840                 5845                 5850

Ala His  Ser Cys Asn Val Asn  Arg Phe Asn Val Ala  Ile Thr Arg
    5855                 5860                 5865

Ala Lys  Ile Gly Ile Leu Cys  Ile Met Ser Asp Arg  Asp Leu Tyr
    5870                 5875                 5880

Asp Lys  Leu Gln Phe Thr Ser  Leu Glu Ile Pro Arg  Arg Asn Val
    5885                 5890                 5895

Ala Thr  Leu Gln Ala Glu Asn  Val Thr Gly Leu Phe  Lys Asp Cys
    5900                 5905                 5910

Ser Lys  Ile Ile Thr Gly Leu  His Pro Thr Gln Ala  Pro Thr His
    5915                 5920                 5925

Leu Ser  Val Asp Ile Lys Phe  Lys Thr Glu Gly Leu  Cys Val Asp
    5930                 5935                 5940

Ile Pro  Gly Ile Pro Lys Asp  Met Thr Tyr Arg Arg  Leu Ile Ser
    5945                 5950                 5955

Met Met  Gly Phe Lys Met Asn  Tyr Gln Val Asn Gly  Tyr Pro Asn
    5960                 5965                 5970

Met Phe  Ile Thr Arg Glu Glu  Ala Ile Arg His Val  Arg Ala Trp
    5975                 5980                 5985

Ile Gly  Phe Asp Val Glu Gly  Cys His Ala Thr Arg  Asp Ala Val
    5990                 5995                 6000

Gly Thr  Asn Leu Pro Leu Gln  Leu Gly Phe Ser Thr  Gly Val Asn
    6005                 6010                 6015

Leu Val  Ala Val Pro Thr Gly  Tyr Val Asp Thr Glu  Asn Asn Thr
    6020                 6025                 6030

Glu Phe  Thr Arg Val Asn Ala  Lys Pro Pro Pro Gly  Asp Gln Phe
    6035                 6040                 6045

Lys His  Leu Ile Pro Leu Met  Tyr Lys Gly Leu Pro  Trp Asn Val
    6050                 6055                 6060

Val Arg  Ile Lys Ile Val Gln  Met Leu Ser Asp Thr  Leu Lys Gly
    6065                 6070                 6075

Leu Ser  Asp Arg Val Val Phe  Val Leu Trp Ala His  Gly Phe Glu
    6080                 6085                 6090

Leu Thr  Ser Met Lys Tyr Phe  Val Lys Ile Gly Pro  Glu Arg Thr
    6095                 6100                 6105

Cys Cys  Leu Cys Asp Lys Arg  Ala Thr Cys Phe Ser  Thr Ser Ser
    6110                 6115                 6120
```

-continued

```
Asp Thr Tyr Ala Cys Trp Asn His Ser Val Gly Phe Asp Tyr Val
    6125                6130                6135

Tyr Asn Pro Phe Met Ile Asp Val Gln Gln Trp Gly Phe Thr Gly
    6140                6145                6150

Asn Leu Gln Ser Asn His Asp Gln His Cys Gln Val His Gly Asn
    6155                6160                6165

Ala His Val Ala Ser Cys Asp Ala Ile Met Thr Arg Cys Leu Ala
    6170                6175                6180

Val His Glu Cys Phe Val Lys Arg Val Asp Trp Ser Val Glu Tyr
    6185                6190                6195

Pro Ile Ile Gly Asp Glu Leu Arg Val Asn Ser Ala Cys Arg Lys
    6200                6205                6210

Val Gln His Met Val Val Lys Ser Ala Leu Leu Ala Asp Lys Phe
    6215                6220                6225

Pro Val Leu His Asp Ile Gly Asn Pro Lys Ala Ile Lys Cys Val
    6230                6235                6240

Pro Gln Ala Glu Val Glu Trp Lys Phe Tyr Asp Ala Gln Pro Cys
    6245                6250                6255

Ser Asp Lys Ala Tyr Lys Ile Glu Glu Leu Phe Tyr Ser Tyr Ala
    6260                6265                6270

Thr His His Asp Lys Phe Thr Asp Gly Val Cys Leu Phe Trp Asn
    6275                6280                6285

Cys Asn Val Asp Arg Tyr Pro Ala Asn Ala Ile Val Cys Arg Phe
    6290                6295                6300

Asp Thr Arg Val Leu Ser Asn Leu Asn Leu Pro Gly Cys Asp Gly
    6305                6310                6315

Gly Ser Leu Tyr Val Asn Lys His Ala Phe His Thr Pro Ala Phe
    6320                6325                6330

Asp Lys Ser Ala Phe Thr Asn Leu Lys Gln Leu Pro Phe Phe Tyr
    6335                6340                6345

Tyr Ser Asp Ser Pro Cys Glu Ser His Gly Lys Gln Val Val Ser
    6350                6355                6360

Asp Ile Asp Tyr Val Pro Leu Lys Ser Ala Thr Cys Ile Thr Arg
    6365                6370                6375

Cys Asn Leu Gly Gly Ala Val Cys Arg His His Ala Asn Glu Tyr
    6380                6385                6390

Arg Gln Tyr Leu Asp Ala Tyr Asn Met Met Ile Ser Ala Gly Phe
    6395                6400                6405

Ser Leu Trp Ile Tyr Lys Gln Phe Asp Thr Tyr Asn Leu Trp Asn
    6410                6415                6420

Thr Phe Thr Arg Leu Gln Ser Leu Glu Asn Val Ala Tyr Asn Val
    6425                6430                6435

Val Asn Lys Gly His Phe Asp Gly His Ala Gly Glu Ala Pro Val
    6440                6445                6450

Ser Ile Ile Asn Asn Ala Val Tyr Thr Lys Val Asp Gly Ile Asp
    6455                6460                6465

Val Glu Ile Phe Glu Asn Lys Thr Thr Leu Pro Val Asn Val Ala
    6470                6475                6480

Phe Glu Leu Trp Ala Lys Arg Asn Ile Lys Pro Val Pro Glu Ile
    6485                6490                6495

Lys Ile Leu Asn Asn Leu Gly Val Asp Ile Ala Ala Asn Thr Val
    6500                6505                6510

Ile Trp Asp Tyr Lys Arg Glu Ala Pro Ala His Val Ser Thr Ile
```

-continued

```
    6515                6520                6525

Gly Val  Cys Thr Met Thr Asp  Ile Ala Lys Lys Pro  Thr Glu Ser
    6530                6535                6540

Ala Cys  Ser Ser Leu Thr Val  Leu Phe Asp Gly Arg  Val Glu Gly
    6545                6550                6555

Gln Val  Asp Leu Phe Arg Asn  Ala Arg Asn Gly Val  Leu Ile Thr
    6560                6565                6570

Glu Gly  Ser Val Lys Gly Leu  Thr Pro Ser Lys Gly  Pro Ala Gln
    6575                6580                6585

Ala Ser  Val Asn Gly Val Thr  Leu Ile Gly Glu Ser  Val Lys Thr
    6590                6595                6600

Gln Phe  Asn Tyr Phe Lys Lys  Val Asp Gly Ile Ile  Gln Gln Leu
    6605                6610                6615

Pro Glu  Thr Tyr Phe Thr Gln  Ser Arg Asp Leu Glu  Asp Phe Lys
    6620                6625                6630

Pro Arg  Ser Gln Met Glu Thr  Asp Phe Leu Glu Leu  Ala Met Asp
    6635                6640                6645

Glu Phe  Ile Gln Arg Tyr Lys  Leu Glu Gly Tyr Ala  Phe Glu His
    6650                6655                6660

Ile Val  Tyr Gly Asp Phe Ser  His Gly Gln Leu Gly  Gly Leu His
    6665                6670                6675

Leu Met  Ile Gly Leu Ala Lys  Arg Ser Gln Asp Ser  Pro Leu Lys
    6680                6685                6690

Leu Glu  Asp Phe Ile Pro Met  Asp Ser Thr Val Lys  Asn Tyr Phe
    6695                6700                6705

Ile Thr  Asp Ala Gln Thr Gly  Ser Ser Lys Cys Val  Cys Ser Val
    6710                6715                6720

Ile Asp  Leu Leu Leu Asp Asp  Phe Val Glu Ile Ile  Lys Ser Gln
    6725                6730                6735

Asp Leu  Ser Val Ile Ser Lys  Val Val Lys Val Thr  Ile Asp Tyr
    6740                6745                6750

Ala Glu  Ile Ser Phe Met Leu  Trp Cys Lys Asp Gly  His Val Glu
    6755                6760                6765

Thr Phe  Tyr Pro Lys Leu Gln  Ala Ser Gln Ala Trp  Gln Pro Gly
    6770                6775                6780

Val Ala  Met Pro Asn Leu Tyr  Lys Met Gln Arg Met  Leu Leu Glu
    6785                6790                6795

Lys Cys  Asp Leu Gln Asn Tyr  Gly Glu Asn Ala Val  Ile Pro Lys
    6800                6805                6810

Gly Ile  Met Met Asn Val Ala  Lys Tyr Thr Gln Leu  Cys Gln Tyr
    6815                6820                6825

Leu Asn  Thr Leu Thr Leu Ala  Val Pro Tyr Asn Met  Arg Val Ile
    6830                6835                6840

His Phe  Gly Ala Gly Ser Asp  Lys Gly Val Ala Pro  Gly Thr Ala
    6845                6850                6855

Val Leu  Arg Gln Trp Leu Pro  Thr Gly Thr Leu Leu  Val Asp Ser
    6860                6865                6870

Asp Leu  Asn Asp Phe Val Ser  Asp Ala Asp Ser Thr  Leu Ile Gly
    6875                6880                6885

Asp Cys  Ala Thr Val His Thr  Ala Asn Lys Trp Asp  Leu Ile Ile
    6890                6895                6900

Ser Asp  Met Tyr Asp Pro Arg  Thr Lys His Val Thr  Lys Glu Asn
    6905                6910                6915
```

-continued

```
Asp Ser  Lys Glu Gly Phe Phe  Thr Tyr Leu Cys Gly  Phe Ile Lys
    6920                 6925                 6930

Gln Lys  Leu Ala Leu Gly Gly  Ser Ile Ala Val Lys  Ile Thr Glu
    6935                 6940                 6945

His Ser  Trp Asn Ala Asp Leu  Tyr Lys Leu Met Gly  His Phe Ser
    6950                 6955                 6960

Trp Trp  Thr Ala Phe Val Thr  Asn Val Asn Ala Ser  Ser Ser Glu
    6965                 6970                 6975

Ala Phe  Leu Ile Gly Ala Asn  Tyr Leu Gly Lys Pro  Lys Glu Gln
    6980                 6985                 6990

Ile Asp  Gly Tyr Thr Met His  Ala Asn Tyr Ile Phe  Trp Arg Asn
    6995                 7000                 7005

Thr Asn  Pro Ile Gln Leu Ser  Ser Tyr Ser Leu Phe  Asp Met Ser
    7010                 7015                 7020

Lys Phe  Pro Leu Lys Leu Arg  Gly Thr Ala Val Met  Ser Leu Lys
    7025                 7030                 7035

Glu Asn  Gln Ile Asn Asp Met  Ile Tyr Ser Leu Leu  Glu Lys Gly
    7040                 7045                 7050

Arg Leu  Ile Ile Arg Glu Asn  Asn Arg Val Val Val  Ser Ser Asp
    7055                 7060                 7065

Ile Leu  Val Asn Asn
    7070
```

```
<210> SEQ ID NO 28
<211> LENGTH: 2695
<212> TYPE: PRT
<213> ORGANISM: SARS-CoV Urbani

<400> SEQUENCE: 28

Arg Val Cys Gly Val Ser Ala Ala Arg Leu Thr Pro Cys Gly Thr Gly
1               5                   10                  15

Thr Ser Thr Asp Val Val Tyr Arg Ala Phe Asp Ile Tyr Asn Glu Lys
            20                  25                  30

Val Ala Gly Phe Ala Lys Phe Leu Lys Thr Asn Cys Cys Arg Phe Gln
        35                  40                  45

Glu Lys Asp Glu Glu Gly Asn Leu Leu Asp Ser Tyr Phe Val Val Lys
    50                  55                  60

Arg His Thr Met Ser Asn Tyr Gln His Glu Glu Thr Ile Tyr Asn Leu
65                  70                  75                  80

Val Lys Asp Cys Pro Ala Val Ala Val His Asp Phe Phe Lys Phe Arg
                85                  90                  95

Val Asp Gly Asp Met Val Pro His Ile Ser Arg Gln Arg Leu Thr Lys
            100                 105                 110

Tyr Thr Met Ala Asp Leu Val Tyr Ala Leu Arg His Phe Asp Glu Gly
        115                 120                 125

Asn Cys Asp Thr Leu Lys Glu Ile Leu Val Thr Tyr Asn Cys Cys Asp
    130                 135                 140

Asp Asp Tyr Phe Asn Lys Lys Asp Trp Tyr Asp Phe Val Glu Asn Pro
145                 150                 155                 160

Asp Ile Leu Arg Val Tyr Ala Asn Leu Gly Glu Arg Val Arg Gln Ser
                165                 170                 175

Leu Leu Lys Thr Val Gln Phe Cys Asp Ala Met Arg Asp Ala Gly Ile
            180                 185                 190

Val Gly Val Leu Thr Leu Asp Asn Gln Asp Leu Asn Gly Asn Trp Tyr
```

-continued

```
        195                 200                 205

Asp Phe Gly Asp Phe Val Gln Val Ala Pro Gly Cys Gly Val Pro Ile
    210                 215                 220

Val Asp Ser Tyr Tyr Ser Leu Leu Met Pro Ile Leu Thr Leu Thr Arg
225                 230                 235                 240

Ala Leu Ala Ala Glu Ser His Met Asp Ala Asp Leu Ala Lys Pro Leu
                245                 250                 255

Ile Lys Trp Asp Leu Leu Lys Tyr Asp Phe Thr Glu Glu Arg Leu Cys
            260                 265                 270

Leu Phe Asp Arg Tyr Phe Lys Tyr Trp Asp Gln Thr Tyr His Pro Asn
        275                 280                 285

Cys Ile Asn Cys Leu Asp Asp Arg Cys Ile Leu His Cys Ala Asn Phe
    290                 295                 300

Asn Val Leu Phe Ser Thr Val Phe Pro Pro Thr Ser Phe Gly Pro Leu
305                 310                 315                 320

Val Arg Lys Ile Phe Val Asp Gly Val Pro Phe Val Val Ser Thr Gly
                325                 330                 335

Tyr His Phe Arg Glu Leu Gly Val Val His Asn Gln Asp Val Asn Leu
            340                 345                 350

His Ser Ser Arg Leu Ser Phe Lys Glu Leu Leu Val Tyr Ala Ala Asp
        355                 360                 365

Pro Ala Met His Ala Ala Ser Gly Asn Leu Leu Leu Asp Lys Arg Thr
    370                 375                 380

Thr Cys Phe Ser Val Ala Ala Leu Thr Asn Asn Val Ala Phe Gln Thr
385                 390                 395                 400

Val Lys Pro Gly Asn Phe Asn Lys Asp Phe Tyr Asp Phe Ala Val Ser
                405                 410                 415

Lys Gly Phe Phe Lys Glu Gly Ser Ser Val Glu Leu Lys His Phe Phe
            420                 425                 430

Phe Ala Gln Asp Gly Asn Ala Ala Ile Ser Asp Tyr Asp Tyr Tyr Arg
        435                 440                 445

Tyr Asn Leu Pro Thr Met Cys Asp Ile Arg Gln Leu Leu Phe Val Val
    450                 455                 460

Glu Val Val Asp Lys Tyr Phe Asp Cys Tyr Asp Gly Gly Cys Ile Asn
465                 470                 475                 480

Ala Asn Gln Val Ile Val Asn Asn Leu Asp Lys Ser Ala Gly Phe Pro
                485                 490                 495

Phe Asn Lys Trp Gly Lys Ala Arg Leu Tyr Tyr Asp Ser Met Ser Tyr
            500                 505                 510

Glu Asp Gln Asp Ala Leu Phe Ala Tyr Thr Lys Arg Asn Val Ile Pro
        515                 520                 525

Thr Ile Thr Gln Met Asn Leu Lys Tyr Ala Ile Ser Ala Lys Asn Arg
    530                 535                 540

Ala Arg Thr Val Ala Gly Val Ser Ile Cys Ser Thr Met Thr Asn Arg
545                 550                 555                 560

Gln Phe His Gln Lys Leu Leu Lys Ser Ile Ala Ala Thr Arg Gly Ala
                565                 570                 575

Thr Val Val Ile Gly Thr Ser Lys Phe Tyr Gly Gly Trp His Asn Met
            580                 585                 590

Leu Lys Thr Val Tyr Ser Asp Val Glu Thr Pro His Leu Met Gly Trp
        595                 600                 605

Asp Tyr Pro Lys Cys Asp Arg Ala Met Pro Asn Met Leu Arg Ile Met
    610                 615                 620
```

-continued

```
Ala Ser Leu Val Leu Ala Arg Lys His Asn Thr Cys Cys Asn Leu Ser
625                 630                 635                 640

His Arg Phe Tyr Arg Leu Ala Asn Glu Cys Ala Gln Val Leu Ser Glu
                645                 650                 655

Met Val Met Cys Gly Gly Ser Leu Tyr Val Lys Pro Gly Gly Thr Ser
            660                 665                 670

Ser Gly Asp Ala Thr Thr Ala Tyr Ala Asn Ser Val Phe Asn Ile Cys
        675                 680                 685

Gln Ala Val Thr Ala Asn Val Asn Ala Leu Leu Ser Thr Asp Gly Asn
    690                 695                 700

Lys Ile Ala Asp Lys Tyr Val Arg Asn Leu Gln His Arg Leu Tyr Glu
705                 710                 715                 720

Cys Leu Tyr Arg Asn Arg Asp Val Asp His Glu Phe Val Asp Glu Phe
                725                 730                 735

Tyr Ala Tyr Leu Arg Lys His Phe Ser Met Met Ile Leu Ser Asp Asp
            740                 745                 750

Ala Val Val Cys Tyr Asn Ser Asn Tyr Ala Ala Gln Gly Leu Val Ala
        755                 760                 765

Ser Ile Lys Asn Phe Lys Ala Val Leu Tyr Tyr Gln Asn Asn Val Phe
    770                 775                 780

Met Ser Glu Ala Lys Cys Trp Thr Glu Thr Asp Leu Thr Lys Gly Pro
785                 790                 795                 800

His Glu Phe Cys Ser Gln His Thr Met Leu Val Lys Gln Gly Asp Asp
                805                 810                 815

Tyr Val Tyr Leu Pro Tyr Pro Asp Pro Ser Arg Ile Leu Gly Ala Gly
            820                 825                 830

Cys Phe Val Asp Asp Ile Val Lys Thr Asp Gly Thr Leu Met Ile Glu
        835                 840                 845

Arg Phe Val Ser Leu Ala Ile Asp Ala Tyr Pro Leu Thr Lys His Pro
    850                 855                 860

Asn Gln Glu Tyr Ala Asp Val Phe His Leu Tyr Leu Gln Tyr Ile Arg
865                 870                 875                 880

Lys Leu His Asp Glu Leu Thr Gly His Met Leu Asp Met Tyr Ser Val
                885                 890                 895

Met Leu Thr Asn Asp Asn Thr Ser Arg Tyr Trp Glu Pro Glu Phe Tyr
            900                 905                 910

Glu Ala Met Tyr Thr Pro His Thr Val Leu Gln Ala Val Gly Ala Cys
        915                 920                 925

Val Leu Cys Asn Ser Gln Thr Ser Leu Arg Cys Gly Ala Cys Ile Arg
    930                 935                 940

Arg Pro Phe Leu Cys Cys Lys Cys Cys Tyr Asp His Val Ile Ser Thr
945                 950                 955                 960

Ser His Lys Leu Val Leu Ser Val Asn Pro Tyr Val Cys Asn Ala Pro
                965                 970                 975

Gly Cys Asp Val Thr Asp Val Thr Gln Leu Tyr Leu Gly Gly Met Ser
            980                 985                 990

Tyr Tyr Cys Lys Ser His Lys Pro  Pro Ile Ser Phe Pro  Leu Cys Ala
        995                 1000                 1005

Asn Gly  Gln Val Phe Gly Leu  Tyr Lys Asn Thr Cys  Val Gly Ser
    1010                 1015                 1020

Asp Asn  Val Thr Asp Phe Asn  Ala Ile Ala Thr Cys  Asp Trp Thr
    1025                 1030                 1035
```

-continued

Asn Ala Gly Asp Tyr Ile Leu Ala Asn Thr Cys Thr Glu Arg Leu
1040 1045 1050

Lys Leu Phe Ala Ala Glu Thr Leu Lys Ala Thr Glu Glu Thr Phe
1055 1060 1065

Lys Leu Ser Tyr Gly Ile Ala Thr Val Arg Glu Val Leu Ser Asp
1070 1075 1080

Arg Glu Leu His Leu Ser Trp Glu Val Gly Lys Pro Arg Pro Pro
1085 1090 1095

Leu Asn Arg Asn Tyr Val Phe Thr Gly Tyr Arg Val Thr Lys Asn
1100 1105 1110

Ser Lys Val Gln Ile Gly Glu Tyr Thr Phe Glu Lys Gly Asp Tyr
1115 1120 1125

Gly Asp Ala Val Val Tyr Arg Gly Thr Thr Thr Tyr Lys Leu Asn
1130 1135 1140

Val Gly Asp Tyr Phe Val Leu Thr Ser His Thr Val Met Pro Leu
1145 1150 1155

Ser Ala Pro Thr Leu Val Pro Gln Glu His Tyr Val Arg Ile Thr
1160 1165 1170

Gly Leu Tyr Pro Thr Leu Asn Ile Ser Asp Glu Phe Ser Ser Asn
1175 1180 1185

Val Ala Asn Tyr Gln Lys Val Gly Met Gln Lys Tyr Ser Thr Leu
1190 1195 1200

Gln Gly Pro Pro Gly Thr Gly Lys Ser His Phe Ala Ile Gly Leu
1205 1210 1215

Ala Leu Tyr Tyr Pro Ser Ala Arg Ile Val Tyr Thr Ala Cys Ser
1220 1225 1230

His Ala Ala Val Asp Ala Leu Cys Glu Lys Ala Leu Lys Tyr Leu
1235 1240 1245

Pro Ile Asp Lys Cys Ser Arg Ile Ile Pro Ala Arg Ala Arg Val
1250 1255 1260

Glu Cys Phe Asp Lys Phe Lys Val Asn Ser Thr Leu Glu Gln Tyr
1265 1270 1275

Val Phe Cys Thr Val Asn Ala Leu Pro Glu Thr Thr Ala Asp Ile
1280 1285 1290

Val Val Phe Asp Glu Ile Ser Met Ala Thr Asn Tyr Asp Leu Ser
1295 1300 1305

Val Val Asn Ala Arg Leu Arg Ala Lys His Tyr Val Tyr Ile Gly
1310 1315 1320

Asp Pro Ala Gln Leu Pro Ala Pro Arg Thr Leu Leu Thr Lys Gly
1325 1330 1335

Thr Leu Glu Pro Glu Tyr Phe Asn Ser Val Cys Arg Leu Met Lys
1340 1345 1350

Thr Ile Gly Pro Asp Met Phe Leu Gly Thr Cys Arg Arg Cys Pro
1355 1360 1365

Ala Glu Ile Val Asp Thr Val Ser Ala Leu Val Tyr Asp Asn Lys
1370 1375 1380

Leu Lys Ala His Lys Asp Lys Ser Ala Gln Cys Phe Lys Met Phe
1385 1390 1395

Tyr Lys Gly Val Ile Thr His Asp Val Ser Ser Ala Ile Asn Arg
1400 1405 1410

Pro Gln Ile Gly Val Val Arg Glu Phe Leu Thr Arg Asn Pro Ala
1415 1420 1425

Trp Arg Lys Ala Val Phe Ile Ser Pro Tyr Asn Ser Gln Asn Ala

-continued

```
    1430                1435                1440

Val Ala  Ser Lys Ile Leu Gly  Leu Pro Thr Gln Thr  Val Asp Ser
    1445                1450                1455

Ser Gln  Gly Ser Glu Tyr Asp  Tyr Val Ile Phe Thr  Gln Thr Thr
    1460                1465                1470

Glu Thr  Ala His Ser Cys Asn  Val Asn Arg Phe Asn  Val Ala Ile
    1475                1480                1485

Thr Arg  Ala Lys Ile Gly Ile  Leu Cys Ile Met Ser  Asp Arg Asp
    1490                1495                1500

Leu Tyr  Asp Lys Leu Gln Phe  Thr Ser Leu Glu Ile  Pro Arg Arg
    1505                1510                1515

Asn Val  Ala Thr Leu Gln Ala  Glu Asn Val Thr Gly  Leu Phe Lys
    1520                1525                1530

Asp Cys  Ser Lys Ile Ile Thr  Gly Leu His Pro Thr  Gln Ala Pro
    1535                1540                1545

Thr His  Leu Ser Val Asp Ile  Lys Phe Lys Thr Glu  Gly Leu Cys
    1550                1555                1560

Val Asp  Ile Pro Gly Ile Pro  Lys Asp Met Thr Tyr  Arg Arg Leu
    1565                1570                1575

Ile Ser  Met Met Gly Phe Lys  Met Asn Tyr Gln Val  Asn Gly Tyr
    1580                1585                1590

Pro Asn  Met Phe Ile Thr Arg  Glu Glu Ala Ile Arg  His Val Arg
    1595                1600                1605

Ala Trp  Ile Gly Phe Asp Val  Glu Gly Cys His Ala  Thr Arg Asp
    1610                1615                1620

Ala Val  Gly Thr Asn Leu Pro  Leu Gln Leu Gly Phe  Ser Thr Gly
    1625                1630                1635

Val Asn  Leu Val Ala Val Pro  Thr Gly Tyr Val Asp  Thr Glu Asn
    1640                1645                1650

Asn Thr  Glu Phe Thr Arg Val  Asn Ala Lys Pro Pro  Pro Gly Asp
    1655                1660                1665

Gln Phe  Lys His Leu Ile Pro  Leu Met Tyr Lys Gly  Leu Pro Trp
    1670                1675                1680

Asn Val  Val Arg Ile Lys Ile  Val Gln Met Leu Ser  Asp Thr Leu
    1685                1690                1695

Lys Gly  Leu Ser Asp Arg Val  Val Phe Val Leu Trp  Ala His Gly
    1700                1705                1710

Phe Glu  Leu Thr Ser Met Lys  Tyr Phe Val Lys Ile  Gly Pro Glu
    1715                1720                1725

Arg Thr  Cys Cys Leu Cys Asp  Lys Arg Ala Thr Cys  Phe Ser Thr
    1730                1735                1740

Ser Ser  Asp Thr Tyr Ala Cys  Trp Asn His Ser Val  Gly Phe Asp
    1745                1750                1755

Tyr Val  Tyr Asn Pro Phe Met  Ile Asp Val Gln Gln  Trp Gly Phe
    1760                1765                1770

Thr Gly  Asn Leu Gln Ser Asn  His Asp Gln His Cys  Gln Val His
    1775                1780                1785

Gly Asn  Ala His Val Ala Ser  Cys Asp Ala Ile Met  Thr Arg Cys
    1790                1795                1800

Leu Ala  Val His Glu Cys Phe  Val Lys Arg Val Asp  Trp Ser Val
    1805                1810                1815

Glu Tyr  Pro Ile Ile Gly Asp  Glu Leu Arg Val Asn  Ser Ala Cys
    1820                1825                1830
```

-continued

```
Arg Lys  Val Gln His Met Val  Val Lys Ser Ala Leu  Leu Ala Asp
    1835                 1840                 1845

Lys Phe  Pro Val Leu His Asp  Ile Gly Asn Pro Lys  Ala Ile Lys
    1850                 1855                 1860

Cys Val  Pro Gln Ala Glu Val  Glu Trp Lys Phe Tyr  Asp Ala Gln
    1865                 1870                 1875

Pro Cys  Ser Asp Lys Ala Tyr  Lys Ile Glu Glu Leu  Phe Tyr Ser
    1880                 1885                 1890

Tyr Ala  Thr His His Asp Lys  Phe Thr Asp Gly Val  Cys Leu Phe
    1895                 1900                 1905

Trp Asn  Cys Asn Val Asp Arg  Tyr Pro Ala Asn Ala  Ile Val Cys
    1910                 1915                 1920

Arg Phe  Asp Thr Arg Val Leu  Ser Asn Leu Asn Leu  Pro Gly Cys
    1925                 1930                 1935

Asp Gly  Gly Ser Leu Tyr Val  Asn Lys His Ala Phe  His Thr Pro
    1940                 1945                 1950

Ala Phe  Asp Lys Ser Ala Phe  Thr Asn Leu Lys Gln  Leu Pro Phe
    1955                 1960                 1965

Phe Tyr  Tyr Ser Asp Ser Pro  Cys Glu Ser His Gly  Lys Gln Val
    1970                 1975                 1980

Val Ser  Asp Ile Asp Tyr Val  Pro Leu Lys Ser Ala  Thr Cys Ile
    1985                 1990                 1995

Thr Arg  Cys Asn Leu Gly Gly  Ala Val Cys Arg His  His Ala Asn
    2000                 2005                 2010

Glu Tyr  Arg Gln Tyr Leu Asp  Ala Tyr Asn Met Met  Ile Ser Ala
    2015                 2020                 2025

Gly Phe  Ser Leu Trp Ile Tyr  Lys Gln Phe Asp Thr  Tyr Asn Leu
    2030                 2035                 2040

Trp Asn  Thr Phe Thr Arg Leu  Gln Ser Leu Glu Asn  Val Ala Tyr
    2045                 2050                 2055

Asn Val  Val Asn Lys Gly His  Phe Asp Gly His Ala  Gly Glu Ala
    2060                 2065                 2070

Pro Val  Ser Ile Ile Asn Asn  Ala Val Tyr Thr Lys  Val Asp Gly
    2075                 2080                 2085

Ile Asp  Val Glu Ile Phe Glu  Asn Lys Thr Thr Leu  Pro Val Asn
    2090                 2095                 2100

Val Ala  Phe Glu Leu Trp Ala  Lys Arg Asn Ile Lys  Pro Val Pro
    2105                 2110                 2115

Glu Ile  Lys Ile Leu Asn Asn  Leu Gly Val Asp Ile  Ala Ala Asn
    2120                 2125                 2130

Thr Val  Ile Trp Asp Tyr Lys  Arg Glu Ala Pro Ala  His Val Ser
    2135                 2140                 2145

Thr Ile  Gly Val Cys Thr Met  Thr Asp Ile Ala Lys  Lys Pro Thr
    2150                 2155                 2160

Glu Ser  Ala Cys Ser Ser Leu  Thr Val Leu Phe Asp  Gly Arg Val
    2165                 2170                 2175

Glu Gly  Gln Val Asp Leu Phe  Arg Asn Ala Arg Asn  Gly Val Leu
    2180                 2185                 2190

Ile Thr  Glu Gly Ser Val Lys  Gly Leu Thr Pro Ser  Lys Gly Pro
    2195                 2200                 2205

Ala Gln  Ala Ser Val Asn Gly  Val Thr Leu Ile Gly  Glu Ser Val
    2210                 2215                 2220
```

-continued

Lys Thr Gln Phe Asn Tyr Phe Lys Lys Val Asp Gly Ile Ile Gln
2225 2230 2235

Gln Leu Pro Glu Thr Tyr Phe Thr Gln Ser Arg Asp Leu Glu Asp
2240 2245 2250

Phe Lys Pro Arg Ser Gln Met Glu Thr Asp Phe Leu Glu Leu Ala
2255 2260 2265

Met Asp Glu Phe Ile Gln Arg Tyr Lys Leu Glu Gly Tyr Ala Phe
2270 2275 2280

Glu His Ile Val Tyr Gly Asp Phe Ser His Gly Gln Leu Gly Gly
2285 2290 2295

Leu His Leu Met Ile Gly Leu Ala Lys Arg Ser Gln Asp Ser Pro
2300 2305 2310

Leu Lys Leu Glu Asp Phe Ile Pro Met Asp Ser Thr Val Lys Asn
2315 2320 2325

Tyr Phe Ile Thr Asp Ala Gln Thr Gly Ser Ser Lys Cys Val Cys
2330 2335 2340

Ser Val Ile Asp Leu Leu Leu Asp Asp Phe Val Glu Ile Ile Lys
2345 2350 2355

Ser Gln Asp Leu Ser Val Ile Ser Lys Val Val Lys Val Thr Ile
2360 2365 2370

Asp Tyr Ala Glu Ile Ser Phe Met Leu Trp Cys Lys Asp Gly His
2375 2380 2385

Val Glu Thr Phe Tyr Pro Lys Leu Gln Ala Ser Gln Ala Trp Gln
2390 2395 2400

Pro Gly Val Ala Met Pro Asn Leu Tyr Lys Met Gln Arg Met Leu
2405 2410 2415

Leu Glu Lys Cys Asp Leu Gln Asn Tyr Gly Glu Asn Ala Val Ile
2420 2425 2430

Pro Lys Gly Ile Met Met Asn Val Ala Lys Tyr Thr Gln Leu Cys
2435 2440 2445

Gln Tyr Leu Asn Thr Leu Thr Leu Ala Val Pro Tyr Asn Met Arg
2450 2455 2460

Val Ile His Phe Gly Ala Gly Ser Asp Lys Gly Val Ala Pro Gly
2465 2470 2475

Thr Ala Val Leu Arg Gln Trp Leu Pro Thr Gly Thr Leu Leu Val
2480 2485 2490

Asp Ser Asp Leu Asn Asp Phe Val Ser Asp Ala Asp Ser Thr Leu
2495 2500 2505

Ile Gly Asp Cys Ala Thr Val His Thr Ala Asn Lys Trp Asp Leu
2510 2515 2520

Ile Ile Ser Asp Met Tyr Asp Pro Arg Thr Lys His Val Thr Lys
2525 2530 2535

Glu Asn Asp Ser Lys Glu Gly Phe Phe Thr Tyr Leu Cys Gly Phe
2540 2545 2550

Ile Lys Gln Lys Leu Ala Leu Gly Gly Ser Ile Ala Val Lys Ile
2555 2560 2565

Thr Glu His Ser Trp Asn Ala Asp Leu Tyr Lys Leu Met Gly His
2570 2575 2580

Phe Ser Trp Trp Thr Ala Phe Val Thr Asn Val Asn Ala Ser Ser
2585 2590 2595

Ser Glu Ala Phe Leu Ile Gly Ala Asn Tyr Leu Gly Lys Pro Lys
2600 2605 2610

Glu Gln Ile Asp Gly Tyr Thr Met His Ala Asn Tyr Ile Phe Trp

-continued

```
    2615                2620                2625

Arg Asn  Thr Asn Pro Ile Gln  Leu Ser Ser Tyr Ser  Leu Phe Asp
    2630                2635                2640

Met Ser  Lys Phe Pro Leu Lys  Leu Arg Gly Thr Ala  Val Met Ser
    2645                2650                2655

Leu Lys  Glu Asn Gln Ile Asn  Asp Met Ile Tyr Ser  Leu Leu Glu
    2660                2665                2670

Lys Gly  Arg Leu Ile Ile Arg  Glu Asn Asn Arg Val  Val Val Ser
    2675                2680                2685

Ser Asp  Ile Leu Val Asn Asn
    2690                2695


<210> SEQ ID NO 29
<211> LENGTH: 7073
<212> TYPE: PRT
<213> ORGANISM: SARS-CoV CUHK-W1

<400> SEQUENCE: 29

Met Glu Ser Leu Val Leu Gly Val Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Ala Leu Ser Glu Ala Arg Glu His Leu Lys Asn
        35                  40                  45

Gly Thr Cys Gly Leu Val Glu Leu Glu Lys Gly Val Leu Pro Gln Leu
    50                  55                  60

Glu Gln Pro Tyr Val Phe Ile Lys Arg Ser Asp Ala Leu Ser Thr Asn
65                  70                  75                  80

His Gly His Lys Val Val Glu Leu Val Ala Glu Met Asp Gly Ile Gln
                85                  90                  95

Tyr Gly Arg Ser Gly Ile Thr Leu Gly Val Leu Val Pro His Val Gly
            100                 105                 110

Glu Thr Pro Ile Ala Tyr Arg Asn Val Leu Leu Arg Lys Asn Gly Asn
        115                 120                 125

Lys Gly Ala Gly Gly His Ser Tyr Gly Ile Asp Leu Lys Ser Tyr Asp
    130                 135                 140

Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Ala Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Tyr Glu His Gln Thr Pro Phe Glu
                245                 250                 255

Ile Lys Ser Ala Lys Lys Phe Asp Thr Phe Lys Gly Glu Cys Pro Lys
            260                 265                 270

Phe Val Phe Pro Leu Asn Ser Lys Val Lys Val Ile Gln Pro Arg Val
        275                 280                 285
```

-continued

```
Glu Lys Lys Lys Thr Glu Gly Phe Met Gly Arg Ile Arg Ser Val Tyr
    290                 295                 300

Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
                325                 330                 335

Leu Lys Ala Thr Cys Glu His Cys Gly Thr Glu Asn Leu Val Ile Glu
            340                 345                 350

Gly Pro Thr Thr Cys Gly Tyr Leu Pro Thr Asn Ala Val Val Lys Met
        355                 360                 365

Pro Cys Pro Ala Cys Gln Asp Pro Glu Ile Gly Pro Glu His Ser Val
    370                 375                 380

Ala Asp Tyr His Asn His Ser Asn Ile Glu Thr Arg Leu Arg Lys Gly
385                 390                 395                 400

Gly Arg Thr Arg Cys Phe Gly Gly Cys Val Phe Ala Tyr Val Gly Cys
                405                 410                 415

Tyr Asn Lys Arg Ala Tyr Trp Val Pro Arg Ala Ser Ala Asp Ile Gly
            420                 425                 430

Ser Gly His Thr Gly Ile Thr Gly Asp Asn Val Glu Thr Leu Asn Glu
        435                 440                 445

Asp Leu Leu Glu Ile Leu Ser Arg Glu Arg Val Asn Ile Asn Ile Val
    450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
                485                 490                 495

Lys Ser Phe Lys Thr Ile Val Glu Ser Cys Gly Asn Tyr Lys Val Thr
            500                 505                 510

Lys Gly Lys Pro Val Lys Gly Ala Trp Asn Ile Gly Gln Gln Arg Ser
        515                 520                 525

Val Leu Thr Pro Leu Cys Gly Phe Pro Ser Gln Ala Ala Gly Val Ile
    530                 535                 540

Arg Ser Ile Phe Ala Arg Thr Leu Asp Ala Ala Asn His Ser Ile Pro
545                 550                 555                 560

Asp Leu Gln Arg Ala Ala Val Thr Ile Leu Asp Gly Ile Ser Glu Gln
                565                 570                 575

Ser Leu Arg Leu Val Asp Ala Met Val Tyr Thr Ser Asp Leu Leu Thr
            580                 585                 590

Asn Ser Val Ile Ile Met Ala Tyr Val Thr Gly Gly Leu Val Gln Gln
        595                 600                 605

Thr Ser Gln Trp Leu Ser Asn Leu Leu Gly Thr Thr Val Glu Lys Leu
    610                 615                 620

Arg Pro Ile Phe Glu Trp Ile Glu Ala Lys Leu Ser Ala Gly Val Glu
625                 630                 635                 640

Phe Leu Lys Asp Ala Trp Glu Ile Leu Lys Phe Leu Ile Thr Gly Val
                645                 650                 655

Phe Asp Ile Val Lys Gly Gln Ile Gln Val Ala Ser Asp Asn Ile Lys
            660                 665                 670

Asp Cys Val Lys Cys Phe Ile Asp Val Val Asn Lys Ala Leu Glu Met
        675                 680                 685

Cys Ile Asp Gln Val Thr Ile Ala Gly Ala Lys Leu Arg Ser Leu Asn
    690                 695                 700

Leu Gly Glu Val Phe Ile Ala Gln Ser Lys Gly Leu Tyr Arg Gln Cys
```

-continued

```
705                 710                 715                 720

Ile Arg Gly Lys Glu Gln Leu Gln Leu Leu Met Pro Leu Lys Ala Pro
                725                 730                 735

Lys Glu Val Thr Phe Leu Glu Gly Asp Ser His Asp Thr Val Leu Thr
            740                 745                 750

Ser Glu Glu Val Val Leu Lys Asn Gly Glu Leu Glu Ala Leu Glu Thr
        755                 760                 765

Pro Val Asp Ser Phe Thr Asn Gly Ala Ile Val Gly Thr Pro Val Cys
    770                 775                 780

Val Asn Gly Leu Met Leu Leu Glu Ile Lys Asp Lys Glu Gln Tyr Cys
785                 790                 795                 800

Ala Leu Ser Pro Gly Leu Leu Ala Thr Asn Asn Val Phe Arg Leu Lys
                805                 810                 815

Gly Gly Ala Pro Ile Lys Gly Val Thr Phe Gly Glu Asp Thr Val Trp
            820                 825                 830

Glu Val Gln Gly Tyr Lys Asn Val Arg Ile Thr Phe Glu Leu Asp Glu
        835                 840                 845

Arg Val Asp Lys Val Leu Asn Glu Lys Cys Ser Val Tyr Thr Val Glu
    850                 855                 860

Ser Gly Thr Glu Val Thr Glu Phe Ala Cys Val Val Ala Glu Ala Val
865                 870                 875                 880

Val Lys Thr Leu Gln Pro Val Ser Asp Leu Leu Thr Asn Met Gly Ile
                885                 890                 895

Asp Leu Asp Glu Trp Ser Val Ala Thr Phe Tyr Leu Phe Asp Asp Ala
            900                 905                 910

Gly Glu Glu Asn Phe Ser Ser Arg Met Tyr Cys Ser Phe Tyr Pro Pro
        915                 920                 925

Asp Glu Glu Glu Glu Asp Asp Ala Glu Cys Glu Glu Glu Glu Ile Asp
    930                 935                 940

Glu Thr Cys Glu His Glu Tyr Gly Thr Glu Asp Asp Tyr Gln Gly Leu
945                 950                 955                 960

Pro Leu Glu Phe Gly Ala Ser Ala Glu Thr Val Arg Val Glu Glu Glu
                965                 970                 975

Glu Glu Glu Asp Trp Leu Asp Asp Thr Thr Glu Gln Ser Glu Ile Glu
            980                 985                 990

Pro Glu Pro Glu Pro Thr Pro Glu  Glu Pro Val Asn Gln  Phe Thr Gly
        995                 1000                1005

Tyr Leu  Lys Leu Thr Asp Asn  Val Ala Ile Lys Cys  Val Asp Ile
    1010                1015                1020

Val Lys  Glu Ala Gln Ser Ala  Asn Pro Met Val Ile  Val Asn Ala
    1025                1030                1035

Ala Asn  Ile His Leu Lys His  Gly Gly Gly Val Ala  Gly Ala Leu
    1040                1045                1050

Asn Lys  Ala Thr Asn Gly Ala  Met Gln Lys Glu Ser  Asp Asp Tyr
    1055                1060                1065

Ile Lys  Leu Asn Gly Pro Leu  Thr Val Gly Gly Ser  Cys Leu Leu
    1070                1075                1080

Ser Gly  His Asn Leu Ala Lys  Lys Cys Leu His Val  Val Gly Pro
    1085                1090                1095

Asn Leu  Asn Ala Gly Glu Asp  Ile Gln Leu Leu Lys  Ala Ala Tyr
    1100                1105                1110

Glu Asn  Phe Asn Ser Gln Asp  Ile Leu Leu Ala Pro  Leu Leu Ser
    1115                1120                1125
```

-continued

```
Ala Gly  Ile Phe Gly Ala Lys  Pro Leu Gln Ser Leu  Gln Val Cys
    1130                 1135                 1140

Val Gln  Thr Val Arg Thr Gln  Val Tyr Ile Ala Val  Asn Asp Lys
    1145                 1150                 1155

Ala Leu  Tyr Glu Gln Val Val  Met Asp Tyr Leu Asp  Asn Leu Lys
    1160                 1165                 1170

Pro Arg  Val Glu Ala Pro Lys  Gln Glu Glu Pro Pro  Asn Thr Glu
    1175                 1180                 1185

Asp Ser  Lys Thr Glu Glu Lys  Ser Val Val Gln Lys  Pro Val Asp
    1190                 1195                 1200

Val Lys  Pro Lys Ile Lys Ala  Cys Ile Asp Glu Val  Thr Thr Thr
    1205                 1210                 1215

Leu Glu  Glu Thr Lys Phe Leu  Thr Asn Lys Leu Leu  Leu Phe Ala
    1220                 1225                 1230

Asp Ile  Asn Gly Lys Leu Tyr  His Asp Ser Gln Asn  Met Leu Arg
    1235                 1240                 1245

Gly Glu  Asp Met Ser Phe Leu  Glu Lys Asp Ala Pro  Tyr Met Val
    1250                 1255                 1260

Gly Asp  Val Ile Thr Ser Gly  Asp Ile Thr Cys Val  Val Ile Pro
    1265                 1270                 1275

Ser Lys  Lys Ala Gly Gly Thr  Thr Glu Met Leu Ser  Arg Ala Leu
    1280                 1285                 1290

Lys Lys  Val Pro Val Asp Glu  Tyr Ile Thr Thr Tyr  Pro Gly Gln
    1295                 1300                 1305

Gly Cys  Ala Gly Tyr Thr Leu  Glu Glu Ala Lys Thr  Ala Leu Lys
    1310                 1315                 1320

Lys Cys  Lys Ser Ala Phe Tyr  Val Leu Pro Ser Glu  Ala Pro Asn
    1325                 1330                 1335

Ala Lys  Glu Glu Ile Leu Gly  Thr Val Ser Trp Asn  Leu Arg Glu
    1340                 1345                 1350

Met Leu  Ala His Ala Glu Glu  Thr Arg Lys Leu Met  Pro Ile Cys
    1355                 1360                 1365

Met Asp  Val Arg Ala Ile Met  Ala Thr Ile Gln Arg  Lys Tyr Lys
    1370                 1375                 1380

Gly Ile  Lys Ile Gln Glu Gly  Ile Val Asp Tyr Gly  Val Arg Phe
    1385                 1390                 1395

Phe Phe  Tyr Thr Ser Lys Glu  Pro Val Ala Ser Ile  Ile Thr Lys
    1400                 1405                 1410

Leu Asn  Ser Leu Asn Glu Pro  Leu Val Thr Met Pro  Ile Gly Tyr
    1415                 1420                 1425

Val Thr  His Gly Phe Asn Leu  Glu Glu Ala Ala Arg  Cys Met Arg
    1430                 1435                 1440

Ser Leu  Lys Ala Pro Ala Val  Val Ser Val Ser Ser  Pro Asp Ala
    1445                 1450                 1455

Val Thr  Thr Tyr Asn Gly Tyr  Leu Thr Ser Ser Ser  Lys Thr Ser
    1460                 1465                 1470

Glu Glu  His Phe Val Glu Thr  Val Ser Leu Ala Gly  Ser Tyr Arg
    1475                 1480                 1485

Asp Trp  Ser Tyr Ser Gly Gln  Arg Thr Glu Leu Gly  Val Glu Phe
    1490                 1495                 1500

Leu Lys  Arg Gly Asp Lys Ile  Val Tyr His Thr Leu  Glu Ser Pro
    1505                 1510                 1515
```

-continued

```
Val Glu  Phe His Leu Asp Gly  Glu Val Leu Ser Leu  Asp Lys Leu
    1520                 1525                 1530

Lys Ser  Leu Leu Ser Leu Arg  Glu Val Lys Thr Ile  Lys Val Phe
    1535                 1540                 1545

Thr Thr  Val Asp Asn Thr Asn  Leu His Thr Gln Leu  Val Asp Met
    1550                 1555                 1560

Ser Met  Thr Tyr Gly Gln Gln  Phe Gly Pro Thr Tyr  Leu Asp Gly
    1565                 1570                 1575

Ala Asp  Val Thr Lys Ile Lys  Pro His Val Asn His  Glu Gly Lys
    1580                 1585                 1590

Thr Phe  Phe Val Leu Pro Ser  Asp Asp Thr Leu Arg  Ser Glu Ala
    1595                 1600                 1605

Phe Glu  Tyr Tyr His Thr Leu  Asp Glu Ser Phe Leu  Gly Arg Tyr
    1610                 1615                 1620

Met Ser  Ala Leu Asn His Thr  Lys Lys Trp Lys Phe  Pro Gln Val
    1625                 1630                 1635

Gly Gly  Leu Thr Ser Ile Lys  Trp Ala Asp Asn Asn  Cys Tyr Leu
    1640                 1645                 1650

Ser Ser  Val Leu Leu Ala Leu  Gln Gln Leu Glu Val  Lys Phe Asn
    1655                 1660                 1665

Ala Pro  Ala Leu Gln Glu Ala  Tyr Tyr Arg Ala Arg  Ala Gly Asp
    1670                 1675                 1680

Ala Ala  Asn Phe Cys Ala Leu  Ile Leu Ala Tyr Ser  Asn Lys Thr
    1685                 1690                 1695

Val Gly  Glu Leu Gly Asp Val  Arg Glu Thr Met Thr  His Leu Leu
    1700                 1705                 1710

Gln His  Ala Asn Leu Glu Ser  Ala Lys Arg Val Leu  Asn Val Val
    1715                 1720                 1725

Cys Lys  His Cys Gly Gln Lys  Thr Thr Thr Leu Thr  Gly Val Glu
    1730                 1735                 1740

Ala Val  Met Tyr Met Gly Thr  Leu Ser Tyr Asp Asn  Leu Lys Thr
    1745                 1750                 1755

Gly Val  Ser Ile Pro Cys Val  Cys Gly Arg Asp Ala  Thr Gln Tyr
    1760                 1765                 1770

Leu Val  Gln Gln Glu Ser Ser  Phe Val Met Met Ser  Ala Pro Pro
    1775                 1780                 1785

Ala Glu  Tyr Lys Leu Gln Gln  Gly Thr Phe Leu Cys  Ala Asn Glu
    1790                 1795                 1800

Tyr Thr  Gly Asn Tyr Gln Cys  Gly His Tyr Thr His  Ile Thr Ala
    1805                 1810                 1815

Lys Glu  Thr Leu Tyr Arg Ile  Asp Gly Ala His Leu  Thr Lys Met
    1820                 1825                 1830

Ser Glu  Tyr Lys Gly Pro Val  Thr Asp Val Phe Tyr  Lys Glu Thr
    1835                 1840                 1845

Ser Tyr  Thr Thr Thr Ile Lys  Pro Val Ser Tyr Lys  Leu Asp Gly
    1850                 1855                 1860

Val Thr  Tyr Thr Glu Ile Glu  Pro Lys Leu Asp Gly  Tyr Tyr Lys
    1865                 1870                 1875

Lys Asp  Asn Ala Tyr Tyr Thr  Glu Gln Pro Ile Asp  Leu Val Pro
    1880                 1885                 1890

Thr Gln  Pro Leu Pro Asn Ala  Ser Phe Asp Asn Phe  Lys Leu Thr
    1895                 1900                 1905

Cys Ser  Asn Thr Lys Phe Ala  Asp Asp Leu Asn Gln  Met Thr Gly
```

-continued

```
    1910                1915                1920

Phe Thr  Lys Pro Ala Ser Arg  Glu Leu Ser Val Thr  Phe Phe Pro
    1925                1930                1935

Asp Leu  Asn Gly Asp Val Val  Ala Ile Asp Tyr Arg  His Tyr Ser
    1940                1945                1950

Ala Ser  Phe Lys Lys Gly Ala  Lys Leu Leu His Lys  Pro Ile Val
    1955                1960                1965

Trp His  Ile Asn Gln Ala Thr  Thr Lys Thr Thr Phe  Lys Pro Asn
    1970                1975                1980

Thr Trp  Cys Leu Arg Cys Leu  Trp Ser Thr Lys Pro  Val Asp Thr
    1985                1990                1995

Ser Asn  Ser Phe Glu Val Leu  Ala Val Glu Asp Thr  Gln Gly Met
    2000                2005                2010

Asp Asn  Leu Ala Cys Glu Ser  Gln Gln Pro Thr Ser  Glu Glu Val
    2015                2020                2025

Val Glu  Asn Pro Thr Ile Gln  Lys Glu Val Ile Glu  Cys Asp Val
    2030                2035                2040

Lys Thr  Thr Glu Val Val Gly  Asn Val Ile Leu Lys  Pro Ser Asp
    2045                2050                2055

Glu Gly  Val Lys Val Thr Gln  Glu Leu Gly His Glu  Asp Leu Met
    2060                2065                2070

Ala Ala  Tyr Val Glu Asn Thr  Ser Ile Thr Ile Lys  Lys Pro Asn
    2075                2080                2085

Glu Leu  Ser Leu Ala Leu Gly  Leu Lys Thr Ile Ala  Thr His Gly
    2090                2095                2100

Ile Ala  Ala Ile Asn Ser Val  Pro Trp Ser Lys Ile  Leu Ala Tyr
    2105                2110                2115

Val Lys  Pro Phe Leu Gly Gln  Ala Ala Ile Thr Thr  Ser Asn Cys
    2120                2125                2130

Ala Lys  Arg Leu Ala Gln Arg  Val Phe Asn Asn Tyr  Met Pro Tyr
    2135                2140                2145

Val Phe  Thr Leu Leu Phe Gln  Leu Cys Thr Phe Thr  Lys Ser Thr
    2150                2155                2160

Asn Ser  Arg Ile Arg Ala Ser  Leu Pro Thr Thr Ile  Ala Lys Asn
    2165                2170                2175

Ser Val  Lys Ser Val Ala Lys  Leu Cys Leu Asp Ala  Gly Ile Asn
    2180                2185                2190

Tyr Val  Lys Ser Pro Lys Phe  Ser Lys Leu Phe Thr  Ile Ala Met
    2195                2200                2205

Trp Leu  Leu Leu Leu Ser Ile  Cys Leu Gly Ser Leu  Ile Cys Val
    2210                2215                2220

Thr Ala  Ala Phe Gly Val Leu  Leu Ser Asn Phe Gly  Ala Pro Ser
    2225                2230                2235

Tyr Cys  Asn Gly Val Arg Glu  Leu Tyr Leu Asn Ser  Ser Asn Val
    2240                2245                2250

Thr Thr  Met Asp Phe Cys Glu  Gly Ser Phe Pro Cys  Ser Ile Cys
    2255                2260                2265

Leu Ser  Gly Leu Asp Ser Leu  Asp Ser Tyr Pro Ala  Leu Glu Thr
    2270                2275                2280

Ile Gln  Val Thr Ile Ser Ser  Tyr Lys Leu Asp Leu  Thr Ile Leu
    2285                2290                2295

Gly Leu  Ala Ala Glu Trp Val  Leu Ala Tyr Met Leu  Phe Thr Lys
    2300                2305                2310
```

-continued

```
Phe Phe  Tyr Leu Leu Gly Leu  Ser Ala Ile Met Gln  Val Phe Phe
    2315                 2320                 2325

Gly Tyr  Phe Ala Ser His Phe  Ile Ser Asn Ser Trp  Leu Met Trp
    2330                 2335                 2340

Phe Ile  Ile Ser Ile Val Gln  Met Ala Pro Val Ser  Ala Met Val
    2345                 2350                 2355

Arg Met  Tyr Ile Phe Phe Ala  Ser Phe Tyr Tyr Ile  Trp Lys Ser
    2360                 2365                 2370

Tyr Val  His Ile Met Asp Gly  Cys Thr Ser Ser Thr  Cys Met Met
    2375                 2380                 2385

Cys Tyr  Lys Arg Asn Arg Ala  Thr Arg Val Glu Cys  Thr Thr Ile
    2390                 2395                 2400

Val Asn  Gly Met Lys Arg Ser  Phe Tyr Val Tyr Ala  Asn Gly Gly
    2405                 2410                 2415

Arg Gly  Phe Cys Lys Thr His  Asn Trp Asn Cys Leu  Asn Cys Asp
    2420                 2425                 2430

Thr Phe  Cys Thr Gly Ser Thr  Phe Ile Ser Asp Glu  Val Ala Arg
    2435                 2440                 2445

Asp Leu  Ser Leu Gln Phe Lys  Arg Pro Ile Asn Pro  Thr Asp Gln
    2450                 2455                 2460

Ser Ser  Tyr Ile Val Asp Ser  Val Ala Val Lys Asn  Gly Ala Leu
    2465                 2470                 2475

His Leu  Tyr Phe Asp Lys Ala  Gly Gln Lys Thr Tyr  Glu Arg His
    2480                 2485                 2490

Pro Leu  Ser His Phe Val Asn  Leu Asp Asn Leu Arg  Ala Asn Asn
    2495                 2500                 2505

Thr Lys  Gly Ser Leu Pro Ile  Asn Val Ile Val Phe  Asp Gly Lys
    2510                 2515                 2520

Ser Lys  Cys Asp Glu Ser Ala  Ser Lys Ser Ala Ser  Val Tyr Tyr
    2525                 2530                 2535

Ser Gln  Leu Met Cys Gln Pro  Ile Leu Leu Leu Asp  Gln Ala Leu
    2540                 2545                 2550

Val Ser  Asp Val Gly Asp Ser  Thr Glu Val Ser Val  Lys Met Phe
    2555                 2560                 2565

Asp Ala  Tyr Val Asp Thr Phe  Ser Ala Thr Phe Ser  Val Pro Met
    2570                 2575                 2580

Glu Lys  Leu Lys Ala Leu Val  Ala Thr Ala His Ser  Glu Leu Ala
    2585                 2590                 2595

Lys Gly  Val Ala Leu Asp Gly  Val Leu Ser Thr Phe  Val Ser Ala
    2600                 2605                 2610

Ala Arg  Gln Gly Val Val Asp  Thr Asp Val Asp Thr  Lys Asp Val
    2615                 2620                 2625

Ile Glu  Cys Leu Lys Leu Ser  His His Ser Asp Leu  Glu Val Thr
    2630                 2635                 2640

Gly Asp  Ser Cys Asn Asn Phe  Met Leu Thr Tyr Asn  Lys Val Glu
    2645                 2650                 2655

Asn Met  Thr Pro Arg Asp Leu  Gly Ala Cys Ile Asp  Cys Asn Ala
    2660                 2665                 2670

Arg His  Ile Asn Ala Gln Val  Ala Lys Ser His Asn  Val Ser Leu
    2675                 2680                 2685

Ile Trp  Asn Val Lys Asp Tyr  Met Ser Leu Ser Glu  Gln Leu Arg
    2690                 2695                 2700
```

-continued

```
Lys Gln  Ile Arg Ser Ala Ala  Lys Lys Asn Asn Ile  Pro Phe Arg
    2705                 2710                 2715

Leu Thr  Cys Ala Thr Thr Arg  Gln Val Val Asn Val  Ile Thr Thr
    2720                 2725                 2730

Lys Ile  Ser Leu Lys Gly Gly  Lys Ile Val Ser Thr  Cys Phe Lys
    2735                 2740                 2745

Leu Met  Leu Lys Ala Thr Leu  Leu Cys Val Leu Ala  Ala Leu Val
    2750                 2755                 2760

Cys Tyr  Ile Val Met Pro Val  His Thr Leu Ser Ile  His Asp Gly
    2765                 2770                 2775

Tyr Thr  Asn Glu Ile Ile Gly  Tyr Lys Ala Ile Gln  Asp Gly Val
    2780                 2785                 2790

Thr Arg  Asp Ile Ile Ser Thr  Asp Asp Cys Phe Ala  Asn Lys His
    2795                 2800                 2805

Ala Gly  Phe Asp Ala Trp Phe  Ser Gln Arg Gly Gly  Ser Tyr Lys
    2810                 2815                 2820

Asn Asp  Lys Ser Cys Pro Val  Val Ala Ala Ile Ile  Thr Arg Glu
    2825                 2830                 2835

Ile Gly  Phe Ile Val Pro Gly  Leu Pro Gly Thr Val  Leu Arg Ala
    2840                 2845                 2850

Ile Asn  Gly Asp Phe Leu His  Phe Leu Pro Arg Val  Phe Ser Ala
    2855                 2860                 2865

Val Gly  Asn Ile Cys Tyr Thr  Pro Ser Lys Leu Ile  Glu Tyr Ser
    2870                 2875                 2880

Asp Phe  Ala Thr Ser Ala Cys  Val Leu Ala Ala Glu  Cys Thr Ile
    2885                 2890                 2895

Phe Lys  Asp Ala Met Gly Lys  Pro Val Pro Tyr Cys  Tyr Asp Thr
    2900                 2905                 2910

Asn Leu  Leu Glu Gly Ser Ile  Ser Tyr Ser Glu Leu  Arg Pro Asp
    2915                 2920                 2925

Thr Arg  Tyr Val Leu Met Asp  Gly Ser Ile Ile Gln  Phe Pro Asn
    2930                 2935                 2940

Thr Tyr  Leu Glu Gly Ser Val  Arg Val Val Thr Thr  Phe Asp Ala
    2945                 2950                 2955

Glu Tyr  Cys Arg His Gly Thr  Cys Glu Arg Ser Glu  Val Gly Ile
    2960                 2965                 2970

Cys Leu  Ser Thr Ser Gly Arg  Trp Val Leu Asn Asn  Glu His Tyr
    2975                 2980                 2985

Arg Ala  Leu Ser Gly Val Phe  Cys Gly Val Asp Ala  Met Asn Leu
    2990                 2995                 3000

Ile Ala  Asn Ile Phe Thr Pro  Leu Val Gln Pro Val  Gly Ala Leu
    3005                 3010                 3015

Asp Val  Ser Ala Ser Val Val  Ala Gly Gly Ile Ile  Ala Ile Leu
    3020                 3025                 3030

Val Thr  Cys Ala Ala Tyr Tyr  Phe Met Lys Phe Arg  Arg Ala Phe
    3035                 3040                 3045

Gly Glu  Tyr Asn His Val Val  Ala Ala Asn Ala Leu  Leu Phe Leu
    3050                 3055                 3060

Met Ser  Phe Thr Ile Leu Cys  Leu Ala Pro Ala Tyr  Ser Phe Leu
    3065                 3070                 3075

Pro Gly  Val Tyr Ser Val Phe  Tyr Leu Tyr Leu Thr  Phe Tyr Phe
    3080                 3085                 3090

Thr Asn  Asp Val Ser Phe Leu  Ala His Leu Gln Trp  Phe Ala Met
```

-continued

```
    3095                3100                3105

Phe Ser  Pro Ile Val Pro Phe  Trp Ile Thr Ala Ile  Tyr Val Phe
    3110                3115                3120

Cys Ile  Ser Leu Lys His Cys  His Trp Phe Phe Asn  Asn Tyr Leu
    3125                3130                3135

Arg Lys  Arg Val Met Phe Asn  Gly Val Thr Phe Ser  Thr Phe Glu
    3140                3145                3150

Glu Ala  Ala Leu Cys Thr Phe  Leu Leu Asn Lys Glu  Met Tyr Leu
    3155                3160                3165

Lys Leu  Arg Ser Glu Thr Leu  Leu Pro Leu Thr Gln  Tyr Asn Arg
    3170                3175                3180

Tyr Leu  Ala Leu Tyr Asn Lys  Tyr Lys Tyr Phe Ser  Gly Ala Leu
    3185                3190                3195

Asp Thr  Thr Ser Tyr Arg Glu  Ala Ala Cys Cys His  Leu Ala Lys
    3200                3205                3210

Ala Leu  Asn Asp Phe Ser Asn  Ser Gly Ala Asp Val  Leu Tyr Gln
    3215                3220                3225

Pro Pro  Gln Thr Ser Ile Thr  Ser Ala Val Leu Gln  Ser Gly Phe
    3230                3235                3240

Arg Lys  Met Ala Phe Pro Ser  Gly Lys Val Glu Gly  Cys Met Val
    3245                3250                3255

Gln Val  Thr Cys Gly Thr Thr  Thr Leu Asn Gly Leu  Trp Leu Asp
    3260                3265                3270

Asp Thr  Val Tyr Cys Pro Arg  His Val Ile Cys Thr  Ala Glu Asp
    3275                3280                3285

Met Leu  Asn Pro Asn Tyr Glu  Asp Leu Leu Ile Arg  Lys Ser Asn
    3290                3295                3300

His Ser  Phe Leu Val Gln Ala  Gly Asn Val Gln Leu  Arg Val Ile
    3305                3310                3315

Gly His  Ser Met Gln Asn Cys  Leu Leu Arg Leu Lys  Val Asp Thr
    3320                3325                3330

Ser Asn  Pro Lys Thr Pro Lys  Tyr Lys Phe Val Arg  Ile Gln Pro
    3335                3340                3345

Gly Gln  Thr Phe Ser Val Leu  Ala Cys Tyr Asn Gly  Ser Pro Ser
    3350                3355                3360

Gly Val  Tyr Gln Cys Ala Met  Arg Pro Asn His Thr  Ile Lys Gly
    3365                3370                3375

Ser Phe  Leu Asn Gly Ser Cys  Gly Ser Val Gly Phe  Asn Ile Asp
    3380                3385                3390

Tyr Asp  Cys Val Ser Phe Cys  Tyr Met His His Met  Glu Leu Pro
    3395                3400                3405

Thr Gly  Val His Ala Gly Thr  Asp Leu Glu Gly Lys  Phe Tyr Gly
    3410                3415                3420

Pro Phe  Val Asp Arg Gln Thr  Ala Gln Ala Ala Gly  Thr Asp Thr
    3425                3430                3435

Thr Ile  Thr Leu Asn Val Leu  Ala Trp Leu Tyr Ala  Ala Val Ile
    3440                3445                3450

Asn Gly  Asp Arg Trp Phe Leu  Asn Arg Phe Thr Thr  Thr Leu Asn
    3455                3460                3465

Asp Phe  Asn Leu Val Ala Met  Lys Tyr Asn Tyr Glu  Pro Leu Thr
    3470                3475                3480

Gln Asp  His Val Asp Ile Leu  Gly Pro Leu Ser Ala  Gln Thr Gly
    3485                3490                3495
```

-continued

```
Ile Ala Val Leu Asp Met Cys Ala Ala Leu Lys Glu Leu Leu Gln
    3500                3505                3510

Asn Gly Met Asn Gly Arg Thr Ile Leu Gly Ser Thr Ile Leu Glu
    3515                3520                3525

Asp Glu Phe Thr Pro Phe Asp Val Val Arg Gln Cys Ser Gly Val
    3530                3535                3540

Thr Phe Gln Gly Lys Phe Lys Lys Ile Val Lys Gly Thr His His
    3545                3550                3555

Trp Met Leu Leu Thr Phe Leu Thr Ser Leu Leu Ile Leu Val Gln
    3560                3565                3570

Ser Thr Gln Trp Ser Leu Phe Phe Phe Val Tyr Glu Asn Ala Phe
    3575                3580                3585

Leu Pro Phe Thr Leu Gly Ile Met Ala Ile Ala Ala Cys Ala Met
    3590                3595                3600

Leu Leu Val Lys His Lys His Ala Phe Leu Cys Leu Phe Leu Leu
    3605                3610                3615

Pro Ser Leu Ala Thr Val Ala Tyr Phe Asn Met Val Tyr Met Pro
    3620                3625                3630

Ala Ser Trp Val Met Arg Ile Met Thr Trp Leu Glu Leu Ala Asp
    3635                3640                3645

Thr Ser Leu Ser Gly Tyr Arg Leu Lys Asp Cys Val Met Tyr Ala
    3650                3655                3660

Ser Ala Leu Val Leu Leu Ile Leu Met Thr Ala Arg Thr Val Tyr
    3665                3670                3675

Asp Asp Ala Ala Arg Arg Val Trp Thr Leu Met Asn Val Ile Thr
    3680                3685                3690

Leu Val Tyr Lys Val Tyr Tyr Gly Asn Ala Leu Asp Gln Ala Ile
    3695                3700                3705

Ser Met Trp Ala Leu Val Ile Ser Val Thr Ser Asn Tyr Ser Gly
    3710                3715                3720

Val Val Thr Thr Ile Met Phe Leu Ala Arg Ala Ile Val Phe Val
    3725                3730                3735

Cys Val Glu Tyr Tyr Pro Leu Leu Phe Ile Thr Gly Asn Thr Leu
    3740                3745                3750

Gln Cys Ile Met Leu Val Tyr Cys Phe Leu Gly Tyr Cys Cys Cys
    3755                3760                3765

Cys Tyr Phe Gly Leu Phe Cys Leu Leu Asn Arg Tyr Phe Arg Leu
    3770                3775                3780

Thr Leu Gly Val Tyr Asp Tyr Leu Val Ser Thr Gln Glu Phe Arg
    3785                3790                3795

Tyr Met Asn Ser Gln Gly Leu Leu Pro Pro Lys Ser Ser Ile Asp
    3800                3805                3810

Ala Phe Lys Leu Asn Ile Lys Leu Leu Gly Ile Gly Gly Lys Pro
    3815                3820                3825

Cys Ile Lys Val Ala Thr Val Gln Ser Lys Met Ser Asp Val Lys
    3830                3835                3840

Cys Thr Ser Val Val Leu Leu Ser Val Leu Gln Gln Leu Arg Val
    3845                3850                3855

Glu Ser Ser Ser Lys Leu Trp Ala Gln Cys Val Gln Leu His Asn
    3860                3865                3870

Asp Ile Leu Leu Ala Lys Asp Thr Thr Glu Ala Phe Glu Lys Met
    3875                3880                3885
```

-continued

```
Val Ser  Leu Leu Ser Val Leu  Leu Ser Met Gln Gly  Ala Val Asp
    3890                 3895                 3900

Ile Asn  Arg Leu Cys Glu Glu  Met Leu Asp Asn Arg  Ala Thr Leu
    3905                 3910                 3915

Gln Ala  Ile Ala Ser Glu Phe  Ser Ser Leu Pro Ser  Tyr Ala Ala
    3920                 3925                 3930

Tyr Ala  Thr Ala Gln Glu Ala  Tyr Glu Gln Ala Val  Ala Asn Gly
    3935                 3940                 3945

Asp Ser  Glu Val Val Leu Lys  Lys Leu Lys Lys Ser  Leu Asn Val
    3950                 3955                 3960

Ala Lys  Ser Glu Phe Asp Arg  Asp Ala Ala Met Gln  Arg Lys Leu
    3965                 3970                 3975

Glu Lys  Met Ala Asp Gln Ala  Met Thr Gln Met Tyr  Lys Gln Ala
    3980                 3985                 3990

Arg Ser  Glu Asp Lys Arg Ala  Lys Val Thr Ser Ala  Met Gln Thr
    3995                 4000                 4005

Met Leu  Phe Thr Met Leu Arg  Lys Leu Asp Asn Asp  Ala Leu Asn
    4010                 4015                 4020

Asn Ile  Ile Asn Asn Ala Arg  Asp Gly Cys Val Pro  Leu Asn Ile
    4025                 4030                 4035

Ile Pro  Leu Thr Thr Ala Ala  Lys Leu Met Val Val  Val Pro Asp
    4040                 4045                 4050

Tyr Gly  Thr Tyr Lys Asn Thr  Cys Asp Gly Asn Thr  Phe Thr Tyr
    4055                 4060                 4065

Ala Ser  Ala Leu Trp Glu Ile  Gln Gln Val Val Asp  Ala Asp Ser
    4070                 4075                 4080

Lys Ile  Val Gln Leu Ser Glu  Ile Asn Met Asp Asn  Ser Pro Asn
    4085                 4090                 4095

Leu Ala  Trp Pro Leu Ile Val  Thr Ala Leu Arg Ala  Asn Ser Ala
    4100                 4105                 4110

Val Lys  Leu Gln Asn Asn Glu  Leu Ser Pro Val Ala  Leu Arg Gln
    4115                 4120                 4125

Met Ser  Cys Ala Ala Gly Thr  Thr Gln Thr Ala Cys  Thr Asp Asp
    4130                 4135                 4140

Asn Ala  Leu Ala Tyr Tyr Asn  Asn Ser Lys Gly Gly  Arg Phe Val
    4145                 4150                 4155

Leu Ala  Leu Leu Ser Asp His  Gln Asp Leu Lys Trp  Ala Arg Phe
    4160                 4165                 4170

Pro Lys  Ser Asp Gly Thr Gly  Thr Ile Tyr Thr Glu  Leu Glu Pro
    4175                 4180                 4185

Pro Cys  Arg Phe Val Thr Asp  Thr Pro Lys Gly Pro  Lys Val Lys
    4190                 4195                 4200

Tyr Leu  Tyr Phe Ile Lys Gly  Leu Asn Asn Leu Asn  Arg Gly Met
    4205                 4210                 4215

Val Leu  Gly Ser Leu Ala Ala  Thr Val Arg Leu Gln  Ala Gly Asn
    4220                 4225                 4230

Ala Thr  Glu Val Pro Ala Asn  Ser Thr Val Leu Ser  Phe Cys Ala
    4235                 4240                 4245

Phe Ala  Val Asp Pro Ala Lys  Ala Tyr Lys Asp Tyr  Leu Ala Ser
    4250                 4255                 4260

Gly Gly  Gln Pro Ile Thr Asn  Cys Val Lys Met Leu  Cys Thr His
    4265                 4270                 4275

Thr Gly  Thr Gly Gln Ala Ile  Thr Val Thr Pro Glu  Ala Asn Met
```

-continued

```
    4280                4285                4290

Asp Gln  Glu Ser Phe Gly Gly  Ala Ser Cys Cys Leu  Tyr Cys Arg
    4295                4300                4305

Cys His  Ile Asp His Pro Asn  Pro Lys Gly Phe Cys  Asp Leu Lys
    4310                4315                4320

Gly Lys  Tyr Val Gln Ile Pro  Thr Thr Cys Ala Asn  Asp Pro Val
    4325                4330                4335

Gly Phe  Thr Leu Arg Asn Thr  Val Cys Thr Val Cys  Gly Met Trp
    4340                4345                4350

Lys Gly  Tyr Gly Cys Ser Cys  Asp Gln Leu Arg Glu  Pro Leu Met
    4355                4360                4365

Gln Ser  Ala Asp Ala Ser Thr  Phe Leu Asn Arg Val  Cys Gly Val
    4370                4375                4380

Ser Ala  Ala Arg Leu Thr Pro  Cys Gly Thr Gly Thr  Ser Thr Asp
    4385                4390                4395

Val Val  Tyr Arg Ala Phe Asp  Ile Tyr Asn Glu Lys  Val Ala Gly
    4400                4405                4410

Phe Ala  Lys Phe Leu Lys Thr  Asn Cys Cys Arg Phe  Gln Glu Lys
    4415                4420                4425

Asp Glu  Glu Gly Asn Leu Leu  Asp Ser Tyr Phe Val  Val Lys Arg
    4430                4435                4440

His Thr  Met Ser Asn Tyr Gln  His Glu Glu Thr Ile  Tyr Asn Leu
    4445                4450                4455

Val Lys  Asp Cys Pro Ala Val  Ala Val His Asp Phe  Phe Lys Phe
    4460                4465                4470

Arg Val  Asp Gly Asp Met Val  Pro His Ile Ser Arg  Gln Arg Leu
    4475                4480                4485

Thr Lys  Tyr Thr Met Ala Asp  Leu Val Tyr Ala Leu  Arg His Phe
    4490                4495                4500

Asp Glu  Gly Asn Cys Asp Thr  Leu Lys Glu Ile Leu  Val Thr Tyr
    4505                4510                4515

Asn Cys  Cys Asp Asp Asp Tyr  Phe Asn Lys Lys Asp  Trp Tyr Asp
    4520                4525                4530

Phe Val  Glu Asn Pro Asp Ile  Leu Arg Val Tyr Ala  Asn Leu Gly
    4535                4540                4545

Glu Arg  Val Arg Gln Ser Leu  Leu Lys Thr Val Gln  Phe Cys Asp
    4550                4555                4560

Ala Met  Arg Asp Ala Gly Ile  Val Gly Val Leu Thr  Leu Asp Asn
    4565                4570                4575

Gln Asp  Leu Asn Gly Asn Trp  Tyr Asp Phe Gly Asp  Phe Val Gln
    4580                4585                4590

Val Ala  Pro Gly Cys Gly Val  Pro Ile Val Asp Ser  Tyr Tyr Ser
    4595                4600                4605

Leu Leu  Met Pro Ile Leu Thr  Leu Thr Arg Ala Leu  Ala Ala Glu
    4610                4615                4620

Ser His  Met Asp Ala Asp Leu  Ala Lys Pro Leu Ile  Lys Trp Asp
    4625                4630                4635

Leu Leu  Lys Tyr Asp Phe Thr  Glu Glu Arg Leu Cys  Leu Phe Asp
    4640                4645                4650

Arg Tyr  Phe Lys Tyr Trp Asp  Gln Thr Tyr His Pro  Asn Cys Ile
    4655                4660                4665

Asn Cys  Leu Asp Asp Arg Cys  Ile Leu His Cys Ala  Asn Phe Asn
    4670                4675                4680
```

-continued

```
Val Leu Phe Ser Thr Val Phe Pro Pro Thr Ser Phe Gly Pro Leu
    4685                4690                4695

Val Arg Lys Ile Phe Val Asp Gly Val Pro Phe Val Val Ser Thr
    4700                4705                4710

Gly Tyr His Phe Arg Glu Leu Gly Val Val His Asn Gln Asp Val
    4715                4720                4725

Asn Leu His Ser Ser Arg Leu Ser Phe Lys Glu Leu Leu Val Tyr
    4730                4735                4740

Ala Ala Asp Pro Ala Met His Ala Ala Ser Gly Asn Leu Leu Leu
    4745                4750                4755

Asp Lys Arg Thr Thr Cys Phe Ser Val Ala Ala Leu Thr Asn Asn
    4760                4765                4770

Val Ala Phe Gln Thr Val Lys Pro Gly Asn Phe Asn Lys Asp Phe
    4775                4780                4785

Tyr Asp Phe Ala Val Ser Lys Gly Phe Phe Lys Glu Gly Ser Ser
    4790                4795                4800

Val Glu Leu Lys His Phe Phe Phe Ala Gln Asp Gly Asn Ala Ala
    4805                4810                4815

Ile Ser Asp Tyr Asp Tyr Tyr Arg Tyr Asn Leu Pro Thr Met Cys
    4820                4825                4830

Asp Ile Arg Gln Leu Leu Phe Val Val Glu Val Val Asp Lys Tyr
    4835                4840                4845

Phe Asp Cys Tyr Asp Gly Gly Cys Ile Asn Ala Asn Gln Val Ile
    4850                4855                4860

Val Asn Asn Leu Asp Lys Ser Ala Gly Phe Pro Phe Asn Lys Trp
    4865                4870                4875

Gly Lys Ala Arg Leu Tyr Tyr Asp Ser Met Ser Tyr Glu Asp Gln
    4880                4885                4890

Asp Ala Leu Phe Ala Tyr Thr Lys Arg Asn Val Ile Pro Thr Ile
    4895                4900                4905

Thr Gln Met Asn Leu Lys Tyr Ala Ile Ser Ala Lys Asn Arg Ala
    4910                4915                4920

Arg Thr Val Ala Gly Val Ser Ile Cys Ser Thr Met Thr Asn Arg
    4925                4930                4935

Gln Phe His Gln Lys Leu Leu Lys Ser Ile Ala Ala Thr Arg Gly
    4940                4945                4950

Ala Thr Val Val Ile Gly Thr Ser Lys Phe Tyr Gly Gly Trp His
    4955                4960                4965

Asn Met Leu Lys Thr Val Tyr Ser Asp Val Glu Thr Pro His Leu
    4970                4975                4980

Met Gly Trp Asp Tyr Pro Lys Cys Asp Arg Ala Met Pro Asn Met
    4985                4990                4995

Leu Arg Ile Met Ala Ser Leu Val Leu Ala Arg Lys His Asn Thr
    5000                5005                5010

Cys Cys Asn Leu Ser His Arg Phe Tyr Arg Leu Ala Asn Glu Cys
    5015                5020                5025

Ala Gln Val Leu Ser Glu Met Val Met Cys Gly Gly Ser Leu Tyr
    5030                5035                5040

Val Lys Pro Gly Gly Thr Ser Ser Gly Asp Ala Thr Thr Ala Tyr
    5045                5050                5055

Ala Asn Ser Val Phe Asn Ile Cys Gln Ala Val Thr Ala Asn Val
    5060                5065                5070
```

-continued

```
Asn Ala  Leu Leu Ser Thr Asp  Gly Asn Lys Ile Ala  Asp Lys Tyr
    5075                 5080                 5085

Val Arg  Asn Leu Gln His Arg  Leu Tyr Glu Cys Leu  Tyr Arg Asn
    5090                 5095                 5100

Arg Asp  Val Asp His Glu Phe  Val Asp Glu Phe Tyr  Ala Tyr Leu
    5105                 5110                 5115

Arg Lys  His Phe Ser Met Met  Ile Leu Ser Asp Asp  Ala Val Val
    5120                 5125                 5130

Cys Tyr  Asn Ser Asn Tyr Ala  Ala Gln Gly Leu Val  Ala Ser Ile
    5135                 5140                 5145

Lys Asn  Phe Lys Ala Val Leu  Tyr Tyr Gln Asn Asn  Val Phe Met
    5150                 5155                 5160

Ser Glu  Ala Lys Cys Trp Thr  Glu Thr Asp Leu Thr  Lys Gly Pro
    5165                 5170                 5175

His Glu  Phe Cys Ser Gln His  Thr Met Leu Val Lys  Gln Gly Asp
    5180                 5185                 5190

Asp Tyr  Val Tyr Leu Pro Tyr  Pro Asp Pro Ser Arg  Ile Leu Gly
    5195                 5200                 5205

Ala Gly  Cys Phe Val Asp Asp  Ile Val Lys Thr Asp  Gly Thr Leu
    5210                 5215                 5220

Met Ile  Glu Arg Phe Val Ser  Leu Ala Ile Asp Ala  Tyr Pro Leu
    5225                 5230                 5235

Thr Lys  His Pro Asn Gln Glu  Tyr Ala Asp Val Phe  His Leu Tyr
    5240                 5245                 5250

Leu Gln  Tyr Ile Arg Lys Leu  His Asp Glu Leu Thr  Gly His Met
    5255                 5260                 5265

Leu Asp  Met Tyr Ser Val Met  Leu Thr Asn Asp Asn  Thr Ser Arg
    5270                 5275                 5280

Tyr Trp  Glu Pro Glu Phe Tyr  Glu Ala Met Tyr Thr  Pro His Thr
    5285                 5290                 5295

Val Leu  Gln Ala Val Gly Ala  Cys Val Leu Cys Asn  Ser Gln Thr
    5300                 5305                 5310

Ser Leu  Arg Cys Gly Ala Cys  Ile Arg Arg Pro Phe  Leu Cys Cys
    5315                 5320                 5325

Lys Cys  Cys Tyr Asp His Val  Ile Ser Thr Ser His  Lys Leu Val
    5330                 5335                 5340

Leu Ser  Val Asn Pro Tyr Val  Cys Asn Ala Pro Gly  Cys Asp Val
    5345                 5350                 5355

Thr Asp  Val Thr Gln Leu Tyr  Leu Gly Gly Met Ser  Tyr Tyr Cys
    5360                 5365                 5370

Lys Ser  His Lys Pro Pro Ile  Ser Phe Pro Leu Cys  Ala Asn Gly
    5375                 5380                 5385

Gln Val  Phe Gly Leu Tyr Lys  Asn Thr Cys Val Gly  Ser Asp Asn
    5390                 5395                 5400

Val Thr  Asp Phe Asn Ala Ile  Ala Thr Cys Asp Trp  Thr Asn Ala
    5405                 5410                 5415

Gly Asp  Tyr Ile Leu Ala Asn  Thr Cys Thr Glu Arg  Leu Lys Leu
    5420                 5425                 5430

Phe Ala  Ala Glu Thr Leu Lys  Ala Thr Glu Glu Thr  Phe Lys Leu
    5435                 5440                 5445

Ser Tyr  Gly Ile Ala Thr Val  Arg Glu Val Leu Ser  Asp Arg Glu
    5450                 5455                 5460

Leu His  Leu Ser Trp Glu Val  Gly Lys Pro Arg Pro  Pro Leu Asn
```

-continued 5465 5470 5475

Arg Asn Tyr Val Phe Thr Gly Tyr Arg Val Thr Lys Asn Ser Lys
5480 5485 5490

Val Gln Ile Gly Glu Tyr Thr Phe Glu Lys Gly Asp Tyr Gly Asp
5495 5500 5505

Ala Val Val Tyr Arg Gly Thr Thr Thr Tyr Lys Leu Asn Val Gly
5510 5515 5520

Asp Tyr Phe Val Leu Thr Ser His Thr Val Met Pro Leu Ser Ala
5525 5530 5535

Pro Thr Leu Val Pro Gln Glu His Tyr Val Arg Ile Thr Gly Leu
5540 5545 5550

Tyr Pro Thr Leu Asn Ile Ser Asp Glu Phe Ser Ser Asn Val Ala
5555 5560 5565

Asn Tyr Gln Lys Val Gly Met Gln Lys Tyr Ser Thr Leu Gln Gly
5570 5575 5580

Pro Pro Gly Thr Gly Lys Ser His Phe Ala Ile Gly Leu Ala Leu
5585 5590 5595

Tyr Tyr Pro Ser Ala Arg Ile Val Tyr Thr Ala Cys Ser His Ala
5600 5605 5610

Ala Val Asp Ala Leu Cys Glu Lys Ala Leu Lys Tyr Leu Pro Ile
5615 5620 5625

Asp Lys Cys Ser Arg Ile Ile Pro Ala Arg Ala Arg Val Glu Cys
5630 5635 5640

Phe Asp Lys Phe Lys Val Asn Ser Thr Leu Glu Gln Tyr Val Phe
5645 5650 5655

Cys Thr Val Asn Ala Leu Pro Glu Thr Thr Ala Asp Ile Val Val
5660 5665 5670

Phe Asp Glu Ile Ser Met Ala Thr Asn Tyr Asp Leu Ser Val Val
5675 5680 5685

Asn Ala Arg Leu Arg Ala Lys His Tyr Val Tyr Ile Gly Asp Pro
5690 5695 5700

Ala Gln Leu Pro Ala Pro Arg Thr Leu Leu Thr Lys Gly Thr Leu
5705 5710 5715

Glu Pro Glu Tyr Phe Asn Ser Val Cys Arg Leu Met Lys Thr Ile
5720 5725 5730

Gly Pro Asp Met Phe Leu Gly Thr Cys Arg Arg Cys Pro Ala Glu
5735 5740 5745

Ile Val Asp Thr Val Ser Ala Leu Val Tyr Asp Asn Lys Leu Lys
5750 5755 5760

Ala His Lys Glu Lys Ser Ala Gln Cys Phe Lys Met Phe Tyr Lys
5765 5770 5775

Gly Val Ile Thr His Asp Val Ser Ser Ala Ile Asn Arg Pro Gln
5780 5785 5790

Ile Gly Val Val Arg Glu Phe Leu Thr Arg Asn Pro Ala Trp Arg
5795 5800 5805

Lys Ala Val Phe Ile Ser Pro Tyr Asn Ser Gln Asn Ala Val Ala
5810 5815 5820

Ser Lys Ile Leu Gly Leu Pro Thr Gln Thr Val Asp Ser Ser Gln
5825 5830 5835

Gly Ser Glu Tyr Asp Tyr Val Ile Phe Thr Gln Thr Thr Glu Thr
5840 5845 5850

Ala His Ser Cys Asn Val Asn Arg Phe Asn Val Ala Ile Thr Arg
5855 5860 5865

-continued

```
Ala Lys Ile Gly Ile Leu Cys Ile Met Ser Asp Arg Asp Leu Tyr
    5870                5875                5880

Asp Lys Leu Gln Phe Thr Ser Leu Glu Ile Pro Arg Arg Asn Val
    5885                5890                5895

Ala Thr Leu Gln Ala Glu Asn Val Thr Gly Leu Phe Lys Asp Cys
    5900                5905                5910

Ser Lys Ile Ile Thr Gly Leu His Pro Thr Gln Ala Pro Thr His
    5915                5920                5925

Leu Ser Val Asp Ile Lys Phe Lys Thr Glu Gly Leu Cys Val Asp
    5930                5935                5940

Ile Pro Gly Ile Pro Lys Asp Met Thr Tyr Arg Arg Leu Ile Ser
    5945                5950                5955

Met Met Gly Phe Lys Met Asn Tyr Gln Val Asn Gly Tyr Pro Asn
    5960                5965                5970

Met Phe Ile Thr Arg Glu Glu Ala Ile Arg His Val Arg Ala Trp
    5975                5980                5985

Ile Gly Phe Asp Val Glu Gly Cys His Ala Thr Arg Asp Ala Val
    5990                5995                6000

Gly Thr Asn Leu Pro Leu Gln Leu Gly Phe Ser Thr Gly Val Asn
    6005                6010                6015

Leu Val Ala Val Pro Thr Gly Tyr Val Asp Thr Glu Asn Asn Thr
    6020                6025                6030

Glu Phe Thr Arg Val Asn Ala Lys Pro Pro Pro Gly Asp Gln Phe
    6035                6040                6045

Lys His Leu Ile Pro Leu Met Tyr Lys Gly Leu Pro Trp Asn Val
    6050                6055                6060

Val Arg Ile Lys Ile Val Gln Met Leu Ser Asp Thr Leu Lys Gly
    6065                6070                6075

Leu Ser Asp Arg Val Val Phe Val Leu Trp Ala His Gly Phe Glu
    6080                6085                6090

Leu Thr Ser Met Lys Tyr Phe Val Lys Ile Gly Pro Glu Arg Thr
    6095                6100                6105

Cys Cys Leu Cys Asp Lys Arg Ala Thr Cys Phe Ser Thr Ser Ser
    6110                6115                6120

Asp Thr Tyr Ala Cys Trp Asn His Ser Val Gly Phe Asp Tyr Val
    6125                6130                6135

Tyr Asn Pro Phe Met Ile Asp Val Gln Gln Trp Gly Phe Thr Gly
    6140                6145                6150

Asn Leu Gln Ser Asn His Asp Gln His Cys Gln Val His Gly Asn
    6155                6160                6165

Ala His Val Ala Ser Cys Asp Ala Ile Met Thr Arg Cys Leu Ala
    6170                6175                6180

Val His Glu Cys Phe Val Lys Arg Val Asp Trp Ser Val Glu Tyr
    6185                6190                6195

Pro Ile Ile Gly Asp Glu Leu Arg Val Asn Ser Ala Cys Arg Lys
    6200                6205                6210

Val Gln His Met Val Val Lys Ser Ala Leu Leu Ala Asp Lys Phe
    6215                6220                6225

Pro Val Leu His Asp Ile Gly Asn Pro Lys Ala Ile Lys Cys Val
    6230                6235                6240

Pro Gln Ala Glu Val Glu Trp Lys Phe Tyr Asp Ala Gln Pro Cys
    6245                6250                6255
```

-continued

```
Ser Asp  Lys Ala Tyr Lys Ile  Glu Glu Leu Phe Tyr  Ser Tyr Ala
    6260                 6265                 6270

Thr His  His Asp Lys Phe Thr  Asp Gly Val Cys Leu  Phe Trp Asn
    6275                 6280                 6285

Cys Asn  Val Asp Arg Tyr Pro  Ala Asn Ala Ile Val  Cys Arg Phe
    6290                 6295                 6300

Asp Thr  Arg Val Leu Ser Asn  Leu Asn Leu Pro Gly  Cys Asp Gly
    6305                 6310                 6315

Gly Ser  Leu Tyr Val Asn Lys  His Ala Phe His Thr  Pro Ala Phe
    6320                 6325                 6330

Asp Lys  Ser Ala Phe Thr Asn  Leu Lys Gln Leu Pro  Phe Phe Tyr
    6335                 6340                 6345

Tyr Ser  Asp Ser Pro Cys Glu  Ser His Gly Lys Gln  Val Val Ser
    6350                 6355                 6360

Asp Ile  Asp Tyr Val Pro Leu  Lys Ser Ala Thr Cys  Ile Thr Arg
    6365                 6370                 6375

Cys Asn  Leu Gly Gly Ala Val  Cys Arg His His Ala  Asn Glu Tyr
    6380                 6385                 6390

Arg Gln  Tyr Leu Asp Ala Tyr  Asn Met Met Ile Ser  Ala Gly Phe
    6395                 6400                 6405

Ser Leu  Trp Ile Tyr Lys Gln  Phe Asp Thr Tyr Asn  Leu Trp Asn
    6410                 6415                 6420

Thr Phe  Thr Arg Leu Gln Ser  Leu Glu Asn Val Ala  Tyr Asn Val
    6425                 6430                 6435

Val Asn  Lys Gly His Phe Asp  Gly His Ala Gly Glu  Ala Pro Val
    6440                 6445                 6450

Ser Ile  Ile Asn Asn Ala Val  Tyr Thr Lys Val Asp  Gly Ile Asp
    6455                 6460                 6465

Val Glu  Ile Phe Glu Asn Lys  Thr Thr Leu Pro Val  Asn Val Ala
    6470                 6475                 6480

Phe Glu  Leu Trp Ala Lys Arg  Asn Ile Lys Pro Val  Pro Glu Ile
    6485                 6490                 6495

Lys Ile  Leu Asn Asn Leu Gly  Val Asp Ile Ala Ala  Asn Thr Val
    6500                 6505                 6510

Ile Trp  Asp Tyr Lys Arg Glu  Ala Pro Ala His Val  Ser Thr Ile
    6515                 6520                 6525

Gly Val  Cys Thr Met Thr Asp  Ile Ala Lys Lys Pro  Thr Glu Ser
    6530                 6535                 6540

Ala Cys  Ser Ser Leu Thr Val  Leu Phe Asp Gly Arg  Val Glu Gly
    6545                 6550                 6555

Gln Val  Asp Leu Phe Arg Asn  Ala Arg Asn Gly Val  Leu Ile Thr
    6560                 6565                 6570

Glu Gly  Ser Val Lys Gly Leu  Thr Pro Ser Lys Gly  Pro Ala Gln
    6575                 6580                 6585

Ala Ser  Val Asn Gly Val Thr  Leu Ile Gly Glu Ser  Val Lys Thr
    6590                 6595                 6600

Gln Phe  Asn Tyr Phe Lys Lys  Val Asp Gly Ile Ile  Gln Gln Leu
    6605                 6610                 6615

Pro Glu  Thr Tyr Phe Thr Gln  Ser Arg Asp Leu Glu  Asp Phe Lys
    6620                 6625                 6630

Pro Arg  Ser Gln Met Glu Thr  Asp Phe Leu Glu Leu  Ala Met Asp
    6635                 6640                 6645

Glu Phe  Ile Gln Arg Tyr Lys  Leu Glu Gly Tyr Ala  Phe Glu His
```

-continued

```
    6650                6655                6660

Ile Val  Tyr Gly Asp Phe Ser  His Gly Gln Leu Gly  Gly Leu His
    6665                6670                6675

Leu Met  Ile Gly Leu Ala Lys  Arg Ser Gln Asp Ser  Pro Leu Lys
    6680                6685                6690

Leu Glu  Asp Phe Ile Pro Met  Asp Ser Thr Val Lys  Asn Tyr Phe
    6695                6700                6705

Ile Thr  Asp Ala Gln Thr Gly  Ser Ser Lys Cys Val  Cys Ser Val
    6710                6715                6720

Ile Asp  Leu Leu Leu Asp Asp  Phe Val Glu Ile Ile  Lys Ser Gln
    6725                6730                6735

Asp Leu  Ser Val Ile Ser Lys  Val Val Lys Val Thr  Ile Asp Tyr
    6740                6745                6750

Ala Glu  Ile Ser Phe Met Leu  Trp Cys Lys Asp Gly  His Val Glu
    6755                6760                6765

Thr Phe  Tyr Pro Lys Leu Gln  Ala Ser Gln Ala Trp  Gln Pro Gly
    6770                6775                6780

Val Ala  Met Pro Asn Leu Tyr  Lys Met Gln Arg Met  Leu Leu Glu
    6785                6790                6795

Lys Cys  Asp Leu Gln Asn Tyr  Gly Glu Asn Ala Val  Ile Pro Lys
    6800                6805                6810

Gly Ile  Met Met Asn Val Ala  Lys Tyr Thr Gln Leu  Cys Gln Tyr
    6815                6820                6825

Leu Asn  Thr Leu Thr Leu Ala  Val Pro Tyr Asn Met  Arg Val Ile
    6830                6835                6840

His Phe  Gly Ala Gly Ser Asp  Lys Gly Val Ala Pro  Gly Thr Ala
    6845                6850                6855

Val Leu  Arg Gln Trp Leu Pro  Thr Gly Thr Leu Leu  Val Asp Ser
    6860                6865                6870

Asp Leu  Asn Asp Phe Val Ser  Asp Ala Asp Ser Thr  Leu Ile Gly
    6875                6880                6885

Asp Cys  Ala Thr Val His Thr  Ala Asn Lys Trp Asp  Leu Ile Ile
    6890                6895                6900

Ser Asp  Met Tyr Asp Pro Arg  Thr Lys His Val Thr  Lys Glu Asn
    6905                6910                6915

Asp Ser  Lys Glu Gly Phe Phe  Thr Tyr Leu Cys Gly  Phe Ile Lys
    6920                6925                6930

Gln Lys  Leu Ala Leu Gly Gly  Ser Ile Ala Val Lys  Ile Thr Glu
    6935                6940                6945

His Ser  Trp Asn Ala Asp Leu  Tyr Lys Leu Met Gly  His Phe Ser
    6950                6955                6960

Trp Trp  Thr Ala Phe Val Thr  Asn Val Asn Ala Ser  Ser Ser Glu
    6965                6970                6975

Ala Phe  Leu Ile Gly Ala Asn  Tyr Leu Gly Lys Pro  Lys Glu Gln
    6980                6985                6990

Ile Asp  Gly Tyr Thr Met His  Ala Asn Tyr Ile Phe  Trp Arg Asn
    6995                7000                7005

Thr Asn  Pro Ile Gln Leu Ser  Ser Tyr Ser Leu Phe  Asp Met Ser
    7010                7015                7020

Lys Phe  Pro Leu Lys Leu Arg  Gly Thr Ala Val Met  Ser Leu Lys
    7025                7030                7035

Glu Asn  Gln Ile Asn Asp Met  Ile Tyr Ser Leu Leu  Glu Lys Gly
    7040                7045                7050
```

-continued

```
Arg Leu  Ile Ile Arg Glu Asn  Asn Arg Val Val Val  Ser Ser Asp
    7055                 7060                 7065

Ile Leu  Val Asn Asn
    7070


<210> SEQ ID NO 30
<211> LENGTH: 1178
<212> TYPE: PRT
<213> ORGANISM: SARS-CoV Shanghai QXC

<400> SEQUENCE: 30

Lys Ser Phe Lys Thr Ile Val Glu Ser Cys Gly Asn Tyr Lys Val Thr
1               5                   10                  15

Lys Gly Lys Pro Val Lys Gly Ala Trp Asn Ile Gly Gln Gln Arg Ser
            20                  25                  30

Val Leu Thr Pro Leu Cys Gly Phe Pro Ser Gln Ala Ala Gly Val Ile
        35                  40                  45

Arg Ser Ile Phe Ala Arg Thr Leu Asp Ala Ala Asn His Ser Ile Pro
    50                  55                  60

Asp Leu Gln Arg Ala Ala Val Thr Ile Leu Asp Gly Ile Ser Glu Gln
65                  70                  75                  80

Ser Leu Arg Leu Val Asp Ala Met Val Tyr Thr Ser Asp Leu Leu Thr
                85                  90                  95

Asn Ser Val Ile Ile Met Ala Tyr Val Thr Gly Gly Leu Val Gln Gln
            100                 105                 110

Thr Ser Gln Trp Leu Ser Asn Leu Leu Gly Thr Thr Val Glu Lys Leu
        115                 120                 125

Arg Pro Ile Phe Glu Trp Ile Glu Ala Lys Leu Ser Ala Gly Val Glu
    130                 135                 140

Phe Leu Lys Asp Ala Trp Glu Ile Leu Lys Phe Leu Ile Thr Gly Val
145                 150                 155                 160

Phe Asp Ile Val Lys Gly Gln Ile Gln Val Ala Ser Asp Asn Ile Lys
                165                 170                 175

Asp Cys Val Lys Cys Phe Ile Asp Val Val Asn Lys Ala Leu Glu Met
            180                 185                 190

Cys Ile Asp Gln Val Thr Ile Ala Gly Ala Lys Leu Arg Ser Leu Asn
        195                 200                 205

Leu Gly Glu Val Phe Ile Ala Gln Ser Lys Gly Leu Tyr Arg Gln Cys
    210                 215                 220

Ile Arg Gly Lys Glu Gln Leu Gln Leu Leu Met Pro Leu Lys Ala Pro
225                 230                 235                 240

Lys Glu Val Thr Phe Leu Glu Gly Asp Ser His Asp Thr Val Leu Thr
                245                 250                 255

Ser Glu Glu Val Val Leu Lys Asn Gly Glu Leu Glu Ala Leu Glu Thr
            260                 265                 270

Pro Val Asp Ser Phe Thr Asn Gly Ala Ile Val Gly Thr Pro Val Cys
        275                 280                 285

Val Asn Gly Leu Met Leu Leu Glu Ile Lys Asp Lys Glu Gln Tyr Cys
    290                 295                 300

Ala Leu Ser Pro Gly Leu Leu Ala Thr Asn Asn Val Phe Arg Leu Lys
305                 310                 315                 320

Gly Gly Ala Pro Ile Lys Gly Val Thr Phe Gly Glu Asp Thr Val Trp
                325                 330                 335

Glu Val Gln Gly Tyr Lys Asn Val Arg Ile Thr Phe Glu Leu Asp Glu
```

-continued

```
            340                 345                 350

Arg Val Asp Lys Val Leu Asn Glu Lys Cys Ser Val Tyr Thr Val Glu
        355                 360                 365

Ser Gly Thr Glu Val Thr Glu Phe Ala Cys Val Val Ala Glu Ala Val
    370                 375                 380

Val Lys Thr Leu Gln Pro Val Ser Asp Leu Leu Thr Asn Met Gly Ile
385                 390                 395                 400

Asp Leu Asp Glu Trp Ser Val Ala Thr Phe Tyr Leu Phe Asp Asp Ala
                405                 410                 415

Gly Glu Glu Asn Phe Ser Ser Arg Met Tyr Cys Ser Phe Tyr Pro Pro
            420                 425                 430

Asp Glu Glu Glu Glu Asp Asp Ala Glu Cys Glu Glu Glu Glu Ile Asp
        435                 440                 445

Glu Thr Cys Glu His Glu Tyr Gly Thr Glu Asp Asp Tyr Gln Gly Leu
    450                 455                 460

Pro Leu Glu Phe Gly Ala Ser Ala Glu Thr Val Arg Val Glu Glu Glu
465                 470                 475                 480

Glu Glu Glu Asp Trp Leu Asp Asp Thr Thr Glu Gln Ser Glu Ile Glu
                485                 490                 495

Pro Glu Pro Glu Pro Thr Pro Glu Glu Pro Val Asn Gln Phe Thr Gly
            500                 505                 510

Tyr Leu Lys Leu Thr Asp Asn Val Ala Ile Lys Cys Val Asp Thr Val
        515                 520                 525

Lys Glu Ala Gln Ser Ala Asn Pro Met Val Ile Val Asn Ala Ala Asn
    530                 535                 540

Ile His Leu Lys His Gly Gly Gly Val Ala Gly Ala Leu Asn Lys Ala
545                 550                 555                 560

Thr Asn Gly Ala Met Gln Lys Glu Ser Asp Asp Tyr Ile Lys Leu Asn
                565                 570                 575

Gly Pro Leu Thr Val Gly Gly Ser Cys Leu Leu Ser Gly His Asn Leu
            580                 585                 590

Ala Lys Lys Cys Leu His Val Val Gly Pro Asn Leu Asn Ala Gly Glu
        595                 600                 605

Asp Ile Gln Leu Leu Lys Ala Ala Tyr Glu Asn Phe Asn Ser Gln Asp
    610                 615                 620

Ile Leu Leu Ala Pro Leu Leu Ser Ala Gly Ile Phe Gly Ala Lys Pro
625                 630                 635                 640

Leu Gln Ser Leu Gln Val Cys Val Gln Thr Val Arg Thr Gln Val Tyr
                645                 650                 655

Ile Ala Val Asn Asp Lys Ala Leu Tyr Glu Gln Val Val Met Asp Tyr
            660                 665                 670

Leu Asp Asn Leu Lys Pro Arg Val Glu Ala Pro Lys Gln Glu Glu Pro
        675                 680                 685

Pro Asn Thr Glu Asp Ser Lys Thr Glu Glu Lys Ser Val Val Gln Lys
    690                 695                 700

Pro Val Asp Val Lys Pro Lys Ile Lys Ala Cys Ile Asp Glu Val Thr
705                 710                 715                 720

Thr Thr Leu Glu Glu Thr Lys Phe Leu Thr Asn Lys Leu Leu Leu Phe
                725                 730                 735

Ala Asp Ile Asn Gly Lys Leu Tyr His Asp Ser Gln Asn Met Leu Arg
            740                 745                 750

Gly Glu Asp Met Ser Phe Leu Glu Glu Asp Ala Pro Tyr Met Val Gly
        755                 760                 765
```

-continued

```
Asp Val Ile Thr Ser Gly Asp Ile Thr Cys Val Val Ile Pro Ser Lys
    770                 775                 780

Lys Ala Gly Gly Thr Thr Glu Met Leu Ser Arg Ala Leu Lys Lys Val
785                 790                 795                 800

Pro Val Asp Glu Tyr Ile Thr Thr Tyr Pro Gly Gln Gly Cys Ala Gly
                805                 810                 815

Tyr Thr Leu Glu Glu Ala Lys Thr Ala Leu Lys Lys Cys Lys Ser Ala
            820                 825                 830

Phe Tyr Val Leu Pro Ser Glu Ala Pro Asn Ala Lys Glu Glu Ile Leu
        835                 840                 845

Gly Thr Val Ser Trp Asn Leu Arg Glu Met Leu Ala His Ala Glu Glu
    850                 855                 860

Ala Arg Lys Leu Met Pro Ile Cys Met Asp Val Arg Ala Ile Met Ala
865                 870                 875                 880

Thr Ile Gln Arg Lys Tyr Lys Gly Val Lys Ile Gln Glu Gly Ile Val
                885                 890                 895

Asp Tyr Gly Val Arg Phe Phe Phe Tyr Thr Ser Lys Glu Pro Val Ala
            900                 905                 910

Ser Ile Ile Thr Lys Leu Asn Ser Leu Asn Glu Pro Leu Val Thr Met
        915                 920                 925

Pro Ile Gly Tyr Val Thr His Gly Phe Asn Leu Glu Glu Ala Ala Arg
    930                 935                 940

Cys Met Arg Ser Leu Lys Ala Pro Ala Val Val Ser Val Ser Ser Pro
945                 950                 955                 960

Asp Ala Val Thr Thr Tyr Asn Gly Tyr Leu Thr Ser Ser Ser Lys Thr
                965                 970                 975

Ser Glu Glu His Phe Val Glu Thr Val Ser Leu Ala Gly Ser Tyr Arg
            980                 985                 990

Asp Trp Ser Tyr Ser Gly Gln Arg  Thr Glu Leu Gly Val  Glu Phe Leu
        995                 1000                1005

Lys Arg  Gly Asp Lys Ile Val  Tyr His Thr Leu Glu  Ser Pro Val
    1010                1015                1020

Glu Phe  His Leu Asp Gly Glu  Val Leu Ser Leu Asp  Lys Leu Lys
    1025                1030                1035

Ser Leu  Leu Ser Leu Arg Glu  Val Lys Thr Ile Lys  Val Phe Thr
    1040                1045                1050

Thr Val  Asp Asn Thr Asn Leu  His Thr Gln Leu Val  Asp Met Ser
    1055                1060                1065

Met Thr  Tyr Gly Gln Gln Phe  Gly Pro Thr Tyr Leu  Asp Gly Ala
    1070                1075                1080

Asp Val  Thr Lys Ile Lys Pro  His Val Asn His Glu  Gly Lys Thr
    1085                1090                1095

Phe Phe  Val Leu Pro Ser Asp  Asp Thr Leu Arg Ser  Glu Ala Phe
    1100                1105                1110

Glu Tyr  Tyr His Thr Leu Asp  Glu Ser Phe Leu Gly  Arg Tyr Met
    1115                1120                1125

Ser Ala  Leu Asn His Thr Lys  Lys Trp Lys Phe Pro  Gln Val Gly
    1130                1135                1140

Gly Leu  Thr Ser Ile Lys Trp  Ala Asp Asn Asn Cys  Tyr Leu Ser
    1145                1150                1155

Ser Val  Leu Leu Ala Leu Gln  Gln Leu Glu Val Lys  Phe Asn Ala
    1160                1165                1170
```

-continued

```
Pro Ala  Leu Gln Glu
    1175


<210> SEQ ID NO 31
<211> LENGTH: 1178
<212> TYPE: PRT
<213> ORGANISM: SARS-CoV Shanghai QXC

<400> SEQUENCE: 31

Lys Ser Phe Lys Thr Ile Val Glu Ser Cys Gly Asn Tyr Lys Val Thr
1               5                   10                  15

Lys Gly Lys Pro Val Lys Gly Ala Trp Asn Ile Gly Gln Gln Arg Ser
            20                  25                  30

Val Leu Thr Pro Leu Cys Gly Phe Pro Ser Gln Ala Ala Gly Val Ile
        35                  40                  45

Arg Ser Ile Phe Ala Arg Thr Leu Asp Ala Ala Asn His Ser Ile Pro
    50                  55                  60

Asp Leu Gln Arg Ala Ala Val Thr Ile Leu Asp Gly Ile Ser Glu Gln
65                  70                  75                  80

Ser Leu Arg Leu Val Asp Ala Met Val Tyr Thr Ser Asp Leu Leu Thr
                85                  90                  95

Asn Ser Val Ile Ile Met Ala Tyr Val Thr Gly Gly Leu Val Gln Gln
            100                 105                 110

Thr Ser Gln Trp Leu Ser Asn Leu Leu Gly Thr Thr Val Glu Lys Leu
        115                 120                 125

Arg Pro Ile Phe Glu Trp Ile Glu Ala Lys Leu Ser Ala Gly Val Glu
    130                 135                 140

Phe Leu Lys Asp Ala Trp Glu Ile Leu Lys Phe Leu Ile Thr Gly Val
145                 150                 155                 160

Phe Asp Ile Val Lys Gly Gln Ile Gln Val Ala Ser Asp Asn Ile Lys
                165                 170                 175

Asp Cys Val Lys Cys Phe Ile Asp Val Val Asn Lys Ala Leu Glu Met
            180                 185                 190

Cys Ile Asp Gln Val Thr Ile Ala Gly Ala Lys Leu Arg Ser Leu Asn
        195                 200                 205

Leu Gly Glu Val Phe Ile Ala Gln Ser Lys Gly Leu Tyr Arg Gln Cys
    210                 215                 220

Ile Arg Gly Lys Glu Gln Leu Gln Leu Leu Met Pro Leu Lys Ala Pro
225                 230                 235                 240

Lys Glu Val Thr Phe Leu Glu Gly Asp Ser His Asp Thr Val Leu Thr
                245                 250                 255

Ser Glu Glu Val Val Leu Lys Asn Gly Glu Leu Glu Ala Leu Glu Thr
            260                 265                 270

Pro Val Asp Ser Phe Thr Asn Gly Ala Ile Val Gly Thr Pro Val Cys
        275                 280                 285

Val Asn Gly Leu Met Leu Leu Glu Ile Lys Asp Lys Glu Gln Tyr Cys
    290                 295                 300

Ala Leu Ser Pro Gly Leu Leu Ala Thr Asn Asn Val Phe Arg Leu Lys
305                 310                 315                 320

Gly Gly Ala Pro Ile Lys Gly Val Thr Phe Gly Glu Asp Thr Val Trp
                325                 330                 335

Glu Val Gln Gly Tyr Lys Asn Val Arg Ile Thr Phe Glu Leu Asp Glu
            340                 345                 350

Arg Val Asp Lys Val Leu Asn Glu Lys Cys Ser Val Tyr Thr Val Glu
        355                 360                 365
```

-continued

```
Ser Gly Thr Glu Val Thr Glu Phe Ala Cys Val Val Ala Glu Ala Val
    370                 375                 380

Val Lys Thr Leu Gln Pro Val Ser Asp Leu Leu Thr Asn Met Gly Ile
385                 390                 395                 400

Asp Leu Asp Glu Trp Ser Val Ala Thr Phe Tyr Leu Phe Asp Asp Ala
                405                 410                 415

Gly Glu Glu Asn Phe Ser Ser Arg Met Tyr Cys Ser Phe Tyr Pro Pro
            420                 425                 430

Asp Glu Glu Glu Glu Asp Asp Ala Glu Cys Glu Glu Glu Glu Ile Asp
        435                 440                 445

Glu Thr Cys Glu His Glu Tyr Gly Thr Glu Asp Asp Tyr Gln Gly Leu
    450                 455                 460

Pro Leu Glu Phe Gly Ala Ser Ala Glu Thr Val Arg Val Glu Glu Glu
465                 470                 475                 480

Glu Glu Glu Asp Trp Leu Asp Asp Thr Thr Glu Gln Ser Glu Ile Glu
                485                 490                 495

Pro Glu Pro Glu Pro Thr Pro Glu Glu Pro Val Asn Gln Phe Thr Gly
            500                 505                 510

Tyr Leu Lys Leu Thr Asp Asn Val Ala Ile Lys Cys Val Asp Thr Val
        515                 520                 525

Lys Glu Ala Gln Ser Ala Asn Pro Met Val Ile Val Asn Ala Ala Asn
    530                 535                 540

Ile His Leu Lys His Gly Gly Gly Val Ala Gly Ala Leu Asn Lys Ala
545                 550                 555                 560

Thr Asn Gly Ala Met Gln Lys Glu Ser Asp Asp Tyr Ile Lys Leu Asn
                565                 570                 575

Gly Pro Leu Thr Val Gly Gly Ser Cys Leu Leu Ser Gly His Asn Leu
            580                 585                 590

Ala Lys Lys Cys Leu His Val Val Gly Pro Asn Leu Asn Ala Gly Glu
        595                 600                 605

Asp Ile Gln Leu Leu Lys Ala Ala Tyr Glu Asn Phe Asn Ser Gln Asp
    610                 615                 620

Ile Leu Leu Ala Pro Leu Leu Ser Ala Gly Ile Phe Gly Ala Lys Pro
625                 630                 635                 640

Leu Gln Ser Leu Gln Val Cys Val Gln Thr Val Arg Thr Gln Val Tyr
                645                 650                 655

Ile Ala Val Asn Asp Lys Ala Leu Tyr Glu Gln Val Val Met Asp Tyr
            660                 665                 670

Leu Asp Asn Leu Lys Pro Arg Val Glu Ala Pro Lys Gln Glu Glu Pro
        675                 680                 685

Pro Asn Thr Glu Asp Ser Lys Thr Glu Glu Lys Ser Val Val Gln Lys
    690                 695                 700

Pro Val Asp Val Lys Pro Lys Ile Lys Ala Cys Ile Asp Glu Val Thr
705                 710                 715                 720

Thr Thr Leu Glu Glu Thr Lys Phe Leu Thr Asn Lys Leu Leu Leu Phe
                725                 730                 735

Ala Asp Ile Asn Gly Lys Leu Tyr His Asp Ser Gln Asn Met Leu Arg
            740                 745                 750

Gly Glu Asp Met Ser Phe Leu Glu Glu Asp Ala Pro Tyr Met Val Gly
        755                 760                 765

Asp Val Ile Thr Ser Gly Asp Ile Thr Cys Val Val Ile Pro Ser Lys
    770                 775                 780
```

-continued

```
Lys Ala Gly Gly Thr Thr Glu Met Leu Ser Arg Ala Leu Lys Lys Val
785                 790                 795                 800

Pro Val Asp Glu Tyr Ile Thr Thr Tyr Pro Gly Gln Gly Cys Ala Gly
                805                 810                 815

Tyr Thr Leu Glu Glu Ala Lys Thr Ala Leu Lys Lys Cys Lys Ser Ala
            820                 825                 830

Phe Tyr Val Leu Pro Ser Glu Ala Pro Asn Ala Lys Glu Glu Ile Leu
        835                 840                 845

Gly Thr Val Ser Trp Asn Leu Arg Glu Met Leu Ala His Ala Glu Glu
    850                 855                 860

Ala Arg Lys Leu Met Pro Ile Cys Met Asp Val Arg Ala Ile Met Ala
865                 870                 875                 880

Thr Ile Gln Arg Lys Tyr Lys Gly Val Lys Ile Gln Glu Gly Ile Val
                885                 890                 895

Asp Tyr Gly Val Arg Phe Phe Phe Tyr Thr Ser Lys Glu Pro Val Ala
            900                 905                 910

Ser Ile Ile Thr Lys Leu Asn Ser Leu Asn Glu Pro Leu Val Thr Met
        915                 920                 925

Pro Ile Gly Tyr Val Thr His Gly Phe Asn Leu Glu Glu Ala Ala Arg
    930                 935                 940

Cys Met Arg Ser Leu Lys Ala Pro Ala Val Val Ser Val Ser Ser Pro
945                 950                 955                 960

Asp Ala Val Thr Thr Tyr Asn Gly Tyr Leu Thr Ser Ser Ser Lys Thr
                965                 970                 975

Ser Glu Glu His Phe Val Glu Thr Val Ser Leu Ala Gly Ser Tyr Arg
            980                 985                 990

Asp Trp Ser Tyr Ser Gly Gln Arg  Thr Glu Leu Gly Val  Glu Phe Leu
        995                 1000                1005

Lys Arg  Gly Asp Lys Ile Val  Tyr His Thr Leu Glu  Ser Pro Val
    1010                1015                1020

Glu Phe  His Leu Asp Gly Glu  Val Leu Ser Leu Asp  Lys Leu Lys
    1025                1030                1035

Ser Leu  Leu Ser Leu Arg Glu  Val Lys Thr Ile Lys  Val Phe Thr
    1040                1045                1050

Thr Val  Asp Asn Thr Asn Leu  His Thr Gln Leu Val  Asp Met Ser
    1055                1060                1065

Met Thr  Tyr Gly Gln Gln Phe  Gly Pro Thr Tyr Leu  Asp Gly Ala
    1070                1075                1080

Asp Val  Thr Lys Ile Lys Pro  His Val Asn His Glu  Gly Lys Thr
    1085                1090                1095

Phe Phe  Val Leu Pro Ser Asp  Asp Thr Leu Arg Ser  Glu Ala Phe
    1100                1105                1110

Glu Tyr  Tyr His Thr Leu Asp  Glu Ser Phe Leu Gly  Arg Tyr Met
    1115                1120                1125

Ser Ala  Leu Asn His Thr Lys  Lys Trp Lys Phe Pro  Gln Val Gly
    1130                1135                1140

Gly Leu  Thr Ser Ile Lys Trp  Ala Asp Asn Asn Cys  Tyr Leu Ser
    1145                1150                1155

Ser Val  Leu Leu Ala Leu Gln  Gln Leu Glu Val Lys  Phe Asn Ala
    1160                1165                1170

Pro Ala  Leu Gln Glu
    1175
```

-continued

<210> SEQ ID NO 32
<211> LENGTH: 507
<212> TYPE: PRT
<213> ORGANISM: SARS-CoV Shanghai LY

<400> SEQUENCE: 32

```
Met Glu Ser Leu Val Leu Gly Val Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Ala Leu Ser Glu Ala Arg Glu His Leu Lys Asn
        35                  40                  45

Gly Thr Cys Gly Leu Val Glu Leu Glu Lys Gly Val Leu Pro Gln Leu
    50                  55                  60

Glu Gln Pro Tyr Val Phe Ile Lys Arg Ser Asp Ala Leu Ser Thr Asn
65                  70                  75                  80

His Gly His Lys Val Val Glu Leu Val Ala Glu Met Asp Gly Ile Gln
                85                  90                  95

Tyr Gly Arg Ser Gly Ile Thr Leu Gly Val Leu Val Pro His Val Gly
            100                 105                 110

Glu Thr Pro Ile Ala Tyr Arg Asn Val Leu Leu Arg Lys Asn Gly Asn
        115                 120                 125

Lys Gly Ala Gly Gly His Ser Tyr Gly Ile Asp Leu Lys Ser Tyr Asp
    130                 135                 140

Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Val Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Cys Glu His Gln Thr Pro Phe Glu
                245                 250                 255

Ile Lys Ser Ala Lys Lys Phe Asp Thr Phe Lys Gly Glu Cys Pro Lys
            260                 265                 270

Phe Val Phe Pro Leu Asn Ser Lys Val Lys Val Ile Gln Pro Arg Val
        275                 280                 285

Glu Lys Lys Lys Thr Glu Gly Phe Met Gly Arg Ile Arg Ser Val Tyr
    290                 295                 300

Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
                325                 330                 335

Leu Lys Ala Thr Cys Glu His Cys Gly Thr Glu Asn Leu Val Ile Glu
            340                 345                 350

Gly Pro Thr Thr Cys Gly Tyr Leu Pro Thr Asn Ala Val Val Lys Met
        355                 360                 365

Pro Cys Pro Ala Cys Gln Asp Pro Glu Ile Gly Pro Glu His Ser Val
    370                 375                 380
```

-continued

```
Ala Asp Tyr His Asn His Ser Asn Ile Glu Thr Arg Leu Arg Lys Gly
385                 390                 395                 400

Gly Arg Thr Arg Cys Phe Gly Gly Cys Val Phe Ala Tyr Val Gly Cys
                405                 410                 415

Tyr Asn Lys Arg Ala Tyr Trp Val Pro Arg Ala Ser Ala Asp Ile Gly
            420                 425                 430

Ser Gly His Thr Gly Ile Thr Gly Asp Asn Val Glu Thr Leu Asn Glu
        435                 440                 445

Asp Leu Leu Glu Ile Leu Ser Arg Glu Arg Val Asn Ile Asn Ile Val
    450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
                485                 490                 495

Lys Ser Phe Lys Thr Ile Val Glu Ser Cys Gly
            500                 505


<210> SEQ ID NO 33
<211> LENGTH: 507
<212> TYPE: PRT
<213> ORGANISM: SARS-CoV Shanghai LY

<400> SEQUENCE: 33

Met Glu Ser Leu Val Leu Gly Val Asn Glu Lys Thr His Val Gln Leu
1               5                   10                  15

Ser Leu Pro Val Leu Gln Val Arg Asp Val Leu Val Arg Gly Phe Gly
            20                  25                  30

Asp Ser Val Glu Glu Ala Leu Ser Glu Ala Arg Glu His Leu Lys Asn
        35                  40                  45

Gly Thr Cys Gly Leu Val Glu Leu Glu Lys Gly Val Leu Pro Gln Leu
    50                  55                  60

Glu Gln Pro Tyr Val Phe Ile Lys Arg Ser Asp Ala Leu Ser Thr Asn
65                  70                  75                  80

His Gly His Lys Val Val Glu Leu Val Ala Glu Met Asp Gly Ile Gln
                85                  90                  95

Tyr Gly Arg Ser Gly Ile Thr Leu Gly Val Leu Val Pro His Val Gly
            100                 105                 110

Glu Thr Pro Ile Ala Tyr Arg Asn Val Leu Leu Arg Lys Asn Gly Asn
        115                 120                 125

Lys Gly Ala Gly Gly His Ser Tyr Gly Ile Asp Leu Lys Ser Tyr Asp
    130                 135                 140

Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Val Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Cys Glu His Gln Thr Pro Phe Glu
                245                 250                 255
```

-continued

```
Ile Lys Ser Ala Lys Lys Phe Asp Thr Phe Lys Gly Glu Cys Pro Lys
            260                 265                 270

Phe Val Phe Pro Leu Asn Ser Lys Val Lys Val Ile Gln Pro Arg Val
        275                 280                 285

Glu Lys Lys Lys Thr Glu Gly Phe Met Gly Arg Ile Arg Ser Val Tyr
    290                 295                 300

Pro Val Ala Ser Pro Gln Glu Cys Asn Asn Met His Leu Ser Thr Leu
305                 310                 315                 320

Met Lys Cys Asn His Cys Asp Glu Val Ser Trp Gln Thr Cys Asp Phe
                325                 330                 335

Leu Lys Ala Thr Cys Glu His Cys Gly Thr Glu Asn Leu Val Ile Glu
            340                 345                 350

Gly Pro Thr Thr Cys Gly Tyr Leu Pro Thr Asn Ala Val Val Lys Met
        355                 360                 365

Pro Cys Pro Ala Cys Gln Asp Pro Glu Ile Gly Pro Glu His Ser Val
    370                 375                 380

Ala Asp Tyr His Asn His Ser Asn Ile Glu Thr Arg Leu Arg Lys Gly
385                 390                 395                 400

Gly Arg Thr Arg Cys Phe Gly Gly Cys Val Phe Ala Tyr Val Gly Cys
                405                 410                 415

Tyr Asn Lys Arg Ala Tyr Trp Val Pro Arg Ala Ser Ala Asp Ile Gly
            420                 425                 430

Ser Gly His Thr Gly Ile Thr Gly Asp Asn Val Glu Thr Leu Asn Glu
        435                 440                 445

Asp Leu Leu Glu Ile Leu Ser Arg Glu Arg Val Asn Ile Asn Ile Val
    450                 455                 460

Gly Asp Phe His Leu Asn Glu Glu Val Ala Ile Ile Leu Ala Ser Phe
465                 470                 475                 480

Ser Ala Ser Thr Ser Ala Phe Ile Asp Thr Ile Lys Ser Leu Asp Tyr
                485                 490                 495

Lys Ser Phe Lys Thr Ile Val Glu Ser Cys Gly
            500                 505
```

<210> SEQ ID NO 34
<211> LENGTH: 422
<212> TYPE: PRT
<213> ORGANISM: SARS-CoV CUHK-W1

<400> SEQUENCE: 34

```
Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
```

-continued

```
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420


<210> SEQ ID NO 35
<211> LENGTH: 1255
<212> TYPE: PRT
<213> ORGANISM: SARS-CoV CUHK-W1

<400> SEQUENCE: 35

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60
```

-continued

```
Asn Val Thr Gly Phe His Thr Ile Asn His Thr Phe Asp Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Thr Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
```

-continued

```
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910
```

-continued

```
Ile Ser Gln Ile Gln Glu Ser Leu Thr Thr Thr Ser Thr Ala Leu Gly
      915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
      995                 1000                1005

Thr Lys  Met Ser Glu Cys Val  Leu Gly Gln Ser Lys  Arg Val Asp
    1010                 1015                1020

Phe Cys  Gly Lys Gly Tyr His  Leu Met Ser Phe Pro  Gln Ala Ala
    1025                 1030                1035

Pro His  Gly Val Val Phe Leu  His Val Thr Tyr Val  Pro Ser Gln
    1040                 1045                1050

Glu Arg  Asn Phe Thr Thr Ala  Pro Ala Ile Cys His  Glu Gly Lys
    1055                 1060                1065

Ala Tyr  Phe Pro Arg Glu Gly  Val Phe Val Phe Asn  Gly Thr Ser
    1070                 1075                1080

Trp Phe  Ile Thr Gln Arg Asn  Phe Phe Ser Pro Gln  Ile Ile Thr
    1085                 1090                1095

Thr Asp  Asn Thr Phe Val Ser  Gly Asn Cys Asp Val  Val Ile Gly
    1100                 1105                1110

Ile Ile  Asn Asn Thr Val Tyr  Asp Pro Leu Gln Pro  Glu Leu Asp
    1115                 1120                1125

Ser Phe  Lys Glu Glu Leu Asp  Lys Tyr Phe Lys Asn  His Thr Ser
    1130                 1135                1140

Pro Asp  Val Asp Leu Gly Asp  Ile Ser Gly Ile Asn  Ala Ser Val
    1145                 1150                1155

Val Asn  Ile Gln Lys Glu Ile  Asp Arg Leu Asn Glu  Val Ala Lys
    1160                 1165                1170

Asn Leu  Asn Glu Ser Leu Ile  Asp Leu Gln Glu Leu  Gly Lys Tyr
    1175                 1180                1185

Glu Gln  Tyr Ile Lys Trp Pro  Trp Tyr Val Trp Leu  Gly Phe Ile
    1190                 1195                1200

Ala Gly  Leu Ile Ala Ile Val  Met Val Thr Ile Leu  Leu Cys Cys
    1205                 1210                1215

Met Thr  Ser Cys Cys Ser Cys  Leu Lys Gly Ala Cys  Ser Cys Gly
    1220                 1225                1230

Ser Cys  Cys Lys Phe Asp Glu  Asp Asp Ser Glu Pro  Val Leu Lys
    1235                 1240                1245

Gly Val  Lys Leu His Tyr Thr
    1250                 1255
```

<210> SEQ ID NO 36
<211> LENGTH: 72
<212> TYPE: DNA
<213> ORGANISM: SARS-CoV Urbani

<400> SEQUENCE: 36

```
atattaggtt tttacctacc caggaaaagc caaccaacct cgatctcttg tagatctgtt     60
```

-continued

```
ctctaaacga ac                                                       72


<210> SEQ ID NO 37
<211> LENGTH: 71
<212> TYPE: DNA
<213> ORGANISM: SARS coronavirus ZMY 1

<400> SEQUENCE: 37

tattaggttt ttacctaccc aggaaaagcc aaccaacctc gatctcttgt agatctgttc   60

tctaaacgaa c                                                        71


<210> SEQ ID NO 38
<211> LENGTH: 68
<212> TYPE: DNA
<213> ORGANISM: SARS coronavirus BJ03

<400> SEQUENCE: 38

taggttttta cctacccagg aaaagccaac caacctcgat ctcttgtaga tctgttctct   60

aaacgaac                                                            68


<210> SEQ ID NO 39
<211> LENGTH: 62
<212> TYPE: DNA
<213> ORGANISM: SARS-CoV Urbani

<400> SEQUENCE: 39

atattaggtt tttacctacc caggaaaagc caaccaacct cgatctcttg tagatctgtt   60

ct                                                                  62


<210> SEQ ID NO 40
<211> LENGTH: 57
<212> TYPE: DNA
<213> ORGANISM: SARS-CoV Urbani

<400> SEQUENCE: 40

atattaggtt tttacctacc caggaaaagc caaccaacct cgatctcttg tagatct      57


<210> SEQ ID NO 41
<211> LENGTH: 53
<212> TYPE: DNA
<213> ORGANISM: SARS-CoV Urbani

<400> SEQUENCE: 41

atattaggtt tttacctacc caggaaaagc caaccaacct cgatctcttg tag          53


<210> SEQ ID NO 42
<211> LENGTH: 45
<212> TYPE: DNA
<213> ORGANISM: SARS-CoV Urbani

<400> SEQUENCE: 42

atattaggtt tttacctacc caggaaaagc caaccaacct cgatc                   45


<210> SEQ ID NO 43
<211> LENGTH: 39
<212> TYPE: DNA
<213> ORGANISM: SARS-CoV Urbani

<400> SEQUENCE: 43

atattaggtt tttacctacc caggaaaagc caaccaacc                          39
```

-continued

<210> SEQ ID NO 44
<211> LENGTH: 34
<212> TYPE: DNA
<213> ORGANISM: SARS-CoV Urbani

<400> SEQUENCE: 44
atattaggtt tttacctacc caggaaaagc caac 34

<210> SEQ ID NO 45
<211> LENGTH: 30
<212> TYPE: DNA
<213> ORGANISM: SARS-CoV Urbani

<400> SEQUENCE: 45
atattaggtt tttacctacc caggaaaagc 30

<210> SEQ ID NO 46
<211> LENGTH: 24
<212> TYPE: DNA
<213> ORGANISM: SARS-CoV Urbani

<400> SEQUENCE: 46
atattaggtt tttacctacc cagg 24

<210> SEQ ID NO 47
<211> LENGTH: 19
<212> TYPE: DNA
<213> ORGANISM: SARS-CoV Urbani

<400> SEQUENCE: 47
atattaggtt tttacctac 19

<210> SEQ ID NO 48
<211> LENGTH: 8
<212> TYPE: DNA
<213> ORGANISM: SARS-CoV Urbani

<400> SEQUENCE: 48 atattagg 8

<210> SEQ ID NO 49
<211> LENGTH: 61
<212> TYPE: DNA
<213> ORGANISM: SARS-CoV Urbani

<400> SEQUENCE: 49
ttacctaccc aggaaaagcc aaccaacctc gatctcttgt agatctgttc tctaaacgaa 60
c 61

<210> SEQ ID NO 50
<211> LENGTH: 48
<212> TYPE: DNA
<213> ORGANISM: SARS-CoV Urbani

<400> SEQUENCE: 50
aaaagccaac caacctcgat ctcttgtaga tctgttctct aaacgaac 48

<210> SEQ ID NO 51
<211> LENGTH: 44
<212> TYPE: DNA
<213> ORGANISM: SARS-CoV Urbani

<400> SEQUENCE: 51

-continued gccaaccaac ctcgatctct tgtagatctg ttctctaaac gaac 44

<210> SEQ ID NO 52
<211> LENGTH: 39
<212> TYPE: DNA
<213> ORGANISM: SARS-CoV Urbani

<400> SEQUENCE: 52
ccaacctcga tctcttgtag atctgttctc taaacgaac 39

<210> SEQ ID NO 53
<211> LENGTH: 34
<212> TYPE: DNA
<213> ORGANISM: SARS-CoV Urbani

<400> SEQUENCE: 53
ctcgatctct tgtagatctg ttctctaaac gaac 34

<210> SEQ ID NO 54
<211> LENGTH: 27
<212> TYPE: DNA
<213> ORGANISM: SARS-CoV Urbani

<400> SEQUENCE: 54
tcttgtagat ctgttctcta aacgaac 27

<210> SEQ ID NO 55
<211> LENGTH: 20
<212> TYPE: DNA
<213> ORGANISM: SARS-CoV Urbani

<400> SEQUENCE: 55
gatctgttct ctaaacgaac 20

<210> SEQ ID NO 56
<211> LENGTH: 9
<212> TYPE: DNA
<213> ORGANISM: SARS-CoV Urbani

<400> SEQUENCE: 56 taaacgaac 9

<210> SEQ ID NO 57
<211> LENGTH: 60
<212> TYPE: DNA
<213> ORGANISM: SARS-CoV Urbani

<400> SEQUENCE: 57
atattaggtt tttacctacc caggaaaagc caaccaacct cgatctcttg tagatctgtt 60

<210> SEQ ID NO 58
<211> LENGTH: 50
<212> TYPE: DNA
<213> ORGANISM: SARS-CoV Urbani

<400> SEQUENCE: 58
atattaggtt tttacctacc caggaaaagc caaccaacct cgatctcttg 50

<210> SEQ ID NO 59
<211> LENGTH: 40
<212> TYPE: DNA
<213> ORGANISM: SARS-CoV Urbani -continued

<400> SEQUENCE: 59
atattaggtt tttacctacc caggaaaagc caaccaacct 40

<210> SEQ ID NO 60
<211> LENGTH: 30
<212> TYPE: DNA
<213> ORGANISM: SARS-CoV Urbani

<400> SEQUENCE: 60
atattaggtt tttacctacc caggaaaagc 30

<210> SEQ ID NO 61
<211> LENGTH: 20
<212> TYPE: DNA
<213> ORGANISM: SARS-CoV Urbani

<400> SEQUENCE: 61
atattaggtt tttacctacc 20

<210> SEQ ID NO 62
<211> LENGTH: 10
<212> TYPE: DNA
<213> ORGANISM: SARS-CoV Urbani

<400> SEQUENCE: 62
atattaggtt 10

<210> SEQ ID NO 63
<211> LENGTH: 62
<212> TYPE: DNA
<213> ORGANISM: SARS-CoV Urbani

<400> SEQUENCE: 63
tttacctacc caggaaaagc caaccaacct cgatctcttg tagatctgtt ctctaaacga 60
ac 62

<210> SEQ ID NO 64
<211> LENGTH: 52
<212> TYPE: DNA
<213> ORGANISM: SARS-CoV Urbani

<400> SEQUENCE: 64
caggaaaagc caaccaacct cgatctcttg tagatctgtt ctctaaacga ac 52

<210> SEQ ID NO 65
<211> LENGTH: 42
<212> TYPE: DNA
<213> ORGANISM: SARS-CoV Urbani

<400> SEQUENCE: 65
caaccaacct cgatctcttg tagatctgtt ctctaaacga ac 42

<210> SEQ ID NO 66
<211> LENGTH: 32
<212> TYPE: DNA
<213> ORGANISM: SARS-CoV Urbani

<400> SEQUENCE: 66
cgatctcttg tagatctgtt ctctaaacga ac 32

<210> SEQ ID NO 67
<211> LENGTH: 22

-continued

<212> TYPE: DNA
<213> ORGANISM: SARS-CoV Urbani

<400> SEQUENCE: 67
tagatctgtt ctctaaacga ac 22

<210> SEQ ID NO 68
<211> LENGTH: 12
<212> TYPE: DNA
<213> ORGANISM: SARS-CoV Urbani

<400> SEQUENCE: 68
ctctaaacga ac 12

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
atattaggtt tttacctacc cagg 24

<210> SEQ ID NO 70
<211> LENGTH: 23
<212> TYPE: DNA
<213> ORGANISM: Artificial Sequence
<220> FEATURE:
<223> OTHER INFORMATION: Synthetic

<400> SEQUENCE: 70
agtatgttga gtgtaattag gag 23

<210> SEQ ID NO 71
<211> LENGTH: 22
<212> TYPE: DNA
<213> ORGANISM: Artificial Sequence
<220> FEATURE:
<223> OTHER INFORMATION: Synthetic

<400> SEQUENCE: 71
tgctaactac attttctgga gg 22

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
catcaccatc ttccaggagc 20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
cttactcctt ggaggccatg 20

<210> SEQ ID NO 74

-continued

<211> LENGTH: 22
<212> TYPE: DNA
<213> ORGANISM: Artificial Sequence
<220> FEATURE:
<223> OTHER INFORMATION: Synthetic

<400> SEQUENCE: 74
tgctaactac atttctgga gg 22

<210> SEQ ID NO 75
<211> LENGTH: 23
<212> TYPE: DNA
<213> ORGANISM: Artificial Sequence
<220> FEATURE:
<223> OTHER INFORMATION: Synthetic

<400> SEQUENCE: 75
agtatgttga gtgtaattag gag 23

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
atattaggtt tttacctacc cagg 24

<210> SEQ ID NO 77
<211> LENGTH: 57
<212> TYPE: DNA
<213> ORGANISM: SARS coronavirus CUHK-Su10

<400> SEQUENCE: 77
ctacccagga aaagccaacc aacctcgatc tcttgtagat ctgttctcta aacgaac 57

<210> SEQ ID NO 78
<211> LENGTH: 56
<212> TYPE: DNA
<213> ORGANISM: SARS coronavirus BJ04

<400> SEQUENCE: 78
tacccaggaa aagccaacca acctcgatct cttgtagatc tgttctctaa acgaac 56

<210> SEQ ID NO 79
<211> LENGTH: 53
<212> TYPE: DNA
<213> ORGANISM: SARS coronavirus BJ01

<400> SEQUENCE: 79
ccaggaaaag ccaaccaacc tcgatctctt gtagatctgt tctctaaacg aac 53

<210> SEQ ID NO 80
<211> LENGTH: 422
<212> TYPE: PRT
<213> ORGANISM: SARS coronavirus Shanhgai LY

<400> SEQUENCE: 80

Met Ser Asp Asn Gly Pro Gln Ser Asn Gln Arg Ser Ala Pro Arg Ile
1 5 10 15

Thr Phe Gly Gly Pro Thr Asp Ser Thr Asp Asn Asn Gln Asn Gly Gly
20 25 30

Arg Asn Gly Ala Arg Pro Lys Gln Arg Arg Pro Gln Gly Leu Pro Asn

-continued

```
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Ala Ala Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420
```

<210> SEQ ID NO 81
<211> LENGTH: 221
<212> TYPE: PRT
<213> ORGANISM: SARS coronavirus Tor2

<400> SEQUENCE: 81

Met Ala Asp Asn Gly Thr Ile Thr Val Glu Glu Leu Lys Gln Leu Leu
1 5 10 15

Glu Gln Trp Asn Leu Val Ile Gly Phe Leu Phe Leu Ala Trp Ile Met
20 25 30

Leu Leu Gln Phe Ala Tyr Ser Asn Arg Asn Arg Phe Leu Tyr Ile Ile
35 40 45

Lys Leu Val Phe Leu Trp Leu Leu Trp Pro Val Thr Leu Ala Cys Phe
50 55 60

Val Leu Ala Ala Val Tyr Arg Ile Asn Trp Val Thr Gly Gly Ile Ala
65 70 75 80

Ile Ala Met Ala Cys Ile Val Gly Leu Met Trp Leu Ser Tyr Phe Val
85 90 95

Ala Ser Phe Arg Leu Phe Ala Arg Thr Arg Ser Met Trp Ser Phe Asn
100 105 110

Pro Glu Thr Asn Ile Leu Leu Asn Val Pro Leu Arg Gly Thr Ile Val
115 120 125

Thr Arg Pro Leu Met Glu Ser Glu Leu Val Ile Gly Ala Val Ile Ile
130 135 140

Arg Gly His Leu Arg Met Ala Gly His Ser Leu Gly Arg Cys Asp Ile
145 150 155 160

Lys Asp Leu Pro Lys Glu Ile Thr Val Ala Thr Ser Arg Thr Leu Ser
165 170 175

Tyr Tyr Lys Leu Gly Ala Ser Gln Arg Val Gly Thr Asp Ser Gly Phe
180 185 190

Ala Ala Tyr Asn Arg Tyr Arg Ile Gly Asn Tyr Lys Leu Asn Thr Asp
195 200 205

His Ala Gly Ser Asn Asp Asn Ile Ala Leu Leu Val Gln
210 215 220

<210> SEQ ID NO 82
<211> LENGTH: 221
<212> TYPE: PRT
<213> ORGANISM: SARS coronavirus Shanghai QXC

<400> SEQUENCE: 82

Met Ala Asp Asn Gly Thr Ile Thr Val Glu Glu Leu Lys Gln Leu Leu
1 5 10 15

Glu Gln Trp Asn Leu Val Ile Gly Phe Leu Phe Leu Ala Trp Ile Met
20 25 30

Leu Leu Gln Phe Ala Tyr Ser Asn Arg Asn Arg Phe Leu Tyr Ile Ile
35 40 45

Lys Leu Val Phe Leu Trp Leu Leu Trp Pro Val Thr Leu Ala Cys Phe
50 55 60

Val Leu Ala Ala Val Tyr Arg Ile Asn Trp Val Thr Gly Gly Ile Ala
65 70 75 80

Ile Ala Met Ala Cys Ile Val Gly Leu Met Trp Leu Ser Tyr Phe Val
85 90 95

Ala Ser Phe Arg Leu Phe Ala Arg Thr Arg Ser Met Trp Ser Phe Asn
100 105 110

Pro Glu Thr Asn Ile Leu Pro Asn Val Pro Leu Arg Gly Thr Ile Val
115 120 125

Thr Arg Pro Leu Met Glu Ser Glu Leu Val Ile Gly Ala Val Ile Ile
130 135 140

-continued

```
Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220


<210> SEQ ID NO 83
<211> LENGTH: 221
<212> TYPE: PRT
<213> ORGANISM: SARS coronavirus Shanghai QXC

<400> SEQUENCE: 83

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe
    50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110

Pro Glu Thr Asn Ile Leu Pro Asn Val Pro Leu Arg Gly Thr Ile Val
        115                 120                 125

Thr Arg Pro Leu Met Glu Ser Glu Leu Val Ile Gly Ala Val Ile Ile
    130                 135                 140

Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220


<210> SEQ ID NO 84
<211> LENGTH: 76
<212> TYPE: PRT
<213> ORGANISM: SARS coronavirus Tor2

<400> SEQUENCE: 84

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30
```

-continued

```
Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75


<210> SEQ ID NO 85
<211> LENGTH: 76
<212> TYPE: PRT
<213> ORGANISM: SARS coronavirus Shanghai QXC

<400> SEQUENCE: 85

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Pro Glu Gly Val Pro Asp Leu Leu Val
65                  70                  75


<210> SEQ ID NO 86
<211> LENGTH: 76
<212> TYPE: PRT
<213> ORGANISM: SARS coronavirus Shanghai QXC

<400> SEQUENCE: 86

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Pro Glu Gly Val Pro Asp Leu Leu Val
65                  70                  75


<210> SEQ ID NO 87
<211> LENGTH: 76
<212> TYPE: PRT
<213> ORGANISM: SARS coronavirus CUHK-W1

<400> SEQUENCE: 87

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75
```